United States Patent
Beatty et al.

(10) Patent No.: US 12,195,447 B2
(45) Date of Patent: *Jan. 14, 2025

(54) AZOLOPYRIMIDINE FOR THE TREATMENT OF CANCER-RELATED DISORDERS

(71) Applicant: ARCUS BIOSCIENCES, INC., Hayward, CA (US)

(72) Inventors: Joel Beatty, San Mateo, CA (US); Laurent Debien, San Francisco, CA (US); Jenna Jeffrey, Oakland, CA (US); Manmohan Reddy Leleti, Dublin, CA (US); Debashis Mandal, Fremont, CA (US); Dillon Miles, Berkeley, CA (US); Jay Powers, Pacifica, CA (US); Brandon Rosen, San Mateo, CA (US); Ehesan Sharif, Menlo Park, CA (US); Rhiannon Thomas-Tran, San Jose, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 217 days.

This patent is subject to a terminal disclaimer.

(21) Appl. No.: 17/507,921

(22) Filed: Oct. 22, 2021

(65) Prior Publication Data

US 2022/0144808 A1    May 12, 2022

Related U.S. Application Data

(63) Continuation of application No. 17/346,918, filed on Jun. 14, 2021, now abandoned, which is a continuation of application No. 16/460,263, filed on Jul. 2, 2019, now Pat. No. 11,072,597, which is a continuation of application No. 15/875,106, filed on Jan. 19, 2018, now Pat. No. 10,399,962.

(60) Provisional application No. 62/479,005, filed on Mar. 30, 2017, provisional application No. 62/448,608, filed on Jan. 20, 2017.

(51) Int. Cl.
| | | |
|---|---|---|
| C07D 401/14 | (2006.01) | |
| A61K 31/506 | (2006.01) | |
| A61K 31/5377 | (2006.01) | |
| A61K 45/06 | (2006.01) | |
| C07D 403/04 | (2006.01) | |
| C07D 403/14 | (2006.01) | |
| C07D 405/14 | (2006.01) | |
| C07D 413/14 | (2006.01) | |
| C07D 417/14 | (2006.01) | |

(52) U.S. Cl.
CPC .......... *C07D 401/14* (2013.01); *A61K 31/506* (2013.01); *A61K 31/5377* (2013.01); *A61K 45/06* (2013.01); *C07D 403/04* (2013.01); *C07D 403/14* (2013.01); *C07D 405/14* (2013.01); *C07D 413/14* (2013.01); *C07D 417/14* (2013.01)

(58) Field of Classification Search
CPC ................ C07D 401/14; C07D 403/04; C07D 417/14; C07D 403/14; C07D 405/14; C07D 413/14; A61K 31/506; A61K 31/5377; A61K 45/06
See application file for complete search history.

(56) References Cited

U.S. PATENT DOCUMENTS

| | | |
|---|---|---|
| 10,399,962 B2 | 9/2019 | Beatty et al. |
| 11,072,597 B2 | 7/2021 | Beatty et al. |
| 2011/0275611 A1 | 11/2011 | Axten et al. |
| 2013/0289017 A1 | 10/2013 | Dorsch et al. |
| 2015/0018351 A1 | 1/2015 | Lind et al. |

FOREIGN PATENT DOCUMENTS

| | | |
|---|---|---|
| EP | 1439175 A1 | 7/2004 |
| WO | 2005058883 A2 | 6/2005 |
| WO | 2008005457 A2 | 1/2008 |
| WO | 2009156737 A1 | 12/2009 |
| WO | 2010059658 A1 | 5/2010 |
| WO | 2012095142 A1 | 7/2012 |
| WO | WO-2015085909 | 6/2015 |
| WO | WO-2017088755 | 6/2017 |

(Continued)

OTHER PUBLICATIONS

Sangaraiah Nagarajan et al. An eco-friendly water mediated synthesis of 1,2,3-triazolyl-2-aminopyrimidine hybrids as highly potent anti-bacterial agents. Chinese Chemical Letters 25 (2014) 419-422 (Year: 2014).*
International Search Report and Written Opinion mailed Mar. 8, 2018 corresponding to PCT/US2018/014352 filed Jan. 19, 2018; 11 pages.
Extended European Search Report for EP Application No. 18741044.4 mailed May 13, 2020, 9 pages.
Davari et al., "Synthesis and biological evaluation of novel pyridine derivatives as potential anticancer agents and phosphodiesteras-3 inhibitors", Bioorganic Chemistry, Dec. 1, 2014, vol. 57, pp. 83-89.
Mitsos "Isoters in Medicinal Chemistry", 2006, https://www.scripps.edu/baran/images/grpmtgpdf/Mitsos_Group Meeting Feb. 1, 2006.pdf; 7 pages.
Murugavel et al., "Synthesis, Crystal /structure aand DFT Studies of 4-(1-Benzyl-5-mthyl-1H-1,2,3-triazol-4-yl)-6-(o-tolyl)pyrimidin-2-amine", Database CAPLUS, Database accession No. 2015:631662, abstract.

(Continued)

*Primary Examiner* — Noble E Jarrell
*Assistant Examiner* — Richard Grant Peckham
(74) *Attorney, Agent, or Firm* — Sheppard Mullin Richter & Hampton LLP

(57) ABSTRACT

Compound that is an inhibitor of at least one of the $A_{2A}$ and $A_{2B}$ adenosine receptors, and compositions containing the compound and methods for synthesizing the compound, are described herein. The use of such compound and compositions for the treatment of a diverse array of diseases, disorders, and conditions, including cancer- and immune-related disorders that are mediated, at least in part, by the adenosine $A_{2A}$ receptor and/or the adenosine $A_{2B}$ receptor.

2 Claims, No Drawings

(56) References Cited

FOREIGN PATENT DOCUMENTS

| WO | 2018136700 A1 | 7/2018 |
|---|---|---|
| WO | 2018152450 A1 | 8/2018 |
| WO | 2018182051 A1 | 10/2018 |
| WO | 2018183418 A1 | 10/2018 |
| WO | 2018183964 A1 | 10/2018 |

OTHER PUBLICATIONS

Nagarajan et al., "An eco-friendly water mediated synthesis of 1,2,3-triazolyl-2-aminopyrimidine hybrids as highly potent antibacterial agents", Chinese Chemical Letter, 2014, vol. 25, pp. 419-422.
Examination Report for Australian Application No. 2022203515 dated Feb. 14, 2023. 3 pages.
Examination Report for New Zealand Application No. 754731 dated Feb. 24, 2022. 4 pages.
Examination Report for New Zealand Application No. 754731 dated Sep. 9, 2022. 2 pages.
Murugavel, S. et al., "Synthesis, Crystal Structure and DFT Studies of 4-(1-Benzyl-5-methyl-1H-1,2,3-triazol-4-yl)-6-(o-tolyl)pyrimidin-2-amine", Asian Journal Of Chemistry 2015, 27(3), 974-978.
Murugavel, S. et al., Crystal structure and DFT studies of 4-(1-benzyl-5-methyl-1H-1,2,3-triazol-4yl)-6-phenylpyrimidin-2-amine, Indian Journal of Pure & Applied Physics 2016, vol. 54, pp. 199-208.
Notice of Preliminary Rejection for Korean Application No. 10-2019-7024140 dated Apr. 12, 2023. 6 pages.
Office Action and Search Report for Taiwan Application No. 107101999 dated Dec. 6, 2021. 8 pages.
Office Action for Argentina Application No. 20180100131 dated Feb. 2, 2022. 4 pages.
Office Action for Brazilian Application No. BR112019014193-6 dated Aug. 17, 2022. 5 pages.
Office Action for Chinese Application No. 201880007563.X dated Apr. 26, 2022. 19 pages.
Office Action for Chinese Application No. 201880007563.X dated Oct. 18, 2022. 7 pages.
Office Action for Vietnam Application No. 1-2019-04437 for Jan. 28, 2022. 3 pages.
Official Action for Japanese Application No. 2022-15648 dated Mar. 23, 2023. 3 pages.
Yang et al., Identification of a New Series of Potent Adenosine A2A Receptor Antagonists Based on 4-Amino-5-carbonitrile Pyrimidine Template for the Treatment of Parkinson's Disease, ACS Chemical Neuroscience 2016, 7(11), 1575-1584.
Examination Report and Search Report for United Arab Emirates Application No. P6001023/2019 dated Oct. 23, 2023. 11 pages.
Examination Report for Malaysian Application No. PI2019003049 dated Oct. 30, 2023. 3 pages.
Official Action for Japanese Application No. 2022-15648 dated Nov. 6, 2023. 5 pages.
Examination Report for Qatar Application No. QA/201907-00373 dated Jan. 31, 2024. 2 pages.
Examiner's Report for Canadian Application No. 3,047,600 dated Dec. 18, 2023. 7 pages.
Extended European Search Report for European Application No. 23194932.2 dated Mar. 11, 2024. 9 pages.
Official Action for Uruguay Application No. 37.574 dated Mar. 5, 2024. 11 pages.

* cited by examiner

AZOLOPYRIMIDINE FOR THE TREATMENT OF CANCER-RELATED DISORDERS

CROSS-REFERENCES TO RELATED APPLICATIONS

This application is a continuation application of U.S. application Ser. No. 17/346,918, filed Jun. 14, 2021, now abandoned, which is a continuation of U.S. application Ser. No. 16/460,263, filed Jul. 2, 2019, now U.S. Pat. No. 11,072,597, which is a continuation of U.S. application Ser. No. 15/875,106, filed Jan. 19, 2018, now U.S. Pat. No. 10,399,962, which claims the benefit of priority to U.S. Provisional Application No. 62/448,608, filed Jan. 20, 2017, and U.S. Provisional Application No. 62/479,005, filed Mar. 30, 2017, the contents of which are herein incorporated by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Adenosine is a purine nucleoside compound comprising a complex of adenine and a ribose sugar molecule (ribofuranose). Adenosine occurs naturally in mammals and plays important roles in several biochemical processes, including energy transfer (as adenosine triphosphate and adenosine monophosphate) and signal transduction (as cyclic adenosine monophosphate). Adenosine also serves in processes associated with vasodilation, including cardiac vasodilation, and acts as a neuromodulator (e.g., it is thought to be involved in promoting sleep). In addition to its involvement in these biochemical processes, adenosine is used as a therapeutic antiarrhythmic agent to treat, for example, supraventricular tachycardia. As discussed further herein, tumors evade host responses by inhibiting immune function and promoting tolerance, and adenosine has been shown to play an important role in mediating tumor evasion of the immune system. Adenosine signaling through $A_{2A}$Rs and $A_{2B}$Rs, expressed on a variety of immune cell subsets and endothelial cells, has been established as having an important role in protecting tissues during inflammatory responses. As such, under certain conditions adenosine protects tumors from immune destruction (see, e.g., Fishman, P, et al. (2009) Handb Exp Pharmacol 193:399-441).

The adenosine receptors are a class of purinergic G protein-coupled receptors with adenosine as the endogenous ligand. The four types of adenosine receptors in humans are referred to as $A_1$, $A_{2A}$, $A_{2B}$ and $A_3$. Modulation of $A_1$ has been proposed for the management and treatment of, for example, neurological disorders, asthma, and heart and renal failure; $A_{2A}$ antagonists have been proposed for the management and treatment of, for example, Parkinson's disease; modulation of $A_{2B}$ has been proposed for the management and treatment of, for example, chronic pulmonary diseases, including asthma; and modulation of $A_3$ has been proposed for the management and treatment of, for example, asthma and chronic obstructive pulmonary diseases, glaucoma, cancer, and stroke.

Historically, modulators of adenosine receptors have been nonselective. This is acceptable in certain indications, such as where the endogenous agonist adenosine, which acts on all four adenosine receptors in cardiac tissue, is administered parenterally for the treatment of severe tachycardia. However, the use of sub-type selective adenosine receptor agonists and antagonists provides the potential for achieving desired outcomes while minimizing or eliminating adverse effects.

As such, there is a need in the art for sub-type selective adenosine receptor agonists. The present invention addresses this need and provides related advantages as well.

BRIEF SUMMARY OF THE INVENTION

The present invention relates to compounds that modulate the adenosine $A_{2A}$ receptor ($A_{2A}$R) and/or the adenosine $A_{2B}$ receptor ($A_{2B}$R), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by the adenosine $A_{2A}$ receptor ($A_{2A}$R) and/or the adenosine $A_{2B}$ receptor ($A_{2B}$R). Such diseases, disorders and conditions are described in detail elsewhere herein. Unless otherwise indicated, when uses of the compounds of the present invention are described herein, it is to be understood that such compounds may be in the form of a composition (e.g., a pharmaceutical composition).

As discussed hereafter, although the compounds of the present invention are believed to effect their activity by inhibition the adenosine $A_{2A}$ receptor ($A_{2A}$R) and/or the adenosine $A_{2B}$ receptor ($A_{2B}$R), a precise understanding of the compounds' underlying mechanism of action is not required to practice the invention. It is envisaged that the compounds may alternatively effect their activity through direct or indirect inhibition of adenylyl cyclase. It is also envisaged that the compounds may effect their activity through inhibition of both $A_{2A}$ receptor ($A_{2A}$R) and/or the adenosine $A_{2B}$ receptor ($A_{2B}$R) as well as adenylyl cyclase. Although the compounds of the invention are generally referred to herein as adenosine $A_{2A}$ receptor ($A_{2A}$R) and/or the adenosine $A_{2B}$ receptor ($A_{2B}$R) inhibitors, it is to be understood that the term "$A_{2A}$R/$A_{2B}$R inhibitors" encompasses compounds that act individually through inhibition of $A_{2A}$R, $A_{2B}$R or adenylyl cyclase, and/or compounds that act through inhibition of $A_{2A}$R, $A_{2B}$R, and adenylyl cyclase.

The $A_{2A}$ and $A_{2B}$ cell surface adenosine receptors are found to be upregulated in various tumor cells. Thus, antagonists of the $A_{2A}$ and/or $A_{2B}$ adenosine receptors represent a new class of promising oncology therapeutics.

Activation of the $A_{2A}$ adenosine receptor results in inhibition of the immune response to tumors via suppression of T regulatory cell function and inhibition of natural killer cell cytotoxicity and tumor-specific CD4+/CD8+ activity. Therefore, inhibition of this receptor subtype by specific antagonists may enhance immunotherapeutics in cancer therapy. Activation of the $A_{2B}$ adenosine receptor plays a role in the development of tumors via upregulation of the expression levels of angiogenic factors in microvascular endothelial cells. [See, e.g., P. Fishman et al., Handb Exp Pharmacol (2009); 193:399-441]. Moreover, adenosine receptor 2A blockade has been shown to increase the efficacy of anti-PD-1 through enhanced anti-tumor T cell responses (P. Beavis, et al., Cancer Immunol Res DOI: 10.1158/2326-6066.CIR-14-0211 Published 11 Feb. 2015). A more comprehensive discussion of the roles of the $A_{2A}$Rs and the $A_{2B}$Rs is set forth hereafter.

Adenosine 2A Receptor ($A_{2A}$R)

The $A_{2A}$R (also referred to as ADORA2A) is a G protein-coupled receptor (GPCR), family members of which possess seven transmembrane alpha helices. Based on its crystallographic structure, the $A_{2A}$R comprises a ligand binding pocket distinct from that of other structurally determined GPCRs (e.g., the beta-2 adrenergic receptor).

As set forth elsewhere herein, adenosine is involved in mediating tumor evasion of the immune system. The $A_{2A}$R plays a critical, nonredundant role in mediating adenosine-induced anti-inflammatory responses. The $A_{2A}$R negatively regulates immune responses, and thus pharmacologic inhibition of $A_{2A}$R activation has been demonstrated to be a viable means of enhancing immunotherapy.

As noted above, activation of the $A_{2A}$R impacts the adaptive immune response; by way of example, the $A_{2A}$R protects the host from excessive tissue destruction by not only acutely inhibiting T-cell function, but by also promoting the development of regulatory T cells. Because $A_{2A}$R activation is a potent inhibitor of adaptive immune responses, tumor-derived adenosine has been implicated in blocking antitumor immunity.

In addition to its other roles, the $A_{2A}$R has been implicated in selectively enhancing anti-inflammatory cytokines, promoting the upregulation of PD-1 and CTLA-4, promoting the generation of LAG-3 and Foxp3+ regulatory T cells, and mediating the inhibition of regulatory T cells. PD-1, CTLA-4 and other immune checkpoints are discussed further herein. As all of these immunosuppressive properties have been identified as mechanisms by which tumors evade host responses, a cancer immunotherapeutic regimen that includes an $A_{2A}$R antagonist may result in enhanced tumor immunotherapy. [See generally, Naganuma, M., et al. (2006) J Immunol 177:2765-769].

$A_{2A}$R antagonists likely play an important role in chemotherapy and radiation therapy. Mechanistically, the concomitant administration of $A_{2A}$R antagonists during chemotherapy or radiation therapy has been proposed to lead to the expansion of tumor-specific T cells while simultaneously preventing the induction of tumor-specific regulatory T cells. Furthermore, combining $A_{2A}$R antagonists with tumor vaccines is thought to provide at least an additive effect in view of their divergent mechanisms of action. Finally, $A_{2A}$R antagonists may most effectively be used in combination with tumor vaccines and other checkpoint blockers. By way of example, blocking PD-1 engagement as well as inhibiting the $A_{2A}$R might mitigate the ability of tumors to turn off tumor-specific effector T cells (see, e.g., Fishman, P, et al. (2009) Handb Exp Pharmacol 193:399-441). Moreover, adenosine signaling through the $A_{2A}$R receptor has been found to be a promising negative feedback loop, and preclinical studies have confirmed that blockade of $A_{2A}$R activation can markedly enhance anti-tumor immunity (Sitkovsky, M V, et al. (2014) Cancer Immun Res 2:598-605).

Adenosine 2B Receptor ($A_{2B}$R)

The $A_{2B}$R (also referred to as ADORA2B) is a GPCR found in many different cell types. It requires higher concentrations of adenosine for activation than other adenosine receptor subtypes (e.g., $A_1$R, $A_{2A}$R, and $A_3$R) (Fredholm B, et al. (2001) Biochem Pharmacol 61:443-448). Such conditions have been seen in, for example, tumors where hypoxia is commonly observed. Contrary to the other adenosine receptor subtypes, the $A_{2B}$R may play an important role in pathophysiological conditions associated with massive adenosine release. Thus, selective blockade or stimulation of this adenosine receptor subtype may not interfere with the numerous important physiological functions of adenosine mediated via other adenosine receptor subtypes. However, the pathway leading to $A_{2B}$R-mediated inhibition is not fully understood.

Angiogenesis represents a pivotal mechanism for tumor growth. The angiogenesis process is highly regulated by an array of angiogenic factors and is triggered by adenosine under particular circumstances that are associated with hypoxia. The $A_{2B}$R is expressed in human microvascular endothelial cells, where it plays an important role in the regulation of the expression of angiogenic factors such as vascular endothelial growth factor (VEGF). In certain tumor types, hypoxia has been observed to cause an upregulation of $A_{2B}$Rs, suggesting that $A_{2B}$Rs play a critical role in mediating the effects of adenosine on angiogenesis. Thus, blockade of $A_{2B}$Rs may limit tumor growth by limiting the oxygen supply to the tumor cells. Furthermore, experiments involving adenylate cyclase activation indicate that $A_{2B}$Rs are the sole adenosine receptor subtype in certain tumor cells, suggesting that $A_{2B}$R antagonists may exhibit effects on particular tumor types (see, e.g., Feoktistov, I. et al. (2003) Circ Res 92:485-492).

Recent data complicate an understanding of the precise role of $A_{2B}$R modulators. As discussed above, data confirm that $A_{2B}$Rs play an important role in mediating the effects of adenosine on tumor growth and progression. Indeed, inhibition of angiogenesis and inhibition of ERK 1/2 phosphorylation represent the most interesting effects for a potential anticancer treatment based on $A_{2B}$R as a target. However, while inhibition of angiogenesis requires the use of $A_{2B}$R antagonists, inhibition of growth signaling via other clinically relevant pathways (e.g., the MAP kinase pathway) might be achieved through treatment with $A_{2B}$R agonists (see, e.g., Graham, S. et al. (2001) Eur J Pharmacol 420:19-26). The results of additional experimentation may indicate that both agonists and antagonists will provide useful options for treatment in combination with other therapeutic measures if used at different stages of the disease and its treatment.

In one particular aspect, the present invention provides compounds having Formula (I):

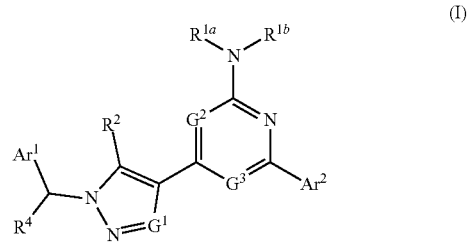

or a pharmaceutically acceptable salt, hydrate, or solvate thereof, wherein, $G^1$ is N or $CR^{3a}$;
$G^2$ is N or $CR^{3b}$;
$G^3$ is N or $CR^{3c}$;

$R^{3a}$, $R^{3b}$, and $R^{3c}$ are each independently H, deuterium or $C_{1-3}$ alkyl;

$R^{1a}$ and $R^{1b}$ are each independently selected from the group consisting of
i) H or deuterium,
ii) $C_{1-8}$ alkyl optionally substituted with from 1-3 $R^5$ substituents,
iii) —$X^1$—O—$C_{1-8}$ alkyl optionally substituted with from 1-3 $R^5$ substituents,
iv) —C(O)—$R^6$,
v) Y optionally substituted with 1-3 $R^7$ substituents, and
vi) —$X^1$—Y optionally substituted with 1-3 $R^7$ substituents; or
vii) $R^{1a}$ and $R^{1b}$ together with the nitrogen to which they are attached form a 5-6 membered heterocycloalkyl ring optionally substituted with from 1-3 $R^8$ substituents, wherein the heterocycloalkyl has 0-2 additional heteroatom ring vertices selected from the group consisting of O, N, and S;

each Y is $C_{3-8}$ cycloalkyl or 4 to 6-membered heterocycloalkyl having 1-3 heteroatom ring vertices selected from the group consisting of O, N, and S;

$R^2$ and $R^4$ are each independently H, deuterium or $C_{1-3}$ alkyl;

$Ar^1$ is phenyl or a 5 to 6-membered heteroaryl, each of which is optionally substituted with 1-3 $R^9$;

$Ar^2$ is phenyl or a 5 to 6-membered heteroaryl, each of which is optionally substituted with 1-3 $R^{10}$;

wherein the 5 to 6-membered heteroaryl of $Ar^1$ and $Ar^2$ each independently have 1-3 heteroatom ring vertices selected from the group consisting of O, N, $N^+$—O— and S;

each $X^1$ is $C_{1-6}$ alkylene;

each $R^5$ is independently selected from the group consisting of hydroxyl, $C_{3-8}$ cycloalkyl, phenyl, —O-phenyl, —C(O)O$R^a$ and oxo;

each $R^6$ is $C_{1-8}$ alkyl or Y, each of which is optionally substituted with 1-3 substituents selected from the group consisting of hydroxyl, —O-phenyl, phenyl, and —O—$C_{1-8}$ alkyl;

each $R^7$ is independently selected from the group consisting of $C_{1-8}$ alkyl, hydroxyl, —O—$C_{1-8}$ alkyl, oxo, and C(O)O$R^a$;

each $R^8$ is independently selected from the group consisting of $C_{1-8}$ alkyl, hydroxyl, and oxo;

each $R^9$ is independently selected from the group consisting of $C_{1-8}$ alkyl, $C_{1-8}$ deuteroalkyl, —O—$C_{1-8}$ alkyl, —O—$C_{1-8}$ deuteroalkyl, —$X^1$—O—$C_{1-8}$ alkyl, —O—$X^1$—O—$C_{1-8}$ alkyl, —$X^1$—O—$X^1$—O—$C_{1-8}$ alkyl, —C(O)O$R^a$, halogen, cyano, —N$R^b R^c$, Y, —$X^1$—$C_{3-8}$ cycloalkyl, and —$X^2$—Z, wherein $X^2$ is selected from the group consisting of $C_{1-6}$ alkylene, —$C_{1-6}$ alkylene-O—, —C(O)—, and —S(O)$_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$;

each $R^{10}$ is independently selected from the group consisting of $C_{1-8}$ alkyl, $C_{1-8}$ deuteroalkyl, halo, cyano, —O—$C_{1-8}$ alkyl, —O—$C_{1-8}$ deuteroalkyl, —$X^1$—O—$C_{1-8}$ alkyl, —O—$X^1$—O—$C_{1-8}$ alkyl, —S(O)$_2$—$C_{1-6}$ alkyl, —C(O)N$R^d R^e$, and 4-6-membered heteroaryl having from 1-3 heteroatom ring vertices selected from the group consisting of O, N, and S, wherein each of said $R^{10}$ substituents is optionally substituted with 1-3 $R^{11}$, or two $R^{10}$ on adjacent ring vertices of $Ar^2$ are optionally combined to form a 5-membered heterocyclic ring optionally substituted with 1-2 halogens;

each $R^{11}$ is independently selected from the group consisting of hydroxyl, halo, cyano, —N$R^d R^e$, —C(O)O$R^a$, phenyl, $C_{3-8}$ cycloalkyl, and $C_{1-4}$ alkyl optionally substituted with C(O)O$R^a$;

each $R^{11}$ is independently selected from the group consisting of halo, cyano, hydroxy, —C(O)O$R^a$; and each $R^a$ is H, deuterium or $C_{1-6}$ alkyl;

each $R^b$ and $R^c$ are independently selected from the group consisting of H, deuterium, $C_{1-8}$ alkyl, —S(O)$_2$—$C_{1-6}$ alkyl, —C(O)O$R^a$, and —$X^1$—C(O)O$R^a$;

each $R^d$ and $R^e$ are independently selected from the group consisting of H, deuterium, $C_{1-8}$ alkyl, —S(O)$_2$—$C_{1-6}$ alkyl; and provided that when $G^1$ and $G^2$ are each N, $G^3$ is CH, $R^2$ is CH$_3$, and $R^{1a}$ and $R^{1b}$ are each H or deuterium, then $Ar^2$ is other than 2-thienyl, phenyl, 2-, 3- or 4-methoxyphenyl, 3- or 4-halophenyl, 2,4-dimethoxyphenyl, 2,4-dichlorophenyl or 2- or 4-methylphenyl.

In some embodiments, the present invention contemplates a compound having the formula:

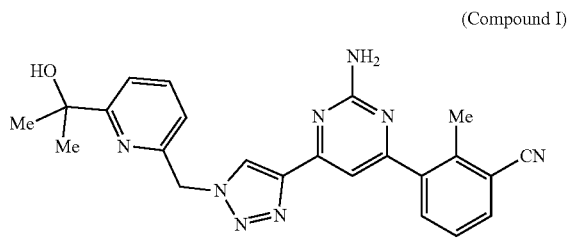 [SMILES: Cc1c(C#N)cccc1-c1cc(-c2cn(Cc3cccc(C(C)(C)O)n3)nn2)nc(N)n1]

(Compound I)

or a pharmaceutically acceptable salt, hydrate, or solvate thereof. As described hereafter, Compound I is a potent antagonist of $A_{2A}R$ and $A_{2B}R$ with a potency on both receptors of less than 10 nM.

In some embodiments, the present invention contemplates methods for treating or preventing cancer in a subject (e.g., a human) comprising administering to the subject a therapeutically effective amount of at least one $A_{2A}R/A_{2B}R$ inhibitor described herein. In some embodiments, the present invention includes methods of treating or preventing a cancer in a subject by administering to the subject at least one of the compounds described herein in an amount effective to reverse or stop the progression of $A_{2A}R$-mediated immunosuppression. In some embodiments, the $A_{2A}R$-mediated immunosuppression is mediated by an antigen-presenting cell (APC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell lung carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an $A_{2A}R/A_{2B}R$ inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one $A_{2A}R/A_{2B}R$ inhibitor (e.g., a novel inhibitor of the instant invention). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present invention contemplates methods for treating or preventing an immune-related disease, disorder or condition in a subject (e.g., a human), comprising administering to the subject a therapeutically effective amount of at least one $A_{2A}R/A_{2B}R$ inhibitor described herein. Examples of immune-related diseases, disorders and conditions are described hereafter.

Other diseases, disorders and conditions that can be treated or prevented, in whole or in part, by modulation of $A_{2A}R/A_{2B}R$ activity are candidate indications for the $A_{2A}R/A_{2B}R$ inhibitor compounds of the present invention.

The present invention further contemplates the use of $A_{2A}R/A_{2B}R$ inhibitors described herein in combination with one or more additional agents. The one or more additional agents may have some adenosine $A_{2A}$ receptor and/or adenosine $A_{2B}$ receptor modulating activity; alternatively, they may function through distinct mechanisms of action. In some embodiments, such agents comprise radiation (e.g., localized radiation therapy or total body radiation therapy) and/or other treatment modalities of a non-pharmacological nature. When combination therapy is utilized, the compound(s) described herein and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In particular embodiments, the present invention contemplates the use of $A_{2A}R/A_{2B}R$ inhibitors described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one $A_{2A}R/A_{2B}R$ inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); anthracycline-based therapies (e.g., doxorubicin, daunorubicin, epirubicin and idarubicin); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the $A_{2A}R/A_{2B}R$ inhibitors in combination with other agents known in the art (e.g., arsenic trioxide) and other chemotherapeutic agents developed in the future.

In some embodiments drawn to methods of treating cancer, the administration of a therapeutically effective amount of an $A_{2A}R/A_{2B}R$ inhibitor described herein in combination with at least one chemotherapeutic agent results in a cancer survival rate greater than the cancer survival rate observed by administering either alone. In further embodiments drawn to methods of treating cancer, the administration of a therapeutically effective amount of an $A_{2A}R/A_{2B}R$ inhibitor described herein in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one $A_{2A}R/A_{2B}R$ inhibitor described herein and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an $A_{2A}R/A_{2B}R$ inhibitor in conjunction with at least one chemotherapeutic agent and/or radiation therapy, wherein the resulting rejection of tumor cells is greater than that obtained by administering either the $A_{2A}R/A_{2B}R$ inhibitor, the chemotherapeutic agent or the radiation therapy alone.

In further embodiments, the present invention provides methods for treating cancer in a subject, comprising administering to the subject a therapeutically effective amount of at least one $A_{2A}R/A_{2B}R$ inhibitor and at least one immunomodulator other than an $A_{2A}R/A_{2B}R$ inhibitors. In particular embodiments, the at least one immunomodulator is selected from the group consisting of CD4OL, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-α/−13, M-CSF, IL-3, GM-CSF, IL-13, anti-IL-10 and indoleamine 2,3-dioxygenase 1 (IDO1) inhibitors. Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one $A_{2A}R/A_{2B}R$ inhibitor described herein and a therapeutically effective amount of an anti-infective agent(s)

In some embodiments of the present invention, the additional therapeutic agent is a cytokine, including, for example granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the compounds described herein to treat (either alone or as a component of combination therapy) infection is discussed further hereafter.

In additional embodiments, treatment of an infective disorder is effected through the co-administration of a vaccine in combination with administration of a therapeutically effective amount of an $A_{2A}R/A_{2B}R$ inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-C SF). In particular embodiments, the vaccine includes one or more immunogenic peptides and/or dendritic cells.

In some embodiments, the present invention contemplates methods of using the compounds described herein in combination with one or more antimicrobial agents.

In certain embodiments drawn to treatment of an infection by administering an $A_{2A}R/A_{2B}R$ inhibitor and at least one additional therapeutic agent, a symptom of infection observed after administering both the $A_{2A}R/A_{2B}R$ inhibitor and the additional therapeutic agent is improved over the same symptom of infection observed after administering either alone. In some embodiments, the symptom of infection observed can be reduction in viral load, increase in $CD4^+$ T cell count, decrease in opportunistic infections, increased survival time, eradication of chronic infection, or a combination thereof.

BRIEF DESCRIPTION OF THE DRAWINGS

NOT APPLICABLE

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Provided herein, for example, are compounds and compositions for inhibition of the adenosine $A_{2A}$ receptor ($A_{2A}R$) and/or the adenosine $A_{2B}$ receptor ($A_{2B}R$), and pharmaceutical compositions comprising the same. Also provided herein are, for example, methods of treating or preventing a disease, disorder or condition, or a symptom thereof, mediated by inhibition of adenosine $A_{2A}$ receptor ($A_{2A}R$) and/or the adenosine $A_{2B}$ receptor ($A_{2B}R$).

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups, often referred to as $X^1$ or $X^2$ groups in the present application, can be substituted or unsubstituted. When a group comprising $X^1$ or $X^2$ is optionally substituted, it is understood that the optional substitutions may be on the alkylene portion of the moiety.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. In some embodiments, the cycloalkyl compounds of the present disclosure are monocyclic $C_{3-6}$ cycloalkyl moieties.

The term "heterocycloalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycylic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A cycloheteroalkyl group can be attached to the remainder of the molecule through a ring carbon or a heteroatom.

As used herein, a wavy line, "〰", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, and alkynyl) can be a variety of groups selected from: halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy, oxo, cycloalkyl and heterocycloalkyl in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, $C_{1-s}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Optional substituents for the cycloalkyl and heterocycloalkyl radicals can be a variety of groups selected from: alkyl optionally substituted with C(O)OR', halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy and oxo. R', R" and R'" each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R"', —NR"C(O)R', —NR"C(O)$_2$R', —NR—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl. Other suitable substituents include each of the above aryl substituents attached to a ring atom by an alkylene tether of from 1-6 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CR$^f$R$^g$)$_r$—B—, wherein A and B are independently —CH$_2$—, —O—, —NH—, —S—, —S(O)—, —S(O)$_2$—, —S(O)$_2$NR'— or a single bond, r is an integer of from 1 to 3, and R$^f$ and R$^g$ are each independently H of halogen. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are described in more detail elsewhere herein.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of $A_{2A}R/A_{2B}R$, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of $A_{2A}R/A_{2B}R$ or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an $A_{2A}R/A_{2B}R$ inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an $A_{2A}R/A_{2B}R$ inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of $A_{2A}R/A_{2B}R$, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Adenosine $A_{2A}$ Receptor and Adenosine $A_{2B}$ Receptor and Inhibition Thereof As set forth above, a precise understanding of the compounds' underlying mechanism of action by which the compounds of the present invention effect their activity is not required to practice the invention, the compounds (or a subset thereof) are believed to inhibit adenosine $A_{2A}$ receptor ($A_{2A}R$) and/or the adenosine $A_{2B}$ receptor ($A_{2B}R$). Alternatively, the compounds (or a subset thereof) may inhibit adenylyl cyclase function. The compounds (or a subset thereof) may also have inhibitor activity on the $A_{2A}$ receptor ($A_{2A}R$), the adenosine $A_{2B}$ receptor ($A_{2B}R$) as well as adenylyl cyclase. Although the compounds of the invention are generally referred to herein as adenosine $A_{2A}$ receptor ($A_{2A}R$) and/or the adenosine $A_{2B}$ receptor ($A_{2B}R$) inhibitors, it is to be understood that the term "$A_{2A}R/A_{2B}R$ inhibitors" encompasses compounds that act individually through inhibition of $A_{2A}R$, $A_{2B}R$ or adenylyl cyclase, and/or compounds that act through inhibition of $A_{2A}R$, $A_{2B}R$, and adenylyl cyclase.

Identification of Adenosine $A_{2A}$ Receptor and Adenosine $A_{2B}$ Receptor Inhibitors Possessing Desirable Characteristics The present invention is drawn, in part, to the identification of inhibitors of the adenosine $A_{2A}$ receptor and/or the adenosine $A_{2B}$ receptor with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

Compounds of the Invention

Provided herein are compounds having the Formula (I)

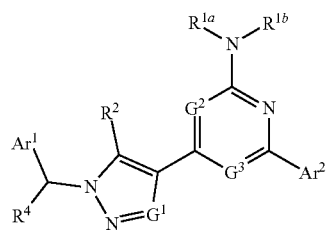

(I)

or a pharmaceutically acceptable salt, hydrate, or solvate thereof, wherein, $G^1$ is N or $CR^{3a}$;
$G^2$ is N or $CR^{3b}$;
$G^3$ is N or $CR^{3c}$;
$R^{3a}$, $R^{3b}$, and $R^{3c}$ are each independently H, deuterium or $C_{1-3}$ alkyl;
$R^{1a}$ and $R^{1b}$ are each independently selected from the group consisting of
  viii) H or deuterium,
  ix) $C_{1-8}$ alkyl optionally substituted with from 1-3 $R^5$ substituents,
  x) —$X^1$—O—$C_{1-8}$ alkyl optionally substituted with from 1-3 $R^5$ substituents,
  xi) —C(O)—$R^6$,
  xii) Y optionally substituted with 1-3 $R^7$ substituents, and
  xiii) —$X^1$—Y optionally substituted with 1-3 $R^7$ substituents; or
  xiv) $R^{1a}$ and $R^{1b}$ together with the nitrogen to which they are attached form a 5-6 membered heterocycloalkyl ring optionally substituted with from 1-3 $R^8$ substituents, wherein the heterocycloalkyl has 0-2 additional heteroatom ring vertices selected from the group consisting of O, N, and S;
each Y is $C_{3-8}$ cycloalkyl or 4 to 6-membered heterocycloalkyl having 1-3 heteroatom ring vertices selected from the group consisting of O, N, and S;
$R^2$ and $R^4$ are each independently H, deuterium or $C_{1-3}$ alkyl;
$Ar^1$ is phenyl or a 5 to 6-membered heteroaryl, each of which is optionally substituted with 1-3 $R^9$;
$Ar^2$ is phenyl or a 5 to 6-membered heteroaryl, each of which is optionally substituted with 1-3 $R^{10}$;
wherein the 5 to 6-membered heteroaryl of $Ar^1$ and $Ar^2$ each independently have 1-3 heteroatom ring vertices selected from the group consisting of O, N, $N^+$—O— and S; each $X^1$ is $C_{1-6}$ alkylene;
each $R^5$ is independently selected from the group consisting of hydroxyl, $C_{3-8}$ cycloalkyl, phenyl, —O-phenyl, —C(O)$OR^a$ and oxo;
each $R^6$ is $C_{1-8}$ alkyl or Y, each of which is optionally substituted with 1-3 substituents selected from the group consisting of hydroxyl, —O-phenyl, phenyl, and —O—$C_{1-8}$ alkyl;
each $R^7$ is independently selected from the group consisting of $C_{1-8}$ alkyl, hydroxyl, —O—$C_{1-8}$ alkyl, oxo, and C(O)$OR^a$;
each $R^8$ is independently selected from the group consisting of $C_{1-8}$ alkyl, hydroxyl, and oxo;
each $R^9$ is independently selected from the group consisting of $C_{1-8}$ alkyl, $C_{1-8}$ deuteroalkyl, —O—$C_{1-8}$ alkyl, —O—$C_{1-8}$ deuteroalkyl, —$X^1$—O—$C_{1-8}$ alkyl, —O—$X^1$—O—$C_{1-8}$ alkyl, —$X^1$—O—$X^1$—O—$C_{1-8}$ alkyl, —C(O)$OR^a$, halogen, cyano, —$NR^bR^c$, Y, —$X^1$—$C_{3-8}$ cycloalkyl, and —$X^2$—Z, wherein $X^2$ is selected from the group consisting of $C_{1-6}$ alkylene, —$C_{1-6}$ alkylene-O—, —C(O)—, and —S(O)$_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$;
each $R^{10}$ is independently selected from the group consisting of $C_{1-8}$ alkyl, $C_{1-8}$ deuteroalkyl, halo, cyano, —O—$C_{1-8}$ alkyl, —O—$C_{1-8}$ deuteroalkyl, —$X^1$—O—$C_{1-8}$ alkyl, —O—$X^1$—O—$C_{1-8}$ alkyl, —S(O)$_2$—$C_{1-6}$ alkyl, —C(O)$NR^dR^e$, and 4-6-membered heteroaryl having from 1-3 heteroatom ring vertices selected from the group consisting of O, N, and S, wherein each of said $R^{10}$ substituents is optionally substituted with 1-3 $R^{12}$, or two $R^{10}$ on adjacent ring vertices of $Ar^2$ are optionally combined to form a 5-membered heterocyclic ring optionally substituted with 1-2 halogens;

each $R^{11}$ is independently selected from the group consisting of hydroxyl, halo, cyano, —$NR^dR^e$, —C(O)OR$^a$, phenyl, $C_{3-8}$ cycloalkyl, and $C_{1-4}$ alkyl optionally substituted with C(O)OR$^a$; each $R^{12}$ is independently selected from the group consisting of halo, cyano, hydroxy, —C(O)OR$^a$; and each $R^a$ is H, deuterium or $C_{1-6}$ alkyl;

each $R^b$ and $R^c$ are independently selected from the group consisting of H, deuterium, $C_{1-8}$ alkyl, —$S(O)_2$—$C_{1-6}$ alkyl, —C(O)OR$^a$, and —$X^1$—C(O)OR$^a$;

each $R^d$ and $R^e$ are independently selected from the group consisting of H, deuterium, $C_{1-8}$ alkyl, —$S(O)_2$—$C_{1-6}$ alkyl; and provided that when $G^1$ and $G^2$ are each N, $G^3$ is CH, $R^2$ is $CH_3$, and $R^{1a}$ and $R^{1b}$ are each H or deuterium, then $Ar^2$ is other than 2-thienyl, phenyl, 2-, 3- or 4-methoxyphenyl, 3- or 4-halophenyl, 2,4-dimethoxyphenyl, 2,4-dichlorophenyl or 2- or 4-methylphenyl.

In one selected group of embodiments, compound of Formula (I) are provided wherein $Ar^1$ is a 5 to 6-membered heteroaryl optionally substituted with 1-3 $R^9$.

In another selected group of embodiments, compounds of Formula (I) are provided wherein $Ar^1$ is selected from the group consisting of pyridyl, pyridyl N-oxide, imidazolyl, pyrazolyl, and thiazolyl optionally substituted with 1-3 $R^9$. In some selected embodiments, $Ar^1$ is pyridyl or pyridyl N-oxide, optionally substituted with 1-3 $R^9$.

In some selected embodiments, compounds of Formula (I) are provided wherein the $G^3$ is $CR^{3c}$.

In some selected embodiments, the compound of Formula (I) is represented by Formula (Ia)

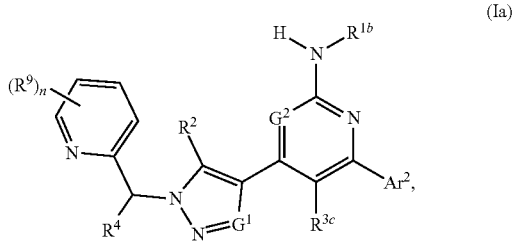

(Ia)

wherein, n is an integer from 0 to 2.

In some selected embodiments, the compound of Formula (I) is represented by Formula (Ib)

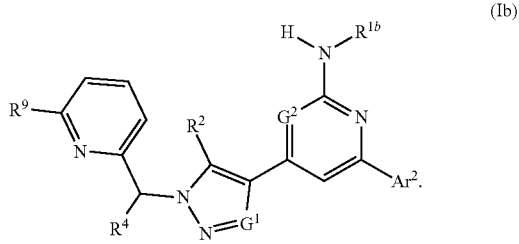

(Ib)

In some selected embodiments, compounds of Formula (I), (Ia), and (Ib) are provided wherein $Ar^2$ is substituted with from 1-3 $R^{10}$. In some embodiments, at least one $R^{10}$ is cyano.

In some selected embodiments, the compound of Formula (I) is represented by Formula (Ic)

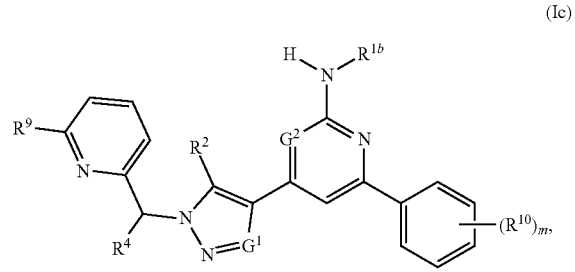

(Ic)

wherein m is an integer from 0 to 2.

In some selected embodiments, the compound of Formula (I) is represented by Formula (Id)

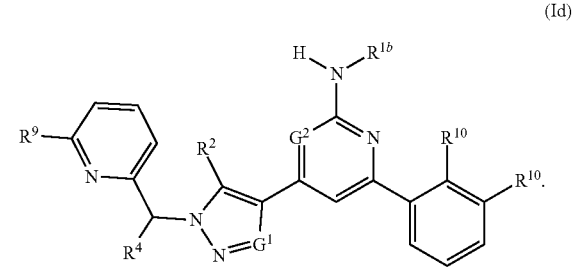

(Id)

In some selected embodiments, compounds of Formula (I), (Ia), (Ib), (Ic), and (Id) are provided wherein each $R^9$ is independently selected from the group consisting of $C_{1-8}$ alkyl, $C_{1-8}$ deuteroalkyl, —O—$C_{1-8}$ alkyl, —O—$C_{1-8}$ deuteroalkyl, —$X^1$—O—$C_{1-8}$ alkyl, —O—$X^1$—O—$C_{1-8}$ alkyl, —$X^1$—O—$X^1$—O—$C_{1-8}$ alkyl, wherein each of said $R^9$ substituents is optionally substituted with 1-3 $R^{11}$.

In some selected embodiments, compounds of Formula (I), (Ia), (Ib), (Ic), and (Id) are provided wherein each $R^9$ is independently selected from the group consisting of —C(O)OR$^a$, —$NR^bR^c$, Y, —$X^1$—$C_{3-8}$ cycloalkyl, and —$X^2$—Z, wherein $X^2$ is selected from the group consisting of $C_{1-6}$ alkylene, —$C_{1-6}$ alkylene-O—, —C(O)—, and —$S(O)_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$.

In some selected embodiments, the compound of Formula (I) is represented by Formula (Ie)

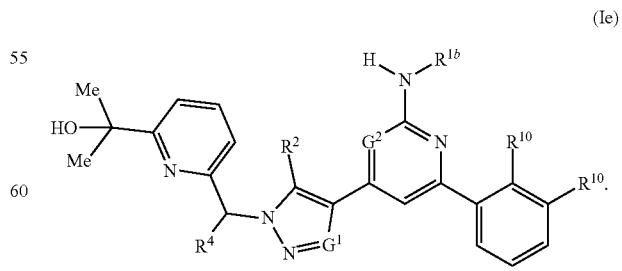

(Ie)

In some selected embodiments, compounds of Formula (I), (Ia), (Ib), (Ic), (Id), and (Ie) are provided wherein $G^2$ is N.

In some selected embodiments, compounds of Formula (I), (Ia), (Ib), (Ic), (Id), and (Ie) are provided wherein $G^1$ is N.

In some selected embodiments, compounds of Formula (I), (Ia), (Ib), (Ic), (Id), and (Ie) are provided wherein $G^1$ is $CR^{3a}$.

In some selected embodiments, compounds of Formula (I), (Ia), (Ib), (Ic), (Id), and (Ie) are provided wherein $R^2$ is H or deuterium.

In some selected embodiments, compounds of Formula (I), (Ia), (Ib), (Ic), (Id), and (Ie) are provided wherein $R^4$ is H or deuterium.

In some selected embodiments, compounds of Formula (I), (Ia), (Ib), (Ic), (Id), and (Ie) are provided wherein $R^{1b}$ is H or deuterium. In some selected embodiments, compounds of Formula (I), (Ia), (Ib), (Ic), (Id), and (Ie) are provided wherein $R^{1b}$ is selected from the group consisting of:
  i) H or deuterium,
  ii) $C_{1-8}$ alkyl optionally substituted with from 1-3 $R^5$ substituents, and
  iii) —$X^1$—O—$C_{1-8}$ alkyl optionally substituted with from 1-3 $R^5$ substituents.

In some selected embodiments, compounds of Formula (I), (Ia), (Ib), (Ic), (Id), and (Ie) are provided wherein $R^{1b}$ is selected from the group consisting of:
  i) H or deuterium,
  iv) —C(O)—$R^6$,
  v) Y optionally substituted with 1-3 $R^7$ substituents, and
  vi) —$X^1$—Y optionally substituted with 1-3 $R^7$ substituents.

In some selected embodiments, compounds of Formula (I), (Ia), (Ib), (Ic), (Id), and (Ie) are provided wherein each $R^{10}$ is independently selected from the group consisting of $C_{1-8}$ alkyl, halo, cyano, —O—$C_{1-8}$ alkyl, —$X^1$—O—$C_{1-8}$ alkyl, —O—$X^1$—O—$C_{1-8}$ alkyl, wherein each of said $R^{10}$ substituents is optionally substituted with 1-3 $R^{12}$, In some embodiments, compounds of Formula (I), (Ia), (Ib), (Ic), (Id), and (Ie) are provided wherein each $R^{10}$ is independently selected from the group consisting of $C_{1-8}$ alkyl, halo, cyano, —O—$C_{1-8}$ alkyl.

In some selected embodiments, compounds of Formula (Ic) are provided where m is at least 1 and at least one $R^{10}$ is cyano. In some selected embodiments, compounds of Formula (Id) and (Ie) are provided wherein at least one $R^{10}$ is cyano.

In some selected embodiments, any one compound of Table 1 is provided.

In some selected embodiments, any one compound of the grouping of compounds shown below is provided:

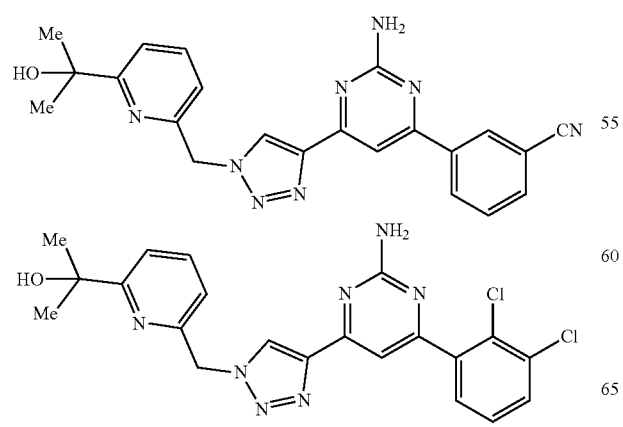

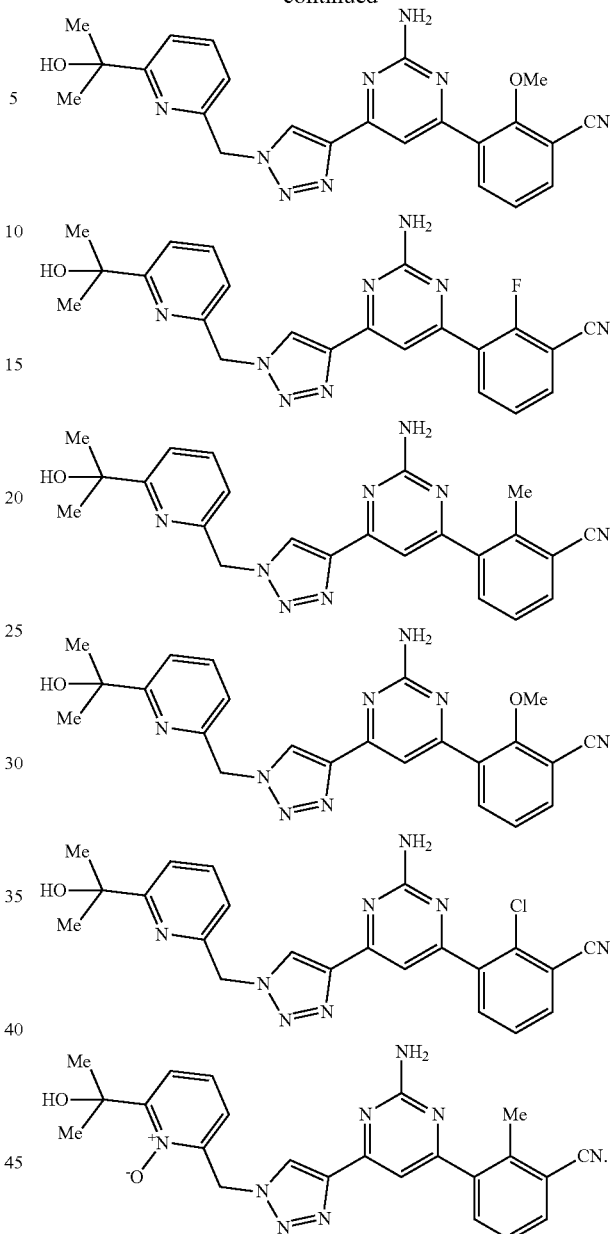

In some selected embodiments, Compound I is provided (Compound I)

In some selected embodiments, deuterated forms of the compounds of Formula (I), (Ia), (Ib), (Ic), (Id), and (Je) are provided. Deuterium may be independently substituted for hydrogen at any position where hydrogen may be present.

Methods of Synthesis

In general, the compounds provided herein can be prepared by conventional methods as described in the Examples below.

Prodrugs and Other Means of Drug Delivery and/or Half-Life Extension

In some aspects of the present invention, compounds described herein are administered in prodrug form.

In order to effect extension of therapeutic activity, drug molecules may be engineered to utilize carriers for delivery. Such carriers are either used in a non-covalent fashion, with the drug moiety physicochemically formulated into a solvent-carrier mixture, or by permanent covalent attachment of a carrier reagent to one of the drug moiety's functional groups (see generally WO 20150202317).

Several non-covalent approaches are favored. By way of example, but not limitation, in certain embodiments depot formulations comprising non-covalent drug encapsulation into polymeric carriers are employed. In such formulations, the drug molecule is combined with carrier material and processed such that the drug molecule becomes distributed inside the bulk carrier. Examples include microparticle polymer-drug aggregates (e.g., Degradex® Microspheres (Phosphorex, Inc.)), which are administered as an injectable suspension; polymer-drug molecule aggregates formulated as gels (e.g., Lupron Depot® (AbbVie Inc.)), which are administered as a single bolus injection; and liposomal formulations (e.g., DepoCyt® (Pacira Pharmaceuticals)), where the carrier may be a polymeric or non-polymeric entity capable of solubilizing the drug. In these formulations, release of the drug molecule may occur when the carrier swells or physically deteriorates. In other instances, chemical degradation allows diffusion of the drug into the biological environment; such chemical degradation processes may be autohydrolytic or enzyme-catalyzed. Among other limitations, non-covalent drug encapsulation requires prevention of uncontrolled release of the drug, and dependence of the release mechanism of the drug upon biodegradation may cause interpatient variability.

In particular embodiments, drug molecules, including both small molecules and large molecules, are conjugated to a carrier through permanent covalent bonds. Certain small molecule therapeutics that exhibit low solubility in aqueous fluids may be solubilized by conjugation to hydrophilic polymers, examples of which are described elsewhere herein. Regarding large molecule proteins, half-life extension may be achieved by, for example, permanent covalent modification with a palmitoyl moiety, and by permanent covalent modification with another protein that itself has an extended half-life (e.g., Albuferon®). In general, drug molecules show decreased biological activity when a carrier is covalently conjugated to the drug.

In certain instances, limitations associated with either drug molecules comprising non-covalent polymer mixtures or permanent covalent attachment may be successfully addressed by employing a prodrug approach for chemical conjugation of the drug to the polymer carrier. In this context, therapeutic agents that are inactive or less active than the drug moiety itself are predictably transformed into active molecular entities. The reduced biological activity of the prodrug as compared to the released drug is advantageous if a slow or controlled release of the drug is desired. In such instances, release of the drug occurs over time, thereby reducing the necessity of repeated and frequent administration of the drug. A prodrug approach may also be advantageous when the drug moiety itself is not absorbed, or has less than optimal absorption, in the gastrointestinal tract; in these instances, the prodrug facilitates absorption of the drug moiety and is then cleaved off at some later time (e.g., via first-pass metabolism). The biologically active drug molecule is typically linked to the polymeric carrier moiety by a temporary bond formed between the carrier moiety and a hydroxy, amino or carboxy group of the drug molecule.

The approaches described above are associated with several limitations. Prodrug activation may occur by enzymatic or non-enzymatic cleavage of the temporary bond between the carrier and the drug molecule, or a sequential combination of both (e.g., an enzymatic step followed by a non-enzymatic modification). In an enzyme-free in vitro environment (e.g., an aqueous buffer solution), a temporary bond such as an ester or amide may undergo hydrolysis, but the corresponding rate of hydrolysis may be such that it is outside the therapeutically useful range. In contrast, in an in vivo environment, esterases or amidases are typically present, and the esterases and amidases may cause significant catalytic acceleration of the kinetics of hydrolysis from two-fold up to several orders of magnitude (see, e.g., Greenwald et al., (1999) J Med Chem 42(18):3857-67).

As described herein, prodrugs may be classified as i) bioprecursors and ii) carrier-linked prodrugs. Bioprecursors do not contain a carrier group and are activated by the metabolic creation of a functional group. In contrast, in carrier-linked prodrugs the active substance is conjugated to a carrier moiety via a temporary linkage at a functional group of the bioactive entity. Preferred functional groups are hydroxyl or amino groups. Both the attachment chemistry and hydrolysis conditions depend on the type of functional group employed. The carrier may be biologically inert (e.g., PEG) or may have targeting properties (e.g., an antibody). Cleavage of the carrier moiety of a carrier-linked prodrug results in the bioactive entity of interest, and the nature of the deprotected functional group of the bioactive entity often contributes to its bioactivity.

The patent and scientific literature describe many macromolecular prodrugs where the temporary linkage is a labile ester bond. In these cases, the functional group of the bioactive entity is either a hydroxyl group or a carboxylic acid (see, e.g. Cheng et al. (2003) Bioconjugate Chem 14:1007-17). In addition, it is often advantageous for biomacromolecules and certain small molecule drugs to link the carrier to an amino group(s) of the bioactive entity (e.g., the N-terminus or lysine amino groups of proteins). During preparation of the prodrug, the amino groups may be more chemoselectively addressed due to their greater nucleophilicity compared to hydroxylic or phenolic groups. This is especially relevant for proteins and peptides containing a great variety of different reactive functionalities, where non-selective conjugation reactions lead to undesired product mixtures requiring extensive characterization or purification, thus decreasing reaction yield and therapeutic efficiency of the active moiety.

In general, amide bonds are more stable against hydrolysis than ester bonds, and the rate of cleavage of the amide bond may be too slow for therapeutic utility in a carrier-linked prodrug. As a result, it may be advantageous to add structural chemical components in order to effect control over the cleavability of the prodrug amide bond. These additional cleavage-controlling chemical components that are provided neither by the carrier entity nor by the drug are generally referred to as "linkers". Prodrug linkers can have a major effect on the rate of hydrolysis of temporary bond, and variation of the chemical nature of the linkers often results in particular properties. Prodrug activation of amine-containing biologically active moieties by specific enzymes for targeted release requires that the structure of the linker display a structural motif recognized as a substrate by a corresponding endogenous enzyme. In these cases, the cleavage of the temporary bond occurs in a one-step process which is catalyzed by the enzyme. For example, the enzymatic release of cytarabin is effected by the protease plasmin, which concentration is relatively high in various kinds of tumor mass.

Interpatient variability is a major drawback of predominant enzymatic cleavage. Enzyme levels may differ significantly between subjects resulting in biological variation of prodrug activation by the enzymatic cleavage. Enzyme levels may also vary depending on the site of administration (e.g., for subcutaneous injection, certain areas of the body yield more predictable therapeutic effects than others). In addition, it is difficult to establish an in vivo—in vitro correlation of the pharmacokinetic properties for enzyme-dependent carrier-linked prodrugs.

Other carrier prodrugs employing temporary linkages to amino groups in the drug moiety are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino group of the drug molecule through a second temporary linkage (e.g., a carbamate). The stability or susceptibility to hydrolysis of the second temporary linkage is dependent on the presence or absence of the masking group. In the presence of the masking group, the second temporary linkage is highly stable and unlikely to release the drug molecule with therapeutically useful kinetics, whereas in the absence of the masking group this linkage becomes highly labile, resulting in rapid cleavage and release of the drug moiety.

The cleavage of the first temporary linkage is the rate-limiting step in the cascade mechanism. The first step may induce a molecular rearrangement of the activating group (e.g., a 1,6-elimination as described in Greenwald et al. (1999) J Med Chem 42:3657-67), and the rearrangement renders the second temporary linkage much more labile such that its cleavage is induced. Ideally, the cleavage rate of the first temporary linkage is identical to the desired release rate for the drug molecule in a given therapeutic scenario. In addition, it is desirable that the cleavage of the second temporary linkage be substantially instantaneous after its lability has been induced by cleavage of the first temporary bond.

Another embodiment comprises polymeric amino-containing prodrugs based on trimethyl lock lactonization (see, e.g., Greenwald et al. (2000) J Med Chem 43(3):457-87). In this prodrug system, substituted o-hydroxyphenyl-dimethylpropionic acid is linked to PEG by an ester, carbonate, or carbamate group as a first temporary linkage and to an amino group of a drug molecule by means of an amide bond as a second temporary linkage. The rate-determining step in drug release is the enzymatic cleavage of the first linkage, which is followed by fast amide cleavage by lactonization, releasing an aromatic lactone side product. The primary disadvantage of the prodrug systems described by Greenwald et al. is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

In certain embodiments of cascade prodrugs comprising aromatic activating groups based on 1,6-elimination, the masking group is structurally separate from the carrier. This may be effected by employing a stable bond between the polymer carrier and the activating group, wherein the stable bond does not participate in the cascade cleavage mechanism. If the carrier is not serving as a masking group and the activating group is coupled to the carrier by means of a stable bond, release of potentially toxic side products (such as the activating group) is avoided. The stable attachment of the activating group and the polymer also suppresses the release of drug-linker intermediates with undefined pharmacology.

A first example of the approach described in the preceding paragraph comprises a polymeric prodrug system based on a mandelic acid activating group (see, e.g., Shabat et al. (2004) Chem Eur J 10:2626-34). In this approach the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released; the activating group is still connected to the polyacrylamide polymer after drug release. A similar prodrug system is based on a mandelic acid activating group and an enzymatically cleavable ester-linked masking group (see, e.g., Lee et al. (2004) Angew Chem 116:1707-10).

When the aforementioned linkers are used, the 1,6-elimination step still generates a highly reactive aromatic intermediate. Even if the aromatic moiety remains permanently attached to the polymeric carrier, side reactions with potentially toxic by-products or immunogenic effects may result. Thus, it is advantageous to generate linker technologies for forming polymeric prodrugs of amine-containing active agents using aliphatic prodrug linkers that are not enzyme-dependent and do not generate reactive aromatic intermediates during cleavage. One such example uses PEG5000-maleic anhydride for the reversible modification of amino groups in tissue-type plasminogen activator and urokinase (see, e.g. (1987) Garman et al. FEBS Lett 223(2):361-65). Regeneration of functional enzyme from PEG-uPA conjugate upon incubation at pH 7.4 buffer by cleavage of the maleamic acid linkage follows first order kinetics with a half-life of roughly 6 hours. A disadvantage of the maleamic acid linkage is the lack of stability of the conjugate at lower pH values.

A further approach comprises a PEG cascade prodrug system based on N,N-bis-(2-hydroxyethyl)glycine amide (bicine) linker (see e.g. (2004) J Med Chem 47:726-34). In this system, two PEG carrier molecules are linked via temporary bonds to a bicine molecule coupled to an amino group of the drug molecule. The first steps in prodrug activation involves the enzymatic cleavage of the first temporary linkages connecting both PEG carrier molecules with the hydroxy groups of the bicine activating group. Different linkages between PEG and bicine result in different prodrug activation kinetics. The second step in prodrug activation involves the cleavage of the second temporary linkage connecting the bicine activating group to the amino group of the drug molecule. A disadvantage of this system is the slow hydrolysis rate of this second temporary bicine amide linkage, which results in the release of a bicine-modified prodrug intermediate that may show different pharmacokinetic, immunogenic, toxicity and pharmacodynamic properties as compared to the native parent drug molecule.

In particular embodiments, dipeptides are utilized for prodrug development for targeting or targeted transport as they are substrates for enzymes or biotransport systems. The non-enzymatic route for dipeptide prodrug formation, that is, the ability to undergo intramolecular cyclization to form the corresponding diketopiperazine (DKP) and release the active drug, is not well defined.

In some embodiments, dipeptides are attached to a drug moiety via ester bonds, as was described for dipeptide esters of the drug paracetamol (Gomes et al. (2005) Bio & Med Chem Lett). In this case, the cyclization reaction consists of a nucleophilic attack of the N-terminal amine of the peptide on the ester carbon atom to form a tetrahedral intermediate, which is followed by a proton transfer from the amine to the leaving group oxyanion with simultaneous formation of a peptide bond to give the cyclic DKP product and free drug. This method is applicable to hydroxyl-containing drugs in vitro but has been found to compete with enzymatic hydrolysis of the ester bond in vivo, as corresponding dipeptide esters released paracetamol at a much faster rate than in buffer (Gomes et al. (Molecules 12 (2007) 2484-2506). Susceptibility of dipeptide-based prodrugs to peptidases may be addressed by incorporating at least one non-natural amino acid in the dipeptide motif. However, endogenous enzymes capable of cleaving ester bonds are not limited to peptidases, and the enzyme-dependence of such prodrug cleavage still gives rise to unpredictable in vivo performance.

In some embodiments, enzyme-dependence is intentionally engineered into DKP prodrugs, such as where dipeptide ester prodrugs are formylated at the amino terminus of the dipeptide, and enzymatic deformylation is used to initiate diketopiperazine formation and subsequent cleavage of the ester-dipeptide bond, followed by release of the drug molecule (see, e.g., U.S. Pat. No. 7,163,923). By way of further example, an octapeptide is attached by an ester linkage to the 4-hydroxyl group of vinblastine and undergoes ester bond cleavage by DKP formation after specific enzymatic removal of the N-terminal hexapeptide (see Brady et al. (2002) J Med Chem 45:4706-15).

The scope of the DKP formation reaction has also been extended to amide prodrugs. By way of example, U.S. Pat. No. 5,952,294 describes prodrug activation using diketopiperazine formation for dipeptidyl amide prodrugs of cytarabine. In this case, the temporary linkage is formed between the carbonyl of a dipeptide and the aromatic amino group of cytarabine. However, it is unlikely that a slow-release effect can be achieved for such conjugates as there is no carrier or other half-life extending moiety or functionality present.

Dipeptide prodrugs comprising bioactive peptides such as GLP-1 capable of releasing the peptide through diketopiperazine formation of the dipeptidic extension have also been described (see, e.g., WO 2009/099763). The bioactive peptide moiety may include an additional PEG chain on one of its amino acid side chain residues to achieve extended circulation of the bioactive peptide. However, this approach is associated with several significant disadvantages. First, the PEG chain has to be linked to the peptide without compromising its bioactivity, which can be difficult to achieve for many peptide-based bioactive agents. Second, as the pegylated peptide itself is bioactive, the dipeptidic promoiety has an effect on the peptide's bioactivity and may negatively affect its receptor binding properties.

Specific exemplary technologies that may be used with the compounds of the present invention include those developed by ProLynx (San Francisco, CA) and Ascendis Pharma (Palo Alto, CA). The ProLynx technology platform utilizes sets of novel linkers that are pre-programmed to cleave at different rates to allow the controlled, predictable and sustained release of small molecules and peptides from circulating semi-solid macromolecular conjugates. The technology allows for maintenance of desired steady-state serum levels of therapeutic agents for weeks to months.

The Ascendis technology platform combines the benefits of prodrug and sustained release technologies to enhance the properties of small molecules and peptides. While in circulation, proprietary prodrugs release the unmodified active parent therapeutic agent at predetermined rates governed by physiological pH and temperature conditions. Because the therapeutic agent is released in its unmodified form, it retains its original mechanism of action.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (*J. Am. Chem. Soc.*, 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Other known modifications include deuteration to improve pharmacokinetics, pharmacodyanics and toxicity profiles. Due to the greater atomic mass of deuterium, cleavage of the carbon-deuterium bond requires more energy than the carbon-hydrogen bond. Because these stronger bonds are more difficult to break, the rate of drug metabolism is slower as compared to non-deuterated forms, which allows for less frequent dosing and may further reduce toxicities. (Charles Schmidt, *Nature Biotechnology*, 2017, 35(6): 493-494; Harbeson, S. and Tung, R., *Medchem News*, 2014(2): 8-22).

Therapeutic and Prophylactic Uses

The present invention contemplates the use of the $A_{2A}R/A_{2B}R$ inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

In some embodiments, the diseases, disorders and/or conditions described herein are mediated, at least in part, by the adenosine $A_{2A}$ receptor ($A_{2A}R$). In some embodiments, the diseases, disorders and/or conditions described herein are mediated, at least in part, by the adenosine $A_{2B}$ receptor ($A_{2B}R$). In some embodiments, the diseases, disorders and/or conditions described herein are mediated, at least in part, by both $A_{2A}R$ and $A_{2B}R$.

In some embodiments, the $A_{2A}R/A_{2B}R$ inhibitors described herein are administered in an amount effective to reverse or stop the progression of $A_{2A}R$-mediated immunosuppression Oncology-related Disorders. In accordance with the present invention, an $A_{2A}R/A_{2B}R$ inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) *Oncogene* 22:3180-87; and Sawaya, et al. (2003) *New Engl. J. Med.* 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an $A_{2A}R/A_{2B}R$ inhibitor and at least one additional therapeutic or diagnostic agent, examples of which are set forth elsewhere herein.

Immune- and Inflammatory-related Disorders. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the $A_{2A}R/A_{2B}R$ inhibitors described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The $A_{2A}R/A_{2B}R$ inhibitors of the present invention can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The $A_{2A}R/A_{2B}R$ inhibitors can also be used to stimulate the immune system of patients suffering from iatrogenically-induced immune suppression, including those who have undergone bone marrow transplants, chemotherapy, or radiotherapy.

In particular embodiments of the present disclosure, the $A_{2A}R/A_{2B}R$ inhibitors are used to increase or enhance an immune response to an antigen by providing adjuvant activity. In a particular embodiment, at least one antigen or vaccine is administered to a subject in combination with at least one $A_{2A}R/A_{2B}R$ inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one $A_{2A}R/A_{2B}R$ inhibitor of the present invention.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of $A_{2A}R/A_{2B}R$ function may also play a role in immunologic tolerance and prevention of fetal rejection in utero.

In some embodiments, an $A_{2A}R/A_{2B}R$ inhibitor described herein can be combined with an immunosuppressive agent to reduce the number of immune effector cells.

Some of the aforementioned diseases, disorders and conditions for which an $A_{2A}R/A_{2B}R$ inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-a and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate—to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Microbial-related Disorders. The present invention contemplates the use of the $A_{2A}R/A_{2B}R$ inhibitors described herein in the treatment and/or prevention of any viral, bacterial, fungal, parasitic or other infective disease, disorder or condition for which treatment with an $A_{2A}R/A_{2B}R$ inhibitor may be beneficial.

Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Further examples of such diseases and disorders include staphylococcal and streptococcal infections (e.g., *Staphylococcus aureus* and *Streptococcus sanguinis*, respectively), *Leishmania, Toxoplasma, Trichomonas, Giardia, Candida albicans, Bacillus anthracis*, and *Pseudomonas aeruginosa*. In some embodiments, diseases or disorders include *Mycobacterium* infection (e.g., *Mycobacterium leprae* or *Mycobacterium tuberculosis*) or an infection caused by *Listeria monocytogenes* or *Toxoplasma gondii*. Compounds of the invention can be used to treat sepsis, decrease or inhibit bacterial growth, and reduce or inhibit inflammatory cytokines.

Further embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale*, or *Plasmodium malariae*. Frequently, anti-parasitic therapy is administered prophylactically (e.g., before a subject travels to an area with a high frequency of parasitic infection).

CNS-related and Neurological Disorders. Inhibition of $A_{2A}R/A_{2B}R$ may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Subjects suffering from multiple sclerosis (MS), a seriously debilitating autoimmune disease comprising multiple areas of inflammation and scarring of the myelin in the brain and spinal cord, may be particularly helped by the $A_{2A}R/A_{2B}R$ inhibitors described herein, as current treatments only alleviate symptoms or delay the progression of disability.

Similarly, the $A_{2A}R/A_{2B}R$ inhibitors may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Other Disorders. Embodiments of the present invention contemplate the administration of the $A_{2A}R/A_{2B}R$ inhibitors described herein to a subject for the treatment or prevention of any other disorder that may benefit from at least some level of $A_{2A}R/A_{2B}R$ inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

Pharmaceutical Compositions

The $A_{2A}R/A_{2B}R$ inhibitors of the present invention may be in the form of compositions suitable for administration to a subject. In general, such compositions are "pharmaceutical compositions" comprising an $A_{2A}R/A_{2B}R$ inhibitor(s) and one or more pharmaceutically acceptable or physiologically acceptable diluents, carriers or excipients. In certain embodiments, the $A_{2A}R/A_{2B}R$ inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of $A_{2A}R/A_{2B}R$ function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an $A_{2A}R/A_{2B}R$ inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an $A_{2A}R/A_{2B}R$ inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the $A_{2A}R/A_{2B}R$ inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the $A_{2A}R/A_{2B}R$ inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The $A_{2A}R/A_{2B}R$ inhibitors contemplated by the present invention may be in the form of any other suitable pharmaceutical composition (e.g., sprays for nasal or inhalation use) currently known or developed in the future.

Routes of Administration

The present invention contemplates the administration of $A_{2A}R/A_{2B}R$ inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the $A_{2A}R/A_{2B}R$ inhibitors disclosed herein over a defined period of time.

Particular embodiments of the present invention contemplate oral administration.

Combination Therapy

The present invention contemplates the use of $A_{2A}R/A_{2B}R$ inhibitors alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the $A_{2A}R/A_{2B}R$ inhibitors are administered or applied sequentially, e.g., where one agent is administered prior to one or more other agents. In other embodiments, the $A_{2A}R/A_{2B}R$ inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The $A_{2A}R/A_{2B}R$ inhibitors of the present invention may be used in combination with at least one other (active) agent in any manner appropriate under the circumstances. In one embodiment, treatment with the at least one active agent and at least one $A_{2A}R/A_{2B}R$ inhibitor of the present invention is maintained over a period of time. In another embodiment, treatment with the at least one active agent is reduced or discontinued (e.g., when the subject is stable), while treatment with an $A_{2A}R/A_{2B}R$ inhibitor of the present invention is maintained at a constant dosing regimen. In a further embodiment, treatment with the at least one active agent is reduced or discontinued (e.g., when the subject is stable), while treatment with an $A_{2A}R/A_{2B}R$ inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the $A_{2A}R/A_{2B}R$ inhibitor of the present invention is increased (e.g., higher dose, more frequent dosing or longer treatment regimen). In yet another embodiment, treatment with the at least one active agent is maintained and treatment with the $A_{2A}R/A_{2B}R$ inhibitor of the present invention is reduced or discontinued (e.g., lower dose, less frequent dosing or shorter treatment regimen). In yet another embodiment, treatment with the at least one active agent and treatment with the $A_{2A}R/A_{2B}R$ inhibitor of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with an $A_{2A}R/A_{2B}R$ inhibitor and at least one additional therapeutic or diagnostic agent. In some embodiments, the additional therapeutic or diagnostic agent is radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, anti-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, TLL IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present invention provides methods for tumor suppression of tumor growth comprising administration of an $A_{2A}R/A_{2B}R$ inhibitor described herein in combination with a signal transduction inhibitor (STI) to achieve additive or synergistic suppression of tumor growth.

As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the $A_{2A}R/A_{2B}R$ inhibitors described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-tri chlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with an $A_{2A}R/A_{2B}R$ inhibitor include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present invention contemplates the use of the compounds described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present invention contemplates the use of the compounds described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

Immune Checkpoint Inhibitors. The present invention contemplates the use of the inhibitors of $A_{2A}R/A_{2B}R$ function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor—ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of $A_{2A}R/A_{2B}R$ function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

In one aspect of the present invention, the claimed $A_{2A}R/A_{2B}R$ inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD4OL, OX-40, OX-40L, CD70, CD27L, CD30, CD3OL, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of the disclosed $A_{2A}R/A_{2B}R$ inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX4OL, GITR, GITRL, CD70, CD27, CD40, DR3 and CD2. Other agents that can be combined with the $A_{2A}R/A_{2B}R$ inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/

119716, WO13/132044) or FPA-008 (WO11/140249; WO13169264; WO14/036357).

In another aspect, the disclosed $A_{2A}R/A_{2B}R$ inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX4OL antagonist, such as an antagonistic OX40 antibody. Suitable OX4OL antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with an $A_{2A}R/A_{2B}R$ inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the $A_{2A}R/A_{2B}R$ inhibitors described herein include various supplements and herbs (e.g., garlic, policosanol, and guggul).

The present invention encompasses pharmaceutically acceptable salts, acids or derivatives of any of the above.

Immune- and Inflammatory-related Disorders. The present invention provides methods for treating and/or preventing immune-related diseases, disorders and conditions; and diseases, disorders and conditions having an inflammatory component; with an $A_{2A}R/A_{2B}R$ inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the $A_{2A}R/A_{2B}R$ inhibitors described herein include interferon-131a (AVONEX); interferon-131b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Microbial Diseases. The present invention provides methods for treating and/or preventing viral, bacterial, fungal and parasitic diseases, disorders and conditions, as well as disorders associated therewith, with an $A_{2A}R/A_{2B}R$ inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an $A_{2A}R/A_{2B}R$ inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, http://en.wikipedia.org/wiki/Fusion_inhibitor ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the inhibitors of $A_{2A}R/A_{2B}R$ function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the $A_{2A}R/A_{2B}R$ inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of antibacterial agents that are appropriate for use in specific bacterial infections.

Embodiments of the present invention contemplate the use of the $A_{2A}R/A_{2B}R$ inhibitors described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The $A_{2A}R/A_{2B}R$ inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the $A_{2A}R/A_{2B}R$ inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the $A_{2A}R/A_{2B}R$ inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired $A_{2A}R/A_{2B}R$ inhibitor is contained in a "unit dosage form". The phrase "unit dosage form" refers to physically discrete units, each unit containing a predetermined amount of the $A_{2A}R/A_{2B}R$ inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound described herein, and pharmaceutical compositions thereof. The kits are generally in the form of a physical structure housing various components, as described below, and may be utilized, for example, in practicing the methods described above.

A kit can include one or more of the compounds disclosed herein (provided in, e.g., a sterile container), which may be in the form of a pharmaceutical composition suitable for administration to a subject. The compounds described herein can be provided in a form that is ready for use (e.g., a tablet or capsule) or in a form requiring, for example, reconstitution or dilution (e.g., a powder) prior to administration. When the compounds described herein are in a form that needs to be reconstituted or diluted by a user, the kit may also include diluents (e.g., sterile water), buffers, pharmaceutically acceptable excipients, and the like, packaged with or separately from the compounds described herein. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); as =amino acid(s); s or sec=second(s); min=minute(s); h or hr=hour(s); ng=nanogram; [tg=microgram; mg=milligram; g=gram; kg=kilogram; dl or dL=deciliter; pl or 1AL=microliter; ml or mL=milliliter; l or L=liter; [iM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., N.Y.).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, CA); and DeCypher™ (TimeLogic Corp., Crystal Bay, NV).

The literature is replete with assays and other experimental techniques that can serve as a basis for evaluation of the compounds described herein. By way of example, mass spectrometry-based ligand binding assays (see, e.g., Massink, A. et al. Purinergic Signaling (2015) 11:581. https://doi.org/10.1007/s11302-015-9477-0; Dionisotti S. et al. J Pharmacol Exp Ther. (1996) 298:726-732) may be utilized to ascertain various properties of the compounds of the present invention.

Functional assays may also be employed to assess the compounds of the present invention. The cAMP assay described in detail below was used to evaluate certain compounds described herein.

An alternative exemplary functional assay, which assesses IFN-γ secretion, is described by Yuan, G. et al. (Int J Med Chem; Volume 2017 (2017), Article ID 4852537; https://doi.org/10.1155/2017/4852537). Briefly, during T cell receptor (TCR) activation by the CD3 ligand, C57BL/6 mice splenocytes T cells are incubated with a receptor agonist to inhibit IFN-γ secretion resulting from receptor $A_{2A}$ Rreceptor—induced immunosuppression via intracellular cAMP. Effective receptor antagonists block the receptor-activated signal, thus restoring secretion of the cytokine to potentiate and prolong the immune response.

Measurement of the Adenosine Receptor Activity of Compound I Using a $A_{2A}$R/TREx CHO cAMP Functional Assay Dose response of NECA (5-N-ethylcarboxamidoadenosine), a non-selective adenosine receptor agonist, was performed daily to determine the $EC_{80}$ of NECA used in the cAMP functional assay. 1000-2500 cells/well of stably expressed $A_{2A}$R TRex CHO cells were seeded to the 384-well Opti plate (Perkin Elmer) followed by incubating NECA at varies concentrations (ranging from 10 μM to 0 μM) at 37° C. for 30 min. After 30 min incubation, 5 μL of Ulight-anti-cAMP (1:150 dilution with conjugate and lysis buffer provided by Perkin Elmer) and 5 μL of Eu-cAMP tracer (1:50 dilution with conjugate and lysis buffer provided by Perkin Elmer) were added to the cell stimulation and incubated for an hour. FRET signal was detected with Envision multilabel plate reader (Perkin Elmer) when Eu-cAMP tracer excitation at 615 nm and emission at 665 nm. Data analysis was performed using GraphPad Prism to determine the $EC_{80}$ of the NECA.

The cAMP antagonist functional assay (Perkin Elmer) was performed on $A_{2A}$R TRex CHO stable cell lines. 1×10⁶ cells were seeded on T75 flasks and grown at 37° C. and 5% $CO_2$ overnight. $A_{2A}$R TRex CHO was induced with 1 μg/mL of tetracycline at ~70% to 80% confluency for at least 16 hours. 1,000-2,500 cells/well of stably-expressed $A_{2A}$R TREx CHO cells were then seeded to a white 384-well Opti plate followed by compound 1 incubation at varies concentration (ranging from 10 μM to 0 μM) at 37° C. for 1 hour. $EC_{80}$ of NECA (Sigma Aldrich) were added to the cell stimulation mixture and incubated for 30 min at 37° C. After 30 min incubation, 5 μL of Ulight-anti-cAMP and 5 μL of Eu-cAMP tracer were added to the cell stimulation and incubated for an hour. FRET signal was detected when Eu-cAMP tracer excitation at 615 nm and emission at 665 nm.

Data analysis was run on GraphPad Prism to measure the $K_B$ of Compound I (less than 10 nM).

EXAMPLES

General Methods:

Those skilled in the art will recognize that there are a variety of methods available to prepare molecules represented in the claims. In general, useful methods for synthesizing compounds represented in the claims consist of four parts, which may be done in any order: Connection of the a and b fragments (or formation of the a-b-c moiety via b ring cyclization), connection of the b and c fragments (or formation of the a-b-c moiety via b ring cyclization), connection of the c and d fragments, and modification of the functional groups present in all fragments. Retrosynthetic disconnection of the compounds of the invention into fragments a-d useful for construction of the compounds is shown below:

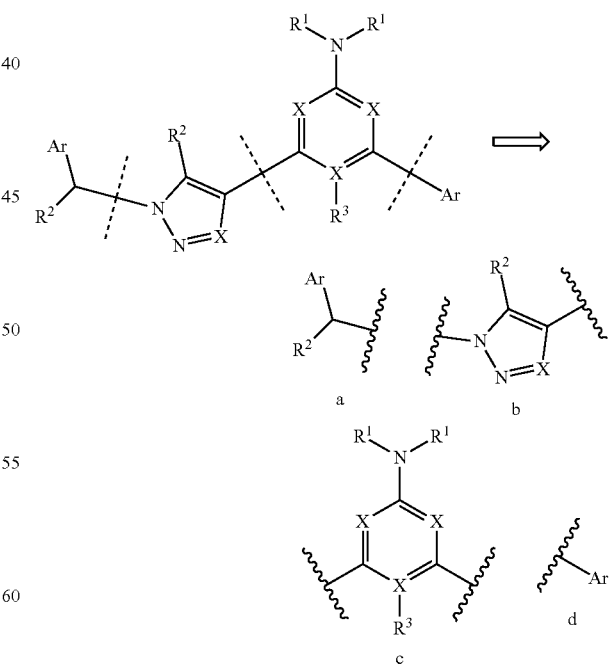

Several methods for the preparation of claimed compounds are exemplary (eq. 1-7). Equation one demonstrates one method of forming the bond between fragments c and d via a Suzuki reaction. In the case of eq. 1, Z may be chosen from an appropriate group such as Cl, Br, I, OTf, etc., and —B(OR)2 is a boronic acid or ester and the coupling is mediated by a transition metal catalyst, preferably palladium with an appropriate ligand.

eq. 1

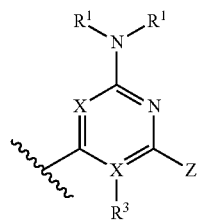 + 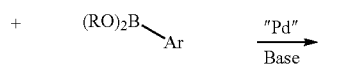 $\xrightarrow{\text{"Pd"}}{\text{Base}}$

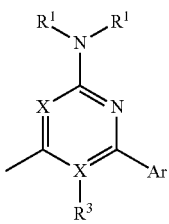

The coupling may be assisted by the use of an organic or inorganic base, and a wide variety of conditions are known in the art to facilitate the Suzuki coupling. The functionalization of the coupling partners may also be reversed as exemplified in eq. 2. Those skilled in the art will recognize that there are other possible combinations which will also result in the desired product.

eq. 2

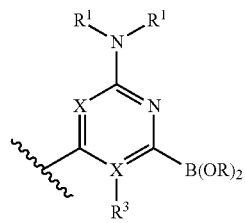 + 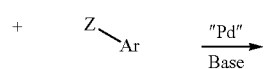 $\xrightarrow{\text{"Pd"}}{\text{Base}}$

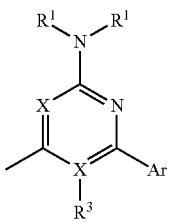

Equation three demonstrates another method of forming the forming the c-d fragment. In the case of eq. 3, condensation of an appropriate aryl acid with Meldrum's acid and appropriate promoting reagents (such as EDCI and DMAP, although other agents will also give the desired product) gives the corresponding arylketoester. Condensation of the ketoester with guanidine then results in formation of the corresponding 2-amino-3-hydroxy-5-arylpyrimidine, which in turn can be converted into the corresponding chloride by treatment with POCl₃ or other suitable reagent.

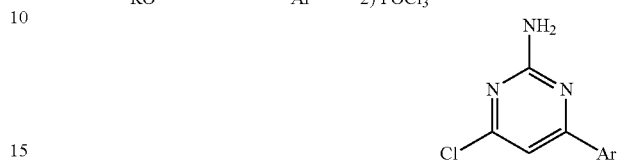

eq. 3

Formation of the bond between the c and b fragments may take place before or after formation of the connection between the c and d fragments, and the groups may be further modified before or after connection of the c and b fragments. Equation four demonstrates one method to connect the c and b fragments via a Suzuki coupling.

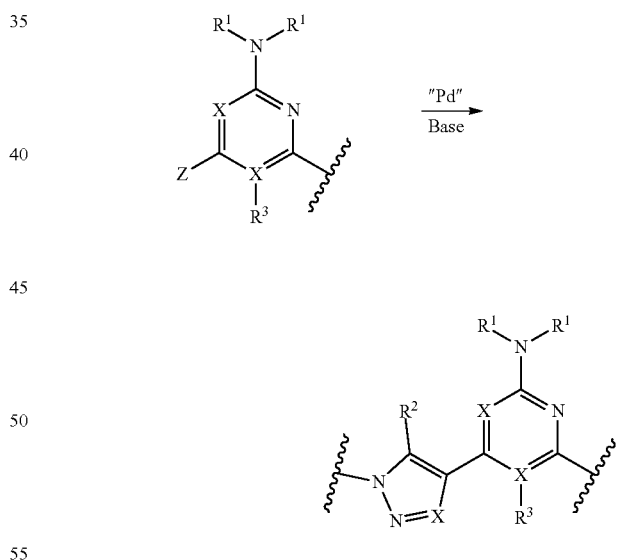

eq. 2

In the case of eq. 4, Z may be chosen from an appropriate group such as Cl, Br, I, OTf, etc., and —B(OR)₂ is a boronic acid or ester and the coupling is mediated by a transition metal catalyst, preferably palladium with an appropriate ligand. The coupling may be assisted by the use of an organic or inorganic base. A wide variety of conditions are known in the art to facilitate the Suzuki coupling. The functionalization of the coupling partners may also be reversed as exemplified in eq. 5. Those skilled in the art will recognize that there are other possible combinations which will also result in the desired product.

eq. 5

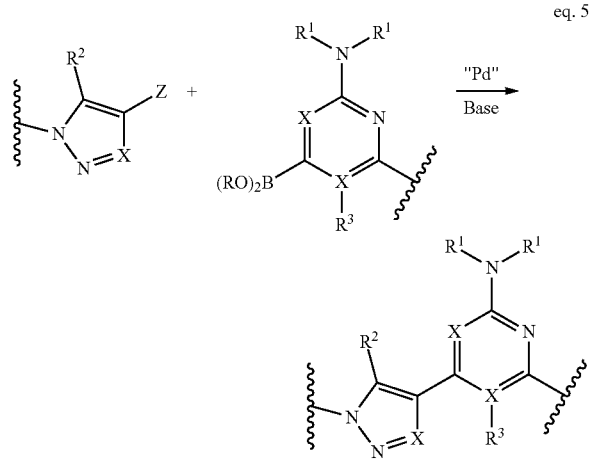

Alternatively, the b fragment may be formed via a cycloaddition between the a and c fragments via an azide-alkyne Huisgen 1,3-dipolar cycloaddition (Equation six). In the case of eq. 6, the appropriately functionalized a and c fragments may be combined together in the cycloaddition reaction between an azide and an alkyne. The reaction may be facilitated via the use of a copper catalyst or other catalyst.

eq. 6

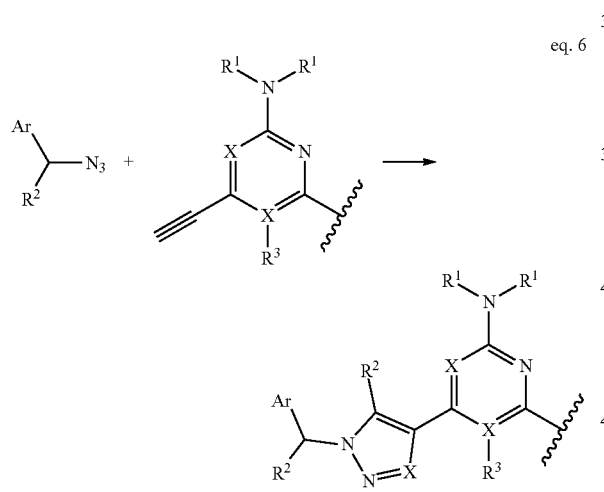

In the case where fragment b is a triazole, the ring may also be synthesized via a palladium mediated addition of sodium azide to alkenyl halides (Barluenga et. al., *Angew. Chem. Int. Ed.*, 2006, 45, 6893-6896), the Amberlyst-15 catalyzed addition of an azide to a nitroalkene (Zhang et. Al., *Synthesis*, 2016, 48, 131-135), the I$_2$/TBPB mediated oxidative cycloaddition of N-tosylhydrozones with anilines (Cai et. Al., *Org. Lett.*, 2014, 16, 5108-5111), and a host of other methods (see "Synthesis of 1,2,3-triazoles" in www-.organic-chemistry.org/synthesis/heterocycles/1,2,3-triazoles.shtm). One skilled in the art will understand that there are a wide variety of methods available to effect this transformation.

Equation seven demonstrates one method of forming the bond between fragments a and b via alkylation. In the case of eq. 7, Z is an appropriate electrophile such as Cl, Br, I, OTf, etc. and the coupling is mediated via an organic or inorganic base. For the most efficient preparation of any particular compound of the invention, one skilled in the art will recognize that the timing and the order of connection of the fragments and modification of the functionality present in any of the fragments may vary in the preparation of any given compound.

eq. 7

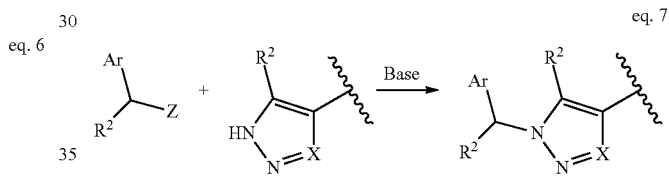

A variety of the methods described above have been used to prepare compounds of the invention, some of which are exemplified in the examples. Deuterated forms of the below examples can be synthesized by using appropriate deuterated intermediates.

Example 1: Synthesis of 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile

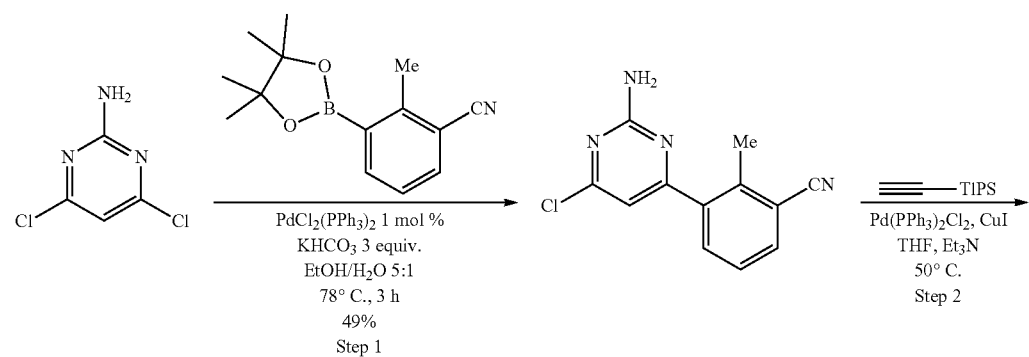

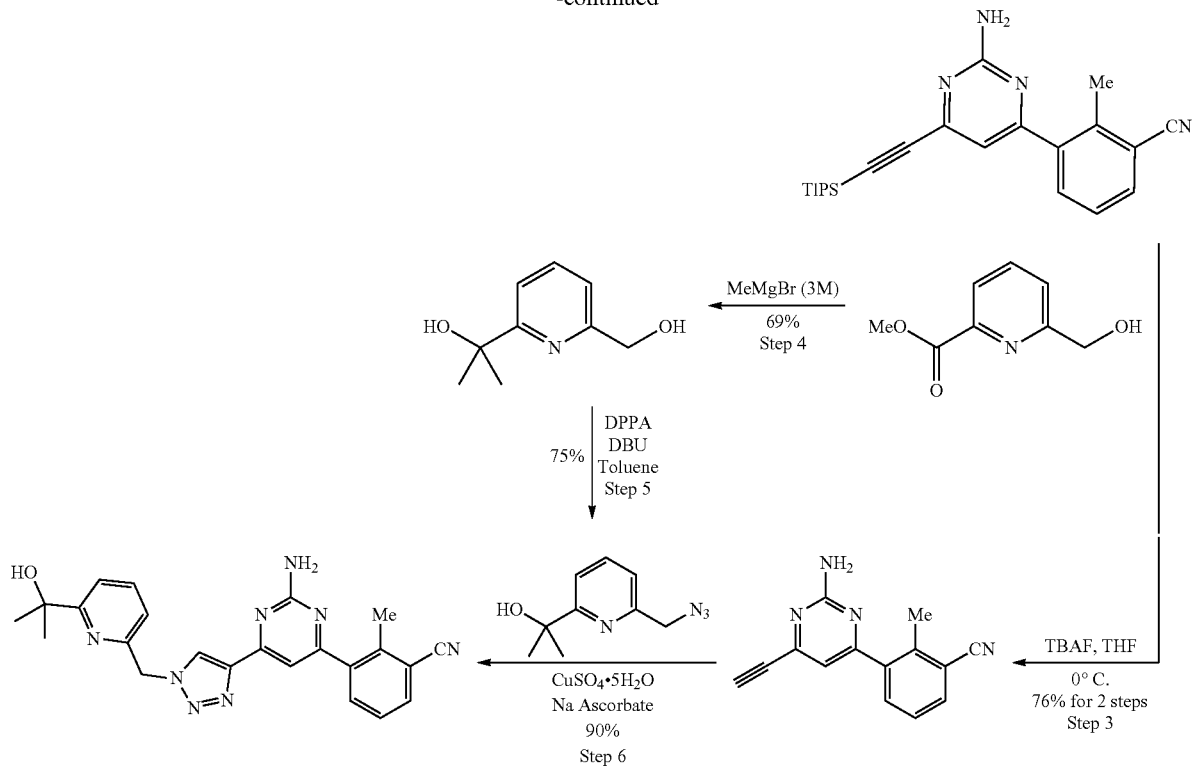

Step 1: In a 250 mL round bottom flask equipped with a magnetic stir bar was successively charged the boronic ester (3.89 g, 16 mmol) and the 2-amino-4,6-dichloropyrimidine (3.67 g, 22.4 mmol). Absolute ethanol (100 mL) was added followed by a solution of KHCO₃ (4.81 g, 48 mmol) in deionized water (19 mL). The resulting suspension was degassed with nitrogen for 5 minutes. PdCl₂(PPh₃)₂ (112 mg, 1 mol %) was then added and the mixture was heated to 78° C. for 3 hours under a nitrogen atmosphere. Ethanol was evaporated under reduced pressure and deionized water (150 mL) was added. The suspension was filtered and the solid was washed with additional water (100 mL). The solid was then dissolved in acetone (220 mL) and collected in a 500 mL round bottom flask. A mixture of silica and celite (1:1, 150 g) was added and the solvent was removed under reduced pressure. The resulting crude material was purified by flash chromatography over silica gel (dichloromethane/ethyl acetate gradient 0% to 15%). The desired product was obtained as a white solid (1.91 g, 49%). LCMS: Method A, retention time=2.93 min, ESI MS [M+H]⁺ for $C_{12}H_9ClN_4$, calcd 245.7, found 245.2.

Step 2: In a round-bottom flask 5.1 g (20.8 mmol) of chloro-pyrimidine was suspended in 42 mL of degassed THF. To this suspension was added 8.68 mL (62.4 mmol) of Et₃N and 5.95 mL (25.0 mmol) of TIPS-acetylene. The reaction mixture was stirred for 5 min, followed by addition of 219 mg (0.312 mmol) of PdCl₂(PPh₃)₂ and 119 mg (0.624 mmol) of CuI. The reaction mixture was stirred at 50° C. for 5 h under N₂. After cooling the reaction to room temp., solvent was removed and the crude material was resuspended in 100 mL EtOAc from which insoluble solid was filtered off. The filtrate was washed with (1:1) NH₄Cl/NH₄OH (2×100 mL) and 10% Na₂S₂O₄ (1×100 mL). The organic layer was dried using Na₂SO₄, concentrated and taken to next step without further purification.

Step 3: In a round-bottom flask the crude TIPS product from previous step was dissolved in 42 mL dry THF and cooled to 0° C. To this was added 25 mL (25.0 mmol) of TBAF (1.0 M in THF). The reaction was stirred at 0° C. for 15 min. Saturated NH₄Cl (100 mL) was added to quench the reaction. The organics were extracted from the aqueous layer with EtOAc (2×100 mL). The combined organic layer was washed with (1:1) NH₄Cl/NH₄OH (2×100 mL) and 10% Na₂S₂O₄ (1×100 mL). The organic layer was dried using Na₂SO₄, concentrated and the pure product 5 was obtained by triturating with 40% CH₂Cl₂/Hexane as a light brown solid. Yield: 3.71 g (76%, 2-steps).

Step 4: To a solution of methylmagnesium bromide (3 M in Et₂O, 40 mL, 120 mmol, 4.0 equiv) at 0° C. under N₂ was added a solution of methyl 2-(hydroxymethyl)pyridine-2-carboxylate (5.0 g, 29.9 mmol) in THF (70 mL, 0.4 M) over the course of 30 minutes. The resulting mixture was allowed to warm to room temperature and stirred for 3 h. The reaction mixture was quenched with NH₄Cl aq (55 mL) and EtOAc (50 mL) was added. The organic phase was separated, and the aqueous phase was extracted with EtOAc (3×40 mL). The combined organic extracts were washed with saturated aqueous sodium bisulfite (7×20 mL), then dried (Na₂SO₄), filtered and concentrated in vacuo to give the title compound (3.45 g, 69% yield; 96% purity as judged by LCMS) as a pale yellow liquid. LCMS: Method A, retention time=0.722 and 1.06 min, ESI MS [M+H]⁺ for $C_9H_{13}NO_2$, calcd 167.09, found 167.2.

Step 5: To a solution of 2-hydroxymethyl-6-(1-hydroxy-1-methylethyl)pyridine (5 g, 29.9 mmol, 1.0 equiv) in PhMe (33 mL, 0.9 M) at 0° C. under N₂ was added diphenylphosphoryl azide (7.73 mL, 35.9 mmol, 1.2 equiv.), followed by 1,8-diazabicyclo[5.4.0]undec-7-ene (5.37 mL, 35.9 mmol, 1.2 equiv.). The resulting mixture was to warm to room temperature and stirred for 14 h. Upon completion, diluted with ethyl acetate and washed with water, the organic layer was dried (Na$_2$SO$_4$), filtered and concentrated. The residue was dissolved in 1N aq HCl (2 eq, 60 mmol) and extracted with MTBE in hexanes (3:7, 100 mL), the organic layer was washed with water (50 mL) and the combined aqueous layer was neutralized with 2N aqueous NaOH and extracted with ethyl acetate (3×75 mL), dried the organic layer (Na$_2$SO$_4$), filtered through a plug of cotton and concentrated the filtrate to afford the pure compound as pale yellow color liquid (3.75 g, 75%). LCMS: Method A, retention time=2.67 min, ESI MS [M+H]$^+$ for C$_9$H$_{12}$N$_4$O, calcd 193.1, found 193.2.

Step 6: A mixture of azide (3.34 g, 17.4 mmol), alkyne (3.71 g, 15.8 mmol), copper(II) sulfate (39 mg; 0.158 mmol), and sodium ascorbate (156 mg, 0.790 mmol) in 2:1 t-BuOH/H$_2$O (158 mL) was heated at 60° C. for 13 h. The solvent was removed in vacuo, the residue dry loaded onto silica gel, and purified by silica gel chromatography (0-100% EtOAc in hexanes) to afford the desired product as an off-white solid (6.08 g, 90%). $^1$H NMR (400 MHz, DMSO-d$_6$) δ 8.69 (s, 1H), 7.90 (d, J=7.8 Hz, 1H), 7.80 (t, J=7.8 Hz, 1H), 7.76 (d, J=7.8 Hz, 1H), 7.61 (d, J=8.0 Hz, 1H), 7.51 (t, J=7.8 Hz, 1H), 7.28 (s, 1H), 7.10 (d, J=7.6 Hz, 2H), 6.90 (s, 2H), 5.81 (s, 2H), 5.23 (s, 1H), 2.55 (s, 3H), 1.38 (s, 6H). ESI MS [M+H]$^+$ for C$_{23}$H$_{23}$N$_8$O, calcd 427.2, found 427.3.

Example 2: Synthesis of 3-[2-amino-6-(1-{[6-(2-hydroxypropan-2-yl)pyridin-2-yl]methyl}-1H-1,2,3-triazol-4-yl)pyrimidin-4-yl]-2-methoxybenzonitrile cooling to room temp., excess MeOH was evaporated under reduced pressure to obtain a thick slurry. To this slurry was added 158 mL (473 mmol) of 3 M aqueous HCl. The product precipitate as a white solid, which was isolated by filtration. The residual water was removed azeotropically using toluene to obtain 26.2 g (94%) of pure product.

Step 2: Meldrum's acid 43 g (297 mmol) and 3-cyano, 2-methoxy-benzoic acid 35 g (198 mmol) was suspended in 660 mL (0.3 M) CH$_2$Cl$_2$. To this suspension was added 57 g (297 mmol) of N-(3-Dimethylaminopropyl)-N'-ethylcarbodiimide hydrochloride (EDC) and 24 g (198 mmol) of 4-Dimethylaminopyridine (DMAP). The reaction mixture was stirred at room temp. for 2 h under N$_2$. At this point, reaction turns homogeneous. The reaction mixture was then transferred to a separatory funnel and 200 mL of CH$_2$Cl$_2$ was added. The organic layer was washed with 1 M HCl (2×300 mL) and saturated NaCl (300 mL). The organic layer was dried using MgSO$_4$, concentrated and the crude material was used in next step without further purification. The crude Meldrum's acid adduct from previous step was suspended in 400 mL of absolute EtOH and refluxed for 1.5 h. After cooling to room temperature, the reaction was concentrated under reduced pressure to ¼$^{th}$ of the initial volume (~100 mL). The product β-keto ester in EtOH was used directly in next step without further purification.

Step 3: In a round-bottom flask 19 g (198 mmol) of guanidine hydrochloride was dissolved in 300 mL (0.7M) EtOH. To this was added 74 mL (198 mmol) of NaOEt (21 wt % in EtOH). The resulting turbid solution was stirred for 10 min at room temperature followed by addition of 4 in 100

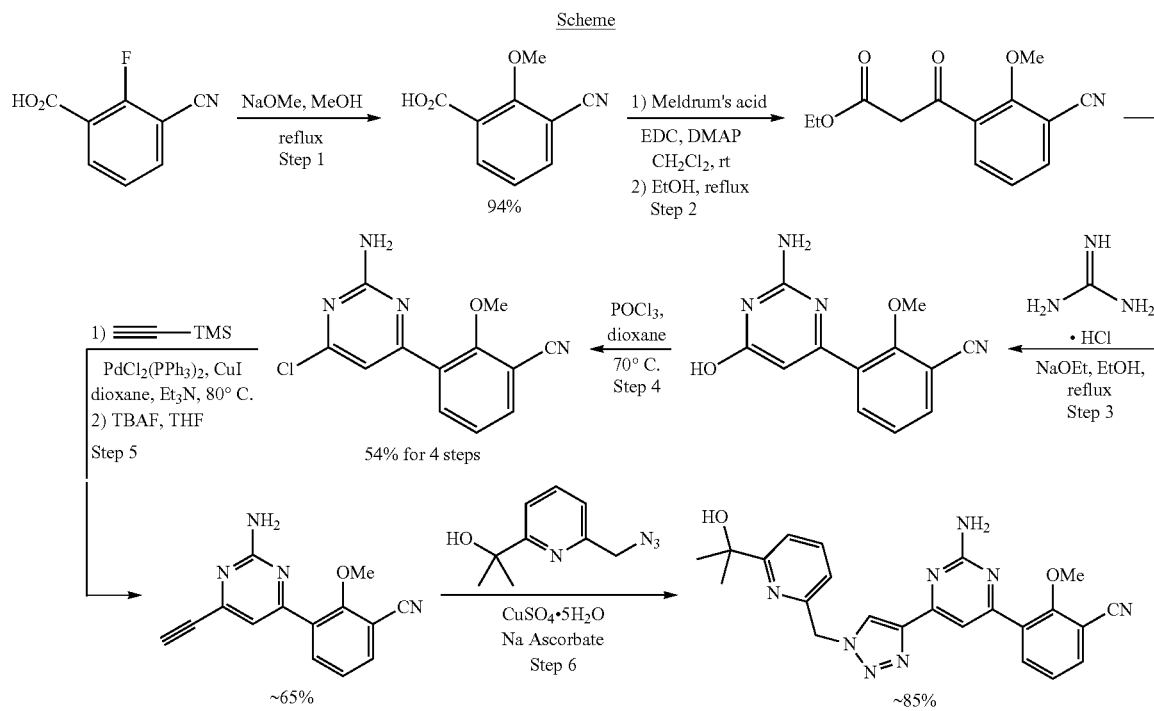

Step 1: In a round-bottom flask 26 g (157.5 mmol) of 3-cyano-2-fluoro-benzoic acid was suspended in 315 mL (0.5 M) dry MeOH. To this suspension was added 144 mL (630 mmol) of NaOMe (25 wt % in MeOH). The resulting reaction mixture was refluxed for 2 h under N$_2$. After mL EtOH (from previous step). The reaction mixture was refluxed for 72 h under N$_2$. After cooling the reaction to room temp., 300 mL hexane was added. The precipitated product was obtained by filtration and used directly in next step without further purification.

Step 4: The crude product κ from previous step was suspended in 200 mL dioxane. To this was added POCl₃ (186 mL, 2000 mmol). The reaction mixture was heated at 70° C. for 1.5 h. After cooling to room temp., the reaction mixture was poured into crushed ice (~1000 g) and stirred. (Caution: Temperature was slowly raised to room temperature allowing excess POCl₃ to quench as the ice melts avoiding vigorous reaction). After POCl₃ has quenched, solid K₂CO₃ (691 g, 5000 mmol) was added in small portion to quench the resulting HCl and H₃PO₄. The aqueous layer was extracted with CH₂C₂ (3×500 mL). The combined organic layer was washed with saturated NaCl (500 mL) and dried over MgSO₄. Solvent was removed under reduced pressure to obtain a brown solid. The crude product was triturated with 10% CH₂Cl₂/Hexane to obtain pure product (28 g, 54% over 4-steps).

Step 5: In a round-bottom flask 7.7 g (29.3 mmol) of chloro-pyrimidine 6 was suspended in 60 mL (1:1 dioxane/Et₃N). To this suspension was added TMS-acetylene (20.3 mL, 146 mmol) followed by PdCl₂(PPh₃)₂ (2.6 g, 2.93 mmol) and CuI (558 mg, 2.93 mmol). The reaction mixture was stirred at 80° C. for 1 h under N₂. After cooling the reaction to room temp., silica gel (~100 g) was added and solvent was removed under reduced pressure. The crude material adsorbed on silica gel was purified by chromatography using 80% (EtOAc/hexane). Yield of 7 was found to be 5.5 g (58%).

under reduced pressure. The crude material adsorbed on silica gel was purified by chromatography using 50% (1:1 hexane:CH₂Cl₂/EtOAc). Yield 3.2 g (80%).

Step 7: To a solution of the azide (example 1, step 5, 294 mg, 1.53 mmol, 1.0 equiv.) and the alkyne (382 mg, 1.53 mmol, 1.0 equiv.) in 2:1 t-BuOH/H₂O (5 mL, 0.3 M) were added CuSO₄ (7.2 mg, 0.029 mmol, 5 mol %) and sodium ascorbate (60.0 mg, 0.305 mmol, 20 mol %). The resulting mixture was stirred at 55° C. for 0.5 h. Upon completion, the reaction mixture was cooled to room temperature and diluted with CH₂Cl₂ (10 mL). The organic phase was separated and the aqueous phase was extracted again with CH₂Cl₂ (10 mL). The combined extracts were concentrated and the resulting residue was purified by column chromatography (CH₂Cl₂→95:5 CH₂Cl₂:MeOH) to give the title compound (604 mg, 89% yield) as a pale beige solid. ¹H NMR (400 MHz, CDCl₃) δ 8.30 (d, J=1.0 Hz, 1H), 8.04-7.98 (m, 1H), 7.92 (d, J=0.8 Hz, 1H), 7.78-7.64 (m, 2H), 7.37 (d, J=7.9 Hz, 1H), 7.28 (td, J=7.8 Hz, 0.8 Hz, 1H), 7.14 (d, J=7.6 Hz, 1H), 5.75 (brs, 2H), 5.15 (brs, 2H), 4.74 (s, 1H), 3.94 (d, J=0.8 Hz, 3H), 1.54 (d, J=0.8 Hz, 6H). ESI calculated for C₂₃H₂₃N₈O₂ [M+H]: 443.19, found: 443.2.

LCMS retention time: 2.8 minutes, Method A

Example 3: Synthesis of 3-[2-amino-6-(1-{[6-(2-hydroxypropan-2-yl)pyridin-2-yl]methyl}-1H-1,2,3-triazol-4-yl)pyrimidin-4-yl]-2-fluorobenzonitrile

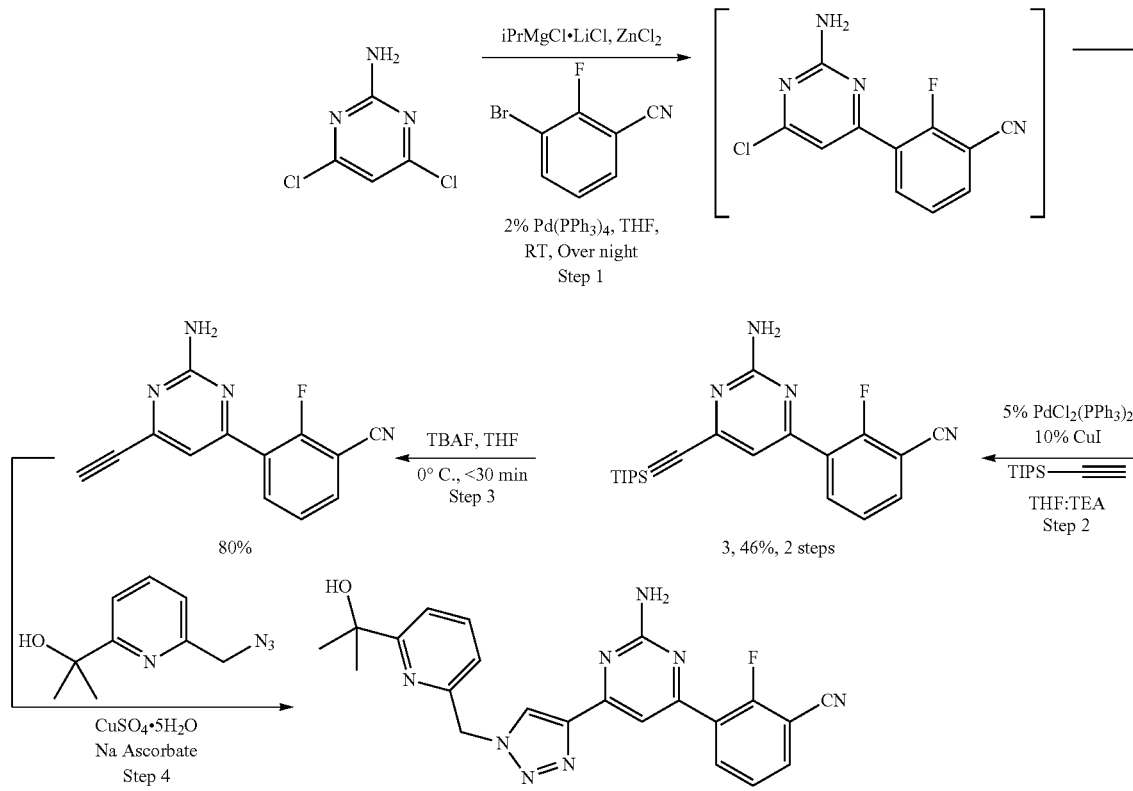

Step 6: In a round-bottom flask 5.1 g (15.7 mmol) of 7 was dissolved in dry THF (30 mL). To this was added 16.5 mL (16.5 mmol) of TBAF (1.0 M in THF). The reaction was stirred at room temperature for 30 min. Silica gel (~100 g) was added to the reaction and the solvent was evaporated Step 1: To a stirred solution of 3-bromo-2-fluoro benzonitrile (26 g, 130 mmol) at 0° C. was added iPrMgCl·LiCl solution (100 mL, 130 mmol, 1.3 M in THF) drop wise over 20 min. The resulted solution was stirred for 50 min at 0° C. and ZnCl₂ (17.72 g, 130 mmol) was added at 0° C. The reaction mixture was warmed to room temperature and stirred for 25 min at the same temperature. Then compound 1 (16.4 g, 100 mmol) was added and stirred for 10 min. Then Pd(PPh$_3$)$_4$ (2.32 g, 2 mmol) was added and stirred at room temperature for 12 h. The reaction mixture was quenched with saturated aqueous NH$_4$Cl solution (500 mL), extracted with EtOAc (3×300 mL), and dried over Na$_2$SO$_4$. The combined organic layer was evaporated to give 28 g of crude 2 which was subjected to next step without further purification.

Step 2: To a stirred solution of compound 3 (24 g, 96.52 mmol) at room temperature were added PdCl$_2$(PPh$_3$)$_2$ (3.38 g, 4.82 mmol), CuI (1.84 g, 9.65 mol), THF/Et$_3$N (1:1, 482 mL) and degassed with N$_2$ for 30 min. Then triisopropyl acetylene (130 mL, 579.15 mmol) was added dropwise over 15 min (reaction mixture turned reddish color) and the reaction mixture was refluxed for 90 min. LCMS and TLC showed full consumption of 2. Solvent was evaporated using rotavapor. Excess Et$_3$N was removed using toluene (2×200 mL) azeotrope. The crude reaction mixture was mixed with silica gel and loaded directly to the flash column. The solvent gradient was changed from 10 to 20 to 30 to 40 to 50% EA in hexane. Pure solid product 3 (15.13 g. 46% over 2 steps) came at 40% EA in hexane.

Step 3: To a stirred solution of compound 4 (15 g, 37.97 mmol) at 0° C. was added TBAF (37.97 mL, 1 M in THF) dropwise over 15 min and stirred at 0° C. for <30 min. TLC shows no SM (LC MS is tricky due to nBuN$^+$ cation). The reaction mixture was quenched with saturated aqueous NH$_4$Cl solution (200 mL) at 0° C., extracted with EtOAc (3×250 mL), dried over Na$_2$SO$_4$ and evaporated to give crude 4. To the crude was added 200 ml of 10% EtOAc in hexane and then sonicated. The supernatant liquid part was separated and to the solid residue was added EtOAc/CH$_2$Cl$_2$ (200 mL, 1:1). To the resulted slurry was added hexane (600 mL) to precipitate and was sonicated for 5 min. The precipitate was filtered and dried under high vacuum to give 4 (7.2 g) in 80% yield.

Step 4: Performed same as in example 1

$^1$H NMR (400 MHz, Acetone-d$_6$) δ 8.62 (s, 1H), 8.45-8.38 (m, 1H), 8.02-7.95 (m, 1H), 7.88-7.81 (m, 2H), 7.65 (dd, J=8.0 Hz, 1H), 7.62-7.56 (m, 1H), 7.24 (d, J=7.8 Hz, 1H), 6.30 (brs, 2H), 5.86 (s, 2H), 4.62 (s, 1H), 1.48 (s, 6H). ESI MS [M+H]$^+$ for C$_{22}$H$_{19}$FN$_8$O, calcd 431.4, found 431.2.

Example 4: 3-[2-amino-6-(1-{[6-(2-hydroxypropan-2-yl)pyridin-2-yl]methyl}-1H-1,2,3-triazol-4-yl)pyrimidin-4-yl]benzonitrile

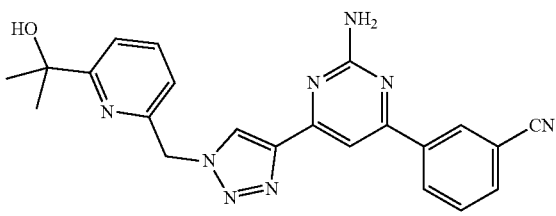 [SMILES: CC(C)(O)c1cccc(Cn2cc(-c3cc(-c4cccc(C#N)c4)nc(N)n3)nn2)n1]

The title compound was prepared similar to example 2 starting from 3-cyanobenzoic acid. $^1$H NMR (400 MHz, DMSO-d$_6$) 8.71 (d, J=1.2 Hz, 1H), 8.59 (q, J=1.5 Hz, 1H), 8.47 (dq, J=8.2, 1.4 Hz, 1H), 8.00 (dq, J=7.7, 1.4 Hz, 1H), 7.87-7.69 (m, 3H), 7.61 (dt, J=8.0, 1.2 Hz, 1H), 7.11 (dt, J=7.7, 1.1 Hz, 1H), 6.92 (s, 2H), 5.83 (s, 2H), 5.23 (d, J=1.2 Hz, 1H), 1.38 (d, J=1.2 Hz, 6H). ESI MS [M+H]$^+$ for C$_{22}$H$_{20}$N$_8$O, calcd 413.2, found 413.3.

Example 5: 3-[2-amino-6-(1-{[6-(2-hydroxypropan-2-yl)pyridin-2-yl]methyl}-1H-1,2,3-triazol-4-yl)pyrimidin-4-yl]-2-chlorobenzonitrile

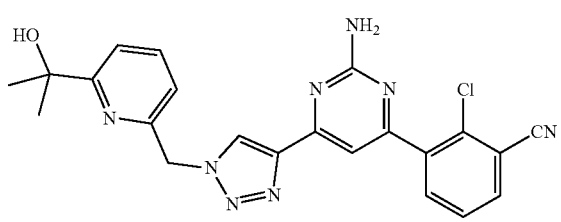 [SMILES: CC(C)(O)c1cccc(Cn2cc(-c3cc(-c4cccc(C#N)c4Cl)nc(N)n3)nn2)n1]

The title compound was prepared similar to example 1 starting from 2-chloro-3-cyanoboronic acid. $^1$H NMR (400 MHz, Acetone-d$_6$) δ 8.67 (s, 1H), 8.02-7.93 (m, 2H), 7.84 (t, J=7.8 Hz, 1H), 7.70 (t, J=7.8 Hz, 1H), 7.66 (d, J=7.6 Hz 1H), 7.62 (s, 1H), 7.25 (d, J=7.7 Hz, 1H), 6.37 (brs, 2H), 5.87 (s, 2H), 4.63 (s, 1H), 1.48 (s, 6H). ESI MS [M+H]$^+$ for C$_{22}$H$_{19}$ClN$_8$O, calcd 447.9, found 447.2.

Example 6: 2-[6-({4-[2-amino-6-(2,3-dichlorophenyl)pyrimidin-4-yl]-1H-1,2,3-triazol-1-yl}methyl)pyridin-2-yl]propan-2-ol

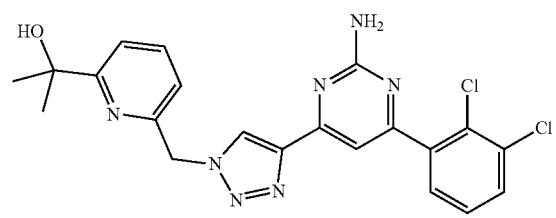 [SMILES: CC(C)(O)c1cccc(Cn2cc(-c3cc(-c4cccc(Cl)c4Cl)nc(N)n3)nn2)n1]

The title compound was prepared similar to example 1 starting from 2,3-dichloroboronic acid. $^1$H NMR (400 MHz, Acetone-d$_6$) δ 8.62 (s, 1H), 7.84 (t, J=7.8 Hz, 1H), 7.74-7.62 (m, 2H), 7.61-7.45 (m, 3H), 7.23 (d, J=7.5 Hz, 1H), 6.21 (s, 1H), 5.85 (s, 2H), 1.48 (s, 9H); LC-MS retention time 2.96 min, Method B, ESI MS [M+H]$^+$ for C$_{21}$H$_{19}$Cl$_2$N$_7$O, calcd 456.1, found 456.2.

Example 7: 3-[2-amino-6-(1-{[6-(2-hydroxypropan-2-yl)pyridin-2-yl]methyl}-1H-pyrazol-4-yl)pyrimidin-4-yl]-2-methoxybenzonitrile

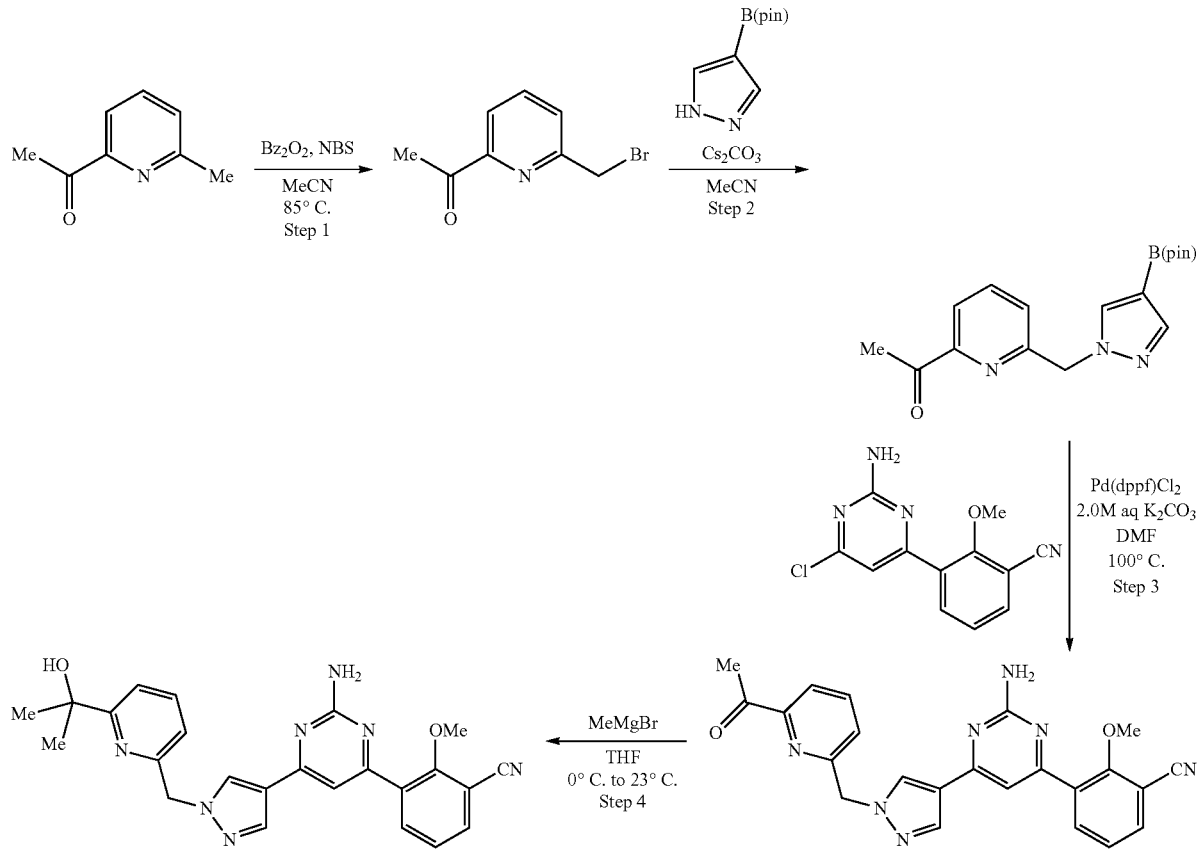

Step 1: To a sparged solution of 2-acetyl-6-methylpyridine (3.0 g, 22.2 mmol, 1.0 equiv) in MeCN (100 mL, 0.2 M) under $N_2$ was added benzoyl peroxide (538 mg, 2.2 mmol, 0.1 equiv) followed by N-bromosuccinimide (4.7 g, 26.6 mmol, 1.2 equiv). The flask was fitted with a reflux condenser and the mixture was heated to 85° C. and stirred for 28 h. Upon completion, saturated aqueous $Na_2SO_2O_3$ (50 mL) was added and the biphasic mixture stirred for 10 minutes. The mixture was transferred to a separatory funnel containing EtOAc (100 mL) and 1:1 water:saturated $Na_2SO_2O_3$ (100 mL). The organic phase was collected and the aqueous phase was extracted with 2×50 mL EtOAc. The combined organic extracts were dried over $MgSO_4$ and concentrated in vacuo. The resulting residue was purified by column chromatography (hexanes→9:1 hexane:EtOAc) to give the title compound (2.65 g, 56% yield) as a pale orange oil.

Step 2: 1-(6-(bromomethyl)pyridin-2-yl)ethan-1-one (1.0 g, 4.7 mmol, 1.0 equiv) and 4-pyrazoleboronic acid pinacol ester (997 mg, 5.1 mmol, 1.1 equiv) were taken up in MeCN (23 mL, 0.2 M) and $Cs_2CO_3$ (1.7 g, 5.1 mmol, 1.1 equiv) was added. The resulting mixture was stirred at room temperature for 4 h. Upon completion, the mixture was diluted with $CH_2Cl_2$ (20 mL) and filtered through a fritted funnel. The filtrate was concentrated in vacuo to afford the title compound which was used in subsequent reactions without further purification.

Step 3: A solution of 1-(6-((4-(4,4,5,5-tetramethyl-1,3,2-dioxaborolan-2-yl)-1H-pyrazol-1-yl)methyl)pyridin-2-yl)ethan-1-one (301 mg, 0.92 mmol, 1.2 equiv) and 3-(2-amino-6-chloropyrimidin-4-yl)-2-methoxybenzonitrile (example 2, step 4, 200 mg, 0.77 mmol, 1.0 equiv) in DMF (33 mL, 0.9 M) and 2.0 M aqueous $K_2CO_3$ (0.8 mL, 2.0 equiv) was sparged with $N_2$ for 10 minutes. Following this time, Pd(dppf)$Cl_2$ (55.6 mg, 0.04 mmol, 0.1 equiv) was added and the reaction mixture heated to 100° C. for 16 h. Upon completion, the reaction mixture was diluted with $CH_2Cl_2$ (10 mL) and $H_2O$ (10 mL). The biphasic mixture was transferred to a separatory funnel and the organic phase collected. The aqueous phase was extracted with 2×10 mL $CH_2Cl_2$ and the combined organic extracts dried over $MgSO_4$ and concentrated in vacuo. The brown residue was purified by column chromatography (7:3 hexane:EtOAc→EtOAc) to give the title compound (190 mg, 58% yield) as a yellow oil.

Step 4: To a solution of 3-(6-(1-(((6-acetylpyridin-2-yl)methyl)-1H-pyrazol-4-yl)-2-aminopyrimidin-4-yl)-2-methoxybenzonitrile (190 mg, 0.45 mmol, 1.0 equiv) in THF (8.2 mL, 0.05 M) at 0° C. under N2 was added MeMgBr (0.8 mL, 1.1 mmol, 2.5 equiv, 1.4 M in 3:1 THF:toluene). The resulting mixture was warmed to room temperature and stirred for 21 h. Upon completion, the reaction was quenched by addition of saturated aqueous $NH_4Cl$ (10 mL). The biphasic mixture was transferred to a separatory funnel and extracted with 3×10 mL EtOAc. The combined organic extracted were washed with brine (10 mL), dried over $MgSO_4$, and concentrated in vacuo. The residue was purified by reversed-phase HPLC (19:1→1:19

H₂O:MeCN with 0.1% CF₃CO₂H) to give the title compound (10 mg, 5% yield) as a white solid. ¹H NMR (400 MHz, Acetone-d₆) δ 8.80 (d, J=14.1 Hz, 1H), 8.35 (d, J=6.3 Hz, 1H), 8.15-8.07 (m, 1H), 7.97-7.77 (m, 3H), 7.65-7.54 (m, 1H), 7.17-7.09 (m, 1H), 5.58 (s, 2H), 4.00 (s, 3H), 2.65 (s, 3H), 1.48 (s, 9H); LC-MS retention time 2.52 min LC-MS, Method B, ESI MS [M+H]⁺ for C₂₄H₂₃N₇O₂, calcd 441.2, found 441.3.

Example 8: 2-[6-({4-[2-Amino-6-(3-fluoro-2-methoxyphenyl)-4-pyrimidinyl]-1H-1,2,3-triazol-1-yl}methyl)-2-pyridyl]-2-propanol

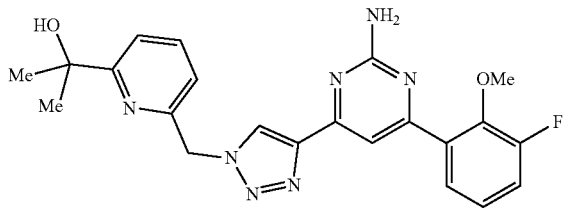 [SMILES: COc1c(F)cccc1-c1cc(-c2cn(Cc3cccc(C(C)(C)O)n3)nn2)nc(N)n1]

The title compound was prepared similar to example 1. ¹H NMR (400 MHz, Chloroform-d) δ 8.30-8.25 (m, 1H), 7.94-7.89 (m, 1H), 7.73 (t, J=7.9 Hz, 1H), 7.56 (d, J=7.7 Hz, 1H), 7.37 (d, J=7.9 Hz, 1H), 7.23-7.05 (m, 3H), 5.75 (s, 2H), 5.07 (s, 2H), 4.74 (s, 1H), 3.94 (s, 3H), 1.55 (s, 6H); LC-MS retention time 2.89 min LC-MS, Method A, ESI MS [M+H]⁺ for C₂₂H₂₃FN₇O₂, calcd 436.2, found 436.3.

Example 9: 2-[6-({4-[2-Amino-6-(3-chloro-2-methoxyphenyl)-4-pyrimidinyl]-1H-1,2,3-triazol-1-yl}methyl)-2-pyridyl]-2-propanol

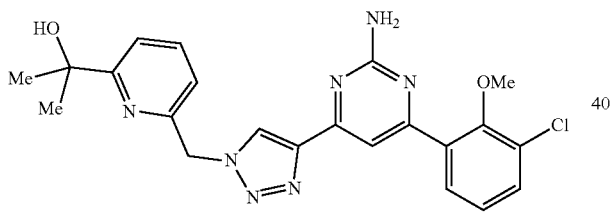

The title compound was prepared similar to example 1. ¹H NMR (400 MHz, Chloroform-d) δ 8.27 (d, J=1.2 Hz, 1H), 7.95 (d, J=1.3 Hz, 1H), 7.77-7.64 (m, 2H), 7.48 (dt, J=8.0, 1.5 Hz, 1H), 7.37 (d, J=8.0 Hz, 1H), 7.19-7.08 (m, 2H), 5.75 (s, 2H), 5.11 (s, 2H), 4.73 (s, 1H), 3.77 (s, 3H), 1.55 (s, 6H); LC-MS retention time 3.04 min LC-MS, Method A, ESI MS [M+H]⁺ for C₂₂H₂₃ClN₇O₂, calcd 452.2, found 452.3.

Example 10: m-(2-Amino-6-{1-[(2-pyridyl)methyl]-1H-1,2,3-triazol-4-yl}-4-pyrimidinyl)benzonitrile

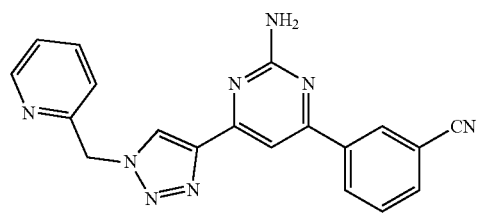 [SMILES: N#Cc1cccc(-c2cc(-c3cn(Cc4ccccn4)nn3)nc(N)n2)c1]

The title compound was prepared similar to example 4. ¹H NMR (400 MHz, Chloroform-d) δ 8.65 (s, 1H), 8.46 (t, J=1.6 Hz, 1H), 8.41-8.34 (m, 1H), 8.31 (dt, J=8.0, 1.4 Hz, 1H), 7.91 (s, 1H), 7.80-7.68 (m, 2H), 7.60 (t, J=7.8 Hz, 1H), 7.34-7.28 (m, 1H), 5.76 (s, 3H), 5.22 (s, 2H); ESI MS [M+H]⁺ for C₁₉H₁₄N₈, calcd 355.1, found 355.2.

Example 11: m-(2-Amino-6-{1-[(3-pyridyl)methyl]-1H-1,2,3-triazol-4-yl}-4-pyrimidinyl)benzonitrile

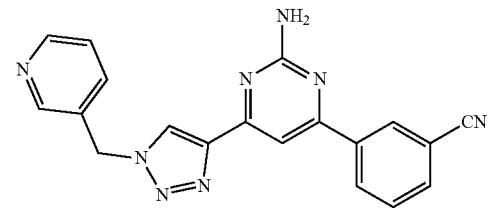 [SMILES: N#Cc1cccc(-c2cc(-c3cn(Cc4cccnc4)nn3)nc(N)n2)c1]

The title compound was prepared similar to example 4 to afford 59 mg of a tan solid. ¹H NMR (400 MHz, DMSO-d₆) δ 8.73 (d, J=1.1 Hz, 1H), 8.68 (dd, J=2.2, 1.0 Hz, 1H), 8.57 (dq, J=3.1, 1.4 Hz, 2H), 8.46 (ddd, J=8.0, 1.9, 1.1 Hz, 1H), 7.99 (dq, J=7.8, 1.3 Hz, 1H), 7.82-7.78 (m, 2H), 7.74 (td, J=7.8, 1.0 Hz, 1H), 7.48-7.40 (m, 1H), 6.89 (s, 2H), 5.78 (s, 2H). ESI MS [M+H]⁺ for C₁₉H₁₄N₈, calcd 355.1, found 355.3.

Example 12: m-(2-Amino-6-{1-[(4-pyridyl)methyl]-1H-1,2,3-triazol-4-yl}-4-pyrimidinyl)benzonitrile

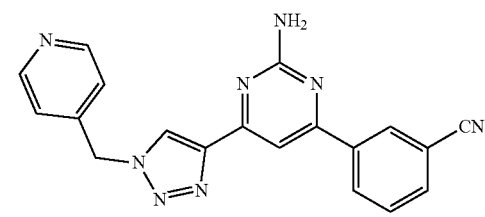 [SMILES: N#Cc1cccc(-c2cc(-c3cn(Cc4ccncc4)nn3)nc(N)n2)c1]

The title compound was prepared similar to example 4 to afford 66 mg of a tan solid. ¹H NMR (400 MHz, DMSO-d₆) δ 8.76 (d, J=1.2 Hz, 1H), 8.63-8.54 (m, 3H), 8.47 (ddd, J=8.0, 1.8, 1.1 Hz, 1H), 8.03-7.96 (m, 1H), 7.81 (d, J=1.3 Hz, 1H), 7.78-7.68 (m, 1H), 7.31-7.23 (m, 2H), 6.90 (s, 2H), 5.81 (s, 2H). ESI MS [M+H]⁺ for C₁₉H₁₄N8, calcd 355.1, found 355.3.

Example 13: m-(2-Amino-6-{1-[(6-methyl-2-pyridyl)methyl]-1H-1,2,3-triazol-4-yl}-4-pyrimidinyl)benzonitrile

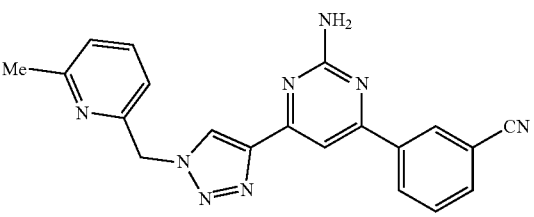 [SMILES: Cc1cccc(Cn2cc(-c3cc(-c4cccc(C#N)c4)nc(N)n3)nn2)n1]

The title compound was prepared similar to example 4 to afford 14 mg of a solid. $^1$H NMR (400 MHz, DMSO-d$_6$) 8.68 (d, J=2.0 Hz, 1H), 8.59 (s, 1H), 8.47 (d, J=8.1 Hz, 1H), 8.03-7.96 (m, 1H), 7.81 (d, J=1.9 Hz, 1H), 7.78-7.69 (m, 2H), 7.24 (d, J=7.8 Hz, 1H), 7.11 (d, J=7.7 Hz, 1H), 6.92 (s, 2H), 5.78 (d, J=2.0 Hz, 2H), 2.45 (s, 3H). ESI MS [M+H]$^+$ for C$_{20}$H$_{16}$N$_8$, calcd 369.2, found 369.3.

Example 14: 3-(2-Amino-6-{1-[(6-methyl-2-pyridyl)methyl]-1H-1,2,3-triazol-4-yl}-4-pyrimidinyl)-2-fluorobenzonitrile

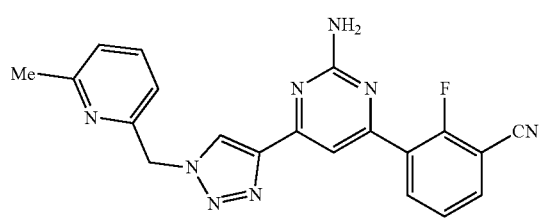 [SMILES: Cc1cccc(Cn2cc(-c3cc(-c4cccc(C#N)c4F)nc(N)n3)nn2)n1]

The title compound was prepared similar to example 3 to afford 13 mg of a tan solid. $^1$H NMR (400 MHz, DMSO-d$_6$) 8.67 (s, 1H), 8.35-8.27 (m, 1H), 8.26-8.18 (m, 1H), 8.09 (dd, J=7.7, 6.1 Hz, 2H), 7.72 (t, J=7.7 Hz, 1H), 7.62 (d, J=2.4 Hz, 1H), 7.23 (d, J=7.8 Hz, 1H), 6.98 (s, 2H), 5.78 (s, 2H), 2.45 (s, 3H). ESI MS [M+H]$^+$ for C$_{20}$H$_{15}$FN$_8$, calcd 387.1, found 387.3.

Example 15: 6-(2-Amino-6-{1-[(6-methyl-2-pyridyl)methyl]-1H-1,2,3-triazol-4-yl}-4-pyrimidinyl)-2-toluonitrile

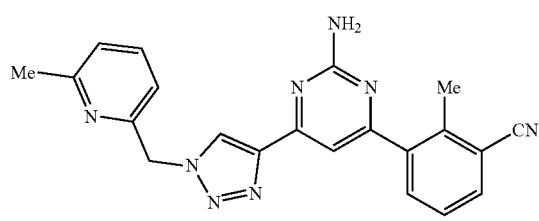 [SMILES: Cc1cccc(Cn2cc(-c3cc(-c4cccc(C#N)c4C)nc(N)n3)nn2)n1]

The title compound was prepared similar to example 1 to afford 75 mg of a tan solid. $^1$H NMR (400 MHz, DMSO-d$_6$) 8.66 (d, J=1.3 Hz, 1H), 7.95-7.86 (m, 1H), 7.80-7.67 (m, 2H), 7.52 (t, J=7.8 Hz, 1H), 7.27 (d, J=1.4 Hz, 1H), 7.23 (d, J=7.8 Hz, 1H), 7.09 (d, J=7.7 Hz, 1H), 6.90 (s, 2H), 5.77 (s, 2H), 2.55 (s, 3H), 2.45 (s, 3H). ESI MS [M+H]$^+$ for C$_{21}$H$_{18}$N$_8$, calcd 383.2, found 383.3.

Example 16: 3-(2-Amino-6-{1-[(6-methyl-2-pyridyl)methyl]-1H-1,2,3-triazol-4-yl}-4-pyrimidinyl)-2-anisonitrile

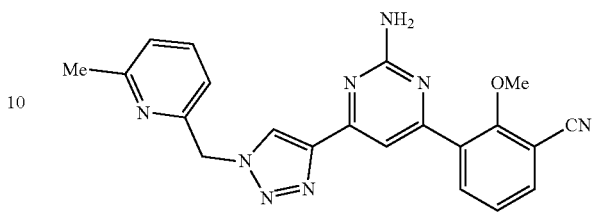

The title compound was prepared similar to example 2 to afford 84 mg of a tan solid. $^1$H NMR (400 MHz, DMSO-d$_6$) 8.65 (d, J=1.1 Hz, 1H), 8.07 (ddd, J=7.8, 1.8, 1.0 Hz, 1H), 7.99-7.90 (m, 1H), 7.72 (t, J=7.7 Hz, 1H), 7.63 (d, J=1.0 Hz, 1H), 7.49-7.39 (m, 1H), 7.23 (d, J=7.8 Hz, 1H), 7.11 (d, J=7.7 Hz, 1H), 6.90 (s, 2H), 5.77 (s, 2H), 3.84 (d, J=1.7 Hz, 3H), 2.45 (s, 3H). ESI MS [M+H]$^+$ for C$_{21}$H$_{18}$N$_8$O, calcd 399.2, found 399.3.

Example 17: m-(2-Amino-6-{1-[(3-methyl-2-pyridyl)methyl]-1H-1,2,3-triazol-4-yl}-4-pyrimidinyl)benzonitrile

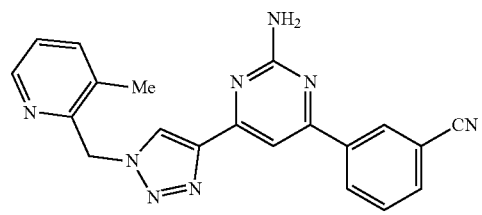 [SMILES: Cc1cccnc1Cn1cc(-c2cc(-c3cccc(C#N)c3)nc(N)n2)nn1]

The title compound was prepared similar to example 4. $^1$H NMR (400 MHz, DMSO-d$_6$) δ 8.69 (d, J=2.1 Hz, 1H), 8.60-8.57 (m, 1H), 8.50-8.44 (m, 1H), 8.37 (d, J=4.6 Hz, 1H), 8.03-7.98 (m, 1H), 7.85 (d, J=2.3 Hz, 1H), 7.75 (td, J=7.7, 2.4 Hz, 2H), 7.35 (dd, J=7.0, 4.3 Hz, 1H), 5.91 (d, J=2.3 Hz, 2H), 4.70 (bs, 2H), 2.41 (s, 3H); ESI MS [M+H]$^+$ for C$_{20}$H$_{16}$N$_8$O$_3$, calcd 369.2, found 369.2.

Example 18: Synthesis of m-[2-Amino-6-(1-{[6-(trifluoromethyl)-2-pyridyl]methyl}-1H-1,2,3-triazol-4-yl)-4-pyrimidinyl]benzonitrile

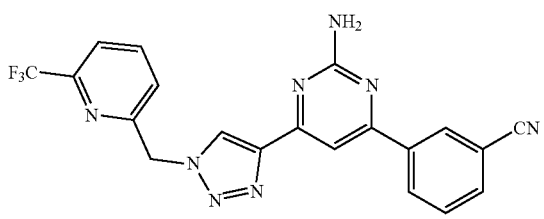 [SMILES: N#Cc1cccc(-c2cc(-c3cn(Cc4cccc(C(F)(F)F)n4)nn3)nc(N)n2)c1]

The title compound was prepared similar to example 4 to afford 74 mg of a tan solid. $^1$H NMR (400 MHz, DMSO-d$_6$) δ 8.77 (d, J=1.1 Hz, 1H), 8.59 (d, J=1.4 Hz, 1H), 8.47 (ddt, J=8.0, 1.9, 1.2 Hz, 1H), 8.16 (t, J=7.9 Hz, 1H), 8.00 (dq, J=7.7, 1.3 Hz, 1H), 7.91 (d, J=7.8 Hz, 1H), 7.85-7.80 (m, 1H), 7.75 (t, J=7.9 Hz, 1H), 7.61 (d, J=7.9 Hz, 1H), 6.93 (s, 2H), 5.99 (s, 2H). ESI MS [M+H]+ for $C_{20}H_{13}F3N_8$, calcd 423.1, found 423.2.

Example 19: m-[2-Amino-6-(1-{[6-(hydroxymethyl)-2-pyridyl]methyl}-1H-1,2,3-triazol-4-yl)-4-pyrimidinyl]benzonitrile

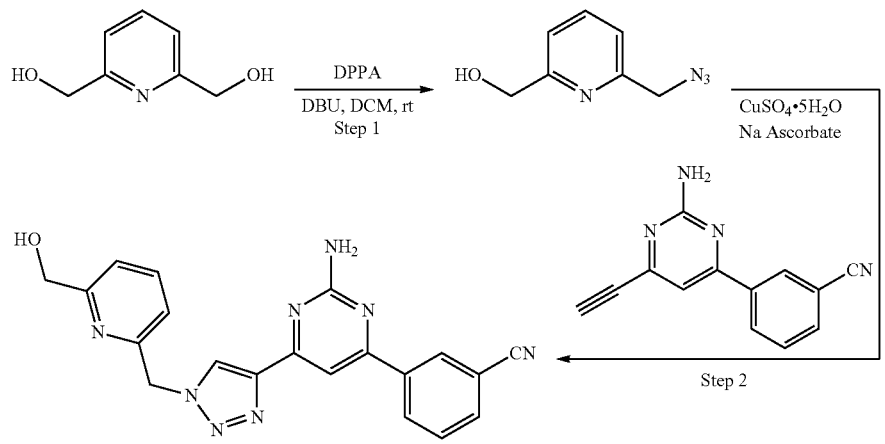 [SMILES: OCc1cccc(CO)n1 ; [N-]=[N+]=NCc1cccc(CO)n1 ; N#Cc1cccc(-c2cc(-c3cn(Cc4cccc(CO)n4)nn3)nc(N)n2)c1 ; C#Cc1cc(-c2cccc(C#N)c2)nc(N)n1]

Step 1. A mixture of diol (696 mg, 5 mmol) and DBU (0.9 mL, 6 mmol) in dichloromethane (15 mL) was cooled to 0° C. DPPA (1.3 mL, 6 mmol) was added dropwise and the resulting mixture was stirred at 0° C. for 15 minutes and at room temperature overnight. Celite (5 g) was added and the mixture was evaporated to dryness and purified by silica gel chromatography (Hexanes/EtOAc 90:10 to 60:40) to afford the desired azide (83 mg, 10%).

Step 2. The title compound was synthesized in a similar fashion to step 6 of example 1 using the azide derivative and m-(2-amino-6-ethynyl-4-pyrimidinyl)benzonitrile (from example 4). $^1$H NMR (400 MHz, DMSO-d$_6$) δ 8.69 (s, 1H), 8.59 (dd, J=1.8, 1.8 Hz, 1H), 8.47 (ddd, J=8.0, 1.8, 1.1 Hz, 1H), 8.00 (ddd, J=7.7, 1.7, 1.2 Hz, 1H), 7.85 (dd, J=7.7, 7.7 Hz, 1H), 7.82 (s, 1H), 7.75 (dd, J=7.7, 7.7 Hz, 1H), 7.46 (d, J=7.8 Hz, 1H), 7.18 (d, J=7.8 Hz, 1H), 6.93 (s, 2H), 5.81 (s, 2H), 4.54 (d, J=5.8 Hz, 3H). MS [M+H]+ for $C_{20}H_{16}N_8O$, calcd 385.2, found 385.2.

Example 20: m-[2-Amino-6-(1-{[6-(methoxymethyl)-2-pyridyl]methyl}-1H-1,2,3-triazol-4-yl)-4-pyrimidinyl]benzonitrile

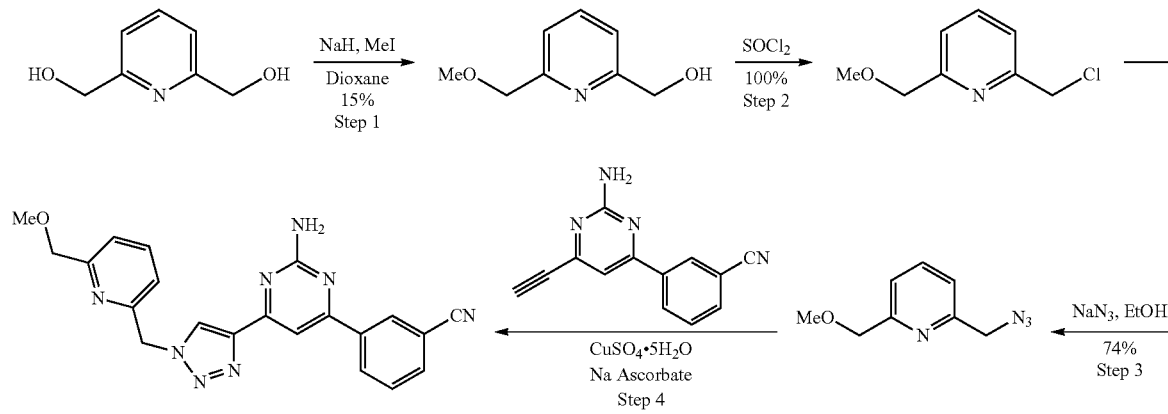

Step 1: At room temperature under nitrogen atmosphere, 12 g of sodium hydride (300 mmol, 60% dispersion in mineral oil, 1 e.q.) in dioxane (100 mL) was added a suspension of 2,6-pyridine dimethanol (41.8 g, 300 mmol) in dioxane (600 mL). The suspension was stirred for 15 minutes. methyl iodide (42.6 g, 300 mmol) was added and the resulting mixture was heated to 50° C. for 2 hours. TLC analysis suggested ~50% starting material was converted. The reaction was quenched with water, then extracted with ethyl acetate (500 mL×3). The ethyl acetate layer was washed with water (200 mL) and brine. The ethyl acetate solution was dried over sodium sulfate for 1 hour, filtered and concentrated. The resulting oil residue was purified by silica gel column, eluted with dichloromethane/methanol (from 2% to 5% of methanol) to give 6.6 g compound 1 as a pink oil, in 15% yield.

Step 2: Product from step 1 (3.4 g, 17.0 mmol) in $SOCl_2$ (30 mL) was stirred at 40° C. for overnight. The mixture was concentrated to obtain the product as a white solid (3.6 g, 100%).

Step 3: A Product from step 2 (1.16 g, 6.8 mmol, 1.0 eq) and $NaN_3$ (1.3 g, 20.3 mmol, 3.0 eq) in EtOH was heated to reflux overnight. The mixture was concentrated to get a crude, which was purified on FCC (PE/EA=5/1) to give the product as a white solid (0.9 g, 74%).

Step 4: Using the General Procedure from example 1, the title compound was synthesized to afford 64 mg of a yellow-brown solid. $^1$H NMR (400 MHz, DMSO-$d_6$) δ 8.70 (s, 1H), 8.59 (td, J=1.8, 0.6 Hz, 1H), 8.47 (ddd, J=8.0, 1.8, 1.1 Hz, 1H), 8.04-7.96 (m, 1H), 7.86 (t, J=7.8 Hz, 1H), 7.81 (s, 1H), 7.77-7.69 (m, 1H), 7.40-7.36 (m, 1H), 7.25-7.19 (m, 1H), 6.92 (bs, 2H), 5.83 (s, 2H), 4.46 (s, 2H), 3.35 (s, 3H). ESI MS [M+H]$^+$ for $C_{21}H_{18}N_8O$, calcd 399.2, found 399.3.

The above title compound can also be obtained as shown below.

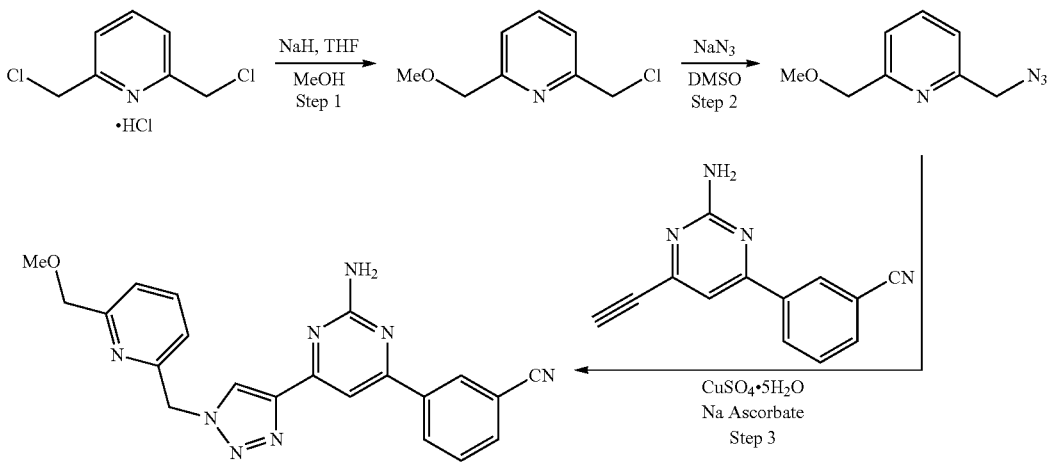

Example 21: 6-(3-Fluoro-2-methoxyphenyl)-4-(1-{[6-(methoxymethyl)-2-pyridyl]methyl}-1H-1,2,3-triazol-4-yl)-2-pyrimidinylamine

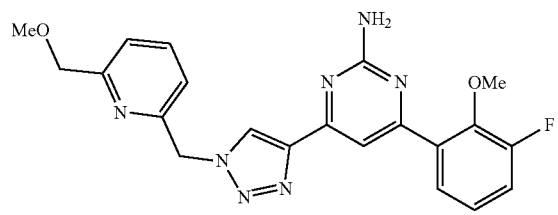 [SMILES: COCc1cccc(Cn2cc(-c3cc(-c4cccc(F)c4OC)nc(N)n3)nn2)n1]

The title compound was prepared similar to example 20. $^1$H NMR (400 MHz, DMSO-$d_6$) δ 8.64 (s, 1H), 7.85 (t, J=7.8 Hz, 1H), 7.64 (s, 1H), 7.60 (dt, J=7.9, 1.5 Hz, 1H), 7.45-7.36 (m, 2H), 7.28-7.18 (m, 2H), 6.81 (s, 2H), 5.81 (s, 2H), 4.46 (s,H), 3.84 (s, 3H), 3.35 (s, 3H). ESI MS [M+H]$^+$ for $C_{21}H_{21}FN_7O_2$, calcd 422.2, found 422.3.

Example 22: 3-[2-Amino-6-(1-{[6-(methoxymethyl)-2-pyridyl]methyl}-1H-1,2,3-triazol-4-yl)-4-pyrimidinyl]-2-anisonitrile

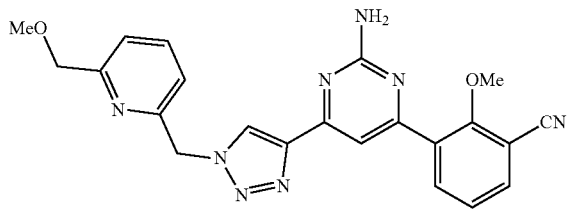 [SMILES: COCc1cccc(Cn2cc(-c3cc(-c4cccc(C#N)c4OC)nc(N)n3)nn2)n1]

The title compound was prepared similar to example 20 from the corresponding azide and alkyne. $^1$H NMR (400 MHz, DMSO-$d_6$) δ 8.82 (s, 1H), 8.08 (dd, J=7.9, 1.7 Hz, 1H), 7.99 (dd, J=7.7, 1.7 Hz, 1H), 7.88 (t, J=7.7 Hz, 1H), 7.69 (s, 1H), 7.47 (t, J=7.8 Hz, 1H), 7.41 (d, J=7.9 Hz, 1H), 7.28 (d, J=8.0 Hz, 1H), 5.86 (s, 2H), 4.47 (s, 2H), 3.88 (s, 3H), 3.35 (s, 3H). ESI MS [M+H]$^+$ for $C_{22}H_{21}N_8O_2$, calcd 429.2, found 429.3.

Example 23: 6-(3-Chloro-2-methoxyphenyl)-4-(1-{[6-(methoxymethyl)-2-pyridyl]methyl}-1H-1,2,3-triazol-4-yl)-2-pyrimidinylamine

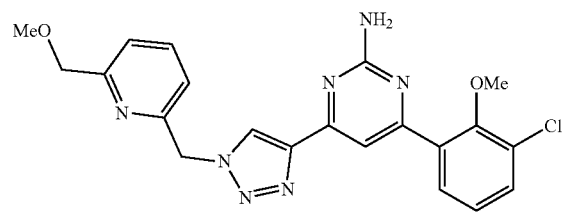 [SMILES: COCc1cccc(Cn2cc(-c3cc(-c4cccc(Cl)c4OC)nc(N)n3)nn2)n1]

The title compound was prepared similar to example 20 from the corresponding azide and alkyne. $^1$H NMR (400 MHz, CDCl$_3$) δ 8.28 (d, J=0.9 Hz, 1H), 7.94-7.88 (m, 1H), 7.73-7.62 (m, 2H), 7.50-7.43 (m, 1H), 7.40 (d, J=7.8 Hz, 1H), 7.19-7.07 (m, 2H), 5.71 (s, 2H), 5.24 (s, 2H), 4.58 (s, 2H), 3.88-3.61 (s, 3H), 3.48 (s, 3H). ESI MS [M+H]$^+$ for $C_{21}H_{20}ClN_7O_2$, calcd 438.1, found 438.3.

Example 24: 5-[2-Amino-6-(1-{[6-(methoxymethyl)-2-pyridyl]methyl}-1H-1,2,3-triazol-4-yl)-4-pyrimidinyl]-3-toluonitrile

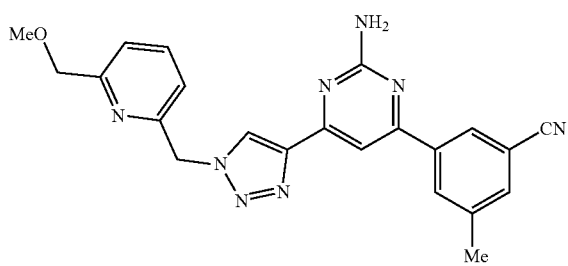 [SMILES: COCc1cccc(Cn2cc(-c3cc(-c4cc(C)cc(C#N)c4)nc(N)n3)nn2)n1]

The title compound was prepared similar to example 20 from the corresponding azide and alkyne. $^1$H NMR (400 MHz, DMSO-$d_6$) δ 8.70 (s, 1H), 8.42-8.36 (m, 1H), 8.32 (d, J=0.8 Hz, 1H), 7.86 (t, J=7.8 Hz, 1H), 7.83 (s, 1H), 7.81 (s, 1H), 7.39 (dd, J=7.8, 0.9 Hz, 1H), 7.26-7.20 (m, 1H), 6.92 (s, 2H), 5.83 (s, 2H), 4.47 (s, 2H), 3.35 (s, 3H), 2.46 (s, 3H). ESI MS [M+H]$^+$ for $C_{22}H_{20}N_8O$, calcd 413.2, found 413.3.

Example 25: 3-[2-Amino-6-(1-{[6-(methoxymethyl)-2-pyridyl]methyl}-1H-1,2,3-triazol-4-yl)-4-pyrimidinyl]-5-chlorobenzonitrile

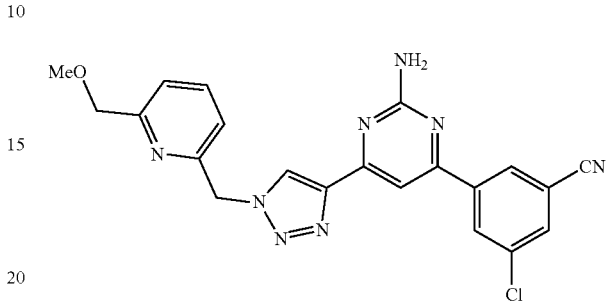

The title compound was prepared similar to example 20 from the corresponding azide and alkyne. $^1$H NMR (400 MHz, DMSO-$d_6$) δ 8.72 (s, 1H), 8.62 (t, J=1.5 Hz, 1H), 8.54 (dd, J=2.1, 1.6 Hz, 1H), 8.22 (dd, J=2.1, 1.4 Hz, 1H), 7.90-7.82 (m, 2H), 7.42-7.36 (m, 1H), 7.26-7.19 (m, 1H), 7.00 (s, 2H), 5.83 (s, 2H), 4.47 (s, 2H), 3.35 (s, 3H). ESI MS [M+H]$^+$ for $C_{21}H_{17}ClN_8O$, calcd 433.1, found 433.2.

Example 26: m-[2-Amino-6-(1-{[6-(methoxymethyl)-2-pyridyl]methyl}-1H-1,2,3-triazol-4-yl)-5-methyl-4-pyrimidinyl]benzonitrile

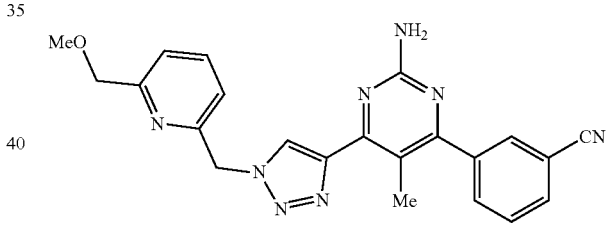

The title compound was prepared similar to example 20 from the corresponding azide and alkyne. $^1$H NMR (400 MHz, DMSO-$d_6$) δ 8.63 (s, 1H), 8.02 (s, 1H), 7.97-7.92 (m, 1H), 7.88 (m, 2H), 7.71 (t, J=7.8 Hz, 1H), 7.39 (d, J=7.7 Hz, 1H), 7.21 (d, J=7.7 Hz, 1H), 6.61 (s, 2H), 5.83 (s, 2H), 4.47 (s, 2H), 3.35 (s, 3H), 2.37 (s, 3H). ESI MS [M+H]$^+$ for $C_{22}H_{20}N_8O$, calcd 413.2, found 413.2.

Example 27: 4-(1-{[6-(Methoxymethyl)-2-pyridyl]methyl}-1H-1,2,3-triazol-4-yl)-6-(o-methoxyphenyl)-2-pyrimidinylamine

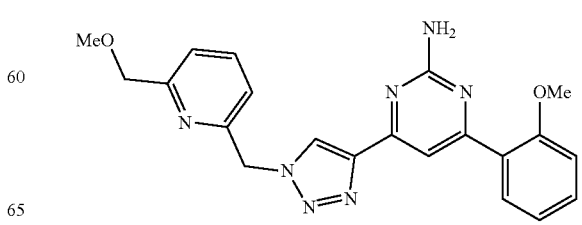

The title compound was synthesized in a similar fashion to step 6 of example 1 using 2-(azidomethyl)-6-(methoxymethyl)pyridine and 4-ethynyl-6-(o-methoxyphenyl)-2-pyrimidinylamine (this was prepared similar to steps 1-3 of example 1). $^1$H NMR (400 MHz, CDCl$_3$) δ 8.27 (s, 1H), 7.99 (s, 1H), 7.83 (dd, J=7.7, 1.8 Hz, 1H), 7.69 (dd, J=7.8, 7.8 Hz, 1H), 7.44-7.36 (m, 2H), 7.11-6.96 (m, 3H), 5.71 (s, 2H), 5.12 (s, 2H), 4.58 (s, 2H), 3.90 (s, 3H), 3.49 (s, 3H). ESI MS [M+H]$^+$ for C$_{21}$H$_{21}$N$_7$O$_2$, calcd 404.2, found 404.2.

Example 28: 4-(1-{[6-(Methoxymethyl)-2-pyridyl]methyl}-1H-1,2,3-triazol-4-yl)-6-(o-methylphenyl)-2-pyrimidinylamine

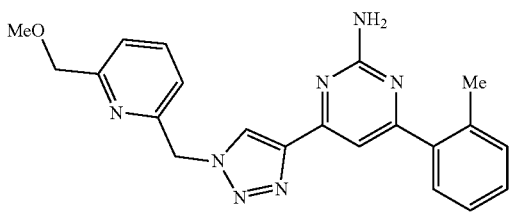 [SMILES: COCc1cccc(Cn2cc(-c3cc(-c4ccccc4C)nc(N)n3)nn2)n1]

The title compound was synthesized in a similar fashion to step 6 of example 1 using 2-(azidomethyl)-6-(methoxymethyl)pyridine and 4-ethynyl-6-(o-methylphenyl)-2-pyrimidinylamine (this was prepared similar to steps 1-3 of example 1). $^1$H NMR (400 MHz, CDCl$_3$) δ 8.29 (s, 1H), 7.70 (dd, J=7.8, 7.8 Hz, 1H), 7.56 (s, 1H), 7.50-7.38 (m, 2H), 7.37-7.27 (m, 3H), 7.09 (d, J=8.0 Hz, 1H), 5.72 (s, 2H), 5.19 (s, 2H), 4.59 (s, 2H), 3.49 (s, 3H), 2.44 (s, 3H). ESI MS [M+H]$^+$ for C$_{21}$H$_{21}$N$_7$O, calcd 388.2, found 388.3.

Example 29: 4-(1-{[6-(Methoxymethyl)-2-pyridyl]methyl}-1H-1,2,3-triazol-4-yl)-6-(p-fluorophenyl)-2-pyrimidinylamine

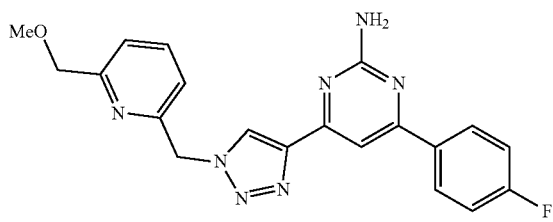 [SMILES: COCc1cccc(Cn2cc(-c3cc(-c4ccc(F)cc4)nc(N)n3)nn2)n1]

The title compound was synthesized in a similar fashion to step 6 of example 1 using 2-(azidomethyl)-6-(methoxymethyl)pyridine and 4-ethynyl-6-(p-fluorophenyl)-2-pyrimidinylamine (this was prepared similar to steps 1-3 of example 1). $^1$H NMR (400 MHz, CDCl$_3$) δ 8.29 (s, 1H), 8.16-8.07 (m, 2H), 7.88 (s, 1H), 7.71 (d, J=7.8, 7.8 Hz, 1H), 7.40 (d, J=7.8 Hz, 1H), 7.21-7.13 (m, 2H), 7.10 (d, J=7.8 Hz, 1H), 5.73 (s, 2H), 5.08 (s, 2H), 4.59 (s, 2H), 3.50 (s, 3H). MS [M+H]$^+$ for C$_{20}$H$_{18}$FN$_7$O, calcd 392.2, found 392.2.

Example 30: 4-(1-{[6-(Methoxymethyl)-2-pyridyl]methyl}-1H-1,2,3-triazol-4-yl)-6-(o-fluorophenyl)-2-pyrimidinylamine

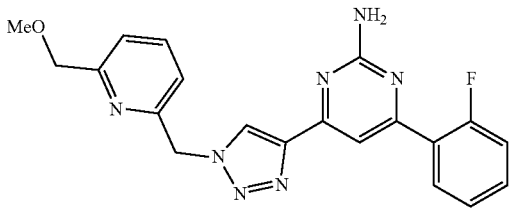 [SMILES: COCc1cccc(Cn2cc(-c3cc(-c4ccccc4F)nc(N)n3)nn2)n1]

The title compound was synthesized in a similar fashion to step 6 of example 1 using 2-(azidomethyl)-6-(methoxymethyl)pyridine and 4-ethynyl-6-(o-fluorophenyl)-2-pyrimidinylamine (this was prepared similar to steps 1-3 of example 1). $^1$H NMR (400 MHz, CDCl$_3$) δ 8.29 (s, 1H), 8.00 (ddd, J=7.8, 7.8, 1.9 Hz, 1H), 7.92 (d, J=2.2 Hz, 1H), 7.71 (dd, J=7.8, 7.8 Hz, 1H), 7.48-7.37 (m, 2H), 7.27 (ddd, J=7.8, 7.8, 1.2 Hz, 1H), 7.17 (ddd, J=11.3, 8.3, 1.1 Hz, 1H), 7.0.9 (d, J=8.3 Hz, 1H), 5.72 (s, 2H), 5.16 (s, 2H), 4.59 (s, 2H), 3.49 (s, 3H). MS [M+H]$^+$ for C$_{20}$H$_{18}$FN$_7$O, calcd 392.2, found 392.3.

Example 31: 4-(1-{[6-(Methoxymethyl)-2-pyridyl]methyl}-1H-1,2,3-triazol-4-yl)-6-(o-chlorophenyl)-2-pyrimidinylamine

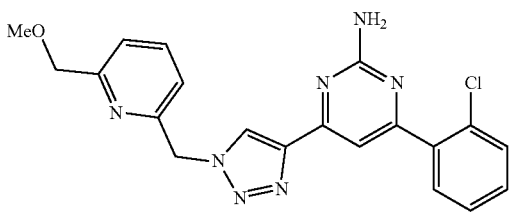 [SMILES: COCc1cccc(Cn2cc(-c3cc(-c4ccccc4Cl)nc(N)n3)nn2)n1]

The title compound was synthesized in a similar fashion to step 6 of example 1 using 2-(azidomethyl)-6-(methoxymethyl)pyridine and 4-ethynyl-6-(o-chlorophenyl)-2-pyrimidinylamine (this was prepared similar to steps 1-3 of example 1). $^1$H NMR (400 MHz, CDCl$_3$) δ 8.30 (s, 1H), 7.74 (s, 1H), 7.69 (dd, J=7.8, 7.8 Hz, 1H), 7.66-7.54 (m, 1H), 7.54-7.45 (m, 1H), 7.40 (d, J=8.0 Hz, 1H), 7.40-7.34 (m, 2H), 7.10 (d, J=8.0 Hz, 1H), 5.72 (s, 2H), 5.16 (s, 2H), 4.59 (s, 2H), 3.50 (s, 3H). MS [M+H]$^+$ for C$_{20}$H$_{18}$ClN$_7$O, calcd 408.1, found 408.3.

Example 32: 4-(1-{[6-(Methoxymethyl)-2-pyridyl]methyl}-1H-1,2,3-triazol-4-yl)-6-(o-trifluoromethoxyphenyl)-2-pyrimidinylamine

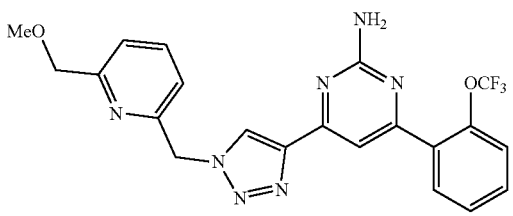 [SMILES: COCc1cccc(Cn2cc(-c3cc(-c4ccccc4OC(F)(F)F)nc(N)n3)nn2)n1]

The title compound was synthesized in a similar fashion to step 6 of example 1 using 2-(azidomethyl)-6-(methoxymethyl)pyridine and 4-ethynyl-6-(o-trifluoromethoxyphenyl)-2-pyrimidinylamine (this was prepared similar to steps 1-3 of example 1). ¹H NMR (400 MHz, CDCl₃) δ 8.29 (s, 1H), 7.83-7.80 (dd, J=7.8, 1.6 Hz, 1H), 7.77 (s, 1H), 7.71 (dd, J=7.8, 7.8 Hz, 1H), 7.52-7.36 (m, 4H), 7.11 (d, J=7.8 Hz, 1H), 5.72 (s, 2H), 5.15 (s, 2H), 4.59 (s, 2H), 3.49 (s, 3H). MS [M+H]⁺ for C₂₁H₁₈F₃N₇O₂, calcd 458.1, found 458.2.

Example 33: 4-[o-(Methoxymethyl)phenyl]-6-(1-{[6-(methoxymethyl)-2-pyridyl]methyl}-1H-1,2,3-triazol-4-yl)-2-pyrimidinylamine

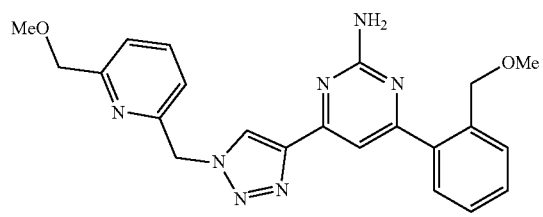 [SMILES: COCc1cccc(Cn2cc(-c3cc(-c4ccccc4COC)nc(N)n3)nn2)n1]

The title compound was synthesized in a similar fashion to step 6 of example 1 using 2-(azidomethyl)-6-(methoxymethyl)pyridine and 6-ethynyl-4-[o-(methoxymethyl)phenyl]-2-pyrimidinylamine (this was prepared similar to steps 1-3 of example 1). ¹H NMR (400 MHz, CDCl₃) δ 8.29 (s, 1H), 7.70 (dd, J=7.7, 7.7 Hz, 1H), 7.65 (s, 1H), 7.60-7.52 (m, 2H), 7.51-7.34 (m, 3H), 7.10 (d, J=7.7 Hz 1H), 5.72 (s, 2H), 5.12 (s, 2H), 4.64 (s, 2H), 4.59 (s, 2H), 3.50 (s, 3H), 3.35 (s, 2H). MS [M+H]⁺ for C₂₂H₂₃N₇O₂, calcd 418.2, found.

Example 34: 4-[2-Amino-6-(1-{[6-(methoxymethyl)-2-pyridyl]methyl}-1H-1,2,3-triazol-4-yl)-4-pyrimidinyl]-2-toluonitrile

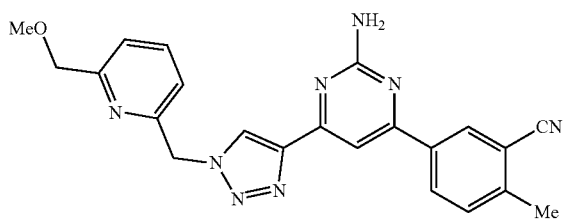 [SMILES: COCc1cccc(Cn2cc(-c3cc(-c4ccc(C)c(C#N)c4)nc(N)n3)nn2)n1]

The title compounds was synthesized in a similar fashion to step 6 of example 1 using 2-(azidomethyl)-6-(methoxymethyl)pyridine and 4-(2-amino-6-ethynyl-4-pyrimidinyl)-2-toluonitrile (this was prepared similar to steps 1-3 of example 1). ¹H NMR (400 MHz, CDCl₃) δ 8.41 (s, 1H), 8.32 (s, 1H), 8.19 (d, J=8.0 Hz, 1H), 7.88 (s, 1H), 7.72 (dd, J=8.0, 8.0 Hz, 1H), 7.43 (dd, J=8.0, 8.0 Hz, 2H), 7.12 (d, J=7.6 Hz, 1H), 5.73 (s, 2H), 5.17 (s, 2H), 4.59 (s, 2H), 3.50 (s, 3H), 2.62 (s, 3H). MS [M+H]⁺ for C₂₂H₂₀N₈O, calcd 413.2, found 413.3.

Example 35: 6-(3,5-Difluorophenyl)-4-(1-{[6-(methoxymethyl)-2-pyridyl]methyl}-1H-1,2,3-triazol-4-yl)-2-pyrimidinylamine

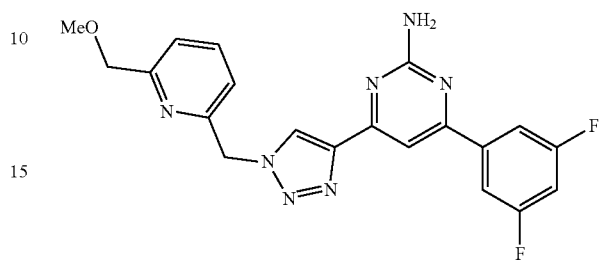

The title compounds was synthesized in a similar fashion to step 6 of example 1 using 2-(azidomethyl)-6-(methoxymethyl)pyridine and 4-(3,5-difluorophenyl)-6-ethynyl-2-pyrimidinylamine (this was prepared similar to steps 1-3 of example 1). ¹H NMR (400 MHz, DMSO-d₆) δ 8.81 (s, 1H), 7.92-7.83 (m, 5H), 7.51-7.42 (m, 1H), 7.40 (d, J=7.6 Hz, 1H), 7.26 (d, J=7.6 Hz, 1H), 6.95 (bs, 1H), 5.86 (s, 1H), 4.47 (s, 3H), 3.35 (s, 3H). MS [M+H]⁺ for C₂₀H₁₇F₂N₇O, calcd 410.1, found 410.2.

Example 36: 6-(3,5-Dimethoxyphenyl)-4-(1-{[6-(methoxymethyl)-2-pyridyl]methyl}-1H-1,2,3-triazol-4-yl)-2-pyrimidinylamine

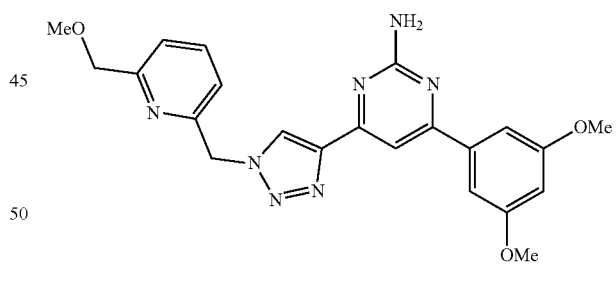

The title compounds was synthesized in a similar fashion to step 6 of example 1 using 2-(azidomethyl)-6-(methoxymethyl)pyridine and 4-(3,5-dimethoxyphenyl)-6-ethynyl-2-pyrimidinylamine (this was prepared similar to steps 1-3 of example 1). ¹H NMR (400 MHz, DMSO-d₆) δ 8.75 (brs, 1H), 7.86 (dd, J=7.7 Hz, 1H), 7.70 (s, 1H), 7.39 (d, J=7.7 Hz, 1H), 7.28 (d, J=2.3 Hz, 2H), 7.23 (d, J=7.7 Hz, 1H), 6.82 (brs, 2H), 6.67 (s, 1H), 5.84 (s, 2H), 4.47 (s, 2H), 3.84 (s, 6H), 3.35 (s, 3H). MS [M+H]⁺ for C₂₂H₂₃N₇O₃, calcd 434.2, found 434.3.

Example 37: p-[2-Amino-6-(1-{[6-(methoxymethyl)-2-pyridyl]methyl}-1H-1,2,3-triazol-4-yl)-4-pyrimidinyl]benzonitrile

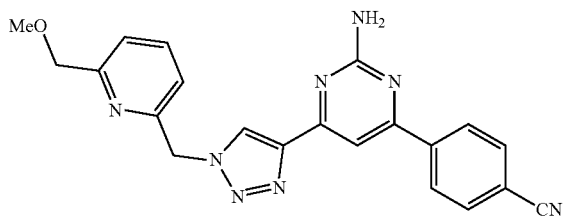 [SMILES: COCc1cccc(Cn2cc(-c3cc(-c4ccc(C#N)cc4)nc(N)n3)nn2)n1]

The title compound was prepared similar to example 20 from the corresponding azide and alkyne. $^1$H NMR (400 MHz, DMSO-d$_6$) δ 8.68 (s, 1H), 8.34-8.26 (m, 2H), 8.03-7.90 (m, 1H), 7.88-7.79 (m, 1H), 7.76 (s, 1H), 7.37 (dd, J=7.9, 7.9 Hz, 1H), 7.21 (dd, J=7.9, 7.9 Hz, 1H), 6.90 (s, 2H), 5.81 (s, 2H), 4.45 (s, 2H), 3.35 (s, 3H). MS [M+H]$^+$ for C$_{21}$H$_{18}$N$_8$O, calcd 399.2, found: 399.3.

Example 38: o-[2-Amino-6-(1-{[6-(methoxymethyl)-2-pyridyl]methyl}-1H-1,2,3-triazol-4-yl)-4-pyrimidinyl]benzonitrile

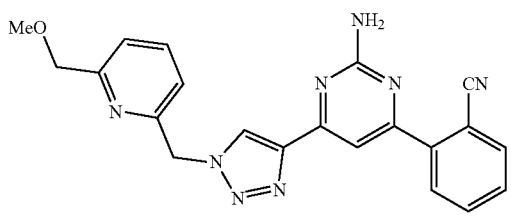 [SMILES: COCc1cccc(Cn2cc(-c3cc(-c4ccccc4C#N)nc(N)n3)nn2)n1]

The title compound was prepared similar to example 20 from the corresponding azide and alkyne. $^1$H NMR (400 MHz, CDCl$_3$) δ 8.34 (s, 1H), 7.88 (d, J=7.8 Hz, 1H), 7.82 (d, J=7.8 Hz, 1H), 7.80 (s, 1H), 7.74-7.63 (m, 2H), 7.55 (d, J=7.8 Hz, 1H), 7.40 (d, J=7.8 Hz, 1H), 7.11 (d, J=7.8 Hz, 1H), 5.72 (s, 2H), 5.31 (s, 2H), 4.58 (s, 2H), 3.51-3.43 (s, 3H). MS [M+H]$^+$ for C$_{21}$H$_{18}$N$_8$O, calcd 399.2, found: 399.3.

Example 39: 2-{m-[2-Amino-6-(1-{[6-(methoxymethyl)-2-pyridyl]methyl}-1H-1,2,3-triazol-4-yl)-4-pyrimidinyl]phenyl}-2-propanol

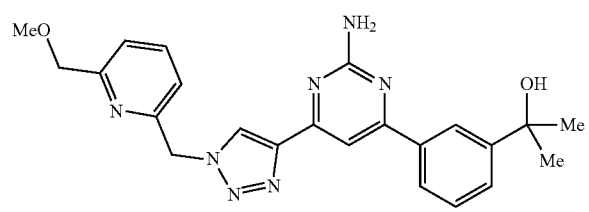 [SMILES: COCc1cccc(Cn2cc(-c3cc(-c4cccc(C(C)(C)O)c4)nc(N)n3)nn2)n1]

The title compound was prepared similar to example 20 from the corresponding azide and alkyne. $^1$H NMR (400 MHz, CDCl$_3$) δ 8.30 (s, 1H), 8.24 (s, 1H), 7.96 (d, J=8.0 Hz, 1H), 7.92 (s, 1H), 7.70 (dd, J=8.0 Hz, 1H), 7.61 (d, J=8.0 Hz, 1H), 7.45 (dd, J=8.0 Hz, 1H), 7.40 (d, J=8.0 Hz, 1H), 7.10 (d, J=8.0 Hz, 1H), 5.72 (s, 2H), 5.30 (s, 1H), 5.16 (s, 2H), 4.58 (s, 1H), 3.48 (s, 3H), 1.64 (s, 6H). MS [M+H]$^+$ for C$_{25}$H$_{25}$N$_7$O$_2$, calcd 432.2, found 432.2.

Example 40: 6-(m-Cumenyl)-4-(1-{[6-(methoxymethyl)-2-pyridyl]methyl}-1H-1,2,3-triazol-4-yl)-2-pyrimidinylamine

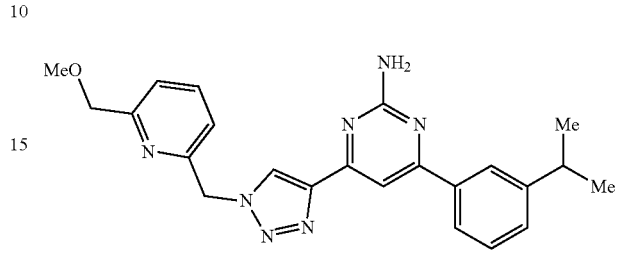

The title compound was prepared similar to example 20 from the corresponding azide and alkyne. $^1$H NMR (400 MHz, Chloroform-d) δ 8.30 (s, 1H), 7.96 (s, 1H), 7.94-7.87 (m, 2H), 7.71 (dd, J=7.7, 7.7 Hz, 1H), 7.49-7.33 (m, 3H), 7.10 (d, J=7.7 Hz, 1H), 5.73 (s, 2H), 5.10 (brs, 2H), 4.59 (s, 2H), 3.50 (s, 3H), 3.00 (h, J=6.9 Hz, 1H), 1.31 (d, J=6.9 Hz, 6H). MS [M+H]$^+$ for C$_{23}$H$_{25}$N$_7$O, calcd 416.2, found 416.4.

Example 41: Ethyl 3-{m-[2-amino-6-(1-{[6-(methoxymethyl)-2-pyridyl]methyl}-1H-1,2,3-triazol-4-yl)-4-pyrimidinyl]phenyl}propionate

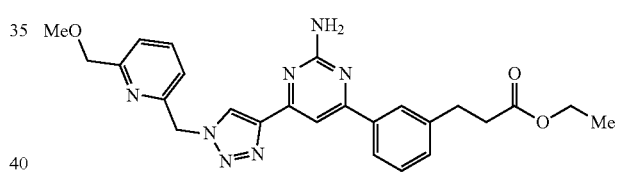

The title compound was prepared similar to example 20 from the corresponding azide and alkyne. $^1$H NMR (400 MHz, Chloroform-d) δ 8.29 (s, 1H), 7.97 (s, 1H), 7.96-7.91 (m, 1H), 7.90 (s, 1H), 7.71 (dd, J=7.8 Hz, 1H), 7.46-7.36 (m, 2H), 7.33 (d, J=7.8 Hz, 1H), 7.10 (d, J=7.8 Hz, 1H), 5.73 (s, 2H), 5.10 (brs, 2H), 4.59 (s, 2H), 4.14 (q, J=7.2 Hz, 2H), 3.49 (s, 3H), 3.04 (t, J=7.9 Hz, 3H), 2.68 (t, J=7.9 Hz, 3H), 1.24 (t, J=7.2 Hz, 3H). MS [M+H]$^+$ for C$_{25}$H$_{27}$N$_7$O$_3$, calcd 474.2, found 474.3.

Example 42: 4-[m-(2-Methoxyethoxy)phenyl]-6-(1-{[6-(methoxymethyl)-2-pyridyl]methyl}-1H-1,2,3-triazol-4-yl)-2-pyrimidinylamine

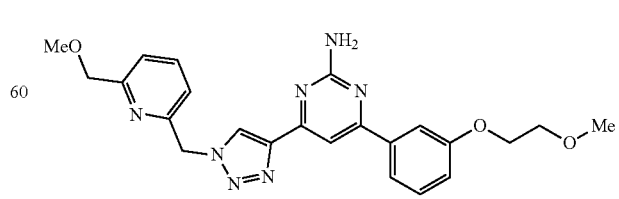

The title compound was prepared similar to example 20 from the corresponding azide and alkyne. $^1$H NMR (400

MHz, Chloroform-d) δ 8.29 (s, 1H), 7.89 (s, 1H), 7.75-7.64 (m, 3H), 7.50-7.29 (m, 2H), 7.11 (d, J=7.6 Hz, 1H)=, 7.09-7.03 (m, 1H), 5.72 (s, 2H), 5.08 (brs, 2H), 4.59 (s, 2H), 4.32-4.18 (m, 2H), 3.83-3.75 (m, 2H), 3.50 (s, 3H), 3.47 (s, 3H). MS [M+H]$^+$ for $C_{23}H_{25}N_7O_3$, calcd 448.2, found 448.3.

Example 43: 3-{m-[2-Amino-6-(1-{[6-(methoxymethyl)-2-pyridyl]methyl}-1H-1,2,3-triazol-4-yl)-4-pyrimidinyl]phenyl}propionic acid

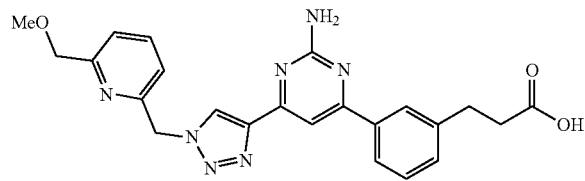 [SMILES: COCc1cccc(Cn2cc(-c3cc(-c4cccc(CCC(=O)O)c4)nc(N)n3)nn2)n1]

The title compound was prepared similar to example 20 from the corresponding azide and alkyne. $^1$H NMR (400 MHz, DMSO-d$_6$) δ 12.15 (brs, 1H), 8.63 (s, 1H), 7.98 (s, 1H), 7.93 (d, J=7.6 Hz, 1H), 7.84 (dd, J=7.6 Hz, 1H), 7.68 (s, 1H), 7.47-7.30 (m, 3H), 7.20 (d, J=7.6 Hz, 1H), 6.74 (s, 1H), 5.80 (s, 2H), 4.45 (s, 2H), 3.34 (s, 3H), 2.90 (t, J=7.6 Hz, 2H), 2.58 (t, J=7.6 Hz, 2H). MS [M+H]$^+$ for $C_{23}H_{23}N_7O_3$, calcd 446.2, found 446.3.

Example 44: 3-[2-Amino-6-(1-{[6-(methoxymethyl)-2-pyridyl]methyl}-1H-1,2,3-triazol-4-yl)-4-pyrimidinyl]-4-fluorobenzonitrile

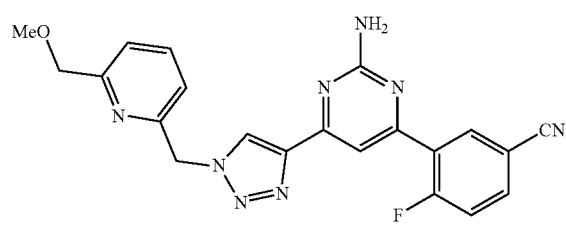 [SMILES: COCc1cccc(Cn2cc(-c3cc(-c4cc(C#N)ccc4F)nc(N)n3)nn2)n1]

The title compound was prepared similar to example 20 from the corresponding azide and alkyne. $^1$H NMR (400 MHz, DMSO-d$_6$) δ 8.70 (s, 1H), 8.50-8.43 (m, 1H), 8.14-8.03 (m, 1H), 7.84 (dd, J=8.0, 8.0 Hz, 1H), 7.70-7.57 (m, 2H), 7.38 (d, J=7.7 Hz, 1H), 7.22 (d, J=8.0 Hz, 1H), 5.82 (s, 2H), 4.45 (s, 2H), 3.53 (s, 3H). MS [M+H]$^+$ for $C_{21}H_{17}FN_8O$, calcd 417.2, found 417.3.

Example 45: 3-[2-Amino-6-(1-{[6-(methoxymethyl)-2-pyridyl]methyl}-1H-1,2,3-triazol-4-yl)-4-pyrimidinyl]-2-fluorobenzonitrile

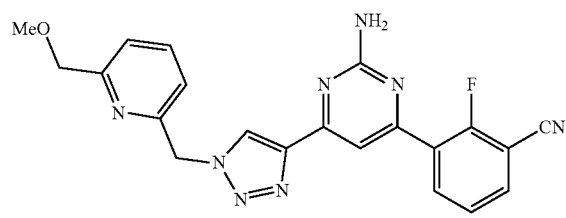 [SMILES: COCc1cccc(Cn2cc(-c3cc(-c4cccc(C#N)c4F)nc(N)n3)nn2)n1]

The title compound was prepared similar to example 20 from the corresponding azide and alkyne. $^1$H NMR (400 MHz, DMSO-d$_6$) δ 8.66 (s, 1H), 8.29 (dd, J=7.9, 7.9 Hz, 1H), 8.07 (ddd, J=7.6, 7.6 Hz, 1H), 7.84 (dd, J=7.9, 7.9 Hz, 1H), 7.61 (s, 1H), 7.56 (dd, J=7.9, 7.9 Hz, 1H), 7.37 (d, J=7.6 Hz, 1H), 7.21 (d, J=7.6 Hz, 1H), 6.94 (s, 2H), 5.79 (s, 2H), 4.44 (s, 2H). MS [M+H]$^+$ for $C_{21}H_{17}FN_8O$, calcd 417.2, found: 417.3.

Example 46: 6-(2,3-Difluorophenyl)-4-(1-{[6-(methoxymethyl)-2-pyridyl]methyl}-1H-1,2,3-triazol-4-yl)-2-pyrimidinylamine

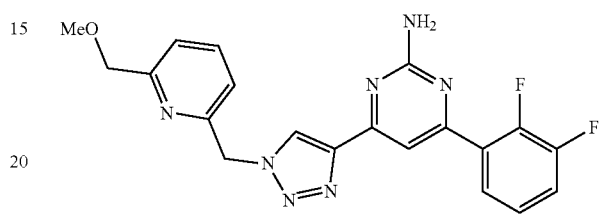

$^1$H NMR (400 MHz, DMSO-d$_6$) δ 8.69 (s, 1H), 7.89-7.72 (m, 2H), 7.63-7.49 (m, 2H), 7.41-7.29 (m, 2H), 7.21 (d, J=7.8 Hz, 1H), 6.99 (brs, 2H), 5.81 (s, 2H), 4.45 (s, 2H), 3.55 (s, 3H). MS [M+H]$^+$ for $C_{20}H_{17}F_2N_7O_2$, calcd 410.1, found.

Example 47: 4-(1-{[6-(Methoxymethyl)-2-pyridyl]methyl}-1H-1,2,3-triazol-4-yl)-6-(m-tolyl)-2-pyrimidinylamine

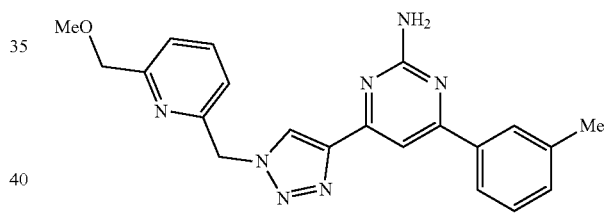

The title compound was prepared similar to example 20 from the corresponding azide and alkyne to afford 9 mg of a yellow-brown solid. $^1$H NMR (400 MHz, DMSO-d$_6$) δ 8.25 (s, 1H), 7.89-7.85 (m, 1H), 7.83 (d, J=7.2 Hz, 1H), 7.65 (t, J=7.7 Hz, 1H), 7.37-7.33 (m, 1H), 7.31 (d, J=7.6 Hz, 1H), 7.26-7.22 (m, 1H), 7.21 (s, 1H), 7.07-7.03 (m, 1H), 5.67 (s, 2H), 5.13 (s, 2H), 4.53 (s, 2H), 3.44 (s, 3H), 2.40-2.37 (m, 3H). ESI MS [M+H]$^+$ for $C_{21}H_{21}N_7O$, calcd 388.1, found 388.3.

Example 48: 4-(1-{[6-(Methoxymethyl)-2-pyridyl]methyl}-1H-1,2,3-triazol-4-yl)-6-(m-methoxyphenyl)-2-pyrimidinylamine

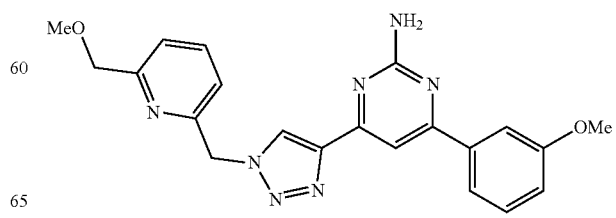

The title compound was prepared similar to example 20 from the corresponding azide and alkyne to afford 37 mg of a yellow-brown solid. $^1$H NMR (400 MHz, DMSO-d$_6$) δ 8.67 (s, 1H), 7.85 (t, J=7.8 Hz, 1H), 7.71-7.63 (m, 3H), 7.48-7.34 (m, 2H), 7.24-7.17 (m, 1H), 7.09 (ddd, J=8.2, 2.7, 0.9 Hz, 1H), 6.80 (bs, 2H), 5.81 (s, 2H), 4.46 (s, 2H), 3.84 (s, 3H), 3.34 (s, 3H). ESI MS [M+H]$^+$ for C$_{21}$H$_{21}$N$_7$O$_2$, calcd 404.2, found 404.2.

Example 49: 6-(m-Fluorophenyl)-4-(1-{[6-(methoxymethyl)-2-pyridyl]methyl}-1H-1,2,3-triazol-4-yl)-2-pyrimidinylamine

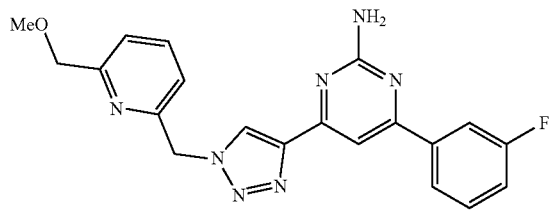 [SMILES: COCc1cccc(Cn2cc(-c3cc(-c4cccc(F)c4)nc(N)n3)nn2)n1]

The title compound was prepared similar to example 20 from the corresponding azide and alkyne. to afford 32 mg of a yellow solid. $^1$H NMR (400 MHz, DMSO-d$_6$) δ 8.69 (s, 1H), 8.01-7.98 (m, 1H), 7.94 (ddd, J=10.6, 2.7, 1.5 Hz, 1H), 7.86 (t, J=7.7 Hz, 1H), 7.73 (s, 1H), 7.58 (td, J=8.0, 6.0 Hz, 1H), 7.42-7.34 (m, 2H), 7.26-7.20 (m, 1H), 6.87 (bs, 2H), 5.83 (s, 2H), 4.47 (s, 2H), 3.35 (s, 3H). ESI MS [M+H]$^+$ for C$_{20}$H$_{18}$FN$_7$O, calcd 392.2, found 392.2.

Example 50: 6-(1-{[6-(Methoxymethyl)-2-pyridyl]methyl}-1H-1,2,3-triazol-4-yl)-4-[m-(trifluoromethyl)phenyl]-2-pyrimidinylamine

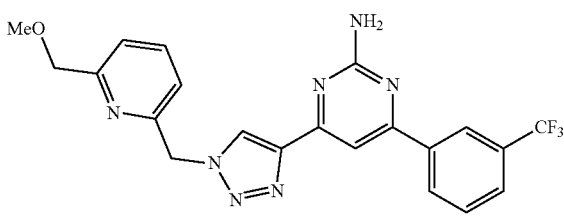 [SMILES: COCc1cccc(Cn2cc(-c3cc(-c4cccc(C(F)(F)F)c4)nc(N)n3)nn2)n1]

The title compound was prepared similar to example 20 from the corresponding azide and alkyne to afford an orange solid. $^1$H NMR (400 MHz, DMSO-d$_6$) δ 8.70 (s, 1H), 8.48 (d, J=2.1 Hz, 1H), 8.45 (d, J=7.9 Hz, 1H), 7.95-7.83 (m, 2H), 7.79 (d, J=11.5 Hz, 2H), 7.67-7.52 (m, 2H), 7.42-7.36 (m, 1H), 7.25-7.18 (m, 1H), 6.94 (s, 2H), 5.83 (s, 2H), 4.47 (s, 2H), 3.35 (s, 3H). ESI MS [M+H]$^+$ for C$_{21}$H$_{18}$F$_3$N$_7$O, calcd 442.2, found 442.2.

Example 51: 6-(1-{[6-(Methoxymethyl)-2-pyridyl]methyl}-1H-1,2,3-triazol-4-yl)-4-[m-(methylsulfonyl)phenyl]-2-pyrimidinylamine

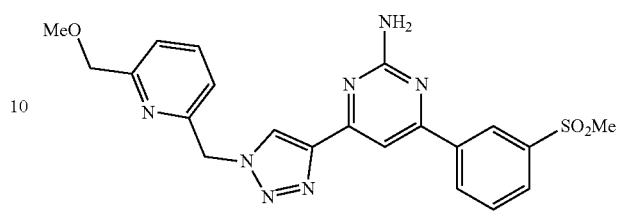

The title compound was prepared similar to example 20 from the corresponding azide and alkyne to afford a yellow-brown solid. $^1$H NMR (400 MHz, DMSO-d$_6$) δ 8.77-8.59 (m, 2H), 8.49 (ddd, J=7.9, 1.8, 1.1 Hz, 1H), 8.08 (ddd, J=7.8, 1.9, 1.1 Hz, 1H), 7.90-7.76 (m, 3H), 7.45-7.36 (m, 1H), 7.31-7.17 (m, 1H), 6.96 (s, 2H), 5.83 (s, 2H), 4.46 (s, 2H), 3.35 (s, 3H), 3.30 (s, 3H). ESI MS [M+H]$^+$ for C$_{21}$H$_{21}$N$_7$O$_3$S, calcd 452.2, found 452.2.

Example 52: 6-(m-Chlorophenyl)-4-(1-{[6-(methoxymethyl)-2-pyridyl]methyl}-1H-1,2,3-triazol-4-yl)-2-pyrimidinylamine

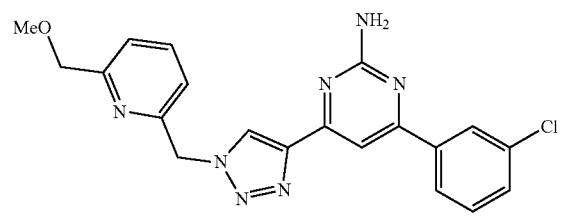 [SMILES: COCc1cccc(Cn2cc(-c3cc(-c4cccc(Cl)c4)nc(N)n3)nn2)n1]

The title compound was prepared similar to example 20 from the corresponding azide and alkyne to afford 71 mg of a tan solid. $^1$H NMR (400 MHz, DMSO-d$_6$) δ 8.69 (s, 1H), 8.25-8.15 (m, 1H), 8.10 (dt, J=7.4, 1.6 Hz, 1H), 7.86 (t, J=7.7 Hz, 1H), 7.73 (s, 1H), 7.66-7.50 (m, 2H), 7.44-7.34 (m, 1H), 7.30-7.16 (m, 1H), 6.88 (s, 2H), 5.82 (s, 2H), 4.46 (s, 2H), 3.35 (s, 3H). ESI MS [M+H]$^+$ for C$_{20}$H$_{18}$ClN$_7$O, calcd 408.1, found 408.2.

Example 53: 3-[2-Amino-6-(1-{[6-(methoxymethyl)-2-pyridyl]methyl}-1H-1,2,3-triazol-4-yl)-4-pyrimidinyl]-5-fluorobenzonitrile

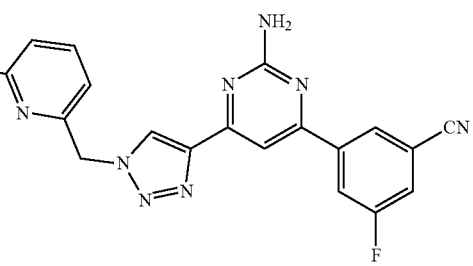

The title compound was prepared similar to example 20 from the corresponding azide and alkyne to afford 3 mg of a white solid. ¹H NMR (400 MHz, CDCl₃) δ 8.33 (s, 1H), 8.25 (t, J=1.2 Hz, 1H), 8.15-8.05 (m, 1H), 7.88 (s, 1H), 7.73-7.71 (m, 1H), 7.44-7.27 (m, 2H), 7.13 (d, J=8.4 Hz, 1H), 5.74 (s, 2H), 5.16 (bs, 2H), 4.60 (s, 2H), 3.51 (s, 3H). ESI MS [M+H]⁺ for C₂₁H₁₇FN₈O, calcd 417.2, found 417.3.

Example 54: 3-[2-Amino-6-(1-{[6-(methoxymethyl)-2-pyridyl]methyl}-1H-1,2,3-triazol-4-yl)-4-pyrimidinyl]-5-anisonitrile

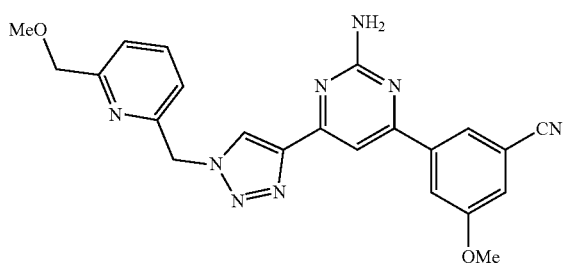 [SMILES: COCc1cccc(Cn2cc(-c3cc(-c4cc(C#N)cc(OC)c4)nc(N)n3)nn2)n1]

The title compound was prepared similar to example 20 from the corresponding azide and alkyne to afford 56 mg of a white solid. ¹H NMR (400 MHz, DMSO-d₆) δ 8.72 (s, 1H), 8.18 (d, J=1.2 Hz, 1H), 7.99 (d, J=1.6 Hz, 1H), 7.87-7.85 (m, 1H), 7.81 (s, 1H), 7.60-7.56 (m, 2H), 7.39 (d, J=8 Hz, 1H), 7.22 (J=8 Hz, 1H), 6.92 (bs, 1H), 5.83 (s, 2H), 4.47 (s, 2H), 3.92 (s, 3H), 3.35 (s, 3H). ESI MS [M+H]⁺ for C₂₂H₂₀N₈O₂, calcd 429.2, found 429.3.

Example 55: 6-[2-Amino-6-(1-{[6-(methoxymethyl)-2-pyridyl]methyl}-1H-1,2,3-triazol-4-yl)-4-pyrimidinyl]-2-toluonitrile

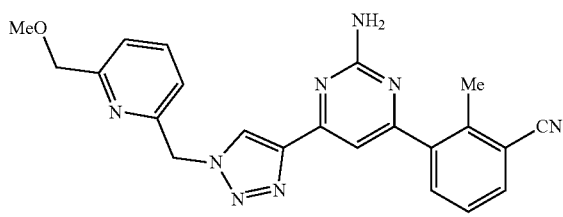 [SMILES: COCc1cccc(Cn2cc(-c3cc(-c4cccc(C#N)c4C)nc(N)n3)nn2)n1]

The title compound was prepared similar to example 20 from the corresponding azide and alkyne to afford 78 mg of a tan solid. ¹H NMR (400 MHz, DMSO-d₆) 8.67 (d, J=0.8 Hz, 1H), 7.94-7.81 (m, 2H), 7.75 (dd, J=7.8, 1.3 Hz, 1H), 7.52 (t, J=7.8 Hz, 1H), 7.39 (d, J=7.8 Hz, 1H), 7.27 (d, J=0.9 Hz, 1H), 7.21 (d, J=7.7 Hz, 1H), 6.88 (s, 2H), 5.81 (s, 2H), 4.46 (s, 2H), 3.35 (s, 3H), 2.55 (s, 3H). ESI MS [M+H]⁺ for C₂₂H₂₀N₈O, calcd 413.2, found 413.3.

Example 56: 6-(2,2-Difluoro-2H-1,3-benzodioxol-5-yl)-4-(1-{[6-(methoxymethyl)-2-pyridyl]methyl}-1H-1,2,3-triazol-4-yl)-2-pyrimidinylamine

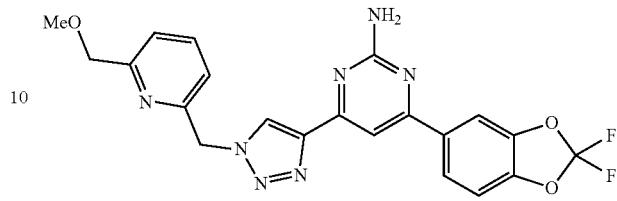

The title compound was prepared similar to example 20 from the corresponding azide and alkyne to afford 30 mg of a yellow solid. H NMR (400 MHz, DMSO-d₆) δ 8.67 (s, 1H), 8.15 (dd, J=1.8, 0.4 Hz, 1H), 8.07 (dd, J=8.5, 1.8 Hz, 1H), 7.86 (t, J=7.8 Hz, 1H), 7.73 (s, 1H), 7.56 (dd, J=8.5, 0.4 Hz, 1H), 7.43-7.35 (m, 1H), 7.22 (dd, J=7.7, 0.9 Hz, 1H), 6.84 (s, 2H), 5.82 (s, 2H), 4.46 (s, 2H), 3.35 (s, 3H). ESI MS [M+H]⁺ for C₂₁H₁₇F₂N₇O₃, calcd 454.1, found 454.3.

Example 57: 4-(1-{[6-(Methoxymethyl)-2-pyridyl]methyl}-1H-1,2,3-triazol-4-yl)-6-(m-trifluoromethoxyphenyl)-2-pyrimidinylamine

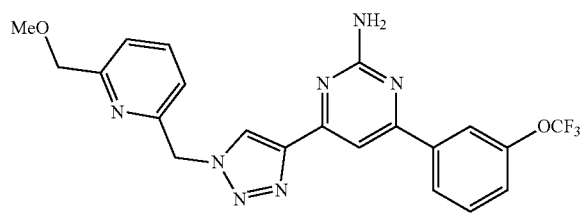 [SMILES: COCc1cccc(Cn2cc(-c3cc(-c4cccc(OC(F)(F)F)c4)nc(N)n3)nn2)n1]

The title compound was prepared similar to example 20 from the corresponding azide and alkyne to afford 100 mg of a white solid. ¹H NMR (400 MHz, DMSO-d₆) δ 8.70 (s, 1H), 8.20-8.17 (m, 1H), 8.12 (s, 1H), 8.12 (bs, 1H), 7.86 (t, J=8 Hz, 1H), 7.76 (s, 1H), 7.66 (t, J=8 Hz, 1H), 7.56-7.54 (m, 1H), 7.39 (d, J=3.2 Hz, 1H), 7.22 (d, J=3.2 Hz, 1H), 6.90 (bs, 2H), 5.83 (s, 2H), 4.47 (s, 2H), 3.35 (s, 3H). ESI MS [M+H]⁺ for C₂₁H₁₈F₃N₇O₂, calcd 458.2, found 458.3.

Example 58: {m-[2-Amino-6-(1-{[6-(methoxymethyl)-2-pyridyl]methyl}-1H-1,2,3-triazol-4-yl)-4-pyrimidinyl]phenyl}(dimethylamino)formaldehyde

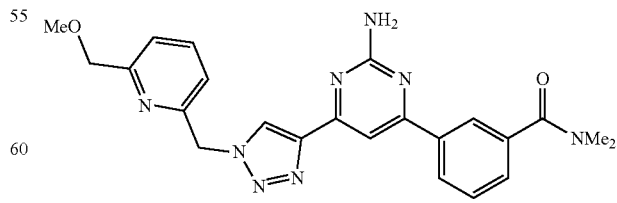

The title compound was prepared similar to example 20 from the corresponding azide and alkyne to afford 48 mg of a tan solid. ¹H NMR (400 MHz, DMSO-d₆) δ 8.68 (dd, J=3.7, 1.1 Hz, 1H), 8.23-8.12 (m, 2H), 7.86 (td, J=7.8, 4.1

Hz, 1H), 7.74 (dd, J=3.6, 1.1 Hz, 1H), 7.63-7.51 (m, 2H), 7.39 (dd, J=7.8, 3.5 Hz, 1H), 7.22 (dd, J=7.7, 3.5 Hz, 1H), 6.82 (d, J=3.5 Hz, 2H), 5.82 (d, J=3.6 Hz, 2H), 4.47 (d, J=3.8 Hz, 2H), 3.35 (dd, J=3.7, 1.1 Hz, 3H), 3.02 (s, 3H), 2.94 (s, 3H). ESI MS [M+H]+ for $C_{23}H_{24}N_8O_2$, calcd 445.2, found 445.3.

Example 59: {m-[2-Amino-6-(1-{[6-(methoxymethyl)-2-pyridyl]methyl}-1H-1,2,3-triazol-4-yl)-4-pyrimidinyl]phenylaminohydroxysulfeno}methane

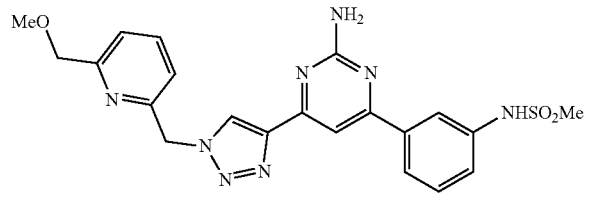

The title compound was prepared similarly to example 1 starting from 3-(methylsulfonylamino)phenylboronic acid. 1H NMR (400 MHz, D$_2$O) δ 8.65 (m, 1H), 8.16-7.94 (m, 1H), 7.68-7.04 (m, 8H), 5.79 (m, 2H), 3.31 (m, 3H), 3.19 (m, 1H), 2.95 (m, 3H); LC-MS retention time 2.28 min LC-MS, Method A, ESI MS [M+H]+ for $C_{21}H_{23}N_8O_3S$, calcd 467.2, found 467.2.

Example 60: 6-(m-Ethylphenyl)-4-(1-{[6-(methoxymethyl)-2-pyridyl]methyl}-1H-1,2,3-triazol-4-yl)-2-pyrimidinylamine

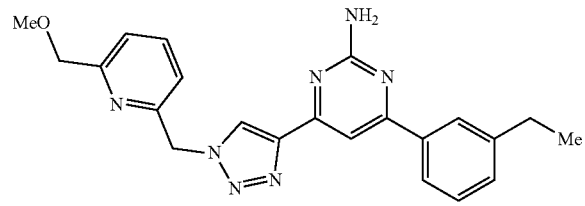 [SMILES: CCc1cccc(-c2cc(-c3cn(Cc4cccc(COC)n4)nn3)nc(N)n2)c1]

The title compound was prepared similarly to example 1 starting from 3-ethylphenylboronic acid. $^1$H NMR (400 MHz, DMSO-d$_6$) δ 8.97 (s, 1H), 8.04 (s, 1H), 7.99 (d, J=7.1 Hz, 1H), 7.92-7.81 (m, 2H), 7.53-7.43 (m, 2H), 7.39 (d, J=7.8 Hz, 1H), 7.28 (d, J=7.7 Hz, 1H), 5.86 (s, 2H), 4.45 (s, 2H), 3.33 (s, 2H), 2.71 (q, J=7.6 Hz, 2H), 1.23 (td, J=7.6, 1.0 Hz, 3H); LC-MS retention time 2.66 min LC-MS, Method A, ESI MS [M+H]+ for $C_{22}H_{24}N_7O$, calcd 402.2, found 402.3.

Example 61: {m-[2-Amino-6-(1-{[6-(methoxymethyl)-2-pyridyl]methyl}-1H-1,2,3-triazol-4-yl)-4-pyrimidinyl]phenyl}acetonitrile

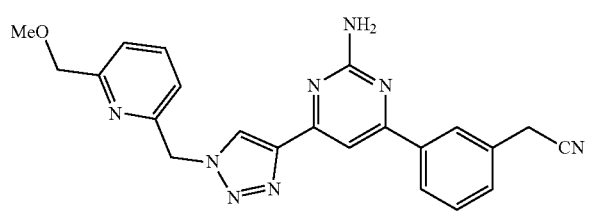 [SMILES: COCc1cccc(Cn2cc(-c3cc(-c4cccc(CC#N)c4)nc(N)n3)nn2)n1]

The title compound was prepared similar to example 20 from the corresponding azide and alkyne to afford 103 mg of a tan solid. $^1$H NMR (400 MHz, DMSO-d$_6$) δ 8.66 (d, J=1.1 Hz, 1H), 8.14 (s, 1H), 8.09 (d, J=7.7 Hz, 1H), 7.90-7.79 (m, 1H), 7.72 (d, J=1.1 Hz, 1H), 7.59-7.47 (m, 2H), 7.39 (d, J=7.8 Hz, 1H), 7.22 (d, J=7.8 Hz, 1H), 6.82 (s, 2H), 5.82 (s, 2H), 4.47 (s, 2H), 4.16 (s, 2H), 3.35 (d, J=1.2 Hz, 3H). ESI MS [M+H]+ for $C_{22}H_{20}N_8O$, calcd 413.2, found 413.3.

Example 62: 6-(1-{[6-(Methoxymethyl)-2-pyridyl]methyl}-1H-1,2,3-triazol-4-yl)-4-[m-(1,3-oxazol-2-yl)phenyl]-2-pyrimidinylamine

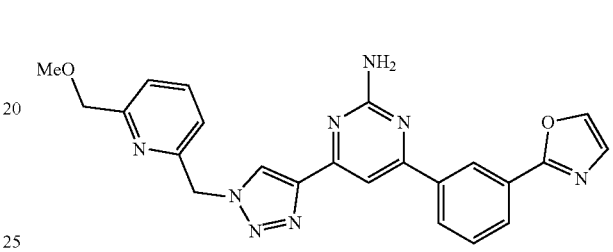

The title compound was prepared similar to example 20 from the corresponding azide and alkyne to afford 110 mg of a tan solid. H NMR (400 MHz, DMSO-d$_6$) δ 8.79 (d, J=1.8 Hz, 1H), 8.73-8.67 (m, 1H), 8.32-8.24 (m, 2H), 8.13 (d, J=7.7 Hz, 1H), 7.91-7.82 (m, 1H), 7.78 (d, J=2.0 Hz, 1H), 7.71 (dt, J=8.6, 4.3 Hz, 1H), 7.47-7.43 (m, 1H), 7.39 (d, J=7.8 Hz, 1H), 7.23 (d, J=7.8 Hz, 1H), 6.91 (s, 2H), 5.83 (d, J=2.0 Hz, 2H), 4.47 (d, J=2.0 Hz, 2H), 3.35 (q, J=1.4 Hz, 3H). ESI MS [M+H]+ for $C_{23}H_{20}N_8O_2$, calcd 441.2, found 441.3.

Example 63: 4-(1-{[6-(Methoxymethyl)-2-pyridyl]methyl}-1H-1,2,3-triazol-4-yl)-6-(3-pyridyl)-2-pyrimidinylamine

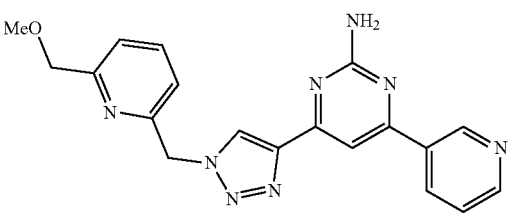 [SMILES: COCc1cccc(Cn2cc(-c3cc(-c4cccnc4)nc(N)n3)nn2)n1]

The title compound was synthesized in a similar fashion to step 6 of example 1 using 2-(azidomethyl)-6-(methoxymethyl)pyridine and 6-ethynyl-4-(3-pyridyl)-2-pyrimidinylamine (this was prepared similar to steps 1-3 of example 1). $^1$H NMR (400 MHz, Chloroform-d) δ 9.32 (d, J=2.4 Hz, 1H), 8.71 (dd, J=4.8, 1.7 Hz, 1H), 8.37 (ddd, J=8.0, 2.3, 1.7 Hz, 1H), 8.31 (s, 1H), 7.92 (s, 1H), 7.71 (dd, J=7.8, 7.8 Hz, 1H), 7.46-7.39 (m, 2H), 7.11 (d, J=7.8 Hz, 1H), 5.73 (s, 2H), 5.15 (s, 2H), 4.59 (s, 2H), 3.50 (s, 3H). MS [M+H]+ for $C_{19}H_{18}N_8O$, calcd 375.2, found 375.3.

Example 64: 6-(2-Furyl)-4-(1-{[6-(methoxymethyl)-2-pyridyl]methyl}-1H-1,2,3-triazol-4-yl)-2-pyrimidinylamine

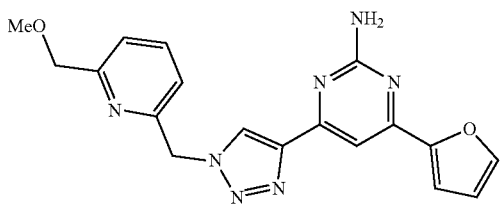 [SMILES: COCc1cccc(Cn2cc(-c3cc(-c4ccco4)nc(N)n3)nn2)n1]

The title compound was synthesized in a similar fashion to step 6 of example 1 using 2-(azidomethyl)-6-(methoxymethyl)pyridine and 6-ethynyl-4-(2-furyl)-2-pyrimidinylamine. $^1$H NMR (400 MHz, Chloroform-d) δ 8.27 (s, 1H), 7.80 (s, 1H), 7.71 (t, J=7.8 Hz, 1H), 7.61 (dd, J=1.8, 0.8 Hz, 1H), 7.43-7.39 (m, 1H), 7.20 (dd, J=3.5, 0.8 Hz, 1H), 7.12-7.08 (m, 1H), 6.57 (dd, J=3.5, 1.8 Hz, 1H), 5.73 (s, 2H), 5.08 (s, 2H), 4.59 (s, 2H), 3.50 (s, 3H); ESI MS [M+H]$^+$ for $C_{18}H_{17}N_7O_2$, calcd 364.1, found 364.2.

Example 65: 4-(1-{[6-(Methoxymethyl)-2-pyridyl]methyl}-1H-1,2,3-triazol-4-yl)-6-(1,3-thiazol-2-yl)-2-pyrimidinylamine containing activated acid derivative was added to the other flask at r.t. The combined reaction mixture was stirred at 50° C. for 16 hours. The mixture was cooled to r.t. and 2M HCl$_{(aq)}$ (100 mL) was added. The mixture was extracted with ethyl acetate (2×150 mL), washed with sat. NaHCO$_3$, brine and filtered through a silica gel plug to afford the desired β-ketoester product as a brown oil (9.11 g; 91%).

Step 2: To a solution of guanidine hydrochloride (1.91 g, 20.0 mmol) and ethanol (40 mL) was added sodium ethoxide (1.36 g, 20.0 mmol). The mixture was stirred at r.t. for 10 minutes, at which time the above β-ketoester (3.98 g, 20.0 mmol) was added. The mixture was stirred at 100° C. for 16 hours. Upon cooling to r.t., hexanes (100 mL) was added. The precipitated solids were collected by filtration to afford the desired product as a yellow solid (2.88 g, 74%).

Step 3: A mixture of the step 2 product (2.88 g, 14.8 mmol), and POCl$_3$ (13.8 mL, 148 mmol) in dioxane (59 mL) was stirred at 70° C. for two hours. The mixture was then cooled, poured onto ice (75 g), neutralized with sat. NaHCO$_3$, extracted with ethyl acetate (2×150 mL), and dried over Na$_2$SO$_4$. The crude product was purified by silica gel chromatography (0 to 5% MeOH in CH$_2$Cl$_2$) to afford the desired product chloropyrimidine derivative as a brown solid (1.29 g; 41%).

Steps 4 and 5: A mixture of step 3 product (1.29 g; 6.07 mmol), trimethylsilylacetylene (2.59 mL, 18.2 mmol), bis(triphenylphosphine)palladium chloride (428 mg; 0.61 mmol), copper(I) iodide (116 mg, 0.61 mmol), triethylamine (3 mL), and DMF (3 mL) was stirred at 80° C. for 12 hours.

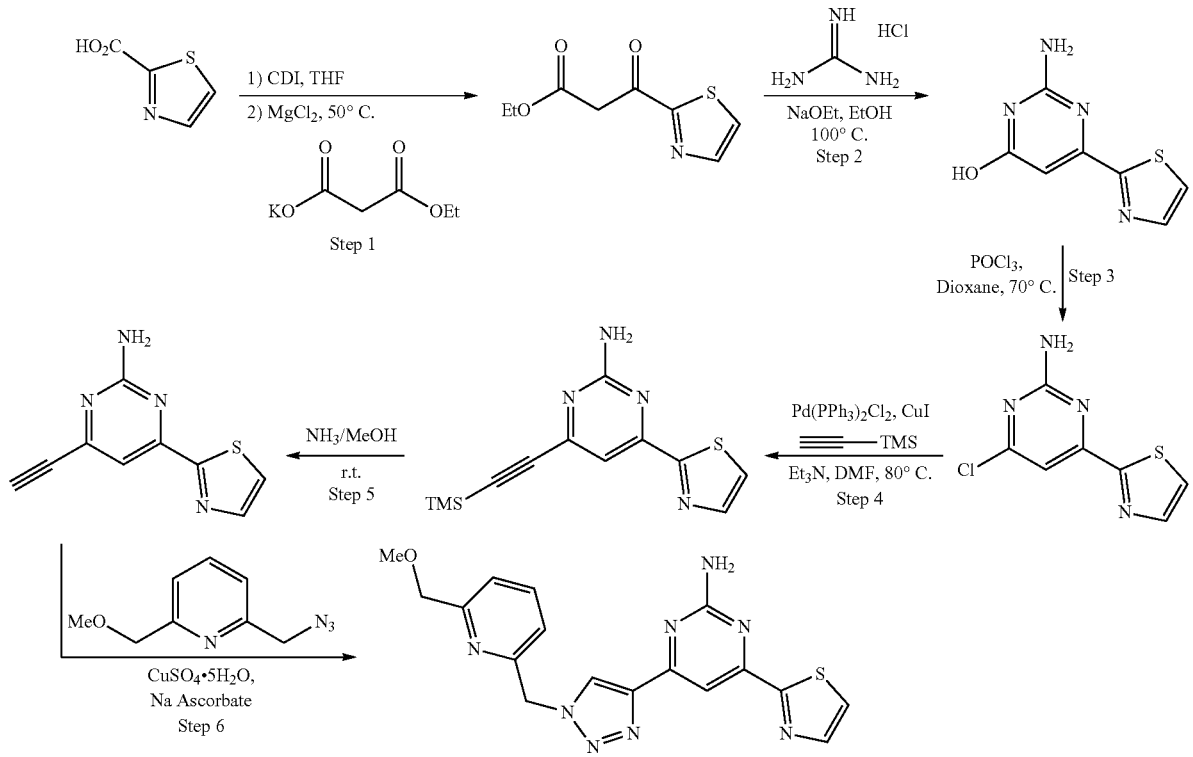

Step 1: To a solution of the thiazole acid derivative (6.46 g, 50.0 mmol) and THF (100 mL) at 0° C. was added CDI (9.72 g, 60.0 mmol) in one portion. The mixture was then stirred at r.t. for 4 hours. In a separate flask, a mixture of ethyl potassium malonate (25.5 g, 150 mmol), MgCl$_2$ (14.3 g, 150 mmol), and THF (100 mL) was stirred at 75° C. for 4 hours. Upon completion of the two reactions, the mixture The volatiles were removed and the crude product was purified by silica gel chromatography (0 to 100% EtOAc in hexanes) to afford the alkyne derivative. It was dissolved in MeOH (30 mL), ammonia (4.3 mL, 7 M in MeOH) was added, and the mixture stirred at r.t. for 30 minutes. The volatiles were removed and the crude product was purified by silica gel chromatography (0 to 50% EtOAc in CH$_2$Cl$_2$/hexanes (1:1)) to afford the desired product as an orange solid (254 mg; 21%).

Step 6: The product was synthesized in a similar manner to example 1, step 6: off-white solid (34 mg, 30%). $^1$H NMR (400 MHz, DMSO-d$_6$) δ 8.85 (s, 1H), 8.13 (s, 1H), 8.05 (s, 1H), 7.97-7.85 (m, 2H), 7.43 (d, J=8.4 Hz, 1H), 7.30 (d, J=7.6 Hz, 1H), 5.87 (s, 2H), 4.49 (s, 2H), 3.36 (s, 3H). ESI MS [M+H]$^+$ for C$_{17}$H$_{17}$N$_8$OS, calcd 381.1, found 381.2.

Example 66: 4-(1-{[6-(Methoxymethyl)-2-pyridyl]methyl}-1H-1,2,3-triazol-4-yl)-6-(4-methyl-1,3-thiazol-2-yl)-2-pyrimidinylamine

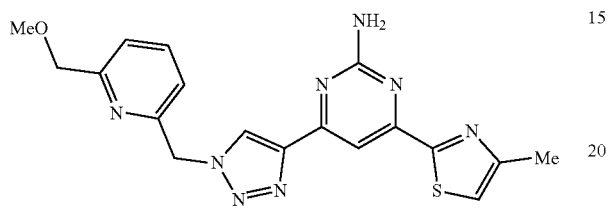

The title compound was synthesized similar to above example 65. $^1$H NMR (400 MHz, Chloroform-d) δ 8.30 (s, 1H), 8.13 (s, 1H), 7.71 (t, J=7.8 Hz, 1H), 7.44-7.36 (m, 1H), 7.14-7.09 (m, 1H), 7.07 (t, J=0.9 Hz, 1H), 5.72 (s, 2H), 5.32 (s, 2H), 4.59 (s, 2H), 3.49 (s, 3H), 2.54 (s, 3H). ESI MS [M+H]$^+$ for C$_{18}$H$_{18}$N$_8$OS, calcd 395.1, found 395.2.

Example 67: 4-(1-{[6-(Methoxymethyl)-2-pyridyl]methyl}-1H-1,2,3-triazol-4-yl)-6-(3-methyl-2-pyrazinyl)-2-pyrimidinylamine

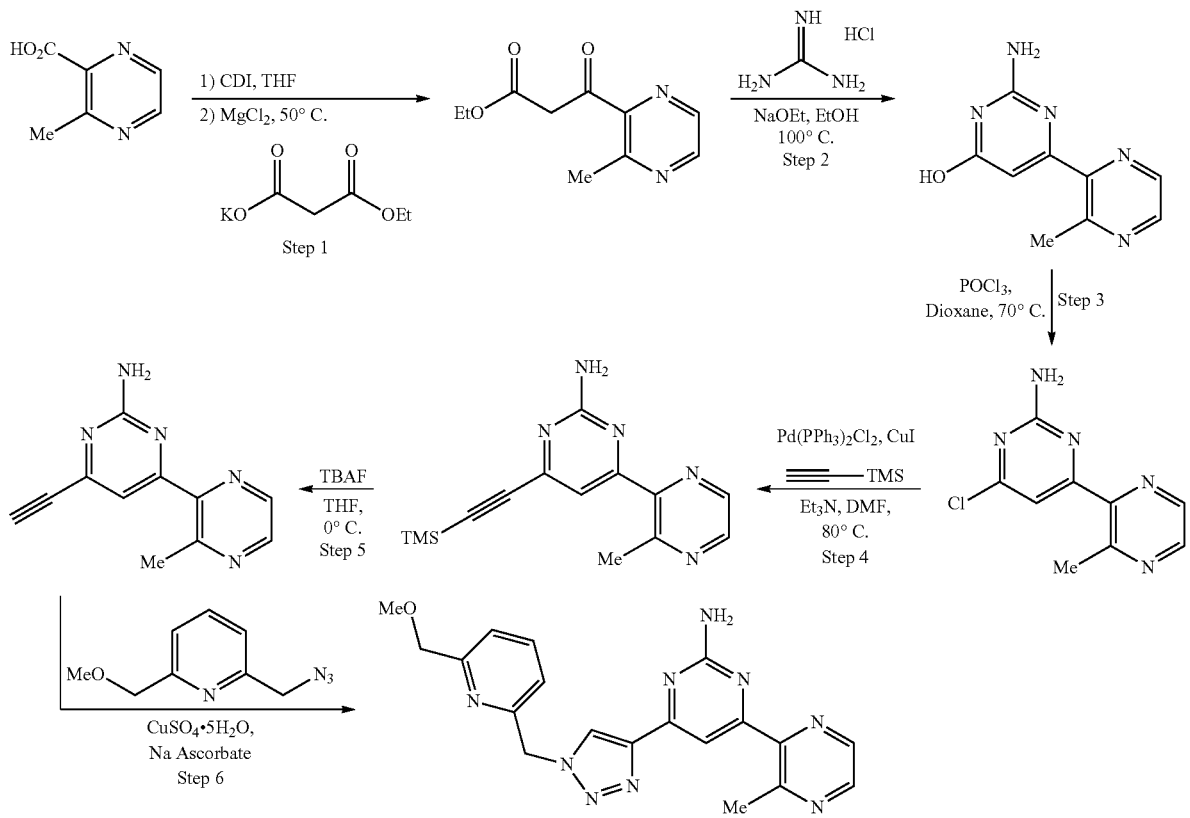

Steps 1-4: the TMS alkyne derivative was synthesized in a similar manner to example 65: Brown solid (193 mg, 1.3% (4 steps)).

Step 5: To a solution of the TMS alkyne derivative (193 mg, 0.682 mmol) in THF (3.4 mL) at 0° C. was added TBAF (3.4 mL, 0.750 mmol, 1 M in THF) dropwise. The mixture was stirred at 0° C. for 15 minutes. The mixture was concentrated and purified by silica gel chromatography (0 to 5% MeOH in $CH_2Cl_2$) to afford the desired product as a brown solid (93 mg; 65%).

Step 6: The product was synthesized in a similar manner to example 1, step 6: off-white solid (7 mg, 6%). $^1$H NMR (400 MHz, DMSO-$d_6$) δ 8.81 (s, 1H), 8.70-8.62 (m, 2H), 7.93-7.83 (m, 1H), 7.76 (s, 1H), 7.40 (d, J=7.9 Hz, 1H), 7.26 (d, J=7.8 Hz, 1H), 5.85 (s, 2H), 4.47 (s, 2H), 3.34 (s, 3H), 2.80 (s, 3H). ESI MS [M+H]$^+$ for $C_{19}H_{20}N_9O$, calcd 390.2, found 390.2.

Example 68: 4-(1-{[6-(Methoxymethyl)-2-pyridyl]methyl}-1H-1,2,3-triazol-4-yl)-6-(2H-pyrazol-3-yl)-2-pyrimidinylamine

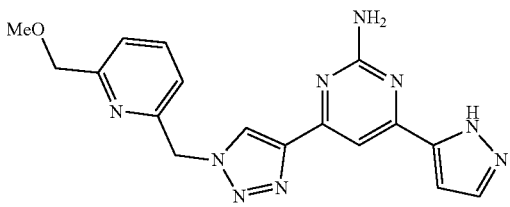 [SMILES: COCc1cccc(Cn2cc(-c3cc(-c4ccn[nH]4)nc(N)n3)nn2)n1]

The title compound was prepared similar to example 20 from the corresponding azide and alkyne to afford 92 mg of a pale yellow solid. $^1$H NMR (400 MHz, DMSO-$d_6$) δ 8.60 (s, 1H), 7.90-7.81 (m, 2H), 7.77 (s, 1H), 7.38 (d, J=7.7 Hz, 1H), 7.21 (d, J=7.7 Hz, 1H), 6.82 (t, J=2.1 Hz, 1H), 6.68 (bs, 2H), 5.80 (s, 2H), 4.46 (s, 2H), 3.35 (s, 3H). ESI MS [M+H]$^+$ for $C_{17}H_{17}N_9O$, calcd 364.2, found 364.3.

Example 69: 4-(1-{[6-(Methoxymethyl)-2-pyridyl]methyl}-1H-1,2,3-triazol-4-yl)-6-(1H-pyrazol-4-yl)-2-pyrimidinylamine

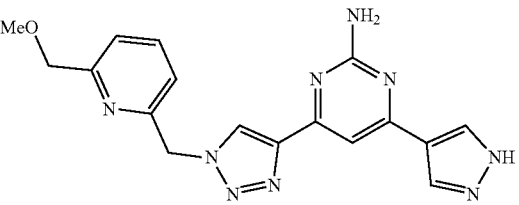 [SMILES: COCc1cccc(Cn2cc(-c3cc(-c4cn[nH]c4)nc(N)n3)nn2)n1]

The title compound was prepared similar to example 20 from the corresponding azide and alkyne to afford 2.4 mg of a yellow-brown solid. $^1$H NMR (400 MHz, DMSO-$d_6$) δ 8.57 (s, 1H), 8.45 (s, 1H), 8.09 (s, 1H), 7.85 (t, J=7.8 Hz, 1H), 7.49 (s, 1H), 7.38 (dd, J=7.9, 0.9 Hz, 1H), 7.20 (d, J=7.7 Hz, 1H), 6.57 (s, 2H), 5.81 (s, 2H), 4.46 (s, 2H), 3.35 (s, 3H). ESI MS [M+H]$^+$ for $C_{17}H_{17}N_9O$, calcd 364.2, found 364.2.

Example 70: 6-(1H-Indazol-6-yl)-4-(1-{[6-(methoxymethyl)-2-pyridyl]methyl}-1H-1,2,3-triazol-4-yl)-2-pyrimidinylamine

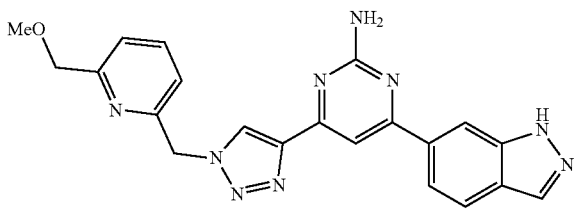 [SMILES: COCc1cccc(Cn2cc(-c3cc(-c4ccc5cn[nH]c5c4)nc(N)n3)nn2)n1]

The title compound was prepared similar to example 20 from the corresponding azide and alkyne. $^1$H NMR (400 MHz, DMSO-$d_6$) δ 9.23 (s, 1H), 8.50 (s, 1H), 8.22 (s, 1H), 8.08 (s, 1H), 8.01-7.85 (m, 3H), 7.43 (d, J=7.9 Hz, 1H), 7.36 (d, J=7.9 Hz, 1H), 5.93 (s, 2H), 4.48 (s, 2H), 3.33 (s, 3H). MS [M+H]$^+$ for $C_{21}H_{19}N_9O$, calcd 414.2, found 414.3.

Example 71: 4-(1-{[6-(Methoxymethyl)-2-pyridyl]methyl}-1H-1,2,3-triazol-4-yl)-6-(7-quinolyl)-2-pyrimidinylamine

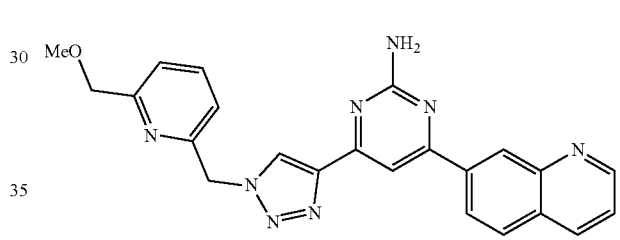

The title compound was prepared similar to example 20 from the corresponding azide and alkyne to afford 61 mg of a tan solid. $^1$H NMR (400 MHz, DMSO-$d_6$) δ 8.99 (dd, J=4.3, 1.9 Hz, 1H), 8.79 (s, 1H), 8.73 (d, J=1.5 Hz, 1H), 8.45 (d, J=8.2 Hz, 1H), 8.38-8.31 (m, 1H), 8.13 (d, J=8.2 Hz, 1H), 7.94-7.80 (m, 2H), 7.66-7.54 (m, 1H), 7.40 (d, J=7.7 Hz, 1H), 7.24 (d, J=7.6 Hz, 1H), 6.90 (s, 2H), 5.84 (s, 2H), 4.52-4.41 (m, 2H), 3.36 (d, J=1.3 Hz, 3H). ESI MS [M+H]$^+$ for $C_{23}H_{20}N_8O$, calcd 425.2, found 425.3.

Example 72: 4-(1-{[6-(Methoxymethyl)-2-pyridyl]methyl}-1H-1,2,3-triazol-4-yl)-6-(8-quinolyl)-2-pyrimidinylamine

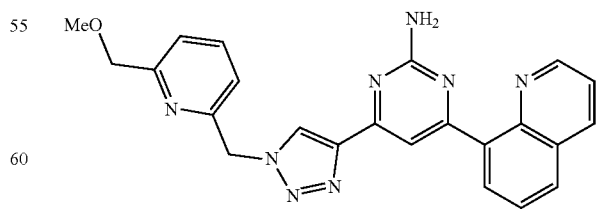

The title compound was prepared similar to example 20 from the corresponding azide and alkyne to afford 31 mg of a tan solid. $^1$H NMR (400 MHz, DMSO-$d_6$) δ 8.98 (dt, J=4.2, 1.5 Hz, 1H), 8.65 (d, J=1.2 Hz, 1H), 8.49 (dd, J=8.4, 1.8 Hz, 1H), 8.21-8.09 (m, 2H), 7.93 (d, J=1.2 Hz, 1H), 7.89-7.79 (m, 1H), 7.75 (ddd, J=8.2, 7.2, 1.1 Hz, 1H), 7.62 (ddd, J=8.3, 4.2, 1.1 Hz, 1H), 7.39 (d, J=7.8 Hz, 1H), 7.21 (d, J=7.8 Hz, 1H), 6.73 (s, 2H), 5.82 (s, 2H), 4.47 (s, 2H), 3.36 (d, J=1.1 Hz, 3H). ESI MS [M+H]$^+$ for $C_{23}H_{20}N_8O$, calcd 425.2, found 425.3.

Example 73: 4-(1-{[6-(Methoxymethyl)-2-pyridyl]methyl}-1H-1,2,3-triazol-4-yl)-6-(1H-pyrazol-1-yl)-2-pyrimidinylamine

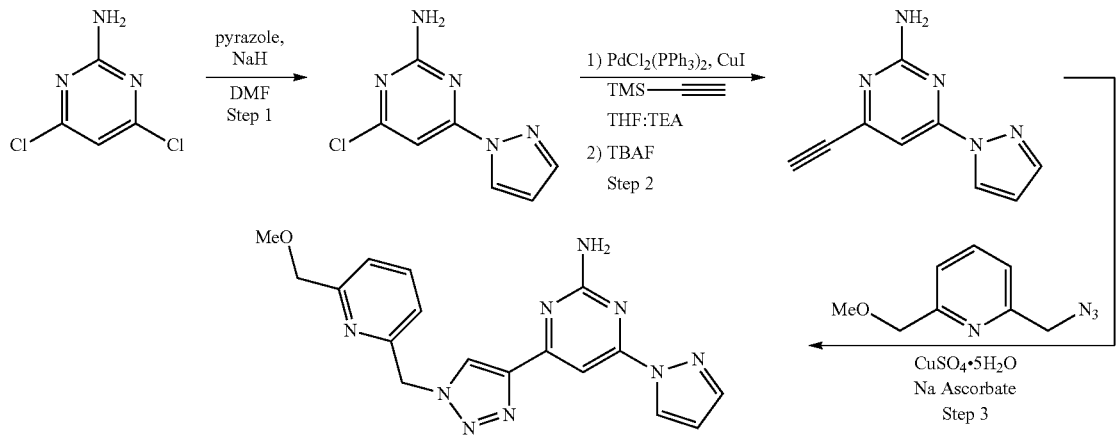

Step 1: NaH (60% dispersion in mineral oil, 840 mg, 21 mmol, 1.05 equiv.) was suspended in DMF (80 mL), and the suspension was cooled in an ice/water bath. Pyrazole (1.43 g, 21 mmol, 1.05 equiv.) was added. After 45 minutes, solid dichloropyrimidine (3.26 g, 20 mmol, 1 equiv.) was added and the ice bath was removed. After 2 hours, water was added, and the reaction mixture was filtered to afford the title compound as 2.99 g of a pale yellow solid.

Steps 2 and 3: Similar to example 1, 30 mg of a yellow solid was obtained. $^1$H NMR (400 MHz, DMSO-d$_6$) δ 8.64 (s, 1H), 8.52 (dd, J=2.7, 0.7 Hz, 1H), 7.90 (dd, J=1.7, 0.7 Hz, 1H), 7.85 (t, J=7.8 Hz, 1H), 7.68 (s, 1H), 7.38 (d, J=7.7 Hz, 1H), 7.22 (d, J=7.7 Hz, 1H), 7.01 (s, 2H), 6.62 (dd, J=2.7, 1.6 Hz, 1H), 5.81 (s, 2H), 4.46 (s, 2H), 3.35 (s, 3H). ESI MS [M+H]$^+$ for $C_{17}H_{17}N_9O$, calcd 364.2, found 364.2.

Example 74: m-[2-Amino-6-(1-{[6-(methoxymethyl)-2-pyridyl]methyl}-5-methyl-1H-1,2,3-triazol-4-yl)-4-pyrimidinyl]benzonitrile

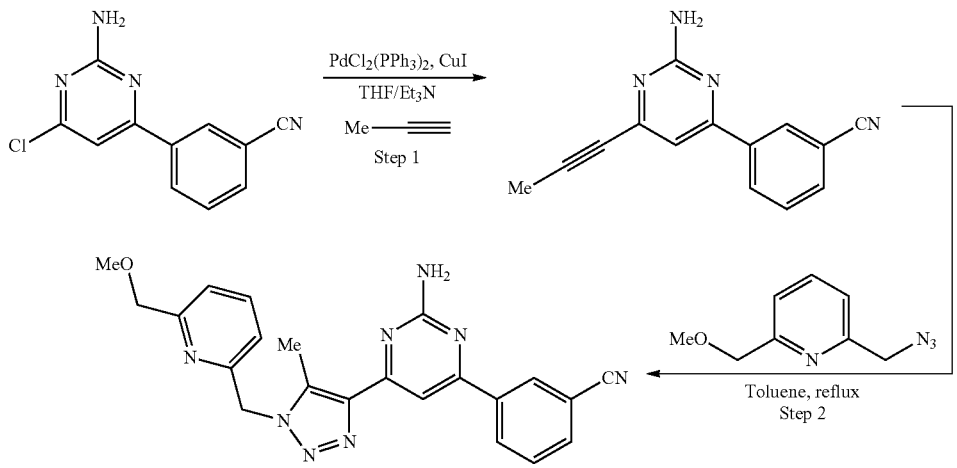

Step 1. The alkyne was prepared in a similar fashion to step 2 of example 1 by using propyne as the reagent to afford the product.

Step 2. A mixture of azide derivative (18 mg, 0.1 mmol) and alkyne (23 mg, 0.1 mmol) in toluene (1 mL) was heated to 120° C. in a sealed tube for 20 hours. The mixture was cooled to room temperature, evaporated to dryness and purified by silica gel chromatography (hexanes/EtOAc 70:30 to 0:100) to afford the desired product (4 mg, 10%) together with its regioisomer (2 mg, 5%). $^1$H NMR (400 MHz, Chloroform-d) δ 8.47 (ddd, J=1.7, 1.7, 0.6 Hz, 1H), 8.32 (ddd, J=8.0, 1.9, 1.2 Hz, 1H), 7.99 (s, 1H), 7.75 (ddd, J=7.7, 1.7, 1.2 Hz, 1H), 7.67 (dd, J=7.8. 7.8 Hz, 1H), 7.60 (ddd, J=7.8, 7.8, 0.6 Hz, 1H), 7.37 (d, J=7.8 Hz, 1H), 6.89 (d, J=7.8 Hz, 1H), 5.69 (s, 2H), 5.09 (s, 2H), 4.57 (s, 2H), 3.49 (s, 3H), 2.71 (s, 3H). MS [M+H]$^+$ for $C_{22}H_{20}N_8O$, calcd 413.2, found 413.3.

Example 75: m-[2-Amino-6-(1-{[6-(ethoxymethyl)-2-pyridyl]methyl}-1H-1,2,3-triazol-4-yl)-4-pyrimidinyl]benzonitrile

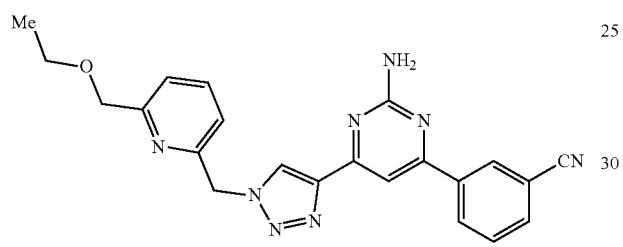

The title compound was prepared similar to example 20 from the corresponding azide and alkyne. $^1$H NMR (400 MHz, DMSO-d$_6$) δ 8.90 (s, 1H), 8.63 (s, 1H), 8.50 (d, J=7.9 Hz, 1H), 8.06 (d, J=7.8 Hz, 1H), 7.95 (s, 1H), 7.90 (t, J=7.8 Hz, 1H), 7.79 (t, J=7.7 Hz, 1H), 7.43 (d, J=7.9 Hz, 1H), 7.28 (d, J=7.3 Hz, 1H), 5.88 (s, 2H), 4.51 (s, 2H), 3.54 (q, J=7.0 Hz, 2H), 1.16 (t, J=7.0 Hz, 3H). ESI MS [M+H]$^+$ for $C_{22}H_{21}N_8O$, calcd 413.2, found 413.3.

Example 76: m-[2-Amino-6-(1-{[6-(isopropoxymethyl)-2-pyridyl]methyl}-1H-1,2,3-triazol-4-yl)-4-pyrimidinyl]benzonitrile

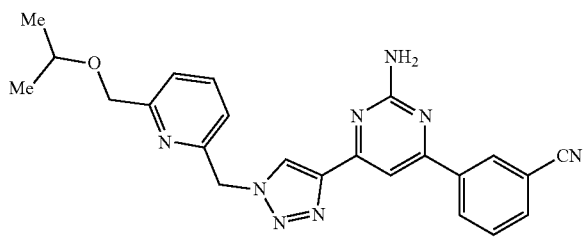 [SMILES: CC(C)OCc1cccc(Cn2cc(-c3cc(-c4cccc(C#N)c4)nc(N)n3)nn2)n1]

The title compound was prepared similar to example 20 from the corresponding azide and alkyne. $^1$H NMR (400 MHz, DMSO-d$_6$) δ 8.93 (s, 1H), 8.64 (s, 1H), 8.51 (d, J=8.0 Hz, 1H), 8.06 (d, J=7.7 Hz, 1H), 7.97 (d, J=3.4 Hz, 1H), 7.93-7.86 (m, 1H), 7.82-7.76 (m, 1H), 7.44 (d, J=7.8 Hz, 1H), 7.29 (d, J=7.3 Hz, 1H), 5.88 (s, 2H), 4.52 (s, 2H), 3.74-3.62 (m, 1H), 1.14 (d, J=6.1 Hz, 6H). ESI MS [M+H]$^+$ for $C_{23}H_{23}N_8O$, calcd 427.2, found 427.3.

Example 77: m-[2-Amino-6-(1-{[6-(1-methoxyethyl)-2-pyridyl]methyl}-1H-1,2,3-triazol-4-yl)-4-pyrimidinyl]benzonitrile

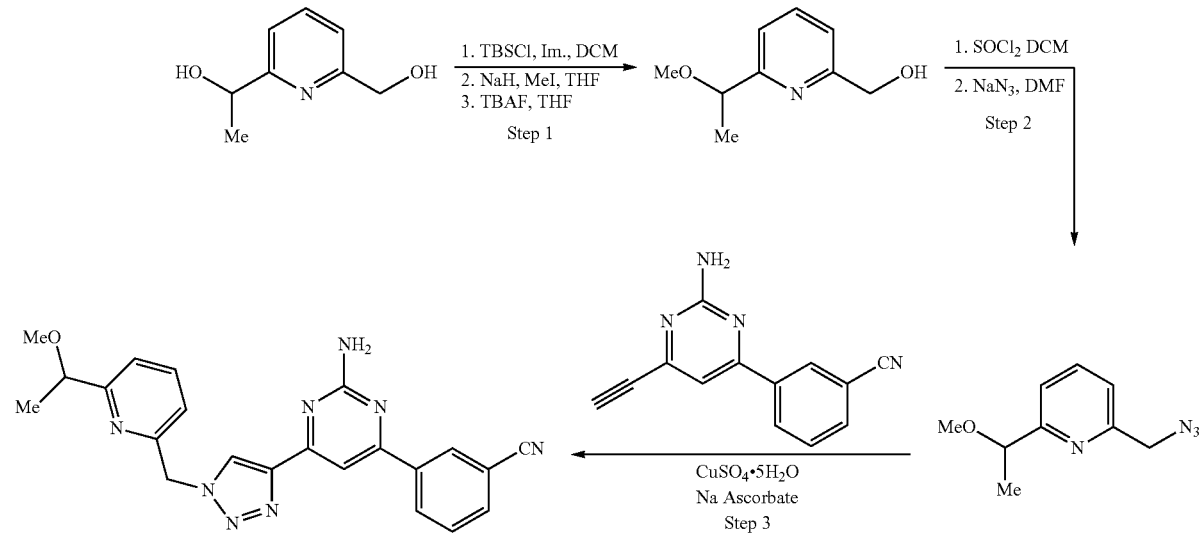

Step 1. The diol (700 mg, 4.6 mmol) was dissolved in CH$_2$Cl$_2$ (10 mL). Imidazole (640 mg, 9.4 mmol) and TBSCl (754 mg, 5 mmol) were added and the mixture was stirred until full conversion of the starting diol. The crude mixture was directly taken on silica gel column (Hex/EtOAc 95:5) to afford the mono-protected alcohol (794 mg, 65%). The TBS protected alcohol from above step (794 mg, 3 mmol) was dissolved in THF (6 mL) and NaH (60% in mineral oil, 144 mg, 3.6 mmol) was added, stirred for 10 minutes and methyl iodide (374 μL, 6 mmol) was added. Upon full conversion of the starting alcohol, the mixture was quenched with saturated NH₄Cl and after usual work-up, the residue was purified by silica gel chromatography (Hex/EtOAc 95:5) to afford the desired ether (800 mg, 96%).

The above TBS derivative (800 mg, 2.8 mmol) was dissolved in THF (5 mL) and the solution was cooled to 0° C. at which point a solution of TBAF (1M in THF, 3 mL) was added dropwise. Upon completion of the reaction, the mixture was quenched with saturated NH₄Cl and after usual work-up, the residue was purified by silica gel chromatography (Hex/EtOAc 90:10 to 60:40) to afford the desired primary alcohol (475 mg, quant.).

Step 2. The alcohol obtained in step 1 (475 mg, 2.8 mmol) was dissolved in CH₂Cl₂ (3 mL) and SOCl₂ (397 μL, 2 equiv., 5.6 mmol) was added. The resulting solution was stirred until full conversion of the starting alcohol at which point the mixture was evaporated to dryness. The resulting residue was used without further purification. The crude material obtained was dissolved in DMF (5 mL) and sodium azide (273 mg, 4.2 mmol) was added. The resulting mixture was stirred at 50° C. for 8 hours then cooled to room temperature. The crude was partitioned between water and dichloromethane. The organic layer was evaporated to dryness and the residue was purified by silica gel chromatography (Hex/EtOAc 90:10) to afford the desired azide (200 mg, 37% over 2 steps).

Step 3: The title compound was synthesized in a similar fashion to step 6 of example 1 using the azide derivative and m-(2-amino-6-ethynyl-4-pyrimidinyl)benzonitrile (from example 4). ¹H NMR (400 MHz, Chloroform-d) δ 8.46 (s, 1H), 8.39-8.24 (m, 2H), 7.92 (s, 1H), 7.82-7.66 (m, 2H), 7.61 (dd, J=7.8, 7.8 Hz 1H), 7.40 (d, J=7.8 Hz, 1H), 7.09 (d, J=7.8 Hz, 1H), 5.74 (s, 2H), 5.14 (s, 2H), 4.49-4.36 (m, 1H), 3.33 (s, 3H), 1.47 (d, J=6.9 Hz, 3H). MS [M+H]⁺ for C₂₂H₂₀N₈O, calcd 413.2, found 413.3.

Example 78: 4-(1-{[6-(1-Methoxyethyl)-2-pyridyl]methyl}-1H-1,2,3-triazol-4-yl)-6-(1,3-oxazol-2-yl)-2-pyrimidinylamine

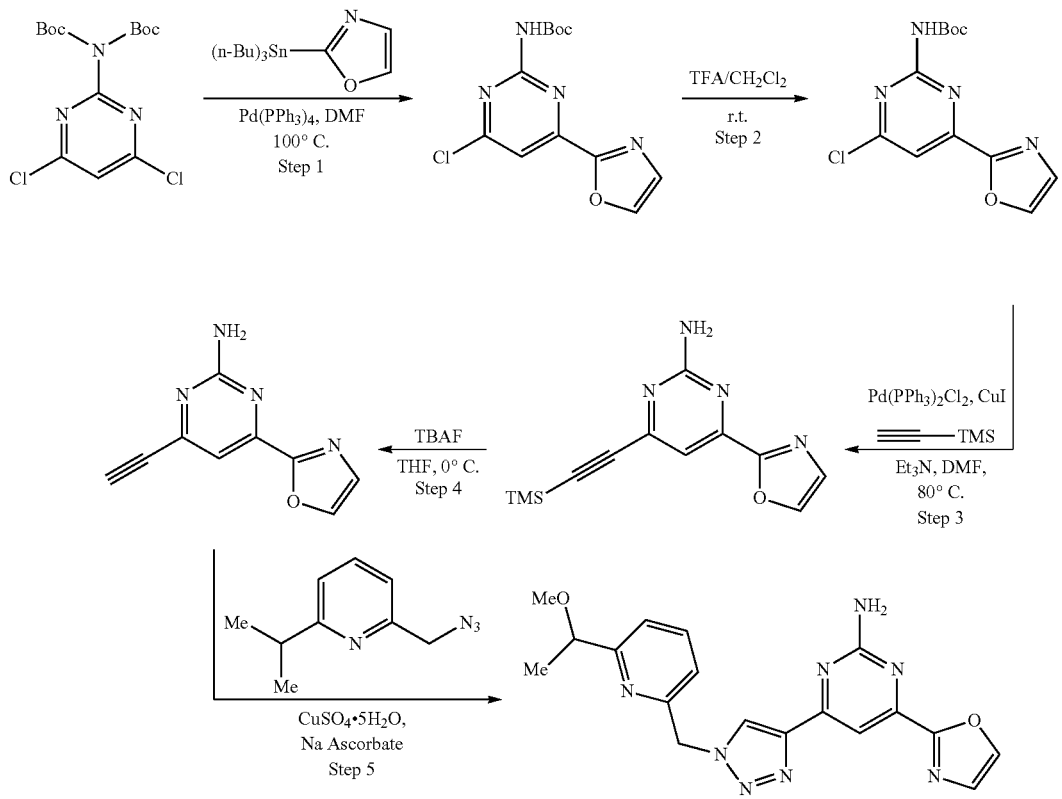

Steps 1 and 2: A mixture of the pyrimidine derivative (3.64 g, 10.0 mmol), 2-(tri-n-butylstannyl)oxazole (2.10 mL, 10.0 mmol), and Pd(PPh₃)₄ (1.16 g; 1.00 mmol), in DMF (20 mL) was stirred at 100° C. for 5 hours. The mixture was cooled to r.t. and ethyl acetate (200 mL) was added. The organics were washed with brine (4×200 mL) and dried over MgSO₄. The crude product was purified by silica gel chromatography (0 to 30% EtOAc in hexanes) to afford the desired product. To this was added TFA (1 mL) and CH₂Cl₂ (5 mL) and the mixture stirred at r.t. for 10 minutes. The mixture was neutralized with sat. NaHCO₃, diluted with ethyl acetate and dried over Na₂SO₄ to afford the desired product as a yellow solid (322 mg; 8%).

Steps 3 and 4: The terminal alkyne was synthesized in a similar manner to example 65: Brown solid (63 mg, 21%, 2 steps).

Step 5: The product was synthesized in a similar manner to example 1, step 6: Yellow solid (13 mg, 10%). ¹H NMR (400 MHz, DMSO-d₆) δ 8.75 (s, 1H), 8.37 (s, 1H), 7.87 (t, J=7.8 Hz, 1H), 7.82 (s, 1H), 7.54 (s, 1H), 7.39 (d, J=7.8 Hz, 1H), 7.19 (d, J=7.7 Hz, 1H), 5.85 (s, 2H), 4.35 (q, J=6.4 Hz, 1H), 3.19 (s, 3H), 1.32 (d, J=6.6 Hz, 3H). ESI MS [M+H]⁺ for C₁₈H₁₉N₈O₂, calcd 379.2, found 379.3.

Example 79: m-[2-Amino-6-(1-{[6-(1-methoxypropyl)-2-pyridyl]methyl}-1H-1,2,3-triazol-4-yl)-4-pyrimidinyl]benzonitrile

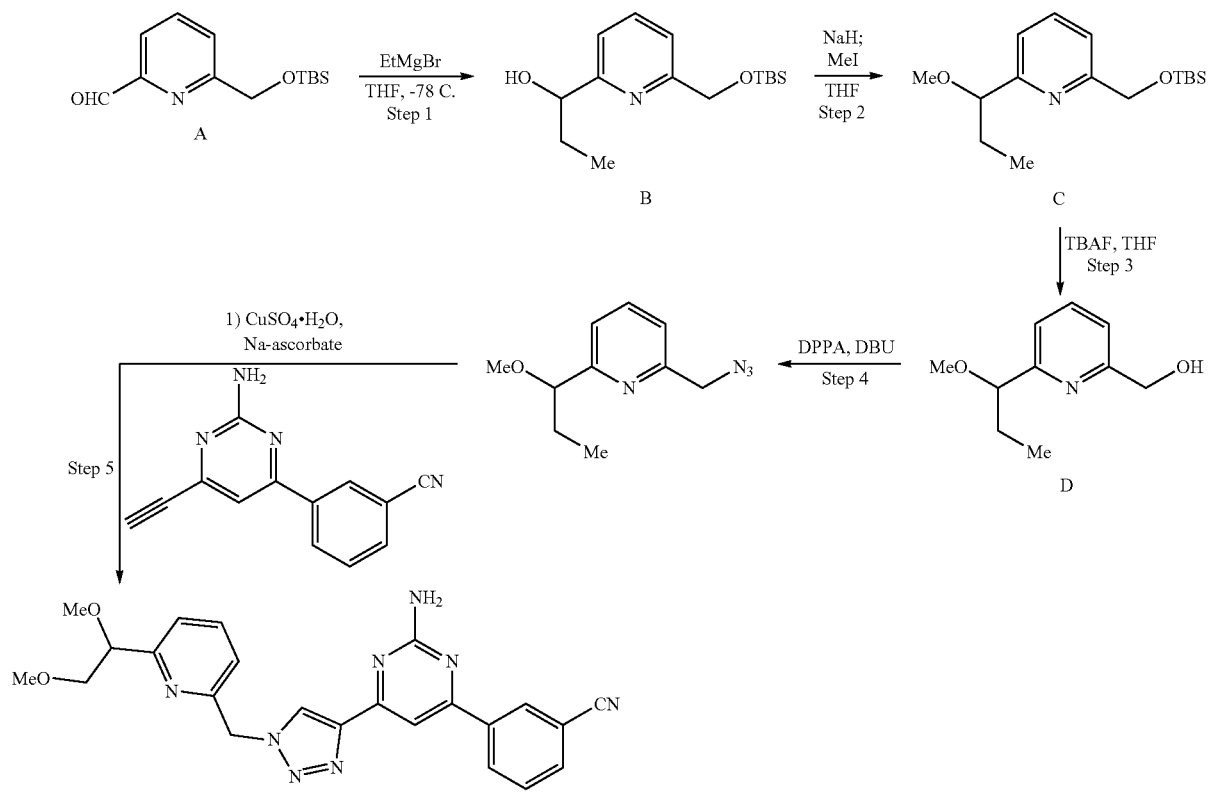

Step 1: A solution of aldehyde A (1.0 g, 4 mmol) in THF (20 mL) was cooled in a dry ice/acetone bath. EtMgBr (3 M in THF, 2 mL, 6 mmol, 1.5 equiv.) was added along the side of the flask. After 1.5 hours, the reaction was quenched with NH$_4$Cl and extracted with EtOAc. The organic layers were concentrated onto Celite® and purified by flash chromatography on SiO$_2$ to afford alcohol B (537 mg) as a white solid.

Step 2: To a solution of alcohol B (537 mg, 1.9 mmol) in THF (8 mL) was added NaH (60% dispersion in mineral oil, 99 mg, 2.5 mmol, 1.3 equiv.). After 30 minutes, MeI (0.18 mL, 2.9 mmol, 1.5 equiv.) was added. The reaction mixture stirred overnight and was quenched with H$_2$O, extracted with MTBE, dried, and concentrated to afford ether C (559 mg) as a yellow oil.

Step 3: To a solution of ether C (1.9 mmol) in THF (2 mL) was added TBAF (1 M in THF, 2 mL). After 1.5 hours, the reaction mixture was concentrated, and the crude residue was purified by flash chromatography on SiO$_2$ to afford alcohol D (299 mg) as a colorless oil.

Steps 4 and 5: Using example 1 procedure, the title compound was synthesized to afford 81 mg of a tan solid. $^1$H NMR (400 MHz, DMSO-d$_6$) δ 8.71 (dd, J=5.4, 1.9 Hz, 1H), 8.58 (q, J=3.1, 1.7 Hz, 1H), 8.54-8.40 (m, 1H), 8.06-7.94 (m, 1H), 7.91-7.69 (m, 3H), 7.35 (t, J=7.1 Hz, 1H), 7.17 (t, J=6.6 Hz, 1H), 6.90 (s, 2H), 5.84 (d, J=6.0 Hz, 2H), 4.13 (t, J=6.3 Hz, 1H), 3.19 (dd, J=5.4, 1.8 Hz, 3H), 1.75-1.62 (m, 2H), 0.86-0.70 (m, 3H). ESI MS [M+H]$^+$ for C$_{23}$H$_{22}$N$_8$O, calcd 427.2, found 427.3.

Example 80: m-[2-Amino-6-(1-{[6-(1-methoxy-2-methylpropyl)-2-pyridyl]methyl}-1H-1,2,3-triazol-4-yl)-4-pyrimidinyl]benzonitrile

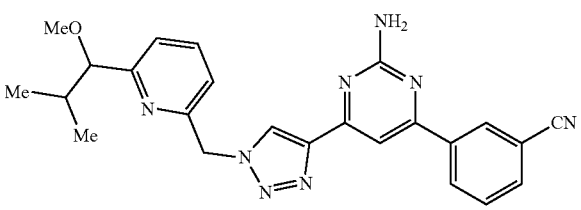 [SMILES: COC(c1cccc(Cn2cc(-c3cc(-c4cccc(C#N)c4)nc(N)n3)nn2)n1)C(C)C]

The title compound was prepared similar to example 79 to afford 86 mg of a tan solid. $^1$H NMR (400 MHz, DMSO-d$_6$) δ 8.71 (d, J=2.0 Hz, 1H), 8.58 (t, J=2.0 Hz, 1H), 8.47 (dd, J=8.1, 1.7 Hz, 1H), 8.04-7.96 (m, 1H), 7.90-7.79 (m, 2H), 7.74 (td, J=7.9, 2.0 Hz, 1H), 7.30 (d, J=7.8 Hz, 1H), 7.18 (dd, J=7.5, 1.8 Hz, 1H), 6.89 (s, 2H), 5.83 (d, J=1.7 Hz, 2H), 3.92 (dd, J=6.2, 2.0 Hz, 1H), 3.20-3.14 (m, 3H), 1.95 (dt, J=12.2, 7.3 Hz, 1H), 0.80 (dd, J=6.8, 2.0 Hz, 3H), 0.71 (dd, J=6.8, 2.0 Hz, 3H). ESI MS [M+H]$^+$ for C$_{24}$H$_{24}$N$_8$O, calcd 441.2, found 441.5.

Example 81: m-[2-Amino-6-(1-{[6-(cyclopropyl-methoxymethyl)-2-pyridyl]methyl}-1H-1,2,3-triazol-4-yl)-4-pyrimidinyl]benzonitrile

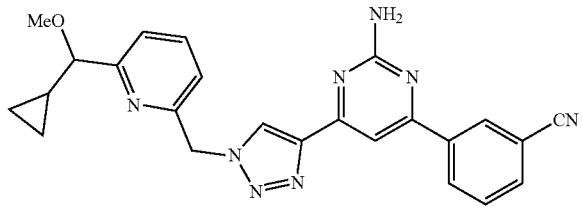 [SMILES: COC(c1cccc(Cn2cc(-c3cc(-c4cccc(C#N)c4)nc(N)n3)nn2)n1)C1CC1]

The title compound was prepared similar to example 79 to afford 87 mg of a tan solid. $^1$H NMR (400 MHz, DMSO-d$_6$) δ 8.73-8.69 (m, 1H), 8.58 (q, J=1.8 Hz, 1H), 8.50-8.44 (m, 1H), 8.02-7.96 (m, 1H), 7.89-7.79 (m, 2H), 7.79-7.71 (m, 1H), 7.38 (d, J=7.5 Hz, 1H), 7.20 (d, J=7.3 Hz, 1H), 6.90 (s, 2H), 5.84 (d, J=3.0 Hz, 2H), 3.67 (dd, J=7.9, 3.1 Hz, 1H), 3.22-3.15 (m, 3H), 1.11-1.02 (m, 1H), 0.55-0.36 (m, 2H), 0.25 (ddd, J=37.8, 9.0, 4.6 Hz, 2H). ESI MS [M+H]$^+$ for C$_{24}$H$_{22}$N$_8$O, calcd 439.2, found 439.3.

Example 82: m-[2-Amino-6-(1-{[6-(cyclopentyl-methoxymethyl)-2-pyridyl]methyl}-1H-1,2,3-triazol-4-yl)-4-pyrimidinyl]benzonitrile

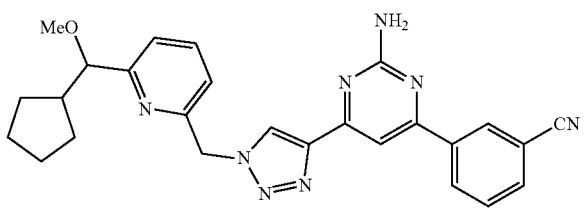 [SMILES: COC(c1cccc(Cn2cc(-c3cc(-c4cccc(C#N)c4)nc(N)n3)nn2)n1)C1CCCC1]

The title compound was prepared similar to example 79 to afford 81 mg of a tan solid. $^1$H NMR (400 MHz, DMSO-d$_6$) δ 8.71 (d, J=1.1 Hz, 1H), 8.61-8.58 (m, 1H), 8.51-8.42 (m, 1H), 8.01-7.97 (m, 1H), 7.89-7.79 (m, 2H), 7.74 (t, J=7.8 Hz, 1H), 7.33 (d, J=7.8 Hz, 1H), 7.19 (d, J=7.7 Hz, 1H), 6.89 (s, 2H), 5.84 (s, 2H), 4.01-3.93 (m, 1H), 3.13 (s, 3H), 2.16 (q, J=7.9 Hz, 1H), 1.60 (d, J=8.8 Hz, 1H), 1.52-1.09 (m, 7H). ESI MS [M+H]$^+$ for C$_{26}$H$_{26}$N$_8$O, calcd 467.2, found 467.3.

Example 83: m-[2-Amino-6-(1-{[6-(methoxyphe-nylmethyl)-2-pyridyl]methyl}-1H-1,2,3-triazol-4-yl)-4-pyrimidinyl]benzonitrile

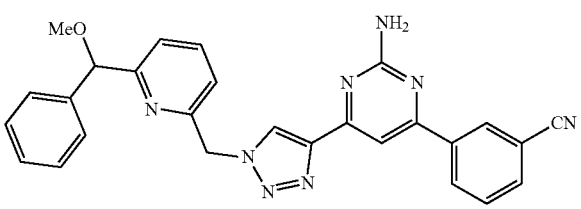 [SMILES: COC(c1ccccc1)c1cccc(Cn2cc(-c3cc(-c4cccc(C#N)c4)nc(N)n3)nn2)n1]

The title compound was prepared similar to example 79 to afford 90 mg of a tan solid. $^1$H NMR (400 MHz, DMSO-d$_6$) δ 8.72-8.65 (m, 1H), 8.60 (t, J=2.0 Hz, 1H), 8.52-8.45 (m, 1H), 8.00 (ddd, J=7.8, 2.7, 1.5 Hz, 1H), 7.88-7.80 (m, 2H), 7.75 (td, J=7.9, 2.0 Hz, 1H), 7.49 (d, J=7.8 Hz, 1H), 7.34 (dd, J=7.2, 1.8 Hz, 2H), 7.26 (tt, J=7.4, 1.4 Hz, 2H), 7.23-7.12 (m, 2H), 6.91 (s, 2H), 5.85-5.76 (m, 2H), 5.32 (d, J=1.9 Hz, 1H), 3.33-3.31 (m, 3H). ESI MS [M+H]$^+$ for C$_{27}$H$_{22}$N$_8$O, calcd 475.2, found 475.3.

Example 84: m-{6-[1-({6-[(R)-1-Methoxyethyl]-2-pyridyl}methyl)-1H-1,2,3-triazol-4-yl]-2-amino-4-pyrimidinyl}benzonitrile

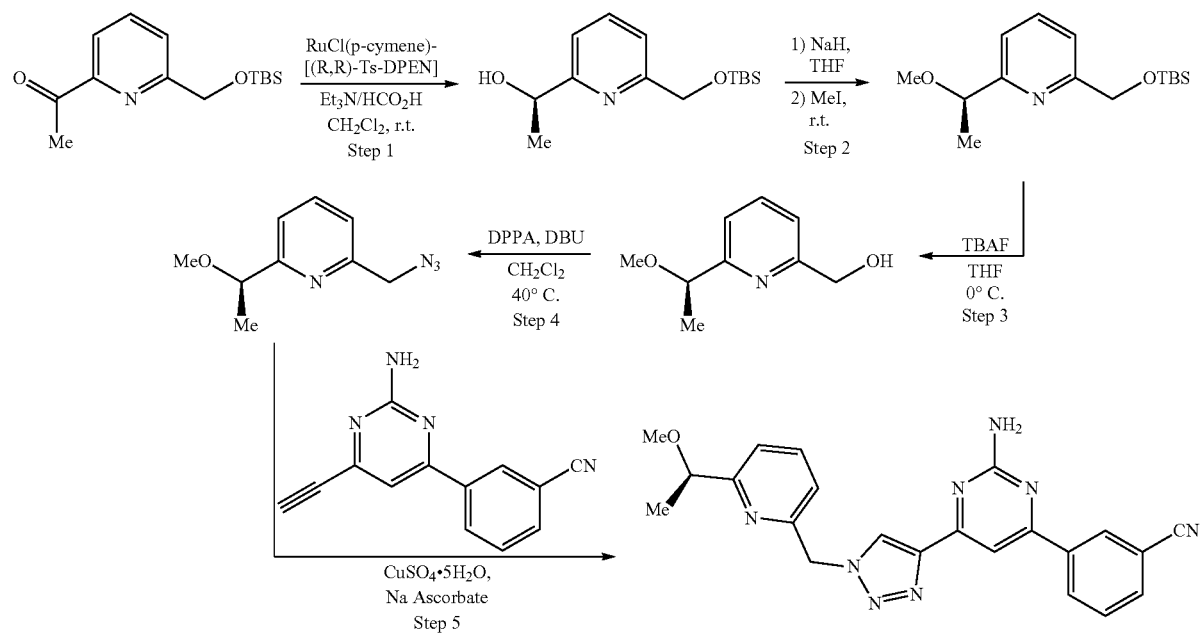

Step 1: To triethylamine (13.6 mL) at 0° C. was added formic acid (8.0 mL) dropwise. The mixture was the degassed before adding the ketone (2.68 g, 10.0 mmol), RuCl(p-cymene)-[(R,R)-Ts-DPEN] (129 mg, 0.200 mmol), and CH$_2$Cl$_2$ (2.6 mL). The mixture was stirred at r.t. for 14 hours, quenched with sat. NaHCO$_3$ (aq), diluted with EtOAc (200 mL), washed with brine, and dried over Na$_2$SO$_4$. The crude product was purified by silica gel chromatography (0 to 5% MeOH in CH$_2$Cl$_2$) to afford the desired product as a brown oil (896 mg; 33%).

Step 2: To a solution of the step 2 product (1.14 g, 4.26 mmol) in THF (21 mL) at 0° C. was added NaH (204 mg, 5.11 mmol, 60% in oil) in one portion. The mixture was stirred at r.t. for 15 minutes, cooled to 0° C., and methyl iodide (265 μL, 4.26 mmol) was added dropwise. The mixture was stirred at r.t. for 2 hours and was concentrated onto silica gel. The crude product was purified by silica gel chromatography (0 to 30% EtOAc in hexanes) to afford the desired product as a colorless oil (803 mg; 67%).

Steps 3-4: The azide was synthesized in a similar manner to example 79 and the product was obtained as colorless oil (373 mg, 68% (2 steps)).

Step 5: The product was synthesized in a similar manner to example 1, step 6: Off-white solid (97 mg, 79%). The compound was synthesized in a similar fashion to Example 1, Step 6. $^1$H NMR (400 MHz, DMSO-d$_6$) δ 8.76 (s, 1H), 8.62-8.56 (m, 1H), 8.52-8.43 (m, 1H), 8.04-7.97 (m, 1H), 7.90-7.82 (m, 2H), 7.75 (t, J=7.8 Hz, 1H), 7.39 (d, J=8.2 Hz, 1H), 7.18 (d, J=6.7 Hz, 1H), 5.85 (s, 2H), 4.34 (q, J=6.5 Hz, 1H), 3.19 (s, 3H), 1.32 (d, J=6.5 Hz, 3H). ESI MS [M+H]$^+$ for C$_{22}$H$_{21}$N$_8$O, calcd 413.2, found 413.3.

Example 85: 3-{6-[1-({6-[(R)-1-Methoxyethyl]-2-pyridyl}methyl)-1H-1,2,3-triazol-4-yl]-2-amino-4-pyrimidinyl}-2-fluorobenzonitrile

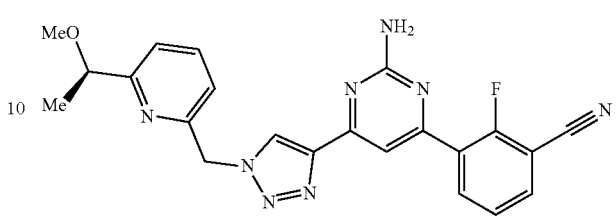

The compound was synthesized in a similar fashion to example 84 from the corresponding alkyne. $^1$H NMR (400 MHz, DMSO-d$_6$) δ 8.74 (s, 1H), 8.35-8.26 (m, 1H), 8.14-8.05 (m, 1H), 7.91-7.82 (m, 1H), 7.68-7.62 (m, 1H), 7.62-7.53 (m, 1H), 7.39 (d, J=7.6 Hz, 1H), 7.18 (d, J=7.0 Hz, 1H), 5.84 (s, 2H), 4.39-4.30 (m, 1H), 3.19 (s, 3H), 1.32 (d, J=6.6 Hz, 3H). ESI MS [M+H]$^+$ for C$_{22}$H$_{20}$FN$_8$O, calcd 431.2, found 431.3.

Example 86: m-{6-[1-({6-[(S)-1-Methoxyethyl]-2-pyridyl}methyl)-1H-1,2,3-triazol-4-yl]-2-amino-4-pyrimidinyl}benzonitrile

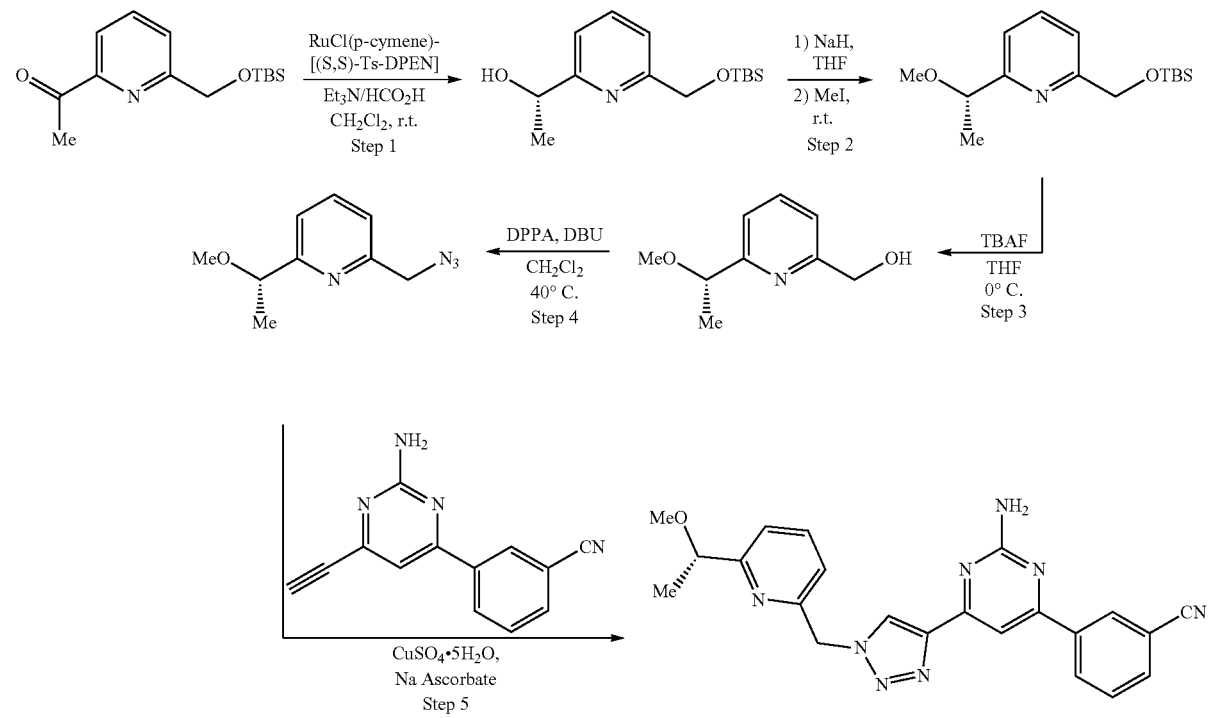

Synthesis: The azide was synthesized in a similar manner to example 84, except RuCl(p-cymene)-[(S,S)-Ts-DPEN] was used as catalyst in step 2.

Step 6: The product was synthesized in a similar manner to example 1, step 6: off-white solid (96 mg, 78%). $^1$H NMR (400 MHz, DMSO-d$_6$) δ 8.78 (s, 1H), 8.63-8.57 (m, 1H), 8.53-8.44 (m, 1H), 8.04-7.99 (m, 1H), 7.92-7.82 (m, 2H), 7.80-7.73 (m, 1H), 7.39 (d, J=8.2 Hz, 1H), 7.19 (d, J=7.9 Hz, 1H), 5.85 (s, 2H), 4.38-4.30 (m, 1H), 3.19 (s, 3H), 1.32 (d, J=6.5 Hz, 3H). ESI MS [M+H]+ for $C_{22}H_{21}N_8O$, calcd 413.2, found 413.3.

Example 87: 3-{6-[1-({6-[(S)-1-Methoxyethyl]-2-pyridyl}methyl)-1H-1,2,3-triazol-4-yl]-2-amino-4-pyrimidinyl}-2-fluorobenzonitrile

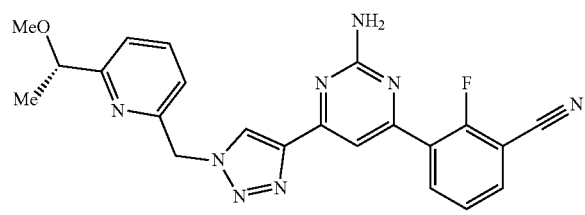 [SMILES: CO[C@@H](C)c1cccc(Cn2cc(-c3cc(-c4cccc(C#N)c4F)nc(N)n3)nn2)n1]

The compound was synthesized in a similar fashion to example 86 from the corresponding alkyne. $^1$H NMR (400 MHz, DMSO-$d_6$) δ 8.76 (s, 1H), 8.31 (td, J=7.8, 1.8 Hz, 1H), 8.13-8.06 (m, 1H), 7.87 (t, J=7.8 Hz, 1H), 7.65 (d, J=2.4 Hz, 1H), 7.58 (t, J=7.8 Hz, 1H), 7.40 (d, J=7.8 Hz, 1H), 7.19 (d, J=7.3 Hz, 1H), 5.85 (s, 2H), 4.35 (q, J=6.5 Hz, 1H), 3.19 (s, 3H), 1.32 (d, J=6.5 Hz, 3H). ESI MS [M+H]+ for $C_{22}H_{20}FN_8O$, calcd 431.2, found 431.2.

Example 88: m-[2-Amino-6-(1-{1-[6-(methoxymethyl)-2-pyridyl]ethyl}-1H-1,2,3-triazol-4-yl)-4-pyrimidinyl]benzonitrile Step 1. A solution of aldehyde (756 mg, 5.0 mmol) in THF (10 mL) was cooled to −78° C. MeMgBr (3N in Et$_2$O, 2 mL, 1.2 equiv.) was added dropwise. The resulting mixture was slowly warmed up to 0° C. over 2 hours and was subsequently quenched with a saturated solution of NH$_4$Cl. After usual work-up (H$_2$O/EtOAc) the organics were dried over sodium sulfate, filtered and evaporated to dryness. The residue was purified by silica gel chromatography (Hex/EtOAc 90:10 to 60:40) to afford the corresponding alcohol (635 mg, 76%).

The alcohol obtained in step 1 (600 mg, 3.6 mmol) was dissolved in CH$_2$Cl$_2$ (4 mL) and SOCl$_2$ (525 µL, 2 equiv., 7.4 mmol) was added. The resulting solution was stirred until full conversion of the starting alcohol at which point the mixture was evaporated to dryness. The resulting residue was used without further purification.

Step 2. Crude material obtained in step 1 was dissolved in DMF (7 mL) and sodium azide (325 mg, 5 mmol) was added. The resulting mixture was stirred at 80° C. for 8 hours then cooled to room temperature. The crude was partitioned between water and dichloromethane. The organic layer was evaporated to dryness and the residue was purified by silica gel chromatography (Hex/EtOAc 90:10) to afford the desired azide (580 mg, 84% over 2 steps).

Step 3: The title compound was synthesized in a similar fashion to step 6 of example 1 using the azide derivative and m-(2-amino-6-ethynyl-4-pyrimidinyl)benzonitrile (from example 4). $^1$H NMR (400 MHz, Chloroform-d) δ 8.47-8.43 (m, 1H), 8.40 (s, 1H), 8.30 (ddd, J=8.0, 1.8, 1.2 Hz, 1H), 7.89 (s, 1H), 7.75 (ddd, J=7.7, 1.7, 1.2 Hz, 1H), 7.69 (dd, J=7.8, 7.8 Hz, 1H), 7.60 (dd, J=7.8, 7.8 Hz, 1H), 7.39 (d, J=7.8 Hz, 1H), 7.12 (d, J=7.8 Hz, 1H), 5.18 (s, 2H), 4.59 (s, 2H), 3.49 (s, 3H), 2.03 (d, J=7.2 Hz, 3H). MS [M+H]+ for $C_{22}H_{20}N_8O$, calcd 413.2, found 413.3.

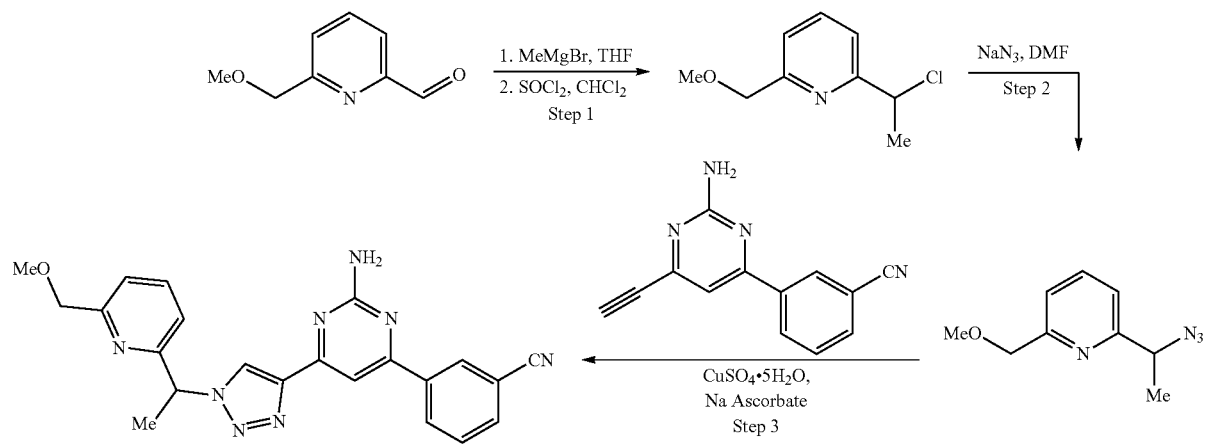

Example 89: m-(6-{1-[(6-{[(S)-Tetrahydrofur-3-yloxy]methyl}-2-pyridyl)methyl]-1H-1,2,3-triazol-4-yl}-2-amino-4-pyrimidinyl)benzonitrile

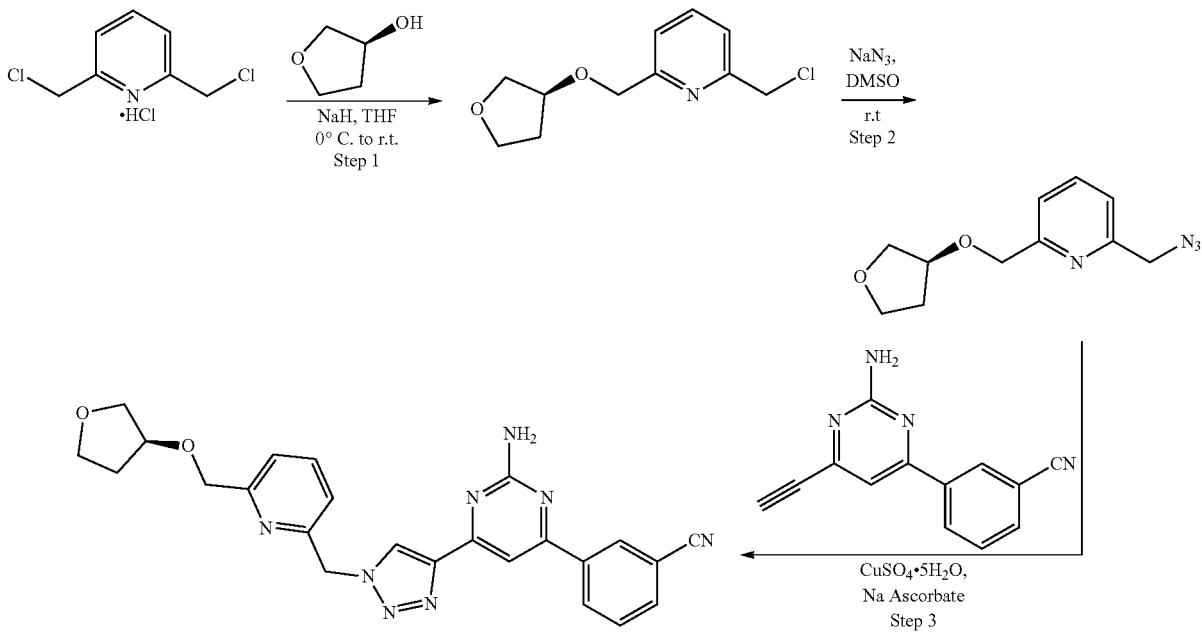

Step 1. To a 0° C. stirred solution of the 3(S)-hydroxytetrahydrofuran (440 mg, 5 mmol) in dry THF (20 mL) was added NaH (60%, 400 mg, 10 mmol) in 5 portions. It was stirred at this temperature for 30 min. A gray color suspension was obtained, to this reaction mixture was added 2,6-bis(chloromethyl)pyridine hydrochloride (1.06 g, 5 mmol) in one portion at 0° C. The reaction mixture was stirred at room temperature for overnight. It was cooled to 0° C., quenched with saturated aqueous NH₄Cl solution, diluted with MTBE (10 mL), the layers were separated, aqueous layer was extracted with MTBE and the organics were combined, dried (Na₂SO₄), filtered and concentrated on rotavapor. The oily residue was dissolved in dichloromethane purified by flash column (ISCO, 40 g column, 5-60% ethyl acetate in hexanes) to get the pure compound as colorless liquid (480 mg, 42%).

Step 2. The above product (480 mg, 2.1 mmol) was dissolved in dry DMSO (2 mL), NaN₃ (164 mg, 2.53 mmol) was added and stirred at r.t for 2 hours. LCMS indicated completion of the reaction, it was diluted with water (15 mL), extracted with MTBE (3×15 mL), dried (Na₂SO₄), filtered, and concentrated on rotavapor. The oily residue was dried under high vacuum to afford the product (455 mg, 92%).

Step 3. The title compound was prepared similar to example 1, step 6 from the above azide and corresponding alkyne. ¹H NMR (400 MHz, DMSO-d₆) δ 8.72 (d, J=1.1 Hz, 1H), 8.60 (t, J=1.5 Hz, 1H), 8.48 (ddd, J=8.0, 1.9, 1.2 Hz, 1H), 8.01 (dt, J=7.7, 1.3 Hz, 1H), 7.87 (t, J=7.7 Hz, 1H), 7.83 (d, J=0.8 Hz, 1H), 7.75 (t, J=7.9 Hz, 1H), 7.41 (dd, J=7.8, 1.0 Hz, 1H), 7.25 (d, J=7.3 Hz, 1H), 6.99 (s, 2H), 5.84 (s, 2H), 4.52 (d, J=1.8 Hz, 2H), 4.30-4.21 (m, 1H), 3.79-3.70 (m, 2H), 3.70-3.61 (m, 2H), 1.97-1.92 (m, 2H); ESI MS [M+H]⁺ for C₂₄H₂₂N₈O₂, calcd 455.2, found 455.3.

Example 90: m-(6-{1-[(6-{[(R)-Tetrahydrofur-3-yloxy]methyl}-2-pyridyl)methyl]-1H-1,2,3-triazol-4-yl}-2-amino-4-pyrimidinyl)benzonitrile

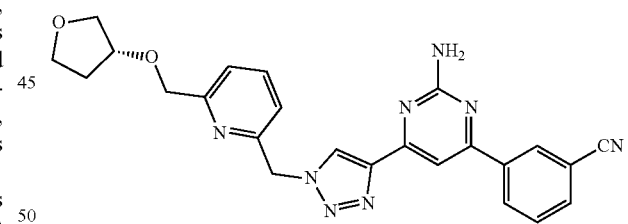

The title compound was prepared similar to example 89 from the corresponding azide and alkyne. ¹H NMR (400 MHz, DMSO-d₆) δ 8.73 (t, J=1.2 Hz, 1H), 8.60 (dt, J=1.8, 1.0 Hz, 1H), 8.48 (ddd, J=8.0, 1.9, 1.2 Hz, 1H), 8.01 (dt, J=7.7, 1.4 Hz, 1H), 7.87 (t, J=7.8 Hz, 1H), 7.84 (d, J=1.1 Hz, 1H), 7.76 (t, J=7.9 Hz, 1H), 7.41 (dd, J=7.8, 0.9 Hz, 1H), 7.25 (d, J=7.7 Hz, 1H), 7.04 (s, 2H), 5.84 (s, 2H), 4.53 (d, J=1.8 Hz, 2H), 4.31-4.19 (m, 1H), 3.83-3.58 (m, 4H), 1.97-1.92 (m, 2H); ESI MS [M+H]⁺ for C₂₄H₂₂N₈O₂, calcd 455.2, found 455.3.

Example 91: m-{2-Amino-6-[1-({6-[(2-methoxyethoxy)methyl]-2-pyridyl}methyl)-1H-1,2,3-triazol-4-yl]-4-pyrimidinyl}benzonitrile

Example 92: 3-{2-Amino-6-[1-({6-[(2-methoxyethoxy)methyl]-2-pyridyl}methyl)-1H-1,2,3-triazol-4-yl]-4-pyrimidinyl}-2-anisonitrile

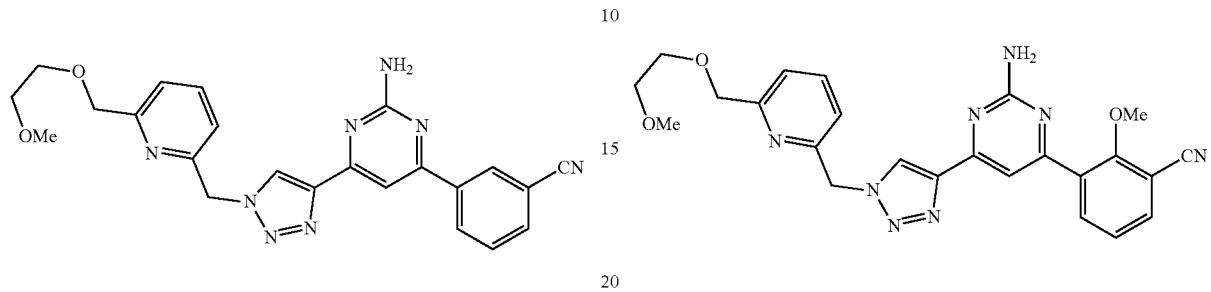

The title compound was prepared similar to example 89 from the corresponding azide and alkyne. ¹H NMR (400 MHz, DMSO-d₆) δ 8.70 (s, 1H), 8.59 (td, J=1.8, 0.6 Hz, 1H), 8.47 (ddd, J=8.0, 1.8, 1.2 Hz, 1H), 8.00 (ddd, J=7.7, 1.7, 1.1 Hz, 1H), 7.87 (t, J=7.8 Hz, 1H), 7.82 (s, 1H), 7.77-7.71 (m, 1H), 7.43-7.39 (m, 1H), 7.25-7.21 (m, 1H), 6.93 (s, 2H), 5.83 (s, 2H), 4.54 (s, 2H), 3.66-3.57 (m, 2H), 3.52-3.43 (m, 2H), 3.24 (s, 3H); ESI MS [M+H]⁺ for C₂₃H₂₂N₈O₂, calcd 443.2, found 443.3.

The title compound was prepared similar to example 89 from the corresponding azide and alkyne. ¹H NMR (400 MHz, Chloroform-d) δ 8.30 (s, 1H), 8.01 (dd, J=7.9, 1.8 Hz, 1H), 7.91 (s, 1H), 7.78-7.62 (m, 2H), 7.48 (d, J=8.0 Hz, 1H), 7.35-7.26 (m, 1H), 7.12 (d, J=7.7 Hz, 1H), 5.71 (s, 2H), 5.12 (s, 2H), 4.70 (s, 2H), 3.94 (m, 3H), 3.77-3.71 (m, 2H), 3.65-3.59 (m, 2H), 3.41 (s, 3H); ESI MS [M+H]⁺ for C₂₄H₂₄N₈O₃, calcd 473.2, found 473.3.

Example 93: 3-(2-Amino-6-{1-[(6-cyclopropyl-2-pyridyl)methyl]-1H-1,2,3-triazol-4-yl}-4-pyrimidinyl)-2-anisonitrile

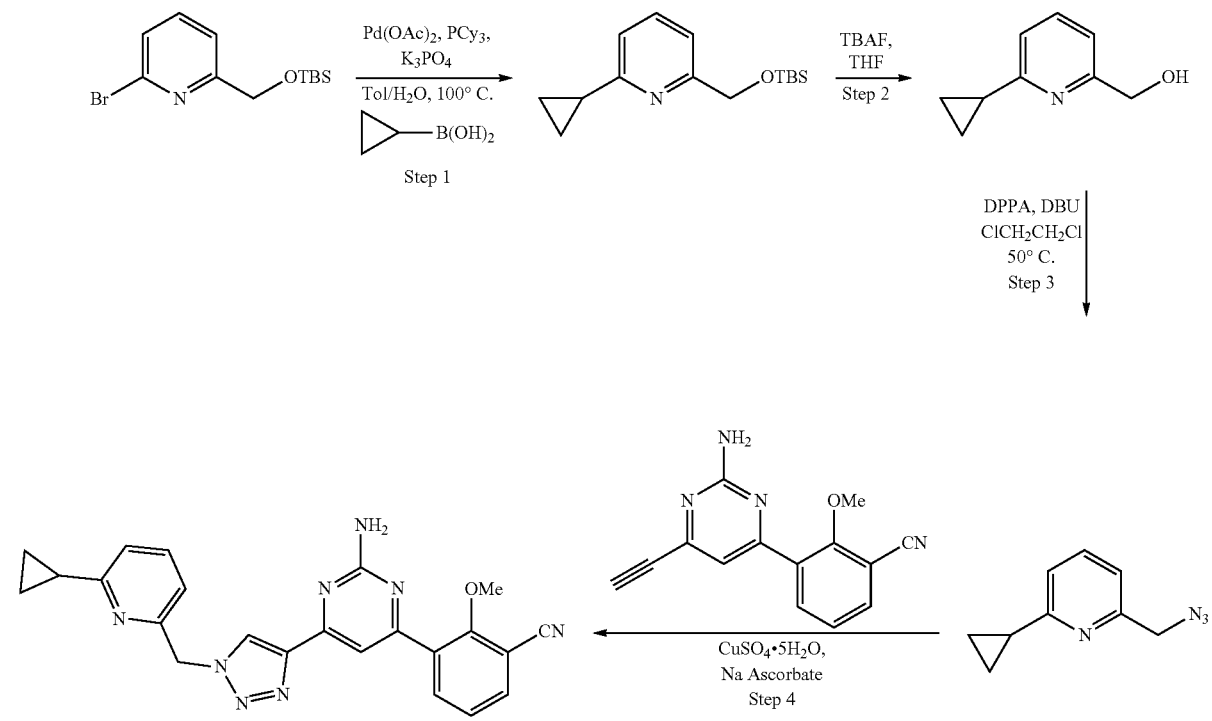

Step 1: To a mixture of 2-bromo-pyridine derivative (14 g, 46.4 mmol), cyclopropyl-boronic acid (8 g, 93 mmol), $K_3PO_4$ (34.5 g, 162.4 mmol) and $PCy_3$ (1.3 g, 4.64 mmol) in 210 mL of 20:1 toluene/$H_2O$ was added $Pd(OAc)_2$ (516 mg, 2.3 mmol). The reaction mixture was stirred at 100° C. for 12 hours under $N_2$. Saturated $NH_4Cl$ (50 mL) was added to quench the reaction and the aqueous layer was extracted with EtOAc (2×70 mL). The pooled organic layer was dried over $Na_2SO_4$, concentrated and taken to next step without further purification.

Step 2: The crude TBS-ether from previous step was dissolved in 100 mL THE and was added 46.4 mL of 1M TBAF in THF dropwise. After 15 min, 50 mL saturated $NH_4Cl$ was added to quench the reaction and the aqueous layer was extracted with EtOAc (2×70 mL). The pooled organic layer was dried over $Na_2SO_4$, concentrated and purified by silica gel chromatography to obtain the desired alcohol (6.3 g, 91% in 2-steps).

Step 3: The azide was synthesized in a similar manner to step 5 in example 1: Colorless oil (6.2 g, 85%).

Step 4: The title compound was synthesized in a similar manner to step 6 in example 1. $^1$H NMR (400 MHz, DMSO-$d_6$) δ 8.62 (s, 1H), 8.04 (d, J=7.9 Hz, 1H), 7.93 (d, J=7.5 Hz, 1H), 7.66 (dd, J=7.7, 7.7 Hz, 1H), 7.62 (s, 1H), 7.42 (dd, J=7.5, 7.5 Hz, 1H), 7.22 (d, J=7.8 Hz, 1H), 7.02 (d, J=7.6 Hz, 1H), 5.73 (s, 2H), 3.83 (s, 3H), 2.09-2.02 (m, 1H), 0.93-0.88 (m, 2H), 0.82-0.78 (m, 2H). ESI MS [M+H]$^+$ for $C_{23}H_{20}N_8O$, calcd 425.2, found 425.3.

Example 94: m-(2-Amino-6-{1-[(6-cyclopropyl-2-pyridyl)methyl]-1H-1,2,3-triazol-4-yl}-4-pyrimidinyl)benzonitrile

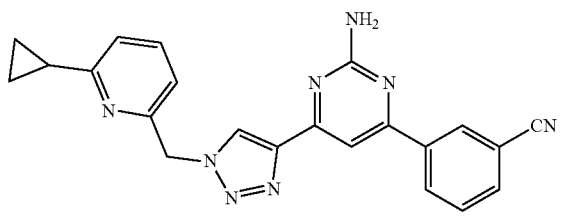 [SMILES: N#Cc1cccc(-c2cc(-c3cn(Cc4cccc(C5CC5)n4)nn3)nc(N)n2)c1]

The title compound was prepared similar to example 93 from the corresponding azide and alkyne. $^1$H NMR (400 MHz, Chloroform-d) δ 8.49-8.39 (m, 1H), 8.35-8.23 (m, 2H), 7.93-7.81 (m, 1H), 7.80-7.68 (m, 1H), 7.63-7.45 (m, 2H), 7.14-7.03 (m, 1H), 7.02-6.89 (m, 1H), 5.63 (s, 2H), 5.25 (s, 2H), 2.08-1.95 (m, 1H), 1.05-0.92 (m, 4H); LC-MS retention time 3.15 min LC-MS, Method A, ESI MS [M+H]$^-$ for $C_{22}H_{19}N_8$, calcd 395.2, found 395.3.

Example 95: 3-(2-Amino-6-{1-[(6-cyclopropyl-2-pyridyl)methyl]-1H-1,2,3-triazol-4-yl}-4-pyrimidinyl)-2-fluorobenzonitrile

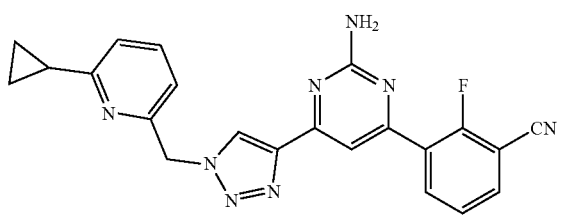 [SMILES: N#Cc1cccc(-c2cc(-c3cn(Cc4cccc(C5CC5)n4)nn3)nc(N)n2)c1F]

The title compound was prepared similar to example 93 from the corresponding azide and alkyne. $^1$H NMR (400 MHz, Chloroform-d) δ 8.38-8.18 (m, 2H), 7.91-7.82 (m, 1H), 7.76-7.64 (m, 1H), 7.57-7.46 (m, 1H), 7.42-7.31 (m, 1H), 7.14-7.04 (m, 1H), 7.00-6.91 (m, 1H), 5.62 (s, 2H), 5.29 (s, 2H), 2.09-1.95 (m, 1H), 1.07-0.89 (m, 4H); LC-MS retention time 3.15 min LC-MS, Method A, ESI MS [M+H] for $C_{22}H_{18}FN_8$, calcd 413.2, found 413.3.

Example 96: 4-{1-[(6-Cyclopropyl-2-pyridyl)methyl]-1H-1,2,3-triazol-4-yl}-6-(2,3-difluorophenyl)-2-pyrimidinylamine

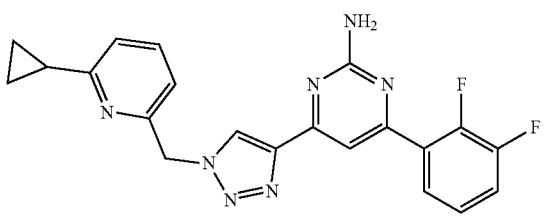 [SMILES: Nc1nc(-c2cn(Cc3cccc(C4CC4)n3)nn2)cc(-c2cccc(F)c2F)n1]

The title compound was prepared similar to example 93 from the corresponding azide and alkyne. $^1$H NMR (400 MHz, Chloroform-d) δ 8.29 (s, 1H), 7.87 (s, 1H), 7.78-7.69 (m, 1H), 7.52 (dd, J=7.8, 7.8 Hz, 1H), 7.32-7.13 (m, 2H), 7.09 (d, J=7.8 Hz, 1H), 6.95 (d, J=7.6 Hz, 1H), 5.62 (s, 2H), 5.19 (brs, 2H), 2.08-1.98 (m, 1H), 1.05-0.94 (m, 4H). MS [M+H]$^+$ for $C_{21}H_{17}F_2N_7$, calcd 406.2, found 406.3.

Example 97: 4-{1-[(6-Cyclopropyl-2-pyridyl)methyl]-1H-1,2,3-triazol-4-6-(m-fluorophenyl)-2-pyrimidinylamine

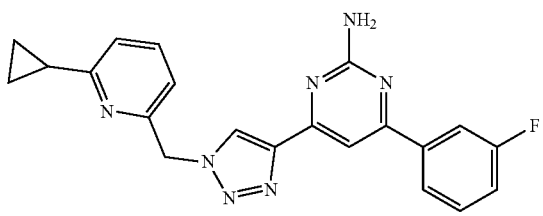 [SMILES: Nc1nc(-c2cccc(F)c2)cc(-c2cn(Cc3cccc(C4CC4)n3)nn2)n1]

The title compound was prepared similar to example 93 from the corresponding azide and alkyne. $^1$H NMR (400 MHz, $CD_3OD$-$d_4$) 8.60 (s, 1H), 7.93 (d, J=8.0 Hz, 1H), 7.89 (d, J=12 Hz, 1H), 7.77 (s, 1H), 7.64 (t, J=8 Hz, 1H), 7.52 (q, J=8 Hz, 1H), 7.25 (t, J=8 Hz, 1H), 7.17 (d, J=4 Hz, 1H), 7.09 (d, J=8.0 Hz, 1H), 5.72 (s, 1H), 2.09-2.02 (m, 1H), 0.98-0.91 (m, 4H). ESI MS [M+H]$^+$ for $C_{21}H_{18}FN_7$, calcd 388.4, found 388.3.

Example 98: 3-(2-Amino-6-{1-[(6-isopropyl-2-pyridyl)methyl]-1H-1,2,3-triazol-4-yl}-4-pyrimidinyl)-2-anisonitrile

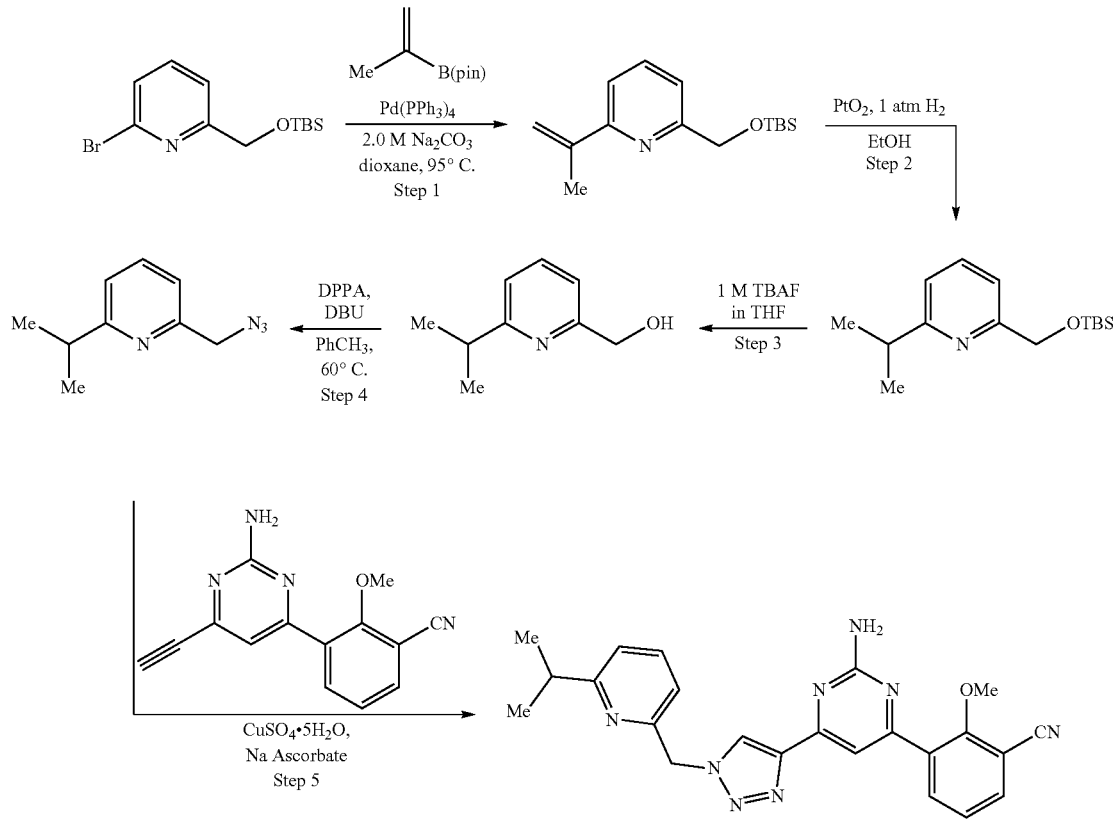

Step 1: A solution of 2-bromo-6-(({[dimethyl(2-methyl-2-propanyl)silyl]oxy}methyl)pyridine (2.8 g, 9.2 mmol, 1.0 equiv) and isopropenylboronic acid pinacol ester (2.3 g, 13.9 mmol, 1.5 equiv) in dioxane (37 mL, 0.25 M) and 2.0 M aqueous $Na_2CO_3$ (14 mL, 3.0 equiv) was sparged with $N_2$ for 10 minutes. Following this time, $Pd(PPh_3)_4$ (717 mg, 0.46 mmol, 0.05 equiv) was added and the reaction mixture heated to 95° C. for 18 h. Following this time, the reaction mixture was diluted with $CH_2Cl_2$ (100 mL), transferred to a separatory funnel and washed with $H_2O$ (100 mL). The organic phase was collected and the aqueous phase was extracted with $CH_2Cl_2$ (2×100 mL). The combined organic extracts were dried over $MgSO_4$, and concentrated in vacuo. The resulting oil was purified by column chromatography (0:1 EtOAc:hexanes→1:9 EtOAc:hexanes) to give the title compound (2.2 g, 90% yield) as a colorless oil.

Step 2: A solution of the isopropenyl pyridine from step 1 (2.2 g, 8.4 mmol, 1.0 equiv) in methanol (20 mL, 0.5 M) with acetic acid (0.1 mL) was sparged with $N_2$ for 5 minutes and then $PtO_2$ (117 mg, 0.52 mmol, 0.05 equiv) was added. The suspension was sparged with a balloon of $H_2$ for 10 minutes and then the reaction stirred under $H_2$ atmosphere (balloon) for 20 h. Upon completion, the reaction mixture was filtered over celite, the filter cake washed with methanol (2×10 mL), and the filtrate concentrated in vacuo. The resulting oil used in the following step without further purification.

Step 3: The intermediate from the previous step was taken up in 1.0 M TBAF in THF (20 mL, 2.0 equiv) and the solution stirred at room temperature for 45 minutes. The reaction mixture was then loaded directly onto $SiO_2$ and purified by column chromatography (0:1 MeOH:$CH_2Cl_2$→1:9 MeOH:$CH_2Cl_2$) to give (6-isopropyl-2-pyridyl)methanol (1.1 g, 87% yield) as a colorless oil.

Step 4: To a solution of (6-isopropyl-2-pyridyl)methanol (1.1 g, 7.0 mmol, 1.0 equiv) in toluene (14 mL, 0.5 M) was added diphenylphosphoryl azide (1.8 mL, 8.4 mmol, 1.2 equiv.), followed by 1,8-diazabicyclo[5.4.0]undec-7-ene (1.3 mL, 8.4 mmol, 1.2 equiv.). The resulting mixture was heated to 60° C. for 1.5 h. The reaction mixture was then loaded directly onto $SiO_2$ and purified by column chromatography (0:1 EtOAc:hexanes→1:19 EtOAc:hexanes) to give 2-(azidomethyl)-6-isopropylpyridine (890 mg, 72% yield) as a colorless oil.

Step 5: The title compound was synthesized in a similar fashion to step 6 of example 1. $^1$H NMR (400 MHz, DMSO-$d_6$) δ 8.71 (s, 1H), 8.05 (d, J=7.8 Hz, 1H) 7.94 (d, J=7.7 Hz, 1H), 7.80-7.75 (m, 1H), 7.63 (s, 1H), 7.43 (dd, J=7.7, 7.7 Hz, 1H), 7.29 (d, J=7.9 Hz, 1H), 7.09 (d, J=7.6 Hz, 1H), 5.81 (s, 2H), 3.03-2.96 (m, 1H), 1.19 (d, J=6.9 Hz, 6H). ESI MS $[M+H]^+$ for $C_{23}H_{22}N_8O$, calcd 427.2, found 427.3.

Example 99: m-(2-Amino-6-{1-[(6-isopropyl-2-pyridyl)methyl]-1H-1,2,3-triazol-4-yl}-4-pyrimidinyl)benzonitrile

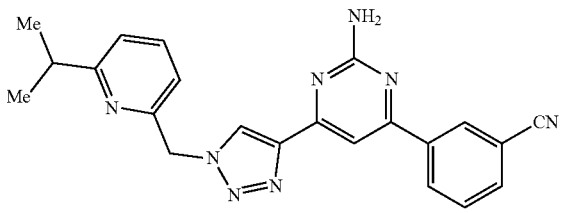 [SMILES: CC(C)c1cccc(Cn2cc(-c3cc(-c4cccc(C#N)c4)nc(N)n3)nn2)n1]

The title compound was prepared similar to example 98 from the corresponding azide and alkyne. ¹H NMR (400 MHz, CD₃OD) δ 8.82 (s, 1H), 8.54 (s, 1H), 8.45 (d, J=8.1 Hz, 1H), 7.94-7.86 (m, overlap, 3H), 7.74 (dd, J=8.0, 8.0 Hz, 1H), 7.39 (d, J=8.0 Hz, 1H), 7.28, J=8.0 Hz, 1H), 5.86 (s, 2H), 3.10 (sept, 7.0 Hz, 1H), 1.29 (d, J=7.0 Hz, 6H). ESI MS [M+H]⁺ for C₂₂H₂₀N₈, calcd 397.2, found 397.3.

Example 100: 6-(m-Fluorophenyl)-4-{1-[(6-isopropyl-2-pyridyl)methyl]-1H-1,2,3-triazol-4-yl}-2-pyrimidinylamine

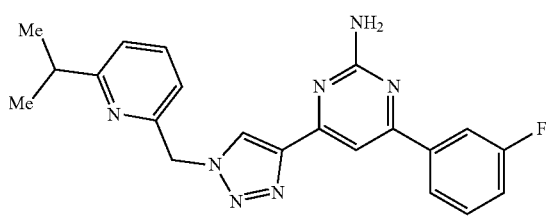 [SMILES: CC(C)c1cccc(Cn2cc(-c3cc(-c4cccc(F)c4)nc(N)n3)nn2)n1]

The title compound was prepared similar to example 98 from the corresponding azide and alkyne. ¹H NMR (400 MHz, CD₃OD-d₄) 8.65 (s, 1H), 7.94 (d, J=8.0 Hz, 1H), 7.89 (d, J=8.0 Hz, 1H), 7.73-7.78 (m, 3H), 7.53 (d, J=8 Hz, 1H), 7.27 (d, J=8 Hz, 1H), 7.16 (d, J=4 Hz, 1H), 7.20 (dt, J=8, 4 Hz, 1H), 7.1 (d, J=8.0 Hz, 1H), 5.79 (s, 2H), 3.04-3.07 (m, 1H), 1.28 (d, J=4 Hz, 6H). ESI MS [M+H]⁺ for C₂₁H₂₀FN₇, calcd 390.4, found 390.3.

Example 101: 3-(2-Amino-6-{1-[(6-isopropyl-2-pyridyl)methyl]-1H-1,2,3-triazol-4-yl}-4-pyrimidinyl)-2-fluorobenzonitrile

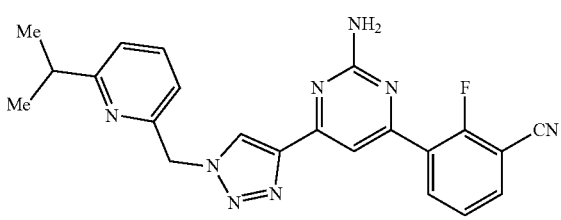 [SMILES: CC(C)c1cccc(Cn2cc(-c3cc(-c4cccc(C#N)c4F)nc(N)n3)nn2)n1]

The title compound was prepared similar to example 98 from the corresponding azide and alkyne. ¹H NMR (400 MHz, Acetone-d₆) δ 8.59 (d, J=0.8 Hz, 1H), 8.45-8.36 (m, 1H), 7.98 (dddd, J=7.7, 6.0, 1.8, 0.8 Hz, 1H), 7.85 (dd, J=2.7, 0.8 Hz, 1H), 7.74 (td, J=7.8, 0.7 Hz, 1H), 7.58 (t, J=7.8 Hz, 1H), 7.25 (d, J=7.8 Hz, 1H), 7.15 (dd, J=7.6, 0.9 Hz, 1H), 6.30 (s, 2H), 5.80 (s, 2H), 3.03 (hept, J=6.8 Hz, 1H), 1.24 (dd, J=6.9, 0.8 Hz, 6H). ESI MS [M+H]⁺ for C₂₂H₁₉FN₈, calcd 415.2, found 415.3.

Example 102: 6-(2,3-Difluorophenyl)-4-{1-[(6-isopropyl-2-pyridyl)methyl]-1H-1,2,3-triazol-4-yl}-2-pyrimidinylamine

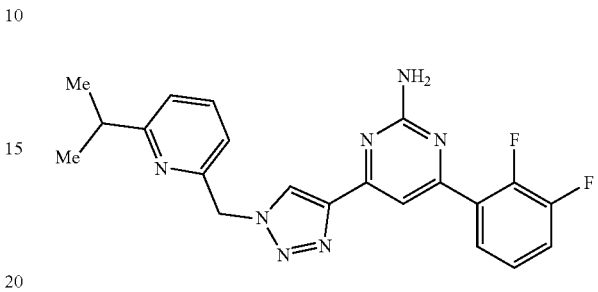

The title compound was prepared similar to example 98 from the corresponding azide and alkyne. ¹H NMR (400 MHz, Acetone-d₆) δ 8.72 (s, 1H), 7.89-7.87 (s, 2H), 7.79 (t, J=7.9 Hz, 1H), 7.51 (q, J=8.6 Hz, 1H), 7.39-7.34 (m, 1H), 7.29 (d, J=7.8 Hz, 1H), 7.21 (d, J=7.7 Hz, 1H), 5.85 (s, 2H), 3.07 (p, J=7.2 Hz, 1H), 1.25 (dd, J=6.9, 1.2 Hz, 6H). ESI MS [M+H]⁺ for C₂₁H₁₉F₂N₇, calcd 408.2, found 408.3.

Example 103: 6-(2-Amino-6-{1-[(6-isopropyl-2-pyridyl)methyl]-1H-1,2,3-triazol-4-yl}-4-pyrimidinyl)-2-toluonitrile

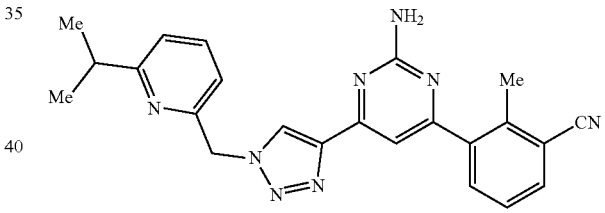

The title compound was prepared similar to example 98 from the corresponding azide and alkyne. ¹H NMR (400 MHz, Acetone-d₆) δ 8.58 (s, 1H), 7.86-7.70 (m, 3H), 7.53 (td, J=7.8, 0.7 Hz, 1H), 7.44 (d, J=0.9 Hz, 1H), 7.26 (d, J=7.8 Hz, 1H), 7.15 (d, J=7.7 Hz, 1H), 6.22 (s, 2H), 5.80 (s, 2H), 3.04 (p, J=6.9 Hz, 1H), 1.25 (dd, J=6.9, 0.9 Hz, 6H). ESI MS [M+H]⁺ for C₂₃H₂₂N₈, calcd 411.2, found 411.3.

Example 104: 3-(2-Amino-6-{1-[(6-isopropyl-2-pyridyl)methyl]-1H-1,2,3-triazol-4-yl}-4-pyrimidinyl)-2-ethoxybenzonitrile

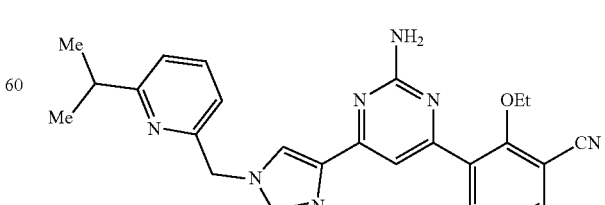

The title compound was prepared similar to example 98 from the corresponding azide and alkyne. ¹H NMR (400 MHz, Acetone-$d_6$) δ 8.72 (d, J=1.7 Hz, 1H), 8.25-8.18 (m, 1H), 8.05 (d, J=1.8 Hz, 1H), 7.89 (dd, J=7.7, 2.0 Hz, 1H), 7.82-7.73 (m, 1H), 7.47 (td, J=7.7, 1.8 Hz, 1H), 7.28 (d, J=7.8 Hz, 1H), 7.22 (d, J=7.9 Hz, 1H), 5.84 (d, J=1.7 Hz, 3H), 4.16 (q, J=8.0 Hz, 2H), 3.05 (p, J=6.6 Hz, 1H), 1.38 (td, J=7.0, 1.8 Hz, 4H), 1.25 (dd, J=6.9, 1.9 Hz, 6H). ESI MS [M+H]⁺ for $C_{24}H_{24}N_8O$, calcd 441.2, found 441.3.

Example 105: m-[2-Amino-6-(1-{[6-(tert-butyl)-2-pyridyl]methyl}-1H-1,2,3-triazol-4-yl)-4-pyrimidinyl]benzonitrile

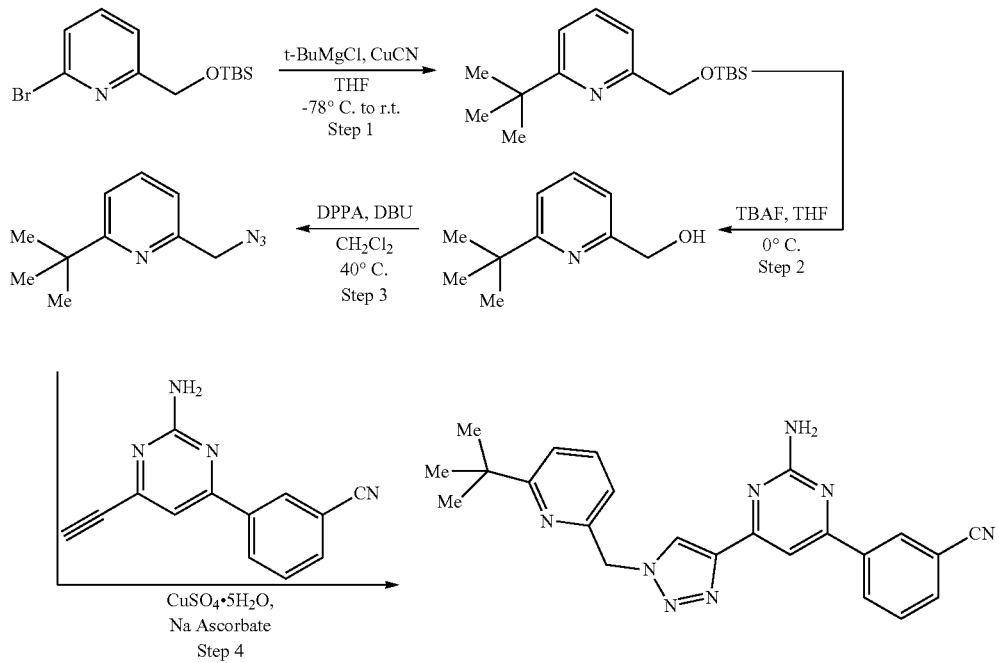

Step 1: To a suspension of CuCN (2.24 g, 25.0 mmol) in THF (50 mL) at −78° C. was added t-BuMgCl (50.0 mL, 50.0 mmol, 1 M in THF). The mixture was stirred for −78° C. for 30 minutes. The bromopyridine derivative (1.51 g, 5.00 mmol) was added dropwise and the mixture stirred at −78° C. for 2 hours. The mixture was warmed to r.t. over 14 hours and $NH_3$ (50 mL, 25% in water) followed by 50 mL ethyl acetate were added. The mixture was stirred at r.t. for 30 minutes and filtered to remove any solids. The organic phase was dried with brine and $MgSO_4$ and passed through a plug of silica gel, eluting with ethyl acetate. The organic phase was concentrated to afford the desired product as a yellow oil, which was used directly in the next step.

Steps 2-3: The azide was synthesized in a similar manner to example 79: Colorless oil (253 mg, 27%, 3 steps).

Step 4: The product was synthesized in a similar manner to example 1, step 6: Yellow solid (86 mg, 70%). ¹H NMR (400 MHz, DMSO-$d_6$) δ 8.90 (s, 1H), 8.63 (s, 1H), 8.50 (d, J=8.7 Hz, 1H), 8.05 (d, J=7.7 Hz, 1H), 7.95 (s, 1H), 7.84-7.73 (m, 2H), 7.53-7.33 (m, 1H), 7.14 (dd, J=7.7, 0.9 Hz, 1H), 5.88 (s, 2H), 1.25 (s, 9H). ESI MS [M+H]⁺ for $C_{23}H_{23}N_8$, calcd 411.2, found 411.3.

Example 106: 6-(3-Chloro-2-methoxyphenyl)-4-(1-{[6-(tert-butyl)-2-pyridyl]methyl}-1H-1,2,3-triazol-4-yl)-2-pyrimidinylamine

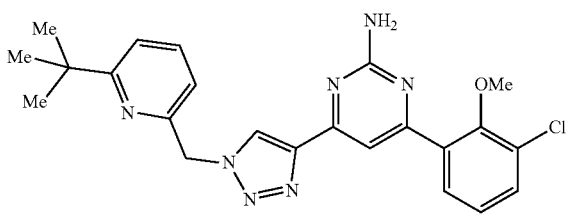 [SMILES: COc1c(Cl)cccc1-c1cc(-c2cn(Cc3cccc(C(C)(C)C)n3)nn2)nc(N)n1]

The title compound was prepared similar to example 105 from the corresponding azide and alkyne. ¹H NMR (400 MHz, CDCl₃) δ 8.35 (d, J=2.3 Hz, 1H), 7.92 (d, J=2.3 Hz, 1H), 7.66 (dd, J=7.8, 1.9 Hz, 1H), 7.62-7.55 (m, 1H), 7.49-7.42 (m, 1H), 7.31-7.24 (m, 1H), 7.19-7.11 (m, 1H), 7.01 (d, J=7.6 Hz, 1H), 5.68 (s, 2H), 5.23 (s, 2H), 3.75 (s, 2H), 1.34 (s, 9H). ESI MS [M+H]⁺ for $C_{23}H_{24}ClN_7O$, calcd 450.2, found 450.3.

Example 107: 6-(3-Fluoro-2-methoxyphenyl)-4-(1-{[6-(tert-butyl)-2-pyridyl]methyl}-1H-1,2,3-triazol-4-yl)-2-pyrimidinylamine

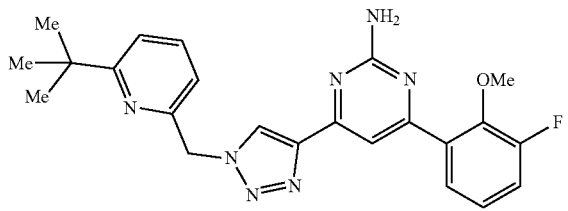 [SMILES: COc1c(F)cccc1-c1cc(-c2cn(Cc3cccc(C(C)(C)C)n3)nn2)nc(N)n1]

The title compound was prepared similar to example 105 from the corresponding azide and alkyne. $^1$H NMR (400 MHz, DMSO-$d_6$) δ 8.65 (s, 1H), 7.79-7.71 (m, 1H), 7.65-7.57 (m, 2H), 7.45-7.36 (m, 2H), 7.28-7.19 (m, 1H), 7.07 (d, J=7.4 Hz, 1H), 6.80 (s, 2H), 5.80 (s, 2H), 3.85 (s, 3H), 1.26 (s, 9H). ESI MS [M+H]$^+$ for $C_{23}H_{25}FN_7O$, calcd 434.2, found 434.4.

Example 108: 3-[2-Amino-6-(1-{[6-(tert-butyl)-2-pyridyl]methyl}-1H-1,2,3-triazol-4-yl)-4-pyrimidinyl]-2-anisonitrile

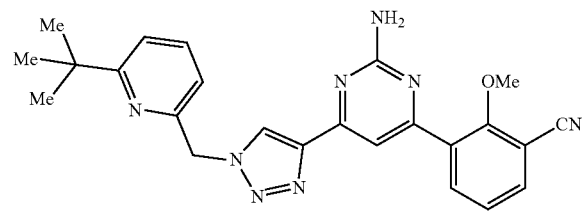 [SMILES: COc1c(C#N)cccc1-c1cc(-c2cn(Cc3cccc(C(C)(C)C)n3)nn2)nc(N)n1]

The title compound was prepared similar to example 105 from the corresponding azide and alkyne. $^1$H NMR (400 MHz, DMSO-$d_6$) δ 8.76 (s, 1H), 8.07 (dd, J=7.9, 1.7 Hz, 1H), 7.99-7.95 (m, 1H), 7.77 (t, J=7.8 Hz, 1H), 7.66 (s, 1H), 7.46 (t, J=7.8 Hz, 1H), 7.40 (d, J=7.9 Hz, 1H), 7.11 (d, J=8.5 Hz, 1H), 5.83 (s, 2H), 3.86 (s, 3H), 1.26 (s, 9H). ESI MS [M+H]$^+$ for $C_{24}H_{25}N_8O$, calcd 441.2, found 441.3.

Example 109: 3-[2-Amino-6-(1-{[6-(tert-butyl)-2-pyridyl]methyl}-1H-1,2,3-triazol-4-yl)-4-pyrimidinyl]-2-fluorobenzonitrile

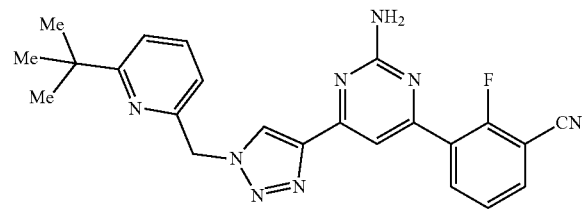 [SMILES: CC(C)(C)c1cccc(Cn2cc(-c3cc(-c4cccc(C#N)c4F)nc(N)n3)nn2)n1]

The title compound was prepared similar to example 105 from the corresponding azide and alkyne. $^1$H NMR (400 MHz, DMSO-$d_6$) δ 8.75 (s, 1H), 8.31 (td, J=7.8, 1.8 Hz, 1H), 8.13-8.07 (m, 1H), 7.77 (t, J=7.8 Hz, 1H), 7.66 (d, J=2.4 Hz, 1H), 7.58 (t, J=7.8 Hz, 1H), 7.40 (d, J=7.1 Hz, 1H), 7.11 (d, J=7.7 Hz, 1H), 5.84 (s, 2H), 1.25 (s, 9H). ESI MS [M+H]$^+$ for $C_{23}H_{22}FN_8$, calcd 429.2, found 429.3.

Example 110: 6-(2,3-Difluorophenyl)-4-(1-{[6-(tert-butyl)-2-pyridyl]methyl}-1H-1,2,3-triazol-4-yl)-2-pyrimidinylamine

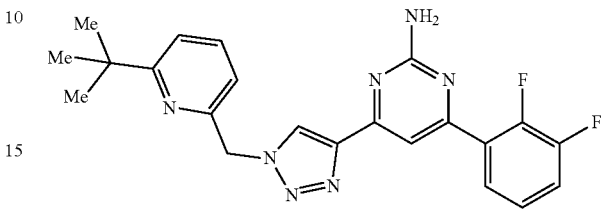

The title compound was prepared similar to example 105 from the corresponding azide and alkyne. $^1$H NMR (400 MHz, CDCl$_3$) δ 8.38 (s, 1H), 7.87 (s, 1H), 7.77-7.70 (m, 1H), 7.60 (dd, J=8.0, 8.0 Hz, 1H), 7.29 (d, J=8.0 Hz, 1H), 7.28-7.13 (m, 2H), 7.02 (d, J=7.8 Hz, 1H), 5.69 (s, 2H), 5.17 (brs, 2H), 1.35 (s, 9H). MS [M+H]$^+$ for $C_{22}H_{21}F_2N_7$, calcd 422.2, found 422.3.

Example 111: 6-[2-Amino-6-(1-{[6-(tert-butyl)-2-pyridyl]methyl}-1H-1,2,3-triazol-4-yl)-4-pyrimidinyl]-2-toluonitrile

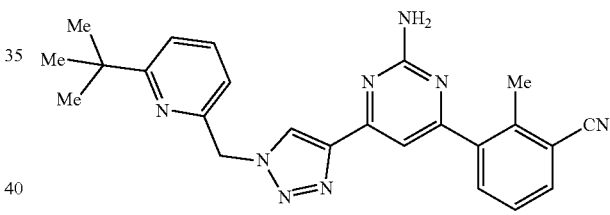

The title compound was prepared similar to example 105 from the corresponding azide and alkyne to afford 73 mg of a tan solid. $^1$H NMR (400 MHz, DMSO-$d_6$) 8.70 (s, 1H), 7.90 (dt, J=7.7, 1.3 Hz, 1H), 7.75 (td, J=7.8, 1.2 Hz, 2H), 7.52 (t, J=7.7 Hz, 1H), 7.46-7.33 (m, 1H), 7.28 (d, J=1.2 Hz, 1H), 7.07 (d, J=7.6 Hz, 1H), 6.90 (s, 2H), 5.81 (s, 2H), 2.55 (d, J=1.1 Hz, 3H), 1.26 (d, J=1.3 Hz, 9H). ESI MS [M+H]$^+$ for $C_{24}H_{24}N_8$, calcd 425.2, found 425.4.

Example 112: 6-(m-Fluorophenyl)-4-(1-{[6-tert-butyl)2-pyridyl]methyl}-1H-1,2,3-triazol-4-yl)-2-pyrimidinylamine

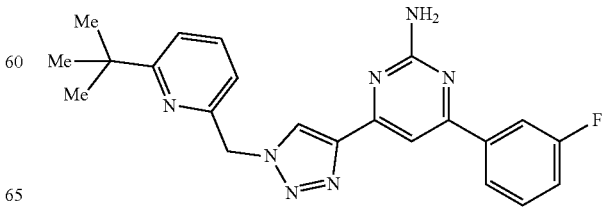

The title compound was prepared similar to example 105 from the corresponding azide and alkyne. ¹H NMR (400 MHz, CD₃OD) 8.64 (s, 1H), 7.89 (d, J=8.0 Hz, 1H), 7.84 (d, J=8.0 Hz, 1H), 7.74 (s, 1H), 7.67 (t, J=8 Hz, 1H), 7.47 (q, J=8 Hz, 1H), 7.34 (d, J=8 Hz, 1H), 7.20 (dt, J=8, 4 Hz, 1H), 7.1 (d, J=8.0 Hz, 1H), 5.75 (s, 2H), 1.28 (s, 9H). ESI MS [M+H]⁺ for $C_{22}H_{22}FN_7$, calcd 404.4, found 404.4.

Example 113: 2-[6-({4-[2-Amino-6-(o-fluorophenyl)-4-pyrimidinyl]-1H-1,2,3-triazol-1-yl}methyl)-2-pyridyl]-2-methylpropiononitrile

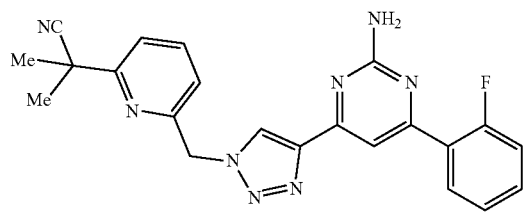 [SMILES: CC(C)(C#N)c1cccc(Cn2cc(-c3cc(-c4ccccc4F)nc(N)n3)nn2)n1]

The title compound was prepared similar to example 1 from the corresponding azide and alkyne. ¹H NMR (400 MHz, Chloroform-d) δ 8.34 (s, 1H), 8.01 (ddd, J=7.8, 7.8, 1.9 Hz, 1H), 7.92 (d, J=2.2 Hz, 1H), 7.74 (dd, J=7.8, 7.8 Hz, 1H), 7.55 (d, J=7.8 Hz, 1H), 7.48-7.42 (m, 1H), 7.31-7.22 (m, 1H), 7.22-7.14 (m, 2H), 5.74 (s, 2H), 5.30 (s, 2H), 5.14 (brs, 2H), 1.74 (s, 6H). MS [M+H]⁺ for $C_{22}H_{17}FN_8$, calcd 415.2, found 415.2.

Example 114: 5-[2-Amino-6-(m-cyanophenyl)-4-pyrimidinyl]-3-{[6-(tert-butyl)-2-pyridyl]methyl}-3H-1,2,3-triazole-4-carboxylic acid Step 1. A mixture of chloride (500 mg, 2.17 mmol) and propynol (0.5 mL) in DMF (3 mL) and Et₃N (5 mL) was degassed for 5 minutes. PdCl₂(dppf) (79 mg, 5 mol %) and CuI (41 mg, 10 mol %) were added and the mixture was heated to 75° C. for 1 hour. Usual work-up followed by purification over silica gel ((hexanes/CH₂Cl₂) (1:1)/EtOAc 100:0 to 0:100) afforded the desired alkyne (210 mg, 39%).

Step 2. A mixture of the alkyne derivative (70 mg) and the azide derivative (60 mg, 1.1 eq.) was heated in toluene at 120° C. for 30 hours. Excess solvent was removed in vacuo and the residue was purified by flash column to afford m-{2-amino-6-[5-(hydroxymethyl)-1-{[6-(tert-butyl)-2-pyridyl]methyl}-1H-1,2,3-triazol-4-yl]-4-pyrimidinyl}benzonitrile. ¹H NMR (400 MHz, Chloroform-d) δ 8.42 (s, 1H), 8.35-8.25 (m, 1H), 8.02 (s, 1H), 7.76 (d, J=7.8 Hz, 1H), 7.64-7.53 (m, 2H), 7.32 (d, J=7.8 Hz, 1H), 7.17 (d, J=7.8 Hz, 1H), 6.63 (brs, 1H), 5.73 (s, 2H), 5.23 (s, 2H), 5.07 (brs, 2H), 1.24 (s, 9H). MS [M+H]⁺ for $C_{24}H_{24}N_8O$, calcd 441.2, found 441.4.

Step 3. m-{2-Amino-6-[5-(hydroxymethyl)-1-{[6-(tert-butyl)-2-pyridyl]methyl}-1H-1,2,3-triazol-4-yl]-4-pyrimidinyl}benzonitrile (35 mg, 0.08 mmol) was taken in CH₂Cl₂ (3 mL) and MnO₂ (1.05 g) was added. The resulting mixture was stirred for 24 hours at room temperature. Filtration over celite followed by purification by chromatography over silica gel (CH₂Cl₂/EtOAc 90:10 to 20:80) afforded the corresponding aldehyde (15 mg, 43%) and acid (11 mg, 31%). ¹H NMR (400 MHz, DMSO-d₆) δ 8.71 (s, 1H), 8.63 (d, J=7.9 Hz, 1H), 8.29 (s, 1H), 8.02 (d, J=7.9 Hz, 1H), 7.84 (dd, J=7.9, 7.9 Hz, 1H), 7.71 (dd, J=7.9, 7.9 Hz, 2H), 7.30 (d, J=7.9 Hz, 1H), 7.20 (brs, 2H), 7.13 (d, J=7.9 Hz, 1H), 6.31 (s, 2H), 1.18 (s, 9H). MS [M+H]⁺ for $C_{24}H_{22}N_8O_2$, calcd 455.2, found 455.3.

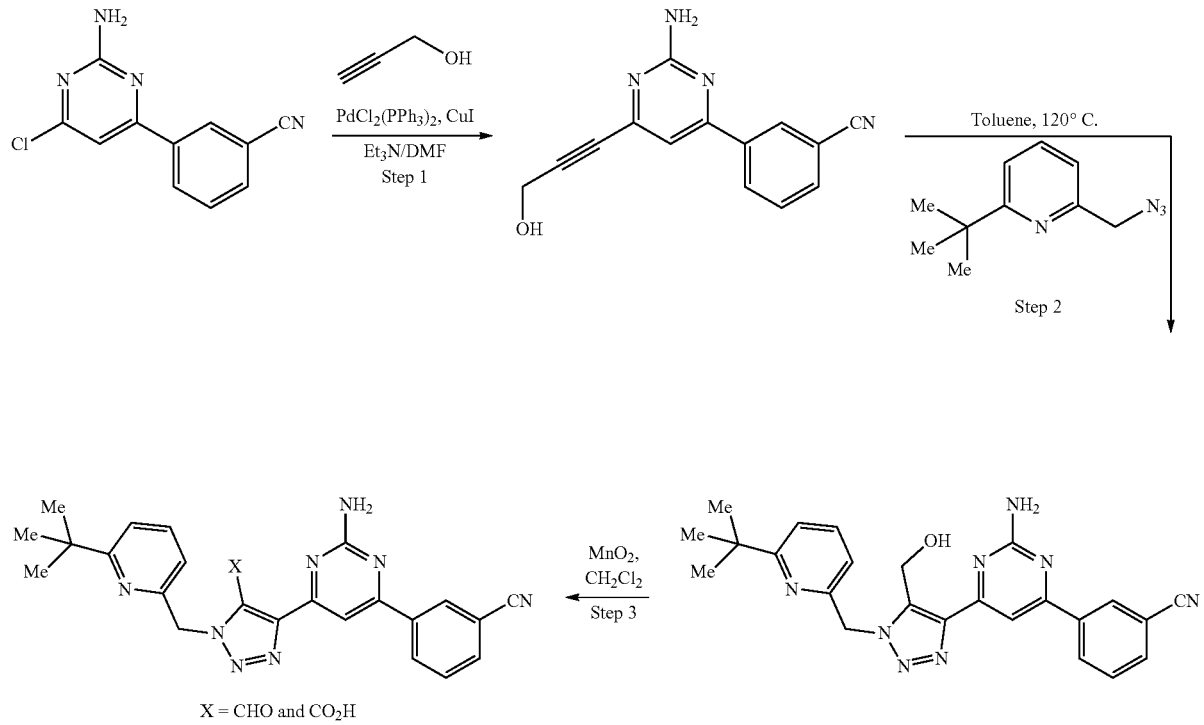

Example 115: m-[2-Amino-6-(1-{[6-(1-hydroxycyclobutyl)-2-pyridyl]methyl}-1H-1,2,3-triazol-4-yl)-4-pyrimidinyl]benzonitrile

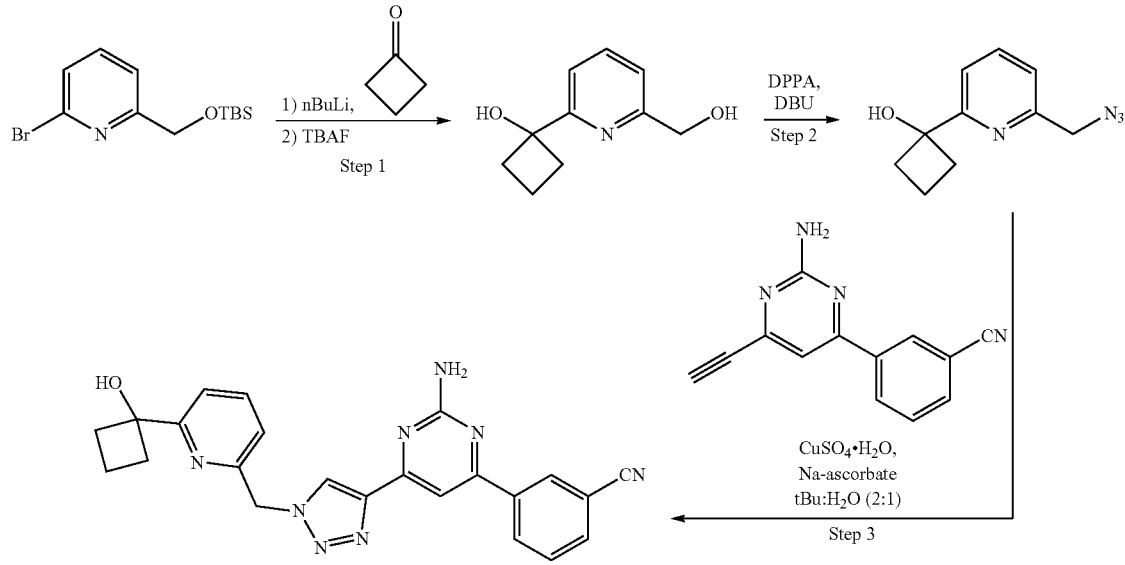 [SMILES: CC(C)(C)[Si](C)(C)OCc1cccc(Br)n1 ; O=C1CCC1 ; OCc1cccc(C2(O)CCC2)n1 ; [N-]=[N+]=NCc1cccc(C2(O)CCC2)n1 ; N#Cc1cccc(-c2cc(-c3cn(Cc4cccc(C5(O)CCC5)n4)nn3)nc(N)n2)c1 ; C#Cc1cc(-c2cccc(C#N)c2)nc(N)n1]

Step 1: A round-bottom flask was charged with 2.0 g (6.7 mmol) of commercially available 2-bromo-pyridine derivative. To this flask was added 13.0 mL of dry THF and cooled to −78° C. under N₂. nBuLi 2.7 mL (2.5 M in THF) was added dropwise to the reaction at −78° C. and stirred for 30 min. Cyclobutanone (0.58 mL, 7.9 mmol) was then added in one-portion and the reaction warmed to room temperature over 2 h (LCMS shows formation of the desired addition product). The reaction mixture was cooled back to 0° C. and 6.7 mL of TBAF (1 M in THF) was added. After stirring the reaction for 15 min at 0° C., 50.0 mL saturated aqueous NH₄Cl was added to quench the reaction. The aqueous layer was extracted with EtOAc (2×50 mL), dried over Na₂SO₄ and concentrated. The crude material was purified by silica gel chromatography to obtain the desired pyridine-diol (570 mg, 48% in 2-steps).

Step 2: To a solution of the diol (570.0 mg, 3.2 mmol) from step 1 in CH₂Cl₂ (4.0 mL) was added diphenylphosphorylazide (0.8 mL, 3.8 mmol) and DBU (0.6 mL, 3.8 mmol) at room temperature. The reaction mixture was stirred at room temperature for 10 h under N₂. After removing CH₂Cl₂, the residue was re-dissolved in EtOAc and subsequently washed with H₂O (2×25 mL). The organic layer was dried over Na₂SO₄ and concentrated. The crude material was purified by silica gel chromatography to obtain the desired azide (450 mg, 69%).

Step 3: The title compound was prepared similar to example 1 (step 6) from the corresponding azide and alkyne. ¹H NMR (400 MHz, Chloroform-d) δ 8.43 (td, J=1.8, 0.6 Hz, 1H), 8.33 (s, 1H), 8.29 (ddd, J=8.0, 1.8, 1.2 Hz, 1H), 7.88 (s, 1H), 7.81-7.72 (m, 1H), 7.62-7.54 (m, 2H), 7.16 (dd, J=7.6, 0.9 Hz, 1H), 5.74 (s, 2H), 5.37 (s, 2H), 5.03 (s, 1H), 2.68-2.38 (m, 4H), 2.18-2.07 (m, 1H), 1.93-1.75 (m, 1H). ESI MS [M+H]⁺ for C₂₃H₂₀N₈O, calcd 425.2, found 425.3.

Example 116: m-[2-Amino-6-(1-{[6-(1-hydroxycyclopentyl)-2-pyridyl]methyl}-1H-1,2,3-triazol-4-yl)-4-pyrimidinyl]benzonitrile

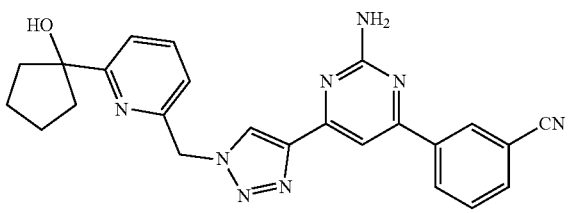 [SMILES: N#Cc1cccc(-c2cc(-c3cn(Cc4cccc(C5(O)CCCC5)n4)nn3)nc(N)n2)c1]

The title compound was prepared similar to example 115 from the corresponding azide and alkyne. ¹H NMR (400 MHz, Chloroform-d) δ 8.46 (td, J=1.7, 0.6 Hz, 1H), 8.36-8.28 (m, 2H), 7.91 (s, 1H), 7.80-7.69 (m, 2H), 7.61 (td, J=7.8, 0.6 Hz, 1H), 7.39 (dd, J=8.0, 0.9 Hz, 1H), 7.13 (dd, J=7.6, 0.9 Hz, 1H), 5.76 (s, 2H), 5.18 (s, 2H), 4.70 (s, 1H), 2.10-1.78 (m, 8H). ESI MS [M+H]⁺ for C₂₄H₂₂N₈O, calcd 439.2, found 439.3.

Example 117: 1-[6-({4-[2-Amino-6-(2,3-difluorophenyl)-4-pyrimidinyl]-1H-1,2,3-triazol-1-yl}methyl)-2-pyridyl]cyclopentanol

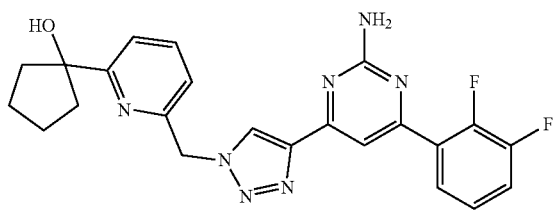 [SMILES: Nc1nc(-c2cn(Cc3cccc(C4(O)CCCC4)n3)nn2)cc(-c2cccc(F)c2F)n1]

The title compound was prepared similar to example 115 from the corresponding azide and alkyne. ¹H NMR (400 MHz, Chloroform-d) δ 8.30 (s, 1H), 7.89 (d, J=2.1 Hz, 1H), 7.78-7.71 (m, 1H), 7.71 (dd, J=7.9, 7.9 Hz, 1H), 7.37 (d, J=7.9 Hz, 1H), 7.30-7.22 (m, 1H), 7.22-7.14 (m, 1H), 7.11 (d, J=7.6 Hz, 1H), 5.74 (s, 2H), 5.16 (s, 2H), 2.12-1.79 (m, 8H). MS [M+H]⁺ for $C_{23}H_{21}F_2N_7O$, calcd 450.2, found 450.3.

Example 118: 3-[2-Amino-6-(1-{[6-(1-hydroxycyclopentyl)-2-pyridyl]methyl}-1H-1,2,3-triazol-4-yl)-4-pyrimidinyl]-2-fluorobenzonitrile

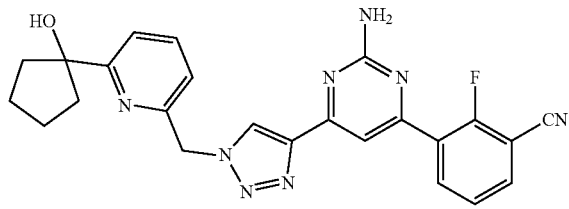 [SMILES: N#Cc1cccc(-c2cc(-c3cn(Cc4cccc(C5(O)CCCC5)n4)nn3)nc(N)n2)c1F]

The title compound was prepared similar to example 115 from the corresponding azide and alkyne. ¹H NMR (400 MHz, Chloroform-d) δ 8.34 (s, 1H), 8.33-8.22 (m, 1H), 7.92-7.85 (m, 1H), 7.81-7.61 (m, 2H), 7.47-7.34 (m, 2H), 7.12 (d, J=7.6 Hz, 1H), 5.75 (s, 2H), 5.24 (s, 2H), 4.63 (brs, 1H), 2.13-1.61 (m, 8H). MS [M+H]⁺ for $C_{24}H_{21}FN_8O$, calcd 457.2, found: 457.4.

Example 119: 1-[6-({4-[2-Amino-6-(o-fluorophenyl)-4-pyrimidinyl]-1H-1,2,3-triazol-1-yl}methyl)-2-pyridyl]cyclopentanol

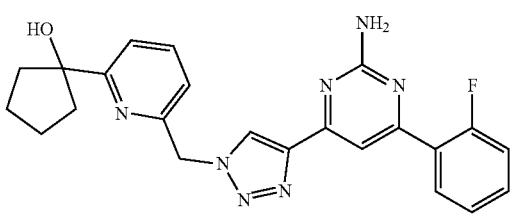 [SMILES: Nc1nc(-c2cn(Cc3cccc(C4(O)CCCC4)n3)nn2)cc(-c2ccccc2F)n1]

The title compound was prepared similar to example 115 from the corresponding azide and alkyne. ¹H NMR (400 MHz, Chloroform-d) δ 8.29 (s, 1H), 8.01 (dd, J=7.7, 7.7 Hz, 1H), 7.94 (s, 1H), 7.71 (dd, J=7.4, 7.4 Hz, 1H), 7.44 (s, 1H), 7.37 (d, J=7.7 Hz, 1H), 7.22-7.14 (m, 1H), 7.10 (d, J=7.4 Hz, 1H), 5.75 (s, 2H), 5.10 (s, 2H), 4.68 (brs, 1H), 2.12-1.77 (m, 8H). MS [M+H]⁺ for $C_{23}H_{22}FN_7O$, calcd 432.2, found 432.3.

Example 120: 3-{6-[1-({6-[(S)-3-Hydroxy-1-pyrrolidinyl]-2-pyridyl}methyl)-1H-1,2,3-triazol-4-yl]-2-amino-4-pyrimidinyl}-2-anisonitrile

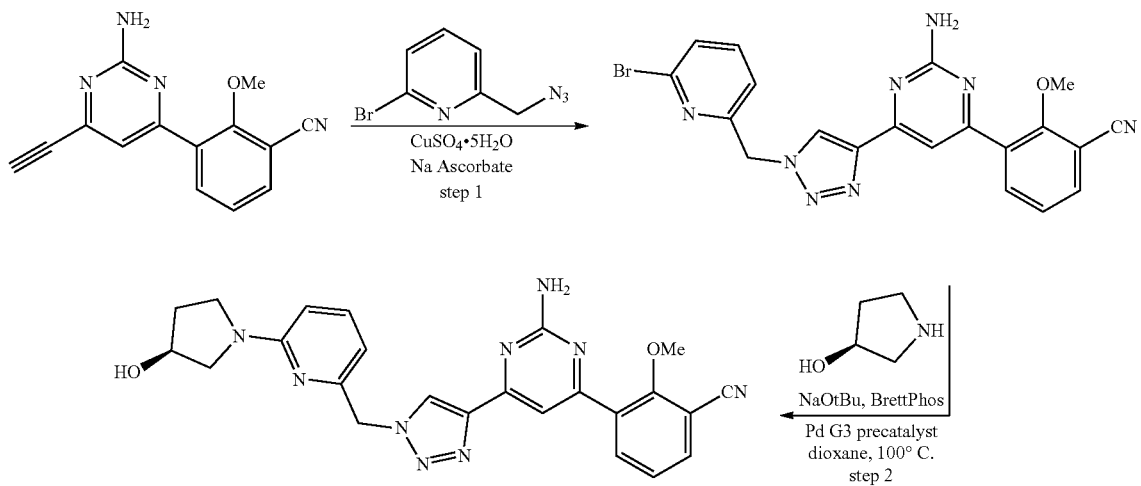 [SMILES: C#Cc1cc(-c2cccc(C#N)c2OC)nc(N)n1 ; [N-]=[N+]=NCc1cccc(Br)n1 ; COc1c(C#N)cccc1-c1cc(-c2cn(Cc3cccc(Br)n3)nn2)nc(N)n1 ; COc1c(C#N)cccc1-c1cc(-c2cn(Cc3cccc(N4CC[C@H](O)C4)n3)nn2)nc(N)n1 ; O[C@H]1CCNC1]

Step 1: An 8 mL glass vial equipped with a magnetic stir bar was charged with the azide (96.2 mg, 0.451 mmol), the alkyne (113 mg, 0.451 mmol), CuSO$_4$ 5H$_2$O (6 mg, 22.6 µmol, 5 mol %), sodium ascorbate (17.9 mg, 90.3 µmol, 20 mol %) and 2:1 tBuOH/H$_2$O (1.81 mL, 0.25 M). The resulting mixture was heated at 55° C. for 2 h. Upon completion, the mixture was cooled to room temperature and diluted with CH$_2$Cl$_2$ (3 mL). The phases were separated and the aqueous phase was extracted again with CH$_2$Cl$_2$ (3 mL). The combined organic extracts were concentrated in vacuo. The crude residue was purified by flash column chromatography over silica (CH$_2$Cl$_2$/MeOH gradient) to afford the product (176 mg, 84% yield) as a beige solid.

Step 2: A 1-dram vial equipped with a magnetic stir bar was charged with the bromopyridine substrate (20.0 mg, 43.1 µmol, 1.0 equiv), (S)-3-hydroxypyrrolidine (4.50 mg, 51.7 µmol, 1.2 equiv), NaOtBu (8.30 mg, 86.2 µmol, 2.0 equiv), Pd G3 precatalyst (300 µg, 0.431 µmol, 1 mol %), BrettPhos (200 µg, 0.431 µmol, 1 mol %), and dioxane (100 µL, 0.45 M). The resulting mixture was degassed by evacuating and backfilling with N$_2$ (3×) and then stirred at 100° C. for 3 h. Upon completion, the reaction mixture was cooled to room temperature, diluted with EtOAc, and filtered over Celite. The filtrate was concentrated in vacuo and the crude residue was purified by flash column chromatography over silica (CH$_2$Cl$_2$/MeOH gradient) to afford the product (5 mg, 25% yield) as an off-white solid. $^1$H NMR (400 MHz, Chloroform-d) δ 8.38 (s, 1H), 8.03-7.97 (m, 1H), 7.90 (s, 1H), 7.70-7.63 (m, 1H), 7.46-7.35 (m, 1H), 7.32-7.26 (m, 1H), 6.50 (d, J=7.2 Hz, 1H), 6.32 (d, J=8.5 Hz, 1H), 5.52 (s, 2H), 5.16 (s, 2H), 4.67-4.55 (m, 1H), 3.94 (s, 3H), 3.65-3.50 (m, 4H), 2.22-2.06 (m, 2H); LC-MS retention time 2.32 min LC-MS, Method A, ESI MS [M+H$^+$] for C$_{24}$H$_{24}$N$_9$O$_2$, calcd 470.2, found 470.3.

Example 121: 3-{6-[1-({6-[(R)-3-Hydroxy-1-pyrrolidinyl]-2-pyridyl}methyl)-1H-1,2,3-triazol-4-yl]-2-amino-4-pyrimidinyl}-2-anisonitrile

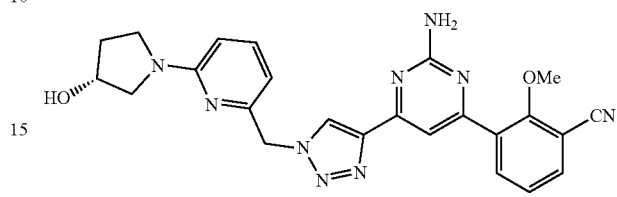

The title compound was prepared similar to example 120 from the corresponding azide and alkyne. $^1$H NMR (400 MHz, Chloroform-d) δ 8.38 (s, 1H), 8.01 (dd, J=7.6, 1.7 Hz, 1H), 7.89 (s, 1H), 7.72-7.64 (m, 1H), 7.45-7.38 (m, 1H), 7.31-7.26 (m, 1H), 6.50 (d, J=7.1 Hz, 1H), 6.32 (d, J=8.4 Hz, 1H), 5.52 (s, 2H), 5.16 (s, 2H), 4.65-4.59 (m, 1H), 3.93 (s, 3H), 3.64-3.51 (m, 4H), 2.20-2.07 (m, 2H); LC-MS retention time 2.32 min LC-MS, Method A, ESI MS [M+H$^+$] for C$_{24}$H$_{24}$N$_9$O$_2$, calcd 470.2, found 470.4.

Example 122: 1-{[6-({4-[2-Amino-6-(m-cyanophenyl)-4-pyrimidinyl]-1H-1,2,3-triazol-1-yl}methyl)-2-pyridyl]carbonyl}-4-piperidinecarboxylic acid

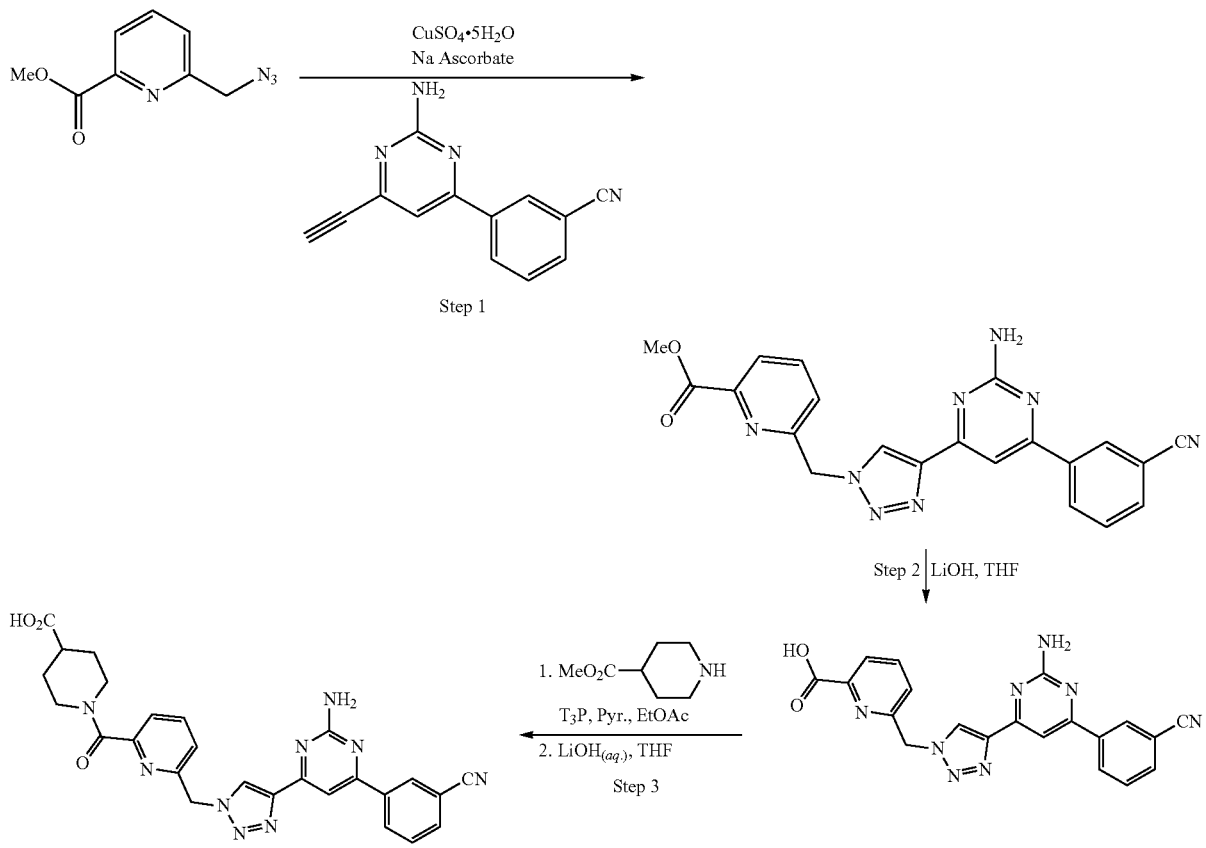

Step 1. Cycloaddition was performed in a similar fashion to step 6 of example 1 to yield methyl 6-({4-[2-amino-6-(m-cyanophenyl)-4-pyrimidinyl]-1H-1,2,3-triazol-1-yl}methyl)-2-pyridinecarboxylate. $^1$H NMR (400 MHz, DMSO-d$_6$) δ 8.75 (s, 1H), 8.59 (dt, J=1.8, 1.0 Hz, 1H), 8.48 (ddd, J=8.0, 1.8, 1.1 Hz, 1H), 8.09-8.03 (m, 2H), 8.00 (dt, J=7.7, 1.3 Hz, 1H), 7.82 (s, 1H), 7.78-7.72 (m, 1H), 7.55 (dd, J=6.5, 2.3 Hz, 1H), 6.95 (s, 2H), 5.94 (s, 2H), 3.88 (s, 3H). ESI MS [M+H]$^+$ for C$_{21}$H$_{16}$N$_8$O$_2$, calcd 413.1, found 413.2.

Step 2. To a solution of methyl 6-({4-[2-amino-6-(m-cyanophenyl)-4-pyrimidinyl]-1H-1,2,3-triazol-1-yl}methyl)-2-pyridinecarboxylate (10 mg, 0.024 mmol) in t-BuOH (0.2 mL) and H$_2$O (0.1 mL) was added LiOH·H$_2$O (1.5 mg, 0.036 mmol, 1.5 equiv.) at room temperature. The mixture stirred overnight and was washed with MTBE. The reaction was quenched by addition of 1 M HCl (ca. 50 μL), extracted with EtOAc, and concentrated to yield the 9.7 mg of the compound as a tan solid. $^1$H NMR (400 MHz, DMSO-d$_6$) δ 8.61 (td, J=1.8, 0.6 Hz, 1H), 8.49 (ddd, J=8.0, 1.9, 1.1 Hz, 1H), 8.13-7.99 (m, 3H), 7.89 (s, 1H), 7.84-7.71 (m, 1H), 7.55 (dd, J=6.8, 2.1 Hz, 1H), 5.95 (s, 2H), 5.36 (bs, 3H). ESI MS [M+H]$^+$ for C$_{20}$H$_{14}$N$_8$O$_2$, calcd 399.1, found 399.2.

Step 3. A mixture of the above acid (30 mg, 0.075 mmol), amine (50 mg, 0.15 mmol), pyridine (0.5 mL) and T$_3$P (0.2 mL) was stirred at 50° C. for one hour. The mixture was directly taken on silica gel for purification (CH$_2$Cl$_2$:MeOH 100:0 to 95:5) to afford the amide (35 mg, 90%). Hydrolysis of this ester yielded the title acid (23 mg, 66%). $^1$H NMR (400 MHz, Acetone-d$_6$) δ 8.63 (s, 1H), 8.58 (s, 1H), 8.50 (d, J=8.0 Hz, 1H), 7.98 (dd, J=8.0, 8.0 Hz, 1H), 7.94-7.86 (m, 1H), 7.89 (s, 1H), 7.75 (dd, J=8.0, 8.0 Hz, 1H), 7.60 (d, J=8.0 Hz, 1H), 7.54 (d, J=8.0 Hz, 1H), 6.30 (brs, 1H), 5.91 (s, 2H), 4.48-4.39 (m, 1H), 3.84-3.75 (m, 1H), 3.15-2.95 (m, 2H), 2.69-2.57 (m, 1H), 2.06-1.84 (m, 3H), 1.73-1.59 (m, 2H). MS [M+H]$^+$ for C$_{26}$H$_{23}$N$_9$O$_3$, calcd 510.2, found 510.3.

Example 123: 6-({4-[2-Amino-6-(m-cyanophenyl)-4-pyrimidinyl]-1H-1,2,3-triazol-1-yl}methyl)nicotinic acid

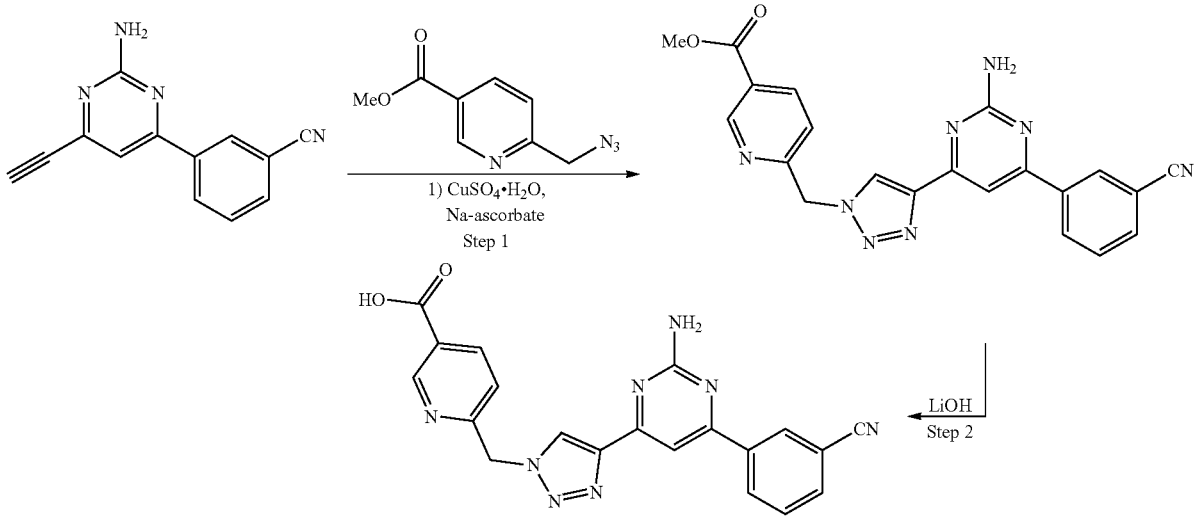

Step 1. Methyl 6-({4-[2-amino-6-(m-cyanophenyl)-4-pyrimidinyl]-1H-1,2,3-triazol-1-yl}methyl)nicotinate was synthesized similar to example 122. $^1$H NMR (400 MHz, Chloroform-d) δ 9.22 (dd, J=2.1, 0.9 Hz, 1H), 8.46 (s, 1H), 8.40 (s, 1H), 8.32 (dd, J=8.1, 2.1 Hz, 2H), 7.91 (s, 1H), 7.77 (dt, J=7.7, 1.4 Hz, 1H), 7.61 (t, J=7.8 Hz, 1H), 7.37-7.30 (m, 1H), 5.81 (s, 2H), 5.23 (s, 2H), 3.96 (s, 3H). ESI MS [M+H]$^+$ for C$_{21}$H$_{16}$N$_8$O$_2$, calcd 413.1, found 413.2.

Step 2. Saponification of methyl 6-({4-[2-amino-6-(m-cyanophenyl)-4-pyrimidinyl]-1H-1,2,3-triazol-1-yl}methyl)nicotinate afforded the title compound: $^1$H NMR (400 MHz, DMSO-d$_6$) δ 9.10-8.94 (m, 1H), 8.81 (s, 1H), 8.61 (s, 1H), 8.49 (d, J=8.1 Hz, 1H), 8.33 (dd, J=8.1, 2.2 Hz, 1H), 8.02 (dd, J=7.8, 1.4 Hz, 1H), 7.86 (s, 1H), 7.76 (t, J=7.9 Hz, 1H), 7.49 (d, J=8.2 Hz, 1H), 5.98 (s, 2H). ESI MS [M+H]$^+$ for C$_{20}$H$_{14}$N$_8$O$_2$, calcd 399.1, found 399.2.

Example 124: 2-({4-[2-Amino-6-(m-cyanophenyl)-4-pyrimidinyl]-1H-1,2,3-triazol-1-yl}methyl)isonicotinic acid

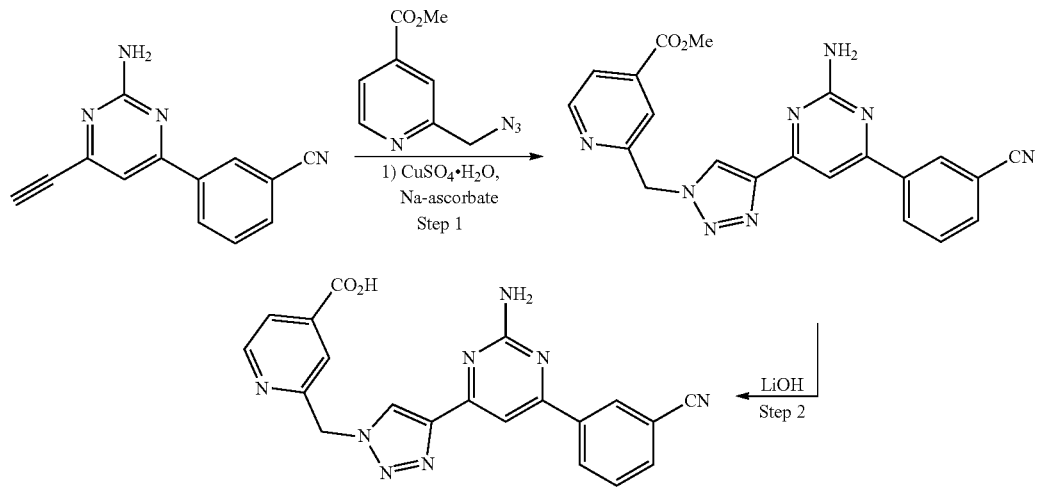

Step 1. Methyl 2-({4-[2-amino-6-(m-cyanophenyl)-4-pyrimidinyl]-1H-1,2,3-triazol-1-yl}methyl)isonicotinate was synthesized to example 122 to afford 88 mg of a tan solid. $^1$H NMR (400 MHz, DMSO-$d_6$) δ 8.83-8.71 (m, 2H), 8.59 (t, J=1.6 Hz, 1H), 8.47 (dt, J=8.2, 1.3 Hz, 1H), 8.00 (dt, J=7.8, 1.3 Hz, 1H), 7.88 (t, J=1.2 Hz, 1H), 7.84-7.80 (m, 2H), 7.74 (t, J=7.9 Hz, 1H), 6.93 (s, 2H), 5.98 (s, 2H), 3.90 (s, 3H). ESI MS [M+H]$^+$ for $C_{21}H_{16}N_8O_2$, calcd 413.1, found 413.2.

Step 2. Saponification of methyl 2-({4-[2-amino-6-(m-cyanophenyl)-4-pyrimidinyl]-1H-1,2,3-triazol-1-yl}methyl)isonicotinate afforded the title compound. $^1$H NMR (400 MHz, DMSO-$d_6$) δ 8.88 (s, 1H), 8.75 (d, J=5.0 Hz, 1H), 8.62 (t, J=1.7 Hz, 1H), 8.50 (d, J=8.0 Hz, 1H), 8.04 (d, J=7.7 Hz, 1H), 7.90 (s, 1H), 7.85 (s, 1H), 7.84-7.71 (m, 2H), 6.00 (s, 2H), 5.44 (bs, 3H). ESI MS [M+H]$^+$ for $C_{20}H_{14}N_8O_2$, calcd 399.1, found 399.2.

Example 125: 3-[6-({4-[2-Amino-6-(m-cyanophenyl)-4-pyrimidinyl]-1H-1,2,3-triazol-1-yl}methyl)-2-pyridyl]propionic acid

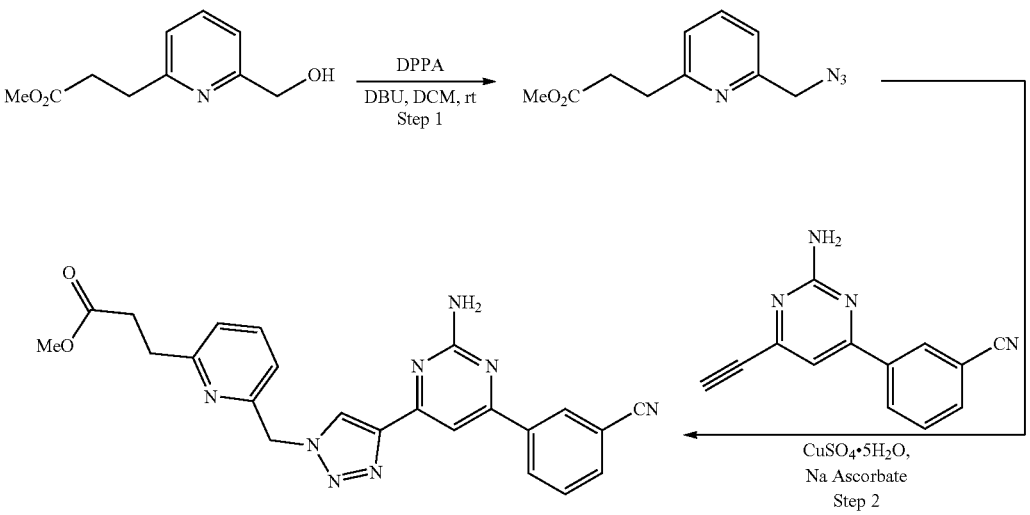

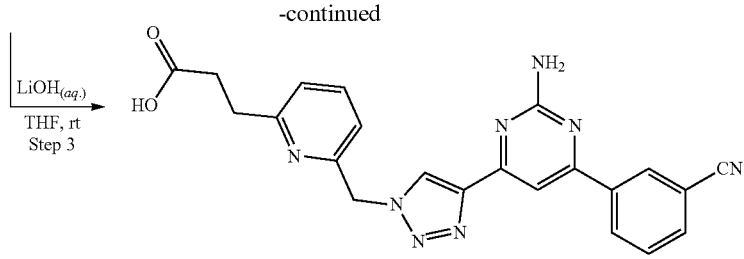

Step 1: The azide derivative synthesis was similar to step 5 of example 1. 500 mg (2.6 mmol) alcohol afforded the desired azide (265 mg, 46%) after silica gel chromatography (hexanes/EtOAc 90:10 to 70:30).

Step 2: Azide and alkyne derivatives cyclo addition was performed similar to step 6 of example 1 to afford methyl 3-[6-({4-[2-amino-6-(m-cyanophenyl)-4-pyrimidinyl]-1H-1,2,3-triazol-1-yl}methyl)-2-pyridyl]propionate. $^1$H NMR (400 MHz, Chloroform-d) δ 8.46 (ddd, J=1.7, 1.7, 0.6 Hz, 1H), 8.35 (s, 1H), 8.32 (ddd, J=8.0, 1.9, 1.2 Hz, 1H), 7.90 (s, 1H), 7.76 (ddd, J=7.7, 1.7, 1.2 Hz, 1H), 7.71-7.52 (m, 2H), 7.17 (d, J=8.0 Hz, 1H), 7.08 (m, J=8.0 Hz, 1H), 5.67 (s, 2H), 5.16 (s, 2H), 3.66 (s, 3H), 3.14 (t, J=7.3 Hz, 2H), 2.83 (t, J=7.3 Hz, 2H). MS [M+H]$^+$ for $C_{23}H_{20}N_8O_2$, calcd 441.2, found 441.3.

Step 3: To a solution of methyl ester (45 mg, 0.1 mmol) in THF (1 mL) was added an aqueous solution of LiOH (0.2 mL, 1M). The resulting mixture was vigorously stirred at room temperature for 6 hours. It was then quenched by the addition of acetic acid (excess) and evaporated onto silica. The residue was purified by silica gel chromatography ($CH_2Cl_2$/MeOH 100:0 to 90:10) to afford 3-[6-({4-[2-amino-6-(m-cyanophenyl)-4-pyrimidinyl]-1H-1,2,3-triazol-1-yl}methyl)-2-pyridyl]propionic acid (40 mg, 95%). $^1$H NMR (400 MHz, DMSO-d$_6$) δ 8.76 (s, 1H), 8.60 (s, 1H), 8.48 (d, J=8.0 Hz, 1H), 8.02 (d, J=8.0 Hz, 1H), 7.86 (s, 1H), 7.77 (dd, J=7.7, 7.7 Hz, 1H), 7.30 (d, J=7.7 Hz, 1H), 7.14 (d, J=7.7 Hz, 1H), 5.82 (s, 1H), 2.96 (t, J=7.2 Hz, 2H), 2.64 (t, J=7.2 Hz, 2H). MS [M+H]$^+$ for $C_{22}H_{18}N_8O_2$, calcd 427.2, found 427.2.

Example 126: 3-[6-({4-[2-Amino-6-(m-cyanophenyl)-4-pyrimidinyl]-1H-1,2,3-triazol-1-yl}methyl)-2-pyridyl]-2,2-dimethylpropionic acid

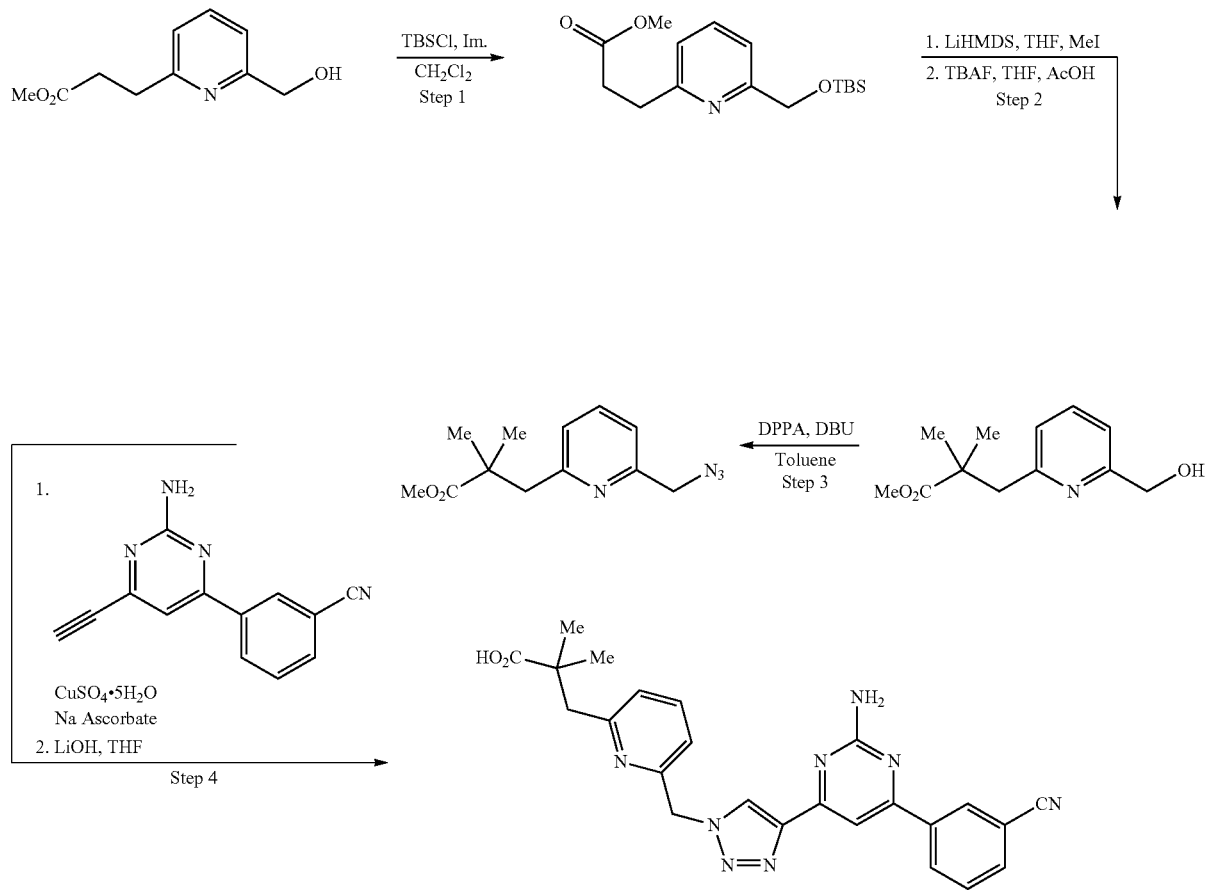

Step 1. TBSCl (723 mg, 4.8 mmol) was added to a mixture of alcohol (781 mg, 4 mmol) and imidazole (465 mg, 8 mmol) in CH$_2$Cl$_2$ (15 mL). After full conversion of the starting material, silica was added and the resulting mixture was evaporated to dryness. Purification by silica gel chromatography (hexanes/EtOAc 95:5 to 80:20) afforded the silylether as a pale yellow oil (1.14 g, 92%).

Step 2. A mixture of ester (1.5 g, 5 mmol) in THF (8 mL) was treated with LiHMDS (1M in THF, 12 mL) at −78° C. The solution was stirred for 20 minutes at this temperature and MeI (13 mmol) was added. The mixture was stirred from −78° C. to room temperature overnight. After usual work-up, the residue was purified by chromatography over silica gel (hexanes/EtOAc 95:5 to 85:15) to give rise to the di-alkylated ester (350 mg, 21%). The silylether (350 mg, 1.05 mmol) was dissolved in THF (2 mL) and acetic acid (20 μL) was added followed by TBAF (1 M in THF, 2 mL). The mixture was stirred for 2 hours at room temperature and after usual work-up the residue was purified by silica gel chromatography (CH$_2$Cl$_2$/hexanes (1:1)/EtOAc 95:5 to 70:30) to furnish the primary alcohol (95 mg, 40%).

Step 3. The azide derivative synthesis was similar to step 5 of example 1 (100 mg, 94%).

Step 4. Cycloaddition was performed in a similar fashion to step 6 of example 1 and hydrolysis of the subsequent ester similar to example 125 afforded the title compound. $^1$H NMR (400 MHz, DMSO-d$_6$) δ 8.82 (s, 1H), 8.62 (s, 1H), 8.58 (d, J=7.9 Hz, 1H), 7.90-7.99 (m, 2H), 7.70-7.82 (m, 2H), 7.36 (d, J=7.9 Hz, 2H), 7.22 (d, J=7.9 Hz, 1H), 6.27 (brs, 2H), 5.79 (s, 2H), 2.63 (s, 2H), 1.30 (s, 6H). MS [M+H]$^+$ for C$_{24}$H$_{22}$N$_8$O$_2$, calcd 455.2, found 455.3.

Example 127: 3-[6-({4-[2-Amino-6-(m-cyanophenyl)-4-pyrimidinyl]-1H-1,2,3-triazol-1-yl}methyl)-2-pyridyl]butyric acid mixture was evaporated to dryness and then purified by silica gel chromatography (hexanes/EtOAc 95:5 to 80:20) to afford a Z:E mixture of α,β-unsaturated ester (1.22 g, 61%).

Pd/C (10%. 60 mg) was added to a degassed solution of α,β-unsaturated ester (660 mg, 1.96 mmol) in THF (10 mL). The suspension was placed under H$_{2(g)}$ and stirred for 4 hours. Filtration over celite and evaporation of the solvent to dryness delivered the reduced alkane (660 mg, quant.).

Step 2. The azide derivative synthesis was similar to example 79 (468 mg, 96% over 2 steps).

Step 3. Cycloaddition and hydrolysis reactions were performed in a similar fashion to example 125 to afford the title compound. $^1$H NMR (400 MHz, DMSO-d$_6$) δ 12.04 (brs, 1H), 8.68 (s, 1H), 8.56 (s, 1H), 8.45 (d, J=8.0 Hz, 1H), 7.97 (d, J=8.0 Hz, 1H), 7.79 (s, 1H), 7.73 (dd, J=7.8, 7.8 Hz, 2H), 7.26 (d, J=7.8 Hz, 1H), 7.05 (d, J=7.8 Hz, 1H), 6.88 (s, 2H), 5.79 (s, 2H), 3.33-3.19 (m, 1H), 2.67 (dd, J=15.8, 7.2 Hz, 1H), 2.44 (dd, J=15.8, 7.3 Hz, 1H), 2.52-2.38 (m, 4H), 1.16 (d, J=7.0 Hz, 3H). MS [M+H]$^+$ for C$_{23}$H$_{20}$N$_8$O$_2$, calcd 441.2, found: 441.3.

Example 128: 3-[6-({4-[2-Amino-6-(2,3-difluorophenyl)-4-pyrimidinyl]-1H-1,2,3-triazol-1-yl}methyl)-2-pyridyl]butyric acid

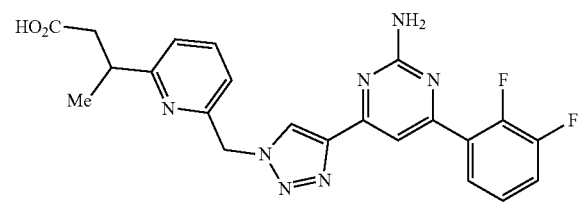

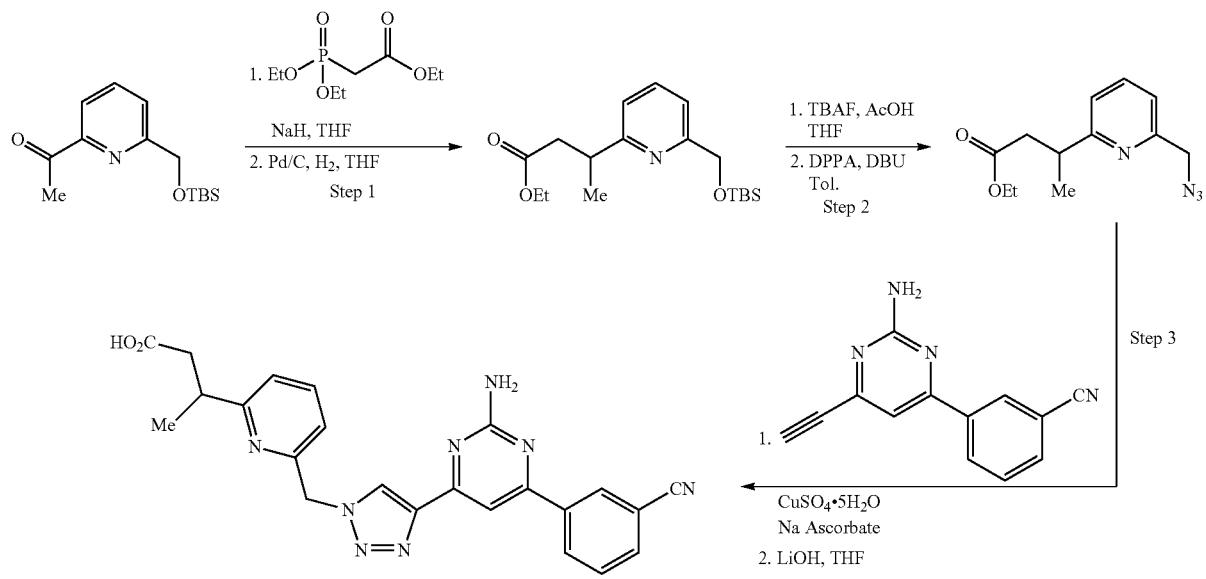

Step 1. A mixture of phosphonate (1.48 g, 6.6 mmol) in THF (10 mL) was treated with NaH (60% in mineral oil, 264 mg, 6.6 mmol) and a solution of ketone (1.59 g, 6 mmol) in THF (2 mL) was added after 10 minutes. The resulting mixture was stirred overnight; celite was added and the Cycloaddition and hydrolysis reactions were performed in a similar fashion to example 125 to afford the title compound. $^1$H NMR (400 MHz, Acetone-d$_6$) δ 8.61 (s, 1H), 7.93-7.85 (m, 1H), 7.84 (s, 1H), 7.75 (dd, J=7.8, 7.8 Hz, 1H), 7.53-7.41 (m, 1H), 7.38-7.31 (m, 1H), 7.31 (d, J=7.8 Hz, 1H), 7.19 (d, J=7.8 Hz, 1H), 6.27 (brs, 2H), 5.80 (s, 2H), 3.40 (qt, J=7.0, 6.6 Hz, 1H), 2.85 (dd, J=15.8, 7.7 Hz, 1H), 2.59 (dd, J=15.8, 6.8 Hz, 1H), 2.08 (s, 2H), 1.29 (dd, J=7.0 Hz, 3H). MS [M+H]$^+$ for $C_{22}H_{21}F_2N_7O_2$, calcd 452.2, found 452.3.

Example 129: 2-[6-({4-[2-Amino-6-(m-cyanophenyl)-4-pyrimidinyl]-1H-1,2,3-triazol-1-yl}methyl)-2-pyridyl]cyclopropanecarboxylic acid

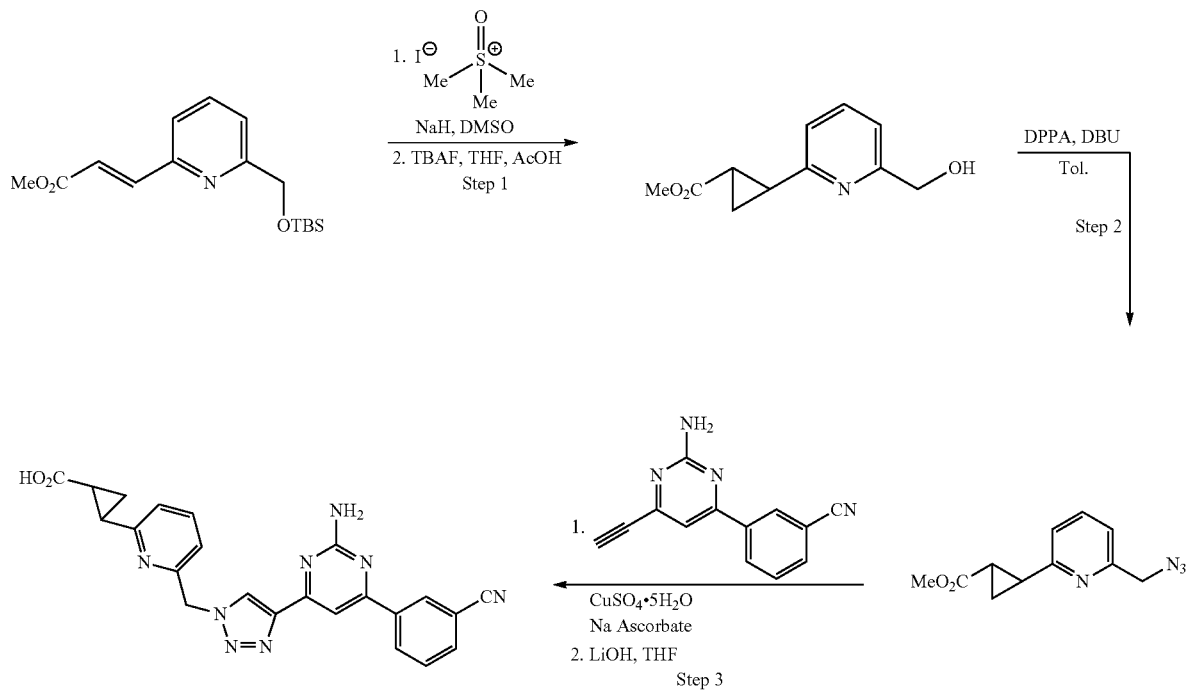

Step 1. A solution of Me$_3$SOI (1.93 g, 8.75 mmol) in DMSO (8 mL) was treated with NaH (60% in mineral oil, 320 mg, 8 mmol). The resulting mixture was stirred for 30 minutes before a solution of α,β-unsaturated ester (1.5 g, 4.9 mmol) in DMSO (4 mL) was added. The mixture obtained was stirred at 50° C. for 2 hours before it was worked-up (EtOAc/H$_2$O). The residue obtained after evaporation of the organics was purified by chromatography over silica gel (hexanes/EtOAc 95:5 to 85:15) to give rise to the cyclopropyl derivative (500 mg, mixture of cis/trans isomers 65:35, 32%). The silylether (500 mg, 3.1 mmol) was dissolved in THF (3 mL) and acetic acid (40 μL) was added followed by TBAF (1 M in THF, 3 mL). The mixture was stirred for 2 hours at room temperature and after usual work-up the residue was purified by silica gel chromatography (CH$_2$Cl$_2$/hexanes (1:1)/EtOAc 95:5 to 50:50) to furnish the primary alcohol (320 mg, mixture of cis/trans isomers 65:35, quant.).

Step 2. The azide derivative synthesis was similar to step 5 of example 1 (275 mg, 76%, 65:35 mixture of isomers).

Step 3. Cycloaddition and hydrolysis reactions were performed in a similar fashion to example 125 to afford the title compound. $^1$H NMR (400 MHz, DMSO-d$_6$) δ 12.33 (brs, 1H), 8.66 (s, 1H), 8.57 (s, 1H), 8.45 (dd, J=8.0 Hz, 1H), 7.98 (d, J=8.0 Hz, 1H), 7.80 (s, 1H), 7.77-7.67 (m, 2H), 7.38 (d, J=8.0 Hz, 1H), 7.10 (dt, J=8.0 Hz, 1H), 6.88 (brs, 2H), 5.75 (s, 2H), 2.59-2.51 (m, 1H), 1.94-1.84 (m, 1H), 1.43-1.28 (m, 1H). MS [M+H]$^+$ for $C_{23}H_{18}N_8O_2$, calcd 439.2, found: 439.3.

Example 130: 3-[6-({4-[2-Amino-6-(m-cyanophenyl)-4-pyrimidinyl]-1H-1,2,3-triazol-1-yl}methyl)-2-pyridyl]-3-methylbutyric acid

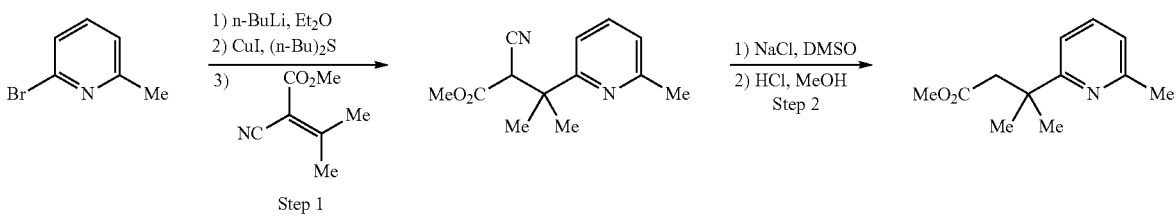

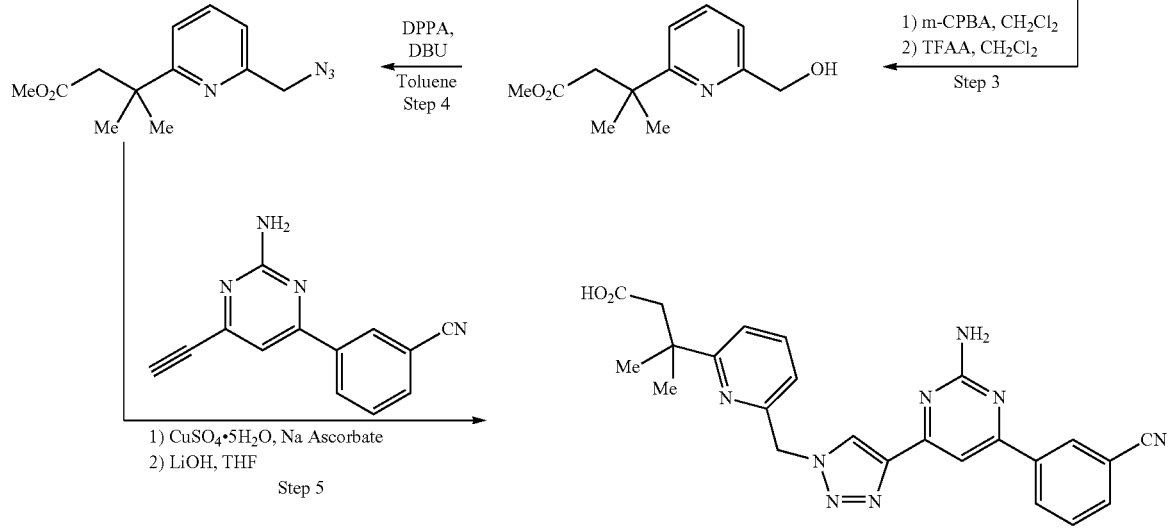

Step 1: A solution of n-butyllithium (144 mL, 360 mmol, 2.5 M in hexanes) in ether (120 mL) was cooled to −78° C. and 2-bromo-6-methylpyridine (41.0 mL, 360 mmol) was added dropwise. The reaction mixture was warmed to 0° C. and stirred at this temperature for 15 minutes. In a separate flask dibutyl sulfide (54.5 mL, 312 mmol) and copper(I) iodide (34.3 g, 180 mmol) were combined and the mixture stirred for 5 minutes until homogeneous. Ether (240 mL) was added, the solution cooled to 0° C., and the pyridine solution from above was added dropwise. The mixture was stirred for an additional 20 minutes at 0° C. at which point a solution of the acrylate (16.7 g, 120 mmol) in ether (120 mL) was added. The reaction mixture was warmed to room temperature over 14 hours. The mixture was quenched with saturated ammonium chloride solution and extracted ethyl acetate (2×200 mL), washed with brine, and dried over sodium sulfate. The crude product was purified by silica gel chromatography (0 to 20% EtOAc in hexanes) to afford the desired Michael addition product as a brown oil (16.44 g; 59%).

Step 2: A mixture of the step 1 product (16.44 g, 70.8 mmol), sodium chloride (1.24 g, 21.2 mmol), water (1.42 mL), and DMSO (71 mL) were stirred at 160° C. for 3 hours. The reaction mixture was cooled, MTBE (500 mL) was added, the organic phase washed with water (4×400 mL), and dried over sodium sulfate. The crude material was dissolved in 3.0 M methanolic HCl (236 mL) and stirred at 50° C. for 60 h. The reaction mixture was slowly quenched with sodium bicarbonate$_{(s)}$, filtered, and concentrated. The crude product was purified by silica gel chromatography (7.5% EtOAc in hexanes) to afford the desired product as a colorless oil (8.73 g; 59%).

Step 3: To a solution of the step 2 product (8.73 g, 42.1 mmol) in dichloromethane (168 mL) at 0° C. was added m-CPBA (19.9 g, 84.2 mmol, 75% in water) slowly as a solid over 5 minutes. The reaction mixture was stirred at 0° C. for 1 hour and at room temperature for 14 hours. The organic layer was washed with 0.1 M NaOH solution, dried over sodium sulfate, and concentrated. The crude material was re-dissolved in dichloromethane (84 mL), cooled to 0° C., and TFAA (59 mL) was added dropwise. The reaction mixture was stirred at room temperature for 3 hours. The reaction mixture was slowly quenched with a saturated $Na_2CO_3$ solution and extracted with ethyl acetate (3×200 mL). The crude material was purified by silica gel chromatography (0 to 75% EtOAc in hexanes) to afford the desired product as a red oil (5.55 g; 59%).

Step 4: To a mixture of the step 3 product (5.55 g, 24.9 mmol), DPPA (6.42 g, 29.8 mmol), and toluene (25 mL) was added DBU (4.46 mL, 29.8 mmol). The reaction mixture was stirred at room temperature for 14 hours. The mixture was purified by silica gel chromatography (0 to 20% EtOAc in hexanes) to afford the desired product as a colorless oil (5.53 g; 89%).

Step 5: Cycloaddition and hydrolysis reactions were performed in a similar fashion to example 125 to afford the title compound to afford the title compound as a white solid (33 mg, 24%). $^1$H NMR (400 MHz, DMSO-d$_6$) δ 11.86 (br s, 1H), 8.69 (s, 1H), 8.59 (s, 1H), 8.47 (d, J=8.3 Hz, 1H), 8.00 (d, J=7.7 Hz, 1H), 7.82 (s, 1H), 7.79-7.69 (m, 2H), 7.38 (d, J=7.9 Hz, 1H), 7.06 (d, J=7.6 Hz, 1H), 6.91 (s, 2H), 5.80 (s, 2H), 2.65 (s, 2H), 1.32 (s, 6H). ESI MS [M+H]$^+$ for $C_{24}H_{23}N_8O_2$, calcd 455.2, found 455.3.

Example 131: 3-[6-({4-[2-Amino-6-(3-cyano-2-methoxyphenyl)-4-pyrimidinyl]-1H-1,2,3-triazol-1-yl}methyl)-2-pyridyl]-3-methylbutyric acid

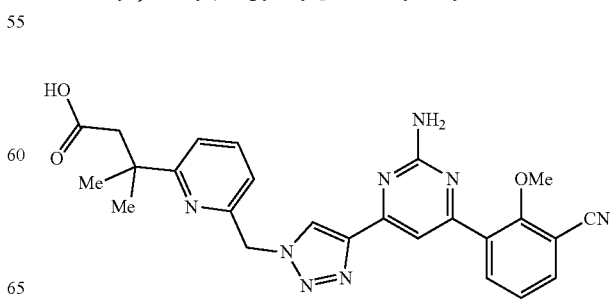

The title compound was prepared similar to example 130 from the corresponding azide and alkyne. $^1$H NMR (400 MHz, DMSO-d$_6$) δ 8.67 (s, 1H), 8.10-8.04 (m, 1H), 7.97-7.90 (m, 1H), 7.67-7.61 (m, 2H), 7.43 (t, J=7.7 Hz, 1H), 7.35 (d, J=8.0 Hz, 1H), 6.97 (d, J=7.6 Hz, 1H), 6.90 (s, 2H), 5.76 (s, 2H), 3.85 (s, 3H), 2.31 (s, 2H), 1.32 (s, 6H). ESI MS [M+H]$^+$ for C$_{25}$H$_{25}$N$_8$O$_3$, calcd 485.2, found 485.3.

Example 132: 3-[6-({4-[2-Amino-6-(3-fluoro-2-methoxyphenyl)-4-pyrimidinyl]-1H-1,2,3-triazol-1-yl}methyl)-2-pyridyl]-3-methylbutyric acid

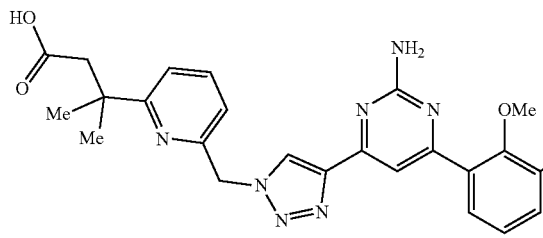

The title compound was prepared similar to example 130 from the corresponding azide and alkyne. $^1$H NMR (400 MHz, DMSO-d$_6$) δ 11.87 (br s, 1H), 8.63 (s, 1H), 7.75 (t, J=7.8 Hz, 1H), 7.64 (s, 1H), 7.60 (d, J=7.8 Hz, 1H), 7.45-7.40 (m, 1H), 7.38 (d, J=7.9 Hz, 1H), 7.23 (td, J=8.0, 5.1 Hz, 1H), 7.05 (d, J=7.6 Hz, 1H), 6.79 (s, 2H), 5.79 (s, 2H), 3.84 (s, 3H), 2.66 (s, 2H), 1.33 (s, 6H). ESI MS [M+H]$^+$ for C$_{24}$H$_{25}$FN$_7$O$_3$, calcd 478.2, found 478.2.

Example 133: 3-[6-({4-[2-Amino-6-(2,3-difluorophenyl)-4-pyrimidinyl]-1H-1,2,3-triazol-1-yl}methyl)-2-pyridyl]-3-methylbutyric acid

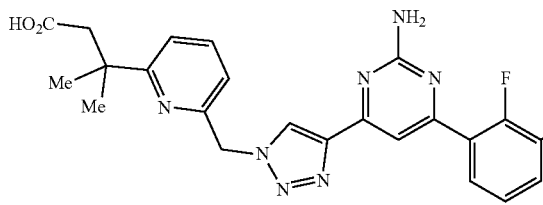

The title compound was prepared similar to example 130 from the corresponding azide and alkyne. $^1$H NMR (400 MHz, Acetone-d$_6$) δ 8.61 (s, 1H), 7.93-7.85 (m, 1H), 7.84 (s, 1H), 7.79 (dd, J=7.8, 7.8 Hz, 1H), 7.53-7.41 (m, 2H), 7.40-7.29 (m, 1H), 7.21 (d, J=7.8 Hz, 1H), 6.26 (s, 2H), 5.81 (s, 2H), 2.70 (s, 2H), 1.44 (s, 6H). MS [M+H]$^+$ for C$_{23}$H$_{21}$F$_2$N$_7$O$_2$, calcd 466.2, found 466.3.

Example 134: 3-[6-({4-[2-Amino-6-(3-cyano-2-fluorophenyl)-4-pyrimidinyl]-1H-1,2,3-triazol-1-yl}methyl)-2-pyridyl]-3-methylbutyric acid

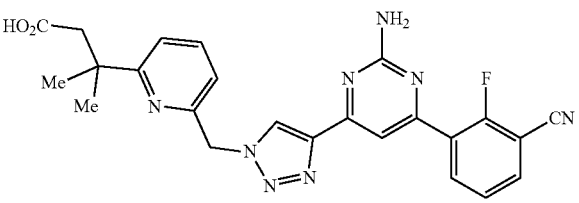

The title compound was prepared similar to example 130 from the corresponding azide and alkyne. $^1$H NMR (400 MHz, DMSO-d$_6$) δ 11.79 (brs, 1H), 8.66 (s, 1H), 8.34-8.24 (m, 1H), 8.07 (ddd, J=7.7, 6.0, 1.9 Hz, 1H), 7.73 (dd, J=7.8, 7.8 Hz, 1H), 7.61 (d, J=2.5 Hz, 1H), 7.56 (dd, J=7.8, 7.8 Hz, 1H), 7.36 (d, J=7.8 Hz, 2H), 7.04 (d, J=7.8 Hz, 1H), 6.95 (s, 2H), 5.78 (s, 2H), 2.63 (s, 2H), 1.30 (s, 6H). MS [M+H]$^+$ for C$_{24}$H$_{21}$FN$_8$O$_2$, calcd 471.2, found 471.2.

Example 135: 3-[6-({4-[2-Amino-6-(2-chloro-3-cyanophenyl)-4-pyrimidinyl]-1H-1,2,3-triazol-1-yl}methyl)-2-pyridyl]-3-methylbutyric acid

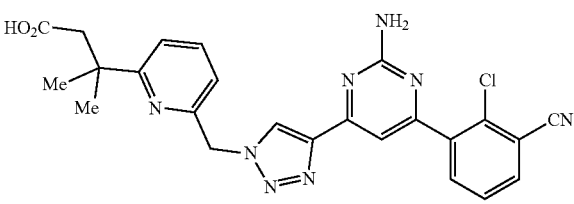

The title compound was prepared similar to example 130 from the corresponding azide and alkyne. $^1$H NMR (400 MHz, Acetone-d$_6$) δ 10.71 (brs, 1H), 8.62 (s, 1H), 7.99 (dd, J=7.7, 1.7 Hz, 1H), 7.94 (dd, J=7.8, 1.7 Hz, 1H), 7.78 (dd, J=7.8, 7.8 Hz, 1H), 7.69 (dd, J=7.8 Hz, 1H), 7.60 (s, 1H), 7.45 (d, J=7.9 Hz, 1H), 7.21 (d, J=7.6 Hz, 1H), 6.37 (brs, 2H), 5.80 (s, 2H), 2.81 (s, 2H), 1.43 (s, 6H). MS [M+H]$^+$ for C$_{24}$H$_{21}$ClN$_8$O$_2$, calcd 489.1, found 489.2.

Example 136: 3-[6-({4-[2-Amino-6-(3-cyanotolyl)-4-pyrimidinyl]-1H-1,2,3-triazol-1-yl}methyl)-2-pyridyl]-3-methylbutyric acid

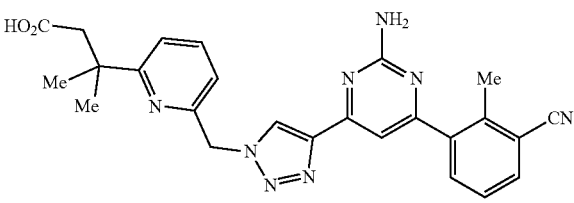

The title compound was prepared similar to example 130 from the corresponding azide and alkyne to afford 73 mg of a tan solid. $^1$H NMR (400 MHz, DMSO-d$_6$) 11.81 (s, 1H), 8.66 (d, J=0.7 Hz, 1H), 7.89 (dd, J=7.7, 1.4 Hz, 1H), 7.80-7.69 (m, 2H), 7.51 (t, J=7.8 Hz, 1H), 7.41-7.35 (m, 1H), 7.27 (d, J=0.5 Hz, 1H), 7.05 (d, J=7.7 Hz, 1H), 6.87 (s, 2H), 5.79 (s, 2H), 2.65 (s, 2H), 2.55 (s, 3H), 1.33 (s, 6H). ESI MS [M+H]+ for C25H24N8O2, calcd 469.2, found 469.3.

Example 137: 3-[6-({4-[2-amino-6-(o-fluorophenyl)-4-pyrimidinyl]-1H-1,2,3-triazol-1-yl}methyl)-2-pyridyl]-3-methylbutyric acid

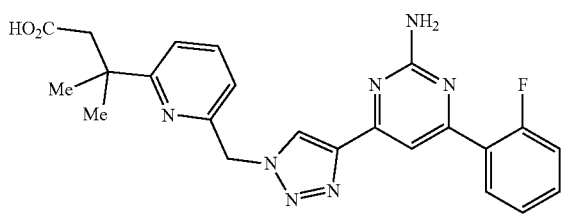

The title compound was prepared similar to example 130 from the corresponding azide and alkyne. 1H NMR (400 MHz, Acetone-d6) δ 8.59 (d, J=1.1 Hz, 1H), 8.12 (tt, J=7.9, 1.5 Hz, 1H), 7.87 (dd, J=2.4, 1.2 Hz, 1H), 7.78 (td, J=7.9, 1.1 Hz, 1H), 7.55 (dd, J=8.2, 7.1 Hz, 1H), 7.46 (dd, J=8.0, 1.1 Hz, 1H), 7.39-7.24 (m, 2H), 7.21 (dt, J=7.6, 1.0 Hz, 1H), 6.22 (s, 2H), 5.80 (s, 2H), 3.31 (s, 2H), 2.05 (p, J=2.2 Hz, 1H), 1.44 (s, 6H). ESI MS [M+H]+ for C23H22FN7O2, calcd 448.2, found 448.3.

Example 138: 3-[6-({4-[2-amino-6-(m-fluorophenyl)-4-pyrimidinyl]-1H-1,2,3-triazol-1-yl}methyl)-2-pyridyl]-3-methylbutyric acid

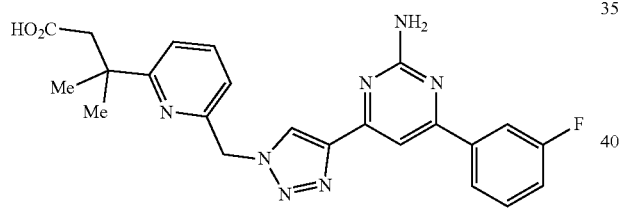

The title compound was prepared similar to example 130 from the corresponding azide and alkyne. 1H NMR (400 MHz, Acetone-d6) δ 8.98 (s, 1H), 8.14-8.06 (m, 1H), 8.06-7.97 (m, 2H), 7.80 (td, J=7.9, 1.3 Hz, 1H), 7.71-7.60 (m, 1H), 7.50-7.37 (m, 2H), 7.33-7.26 (m, 1H), 6.67 (s, 1H), 5.87 (d, J=1.2 Hz, 2H), 2.79 (s, 2H), 1.41 (s, 6H). ESI MS [M+H]+ for C23H22FN7O2, calcd 448.2, found 448.3.

Example 139: 3-[6-({4-[2-Amino-6-(3,4-difluorophenyl)-4-pyrimidinyl]-1H-1,2,3-triazol-1-yl}methyl)-2-pyridyl]-3-methylbutyric acid

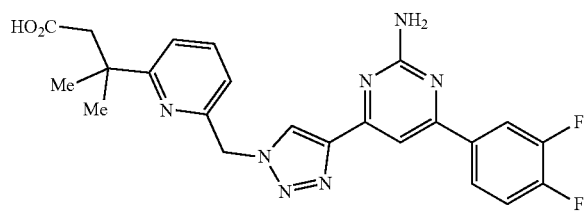

The title compound was prepared similar to example 130 from the corresponding azide and alkyne. 1H NMR (400 MHz, Acetone-d6) δ 8.95 (d, J=1.3 Hz, 1H), 8.25 (ddt, J=11.7, 7.8, 1.8 Hz, 1H), 8.21-8.12 (m, 1H), 7.97 (d, J=1.5 Hz, 1H), 7.80 (td, J=7.9, 1.5 Hz, 1H), 7.56 (dtd, J=10.1, 8.5, 1.4 Hz, 1H), 7.46 (dt, J=8.0, 1.2 Hz, 1H), 7.33-7.25 (m, 1H), 5.86 (s, 2H), 2.08-2.01 (m, 3H), 1.41 (d, J=1.4 Hz, 6H). ESI MS [M+H]+ for C23H21F2N7O2, calcd 466.2, found 466.3.

Example 140: 3-[6-({4-[2-Amino-6-(2,5-difluorophenyl)-4-pyrimidinyl]-1H-1,2,3-triazol-1-yl}methyl)-2-pyridyl]-3-methylbutyric acid

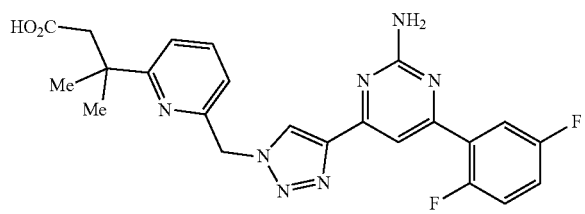

The title compound was prepared similar to example 130 from the corresponding azide and alkyne. 1H NMR (400 MHz, Acetone-d6) δ 8.75 (s, 1H), 7.98-7.85 (m, 2H), 7.79 (td, J=7.9, 1.7 Hz, 1H), 7.50-7.42 (m, 1H), 7.43-7.34 (m, 2H), 7.24 (d, J=7.5 Hz, 1H), 5.83 (s, 2H), 2.80 (s, 2H), 1.43 (s, 6H). ESI MS [M+H]+ for C23H21F2N7O2, calcd 466.2, found 466.2.

Example 141: 3-[6-({4-[2-Amino-6-(3-chloro-2-methoxyphenyl)-4-pyrimidinyl]-1H-1,2,3-triazol-1-yl}methyl)-2-pyridyl]-3-methylbutyric acid

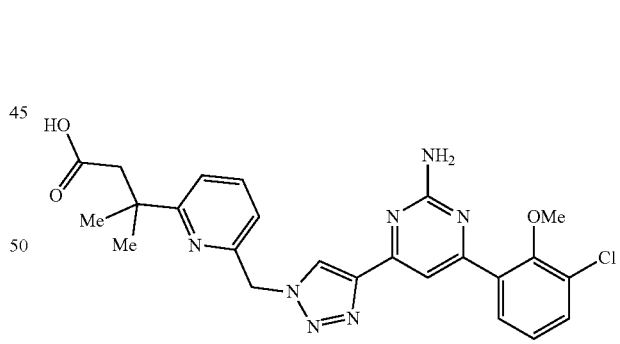

The title compound was prepared similar to example 130 from the corresponding azide and alkyne. 1H NMR (400 MHz, Chloroform-d) δ 8.57 (s, 1H), 7.89 (s, 1H), 7.69 (t, J=7.8 Hz, 1H), 7.60 (dd, J=7.9, 1.6 Hz, 1H), 7.47 (dd, J=8.0, 1.7 Hz, 1H), 7.42-7.38 (m, 1), 7.23 (d, J=7.6 Hz, 1H), 7.14 (t, J=7.9 Hz, 1H), 5.78 (s, 2H), 5.65 (s, 2H), 3.73 (s, 3H), 2.82 (s, 2H), 1.50 (s, 6H). ESI MS [M+H]+ for C24H24ClN7O3, calcd 494.2, found 494.2.

Example 142: 3-[6-({4-[2-Amino-6-(3-cyano-2-ethoxyphenyl)-4-pyrimidinyl]-1H-1,2,3-triazol-1-yl}methyl)-2-pyridyl]-3-methylbutyric acid

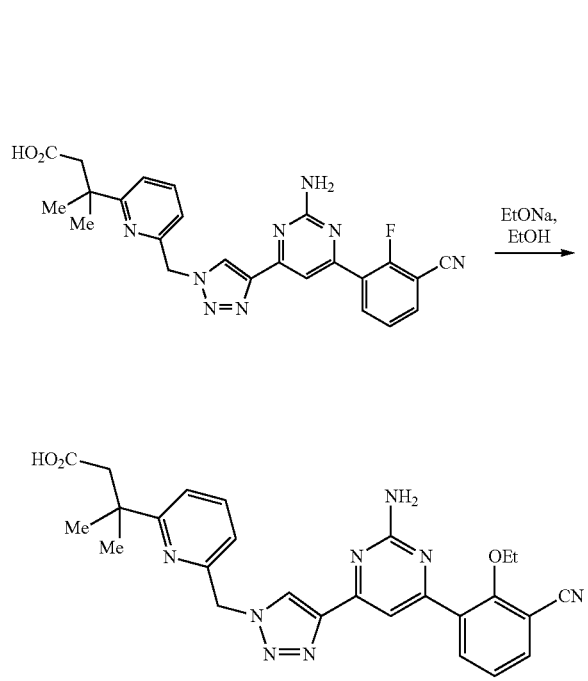

3-[6-({4-[2-Amino-6-(3-cyano-2-fluorophenyl)-4-pyrimidinyl]-1H-1,2,3-triazol-1-yl}methyl)-2-pyridyl]-3-methylbutyric acid (22 mg, 0.044 mmo) was taken in EtOH (1 mL) and excess EtONa was added. The reaction was stirred at 45° C. overnight and then quenched with excess acetic acid. After evaporation of the solvents, the residue was purified by chromatography over silica gel (CH$_2$Cl$_2$/MeOH, 100:0 to 90:10) to afford the desired compound (14 mg, 60%). $^1$H NMR (400 MHz, Acetone-d$_6$) δ 8.61 (s, 1H), 8.20 (dd, J=7.9, 1.4 Hz, 1H), 7.99 (s, 1H), 7.85 (dd, J=7.7 Hz, J=1.8 Hz, 1H), 7.79 (dd, J=7.9, 7.7 Hz, 1H), 7.50-7.39 (m, 2H), 7.23 (dd, J=7.7 Hz, 2H), 6.27 (brs, 2H), 5.80 (s, 2H), 4.11 (q, J=7.0 Hz, 1H), 2.80 (s, 2H), 1.43 (s, 6H), 1.37 (t, J=7.0 Hz, 3H). MS [M−H]$^−$ for C$_{26}$H$_{26}$N$_8$O$_3$, calcd 497.2, found 497.3.

Example 143: 3-[6-({4-[2-Amino-6-(m-cyanophenyl)-4-pyrimidinyl]-5-methyl-1H-1,2,3-triazol-1-yl}methyl)-2-pyridyl]-3-methylbutyric acid

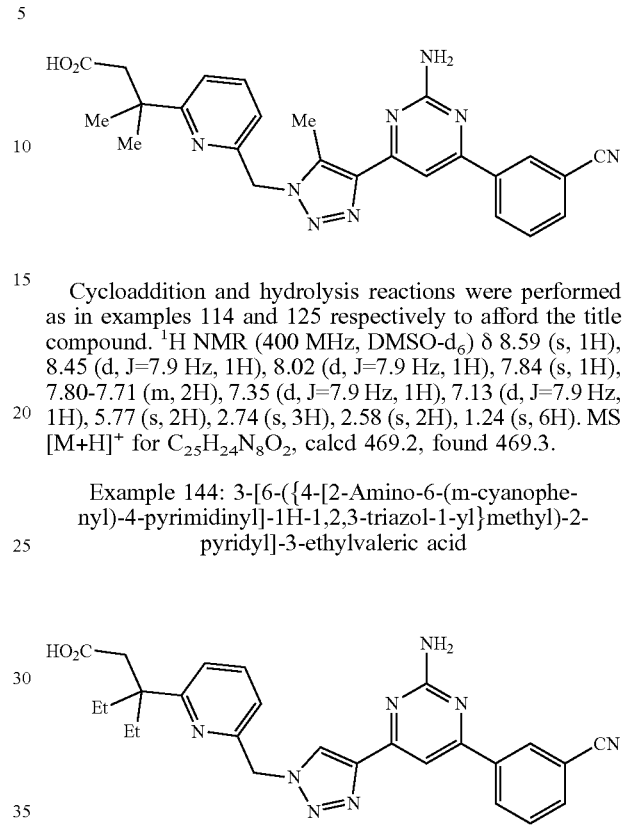

Cycloaddition and hydrolysis reactions were performed as in examples 114 and 125 respectively to afford the title compound. $^1$H NMR (400 MHz, DMSO-d$_6$) δ 8.59 (s, 1H), 8.45 (d, J=7.9 Hz, 1H), 8.02 (d, J=7.9 Hz, 1H), 7.84 (s, 1H), 7.80-7.71 (m, 2H), 7.35 (d, J=7.9 Hz, 1H), 7.13 (d, J=7.9 Hz, 1H), 5.77 (s, 2H), 2.74 (s, 3H), 2.58 (s, 2H), 1.24 (s, 6H). MS [M+H]$^+$ for C$_{25}$H$_{24}$N$_8$O$_2$, calcd 469.2, found 469.3.

Example 144: 3-[6-({4-[2-Amino-6-(m-cyanophenyl)-4-pyrimidinyl]-1H-1,2,3-triazol-1-yl}methyl)-2-pyridyl]-3-ethylvaleric acid The title compound was prepared similar to example 130 from the corresponding azide and alkyne. $^1$H NMR (400 MHz, DMSO-d$_6$) δ 8.91 (s, 1H), 8.62 (s, 1H), 8.49 (d, J=7.9 Hz, 1H), 8.05 (d, J=7.7 Hz, 1H), 7.96 (s, 1H), 7.82-7.73 (m, 2H), 7.32 (d, J=8.0 Hz, 1H), 7.15 (d, J=7.8 Hz, 1H), 5.86 (s, 2H), 2.66 (s, 2H), 1.75 (q, J=7.2 Hz, 4H), 0.54 (t, J=7.2 Hz, 6H). MS [M+H]$^+$ for C$_{26}$H$_{26}$N$_8$O$_2$, calcd 483.2, found 483.3.

Example 145: 3-[6-({4-[2-Amino-6-(3-cyano-2-fluorophenyl)-4-pyrimidinyl]-1H-1,2,3-triazol-1-yl}methyl)-2-pyridyl]-3-methylvaleric acid

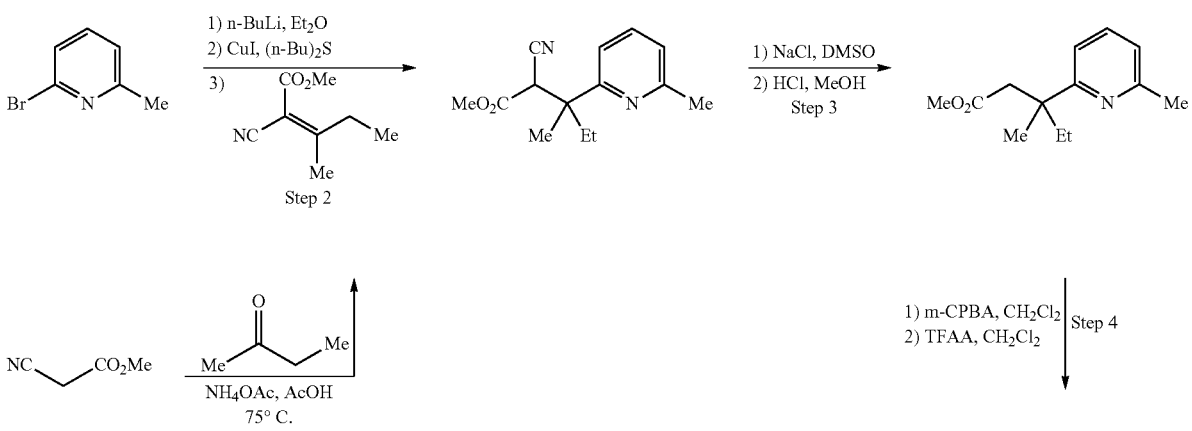

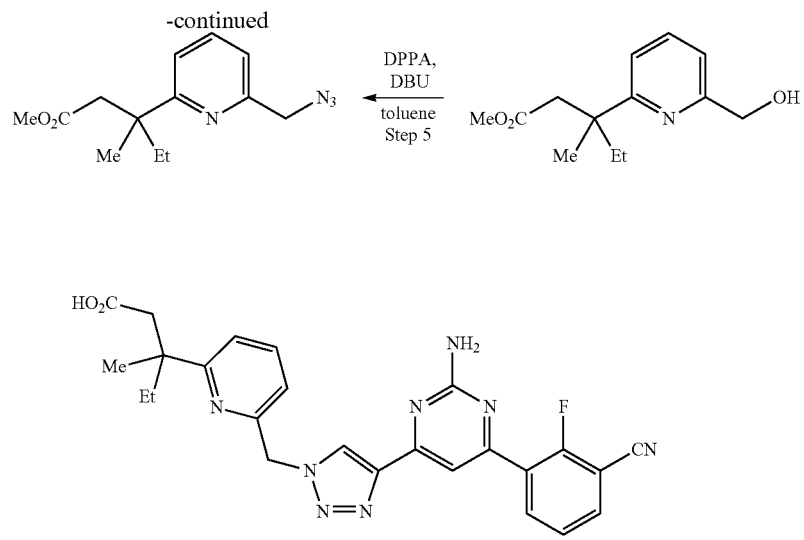

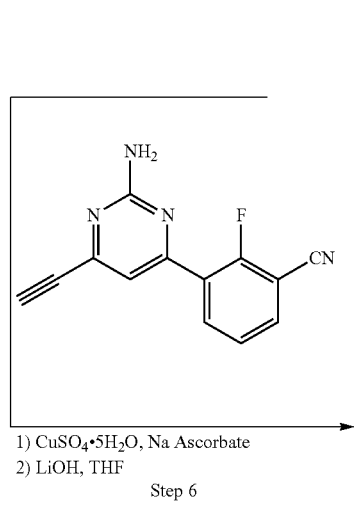

1) CuSO₄·5H₂O, Na Ascorbate
2) LiOH, THF
Step 6

Step 1: A mixture of methyl cyanoacetate (24.8 g, 250 mmol), 2-butanone (112 mL, 1.25 mol), ammonium acetate (1.93 g, 25.0 mmol), and acetic acid (2.86 mL, 50.0 mmol) was stirred at 75° C. for 4 hours. Excess 2-butanone was removed under reduced pressure and the crude material was dissolved in MTBE. The organic phase was washed with sat. NaHCO₃ (aq) and dried with Na₂SO₄. The crude product was purified by silica gel chromatography (0 to 30% EtOAc in hexanes) to afford the desired product as a colorless oil (23.53 g; 61%).

Steps 2-5: The azide was synthesized in a similar manner to example 130: Colorless oil (3.77 g, 25%, 4 steps).

Step 6: The title compound was prepared similar to example 130 from the corresponding azide and alkyne to afford an off-white solid (24 mg, 23%). ¹H NMR (400 MHz, DMSO-d₆) δ 8.67 (s, 1H), 8.35-8.28 (m, 1H), 8.11-8.05 (m, 1H), 7.67 (t, J=7.8 Hz, 1H), 7.64-7.61 (m, 1H), 7.57 (t, J=7.8 Hz, 1H), 7.31 (d, J=8.0 Hz, 1H), 7.01 (d, J=7.7 Hz, 1H), 6.98 (s, 2H), 5.78 (s, 2H), 2.57 (d, J=14.6 Hz, 1H), 2.35 (d, J=14.6 Hz, 1H), 1.80-1.70 (m, 1H), 1.70-1.57 (m, 1H), 1.34 (s, 3H), 0.50 (t, J=8.0 Hz, 3H). ESI MS [M+H]⁺ for C₂₅H₂₄FN₈O₂, calcd 487.2, found 487.3.

Example 146: 3-[6-({4-[2-Amino-6-(m-cyanophenyl)-4-pyrimidinyl]-1H-1,2,3-triazol-1-yl}methyl)-2-pyridyl]-3-methylvaleric acid The title compound was prepared similar to example 130 from the corresponding azide and alkyne. ¹H NMR (400 MHz, DMSO-d₆) δ 8.78 (s, 1H), 8.65-8.58 (m, 1H), 8.51-8.45 (m, 1H), 8.03 (dt, J=7.7, 1.3 Hz, 1H), 7.88 (s, 1H), 7.76 (td, J=7.8, 1.4 Hz, 2H), 7.34 (d, J=8.0 Hz, 1H), 7.11 (d, J=7.7 Hz, 1H), 5.83 (s, 2H), 2.81 (d, J=15.2 Hz, 1H), 2.50 (d, J=15.2 Hz, 1H), 1.71 (dq, J=14.6, 7.3 Hz, 1H), 1.60 (dq, J=14.3, 7.3 Hz, 1H), 1.35 (s, 3H), 0.53 (t, J=7.4 Hz, 3H). ESI MS [M+H]⁺ for C₂₅H₂₅N₈O₂, calcd 469.2, found 469.3.

Example 147: (S)-3-[6-({4-[2-Amino-6-(3-cyano-2-fluorophenyl)-4-pyrimidinyl]-1H-1,2,3-triazol-1-yl}methyl)-2-pyridyl]-3-methylvaleric acid; and Example 148: (R)-3-[6-({4-[2-Amino-6-(3-cyano-2-fluorophenyl)-4-pyrimidinyl]-1H-1,2,3-triazol-1-yl}methyl)-2-pyridyl]-3-methylvaleric acid

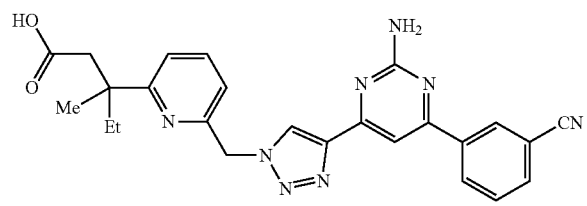

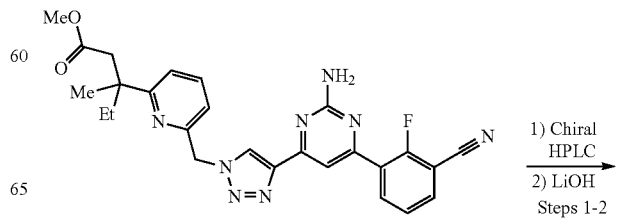

1) Chiral HPLC
2) LiOH
Steps 1-2

-continued

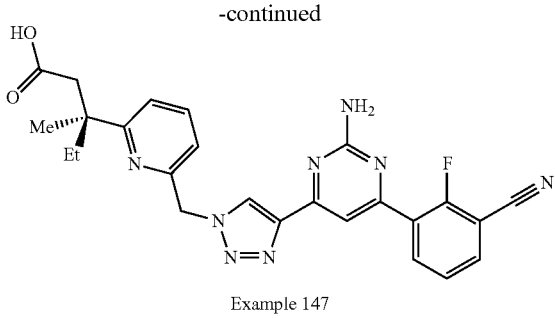

Example 147

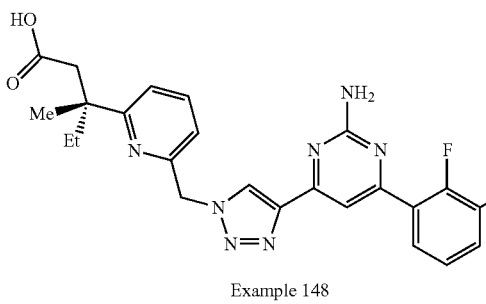

Example 148

Step 1: Methyl 3-[6-({4-[2-amino-6-(3-cyano-2-fluorophenyl)-4-pyrimidinyl]-1H-1,2,3-triazol-1-yl}methyl)-2-pyridyl]-3-methylvalerate obtained from example 145 was separated by chiral HPLC (AD-H; Ethanol+0.5% DEA/ CO$_2$) to afford the desired chiral esters as a white solids. Enantiomer 147A (170 mg, 45%) and enantiomer 148B (174 mg, 46%).

Step 2: Hydrolysis of the enantiomeric esters (147A and 148B) similar to example 125 yielded the title compounds (example 147 and 148)

Example 147: White solid (86 mg, 52%). $^1$H NMR (400 MHz, DMSO-d$_6$) δ 11.83 (br s, 1H), 8.66 (s, 1H), 8.31 (td, J=7.8, 1.8 Hz, 1H), 8.12-8.05 (m, 1H), 7.74 (t, J=7.8 Hz, 1H), 7.62 (d, J=1.8 Hz, 1H), 7.57 (t, J=7.8 Hz, 1H), 7.33 (d, J=7.9 Hz, 1H), 7.07 (d, J=7.6 Hz, 1H), 6.96 (s, 2H), 5.80 (s, 2H), 2.79 (d, J=15.1 Hz, 1H), 2.50 (d, J=15.1 Hz, 1H), 1.79-1.66 (m, 1H), 1.66-1.55 (m, 1H), 1.35 (s, 3H), 0.53 (t, J=7.4 Hz, 3H). ESI MS [M–H]$^-$ for C$_{25}$H$_{22}$FN$_8$O$_2$, calcd 485.2, found 485.2.

Example 148: White solid (89 mg, 53%). $^1$H NMR (400 MHz, DMSO-d$_6$) δ 11.84 (br s, 1H), 8.66 (s, 1H), 8.35-8.27 (m, 1H), 8.13-8.04 (m, 1H), 7.74 (t, J=7.8 Hz, 1H), 7.62 (d, J=2.4 Hz, 1H), 7.57 (t, J=7.8 Hz, 1H), 7.33 (d, J=7.7 Hz, 1H), 7.07 (d, J=7.5 Hz, 1H), 6.96 (s, 2H), 5.80 (s, 2H), 2.79 (d, J=15.1 Hz, 1H), 2.50 (d, J=15.0 Hz, 1H), 1.78-1.66 (m, 1H), 1.66-1.55 (m, 1H), 1.35 (s, 3H), 0.53 (t, J=7.4 Hz, 3H). ESI MS [M–H]$^-$ for C$_{25}$H$_{22}$FN$_8$O$_2$, calcd 485.2, found 485.3.

Example 149: {1-[6-({4-[2-Amino-6-(m-cyanophenyl)-4-pyrimidinyl]-1H-1,2,3-triazol-1-yl}methyl)-2-pyridyl]cyclobutyl}acetic acid

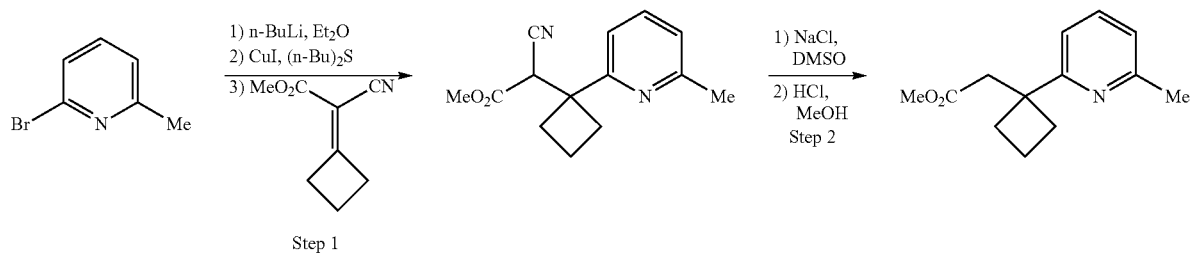

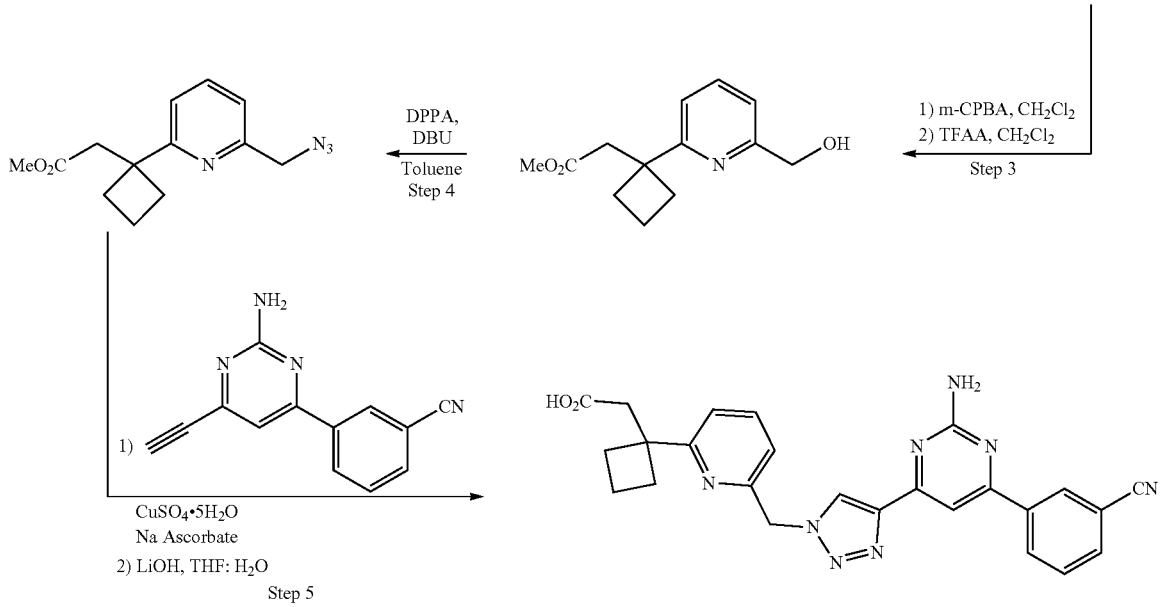

Step 1: To a solution of n-BuLi (2.5 M in hexanes, 5.4 mL, 13.5 mmol, 1.5 equiv), in Et$_2$O (4.5 mL) under N2 at −78° C. was added 2-bromo-6-methylpyridine (1.5 mL, 13.5 mmol, 1.5 equiv) slowly dropwise. In a separate flask, dibutyl sulfide (2.6 mL, 13.5 mmol, 1.5 equiv) and CuI (1.3 g, 6.8 mmol, 0.75 equiv) were combined under N$_2$, stirred for 15 minutes, and then taken up in Et$_2$O (11.3 mL) and cooled to 0° C. After 15 minutes, the solution of 2-bromo-6-methylpyridine was slowly cannulated into the flask containing dibutyl sulfide and CuI. The resulting mixture was stirred at 0° C. for 20 minutes. Following this time, a solution of methyl cyanocyclobutylideneacetate (1.4 g, 9.0 mmol, 1.0 equiv) in Et$_2$O (9.0 mL) was added to the reaction mixture at 0° C. After the addition was complete, the reaction was warmed to room temperature. After 20 h the reaction mixture was cooled to 0° C. and quenched by the addition of saturated aqueous NH$_4$Cl (50 mL). The biphasic mixture was diluted with EtOAc (560 mL) and transferred to a separatory funnel. The organic phase was collected and the aqueous phase was extracted with EtOAc (2×30 mL). The combined organic extracts were dried over MgSO$_4$, and concentrated in vacuo. The resulting residue was purified by column chromatography (1:9 EtOAc:hexanes→2:3 EtOAc:hexanes) to give methyl cyano[1-(6-methyl-2-pyridyl)cyclobutyl]acetate (535 mg, 24% yield).

Step 2: A solution of methyl cyano[1-(6-methyl-2-pyridyl)cyclobutyl]acetate (535 mg, 2.2 mmol, 1.0 equiv) and NaCl (38 mg, 0.65 mmol, 0.3 equiv) in DMSO (2.2 mL, 1.0 M) and H$_2$O (45 µL) was heated to 160° C. for 3.5 h. Following this time, the reaction mixture was cooled to room temperature and diluted with MTBE (10 mL) and H$_2$O (10 mL). The organic phase was collected and the aqueous phase was extracted with MTBE (2×10 mL). The combined organic extracts were dried over Na$_2$SO$_4$, and concentrated in vacuo. The resulting residue was purified by column chromatography (0:1 EtOAc:hexanes+2:3 EtOAc:hexanes) to give [1-(6-methyl-2-pyridyl)cyclobutyl]acetonitrile (161 mg, 39% yield).

A solution of [1-(6-methyl-2-pyridyl)cyclobutyl]acetonitrile (161 mg, 0.86 mmol, 1.0 equiv) in 3 M HCl in methanol (2.9 mL, 0.3 M) was heated to 60° C. for 8.5 h. Following this time, the reaction mixture was concentrated in vacuo. The resulting residue was taken up in CH$_2$Cl$_2$ (10 mL) and washed with 1:1 H$_2$O: saturated aqueous NaHCO$_3$ (10 mL). The organic phase was collected, dried over Na$_2$SO$_4$ and concentrated in vacuo. cooled to room temperature and diluted with MTBE (10 mL) and H$_2$O (10 mL). The organic phase was collected and the aqueous phase was extracted with MTBE (2×10 mL). The resulting residue was purified by column chromatography (1:9 EtOAc:hexanes+2:3 EtOAc:hexanes) to give methyl [1-(6-methyl-2-pyridyl)cyclobutyl]acetate (148 mg, 78% yield).

Step 3: To a solution of methyl [1-(6-methyl-2-pyridyl)cyclobutyl]acetate (148 mg, 0.67 mmol, 1.0 equiv) in CH$_2$Cl$_2$ (2.7 mL, 0.25 M) at 0° C. was added 3-chloroperbenzoic acid (154.9 mg, 0.67 mmol, 1.0 equiv). The reaction was slowly warmed to room temperature and then stirred for 14 h. Following completion, the reaction was loaded directly onto SiO$_2$ and purified by column chromatography (0:1 MeOH:CH$_2$Cl$_2$+1:9 MeOH:CH$_2$Cl$_2$) to give methyl [1-(6-methyl-2-pyridyl)cyclobutyl]acetate N-oxide (157 mg, 99% yield).

To a solution of methyl [1-(6-methyl-2-pyridyl)cyclobutyl]acetate N-oxide (157 mg, 0.67 mmol, 1.0 equiv) in CH$_2$Cl$_2$ (1.3 mL, 0.5 M) at 0° C. was added trifluoroacetic anhydride (940 µL, 6.6 mmol, 10.0 equiv). The solution was stirred at 0° C. for 15 minutes then warmed to room temperature. After 6 h, the reaction mixture was cooled to 0° C. and quenched with 2.0 M Na$_2$CO$_3$ (5 mL). The biphasic mixture was stirred at 0° C. for 1 h and then diluted with CH$_2$Cl$_2$ (10 mL). The organic phase was collected, washed with H$_2$O (10 mL), then dried over MgSO$_4$ and concentrated in vacuo. The residue was purified by column chromatography (0:1 MeOH:CH$_2$Cl$_2$→1:9 MeOH:CH$_2$Cl$_2$) to give methyl {1-[6-(hydroxymethyl)-2-pyridyl]cyclobutyl}acetate: (128 mg, 82% yield).

Step 4: To a solution of methyl {1-[6-(hydroxymethyl)-2-pyridyl]cyclobutyl}acetate (128 mg, 0.55 mmol, 1.0 equiv) in toluene (1.1 mL, 0.5 M) was added diphenylphosphoryl azide (141 µL, 0.65 mmol, 1.2 equiv.), followed by 1,8-diazabicyclo[5.4.0]undec-7-ene (98 µL, 0.65 mmol, 1.2 equiv.). The resulting mixture was heated to 60° C. for 4 h. The reaction mixture was then loaded directly onto SiO$_2$ and purified by column chromatography (0:1 EtOAc:hexanes+3:7 EtOAc:hexanes) to give methyl {1-[6-(azidomethyl)-2-pyridyl]cyclobutyl}acetate (101 mg, 72% yield) as a colorless oil.

Step 5: The title compound was prepared similar to example 130. $^1$H NMR (400 MHz, Acetone-d$_6$) δ 8.66-8.57 (m, 2H), 8.52 (dd, J=8.0, 1.4 Hz, 1H), 7.97-7.87 (m, 2H), 7.83-7.72 (m, 2H), 7.47 (d, J=7.9 Hz, 1H), 7.24-7.17 (m, 1H), 6.35 (s, 2H), 5.79 (s, 2H), 3.31 (s, 1H), 2.58-2.45 (m, 2H), 2.17-2.02 (m, 2H), 1.88 (dd, J=10.3, 5.5 Hz, 1H). ESI MS [M+H]$^+$ for C$_{25}$H$_{22}$N$_8$O$_2$, calcd 467.2, found 467.3.

Example 150: {1-[6-({4-[2-Amino-6-(3-cyano-2-fluorophenyl)-4-pyrimidinyl]-1H-1,2,3-triazol-1-yl}methyl)-2-pyridyl]cyclobutyl}acetic acid

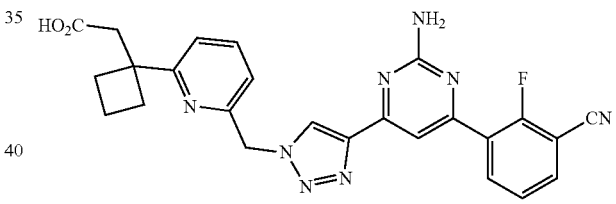

The title compound was prepared similar to example 149 from the corresponding azide and alkyne. $^1$H NMR (400 MHz, Acetone-d$_6$) δ 8.66 (s, 1H), 8.41 (t, J=7.8 Hz, 1H), 8.04-7.96 (m, 1H), 7.88-7.75 (m, 2H), 7.59 (t, J=7.9 Hz, 1H), 7.48 (d, J=8.0 Hz, 1H), 7.22 (d, J=7.6 Hz, 1H), 5.81 (d, J=0.9 Hz, 2H), 2.98 (s, 1H), 2.57-2.46 (m, 2H), 2.33 (s, 2H), 2.16-2.02 (m, 1H), 1.92-1.85 (m, 1H). ESI MS [M+H]$^+$ for C$_{25}$H$_{21}$FN$_8$O$_2$, calcd 485.2, found 485.3.

Example 151: {1-[6-({4-[2-Amino-6-(3-cyano-2-methoxyphenyl)-4-pyrimidinyl]-1H-1,2,3-triazol-1-yl}methyl)-2-pyridyl]cyclobutyl}acetic acid

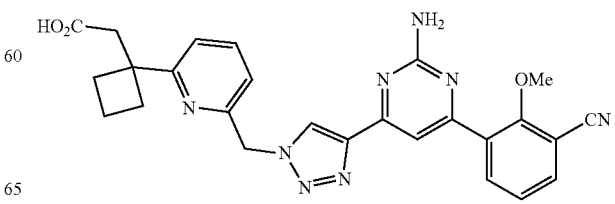

The title compound was prepared similar to example 149 from the corresponding azide and alkyne. ¹H NMR (400 MHz, Acetone-$d_6$) δ 8.80 (s, 1H), 8.16 (dt, J=7.9, 1.6 Hz, 1H), 7.96-7.88 (m, 2H), 7.81 (td, J=7.8, 1.4 Hz, 1H), 7.47 (td, J=7.8, 1.4 Hz, 2H), 7.25 (d, J=7.6 Hz, 1H), 5.83 (s, 2H), 4.00 (s, 3H), 2.98 (d, J=1.4 Hz, 2H), 2.62-2.45 (m, 2H), 2.16-2.02 (m, 1H), 2.35-2.32 (m, 2H), 1.88 (dt, J=10.9, 5.3 Hz, 1H). ESI MS [M+H]⁺ for $C_{26}H_{24}N_8O_3$, calcd 497.2, found 497.3.

Example 152: {3-[6-({4-[2-Amino-6-(m-cyanophenyl)-4-pyrimidinyl]-1H-1,2,3-triazol-1-yl}methyl)-2-pyridyl]tetrahydrofur-3-yl}acetic acid and then transferred via cannula to the flask containing CuI/Bu₂S. The resulting mixture was stirred for 20 minutes at 0° C., then a solution of the Michael acceptor (5 g, 29.9 mmol, 1.0 equiv) in Et₂O (37.5 mL, 0.8 M) was added via cannula. The resulting mixture was stirred for 20 h while slowly warming to room temperature. After 20 h, the reaction mixture was cooled to 0° C., quenched with saturated aqueous NH₄Cl, and diluted with EtOAc. Air was bubbled through the reaction mixture for 6 h. Then, the reaction mixture was extracted with EtOAc and CH₂Cl₂. The combined organic extracts were washed with H₂O (2×), brine, dried (Na₂SO₄), filtered and concentrated in vacuo. The crude residue was purified by flash column chromatography

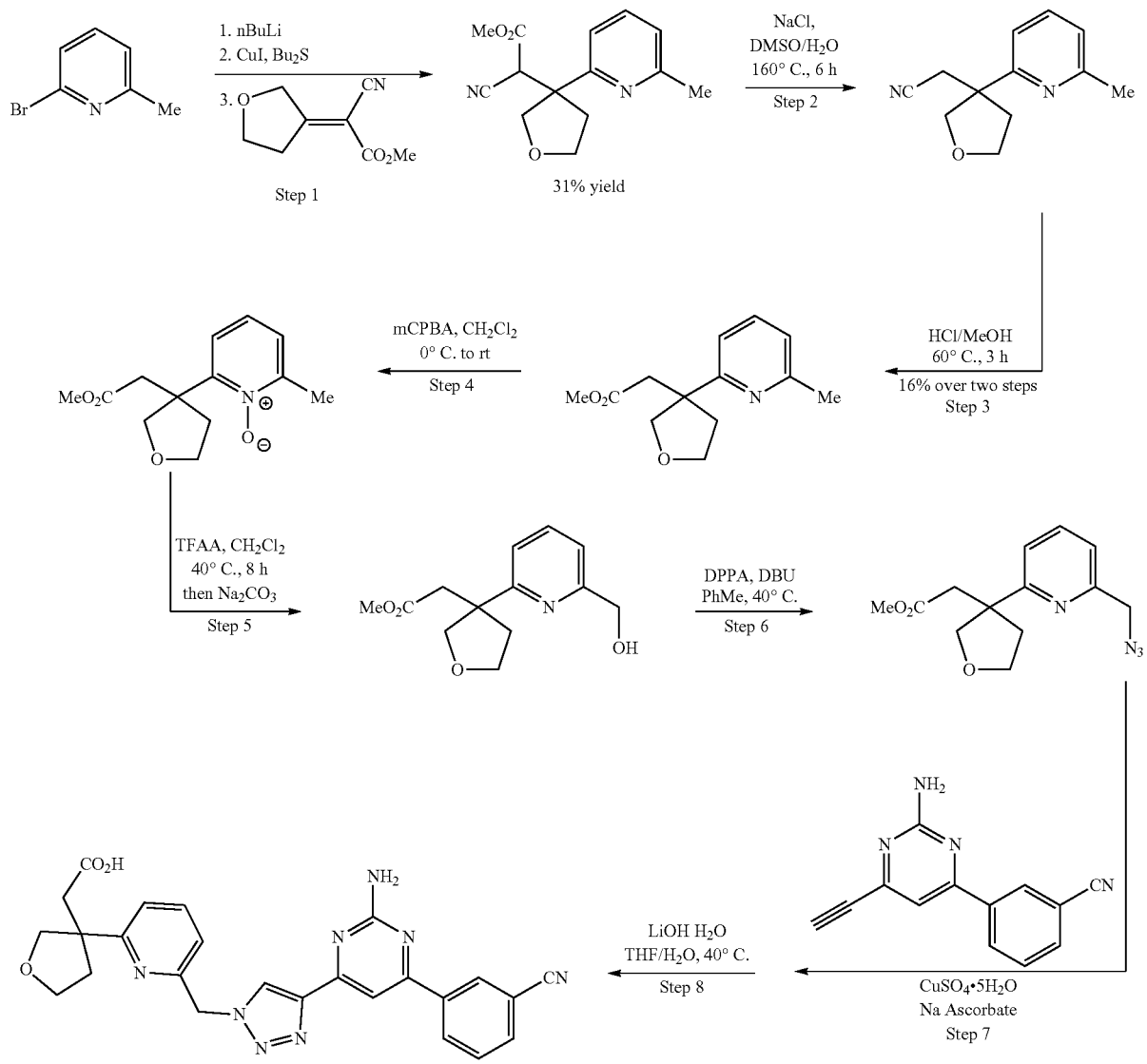

over silica (hexanes+80% hexanes/EtOAc+100% EtOAc) to afford the desired product as a colorless oil (488 mg, 6% yield).

Step 1: CuI (8.57 g, 44.8 mmol, 1.5 equiv) was added to a round-bottom flask and Bu₂S (13.5 mL, 77.5 mmol, 2.6 equiv) was then added. Then Et₂O (70 mL) was added and the solution was cooled to 0° C. In a separate flask, nBuLi (3.8 M in Et₂O, 89.5 mmol, 3.0 equiv) was cooled to −78° C. Bromopicoline (10.2 mL, 89.5 mmol, 3.0 equiv) was then added neat. The resulting mixture was stirred for 10 minutes Step 2: A mixture of the ester (488 mg, 1.88 mmol, 1.0 equiv) and NaCl (33 mg, 0.56 mmol, 0.3 equiv) in DMSO/H₂O (100:1, 3.75 mL, 0.5 M) was heated to 160° C. for 6 h. Upon completion, the reaction mixture was cooled to room temperature and diluted with H₂O and EtOAc (1:1, 10 mL). The layers were separated and the mixture was extracted with EtOAc (3×). The combined organic extracts were washed with brine, dried (Na₂SO₄), filtered, and concentrated in vacuo. The crude residue was used without further purification in Step 3.

Step 3: The crude residue obtained in Step 2 was dissolved in 3 N HCl in MeOH (2.04 mL). The reaction mixture was stirred at 60° C. for 3 h. Upon completion, the reaction mixture was cooled to room temperature and concentrated in vacuo. The residue was taken up in CH₂Cl₂ and washed with saturated aqueous NaHCO₃ solution (3×), dried (Na₂SO₄), filtered and concentrated in vacuo. The crude residue was purified by flash column chromatography over silica (CH₂Cl₂/MeOH gradient) to afford the product (72.8 mg, 16% yield over two steps).

Step 4: To an ice-cooled solution of the pyridine (72.8 mg, 0.309 mmol, 1.0 equiv) in CH₂Cl₂ (0.31 mL, 1 M) was added mCPBA (89 mg, 0.387 mmol, 1.25 equiv). The resulting solution was allowed to warm to room temperature and stirred at room temperature for 3 h. Upon completion, the reaction mixture was diluted with CH₂Cl₂, washed with saturated aqueous K₂CO₃, dried (Na₂SO₄), filtered and concentrated in vacuo. The crude residue was used directly in Step 5 without further purification.

Step 5: To a solution of the crude product obtained in Step 4 in CH₂Cl₂ (0.31 mL) was added TFAA (0.15 mL). The resulting solution was stirred at 40° C. for 8 h. Upon complete conversion to the TFA ester, the reaction mixture was cooled to room temperature and concentrated in vacuo. The crude residue was re-dissolved in CH₂Cl₂ (0.31 mL) and an aqueous solution of Na₂CO₃ (2M, 0.31 mL) was added. The mixture was stirred at room temperature for 1 h. Upon completion, the reaction mixture was extracted with CH₂Cl₂ (3×), dried (Na₂SO₄), filtered and concentrated in vacuo. The crude residue was purified by flash column chromatography over silica (CH₂Cl₂/MeOH gradient) to afford the product (55 mg, 70% yield over two steps).

Step 6: To a solution of the alcohol (55.0 mg, 0.219 mmol, 1.0 equiv) in PhMe (0.23 mL, 0.9 M) at room temperature was added DPPA (0.06 mL, 0.263 mmol, 1.2 equiv), followed by DBU (0.04 mL, 0.263 mmol, 1.2 equiv). The resulting mixture was stirred at room temperature for 10 minutes and then at 40° C. for 4 h. Upon completion, the reaction mixture was concentrated in vacuo and the resulting residue was purified by flash column chromatography over silica (hexanes/EtOAc) to afford the product as a pale colorless oil (31.6 mg, 52% yield).

Steps 7 and 8: Performed similarly to example 130. ¹H NMR (400 MHz, CDCl₃) δ 8.72 (s, 1H), 8.40 (s, 1H), 8.30-8.22 (m, 1H), 7.84 (s, 1H), 7.79-7.68 (m, 2H), 7.58 (t, J=8.0 Hz, 1H), 7.41 (d, J=8.0 Hz, 1H), 7.31 (d, J=7.4 Hz, 1H), 5.71-5.54 (m, 4H), 4.32-4.17 (m, 1H), 4.09-3.95 (m, 3H), 3.10 (d, J=15.6 Hz, 1H), 2.88 (d, J=15.4 Hz, 1H), 2.50-2.27 (m, 2H); LC-MS retention time 2.73 min LC-MS, Method A, ESI MS [M–H⁺]⁻ for C₂₅H₂₃N₈O₃, calcd 483.2, found 483.3.

Example 153: {3-[6-({4-[2-Amino-6-(3-cyano-2-fluorophenyl)-4-pyrimidinyl]-1H-1,2,3-triazol-1-yl}methyl)-2-pyridyl]tetrahydrofur-3-yl}acetic acid

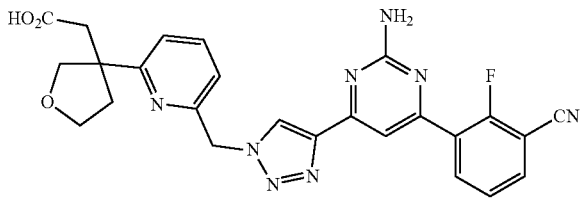

The title compound was prepared similar to example 152. ¹H NMR (400 MHz, Chloroform-d) δ 8.72 (d, J=1.1 Hz, 1H), 8.25 (t, J=7.7 Hz, 1H), 7.89 (s, 1H), 7.73 (t, J=7.9 Hz, 2H), 7.38 (t, J=8.0 Hz, 2H), 7.31 (d, J=7.5 Hz, 1H), 5.70-5.59 (m, 2H), 5.56 (s, 2H), 4.25 (d, J=9.3 Hz, 1H), 4.08-3.99 (m, 3H), 3.07 (d, J=15.5 Hz, 1H), 2.86 (d, J=15.2 Hz, 1H), 2.52-2.26 (m, 2H); LC-MS retention time 2.73 min LC-MS, Method A, ESI MS [M+H+]⁻ for C₂₅H₂₂FN₈O₃, calcd 501.2, found 501.3.

Example 154: {4-[6-({4-[2-Amino-6-(m-cyanophenyl)-4-pyrimidinyl]-1H-1,2,3-triazol-1-yl}methyl)-2-pyridyl]tetrahydro-2H-pyran-4-yl}acetic acid The title compound was prepared similar to example 152. ¹H NMR (400 MHz, Chloroform-d) δ 8.69 (s, 1H), 8.44 (s, 1H), 8.29 (d, J=7.7 Hz, 1H), 7.84-7.70 (m, 3H), 7.60 (t, J=7.8 Hz, 1H), 7.41 (d, J=8.1 Hz, 1H), 7.31 (d, J=7.5 Hz, 1H), 5.82 (s, 2H), 5.68 (s, 2H), 3.91-3.80 (m, 2H), 3.63-3.52 (m, 2H), 2.73 (s, 2H), 2.52-2.39 (m, 2H), 2.13-1.96 (m, 2H); LC-MS retention time 2.76 min LC-MS, Method A, ESI MS [M–H+]⁻ for C₂₆H₂₅N₈O₃, calcd 497.2, found 497.3.

Example 155: {4-[6-({4-[2-Amino-6-(3-cyano-2-fluorophenyl)-4-pyrimidinyl]-1H-1,2,3-triazol-1-yl}methyl)-2-pyridyl]tetrahydro-2H-pyran-4-yl}acetic acid The title compound was prepared similar to example 152. ¹H NMR (400 MHz, Chloroform-d) δ 8.67 (s, 1H), 8.27 (t, J=7.4 Hz, 1H), 7.86-7.82 (m, 1H), 7.80-7.70 (m, 2H), 7.42-7.34 (m, 2H), 7.31 (d, J=7.4 Hz, 1H), 5.80 (s, 2H), 5.68 (s, 2H), 3.91-3.80 (m, 2H), 3.62-3.52 (m, 2H), 2.72 (s, 2H), 2.52-2.37 (m, 2H), 2.13-1.95 (m, 2H); LC-MS retention time 2.76 min LC-MS, Method A, ESI MS [M–H⁺]⁻ for $C_{26}H_{24}FN_8O_3$, calcd 515.2, found 515.3.

Example 156: 4-[6-({4-[2-Amino-6-(3-cyano-2-methoxyphenyl)-4-pyrimidinyl]-1H-1,2,3-triazol-1-yl}methyl)-2-pyridyl]-4-methylvaleric acid tion mixture was filtered to remove imidazolium chloride, and the solid washed with a single portion of $CH_2Cl_2$ (100 ml). Methanol (100 ml) was added to the filtrate, and it was concentrated to a thin, cloudy oil, out of which more salts precipitate during concentration. This crude mixture was filtered through a 3-inch plug of silica gel with 750 ml of 15% ethyl acetate in hexanes. The filtrate was concentrated to a thin oil (121.5 g, 100.8% yield).

Step 2. Dicyclohecylamine (9.08 ml, 9.95 g, 54.9 mmol, 1.3 equiv.) was placed in a flame-dried 2-neck 500 ml

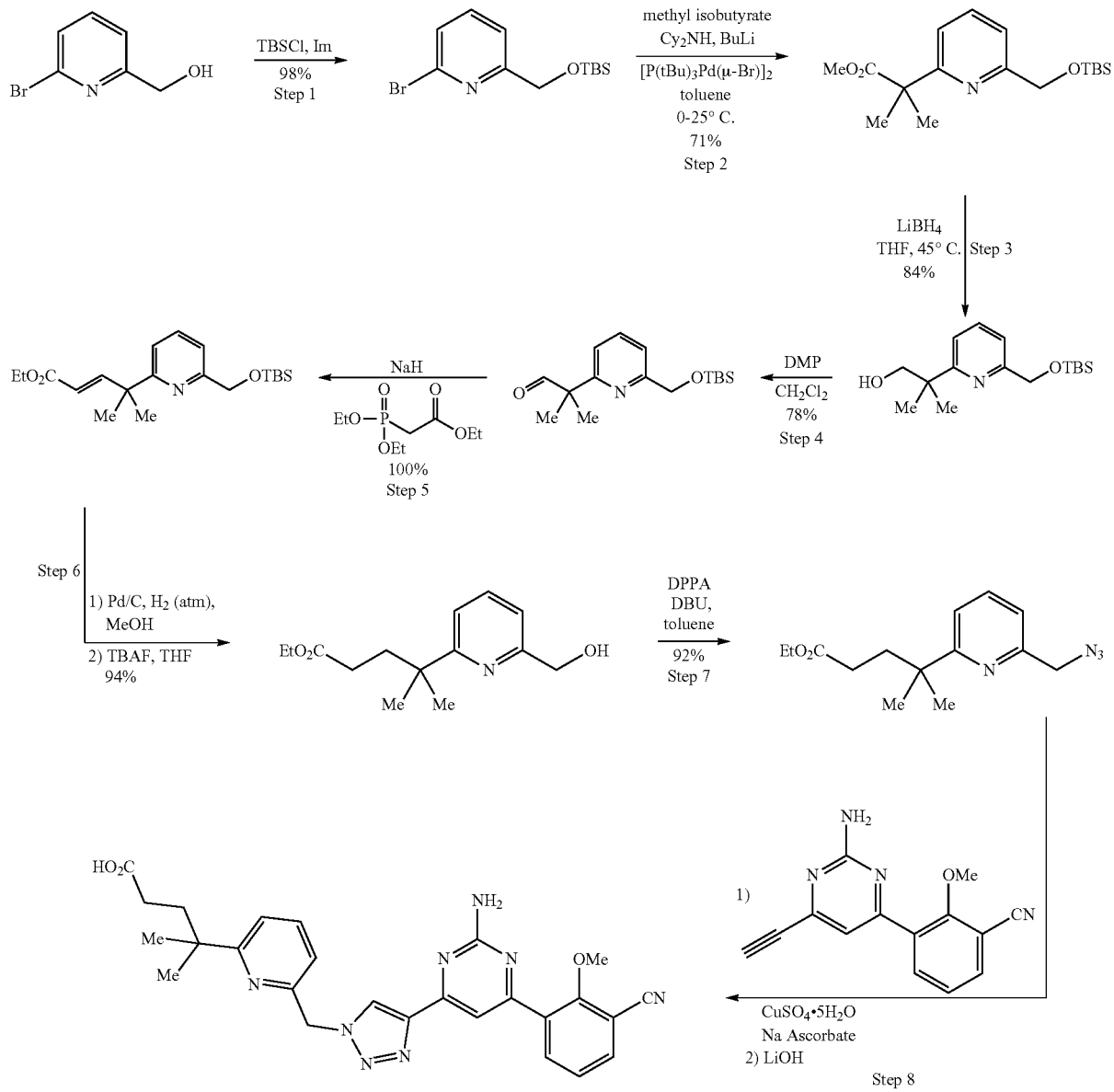

Step 1. (6-Bromo-pyridin-2-yl)methanol (75.0 g, 399.0 mmol, 1.0 equiv.) and imidazole (29.9 g, 439 mmol, 1.1 equiv.) were combined in $CH_2Cl_2$ (800 ml, 0.5 M). TBSCl (66.3 g, 439 mmol, 1.1 equiv.) was added potionwise to the solution at 0° C., which immediately forms a white precipitate. The reaction was warmed to room temperature and stirred for 20 minutes, at which point starting material consumption was confirmed by TLC and LCMS. The reacround-bottom flask and diluted with 100 ml of anhydrous toluene. The resulting solution was cooled to 0° C., and n-BuLi (20.76 ml, 2.5 M in hexanes, 1.23 equiv.) was added dropwise, and the reaction was stirred for 20 minutes at this temperature. Methyl isobutyrate (5.40 ml, 4.80 g, 46.84 mmol, 1.11 equiv.) was then added dropwise over a period of 20-30 minutes. Slow addition in this step is critical to avoid self-condensation of the isobutyrate. The solution was stirred for an additional 30 minutes before addition of the starting bromopyridine (12.76 g [~11 ml], 42.2 mmol, 1.0 equiv.) over 1 minute. The solution becomes a dark reddish brown upon addition of the pyridine. Following this addition, the reaction flask was evacuated and back-filled with nitrogen ×3. Prolonged (~1-2 minute) periods of vacuum are recommended by Hartwig prep. Following this step, bromo (tri-tert-butylphosphine)palladium(I) dimer [P(tBu)$_3$Pd(μ-Br)]$_2$ was added under a stream of nitrogen (24.8 mg, 0.032 mmol, 0.00076 equiv.), after which the reaction was sealed, allowed to warm to room temperature, and stirred for 1 hour. At this point, an additional charge of catalyst was added (27.6 mg, 0.036 mmol, 0.00084 equiv.) and the reaction was stirred an additional 4 hours. There was incomplete conversion of the starting bromide, so an additional charge of catalyst (27.6 mg) was added, and the reaction was stirred overnight. Incomplete conversion after and additional 14 hours. The reaction was quenched by diluting with methyl tert-butyl ether (100 ml) followed by dropwise addition of 1.0 N aqueous HCl (70 ml). The resulting solid was filtered off, and the aqueous layer was removed from the resulting biphasic solution. The organic layer was washed with saturated NaHCO$_3$, brine, dried over Na$_2$SO$_4$, and concentration. The crude reaction oil was chromatographed on silica gel (5-20% ethyl acetate/hexanes) to yield a light yellow oil (9.64 g, 29.85 mmol, 71% yield).

Note: On larger scale (~100 mmol), the dropwise addition of methyl isobutyrate was attempted with an addition funnel. Addition of the isobutyrate neat on this scale was a complication, as the addition funnel's slowest addition rate was too fast for this context. Too fast addition of the isboutyrate results in the formation of byproduct A (shown below) which can only be separated by column chromatography after the LiBH$_4$ reduction step.

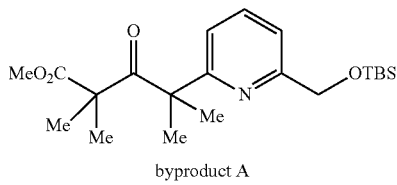 [SMILES: COC(=O)C(C)(C)C(=O)C(C)(C)c1cccc(CO[Si](C)(C)C(C)(C)C)n1]

byproduct A

Step 3. The pyridyl ester starting material (9.64 g, 29.85 mmol, 1.0 equiv) was placed in 60 ml of anhydrous THF (0.5M) and cooled to 0° C. Lithium borohydride (57.7 ml, 2.0 M in THF, 115.4 mmol, 4 equiv) was added dropwise by an addition funnel, after which the reaction was warmed to room temperature and then heated to 45° C. for 6 hours. Upon reaction completion, the reaction was cooled to 0° C. and quenched by dropwise addition of saturated aqueous NH$_4$Cl. Water was intermittently added when salt formation impeded stirring of the reaction mixture. Upon fully quenching remaining borohydride, the reaction was diluted with water to completely dissolve any salts, and the reaction was extracted ×2 with ethyl acetate. The organic layer was washed with brine, dried over sodium sulfate, filtered and concentrated. The crude product oil was wet loaded onto a silica column and chromatographed with a 5-20% ethyl acetate/hexanes gradient. Isolated 7.2 grams of clear oil (84% yield).

Step 4. To the alcohol starting material (11.5 g, 38.8 mmol, 1.0 equiv.) in CH$_2$Cl$_2$ (155 ml, 0.25 M) at room temperature was added Dess Martin periodinane (18.16 g, 42.68 mmol, 1.1 equiv.). The reaction was complete after 15 minutes. Upon completion, the reaction was cooled to 0° C. and 200 ml of a 1:1 mixture of saturated sodium bicarbonate and saturated sodium thiosulfate was added slowly to the reaction mixture. Upon warming to 25° C., mild off-gassing occurs due to protonation of the bicarbonate—this gas evolution will occur violently if the reaction is shaken vigorously before a significant amount of the acetic acid byproduct is quenched. Upon full neutralization of the acetic acid, the organic layer was separated, and the aqueous layer was washed ×1 with another portion of CH$_2$Cl$_2$. The combined organic phase was washed ×1 sat. NaHCO$_3$, ×1 water, ×1 brine, and concentrated. Upon concentration, salts form in the crude reaction oil. It was filtered through a short silica plug with a solution of 20% ethyl acetate in hexanes, and concentrated to a light yellow oil (10.88 g, 96% yield).

Step 5. Triethyl phosphonoacetate (4.15 ml, 4.69 g, 20.9 mmol, 1.1 equiv.) was placed in THF (69 ml, 0.3 M) and cooled to 0° C. NaH (836 mg, 20.9 mmol, 1.1 equiv., 60% in mineral oil) was added portionwise carefully to the resulting solution, and the mixture was stirred for 5 minutes to allow complete deprotonation of the phosphonoacetate. Starting aldehyde (5.59 g, 19.0 mmol) was then added as a solution in THF (19 ml, 1.0 M). The reaction mixture was allowed to warm to room temperature and was stirred overnight (~14 h). Upon reaction completion, the reaction was concentrated directly onto celite and columned with silica gel (0-20% ethyl acetate/hexanes). Isolated 6.91 g of clear oil (100% yield).

Step 6. Palladium on carbon (10 wt %, 689 mg, 10 wt % equiv.) was placed in a 100-ml flask equipped with stir bar. The flask was evacuated and refilled with nitrogen gas three times, before the addition of starting material (6.89 g, 19.0 mmol) in a solution of methanol (0.5M, 38 ml). The solution was sparged with hydrogen gas for ten minutes, and then stirred at room temperature under an H$_2$ atmosphere for 4 hours. The reaction was monitored by LCMS (SM ion m/z 364, product m/z 366). No new peaks by LCMS or new spots by TLC were observed, so LCMS or HNMR are required to monitor reaction progress. Upon complete consumption of starting material, the reaction was filtered through a short plug of silica gel, which was then rinsed with a 1:1 solution of methanol:CH$_2$Cl$_2$. The solution was then concentrated and taken onto the next step without further purification. The starting material (6.94 g, 19.0 mmol, 1.0 equiv.) was dissolved in THF (19 ml, 1.0 M). The resulting solution was cooled to 0° C., and tetrabutylammonium fluoride (19.0 ml, 1.0 M in THF, 1.0 equiv.) was added. The reaction was allowed to warm to room temperature, and the transformation was complete within 15 minutes. The reaction mixture was loaded directly onto celite, and columned (0-50% ethyl acetate/hexanes) to yield 4.46 grams of a clear oil (94% yield, 2 steps).

Step 7. The starting alcohol (4.46 g, 17.77 mmol, 1.0 equiv.) was dissolved in toluene (23.3 ml, 0.8 M). To this solution, diphenylphosphoryl azide (4.62 ml, 5.87 g, 21.32 mmol, 1.2 equiv.) was added, followed by the addition of DBU (3.21 ml, 3.25 g, 21.32 mmol, 1.2 equiv.). The resulting solution turns instantaneously cloudy a few seconds after complete addition of DBU, accompanied by a moderate exotherm. This exotherm is acceptable on small scales but may be a safety concern on larger scales—it is recommended to cool the reaction solution to 0° C. before the addition of DPPA and DBU on larger scales. The reaction was allowed to stir for 14 hours at room temperature, at which time the reaction was deemed complete upon complete consumption of the pyridyl phosphate ester. The reaction was partitioned between ethyl acetate and water. The organics were separated, washed with brine, and dried over sodium sulfate. The crude reaction mixture was columned on silica gel (10% ethyl acetate/hexanes, isocratic) to yield 4.77 g of the product azide as a clear, thin oil (97% yield).

Step 8. A round bottom flask was charged with the azide (414 mg, 1.5 mmol), the alkyne (375 mg, 1.5 mmol), CuSO$_4$·5H$_2$O (19 mg, 5% mol) and sodium ascorbate (59 mg, 20% mol). A 2:1 mixture of tert-butanol and water (mL) was added and the resulting mixture was heated to 65 C. After full consumption of the starting materials as judged by LCMS (2 hours), the mixture was directly loaded onto a silica column and purified by flash chromatography (hexanes/ethyl acetate 0 to 100%) to afford the desired adduct in 97% yield as a yellow pale solid (750 mg). The ester from step a (750 mg, 1.46 mmol) was dissolved in THF (8 mL) and the resulting solution was vigorously stirred. A solution of lithium hydroxide (1 M, 3.0 mL) was then added and the mixture was vigorously stirred at 35° C. until full consumption of the starting ester (12 hours). The medium was cooled to room temperature and excess acetic acid (0.6 mL) was added to quench the reaction mixture. After stirring for 10 minutes, silica (15 grams) was added and the reaction was evaporated to dryness. The residue was purified by flash chromatography over silica gel (CH$_2$Cl$_2$/0.1% acetic acid in ethyl acetate 0 to 100%) to afford the desired acid in 73% yield as a white solid (530 mg). $^1$H NMR (400 MHz, Acetone-d$_6$) δ 8.61 (s, 1H), 8.16 (s, J=7.8 Hz, 1H), 7.88-7.84 (m, 2H), 7.80 (dd, J=7.6, 7.6 Hz, 1H), 6.23 (brs, 2H), 5.83 (s, 2H), 3.93 (s, 3H), 2.85 (brs, 4H), 1.34 (s, 6H). ESI MS [M+H]$^+$ for C$_{26}$H$_{26}$N$_8$O$_3$, calcd 499.2, found 499.3.

Example 157: 4-[6-({4-[2-Amino-6-(m-cyanophenyl)-4-pyrimidinyl]-1H-1,2,3-triazol-1-yl}methyl)-2-pyridyl]-4-methylvaleric acid

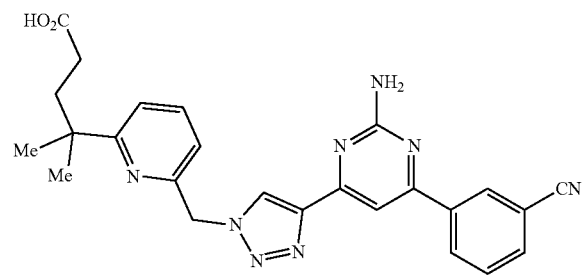

The title compound was prepared similar to example 156. $^1$H NMR (400 MHz, CD$_3$OD) δ 8.92 (m, 1H), 8.58 (s, 1H), 8.49 (d, J=8.2 Hz, 1H), 7.96 (m, 2H), 7.79-7.73 (m, 2H), 7.39 (d, J=8.1 Hz, 1H), 7.27 (dd, J=7.7, 2.7 Hz, 1H), 5.84 (s, 2H), 2.01-1.93 (m, 4H), 1.30 (s, 6H). ESI MS [M+H]$^+$ for C$_{25}$H$_{24}$N$_8$O$_2$ calcd 469.2, found 469.3 Example 158: 4-[6-({4-[2-Amino-6-(3-cyanotolyl)-4-pyrimidinyl]-1H-1,2,3-triazol-1-yl}methyl)-2-pyridyl]-4-methylvaleric acid.

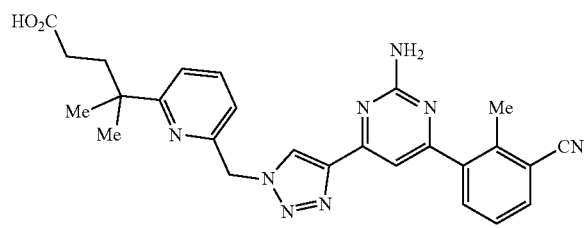

The title compound was prepared similar to example 156 to afford 65 mg of a tan solid. $^1$H NMR (400 MHz, DMSO-d$_6$) 11.93 (s, 1H), 8.68 (d, J=1.0 Hz, 1H), 7.90 (dd, J=7.7, 1.3 Hz, 1H), 7.80-7.73 (m, 2H), 7.51 (t, J=7.8 Hz, 1H), 7.36 (d, J=8.0 Hz, 1H), 7.27 (d, J=1.0 Hz, 1H), 7.06 (d, J=7.7 Hz, 1H), 6.88 (s, 2H), 5.81 (s, 2H), 2.55 (s, 3H), 1.94-1.84 (m, 4H), 1.28-1.20 (m, 6H). ESI MS [M+H]$^+$ for C$_{26}$H$_{26}$N$_8$O$_2$, calcd 483.2, found 483.2.

Example 159: 4-[6-({4-[2-Amino-6-(3-cyano-2-fluorophenyl)-4-pyrimidinyl]-1H-1,2,3-triazol-1-yl}methyl)-2-pyridyl]-4-methylvaleric acid

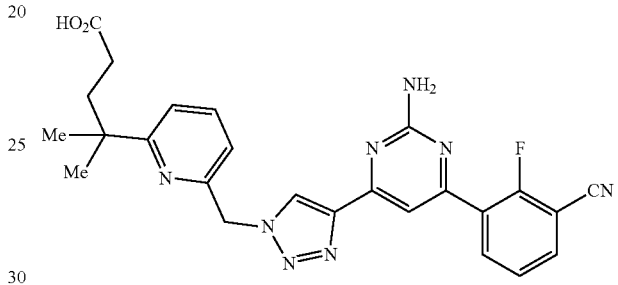

The title compound was prepared similar to example 156. $^1$H NMR (400 MHz, DMSO-d$_6$) δ 8.67 (s, 1H), 8.29 (dd, J=7.2, 7.2 Hz, 1H), 8.07 (dd, J=6.8, 6.8 Hz, 1H), 7.75 (dd, J=7.7, 7.7 Hz, 1H), 7.61 (s, 1H), 7.56 (dd, J=7.8, 7.8 Hz, 1H), 7.34 (d, J=7.9 Hz, 1H), 7.06 (d, J=7.7 Hz, 1H), 6.94 (brs, 2H), 5.80 (s, 2H), 1.87 (brs, 4H), 1.21 (s, 6H). ESI MS [M+H]$^+$ for C$_{25}$H$_{23}$FN$_8$O$_2$, calcd 487.2, found 487.3.

Example 160: 4-[6-({4-[2-Amino-6-(2,3-dichlorophenyl)-4-pyrimidinyl]-1H-1,2,3-triazol-1-yl}methyl)-2-pyridyl]-4-methylvaleric acid

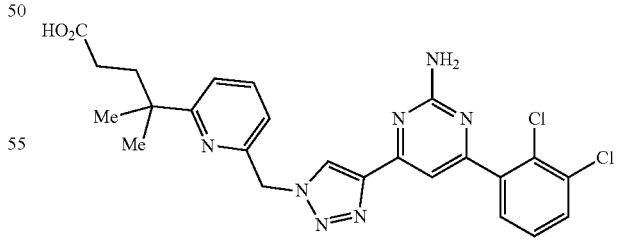

The title compound was prepared similar to example 156. $^1$H NMR (400 MHz, Acetone-d$_6$) δ 8.62 (d, J=1.0 Hz, 1H), 7.84-7.74 (m, 1H), 7.70 (ddd, J=8.0, 1.7, 1.1 Hz, 1H), 7.61-7.44 (m, 2H), 7.42 (d, J=8.0 Hz, 1H), 7.19 (d, J=7.7 Hz, 1H), 6.22 (s, 1H), 5.83 (s, 2H), 1.96 (d, J=1.0 Hz, 4H), 1.34 (s, 6H). ESI MS [M+H]$^+$ for C$_{24}$H$_{23}$Cl$_2$N$_7$O$_2$, calcd 512.1, found 512.2.

Example 161: 4-[6-({4-[2-Amino-6-(3-chloro-2-methoxyphenyl)-4-pyrimidinyl]-1H-1,2,3-triazol-1-yl}methyl)-2-pyridyl]-4-methylvaleric acid

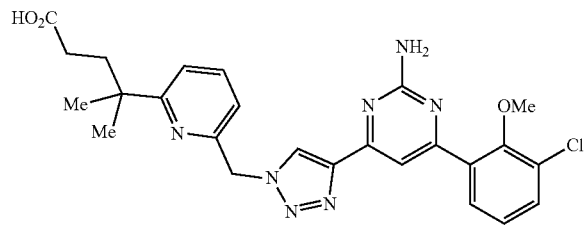

The title compound was prepared similar to example 156. $^1$H NMR (400 MHz, Chloroform-d) δ 11.31 (s, 1H), 8.53 (s, 1H), 7.85 (s, 1H), 7.64 (t, J=7.8 Hz, 1H), 7.56-7.50 (m, 1H), 7.47 (dd, J=8.0, 1.7 Hz, 1H), 7.28 (d, J=8.1 Hz, 1H), 7.18-7.06 (m, 2H), 5.68 (s, 2H), 3.73 (s, 3H), 2.20-2.09 (m, 4H), 1.34 (s, 6H). ESI MS [M+H]$^+$ for $C_{25}H_{26}ClN_7O_3$, calcd 508.2, found 508.2.

Example 162: 4-[6-({4-[2-Amino-6-(3-fluoro-2-methoxyphenyl)-4-pyrimidinyl]-1H-1,2,3-triazol-1-yl}methyl)-2-pyridyl]-4-methylvaleric acid

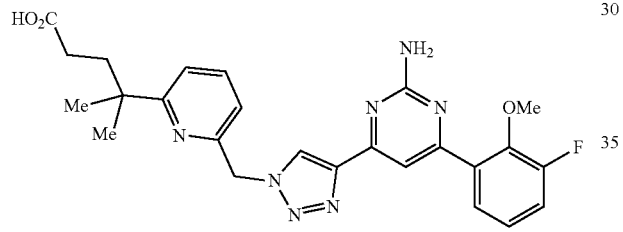

The title compound was prepared similar to example 156. $^1$H NMR (400 MHz, DMSO-d$_6$) δ 12.01 (br s, 1H), 8.65 (s, 1H), 7.76 (t, J=7.8 Hz, 1H), 7.64 (s, 1H), 7.60 (d, J=7.9 Hz, 1H), 7.41 (ddd, J=11.5, 8.2, 1.7 Hz, 1H), 7.36 (d, J=7.9 Hz, 1H), 7.23 (td, J=8.0, 5.1 Hz, 1H), 7.06 (d, J=7.7 Hz, 1H), 6.79 (s, 2H), 5.81 (s, 2H), 3.85 (s, 3H), 1.96-1.82 (m, 4H), 1.24 (s, 6H). ESI MS [M−H]$^-$ for $C_{25}H_{25}FN_7O_3$, calcd 490.2, found 490.2.

Example 163: 4-[6-({4-[2-Amino-6-(3-cyano-2-ethoxyphenyl)-4-pyrimidinyl]-1H-1,2,3-triazol-1-yl}methyl)-2-pyridyl]-4-methylvaleric acid

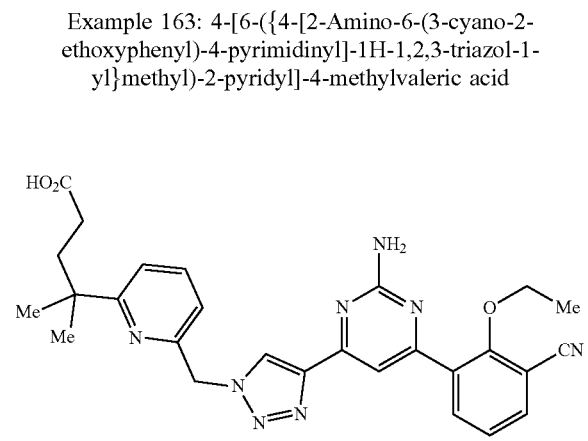

The title compound was prepared similar to example 142. $^1$H NMR (400 MHz, Acetone-d$_6$) δ 8.61 (s, 1H), 8.20 (d, J=7.9 Hz, 1H), 8.00 (s, 1H), 7.85 (d, J=7.9 Hz, 1H), 7.79 (dd, J=7.9, 7.9 Hz, 1H), 7.48-7.38 (m, 2H), 7.21 (d, J=7.7 Hz, 1H), 6.24 (brs, 2H), 5.80 (s, 2H), 4.11 (q, J=7.0 Hz, 2H), 2.07-2.03 (m, 2H), 1.38 (t, J=7.0 Hz, 3H), 1.36-1.26 (m, 2H), 1.34 (s, 6H). MS [M+H]$^+$ for $C_{27}H_{28}N_8O_3$, calcd 513.2, found 513.3.

Example 164: 4-[6-({4-[2-Amino-6-(m-cyanophenyl)-4-pyrimidinyl]-1H-1,2,3-triazol-1-yl}methyl)-2-pyridyl]cyclohexanecarboxylic acid Example 165: 4-[6-({4-[2-Amino-6-(m-cyanophenyl)-4-pyrimidinyl]-1H-1,2,3-triazol-1-yl}methyl)-2-pyridyl]cyclohexanecarboxylic acid

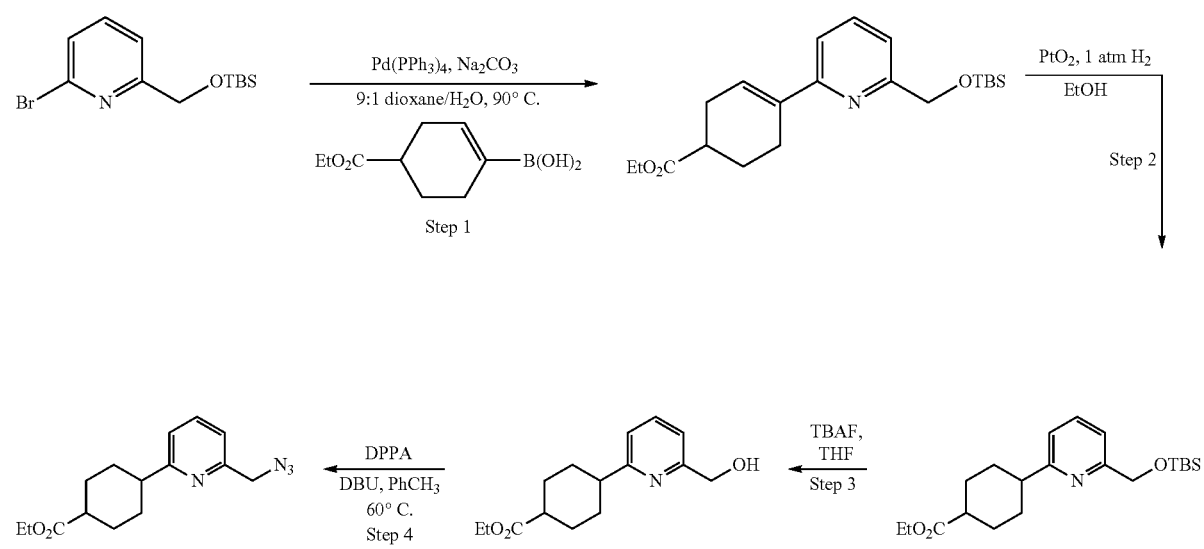

-continued

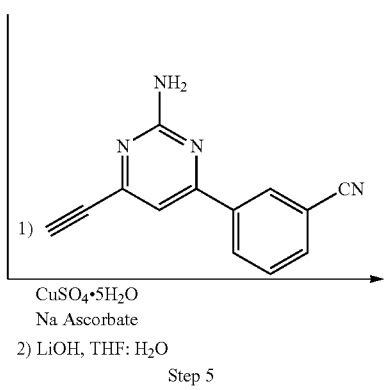

1) CuSO₄·5H₂O
Na Ascorbate
2) LiOH, THF:H₂O

Step 5

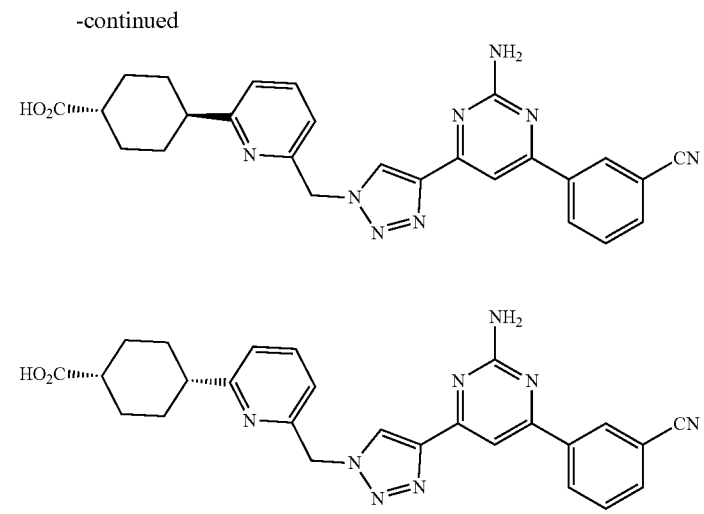

Step 1: A solution of 2-bromo-6-({[dimethyl(2-methyl-2-propanyl)silyl]oxy}methyl)pyridine (1.1 g, 3.6 mmol, 1.0 equiv), 4-ethoxycarbonyl-1-cyclohexenylboronic acid (1.0 g, 3.6 mmol, 1.0 equiv), and K₂CO₃ (1.2 g, 10.7 mmol, 3.0 equiv) in 9:1 dioxane/H₂O (18 mL, 0.2 M) was sparged with N₂ for 10 minutes. Following this time, Pd(PPh₃)₄ (206 mg, 0.18 mmol, 0.05 equiv) was added and the reaction mixture heated to 90° C. for 22 h. Following this time, the reaction mixture was diluted with EtOAc (40 mL), transferred to a separatory funnel and washed with H₂O (40 mL). The organic phase was collected and the aqueous phase was extracted with EtOAc (2×40 mL). The combined organic extracts were dried over MgSO₄, and concentrated in vacuo. The resulting oil was purified by column chromatography (0:1 EtOAc:hexanes→3:17 EtOAc:hexanes) to give the title compound (590 mg, 44% yield) as a colorless oil.

Step 2: A solution of the above product (590 mg, 1.6 mmol, 1.0 equiv) in ethanol (5.2 mL, 0.3 M) was purged with N₂ for 5 minutes and then PtO₂ (36 mg, 0.16 mmol, 0.1 equiv) was added. The suspension was hydrogenated under H₂ atmosphere (balloon) for 4 h. Upon completion, the reaction mixture was filtered over celite, the filter cake washed with EtOH (2×10 mL), and the filtrate concentrated in vacuo. The resulting oil was purified by column chromatography (0:1 EtOAc:hexanes→1:9 EtOAc:hexanes) to give the product (270 mg, 46% yield) as a colorless oil.

Step 3: TBS protected compound from step 2 (270 mg, 0.71 mmol, 1.0 equiv) was taken up in 1.0 M TBAF in THF (1.4 mL, 1.4 mmol, 2.0 equiv) and the solution stirred at room temperature for 30 minutes. The reaction mixture was then loaded directly onto SiO₂ and purified by column chromatography (1:1 EtOAc:hexanes+1:0 EtOAc:hexanes) to give ethyl 4-[6-(hydroxymethyl)-2-pyridyl]cyclohexanecarboxylate (156 mg, 83% yield) as a yellow oil.

Step 4: To a solution of ethyl 4-[6-(hydroxymethyl)-2-pyridyl]cyclohexanecarboxylate (156 mg, 0.59 mmol, 1.0 equiv) in toluene (1.2 mL, 0.5 M) was added diphenylphosphoryl azide (150 μL, 0.71 mmol, 1.2 equiv.), followed by 1,8-diazabicyclo[5.4.0]undec-7-ene (110 μL, 0.71 mmol, 1.2 equiv.). The resulting mixture was heated to 60° C. for 4 h. The reaction mixture was then loaded directly onto SiO₂ and purified by column chromatography (1:9 EtOAc:hexanes+3:7 EtOAc:hexanes) to give ethyl 4-[6-(azidomethyl)-2-pyridyl]cyclohexanecarboxylate (120 mg, 71% yield) as a yellow oil.

Step 5: Target compounds were prepared in a similar fashion to example 125 and cis/trans isomers were separated by reverse phase HPLC. First eluted compound arbitrarily assigned as trans isomer and the second eluted one as cis isomer.

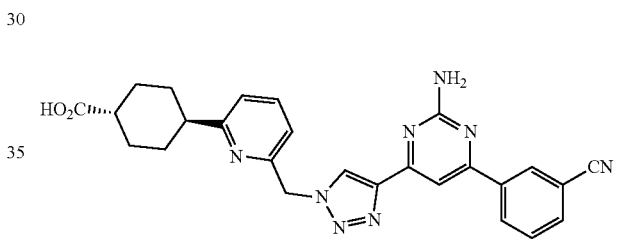

Example 164: ¹H NMR (400 MHz, Acetone-d₆) δ 8.68-8.58 (m, 2H), 8.53 (ddd, J=8.0, 1.9, 1.2 Hz, 1H), 7.99-7.91 (m, 2H), 7.83-7.73 (m, 2H), 7.29 (d, J=7.8 Hz, 1H), 7.19 (d, J=7.7 Hz, 1H), 6.58 (s, 1H), 5.83 (s, 2H), 2.74 (t, J=11.6 Hz, 1H), 2.40-2.30 (m, 1H), 2.12-1.98 (m, 4H), 1.60 (tt, J=24.6, 12.6 Hz, 4H). ESI MS [M+H]⁺ for C₂₆H₂₄N₈O₂, calcd 481.2, found 481.3.

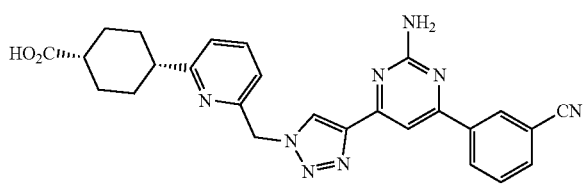

Example 165: ¹H NMR (400 MHz, Acetone-d₆) δ 8.70-8.58 (m, 2H), 8.53 (ddd, J=8.0, 1.9, 1.2 Hz, 1H), 7.97-7.89 (m, 2H), 7.82-7.70 (m, 2H), 7.28-7.16 (m, 2H), 6.42 (s, 2H), 5.80 (s, 2H), 2.70 (p, J=4.3 Hz, 1H), 2.18 (dd, J=13.5, 3.7 Hz, 2H), 2.06 (d, J=2.2 Hz, 1H), 2.03-1.87 (m, 2H), 1.82-1.63 (m, 3H). ESI MS [M+H]⁺ for C₂₆H₂₄N₈O₂, calcd 481.2, found 481.3.

Example 166: 4-{1-[6-({4-[2-Amino-6-(m-cyanophenyl)-4-pyrimidinyl]-1H-1,2,3-triazol-1-yl}methyl)-2-pyridyl]ethyl}cyclohexanecarboxylic acid

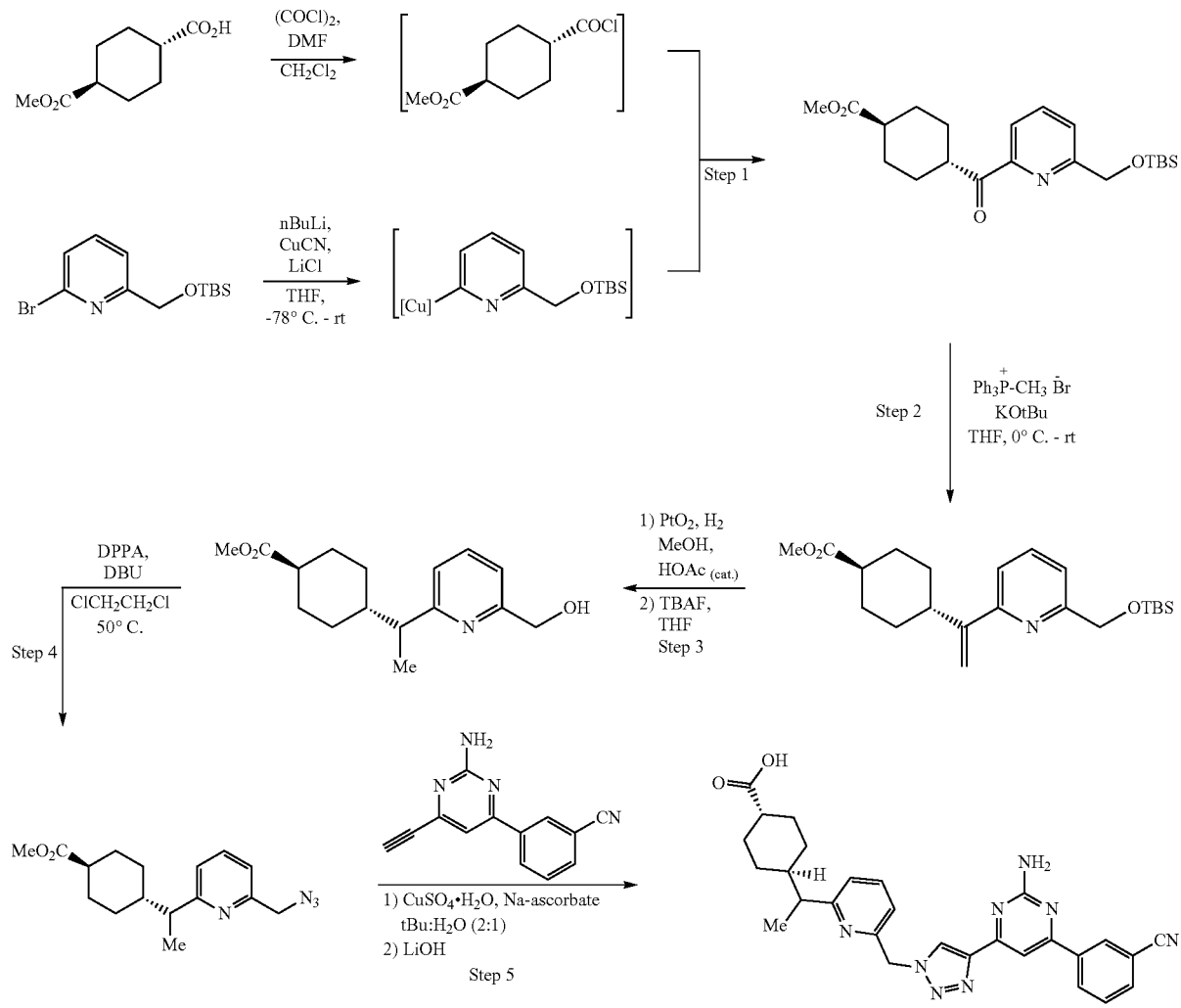

Step 1: To a solution of cyclohexylcarboxylic acid derivative (950 mg, 5.1 mmol) in 10 mL $CH_2Cl_2$ was added oxalylchloride (0.48 mL, 5.61 mmol) dropwise followed by one drop of DMF. The reaction mixture was stirred at room temperature for 10 h. Solvent was removed under reduced pressure and the crude acid-chloride was used in the acylation reaction. In a separate flask, 2.5M nBuLi (2.8 mL, 6.96 mmol) was added dropwise to a cold −78° C. solution of bromopyridine derivative (2.0 g 6.63 mmol) in 22 mL THF and stirred for 15 min. A solution of CuCN (653.5 mg, 7.3 mmol) and LiCl (619 mg, 14.6 mmol) in 7 mL THF was then added and stirred for 15 min. To this reaction mixture was added 5 mL THF solution of acid-chloride prepared above dropwise at −78° C. The reaction was then gradually warmed to ambient temperature over 3 h. The reaction was quenched with $NH_4Cl$ and the aqueous layer was extracted with EtOAc (2×30 mL). The pooled organic layer was dried over $Na_2SO_4$, concentrated and purified by silica gel chromatography to yield the desired product (500 mg, 25%).

Step 2: In a dry vial KOtBu (172 mg, 1.53 mmol) was suspended in 3.5 mL of dry THF. The suspension was cooled to 0° C. and added methyltriphenylphosphonium bromide (548 mg, 1.53 mmol). The reaction was stirred for 1 h at room temperature. To the above yellow reaction mixture was added a 1 mL THF solution ketone (500 mg, 1.3 mmol) obtained from step 1 at 0° C. The reaction was then gradually warmed to ambient temperature over 2 h. The reaction was quenched with saturated $NaHCO_3$ and the aqueous layer was extracted with EtOAc (2×30 mL). The pooled organic layer was dried over $Na_2SO_4$, concentrated and purified by silica gel chromatography to yield the desired product (276 mg, 55%).

Step 3: The alkene from step 2 (276 mg, 0.7 mmol) was dissolved in MeOH and added 2-drops of HOAc. The solution was flushed with $N_2$ and added $PtO_2$ (16 mg, 0.07 mmol). The reaction vial was sealed, purged with $H_2$ and stirred at room temperature under 1 atm $H_2$ pressure for 1 h. The Pt-catalyst was removed by filtration and solvent was removed under reduced pressure. The crude material was re-dissolved in 3 mL THF and was added 0.8 mL 1M TBAF. After 3 h, solvent was removed under reduced pressure and the crude material was purified by silica gel chromatography to obtain the desired alcohol (126 mg, 70% in 2-steps).

Step 4: To a mixture of the step 3 product (133 mg, 0.5 mmol), DPPA (0.13 mL, 0.58 mmol) in ClCH$_2$CH$_2$Cl (1 mL) was added DBU (0.087 mL, 0.58 mmol). The reaction mixture was stirred at 50° C. for 12 hours. The solvent was removed under reduced pressure and the mixture was purified by silica gel chromatography to afford the desired azide as a colorless oil (124 mg; 82%).

Step 5: The title compound synthesized similar to example 125. $^1$H NMR (400 MHz, DMSO-d$_6$) δ 11.99-11.82 (m, 1H), 8.70-8.63 (m, 1H), 8.59-8.51 (m, 1H), 8.44 (dd, J=8.1, 1.5 Hz, 1H), 7.97 (dd, J=7.7, 1.4 Hz, 1H), 7.79 (d, J=1.2 Hz, 1H), 7.71 (t, J=8.0 Hz, 2H), 7.16 (d, J=7.8 Hz, 1H), 7.05 (d, J=7.7 Hz, 1H), 6.87 (s, 2H), 5.79 (s, 2H), 2.57 (p, J=7.0 Hz, 1H), 2.07-1.91 (m, 1H), 1.82 (t, J=16.0 Hz, 2H), 1.71 (m, 1H), 1.48 (m, 1H), 1.32-1.01 (m, 5H), 0.98-0.72 (m, 2H). ESI MS [M+H]$^+$ for C$_{28}$H$_{28}$N$_8$O$_2$, calcd 509.2, found 509.3.

Example 167: Methyl 4-{(R)-1-[6-(hydroxymethyl)-2-pyridyl]ethyl}cyclohexanecarboxylate Example 168: Methyl 4-{(S)-1-[6-(hydroxymethyl)-2-pyridyl]ethyl}cyclohexanecarboxylate

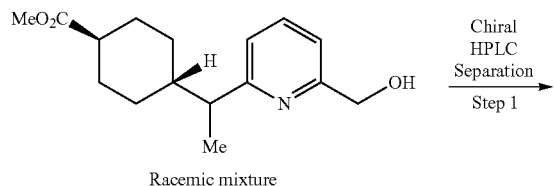

Racemic mixture

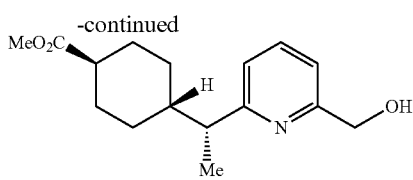

Enatiomer 1: ee = 98%

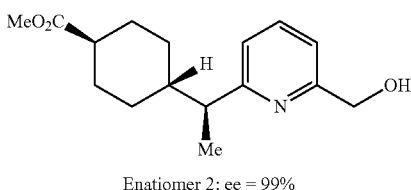

Enatiomer 2: ee = 99%

Step 1: Two enantiomers were separated by using a chiral AD-H column (L=250 mm, ID=30 mm, particle size 5 μm). Mobile phase: MeOH/CO$_2$. Flow rate (g/min): 80. Co-solvent flow rate (mL/min): 10.4. Enantiomer 1: Yield=37%; ee=98%; Enantiomer 2: Yield=38%; ee=99%. Absolute stereochemistry was arbitrarily assigned.

Example 169: 4-[(R)-1-[6-({4-[2-Amino-6-(3-cyano-2-methoxyphenyl)-4-pyrimidinyl]-1H-1,2,3-triazol-1-yl}methyl)-2-pyridyl]ethyl]cyclohexanecarboxylic acid

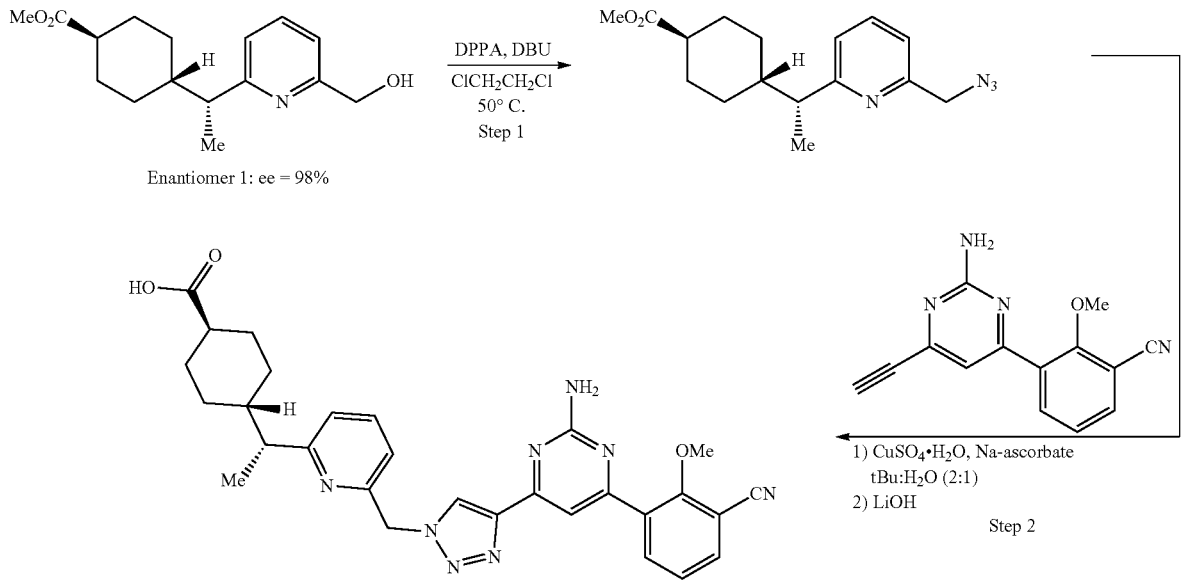 [SMILES: COC(=O)[C@H]1CC[C@H]([C@@H](C)c2cccc(CO)n2)CC1 ; COC(=O)[C@H]1CC[C@H]([C@@H](C)c2cccc(CN=[N+]=[N-])n2)CC1 ; COc1c(C#N)cccc1-c1cc(-c2cn(Cc3cccc([C@H](C)[C@H]4CC[C@H](C(=O)O)CC4)n3)nn2)nc(N)n1 ; C#Cc1cc(-c2cccc(C#N)c2OC)nc(N)n1]

The title compound was prepared similar to example 125 from the corresponding azide and alkyne. ¹H NMR (400 MHz, CDCl₃) δ 8.36 (s, 1H), 7.76-7.63 (m, 3H), 7.65-7.55 (m, 1H), 7.30-7.16 (m, 2H), 7.08 (d, J=7.8 Hz, 1H), 6.87 (s, 2H), 5.75 (d, J=13.8 Hz, 1H), 5.55 (d, J=13.9 Hz, 1H), 3.89 (s, 3H), 2.59 (dq, J=8.5, 6.8 Hz, 1H), 2.24-2.13 (m, 1H), 1.91 (m, 2H), 1.70-1.44 (m, 4H), 1.37 (d, J=13.0 Hz, 1H), 1.30-1.22 (m, 3H), 1.05 (m, 1H), 0.97-0.80 (m, 1H). ESI MS [M+H]⁺ for $C_{29}H_{30}N_8O_3$, calcd 539.2, found 539.3.

Example 170: 4—[(S)-1-[6-({4-[2-Amino-6-(3-cyano-2-methoxyphenyl)-4-pyrimidinyl]-1H-1,2,3-triazol-1-yl}methyl)-2-pyridyl]ethyl]cyclohexanecarboxylic acid

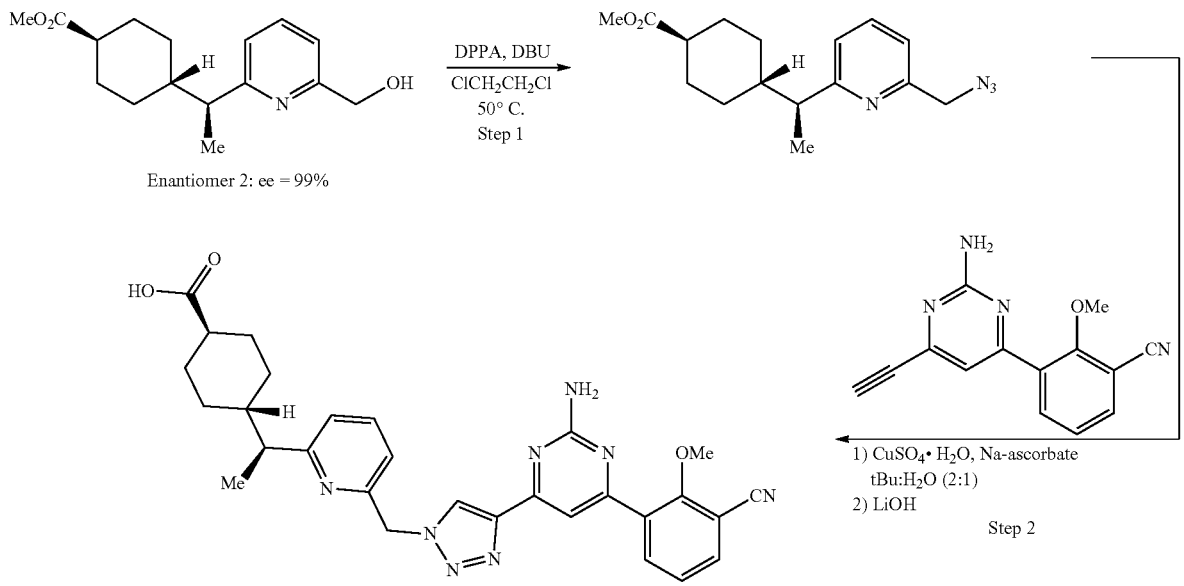 [SMILES: COC(=O)[C@H]1CC[C@H]([C@H](C)c2cccc(CO)n2)CC1 ; COC(=O)[C@H]1CC[C@H]([C@H](C)c2cccc(CN=[N+]=[N-])n2)CC1 ; COc1c(C#N)cccc1-c1cc(-c2cn(Cc3cccc([C@@H](C)[C@H]4CC[C@H](C(=O)O)CC4)n3)nn2)nc(N)n1 ; C#Cc1cc(-c2cccc(C#N)c2OC)nc(N)n1]

The title compound was prepared similar to example 125 from the corresponding azide and alkyne. ¹H NMR (400 MHz, DMSO-d₆) δ 11.97 (br s, 1H), 8.65 (s, 1H), 8.06 (dd, J=8.2, 1.4 Hz, 1H), 7.94 (dd, J=7.7, 1.8 Hz, 1H), 7.72 (t, J=7.7 Hz, 1H), 7.62 (s, 1H), 7.44 (t, J=7.8 Hz, 1H), 7.17 (d, J=7.7 Hz, 1H), 7.07 (d, J=7.7 Hz, 1H), 6.86 (s, 2H), 5.79 (s, 2H), 3.83 (s, 3H), 2.59 (p, J=7.0 Hz, 1H), 2.06-1.95 (m, 1H), 1.92-1.77 (m, 2H), 1.73 (d, J=13.1 Hz, 1H), 1.56-1.42 (m, 1H), 1.34-1.04 (m, 6H), 0.99-0.74 (m, 2H). ESI MS [M+H]⁺ for $C_{29}H_{31}N_8O_3$, calcd 539.2, found 539.3.

Example 171: 2-[6-({4-[2-Amino-6-(m-cyanophenyl)-4-pyrimidinyl]-1H-1,2,3-triazol-1-yl}methyl)-2-pyridyl]cyclopentanecarboxylic acid

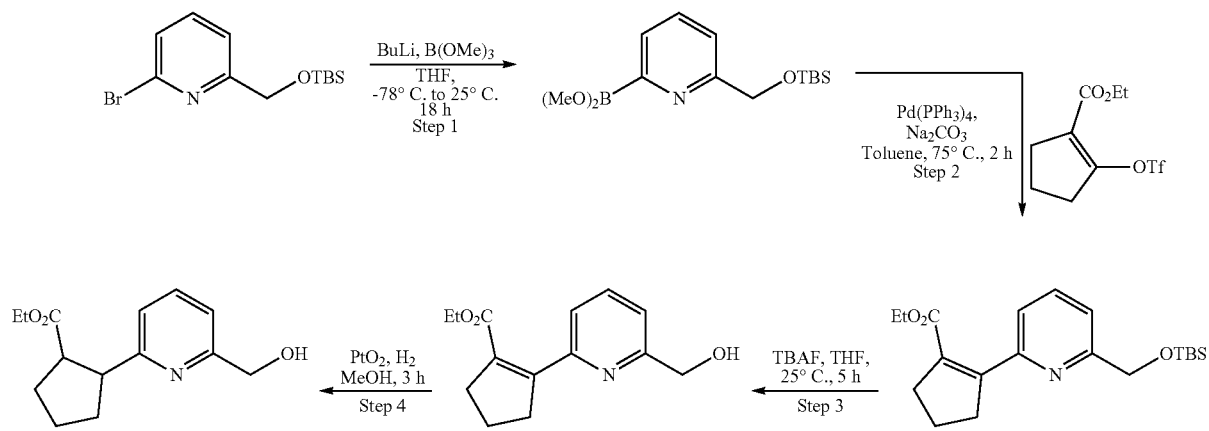

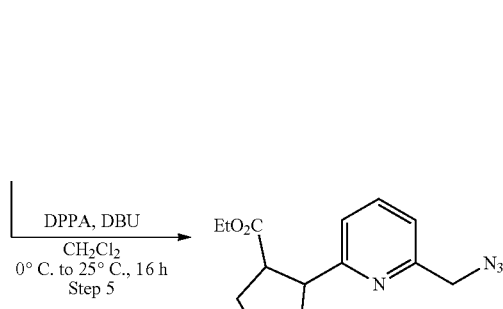
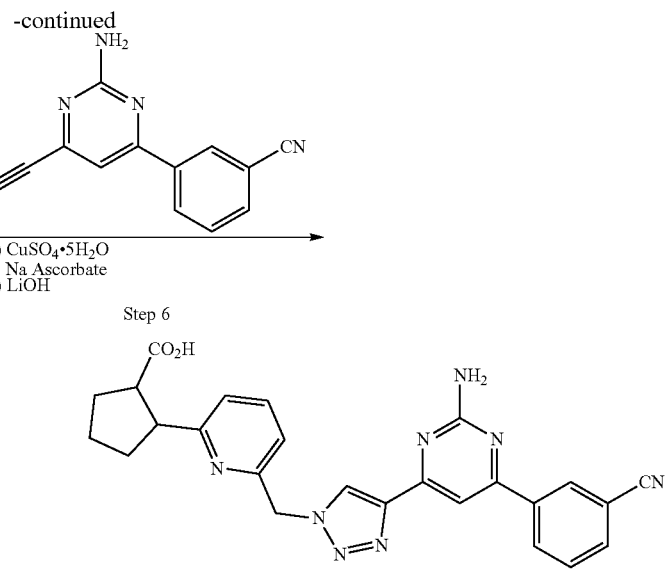

Step 1: The bromopyridine derivative (2.22 g, 7.3 mmol) was dissolved in THF (7.3 ml) and added dropwise to a solution of n-BuLi (2.5 M in hexanes, 3.52 ml, 8.8 mmol) cooled to −78° C. After stirring for 30 minutes, trimethylborate (0.68 ml, 8.8 mmol) was added, the reaction was allowed to warm to room temperature and was stirred overnight. The resulting solution was concentrated and used without further purification.

Step 2: The crude product from step 1 (7.3 mmol) was dissolved in toluene (3.0 ml). The triflate derivative (200 mg, 0.73 mmol) was added, and the solution was degassed by sparging with nitrogen for two minutes. Pd(PPh$_3$)$_4$ (13.0 mg, 0.011 mmol) and Na$_2$CO$_3$ (2M aq., 0.44 ml, 0.88 mmol) were added, and the reaction was sealed under nitrogen and heated to 75° C. for two hours. The reaction was then concentrated and used further without purification.

Step 3: The crude product from step 2 (7.4 mmol) was dissolved in THF (7.4 ml) and TBAF (1.0 M in THF, 7.4 ml, 7.4 mmol) was added at 25° C. The reaction was stirred for 5 hours, concentrated onto celite, and purified by flash chromatography over silica gel (ethyl acetate/hexanes 10% to 20%). Yield: 253 mg (14%, 3 steps).

Step 4: The benzylic alcohol isolated in step 3 (294 mg, 1.19 mmol) was combined with PtO$_2$ (27 mg, 0.12 mmol) in methanol (12 ml) and the resulting solution was sparged with hydrogen for five minutes. The reaction was sealed and stirred vigorously for three hours. The reaction solution was concentrated onto celite and the crude material was purified by flash chromatography over silica gel (ethyl acetate/hexanes 10% to 50%). Yield: 198 mg, (67%).

Step 5: The benzyl alcohol product from step 4 (198.2 mg, 0.80 mmol) was dissolved in toluene (1.0 ml) and cooled to 0° C. before the sequential addition of DPPA (0.21 ml, 0.96 mmol) and DBU (0.15 ml, 0.96 mmol). The reaction was stirred at room temperature for 16 hours. Upon completion, the reaction was partitioned between ethyl acetate and water, the organic layer was collected and concentrated onto celite. The resulting crude material was purified by flash chromatography over silica gel (ethyl acetate/hexanes gradient 0% to 20%). Yield: 207 mg (95%).

Step 6: Cycloaddition and hydrolysis reactions were performed in a similar fashion to example 125 to afford the title compound. $^1$H NMR (400 MHz, CDCl$_3$) δ 8.90 (s, 0.5H) 8.70 (s, 0.5H), 8.44-8.39 (m, 1H), 8.29-8.23 (m, 1H), 7.84-7.82 (m, 1H), 7.77-7.55 (m, 3H), 7.31-7.21 (m, 2H), 5.76 (brs, 0.5H), 5.70-5.57 (m, 2H), 5.37 (brs, 1H), 3.64-3.51 (m, 2H), 3.26 (ddd, J=7.1, 7.1 7.1 Hz, 0.5H), 2.90 (ddd, J=9.3, 9.3, 9.3 Hz, 0.5H), 2.36-1.75 (m, 5H). ESI MS [M+H]$^+$ for C$_{25}$H$_{22}$N$_8$O$_2$, calcd 467.2, found 467.3.

Example 172: 3-[6-({4-[2-Amino-6-(m-cyanophenyl)-4-pyrimidinyl]-1H-1,2,3-triazol-1-yl}methyl)-2-pyridyl]cyclopentanecarboxylic acid

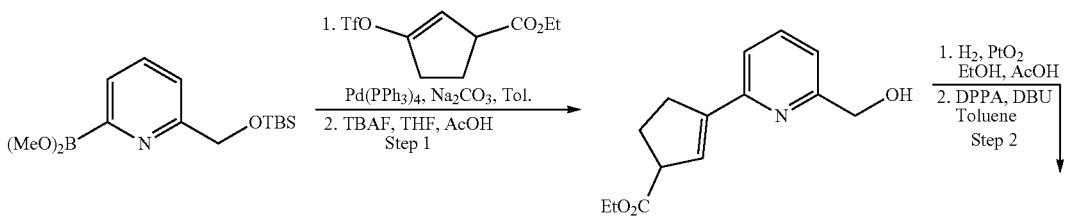

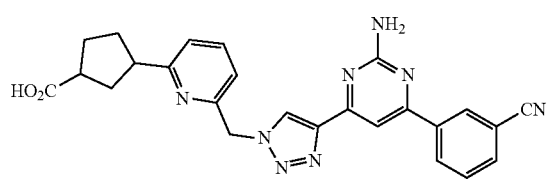
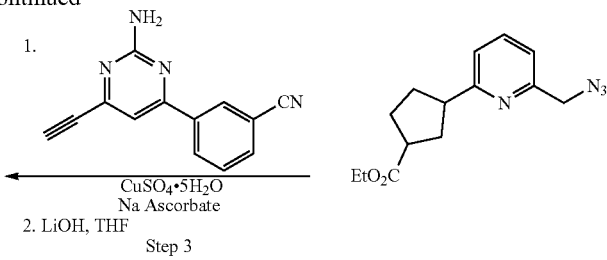

Step 1. A mixture of boronate (830 mg, 1.95 mmol), vinyl triflate (1:1 mixture of regio-isomers, 432 mg, 1.5 mmol), palladium tetrakis (69 mg, 4 mol %) in degassed toluene (4.5 mL) and sodium carbonate (2 M, 1.2 mL) was heated to 75° C. for 2 hours. After usual work-up and chromatography over silica gel (hexanes/EtOAc 100:0 to 80:20) the coupled product was obtained (366 mg, 68%). The product (366 mg, 1.0 mmol) was dissolved in THF (2 mL) and acetic acid (10 µL) was added followed by TBAF (1 M in THF, 1.2 mL). The mixture was stirred for 2 hours at room temperature and after usual work-up, the residue was purified by silica gel chromatography (hexanes/EtOAc 90:10 to 50:50) to furnish the primary alcohol (171 mg, 69%).

Step 2. The alkene mixture (170 mg, 0.69 mmol) was taken in degassed EtOH (2 mL) and AcOH (30 µL). $PtO_2$ (5 mg) was added and the suspension was placed in an atmosphere of $H_2$. After 4 hours at room temperature the mixture was filtered over celite, evaporated to dryness and purified by chromatography over silica gel (hexanes/EtOAc 90:10 to 50:50) to afford the reduced cyclopentane (77 mg, 45%). The azidation step was performed according to example 79 to afford the desired azide derivative (82 mg, 96%).

Step 3. Cycloaddition and hydrolysis reactions were performed in a similar fashion to example 125 to afford the title compound as a 95:5 mixture of diastereoisomers. The minor isomer is not described here. $^1$H NMR (400 MHz, Acetone-$d_6$) δ 8.80 (s, 1H), 8.60 (s, 1H), 8.55-8.48 (m, 1H), 7.97-7.89 (m, 1H), 7.92 (s, 1H), 7.82-7.68 (m, 2H), 7.30 (d, J=8.0 Hz, 1H), 7.26 (d, J=7.8 Hz, 1H), 6.50 (brs, 2H), 5.81 (s, 2H), 3.45-3.27 (m, 1H), 3.09-2.92 (m, 1H), 2.44-2.18 (m, 2H), 2.17-1.94 (m, 4H). MS [M+H]$^+$ for $C_{25}H_{22}N_8O_2$, calcd 467.2, found 467.3.

Example 173: 3-[6-({4-[2-Amino-6-(m-cyanophenyl)-4-pyrimidinyl]-1H-1,2,3-triazol-1-yl}methyl)-2-pyridyl]-3-hydroxycyclopentanecarboxylic acid

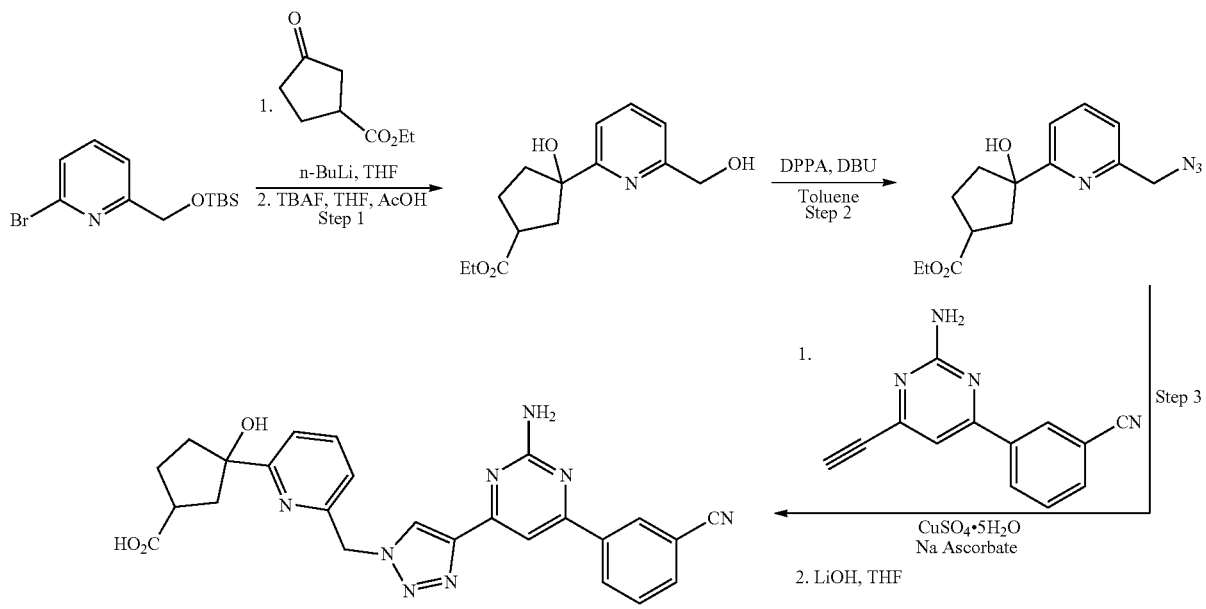

Step 1. n-BuLi (2.5M in hexanes, 1.2 mL, 3 mmol) was added to a −78° C. solution of bromide (903 mg, 3 mmol) in THF (5 mL). The resulting mixture was stirred at −78° C. for 30 minutes before a solution the ketone (460 µL, 3 mmol) was added. After an additional hour, the reaction was quenched with NH$_4$Cl(sat.). Chromatography over silica gel (hexanes/EtOAc 95:5 to 85:15) afforded the tertiary alcohol (680 mg, 60%).

The silylether (680 mg, 1.8 mmol) was dissolved in THF (2 mL) and acetic acid (20 µL) was added followed by TBAF (1 M in THF, 2.5 mL). The mixture was stirred for 2 hours at room temperature and after usual work-up the residue was purified by silica gel chromatography ($CH_2Cl_2$/hexanes (1:1)/EtOAc 95:5 to 70:30) to furnish the primary alcohol (274 mg, 57%).

Step 2. This step was performed according to example 172 to afford the targeted azide (281 mg, 94%).

Step 3. Cycloaddition was performed in a similar fashion to step 6 of example 1 and the hydrolysis of the subsequent ester similar to example 125 yielded 3:1 mixture of diastereoisomers. $^1$H NMR (400 MHz, Acetone-$d_6$) δ 8.79 (s, 0.25H, minor dia), 8.65 (s, 0.75H, major dia), 8.57 (s, 1H), 8.53-8.46 (m, 1H), 7.96-7.86 (m, 1H), 7.90 (s, 1H), 7.82 (dd, J=8.0, 8.0 Hz, 1H), 7.80-7.68 (m, 2H), 7.30 (d, J=8.0 Hz, 0.25H, minor dia), 7.25 (d, J=8.0 Hz, 0.75H, major dia), 6.52 (brs, 0.5H, minor dia), 6.32 (brs, 1.5H, major dia), 5.85 (s, 2H), 3.27-3.17 (m, 0.25H, minor dia), 3.18-3.08 (m, 0.75H, major dia), 2.64-2.10 (m, 5H), 2.07-2.03 (m, 1H), 1.95-1.82 (m, 1H). MS [M+H]$^+$ for $C_{25}H_{22}N_8O_3$, calcd 483.2, found 483.3.

Example 174: 3-[6-({4-[2-Amino-6-(m-cyanophenyl)-4-pyrimidinyl]-1H-1,2,3-triazol-1-yl}methyl)-2-pyridyl]-3-hydroxycyclobutanecarboxylic acid

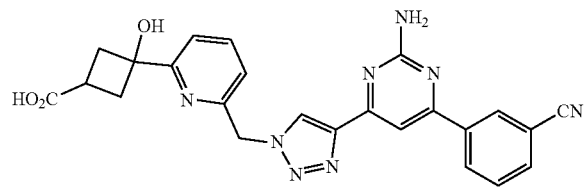 [SMILES: N#Cc1cccc(-c2cc(-c3cn(Cc4cccc(C5(O)CC(C(=O)O)C5)n4)nn3)nc(N)n2)c1]

The title compound was synthesized similar to example 173. $^1$H NMR (400 MHz, Acetone-$d_6$) δ 8.68 (s, 1H), 8.59 (s, 1H), 8.51 (d, J=8.0 Hz, 1H), 7.97-7.88 (m, 1H), 7.90 (s, 1H), 7.86 (dd, J=7.6, 7.9 Hz, 1H), 7.76 (dd, J=7.6, 7.9 Hz, 1H), 7.67 (d, J=7.9 Hz, 1H), 7.32 (d, J=7.6 Hz, 1H), 6.24 (brs, 2H), 5.91 (s, 2H), 3.19-3.05 (m, 1H), 2.79-2.69 (m, 2H), 2.63-2.47 (m, 2H). MS [M+H]$^+$ for $C_{24}H_{20}N_8O_3$, calcd 469.2, found 469.3.

Example 175: {4-[6-({4-[2-Amino-6-(m-cyanophenyl)-4-pyrimidinyl]-1H-1,2,3-triazol-1-yl}methyl)-2-pyridyl]-4-hydroxy-1-piperidyl}acetic acid

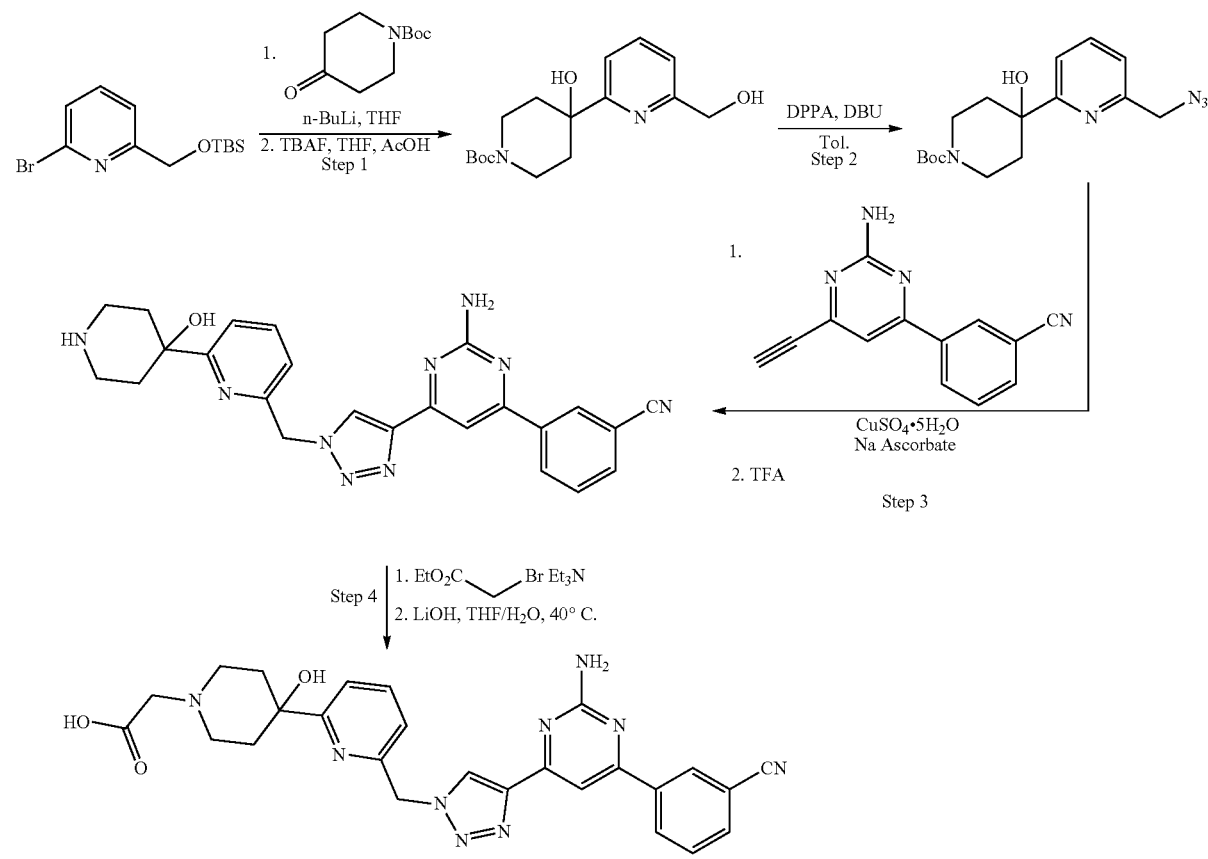

Step 1. n-BuLi (2.5M in hexanes, 2.1 mL, 5.5 mmol) was added to a −78° C. solution of bromide (1.5 g, 5 mmol) in THF (10 mL). The resulting mixture was stirred at −78° C. for 30 minutes before a solution the ketone (996 mg, 5 mmol) in THF (5 mL) was added dropwise. After an additional hour, the reaction was quenched with NH$_4$Cl (sat.). Chromatography over silica gel (hexanes/EtOAc 95:5 to 80:20) afforded the tertiary alcohol (1.3 g, 62%).

The silylether (1.3 g, 3.1 mmol) was dissolved in THF (6 mL) and acetic acid (40 µL) was added followed by TBAF (1 M in THF, 5 mL). The mixture was stirred for 2 hours at room temperature and after usual work-up the residue was purified by silica gel chromatography (CH$_2$Cl$_2$/hexanes (1:1)/EtOAc 95:5 to 50:50) to furnish the primary alcohol (850 mg, 89%).

Step 2. This step was performed according to example 172 to afford the targeted azide (790 mg, 87%).

Step 3. To a mixture of alkyne (66 mg, 0.3 mmol) and azide (100 mg, 0.3 mmol) in tBuOH/H$_2$O (2/1, 1 mL) was added CuSO₄ (2.4 mg) and sodium ascorbate (12 mg). The resulting mixture was stirred at 60° C. for 3 hours. The crude mixture was directly loaded on silica and purified by column chromatography (hexanes/EtOAc 100:0 to 0:100) to afford the cycloadduct (160 mg, 96%). The Boc protected amine (78 mg) was taken in TFA (0.2 mL) and stirred for 30 minutes at room temperature. Evaporation of the volatiles gave rise to the amine TFA salt (77 mg, quant.).

Step 4. The amine TFA salt (77 mg) was dissolved in THF (1 mL) and triethylamine (0.3 mL) was added followed by ethyl bromoacetate (60 μL). The resulting mixture was stirred for 3 hours at room temperature and then purified by column chromatography over silica gel (hexanes/EtOAc 95:5 to 60:40) to deliver the alkylated amine (74 mg, quant). The ester thus obtained (65 mg) was dissolved in THF (1.5 mL) and LiGH (1 M, 0.4 mL) was added. After vigorous stirring at 40° C. for 3 hours, the reaction was quenched by addition of acetic acid (0.2 mL) and the crude was taken directly on silica for column purification (CH₂Cl₂/MeOH 100:0 to 70:30) to deliver the targeted acid (70 mg, 98%). ¹H NMR (400 MHz, DMSO-d₆) δ 8.77 (s, 1H), 8.56 (s, 1H), 8.45 (d, J=7.9 Hz, 1H), 7.97 (d, J=7.9 Hz, 1H), 7.84 (dd, J=7.9, 7.9 Hz, 1H), 7.79 (s, 1H), 7.72 (dd, J=7.9, 7.9 Hz, 1H), 7.62 (d, J=7.9 Hz, 1H), 7.22 (d, J=7.9 Hz, 1H), 6.96 (brs, 2H), 5.81 (s, 2H), 3.28 (s, 1H), 3.18-2.90 (m, 4H), 2.35-2.24 (m, 2H), 1.60 (d, J=13.7 Hz, 2H). MS [M+H]⁺ for C₂₆H₂₅N₉O₃, calcd 512.5, found: 512.3.

Example 176: {4-[6-({4-[2-Amino-6-(m-cyanophenyl)-4-pyrimidinyl]-1H-1,2,3-triazol-1-yl}methyl)-2-pyridyl]-1-piperidyl}acetic acid

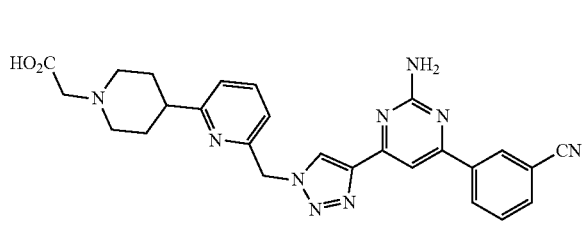 [SMILES: N#Cc1cccc(-c2cc(-c3cn(Cc4cccc(C5CCN(CC(=O)O)CC5)n4)nn3)nc(N)n2)c1]

The title compound was prepared similar to example 125 from the corresponding azide and alkyne. ¹H NMR (400 MHz, CD₃OD) δ 8.75 (d, J=1.4 Hz, 1H), 8.55-8.49 (m, 1H), 8.47-8.37 (m, 1H), 7.90-7.84 (m, 1H), 7.84-7.75 (m, 2H), 7.75-7.66 (m, 1H), 7.32 (dd, J=7.9, 4.0 Hz, 2H), 5.80 (s, 2H), 3.64 (s, 2H), 3.11 (d, J=36.7 Hz, 5H), 2.15 (q, J=15.6, 13.3 Hz, 5H); ESI MS [M+H]⁺ for C₂₆H₂₅N₉O₂, calcd 496.2, found 496.3.

Example 177: [6-({4-[2-Amino-6-(m-cyanophenyl)-4-pyrimidinyl]-1H-1,2,3-triazol-1-yl}methyl)-2-pyridylamino]acetic acid

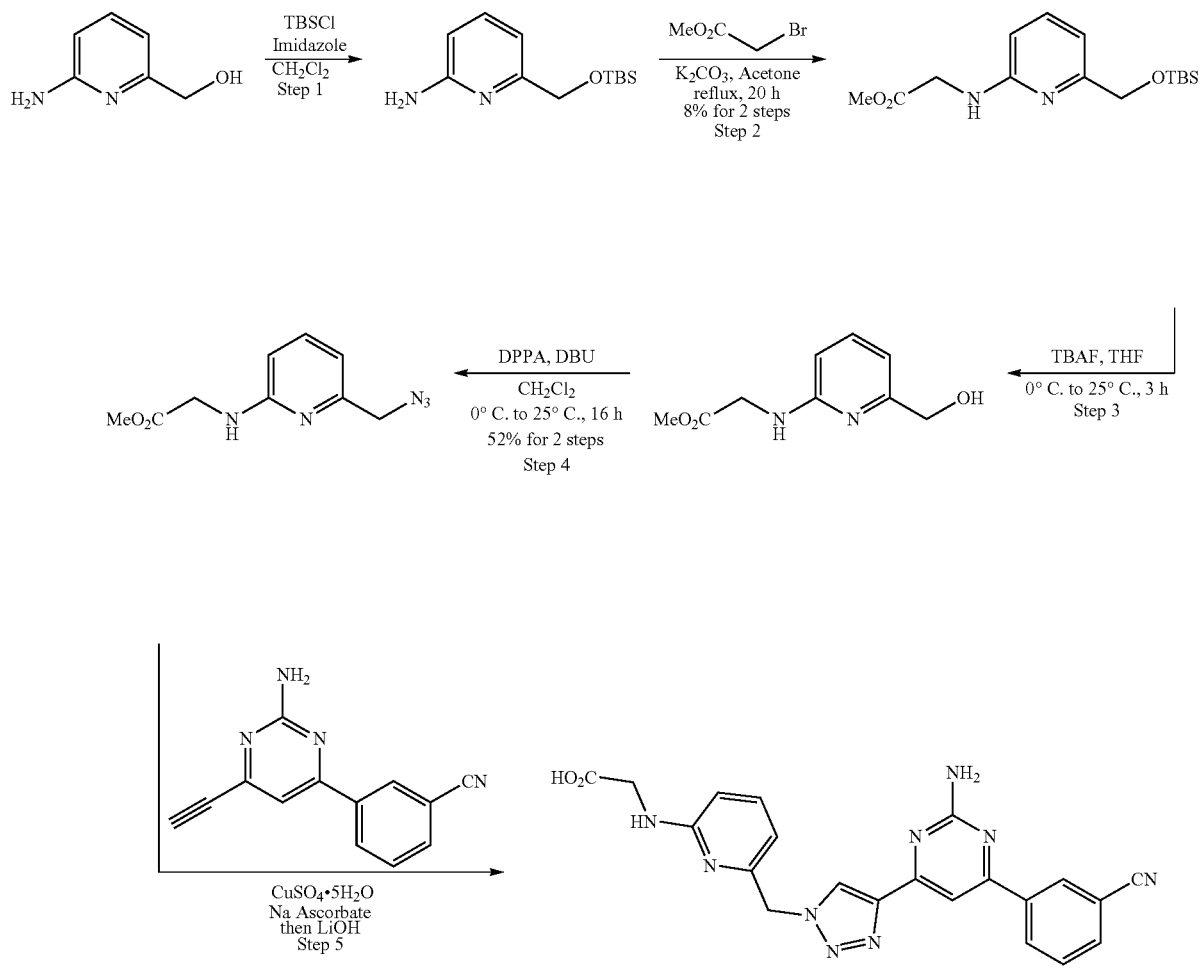

Step 1: To a solution of the aminopyridine (604 mg, 4.06 mmol) and imidazole (332.3 mg, 4.88 mmol) in methylene chloride (8 ml) was added TBSCl (736.9 mg, 4.88 mmol). The reaction was stirred at room temperature for three hours. The reaction was filtered and concentrated onto celite, and the resulting crude material was purified by flash chromatography over silica gel (ethyl acetate/hexanes gradient 20 to 40%). The resulting white crystalline solid was taken to the next step assuming 100% yield.

Step 2: The crude TBS protected product from step 1 (4.06 mmol) was placed in a vial equipped with a pressure-release septum, to which was added $K_2CO_3$ (673 mg, 4.87 mmol) and acetone (3.2 ml). Methyl bromoacetate (384 µl, 4.06 mmol) was added and the solution was heated to reflux for 20 hours. An additional portion of methyl bromoacetate (192 µl, 2.03 mmol) was added, and the reaction was heated for an additional 22 hours. Upon completion, the reaction was partitioned between ethyl acetate and saturated $NaHCO_3$, the aqueous layer was extracted three times with ethyl acetate, and the combined organic layers were washed with brine and dried over sodium sulfate. The resulting solution was concentrated onto celite and purified by flash chromatography over silica gel (ethyl acetate/hexanes gradient 0% to 10%). Yield: 100.1 mg (8%, 2 steps).

Step 3: The aryl glycine product from step 2 (100.1 mg, 0.32 mmol) was dissolved in THF (0.33 ml) and cooled to 0° C. TBAF (1.0 M in THF, 0.33 ml) was added in a single portion, and the solution was allowed to warm to room temperature over one hour. Saturated $NaHCO_3$ was then added, and the reaction was partitioned between ethyl acetate and water. The organic layer was separated, washed with brine, dried over sodium sulfate, concentrated, and taken to the next step without further purification.

Step 4: The crude alcohol product from step 3 (0.32 mmol) was dissolved in methylene chloride (0.4 ml) and cooled to 0° C. DPPA (84.5 µl, 0.39 mmol) and DBU (58.8 µl, 0.39 mmol) were added successively, and the reaction was warmed to room temperature and stirred for three hours. The resulting solution was concentrated onto celite and purified by flash chromatography over silica gel (ethyl acetate/hexanes gradient 0% to 30%). Yield: 37.2 mg, (52%, 2 steps).

Step 5: Cycloaddition and hydrolysis reactions were performed in a similar fashion to example 125 to afford the title compound. $^1$H NMR (400 MHz, DMSO-$d_6$) δ 8.64 (s, 1H), 8.57 (s, 1H), 8.46 (d, J=8.0 Hz, 1H), 7.99 (d, J=7.6 Hz, 1H), 7.81 (s, 1H), 7.73 (dd, J=8.0, 7.6 Hz), 7.44 (m, 1H), 6.56 (m, 1H), 6.41 (m, 1H), 5.58 (s, 2H), 3.93 (s, 2H). ESI MS $[M+H]^+$ for $C_{21}H_{17}N_9O_2$, calcd 428.2, found 428.2.

Example 178: 2-[6-({4-[2-Amino-6-(m-cyanophenyl)-4-pyrimidinyl]-1H-1,2,3-triazol-1-yl}methyl)-2-pyridylamino]-2-methylpropionic acid

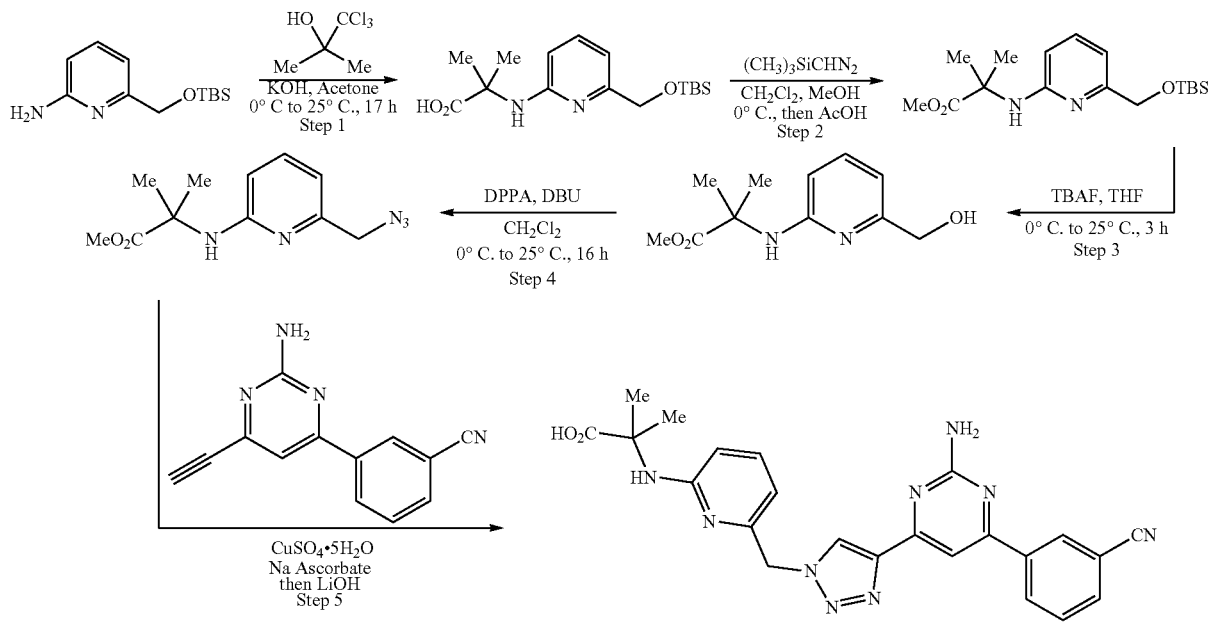

Step 1: Starting aminopyridine derivative (520 mg, 4.2 mmol) was dissolved in acetone (8.4 ml). 1,1,1-Trichloro-2-methyl-2-propanol hemihydrate (1.17 g, 6.3 mmol) was added, and the solution was cooled to 0° C. Powdered KOH (939 mg, 16.8 mmol) was added to the cold solution, and the reaction was stirred for one hour at 0° C. and stirred 16 hours at room temperature for overnight. The reaction was quenched with 2 ml of AcOH, concentrated, and reconstituted in methanol. The solution was filtered and concentrated onto celite. The resulting crude product was purified by flash chromatography over silica gel (methanol/methylene chloride gradient 0% to 10%) as a yellow oil.

Step 2: The resulting carboxylic acid (457 mg, 1.41 mmol) was taken up in methylene chloride (5.6 ml) and methanol (1.4 ml) and cooled to 0° C. Trimethylsilyldiazomethane (1.75 ml, 3.5 mmol) was added dropwise to the cold solution. Upon complete addition, the reaction was quenched with AcOH, concentrated, and re-dissolved in methylene chloride before concentration onto celite. The resulting crude product was purified by flash chromatography over silica gel (ethyl acetate/hexanes gradient 5% to 10%).

Step 3: The carboxylate ester from step 2 (206 mg, 0.61 mmol) was dissolved in THF (6.1 ml) and cooled to 0° C. TBAF (1.0M in THF, 0.61 ml, 0.61 mmol) was added at 0°

C., and the reaction was allowed to warm to room temperature. After stirring for one hour, the reaction was quenched with saturated NaHCO₃, partitioned between ethyl acetate and H₂O. The organic layer was washed with brine, dried over sodium sulfate, and concentrated. The resulting product was taken on to the next step without further purification.

Step 4: The benzyl alcohol from step 3 (136 mg, 0.61 mmol) was dissolved in methylene chloride (6.1 ml) and cooled to 0° C. DPPA (158 µl, 0.72 mmol) and DBU (110 µl, 0.72 mmol) were added sequentially, and the reaction was warmed to 40° C. After 24 h, the reaction was concentrated onto celite and purified by flash chromatography over silica gel (ethyl acetate/hexanes gradient 0% to 30%).

Step 5: Cycloaddition and hydrolysis reactions were performed in a similar fashion to example 125 to afford the title compound. $^1$H NMR (400 MHz, CD₃OD) δ 8.71 (s, 1H), 8.53 (s, 1H), 8.43 (d, J=8.0 Hz, 1H), 7.88-7.81 (m, 2H), 7.68 (dd, J=7.8, 7.8 Hz, 1H), 7.39 (dd, J=8.6, 7.1 Hz, 1H), 6.62 (d, J=7.1 Hz, 1H), 6.49 (d, J=8.6 Hz, 1H), 5.49 (s, 2H, 1.49 (s, 6H). ESI MS [M+H]⁺ for $C_{23}H_{21}N_9O_2$, calcd 456.2, found 456.3.

Example 179: (S)-1-[6-({4-[2-Amino-6-(m-cyanophenyl)-4-pyrimidinyl]-1H-1,2,3-triazol-1-yl}methyl)-2-pyridyl]-2-pyrrolidinecarboxylic acid and then cooled to room temperature at which point methyl iodide (965 µL, 15.5 mmol) was added. The mixture was stirred for an additional 2 hours. After usual work-up (H₂O/EtOAc), the residue was purified by silica gel chromatography (hexanes/EtOAc 90:10 to 80:20) to deliver the coupled product (1.65 g, 61%).

The product from above (1.65 g, 4.7 mmol) was dissolved in THF (4 mL) and acetic acid (40 µL) was added followed by TBAF (1 M in THF, 6 mL). The mixture was stirred for 2 hours at room temperature and after usual work-up the residue was purified by silica gel chromatography (CH₂Cl₂/hexanes (1:1)/EtOAc 95:5 to 50:50) to furnish the primary alcohol (730 mg, 66%).

Step 2. The azide derivative was synthesized like step 5 of example 1 using the above alcohol derivative (380 mg, 1.6 mmol). Purification by silica gel chromatography (hexanes/EtOAc 100:0 to 85:15) delivered the product (330 mg, 79%).

Step 3. (S)-1-[6-({4-[2-amino-6-(m-cyanophenyl)-4-pyrimidinyl]-1H-1,2,3-triazol-1-yl}methyl)-2-pyridyl]-2-pyrrolidinecarboxylate was synthesized in a similar fashion to step 6 of example 1. $^1$H NMR (400 MHz, Chloroform-d) δ 8.46 (s, 1H), 8.35 (d, J=1.4 Hz, 1H), 8.34 (s, 1H), 8.33-8.28 (m, 1H), 7.89 (s, 1H), 7.77-7.70 (m, 1H), 7.58 (dd, J=7.6 Hz, 1H), 7.45 (dd, J=7.6 Hz, 1H), 6.57 (d, J=7.6 Hz, 1H), 6.39

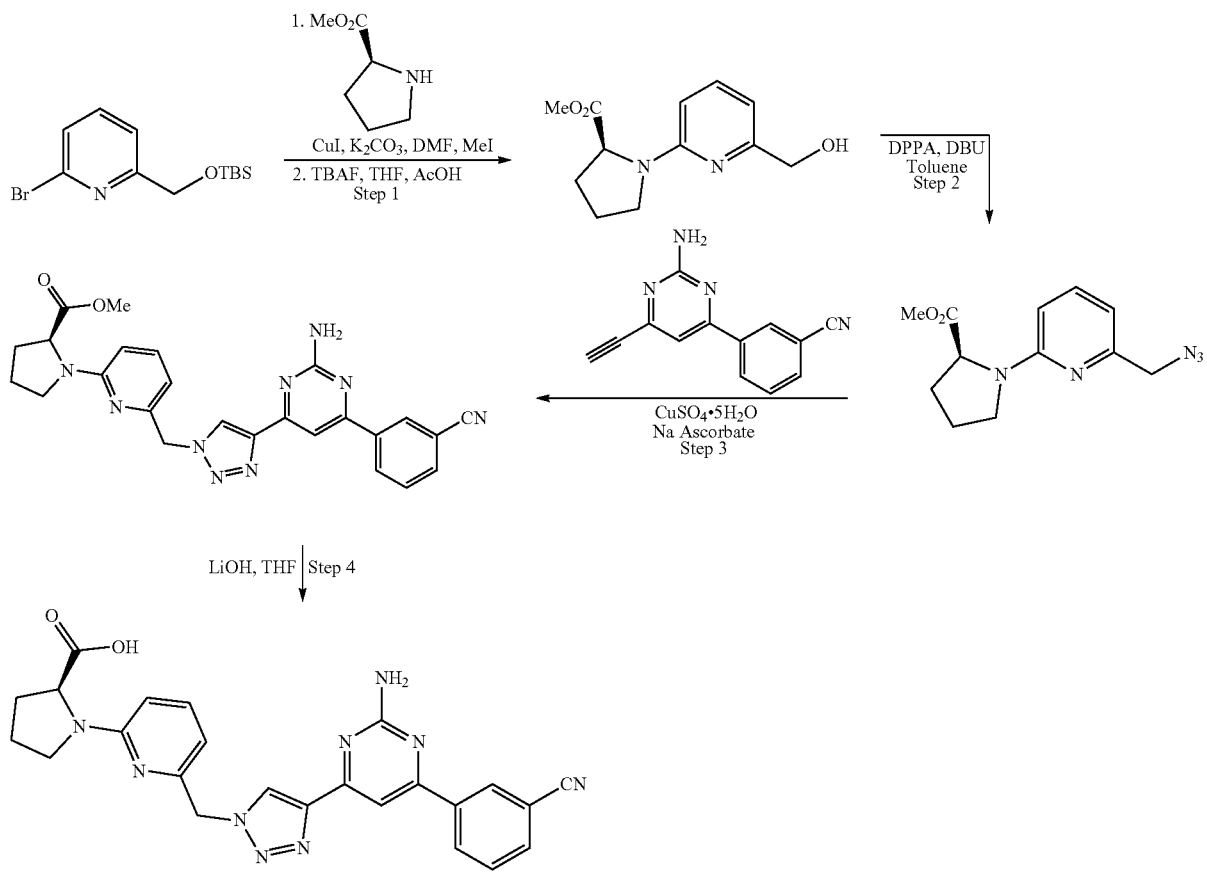

Step 1. A mixture of bromide (2.33 g, 7.75 mmol) and amine (2.0 g, 15.5 mmol) together with CuI (296 mg, 20 mol %) and K₂CO₃ (2.14 g, 15.5 mmol) was taken in DMF (7.8 mL). The resulting mixture was stirred for 2 hours at 90° C.

(d, J=8.0 Hz, 1H), 5.46 (s, 2H), 5.26 (brs, 2H), 4.54 (dd, J=8.7, 3.2 Hz, 1H), 3.66 (s, 3H), 3.64-3.56 (m, 1H), 3.50-3.36 (m, 1H), 2.41-2.08 (m, 3H). MS [M+H]⁺ for $C_{25}H_{23}N_9O_2$, calcd 482.2, found 482.3.

Step 4. To a solution of (S)-1-[6-({4-[2-amino-6-(m-cyanophenyl)-4-pyrimidinyl]-1H-1,2,3-triazol-1-yl}methyl)-2-pyridyl]-2-pyrrolidinecarboxylate (80 mg, 0.17 mmol) in THF (1 mL) was added an aqueous solution of LiGH (0.35 mL, 1M). The resulting mixture was vigorously stirred at room temperature overnight. It was then quenched by the addition of acetic acid (excess) and evaporated onto silica. The residue was purified by silica gel chromatography (CH$_2$Cl$_2$/MeOH 100:0 to 90:10) to afford the targeted acid (40 mg, 52%). $^1$H NMR (400 MHz, DMSO-d$_6$) δ 12.38 (brs, 1H), 8.60 (s, 1H), 8.56 (s, 1H), 8.45 (d, J=7.7 Hz, 1H), 7.97 (dd, J=7.7 Hz, 1H), 7.79 (s, 1H), 7.73 (dd, J=7.9 Hz, 1H), 7.50 (dd, J=7.9 Hz, 1H), 6.87 (s, 1H), 6.45 (d, J=7.2 Hz, 1H), 6.39 (d, J=8.0 Hz, 1H), 5.56 (s, 2H), 4.35 (d, J=7.2 Hz, 1H), 3.53-3.30 (m, 2H), 2.30-2.15 (m, 1H), 2.06-1.84 (m, 3H). MS [M+H]$^+$ for C$_{24}$H$_{21}$N$_9$O$_2$, calcd 468.2, found 468.3.

Example 180: (R)-1-[6-({4-[2-amino-6-(m-cyanophenyl)-4-pyrimidinyl]-1H-1,2,3-triazol-1-yl}methyl)-2-pyridyl]-2-pyrrolidinecarboxylate

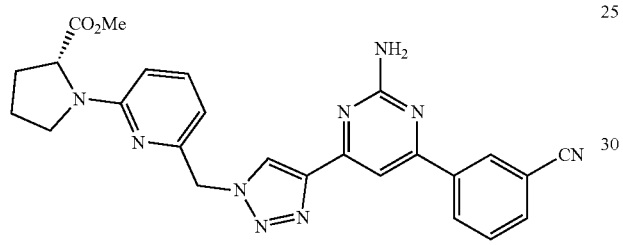

The title compound was synthesized like example 179. $^1$H NMR (400 MHz, Chloroform-d) δ 8.46 (s, 1H), 8.35 (d, J=1.4 Hz, 1H), 8.34 (s, 1H), 8.33-8.28 (m, 1H), 7.89 (s, 1H), 7.77-7.70 (m, 1H), 7.58 (dd, J=7.6 Hz, 1H), 7.45 (dd, J=7.6 Hz, 1H), 6.57 (d, J=7.6 Hz, 1H), 6.39 (d, J=8.0 Hz, 1H), 5.46 (s, 2H), 5.26 (brs, 2H), 4.54 (dd, J=8.7, 3.2 Hz, 1H), 3.66 (s, 3H), 3.64-3.56 (m, 1H), 3.50-3.36 (m, 1H), 2.41-2.08 (m, 3H). MS [M+H]$^+$ for C$_{25}$H$_{23}$N$_9$O$_2$, calcd 482.4, found 482.3.

Example 181: (R)-1-[6-({4-[2-Amino-6-(m-cyanophenyl)-4-pyrimidinyl]-1H-1,2,3-triazol-1-yl}methyl)-2-pyridyl]-2-pyrrolidinecarboxylic acid

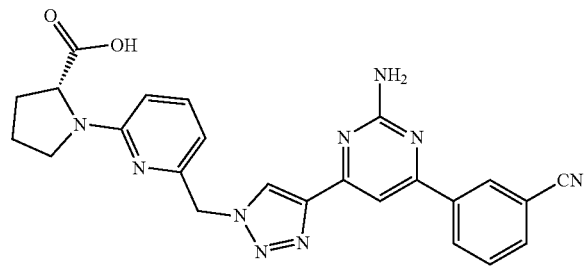 [SMILES: N#Cc1cccc(-c2cc(-c3cn(Cc4cccc(N5CCC[C@@H]5C(=O)O)n4)nn3)nc(N)n2)c1]

The title compound was synthesized like example 179. $^1$H NMR (400 MHz, DMSO-d$_6$) δ 8.60 (s, 1H), 8.56 (s, 1H), 8.45 (d, J=7.7 Hz, 1H), 7.97 (dd, J=7.7 Hz, 1H), 7.79 (s, 1H), 7.73 (dd, J=7.9 Hz, 1H), 7.50 (dd, J=7.9 Hz, 1H), 6.87 (s, 1H), 6.45 (d, J=7.2 Hz, 1H), 6.39 (d, J=8.0 Hz, 1H), 5.56 (s, 2H), 4.35 (d, J=7.2 Hz, 1H), 3.53-3.30 (m, 2H), 2.30-2.15 (m, 1H), 2.06-1.84 (m, 3H). MS [M+H]$^+$ for C$_{24}$H$_{21}$N$_9$O$_2$, calcd 468.2, found 468.3.

Example 182: (R)-1-[6-({4-[2-Amino-6-(3-cyano-2-methoxyphenyl)-4-pyrimidinyl]-1H-1,2,3-triazol-1-yl}methyl)-2-pyridyl]-2-pyrrolidinecarboxylic acid

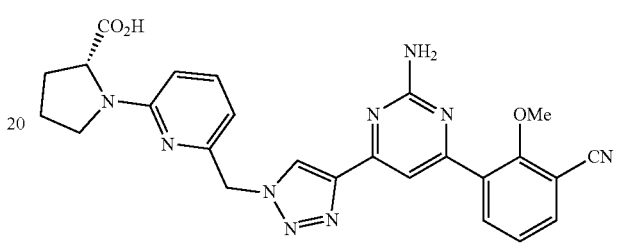

The title compound was synthesized like example 179. $^1$H NMR (400 MHz, Acetone-d$_6$) δ 11.93 (brs, 1H), 8.65 (s, 1H), 8.15 (d, J=7.8 Hz, 1H), 7.89 (s, 1H), 7.85 (d, J=8.0 Hz, 1H), 7.56 (dd, J=7.8, 8.0 Hz, 1H), 7.43 (dd, J=7.8, 8.0 Hz, 1H), 6.68 (d, J=7.2 Hz, 1H), 6.51 (d, J=8.5 Hz, 1H), 6.28 (brs, 2H), 5.61 (d, J=14.7 Hz, 1H), 5.56 (d, J=14.7 Hz, 1H), 4.58-4.56 (m, 1H), 3.95 (s, 3H), 3.61-3.41 (m, 2H), 2.37-2.22 (m, 1H), 2.22-1.99 (m, 3H). MS [M+H]$^+$ for C$_{25}$H$_{23}$N$_9$O$_3$, calcd 498.2, found 498.4.

Example 183: 4-[6-({4-[2-Amino-6-(m-cyanophenyl)-4-pyrimidinyl]-1H-1,2,3-triazol-1-yl}methyl)-2-pyridyl]-3-morpholinecarboxylic acid

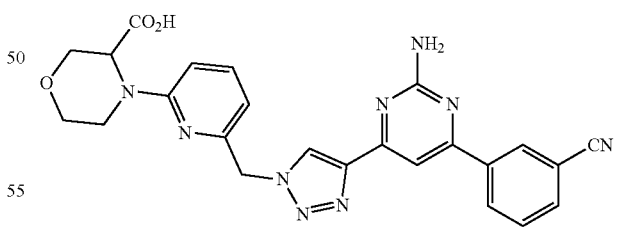

The title compound was synthesized like example 179. $^1$H NMR (400 MHz, DMSO-d$_6$) δ 12.72 (brs, 1H), 8.61 (s, 1H), 8.57 (s, 1H), 8.45 (d, J=7.8 Hz, 1H), 7.97 (d, J=7.8 Hz, 1H), 7.78 (s, 1H), 7.73 (dd, J=7.8, 7.8 Hz, 1H), 7.56 (dd, J=7.8, 7.8 Hz, 1H), 6.86 (s, 2H), 6.73 (d, J=7.8 Hz, 1H), 6.54 (d, J=7.8 Hz, 1H), 5.61 (s, 3H), 4.86 (s, 1H), 4.25 (d, J=11.2 Hz, 1H), 3.90 (d, J=11.2 Hz, 1H), 3.85-3.39 (m, 3H), 3.26-3.11 (m, 1H). MS [M+H]$^+$ for C$_{24}$H$_{21}$N$_9$O$_3$, calcd 484.2, found: 484.3.

Example 184: 1-[6-({4-[2-Amino-6-(m-cyanophenyl)-4-pyrimidinyl]-1H-1,2,3-triazol-1-yl}methyl)-2-pyridyl]-3-azetidinecarboxylic acid

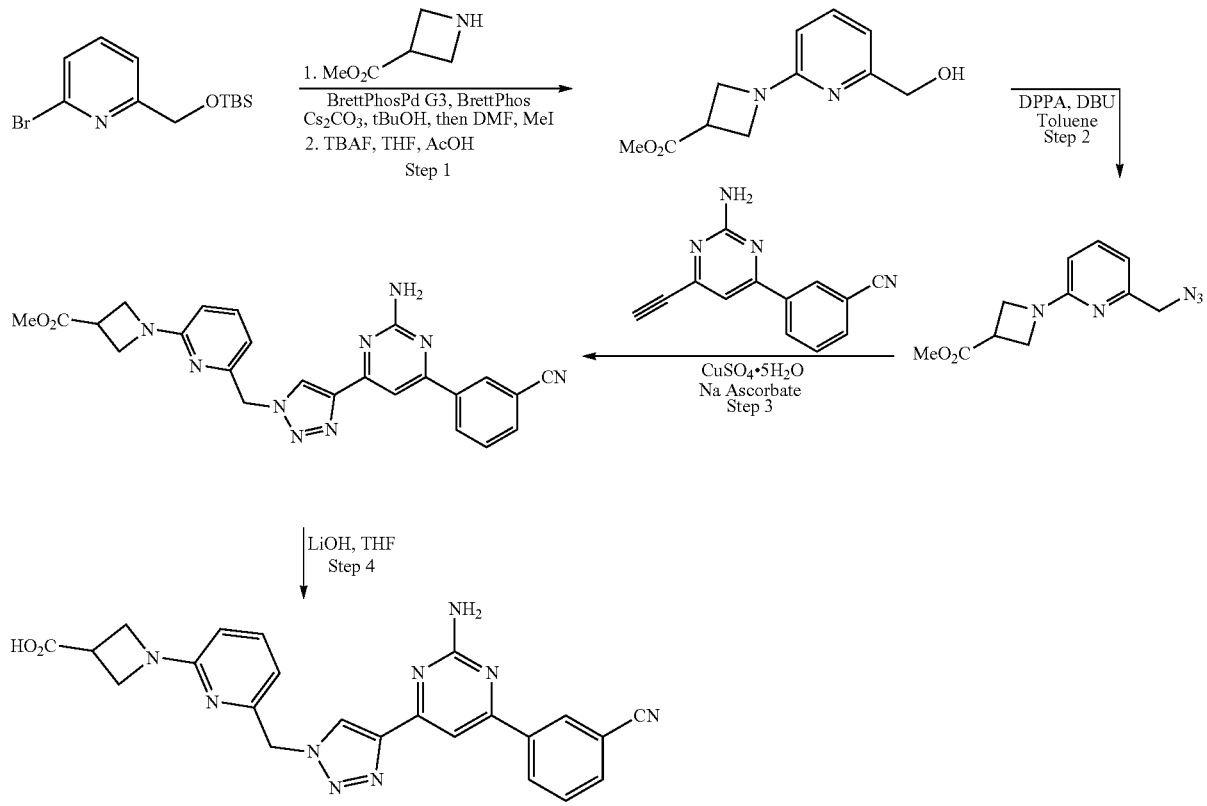

Step 1. A mixture of amine (690 mg, 6 mmol), bromide (1.51 g, 5 mmol), Cs$_2$CO$_3$ (2.44 g, 7.5 mmol), BrettPhosPd G3 (180 mg, 4 mol %) and BrettPhos (107 mg, 4 mol %) in degassed tBuOH (12 mL) was stirred at 100° C. overnight. The mixture was then cooled to room temperature and DMF (3 mL) followed by MeI (373 μL, 6 mmol) were added. The resulting mixture was stirred for an additional 4 hours. After usual work-up and silica gel chromatography (hexanes/EtOAc 95:5 to 85:15) to afford the coupled product (180 mg, 10%).

The silylether (180 mg, 0.5 mmol) was dissolved in THF (1 mL) and acetic acid (10 μL) was added followed by TBAF (1 M in THF, 1.5 mL). The mixture was stirred for 2 hours at room temperature and after usual work-up the residue was purified by silica gel chromatography (CH$_2$Cl$_2$/hexanes (1:1)/EtOAc 95:5 to 50:50) to furnish the primary alcohol (108 mg, quant.).

Step 2. The azide derivative was synthesized like step 5 of example 1 using the above alcohol (90 mg, 68%).

Step 3. Methyl 1-[6-({4-[2-amino-6-(m-cyanophenyl)-4-pyrimidinyl]-1H-1,2,3-triazol-1-yl}methyl)-2-pyridyl]-3-azetidinecarboxylate was synthesized in a similar fashion to step 6 of example 1. $^1$H NMR (400 MHz, Chloroform-d) δ 8.45 (s, 1H), 8.35 (s, 1H), 8.30 (d, J=7.6 Hz, 1H), 7.89 (s, 1H), 7.74 (dd, J=7.8, 7.8 Hz, 1H), 7.59 (dd, J=7.8, 7.8 Hz, 1H), 7.43 (dd, J=7.8, 7.8 Hz, 1H), 6.55 (d, J=7.6 Hz, 1H), 6.25 (d, J=7.6 Hz, 1H), 5.54 (s, 2H), 5.22 (s, 2H), 4.26-4.11 (m, 4H), 3.75 (s, 3H), 3.65-3.48 (m, 1H). MS [M+H]$^+$ for C$_{24}$H$_{21}$N$_9$O$_2$, calcd 468.2, found: 468.2.

Step 4. Methyl 1-[6-({4-[2-amino-6-(m-cyanophenyl)-4-pyrimidinyl]-1H-1,2,3-triazol-1-yl}methyl)-2-pyridyl]-3-azetidinecarboxylate was hydrolyzed using LiOH to afford the title compound. $^1$H NMR (400 MHz, DMSO-d$_6$) δ 8.62 (s, 1H), 8.57 (s, 1H), 8.45 (d, J=7.7 Hz, 1H), 7.97 (d, J=7.7 Hz, 1H), 7.79 (s, 1H), 7.72 (dd, J=7.9, 7.9 Hz, 1H), 7.52 (dd, J=7.9, 7.2 Hz, 1H), 6.88 (s, 2H), 6.49 (d, J=7.2 Hz, 1H), 6.36 (d, J=7.9 Hz, 1H), 5.62 (s, 3H), 4.06 (dd, J=8.4, 5.8 Hz, 2H), 3.93 (dd, J=8.4, 5.8 Hz, 2H), 3.48 (tt, J=8.4, 5.8 Hz, 2H). MS [M+H]$^+$ for C$_{23}$H$_{19}$N$_9$O$_2$, calcd 454.2, found: 454.3.

Example 185: 1-[6-({4-[2-Amino-6-(m-cyanophenyl)-4-pyrimidinyl]-1H-1,2,3-triazol-1-yl}methyl)-2-pyridyl]-3-pyrrolidinecarboxylic acid

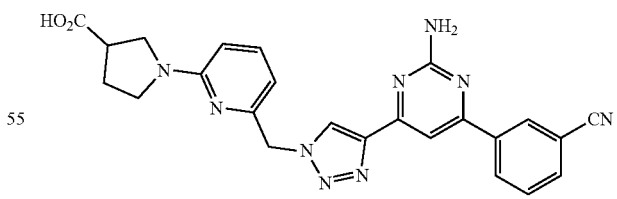

The title compound was synthesized like example 184. $^1$H NMR (400 MHz, DMSO-d$_6$) δ 8.62 (s, 1H), 8.56 (s, 1H), 8.45 (d, J=7.9 Hz, 1H), 7.97 (d, J=7.9 Hz, 1H), 7.79 (s, 1H), 7.72 (dd, J=7.9, 7.9 Hz, 1H), 7.48 (dd, J=7.9, 7.9 Hz, 1H), 6.87 (brs, 2H), 6.43 (d, J=7.9 Hz, 1H), 6.39 (d, J=7.9 Hz, 1H), 5.60 (s, 2H), 3.62-3.20 (m, 5H), 3.18-3.06 (m, 1H), 2.20-2.02 (m, 2H). MS [M+H]$^+$ for C$_{24}$H$_{21}$N$_9$O$_2$, calcd 468.4, found: 468.3.

Example 186: (R)-1-[6-({4-[2-Amino-6-(m-cyanophenyl)-4-pyrimidinyl]-1H-1,2,3-triazol-1-yl}methyl)-2-pyridyl]-3-pyrrolidinecarboxylic acid

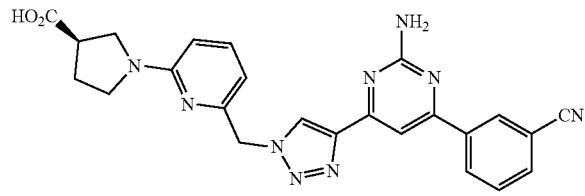

The title compound was synthesized like example 184. $^1$H NMR (400 MHz, DMSO-$d_6$) δ 12.44 (brs, 1H), 8.62 (s, 1H), 8.56 (s, 1H), 8.45 (d, J=7.9 Hz, 1H), 7.97 (d, J=7.9 Hz, 1H), 7.79 (s, 1H), 7.72 (dd, J=7.9, 7.9 Hz, 1H), 7.48 (dd, J=7.9, 7.9 Hz, 1H), 6.87 (brs, 2H), 6.43 (d, J=7.9 Hz, 1H), 6.39 (d, J=7.9 Hz, 1H), 5.60 (s, 2H), 3.62-3.20 (m, 5H), 3.18-3.06 (m, 1H), 2.20-2.02 (m, 2H). MS [M+H]$^+$ for $C_{24}H_{21}N_9O_2$, calcd 468.2, found: 468.3.

Example 187: (S)-1-[6-({4-[2-Amino-6-(m-cyanophenyl)-4-pyrimidinyl]-1H-1,2,3-triazol-1-yl}methyl)-2-pyridyl]-3-pyrrolidinecarboxylic acid

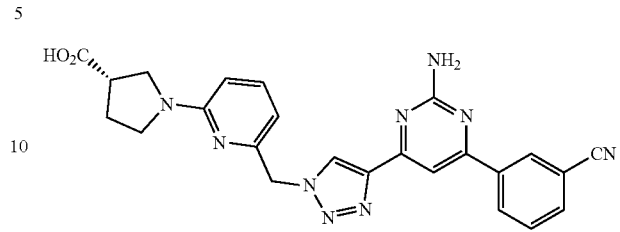

The title compound was synthesized like example 184. $^1$H NMR (400 MHz, DMSO-$d_6$) δ 12.44 (brs, 1H), 8.62 (s, 1H), 8.56 (s, 1H), 8.45 (d, J=7.9 Hz, 1H), 7.97 (d, J=7.9 Hz, 1H), 7.79 (s, 1H), 7.72 (dd, J=7.9, 7.9 Hz, 1H), 7.48 (dd, J=7.9, 7.9 Hz, 1H), 6.87 (brs, 2H), 6.43 (d, J=7.9 Hz, 1H), 6.39 (d, J=7.9 Hz, 1H), 5.60 (s, 2H), 3.62-3.20 (m, 5H), 3.18-3.06 (m, 1H), 2.20-2.02 (m, 2H). MS [M+H]$^+$ for $C_{24}H_{21}N_9O_2$, calcd 468.2, found: 468.3.

Example 188: 1-[6-({4-[2-Amino-6-(m-cyanophenyl)-4-pyrimidinyl]-1H-1,2,3-triazol-1-yl}methyl)-2-pyridyl]-3-piperidinecarboxylic acid

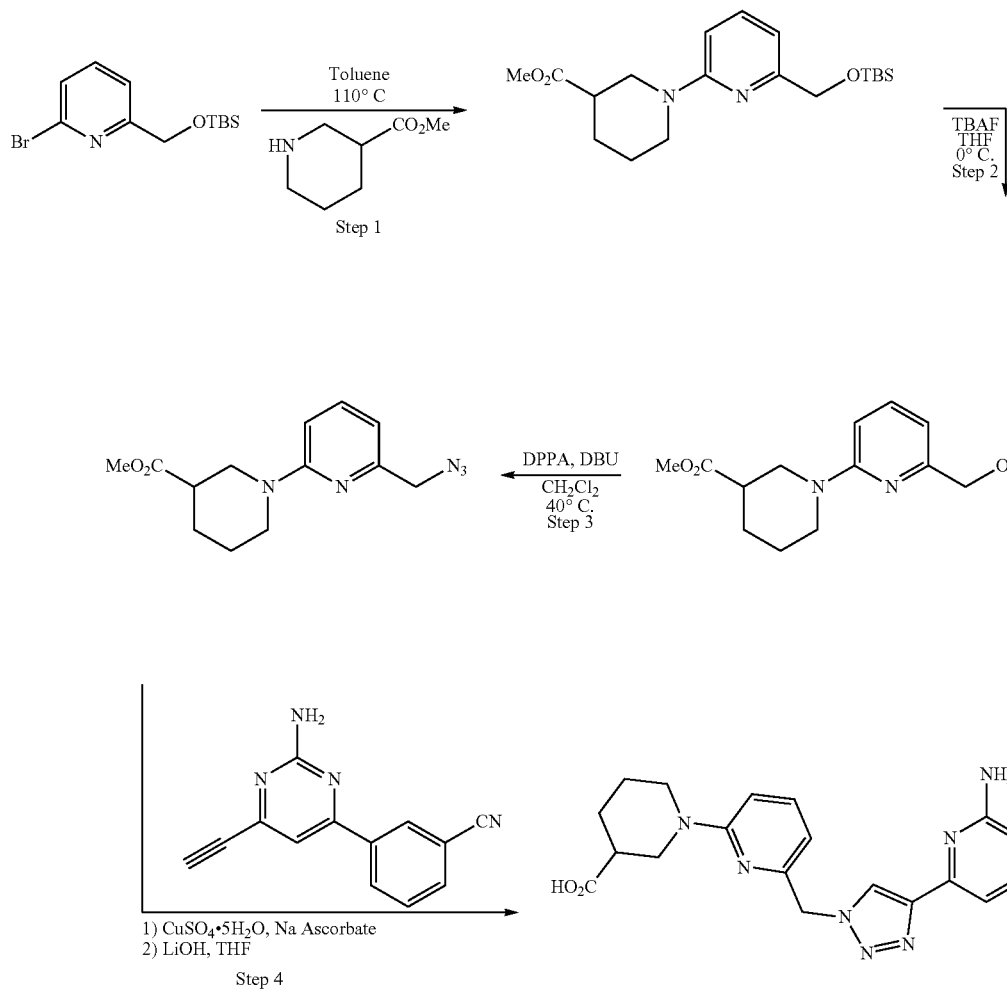

Step 1: A mixture of the bromopyridine derivative (1.51 g, 5.00 mmol), and methyl piperidine-3-carboxylate (1.07 g, 7.50 mmol), in toluene (2.5 mL) was stirred at 110° C. for 14 hours. The mixture was cooled, sat. NaHCO$_3$ was added, and the mixture was extracted with ethyl acetate (3×20 mL). The crude product was purified by silica gel chromatography (0 to 5% MeOH in CH$_2$Cl$_2$) to afford the desired product as a clear oil (481 mg; 26%).

Step 2: To a solution of the step 1 product (481 mg, 1.32 mmol) in THF (2.9 mL) at 0° C. was added TBAF (1.45 mL, 1.45 mmol, 1 M in THF) dropwise. The mixture was stirred at 0° C. for 15 minutes. The mixture was concentrated and purified by silica gel chromatography (0 to 10% MeOH in CH$_2$Cl$_2$) to afford the desired product.

Step 3: To a solution of the step 2 product and DPPA (341 µL, 1.58 mmol) in CH$_2$Cl2 (1.3 mL) was added DBU (236 µL, 1.58 mmol). The mixture was stirred at 40° C. for 14 hours. The mixture was concentrated and purified by silica gel chromatography (0 to 5% MeOH in CH$_2$Cl$_2$) to afford the desired product as a colorless oil (144 mg; 40%, 2 steps).

Step 4: The product was synthesized in a similar manner to example 125: Yellow solid (12 mg, 8%). $^1$H NMR (400 MHz, DMSO-d$_6$) δ 12.32 (br s, 1H), 8.64 (s, 1H), 8.58 (d, J=1.9 Hz, 1H), 8.47 (d, J=8.0 Hz, 1H), 7.99 (d, J=7.7 Hz, 1H), 7.82-7.78 (m, 1H), 7.74 (t, J=7.8 Hz, 1H), 7.56-7.49 (m, 1H), 6.88 (s, 2H), 6.80 (d, J=8.6 Hz, 1H), 6.45 (d, J=7.2 Hz, 1H), 5.63 (s, 2H), 4.27 (d, J=13.1 Hz, 1H), 3.99 (d, J=13.1 Hz, 1H), 3.07-2.86 (m, 2H), 2.44-2.31 (m, 1H), 2.01-1.86 (m, 1H), 1.71-1.52 (m, 2H), 1.49-1.32 (m, 1H). ESI MS [M+H]$^+$ for C$_{25}$H$_{24}$N$_9$O$_2$, calcd 482.2, found 482.3.

Example 189: 1-[6-({4-[2-Amino-6-(m-cyanophenyl)-4-pyrimidinyl]-1H-1,2,3-triazol-1-yl}methyl)-2-pyridyl]-4-piperidinecarboxylic acid

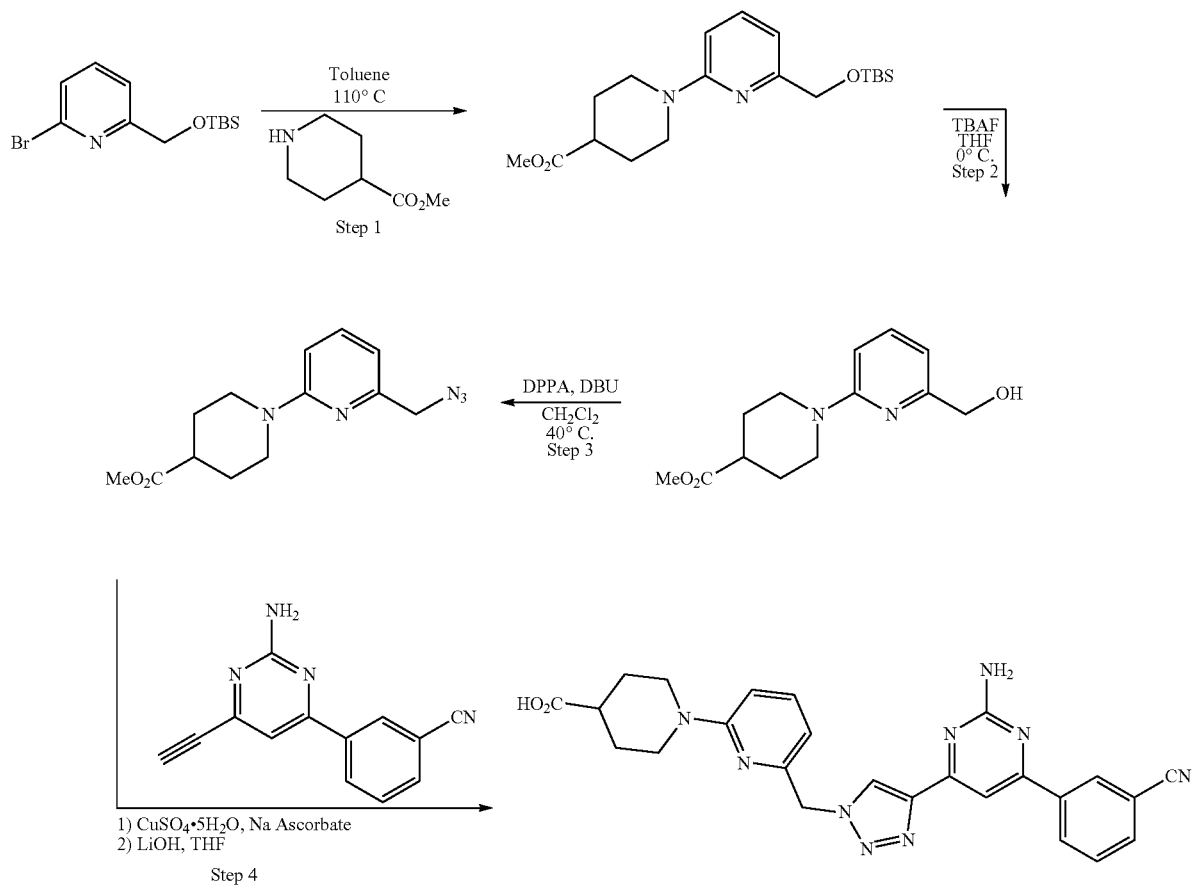

Steps 1-3: The azide was synthesized in a similar manner to example 188: Colorless oil (154 mg, 11%, 3 steps).

Step 4: The product was synthesized in a similar manner to example 125: Yellow solid (12 mg, 19%). $^1$H NMR (400 MHz, DMSO-d$_6$) δ 8.70 (s, 1H), 8.59 (s, 1H), 8.47 (d, J=6.8 Hz, 1H), 8.01 (d, J=7.5 Hz, 1H), 7.83 (s, 1H), 7.75 (t, J=7.2 Hz, 1H), 7.54 (t, J=7.9 Hz, 1H), 6.80 (d, J=8.6 Hz, 1H), 6.49 (d, J=7.2 Hz, 1H), 5.65 (s, 2H), 4.15 (d, J=13.1 Hz, 2H), 2.90 (t, J=12.1 Hz, 2H), 2.48-2.42 (m, 1H), 1.82 (d, J=13.1 Hz, 2H), 1.46 (q, J=11.4 Hz, 2H). ESI MS [M+H]$^+$ for C$_{25}$H$_{24}$N$_9$O$_2$, calcd 482.2, found 482.3.

Example 190: 1-[6-({4-[2-Amino-6-(m-cyanophenyl)-4-pyrimidinyl]-1H-1,2,3-triazol-1-yl}methyl)-2-pyridyl]-2-piperidinecarboxylic acid

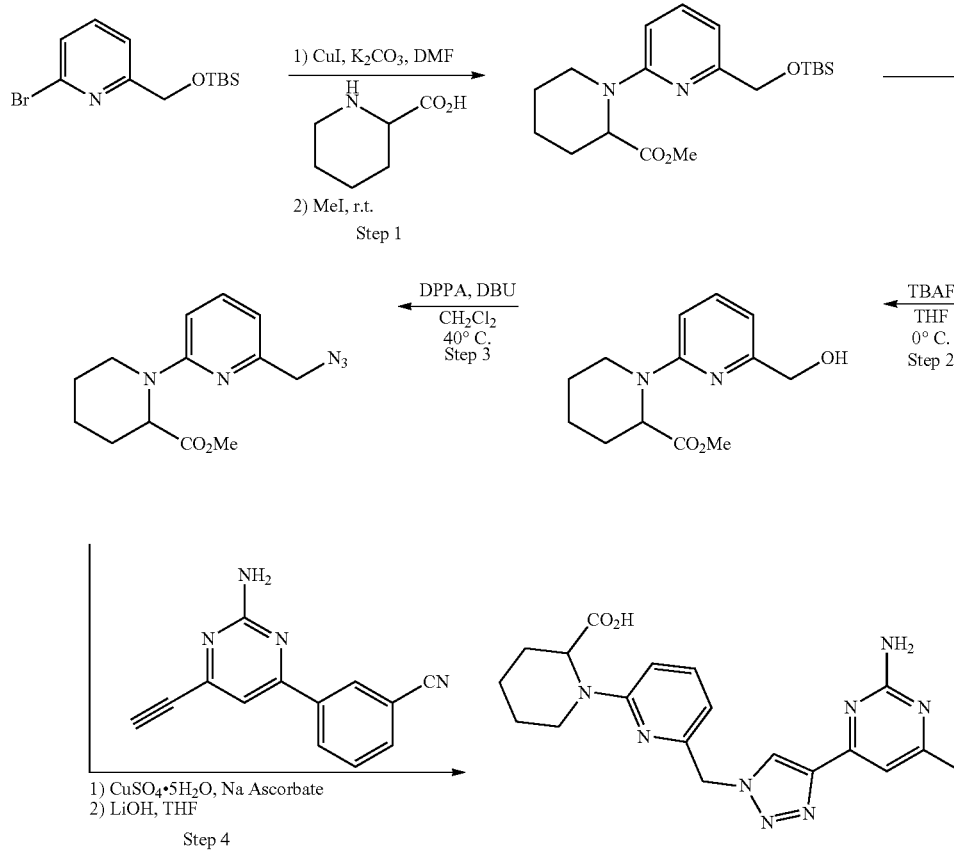

Step 1: Under a nitrogen atmosphere, a mixture of the bromopyridine derivative (3.02 g, 10.0 mmol), pipecolinic acid (2.58 g, 20.0 mmol), copper(I) iodide (380 mg, 2.00 mmol), $K_2CO_3$ (2.74 g, 20.0 mmol), and DMF (10 mL) was stirred at 110° C. for 1 hour. The mixture was cooled to r.t., methyl iodide was added dropwise, and the mixture stirred at r.t. for 14 hours. Ethyl acetate (100 mL) was added, the organic phase washed with brine (4×75 mL), and dried over $Na_2SO_4$. The crude product was purified by silica gel chromatography (0 to 5% MeOH in $CH_2Cl_2$) to afford the desired product as a clear oil (778 mg; 21%).

Steps 2-3: The azide was synthesized in a similar manner to example 188: Colorless oil (354 mg, 60% (2 steps)).

Step 4: The product was synthesized in a similar manner to example 125: Yellow solid (40 mg, 28%). $^1$H NMR (400 MHz, DMSO-$d_6$) δ 12.55 (br s, 1H), 8.64 (s, 1H), 8.59 (s, 1H), 8.47 (d, J=8.2 Hz, 1H), 7.99 (d, J=8.0 Hz, 1H), 7.81 (s, 1H), 7.77-7.70 (m, 1H), 7.56-7.48 (m, 1H), 6.88 (s, 2H), 6.74 (d, J=8.9 Hz, 1H), 6.47 (d, J=7.4 Hz, 1H), 5.60 (s, 2H), 5.14 (s, 1H), 4.02 (d, J=12.5 Hz, 1H), 3.00 (t, J=12.6 Hz, 1H), 2.16 (d, J=12.9 Hz, 1H), 1.81-1.53 (m, 3H), 1.52-1.35 (m, 1H), 1.33-1.18 (m, 1H). ESI MS [M+H]$^+$ for $C_{25}H_{24}N_9O_2$, calcd 482.2, found 482.3.

Example 191: {1-[6-({4-[2-Amino-6-(m-cyanophenyl)-4-pyrimidinyl]-1H-1,2,3-triazol-1-yl}methyl)-2-pyridyl]-4-piperidyl}acetic acid

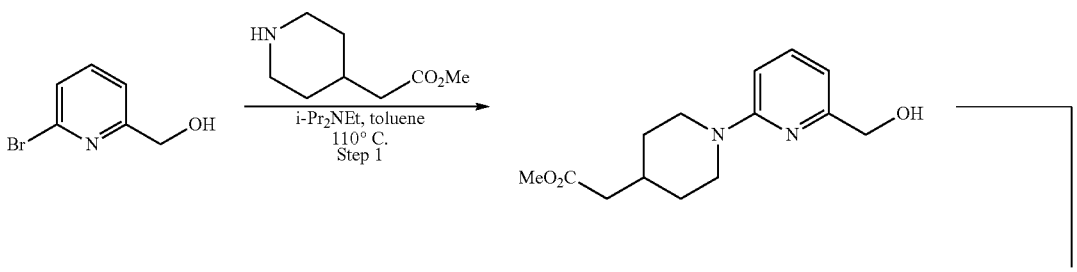

-continued

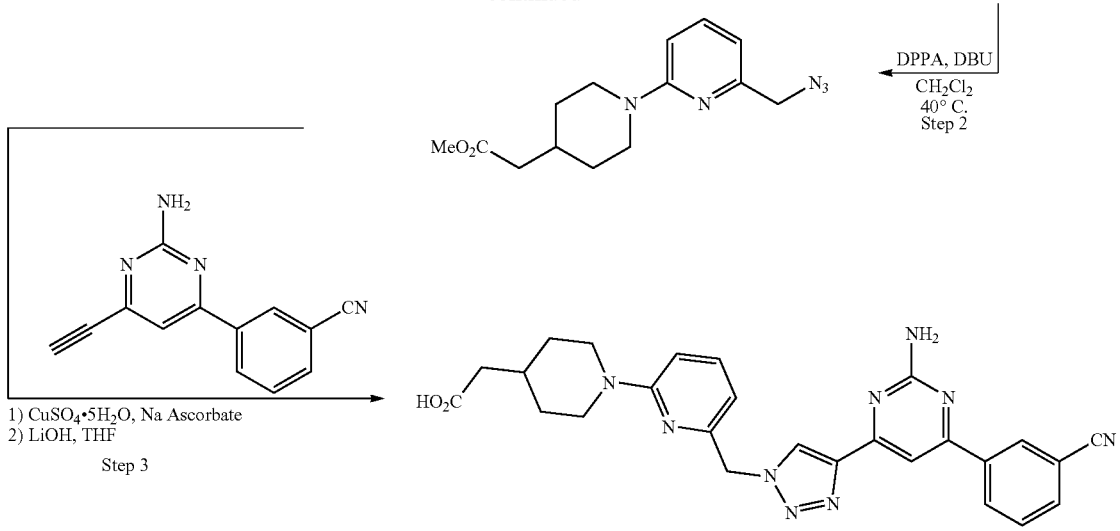

Step 1: A mixture of the bromopyridine derivative (1.88 g, 10.0 mmol), methyl 4-piperidylacetate (1.57 g, 10.0 mmol), diisopropylethylamine (2.61 mL, 15.0 mmol), and toluene was stirred at 110° C. for 2 days. The mixture was concentrated and purified by silica gel chromatography (0 to 10% MeOH in CH$_2$Cl$_2$) to afford the desired product, which was used directly in the next step.

Step 2: The azide was synthesized in a similar manner to example 188 to get the product as a yellow oil (284 mg, 10%, 2 steps).

Step 3: The product was synthesized in a similar manner to example 125: White solid (92 mg, 62%). $^1$H NMR (400 MHz, DMSO-d$_6$) δ 12.05 (br s, 1H), 8.64 (s, 1H), 8.58 (s, 1H), 8.47 (d, J=7.9 Hz, 1H), 7.99 (d, J=6.5 Hz, 1H), 7.81 (s, 1H), 7.74 (t, J=7.9 Hz, 1H), 7.51 (t, J=8.0 Hz, 1H), 6.89 (s, 2H), 6.76 (d, J=8.6 Hz, 1H), 6.45 (d, J=7.2 Hz, 1H), 5.62 (s, 2H), 4.23 (d, J=13.0 Hz, 2H), 2.75 (t, J=12.8, 2.6 Hz, 2H), 2.14 (d, J=6.9 Hz, 2H), 1.95-1.81 (m, 1H), 1.68 (d, J=12.9 Hz, 2H), 1.11 (q, J=12.8, 11.8 Hz, 2H). ESI MS [M+H]$^+$ for C$_{26}$H$_{26}$N$_9$O, calcd 496.2, found 496.4.

Example 192: 1-[6-({4-[2-Amino-6-(m-cyanophenyl)-4-pyrimidinyl]-1H-1,2,3-triazol-1-yl}methyl)-2-pyridyl]-4-methyl-4-piperidinecarboxylic acid

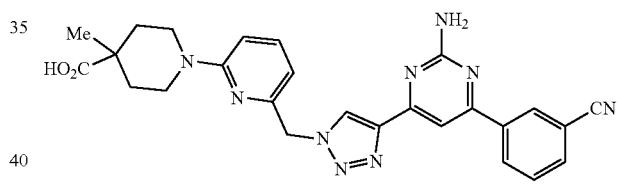

The title compound was synthesized in a similar fashion to example 191. $^1$H NMR (400 MHz, DMSO-d$_6$) δ 12.36 (br s, 1H), 8.65 (s, 1H), 8.58 (t, J=1.7 Hz, 1H), 8.47 (d, J=7.9 Hz, 1H), 7.99 (dt, J=7.7, 1.4 Hz, 1H), 7.81 (s, 1H), 7.74 (t, J=7.9 Hz, 1H), 7.52 (dd, J=8.6, 7.2 Hz, 1H), 6.89 (s, 2H), 6.78 (d, J=8.6 Hz, 1H), 6.47 (d, J=7.2 Hz, 1H), 5.63 (s, 2H), 3.84 (d, J=13.6 Hz, 2H), 3.14-3.04 (m, 2H), 1.98-1.87 (m, 2H), 1.38-1.26 (m, 2H), 1.12 (s, 3H). ESI MS [M+H]$^+$ for C$_{26}$H$_{26}$N$_9$O, calcd 496.2, found 496.3.

Example 193: {4-[6-({4-[2-Amino-6-(m-cyanophenyl)-4-pyrimidinyl]-1H-1,2,3-triazol-1-yl}methyl)-2-pyridyl]-1-piperazinyl}acetic acid

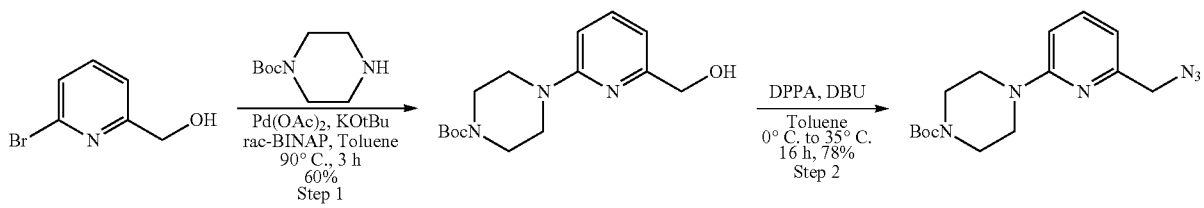

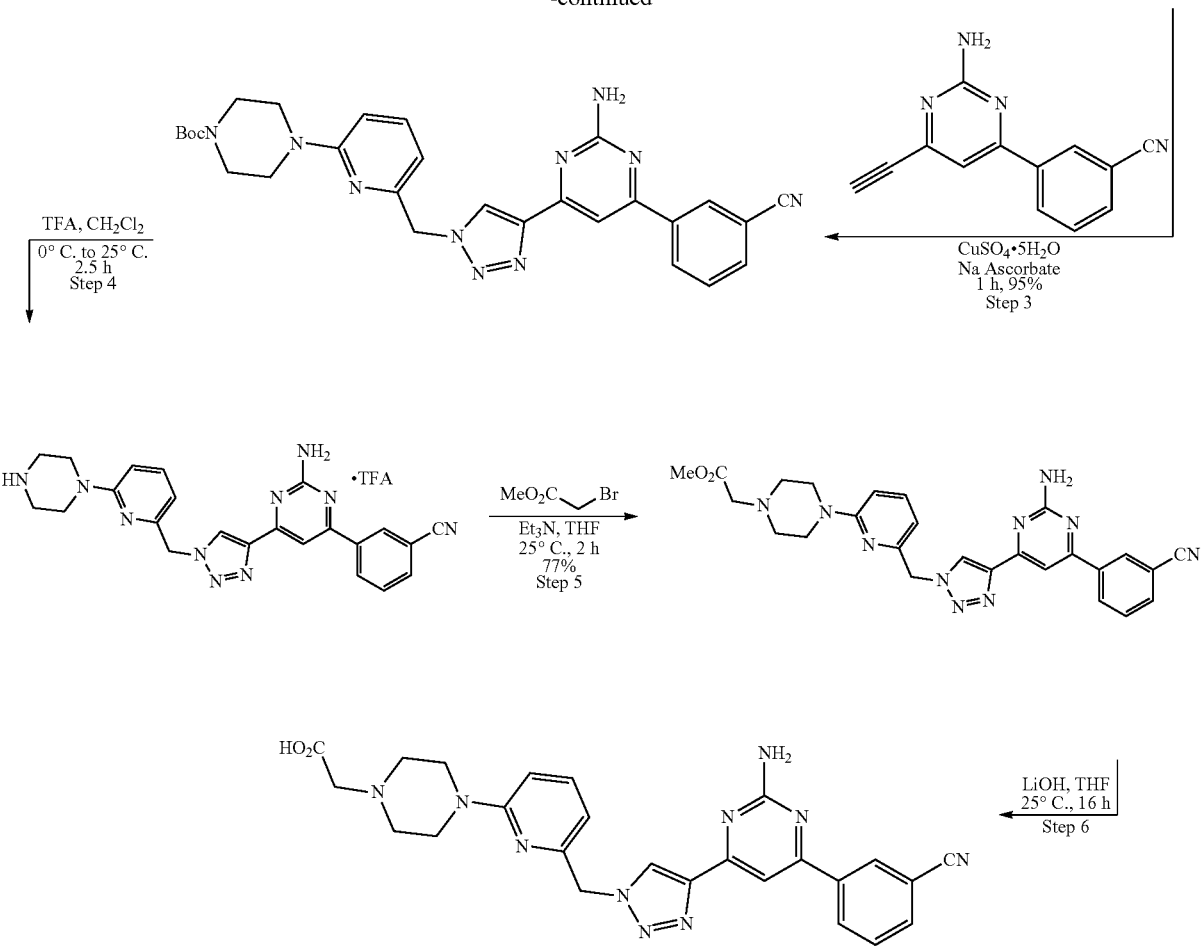

Step 1: To a solution of bromopyridine (3.0 g, 16.0 mmol), 1-Boc-piperazine (2.48 g, 13.3 mmol) in toluene (32 ml) was added KOtBu (2.24 g, 20.0 mmol), followed by racemic BINAP (165.6 mg, 0.266 mmol), and Pd(OAc)$_2$ (29.9 mg, 0.133 mmol). The solution was sparged with nitrogen for one minute, sealed, and heated to 90° C. for 2.5 h. The reaction solution was concentrated onto celite and purified by flash chromatography over silica gel (ethyl acetate/[1:1 hexanes:CH$_2$Cl$_2$] gradient 10% to 50%).

Step 2: The resulting benzyl alcohol (1.0 g, 3.4 mmol) was dissolved in toluene (4.3 ml) and cooled to 0° C. before the sequential addition of DPPA (0.89 ml, 4.1 mmol) and DBU (0.62 ml, 4.1 mmol). The reaction was warmed to 35° C. and stirred for 16 hours. Upon completion the reaction was partitioned between ethyl acetate and water, the organic layer was collected and concentrated onto celite. The resulting crude material was purified by flash chromatography over silica gel (5% ethyl acetate in hexanes).

Step 3: The resulting benzyl azide (79.5 mg, 0.25 mmol), aryl alkyne (55.1 mg, 0.25 mmol), CuSO$_4$ pentahydrate (6.2 mg, 0.025 mmol) and Na ascorbate (10 mg, 0.05 mmol) were combined in 2:1 t-BuOH/H$_2$O (1.0 ml) and methylene chloride (0.5 ml). The reaction was heated at 60° C. for one hour, then concentrated onto celite. The resulting crude product was purified by flash chromatography over silica gel (ethyl acetate/[1:1 hexanes:CH$_2$Cl$_2$] gradient 0% to 100%).

Step 4: The triazole product from step 3 (127.7 mg, 0.24 mmol) was dissolved in methylene chloride (1.2 ml) and cooled to 0° C. before the addition of TFA (1.2 ml) dropwise. The solution was removed from the cooling bath and allowed to warm to room temperature over 2.5 hours of stirring. The resulting solution was concentrated and taken onto the next reaction without further purification.

Step 5: The trifluoroacetate salt product (130.9 mg, 0.24 mmol) was dissolved in THF (0.3 ml) and triethylamine (0.198 ml, 1.42 mmol) was added to the solution. After stirring for two hours the reaction was partitioned between saturated NaHCO$_3$ and ethyl acetate. The organic phase was collected, washed with brine, dried over sodium sulfate, and concentrated onto celite. The resulting crude product was purified by flash chromatography over silica gel (methanol/methylene chloride 0.5% to 5%).

Step 6: To a solution of methyl ester (93.7 mg, 0.18 mmol) in THF (0.9 ml) was added LiGH (aq., 3M, 0.061 ml) at room temperature. The reaction was stirred for 16 hours, then concentrated to dryness. The resulting solid was reconstituted in 1 ml of H$_2$O, and 1N HCl (0.368 ml) was added. The resulting solution was stirred for 10 minutes before it was frozen and lyophilized to provide the title compound. $^1$H NMR (400 MHz, DMSO-d$_6$) δ 8.69 (s, 1H), 8.57 (s, 1H), 8.46 (d, J=8.1 Hz, 1H), 7.98 (d, J=7.7 Hz, 1H), 7.81 (s, 1H), 7.73 (dd, J=7.7, 7.7 Hz, 1H), 7.63 (dd, J=8.6, 7.3 Hz, 1H), 6.94 (brs, 2H), 6.89 (d, J=8.6 Hz, 1H), 6.64 (d, J=7.3 Hz, 1H), 5.67 (s, 2H), 4.13 (s, 2H), 3.44 (brs, 8H). ESI MS [M+H]$^+$ for C$_{25}$H$_{24}$N$_{10}$O$_2$, calcd 497.2, found 497.3.

Example 194: [(S)-4-[6-({4-[2-Amino-6-(m-cyanophenyl)-4-pyrimidinyl]-1H-1,2,3-triazol-1-yl}methyl)-2-pyridyl]-3-methyl-1-piperazinyl]acetic acid

Example 195: [(R)-4-[6-({4-[2-Amino-6-(m-cyanophenyl)-4-pyrimidinyl]-1H-1,2,3-triazol-1-yl}methyl)-2-pyridyl]-3-methyl-1-piperazinyl]acetic acid

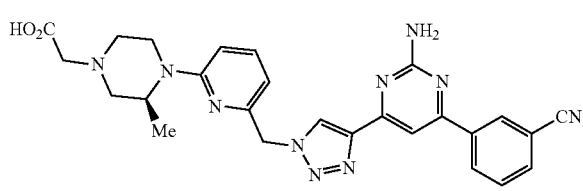 [SMILES: C[C@H]1CN(CC(=O)O)CCN1c1cccc(Cn2cc(-c3cc(-c4cccc(C#N)c4)nc(N)n3)nn2)n1]

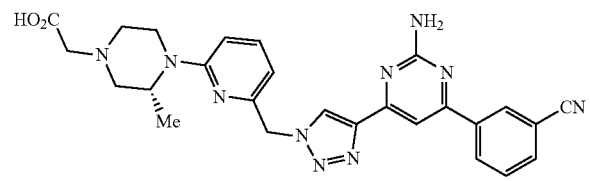 [SMILES: C[C@@H]1CN(CC(=O)O)CCN1c1cccc(Cn2cc(-c3cc(-c4cccc(C#N)c4)nc(N)n3)nn2)n1]

The title compound was synthesized in a similar fashion to example 193. $^1$H NMR (400 MHz, DMSO-d$_6$) δ 10.37 (brs, 1H), 8.73 (s, 1H), 8.58 (s, 1H), 8.47 (d, J=8.1 Hz, 1H), 8.00 (d, J=7.7, 1H), 7.83 (s, 1H), 7.74 (dd, J=7.8, 7.8 Hz, 1H), 7.62 (dd, J=8.6, 7.3 Hz, 1H), 7.01 (brs, 2H), 6.82 (d, J=8.6 Hz, 1H), 6.63 (d, J=7.3 Hz, 1H), 5.67 (s, 2H), 4.74 (brs, 1H), 4.26-4.05 (m, 2H), 3.61-3.45 (m, 3H), 3.26-3.11 (m, 3H), 1.18 (d, J=6.7 Hz, 3H). ESI MS [M+H]$^+$ for C$_{26}$H$_{26}$N$_{10}$O$_2$, calcd 511.2, found 511.3.

The title compound was synthesized in a similar fashion to example 193. $^1$H NMR (400 MHz, DMSO-d$_6$) δ 8.72 (s, 1H), 8.58 (s, 1H), 8.47 (d, J=8.0 Hz, 1H), 8.00 (d, J=7.7, 1H), 7.83 (s, 1H), 7.74 (dd, J=7.8, 7.8 Hz, 1H), 7.62 (dd, J=8.6, 7.3 Hz, 1H), 6.96 (brs, 2H), 6.82 (d, J=8.6 Hz, 1H), 6.63 (d, J=7.3 Hz, 1H), 5.67 (s, 2H), 4.73 (brs, 1H), 4.26-4.05 (m, 2H), 3.61-3.45 (m, 3H), 3.25-3.11 (m, 3H), 1.18 (d, J=6.7 Hz, 3H). ESI MS [M+H]$^+$ for C$_{26}$H$_{26}$N$_{10}$O$_2$, calcd 511.2, found 511.3.

Example 196: 1-{[6-({4-[2-Amino-6-(m-cyanophenyl)-4-pyrimidinyl]-1H-1,2,3-triazol-1-yl}methyl)-2-pyridyl]methyl}-3-pyrrolidinecarboxylic acid

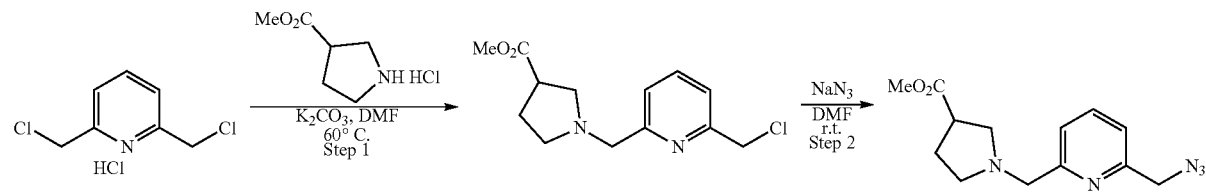

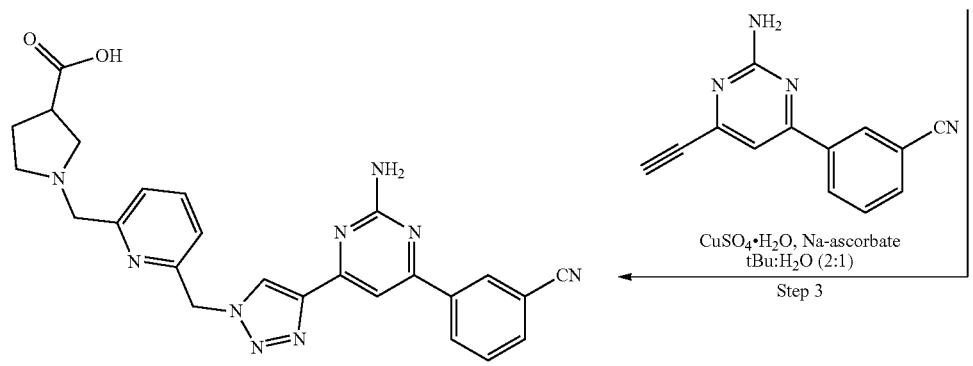

Step 1: To a mixture of dichloromethyl-pyridine derivative (1.0 g, 4.7 mmol) and HCl salt of pyrrolidine 3-methyl carboxylate in 10 mL DMF was added $K_2CO_3$ (2.6 g, 18.4 mmol). The reaction was heated at 90° C. for 10 h. After cooling the reaction to room temperature, solids were filtered off and the crude product (as a solution in DMF) was used in next step without further purification.

Step 2: To the crude product from step 1 (as a solution in DMF) was added $NaN_3$ (336 mg, 5.2 mmol) and stirred for 10 h at room temperature. The reaction mixture was diluted with 30 mL EtOAc and subsequently washed with $H_2O$ (5×30 mL). The organic layer was dried over $Na_2SO_4$, concentrated and purified by silica gel chromatography to yield the desired azide (582 mg, 45% in 2 steps).

Step 3: The title compound was synthesized similar to example 125. $^1$H NMR (400 MHz, DMSO-$d_6$) δ 10.28 (s, 1H), 8.76 (d, J=1.0 Hz, 1H), 8.56 (d, J=1.6 Hz, 1H), 8.44 (dd, J=8.1, 1.5 Hz, 1H), 8.03-7.91 (m, 2H), 7.79 (s, 1H), 7.76-7.70 (m, 1H), 7.47 (d, J=7.8 Hz, 1H), 7.39 (d, J=7.9 Hz, 1H), 6.86 (s, 2H), 5.89 (s, 2H), 4.53 (m, 2H), 3.74 (m, 6H), 2.05 (m, 1H). ESI MS [M+H]$^+$ for $C_{25}H_{23}N_9O_2$, calcd 482.2, found 482.3.

Example 197: 1-{[6-({4-[2-Amino-6-(m-cyanophenyl)-4-pyrimidinyl]-1H-1,2,3-triazol-1-yl}methyl)-2-pyridyl]cyclopropylmethyl}-4-piperidinecarboxylic acid

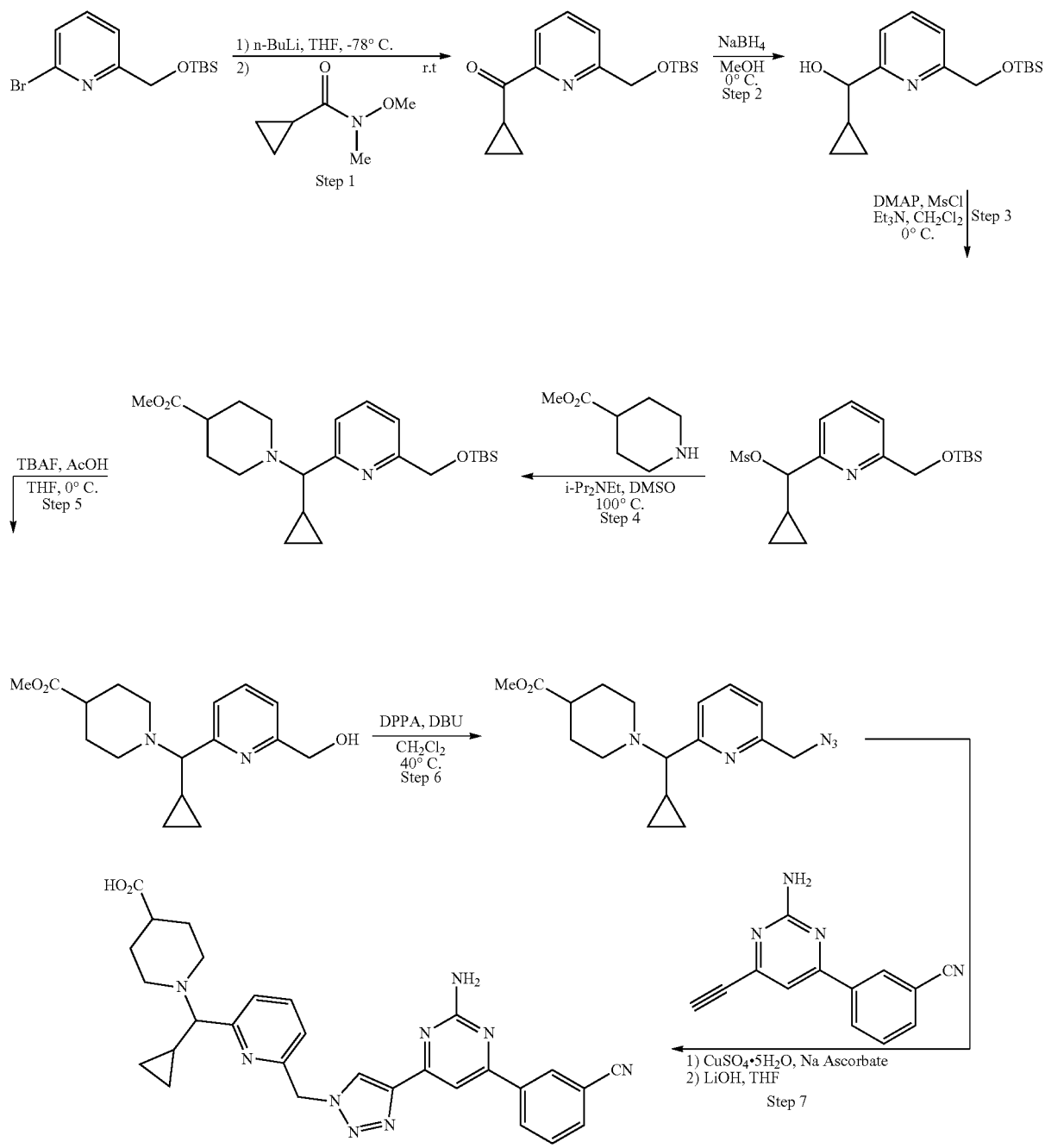

Step 1: To a solution of the bromopyridine derivative (6.05 g, 20.0 mmol) in THF (80 mL) at −78° C. was added n-butyllithium (8.4 mL, 21.0 mmol, 2.5 M in hexanes) dropwise. The mixture was stirred at −78° C. for 30 min and solution of N-methoxy-N-methylcyclopropanamide (2.84 g, 22.0 mmol) in THF (20 mL) was added at this temperature dropwise. The mixture was warmed to r.t. over 14 hours and was quenched with sat. $NH_4Cl_{(aq)}$. Ethyl acetate (100 mL) was added and the organic phase dried with brine and $MgSO_4$. The crude product was purified by silica gel chromatography (0 to 20% EtOAc in hexanes) to afford the desired product as a yellow oil (4.14 g; 71%).

Step 2: To a solution of the step 1 product (1.33 g, 4.55 mmol) in MeOH (23 mL) at 0° C. was added $NaBH_4$ (190 mg, 5.00 mmol) in several portions. The mixture was stirred at r.t. for 30 min. Sat. $NH_4Cl$ was added, the organics extracted with ethyl acetate (2×50 mL), and dried over $Na_2SO_4$ to afford the desired product, which was used directly in the next step.

Step 3: To a solution of the step 2 product, DMAP (56 mg, 0.455 mmol), $Et_3N$ (955 µL, 6.85 mmol), and c (9 mL) at 0° C. was added MsCl (387 µL, 5.00 mmol) dropwise. The mixture was stirred at 0° C. for 15 minutes and concentrated to afford the desired product, which was used directly in the next step.

Step 4: A mixture of the step 3 product, methyl piperidine-4-carboxylate (716 mg, 5.00 mmol), diisopropylethylamine (1.59 mL, 9.10 mmol), and DMSO (5 mL) was stirred at 100° C. for 6 hours. The mixture was cooled, ethyl acetate (100 mL) was added, and the organic phase was washed with brine (4×100 mL). The crude product was purified by silica gel chromatography (0 to 10% MeOH in $CH_2Cl_2$) to afford the desired product as a brown oil (152 mg; 8% (3 steps)).

Steps 5-6: The azide was synthesized in a similar manner to example 79, except AcOH (25 µL, 0.436 mmol) was included in the TBAF deprotection step: brown oil (69 mg, 58% (2 steps)).

Step 7: The product was synthesized in a similar manner to example 125: White solid (43 mg, 38%). $^1$H NMR (400 MHz, DMSO-$d_6$) δ 8.72 (s, 1H), 8.59 (s, 1H), 8.47 (d, J=8.1 Hz, 1H), 7.99 (d, J=7.7 Hz, 1H), 7.82 (s, 1H), 7.78-7.71 (m, 2H), 7.35 (d, J=7.8 Hz, 1H), 7.10 (d, J=7.7 Hz, 1H), 6.92 (s, 2H), 5.82 (s, 2H), 2.77 (d, J=10.6 Hz, 2H), 2.34 (s, 4H), 1.99-1.82 (m, 3H), 1.77 (s, 2H), 1.70 (d, J=12.8 Hz, 2H), 1.47 (q, J=11.4 Hz, 2H). ESI MS [M+H]$^+$ for $C_{29}H_3N_9O_2$, calcd 536.2, found 536.3.

Example 198: 1-{1-[6-({4-[2-Amino-6-(m-cyanophenyl)-4-pyrimidinyl]-1H-1,2,3-triazol-1-yl}methyl)-2-pyridyl]ethyl}-4-piperidinecarboxylic acid

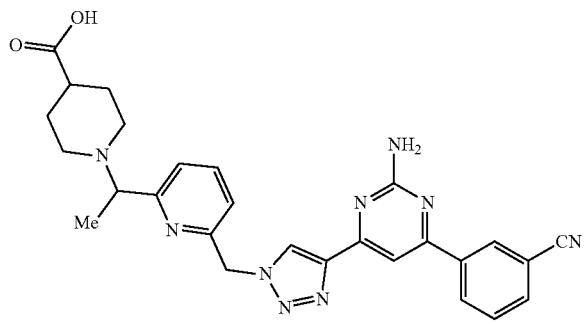

The title compound was synthesized similar to example 197. $^1$H NMR (400 MHz, DMSO-$d_6$) δ 8.65 (d, J=1.2 Hz, 1H), 8.56 (d, J=1.6 Hz, 1H), 8.45 (dd, J=8.1, 1.6 Hz, 1H), 7.97 (dd, J=7.7, 1.3 Hz, 1H), 7.79 (d, J=1.2 Hz, 1H), 7.76-7.68 (m, 2H), 7.36 (d, J=7.8 Hz, 1H), 7.10 (d, J=7.6 Hz, 1H), 6.92 (s, 2H), 5.79 (s, 2H), 3.53 (q, J=6.8 Hz, 1H), 2.74 (m, 1H), 2.60 (m, 1H), 1.89 (t, J=11.1 Hz, 2H), 1.70-1.53 (m, 3H), 1.45 (m, 2H), 1.22 (d, J=6.7 Hz, 3H). ESI MS [M+H]$^+$ for $C_{27}H_{27}N_9O_2$, calcd 510.2, found 510.3.

Example 199: 1-{1-[6-({4-[2-Amino-6-(m-cyanophenyl)-4-pyrimidinyl]-1H-1,2,3-triazol-1-yl}methyl)-2-pyridyl]ethyl}-3-pyrrolidinecarboxylic acid

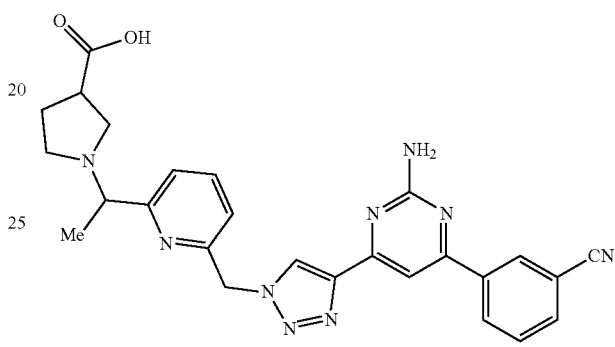

The title compound was synthesized similar to example 197. $^1$H NMR (400 MHz, DMSO-$d_6$) δ 8.67 (m, 1H), 8.57 (s, 1H), 8.45 (d, J=7.2 Hz, 1H), 8.00-7.93 (m, 1H), 7.81-7.69 (m, 3H), 7.37 (dd, J=7.9, 3.4 Hz, 1H), 7.08 (dd, J=7.7, 4.0 Hz, 1H), 6.94 (s, 2H), 5.79 (s, 2H), 2.70-2.60 (m, 1H), 2.45 (s, 1H), 2.38 (m, 1H), 2.33-2.19 (m, 2H), 1.99-1.84 (m, 1H), 1.70 (m, 1H), 1.23 (d, J=6.6 Hz, 3H). ESI MS [M+H]$^+$ for $C_{26}H_{25}N_9O_2$, calcd 496.2, found 496.3.

Example 200: 1-{1-[6-({4-[2-Amino-6-(m-cyanophenyl)-4-pyrimidinyl]-1H-1,2,3-triazol-1-yl}methyl)-2-pyridyl]ethyl}-3-azetidinecarboxylic acid

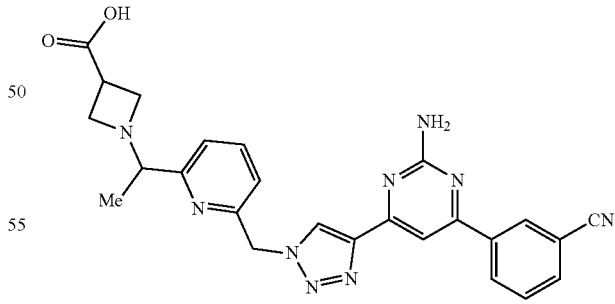

The title compound was synthesized similar to example 197. $^1$H NMR (400 MHz, DMSO-$d_6$) δ 8.67 (s, 1H), 8.57 (d, J=1.6 Hz, 1H), 8.50-8.42 (m, 1H), 7.97 (dd, J=7.5, 1.4 Hz, 1H), 7.81-7.67 (m, 3H), 7.32 (d, J=7.8 Hz, 1H), 7.08 (d, J=7.7 Hz, 1H), 6.94 (s, 2H), 5.78 (s, 2H), 3.26 (m, 1H), 3.07 (m, 2H), 2.95 (t, J=7.1 Hz, 2H), 2.66 (m, 1H), 1.55 (m, 1H), 1.05 (d, J=6.5 Hz, 3H). ESI MS [M+H]$^+$ for $C_{25}H_{23}N_9O_2$, calcd 482.2, found 482.3.

Example 201: (S)-1-[(R)-1-[6-({4-[2-Amino-6-(m-cyanophenyl)-4-pyrimidinyl]-1H-1,2,3-triazol-1-yl}methyl)-2-pyridyl]ethyl]-3-pyrrolidinecarboxylic acid

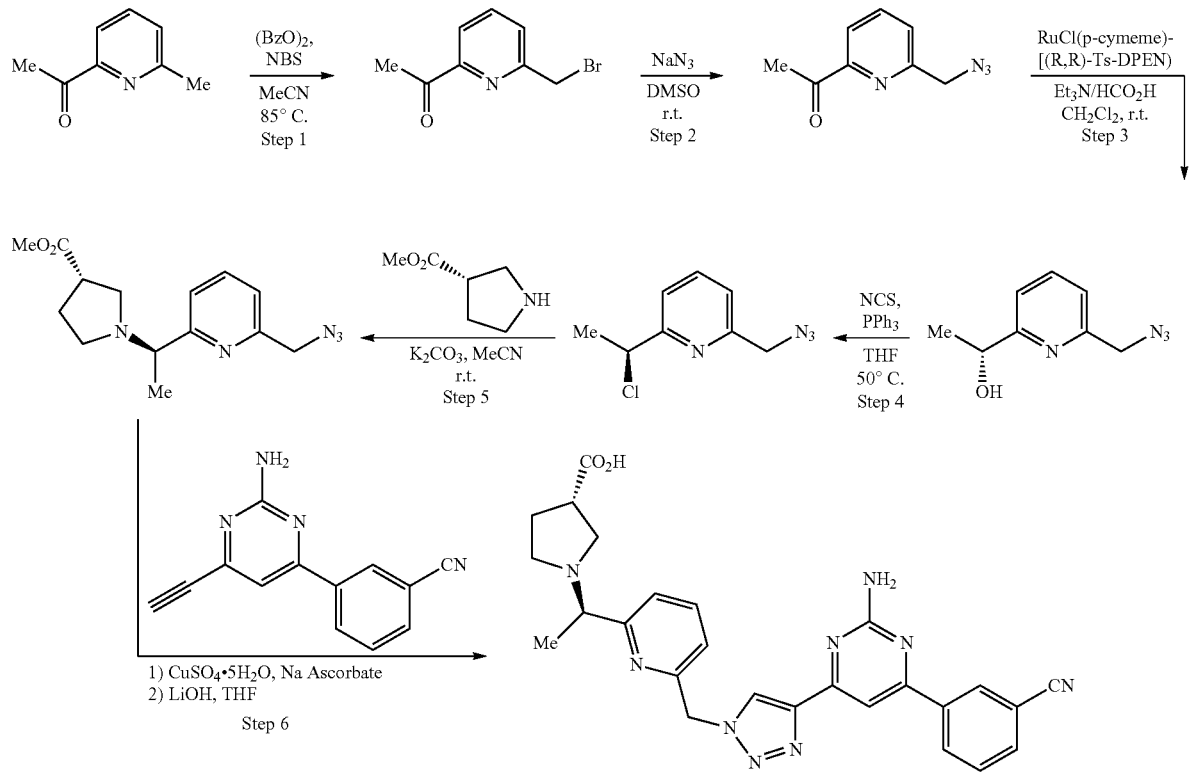

Step 1: Under a nitrogen atmosphere, a mixture of 2-acetyl-6-methylpyridine (20.0 g, 148 mmol), benzoyl peroxide (4.78 g, 14.8 mmol, 75% in water), NBS (29.0 g, 163 mmol), and acetonitrile (300 mL) was stirred at 85° C. for 19 hours. The mixture was cooled, 10% $Na_2SO_2O_3$ (aq) was added, and the acetonitrile removed under reduced pressure. Water (100 mL) and sat. $NaHCO_3$ were added and the mixture was extracted with ethyl acetate (2×200 mL) and the organic phase dried over $Na_2SO_4$. The crude material was purified by silica gel chromatography (0 to 10% EtOAc in hexanes) to afford a mixture of the desired product and 2-acetyl-6-methylpyridine (4:1 molar ratio, respectively) as a yellow oil (19.98 g; 68%).

Step 2: A mixture of the material from step 1, sodium azide (7.88 g, 121 mmol), and DMSO (101 mL) was stirred at r.t. for 4 hours. Ethyl acetate (500 mL) was added. The organic phase was washed with water (4×300 mL), brine (300 mL), and dried over $Na_2SO_4$. The crude product was purified by silica gel chromatography (0 to 10% EtOAc in hexanes) to afford the desired product as a colorless oil (13.8 g; 97%).

Step 3: To triethylamine (13.6 mL) at 0° C. was added formic acid (8.0 mL) dropwise. The mixture was the degassed before adding the step 2 product (1.76 g, 10.0 mmol), RuCl(p-cymene)-[(R,R)-Ts-DPEN] (64 mg, 0.100 mmol), and $CH_2Cl_2$ (2.7 mL). The mixture was stirred at r.t. for 5 hours and concentrated onto silica gel. The crude product was purified by silica gel chromatography (0 to 40% EtOAc in hexanes) to afford the desired product as a colorless oil (1.52 g; 85%).

Step 4: To a solution of NCS (1.48 g, 11.1 mmol) in THF (21 mL) at 0° C. was added a solution of triphenylphosphine (2.91 g, 11.1 mmol) in THF (21 mL). The mixture was stirred at r.t. for 30 minutes and a solution of the step 3 product (1.52 g, 8.53 mmol) in THF (2 mL) was added. The mixture was stirred at 50° C. for 6 hours and concentrated onto silica gel. The crude product was purified by silica gel chromatography (0 to 10% EtOAc in hexanes) to afford the desired product as a colorless oil (1.28 g; 77%).

Step 5: A mixture of the step 4 product (295 mg, 1.50 mmol), (S)-methyl pyrrolidine-3-carboxylate hydrochloride (745 mg, 4.50 mmol), $K_2CO_3$ (1.24 g, 9.00 mmol), and acetonitrile (1.5 mL) was stirred at 60° C. for 14 hours. Water (20 mL) was added, the crude product was extracted with ethyl acetate (2×20 mL), and was concentrated onto silica gel. The crude product was purified by silica gel chromatography (0 to 10% MeOH in $CH_2Cl_2$) to afford the desired product as a colorless oil (419 mg; 97%).

Step 6: The title compound was synthesized similar to example 125: Brown solid (111 mg, 72%). $^1$H NMR (400 MHz, DMSO-$d_6$) δ 8.73 (s, 1H), 8.58 (s, 1H), 8.47 (d, J=8.1 Hz, 1H), 7.99 (d, J=7.7 Hz, 1H), 7.84-7.77 (m, 2H), 7.74 (t, J=7.8 Hz, 1H), 7.38 (d, J=7.8 Hz, 1H), 7.10 (d, J=5.5 Hz, 1H), 6.92 (s, 2H), 5.82 (s, 2H), 3.45-3.34 (m, 1H), 2.90-2.78 (m, 1H), 2.64-2.53 (m, 3H), 2.41-2.29 (m, 1H), 1.95-1.83 (m, 2H), 1.26 (d, J=4.2 Hz, 3H). ESI MS [M+H]$^+$ for $C_{26}H_{26}N_9O_2$, calcd 496.2, found 496.3.

Example 202: (R)-1-[(R)-1-[6-({4-[2-Amino-6-(m-cyanophenyl)-4-pyrimidinyl]-1H-1,2,3-triazol-1-yl}methyl)-2-pyridyl]ethyl]-3-pyrrolidinecarboxylic acid

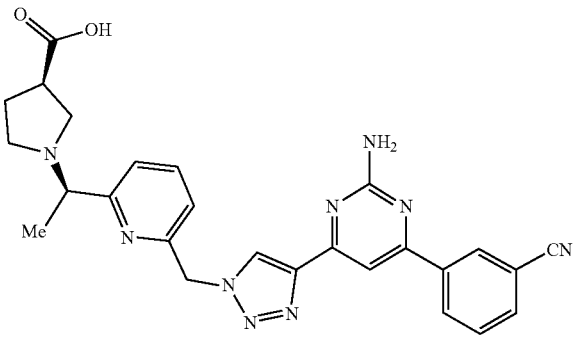 [SMILES: C[C@H](c1cccc(Cn2cc(-c3cc(-c4cccc(C#N)c4)nc(N)n3)nn2)n1)N1CC[C@@H](C(=O)O)C1]

The title compound was synthesized similar to example 201. $^1$H NMR (400 MHz, DMSO-d$_6$) δ 8.73 (s, 1H), 8.58 (s, 1H), 8.47 (d, J=7.9 Hz, 1H), 8.03-7.95 (m, 1H), 7.85-7.77 (m, 2H), 7.75 (t, J=7.8 Hz, 1H), 7.38 (d, J=7.9 Hz, 1H), 7.10 (d, J=7.7 Hz, 1H), 6.92 (s, 2H), 5.82 (s, 2H), 3.47-3.35 (m, 1H), 2.93-2.82 (m, 1H), 2.78-2.68 (m, 1H), 2.63-2.52 (m, 2H), 2.41-2.31 (m, 1H), 1.97-1.82 (m, 2H), 1.31-1.22 (m, 3H). ESI MS [M+H]$^+$ for C$_{26}$H$_{26}$N$_9$O$_2$, calcd 496.2, found 496.3.

Example 203: (S)-1-[(R)-1-[6-({4-[2-Amino-6-(m-cyanophenyl)-4-pyrimidinyl]-1H-1,2,3-triazol-1-yl}methyl)-2-pyridyl]ethyl]-2-pyrrolidinecarboxylic acid

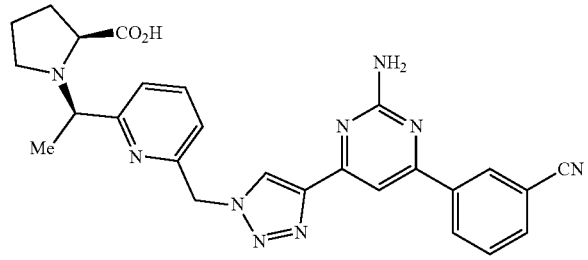

The title compound was synthesized similar to example 201. $^1$H NMR (400 MHz, DMSO-d$_6$) δ 8.77 (s, 1H), 8.58 (s, 1H), 8.49 (d, J=7.8 Hz, 1H), 7.97 (d, J=7.8 Hz, 1H), 7.85 (dd, J=7.8, 7.8 Hz, 1H), 7.82 (s, 1H), 7.72 (dd, J=7.8, 7.8 Hz, 1H), 7.40 (d, J=7.8 Hz, 1H), 7.24 (d, J=7.8 Hz, 1H), 6.89 (brs, 2H), 5.84 (s, 2H), 4.25 (q, J=6.8 Hz, 1H), 3.58-3.47 (m, 1H), 3.06-2.96 (m, 1H), 2.76-2.61 (m, 1H), 1.99-1.77 (m, 2H), 1.68-1.48 (m, 2H), 1.36 (d, J=6.8 Hz, 3H). MS [M+H]$^+$ for C$_{26}$H$_{25}$N$_9$O$_2$, calcd 496.2, found 496.3.

Example 204: 1—[(R)-1-[6-({4-[2-Amino-6-(m-cyanophenyl)-4-pyrimidinyl]-1H-1,2,3-triazol-1-yl}methyl)-2-pyridyl]ethyl]-4-piperidinecarboxylic acid

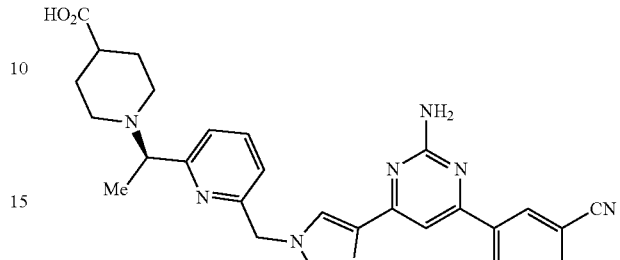

The title compound was synthesized similar to example 201. $^1$H NMR (400 MHz, DMSO-d$_6$) δ 10.26 (s, 1H), 8.84 (s, 1H), 8.58 (s, 1H), 8.46 (d, J=8.0 Hz, 1H), 8.06-7.93 (m, 2H), 7.83 (s, 1H), 7.75 (t, J=7.8 Hz, 1H), 7.57 (d, J=7.8 Hz, 1H), 7.45 (d, J=7.9 Hz, 1H), 6.92 (s, 2H), 5.94 (s, 2H), 4.65-4.53 (m, 1H), 3.62-3.46 (m, 1H), 3.30-3.19 (m, 1H), 2.92-2.75 (m, 1H), 2.74-2.57 (m, 1H), 2.40-2.28 (m, 1H), 1.98-1.69 (m, 4H), 1.57 (d, J=6.7 Hz, 3H); LC-MS retention time 3.25 min LC-MS, Method A, ESI MS [M+H]$^+$ for C$_{27}$H$_{28}$N$_9$O$_2$, calcd 510.2, found 510.3.

Example 205: (R)-1-[(R)-1-[6-({4-[2-Amino-6-(m-cyanophenyl)-4-pyrimidinyl]-1H-1,2,3-triazol-1-yl}methyl)-2-pyridyl]ethyl]-3-piperidinecarboxylic acid

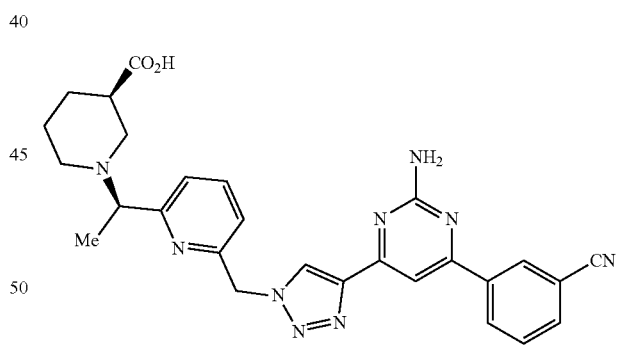

The title compound was synthesized similar to example 201. $^1$H NMR (400 MHz, DMSO-d$_6$) δ 10.63 (s, 1H), 8.88 (s, 1H), 8.60 (s, 1H), 8.49 (d, J=8.2 Hz, 1H), 8.06-7.92 (m, 2H), 7.87 (s, 1H), 7.75 (t, J=7.9 Hz, 1H), 7.60 (d, J=7.7 Hz, 1H), 7.45 (d, J=7.7 Hz, 1H), 6.99 (s, 2H), 5.93 (s, 2H), 4.66 (s, 1H), 3.71-3.61 (m, 1H), 3.59-3.52 (m, 1H), 3.24-3.08 (m, 1H), 3.06-2.83 (m, 1H), 2.83-2.67 (m, 1H), 2.67-2.54 (m, 1H), 1.98-1.83 (m, 1H), 1.82-1.63 (m, 2H), 1.58 (d, J=6.8 Hz, 3H), 1.39-1.24 (m, 1H); LC-MS retention time 2.35 min LC-MS, Method A, ESI MS [M+H]$^+$ for C$_{27}$H$_{28}$N$_9$O$_2$, calcd 510.2, found 510.3.

Example 206: (S)-1-[(R)-1-[6-({4-[2-Amino-6-(m-cyanophenyl)-4-pyrimidinyl]-1H-1,2,3-triazol-1-yl}methyl)-2-pyridyl]ethyl]-3-piperidinecarboxylic acid

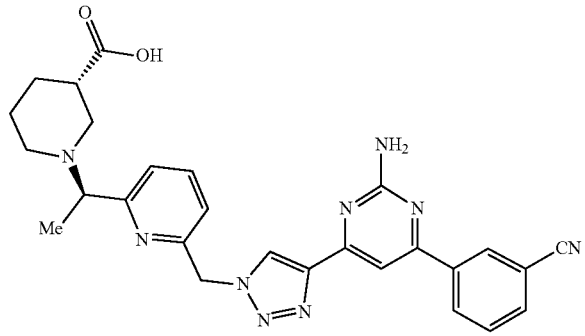 [SMILES: C[C@H](c1cccc(Cn2cc(-c3cc(-c4cccc(C#N)c4)nc(N)n3)nn2)n1)N1CCC[C@H](C(=O)O)C1]

The title compound was synthesized similar to example 201. $^1$H NMR (400 MHz, CD$_3$OD) δ 9.05 (s, 1H), 8.48 (s, 1H), 8.41-8.35 (m, 1H), 7.94 (d, J=8.1 Hz, 1H), 7.87-7.79 (m, 1H), 7.75 (s, 1H), 7.71-7.61 (m, 1H), 7.59-7.53 (m, 1H), 7.52-7.43 (m, 2H), 5.88 (s, 2H), 4.47 (m, 1H), 3.07 (m, 1H), 2.79 m, 4H), 1.95 (m, 2H), 1.84-1.74 (m, 1H), 1.63 (d, J=4.5 Hz, 3H), 1.53 (m, 1H). ESI MS [M+H]$^+$ for C$_{27}$H$_{27}$N$_9$O$_2$, calcd 510.2, found 510.3.

Example 207: 1—[(R)-1-[6-({4-[2-Amino-6-(m-cyanophenyl)-4-pyrimidinyl]-1H-1,2,3-triazol-1-yl}methyl)-2-pyridyl]propyl]-4-piperidinecarboxylic acid

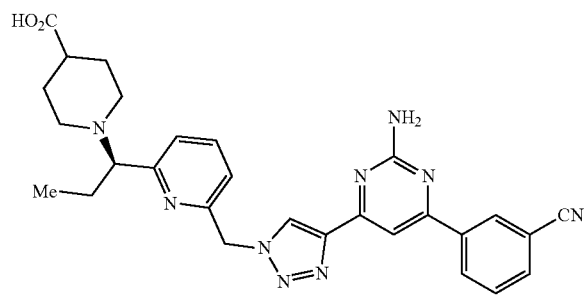 [SMILES: CC[C@H](c1cccc(Cn2cc(-c3cc(-c4cccc(C#N)c4)nc(N)n3)nn2)n1)N1CCC(C(=O)O)CC1]

The title compound was synthesized similar to example 201. $^1$H NMR (400 MHz, DMSO-d$_6$) δ 8.68 (s, 1H), 8.56 (s, 1H), 8.44 (d, J=7.8 Hz, 1H), 7.97 (d, J=7.8, 1H), 7.78 (s, 1H), 7.77-7.67 (m, 2H), 7.22 (d, J=7.8 Hz, 1H), 7.15 (d, J=7.8 Hz, 1H), 6.88 (brs, 2H), 5.81 (s, 2H), 3.47-3.35 (m, 2H), 2.79-2.59 (m, 2H), 1.95-1.28 (m, 8H), 0.66 (t, J=7.4 Hz, 3H). MS [M+H]$^+$ for C$_{28}$H$_{29}$N$_9$O$_2$, calcd 524.2, found 524.4.

Example 208: 1—[(S)-1-[6-({4-[2-Amino-6-(m-cyanophenyl)-4-pyrimidinyl]-1H-1,2,3-triazol-1-yl}methyl)-2-pyridyl]ethyl]-3-azetidinecarboxylic acid

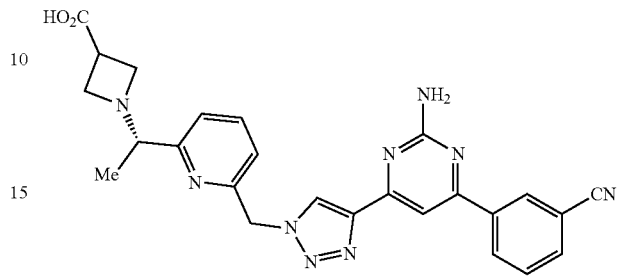

The title compound was synthesized similar to example 201. $^1$H NMR (400 MHz, CD$_3$OD) δ 9.04-8.95 (brm, 1H), 8.57 (s, 1H), 8.49 (d, J=8.0 Hz, 1H), 8.02-7.89 (m, 3H), 7.75 (dd, J=8.1 Hz, 1H), 7.51 (d, J=7.8 Hz, 1H), 7.48 (d, J=7.8 Hz, 1H), 5.91 (s, 1H), 4.85-4.73 (m, 1H), 4.54-4.38 (m, 2H), 4.22-4.09 (m 1H), 4.05-3.97 (m, 1H), 3.75-3.67 (m, 0.5H), 3.59-3.49 (m, 0.5H), 1.53 (d, J=6.3 Hz, 3H). ESI MS [M+H]$^+$ for C$_{25}$H$_{23}$N$_9$O$_2$, calcd 482.2, found 482.3.

Example 209: (R)-1-[(S)-1-[6-({4-[2-Amino-6-(m-cyanophenyl)-4-pyrimidinyl]-1H-1,2,3-triazol-1-yl}methyl)-2-pyridyl]ethyl]-3-pyrrolidinecarboxylic acid

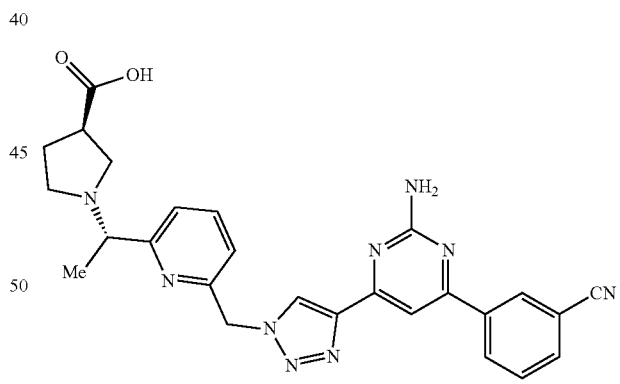

The title compound was synthesized similar to example 201. $^1$H NMR (400 MHz, CD$_3$OD) δ 8.81 (s, 1H), 8.45 (s, 1H), 8.36 (d, J=8.0 Hz, 1H), 7.94-7.87 (m, 1H), 7.84-7.78 (m, 1H), 7.74 (s, 1H), 7.65 (t, J=7.8 Hz, 1H), 7.45 (d, J=7.9 Hz, 2H), 5.93-5.78 (m, 2H), 4.50-4.40 (m, 1H), 3.46 (m, 1H), 3.32-2.97 (m, 4H), 2.30-2.14 (m, 2H), 1.60 (d, J=5.3 Hz, 3H). ESI MS [M+H]$^+$ for C$_{26}$H$_{25}$N$_9$O$_2$, calcd 496.2, found 496.3.

Example 210: (S)-1-[(S)-1-[6-({4-[2-Amino-6-(m-cyanophenyl)-4-pyrimidinyl]-1H-1,2,3-triazol-1-yl}methyl)-2-pyridyl]ethyl]-3-pyrrolidinecarboxylic acid

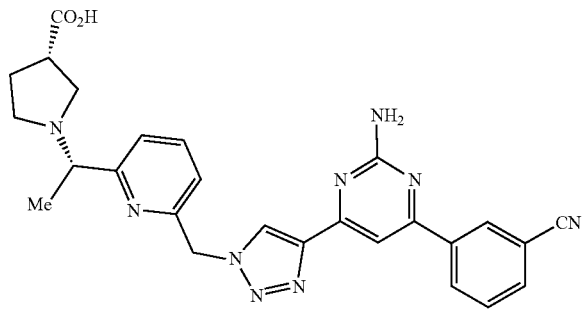 [SMILES: C[C@@H](c1cccc(Cn2cc(-c3cc(-c4cccc(C#N)c4)nc(N)n3)nn2)n1)N1CC[C@H](C(=O)O)C1]

The title compound was synthesized similar to example 201. $^1$H NMR (400 MHz, CD$_3$OD) δ 9.53 (brs, 1H), 8.67-8.61 (m, 2H), 8.19 (brs, 1H), 8.00 (m, 2H), 7.77 (brs, 1H), 7.60 (brs, 1H), 7.49 (brs, 1H). 5.98 (s, 2H), 4.69 (m, 1H), 4.06-3.98 (m, 1H), 3.58-3.48 (m, 2H), 3.29-3.16 (m, 1H), 2.50-2.29 (m, 2H). ESI MS [M+H]$^+$ for C$_{26}$H$_{25}$N$_9$O$_2$, calcd 496.2, found 496.3.

Example 211: (R)-1-[(S)-1-[6-({4-[2-Amino-6-(m-cyanophenyl)-4-pyrimidinyl]-1H-1,2,3-triazol-1-yl}methyl)-2-pyridyl]ethyl]-2-pyrrolidinecarboxylic acid

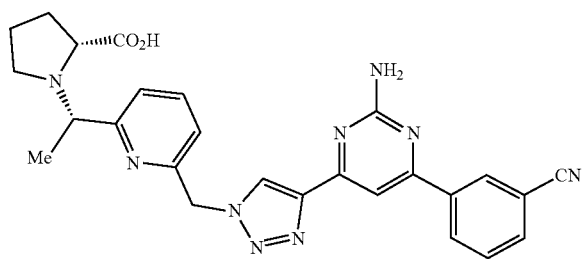

The title compound was synthesized similar to example 201. $^1$H NMR (400 MHz, DMSO-d$_6$) δ 8.77 (s, 1H), 8.59 (s, 1H), 8.48 (d, J=8.0 Hz, 1H), 7.97 (d, J=8.0 Hz, 1H), 7.84 (s, 1H), 7.83 (dd, J=8.0, 8.0 Hz, 1H), 7.72 (dd, J=8.0, 8.0 Hz, 1H), 7.45 (d, J=7.9 Hz, 1H), 7.23 (d, J=7.9 Hz, 1H), 6.90 (brs, 2H), 5.85 (d, J=15.2 Hz, 1H), 5.79 (d, J=15.2 Hz, 1H), 5.74 (s, 2H), 4.26 (q, J=6.6 Hz, 1H), 3.78-3.70 (m, 1H), 3.06-2.90 (m, 1H), 2.64 (q, J=8.4 Hz, 1H), 2.10-2.04 (m, 1H), 1.67-1.54 (m, 1H), 1.37 (d, J=6.6 Hz, 3H). MS [M+H]$^+$ for C$_{26}$H$_{25}$N$_9$O$_2$, calcd 496.2, found 496.3.

Example 212: (R)-1-[(S)-1-[6-({4-[2-Amino-6-(m-cyanophenyl)-4-pyrimidinyl]-1H-1,2,3-triazol-1-yl}methyl)-2-pyridyl]ethyl]-3-piperidinecarboxylic acid

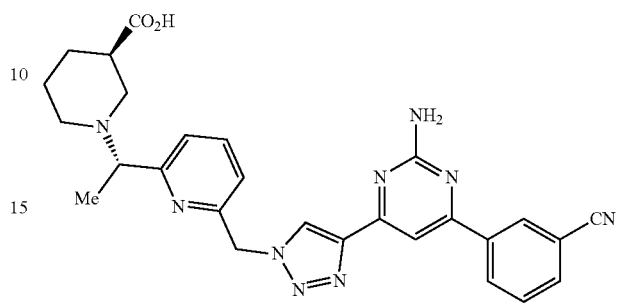

The title compound was synthesized similar to example 201. $^1$H NMR (400 MHz, DMSO-d$_6$) δ 8.81 (s, 1H), 8.58 (s, 1H), 8.50-8.43 (m, 1H), 8.04-7.94 (m, 2H), 7.82 (s, 1H), 7.79-7.70 (m, 1H), 7.60-7.50 (m, 1H), 7.43 (d, J=7.9 Hz, 1H), 6.97-6.82 (brs, 2H), 5.93 (s, 2H), 4.67 (s, 1H), 3.71-3.61 (m, 1H), 3.59-3.52 (m, 1H), 3.24-3.08 (m, 1H), 3.06-2.83 (m, 1H), 2.83-2.67 (m, 1H), 2.67-2.54 (m, 1H), 1.98-1.83 (m, 1H), 1.82-1.63 (m, 2H), 1.58 (d, J=6.8 Hz, 3H), 1.39-1.24 (m, 1H); LC-MS retention time 2.27 min LC-MS, Method A, ESI MS [M+H]$^+$ for C$_{27}$H$_{28}$N$_9$O$_2$, calcd 510.2, found 510.4.

Example 213: (S)-1-[(S)-1-[6-({4-[2-Amino-6-(m-cyanophenyl)-4-pyrimidinyl]-1H-1,2,3-triazol-1-yl}methyl)-2-pyridyl]ethyl]-3-piperidinecarboxylic acid

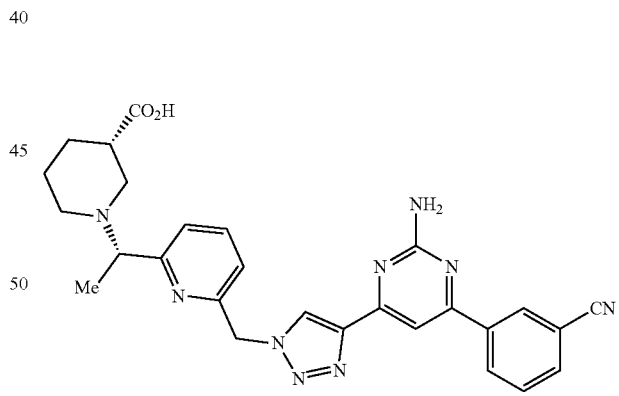

The title compound was synthesized similar to example 201. $^1$H NMR (400 MHz, DMSO-d$_6$) δ8.89-8.85 (m, 1H), 8.58 (s, 1H), 8.47 (d, J=8.1 Hz, 1H), 8.01-7.95 (m, 2H), 7.86-7.85 (m, 1H), 7.73 (dd, J=7.9, 7.9 Hz, 1H), 7.59 (d, J=7.7 Hz, 1H), 7.43 (dd, J=6.8 Hz, 1H), 6.96 (brs, 2H), 5.91 (s, 2H), 4.64 (brs, 1H), 3.66-3.63 (m, 0.5H), 3.54-3.51 (m, 0.5H), 3.32-3.30 (m, 0.5H), 3.18-3.14 (m, 0.5H), 1.89-1.67 (m, 3H), 1.60-1.58 (m, 3H), 1.39-1.21 (m, 1H). ESI MS [M+H]$^+$ for C$_{27}$H$_{27}$N$_9$O$_2$, calcd 510.2, found 510.3.

Example 214: (S)-1-[(S)-1-[6-({4-[2-Amino-6-(m-cyanophenyl)-4-pyrimidinyl]-1H-1,2,3-triazol-1-yl}methyl)-2-pyridyl]ethyl]-2-piperidinecarboxylic acid

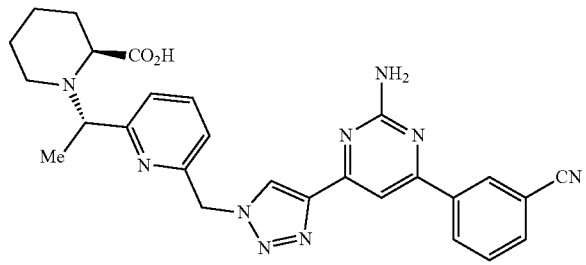

The title compound was synthesized similar to example 201. $^1$H NMR (400 MHz, CD$_3$OD) δ 8.76 (s, 1H), 8.48-8.41 (m, 1H), 8.39-8.27 (m, 1H), 7.93 (td, J=7.8, 0.9 Hz, 1H), 7.80 (dq, J=7.7, 1.1 Hz, 1H), 7.74 (s, 1H), 7.68-7.59 (m, 1H), 7.55-7.44 (m, 2H), 5.90 (s, 2H), 3.65 (s, 1H), 3.35-3.23 (m, 1H), 3.21-2.81 (m, 1H), 2.20-2.04 (m, 1H), 2.00-1.74 (m, 1H), 1.73-1.32 (m, 8H); LC-MS retention time 2.32 min LC-MS, Method A, ESI MS [M+H]$^+$ for C$_{27}$H$_{28}$N$_9$O$_2$, calcd 510.2, found 510.4.

Example 215: (R)-1-[(S)-1-[6-({4-[2-Amino-6-(m-cyanophenyl)-4-pyrimidinyl]-1H-1,2,3-triazol-1-yl}methyl)-2-pyridyl]ethyl]-2-piperidinecarboxylic acid

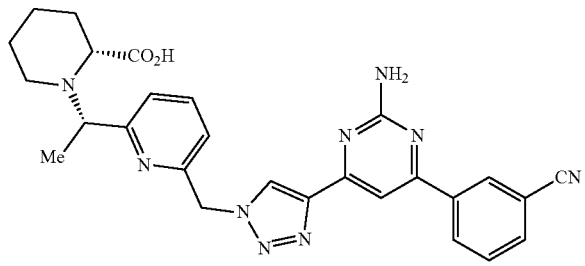

The title compound was synthesized similar to example 201. $^1$H NMR (400 MHz, CD$_3$OD) δ 8.78 (s, 1H), 8.47 (s, 1H), 8.38 (d, J=8.0 Hz, 1H), 7.95 (dd, J=7.8, 7.8 Hz, 1H), 7.83 (d, J=7.7 Hz, 1H), 7.77 (s, 1H), 7.66 (dd, J=7.8, 7.8 Hz, 1H), 7.54-7.50 (m, 2H), 5.92 (s, 2H), 3.68 (m, 1H), 3.31-3.29 (m, 1H), 3.16 (m, 1H), 3.02 (m, 1H), 2.17-2.14 (m, 1H), 1.88 (m, 1H), 1.65-1.51 (m, 6H). ESI MS [M+H]$^+$ for C$_{27}$H$_{27}$N$_9$O$_2$, calcd 510.2, found 510.3.

Example 216: 1—[(S)-1-[6-({4-[2-Amino-6-(m-cyanophenyl)-4-pyrimidinyl]-1H-1,2,3-triazol-1-yl}methyl)-2-pyridyl]ethyl]-4-piperidinecarboxylic acid

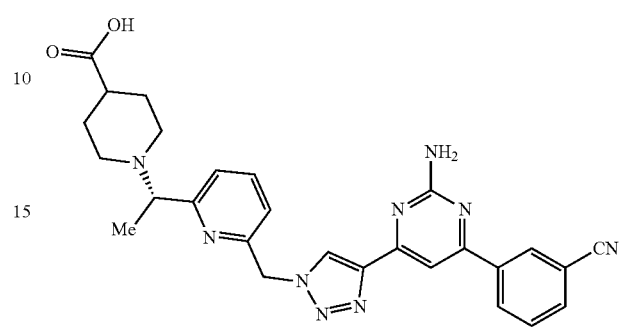

The title compound was synthesized similar to example 201. $^1$H NMR (400 MHz, DMSO-d$_6$) δ 10.50 (s, 1H), 8.93 (s, 1H), 8.63-8.53 (m, 1H), 8.46 (d, J=8.2 Hz, 1H), 8.05-7.92 (m, 2H), 7.88 (s, 1H), 7.74 (t, J=7.8 Hz, 1H), 7.57 (d, J=7.7 Hz, 1H), 7.45 (d, J=7.8 Hz, 1H), 5.93 (s, 2H), 4.58 (m, 1H), 3.52-3.44 (m, 1H), 3.22 (m, 1H), 2.83 (m, 1H), 2.65 (m, 1H), 2.32 (m, 1H), 1.94-1.74 (m, 4H), 1.56 (d, J=6.4 Hz, 3H). ESI MS [M+H]$^+$ for C$_{27}$H$_{27}$N$_9$O$_2$, calcd 510.2, found 510.3.

Example 217: 1—[(S)-1-[6-({4-[2-Amino-6-(m-cyanophenyl)-4-pyrimidinyl]-1H-1,2,3-triazol-1-yl}methyl)-2-pyridyl]propyl]-4-piperidinecarboxylic acid

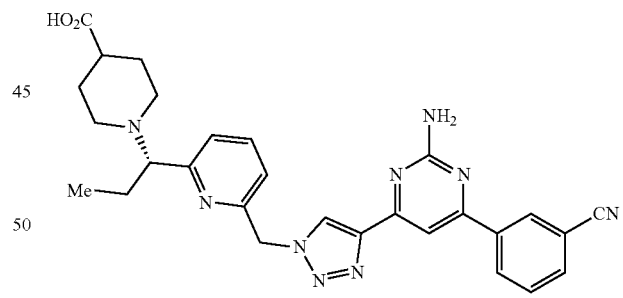

The title compound was synthesized similar to example 201. $^1$H NMR (400 MHz, DMSO-d$_6$) δ 8.68 (s, 1H), 8.56 (s, 1H), 8.44 (d, J=7.8 Hz, 1H), 7.97 (d, J=7.8, 1H), 7.78 (s, 1H), 7.77-7.67 (m, 2H), 7.22 (d, J=7.8 Hz, 1H), 7.15 (d, J=7.8 Hz, 1H), 6.88 (brs, 2H), 5.81 (s, 2H), 3.47-3.35 (m, 2H), 2.79-2.59 (m, 2H), 1.95-1.28 (m, 8H), 0.66 (t, J=7.4 Hz, 3H). MS [M+H]$^+$ for C$_{28}$H$_{29}$N$_9$O$_2$, calcd 524.2, found 524.4.

Example 218: m-{6-[1-({6-[(R)-1-(Methylsulfonylamino)ethyl]-2-pyridyl}methyl)-1H-1,2,3-triazol-4-yl]-2-amino-4-pyrimidinyl}benzonitrile

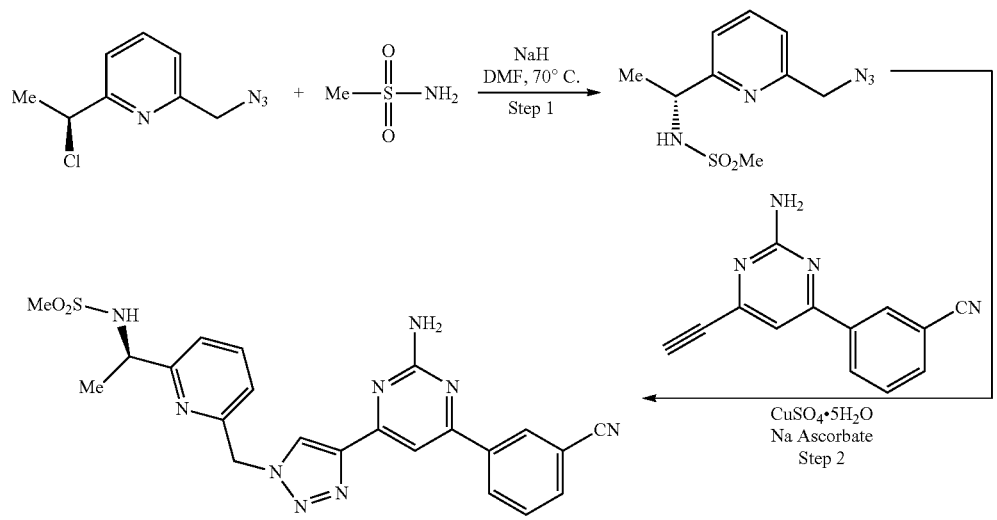 [SMILES: C[C@H](Cl)c1cccc(CN=[N+]=[N-])n1 ; CS(N)(=O)=O ; C[C@@H](NS(C)(=O)=O)c1cccc(CN=[N+]=[N-])n1 ; C[C@@H](NS(C)(=O)=O)c1cccc(Cn2cc(-c3cc(-c4cccc(C#N)c4)nc(N)n3)nn2)n1 ; C#Cc1cc(-c2cccc(C#N)c2)nc(N)n1]

Step 1: To an ice-cooled solution of methanesulfonamide (68.2 mg, 0.717 mmol, 2.0 equiv) in DMF (0.2 mL) was added NaH (60% dispersion in oil, 29 mg, 0.717 mmol, 2.0 equiv). The resulting mixture was stirred at 0° C. for 20 minutes. A solution of the 2-[(S)-1-chloroethyl]-6-(azidomethyl)pyridine derivative (example 201, step 4, 70.5 mg, 0.358 mmol, 1.0 equiv) in DMF (0.2 mL) was added and the resulting mixture was heated to 70° C. and stirred at this temperature for 16 h. Upon completion, the reaction mixture was cooled to 0° C. and residual NaH was quenched by addition of $H_2O$. The mixture was extracted with EtOAc (3×3 mL). The combined extracts were washed with brine, dried ($Na_2SO_4$), filtered and concentrated in vacuo. The resulting residue was purified by flash column chromatography over silica ($CH_2Cl_2$/MeOH gradient) to afford the product (23.3 mg, 25% yield).

Step 2: Performed the same as in example 1 (step 6). $^1$H NMR (400 MHz, CDCl$_3$) δ 8.52-8.41 (m, 2H), 8.35-8.28 (m, 1H), 7.87 (s, 1H), 7.80-7.68 (m, 2H), 7.60 (t, J=7.8 Hz, 1H), 7.30-7.19 (m, 2H), 5.84-5.76 (m, 1H), 5.73 (d, J=6.1 Hz, 2H), 5.27 (s, 3H), 4.75 (p, J=7.1 Hz, 1H), 2.77 (s, 3H), 1.54 (d, J=6.8 Hz, 3H); LC-MS retention time 2.61 min LC-MS, Method A, ESI MS [M+H]$^+$ for $C_{22}H_{22}N_9O_2S$, calcd 476.2, found 476.3.

Example 219: m-{6-[1-({6-[(S)-1-(Methylsulfonylamino)ethyl]-2-pyridyl}methyl)-1H-1,2,3-triazol-4-yl]-2-amino-4-pyrimidinyl}benzonitrile

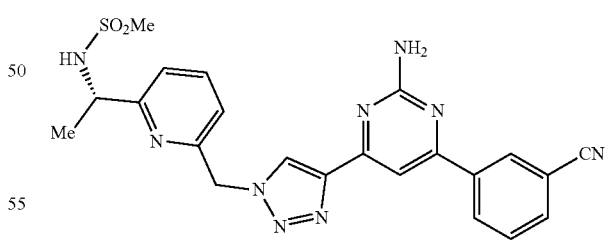

The title compound was synthesized similar to example 218, except 2-[(R)-1-chloroethyl]-6-(azidomethyl)pyridine was used. $^1$H NMR (400 MHz, Chloroform-d) δ 8.52-8.41 (m, 2H), 8.35-8.28 (m, 1H), 7.87 (s, 1H), 7.80-7.68 (m, 2H), 7.60 (t, J=7.8 Hz, 1H), 7.30-7.19 (m, 2H), 5.84-5.76 (m, 1H), 5.73 (d, J=6.1 Hz, 2H), 5.27 (s, 3H), 4.75 (p, J=7.1 Hz, 1H), 2.77 (s, 3H), 1.54 (d, J=6.8 Hz, 3H); LC-MS retention time 2.61 min LC-MS, Method A, ESI MS [M+H]$^+$ for $C_{22}H_{22}N_9O_2S$, calcd 476.2, found 476.2.

Example 220: m-[2-Amino-6-(1-{[6-(methylsulfo-nylamino)-2-pyridyl]methyl}-1H-1,2,3-triazol-4-yl)-4-pyrimidinyl]benzonitrile

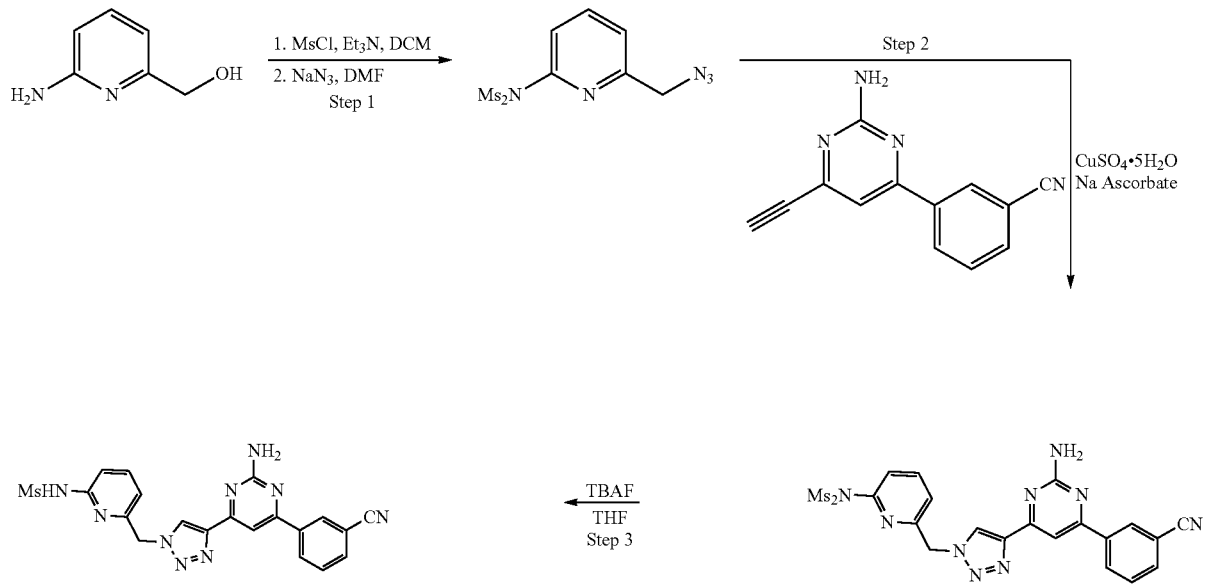

Step 1. A mixture of amino-alcohol (250 mg, 2 mmol) and triethylamine (1.5 mL) in CH₂Cl₂ (8 mL) was cooled to −78° C. Mesyl chloride (575 μL, 6 mmol) was added the resulting mixture was stirred from −78° C. to room temperature overnight. Celite was added and the mixture evaporated to dryness. Purification by silica gel chromatography (hexanes/EtOAc 90:10 to 60:40) afforded the trimesylated product (538 mg, 75%).

The compound obtained above (538 mg, 1.5 mmol) was dissolved in DMF (3 mL) and sodium azide (146 mg, 2.25 mmol) was added. The resulting mixture was stirred at 50° C. for 3 hours. After usual work-up the residue was purified by silica gel chromatography (hexanes/EtOAc 90:10 to 70:30) to afford the targeted azide (415 mg, 93%).

Step 2. m-{2-Amino-6-[1-({6-[bis(methylsulfonyl)amino]-2-pyridyl}methyl)-1H-1,2,3-triazol-4-yl]-4-pyrimidinyl}benzonitrile was synthesized in a similar fashion to step 6 of example 1 using bis(methylsulfonyl)[6-(azidomethyl)-2-pyridyl]amine and m-[6-ethynyl-2-(methylamino)-4-pyrimidinyl]benzonitrile. ¹H NMR (400 MHz, DMSO-d₆) δ 8.74 (s, 1H), 8.58 (s, 1H), 8.46 (d, J=7.8 Hz, 1H), 8.05 (dd, J=7.8, 7.8 Hz, 1H), 8.01-7.95 (m, 1H), 7.79 (s, 1H), 7.76-7.65 (m, 2H), 7.49 (d, J=7.8 Hz, 1H), 6.90 (brs, 2H), 5.95 (s, 2H), 3.55 (s, 6H). MS [M+H]⁺ for C₂₁H₁₉N₉O₄S₂, calcd 526.1, found 526.3.

Step 3. m-{2-Amino-6-[1-({6-[bis(methylsulfonyl)amino]-2-pyridyl}methyl)-1H-1,2,3-triazol-4-yl]-4-pyrimidinyl}benzonitrile (110 mg, 0.2 mmol) was dissolved in THF (1 mL) and a solution of TBAF (1M in THF, 0.3 mL) was added. The solution was stirred at room temperature for 2 hours. The crude mixture was directly loaded on silica gel and purified by chromatography (hexanes/EtOAc 90:10 to 0:100) to give rise to the title compound (78 mg, 87%). ¹H NMR (400 MHz, DMSO-d₆) δ 10.66 (s, 1H), 8.68 (s, 1H), 8.57 (s, 1H), 8.45 (d, J=8.0 Hz, 1H), 7.98 (d, J=7.6 Hz, 1H), 7.78 (s, 1H), 7.77-7.66 (m, 2H), 6.99 (d, J=7.4 Hz, 1H), 6.90 (s, 1H), 6.86 (d, J=8.0 Hz, 1H), 5.77 (s, 2H), 3.18 (s, 3H). MS [M+H]⁺ for C₂₀H₁₇N₉O₂S, calcd 448.1, found 448.3.

Example 221: m-{2-Amino-6-[1-({6-[(methylsulfo-nylamino)methyl]-2-pyridyl}methyl)-1H-1,2,3-tri-azol-4-yl]-4-pyrimidinyl}benzonitrile

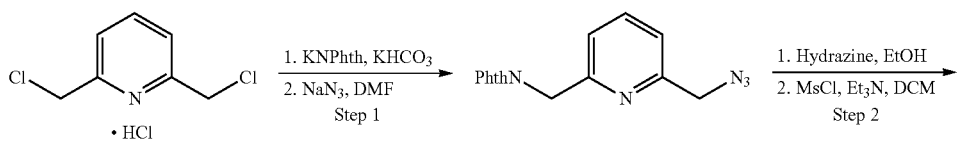

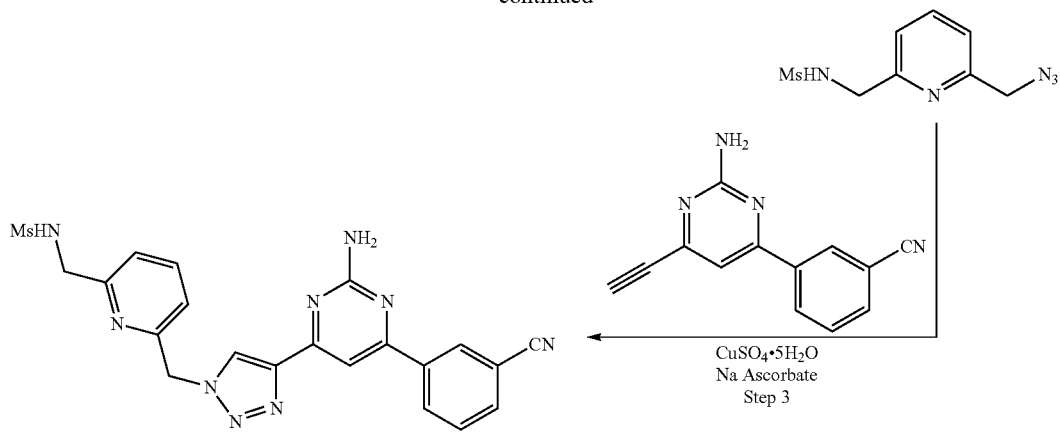

Step 1. The dichloride HCl salt (2.5 g, 11.8 mmol) was dissolved in DMF (20 mL). KHCO$_3$ (2.36 g, 23.6 mmol) and Potassium phthalimide (4.37 g, 23.6 mmol) were added and the resulting mixture was stirred for 2 days. After work-up (CH$_2$Cl$_2$/H$_2$O), the residue was purified by chromatography (hexanes/EtOAc 90:10 to 70:30) to give rise to the phthalimide derivative (2.0 g, 59%).

The above product (2.0 g, 7 mmol) and sodium azide (683 mg, 10.5 mmol) were mixed in DMF (10 mL). The mixture was stirred overnight at room temperature and then partitioned between CH$_2$Cl$_2$ and water. The organic layer was evaporated to dryness and the residue was purified by silica gel chromatography (hexanes/EtOAc 95:15 to 80:20) to deliver the corresponding azide (1.8 g, 88%).

Step 2. Product from step 1 (1.4 g, 4.77 mmol) was dissolved in EtOH (12 mL) and hydrazine hydrate (300 μL, 5.25 mmol) was added. The resulting mixture was stirred for one hour at room temperature and 5 hours at 50° C. Excess solvent was removed in vacuo and the crude was adsorbed on silica and purified by silica gel chromatography (CH$_2$Cl$_2$/MeOH 100:0 to 90:10) to deliver the primary amine (500 mg, 64%). The primary amine (500 mg, 3 mmol) and triethylamine (1 mL) were mixed in CH$_2$Cl$_2$ (5 mL) and the mixture was cooled to −30° C. Mesyl chloride (232 μL, 3 mmol) was added and the mixture was stirred from −30° C. to room temperature overnight. Celite was added and the mixture was evaporated to dryness, then purified by silica gel chromatography (hexanes/EtOAc 90:10 to 70:30) to deliver the mesylated azide (150 mg, 21%).

Step 3. The title compound was synthesized in a similar fashion to step 6 of example 1. $^1$H NMR (400 MHz, CDCl$_3$) δ 8.20 (s, 1H), 7.69 (dd, J=7.8, 7.8 Hz, 1H), 7.50-7.37 (m, 2H), 7.29-7.22 (m, 1H), 7.22-7.12 (m, 2H), 7.0.7 (d, J=7.8 Hz, 1H), 6.90 (s, 1H), 5.68 (s, 2H), 4.98 (bs, 2H), 4.57 (s, 2H), 3.48 (d, J=0.8 Hz, 3H). MS [M+H]$^+$ for C$_{21}$H$_{19}$N$_9$O$_2$S, calcd 462.1, found 462.2.

Example 222: m-{2-Amino-6-[1-({6-[1,1-dimethyl-2-(methylsulfonylamino)ethyl]-2-pyridyl}methyl)-1H-1,2,3-triazol-4-yl]-4-pyrimidinyl}benzonitrile

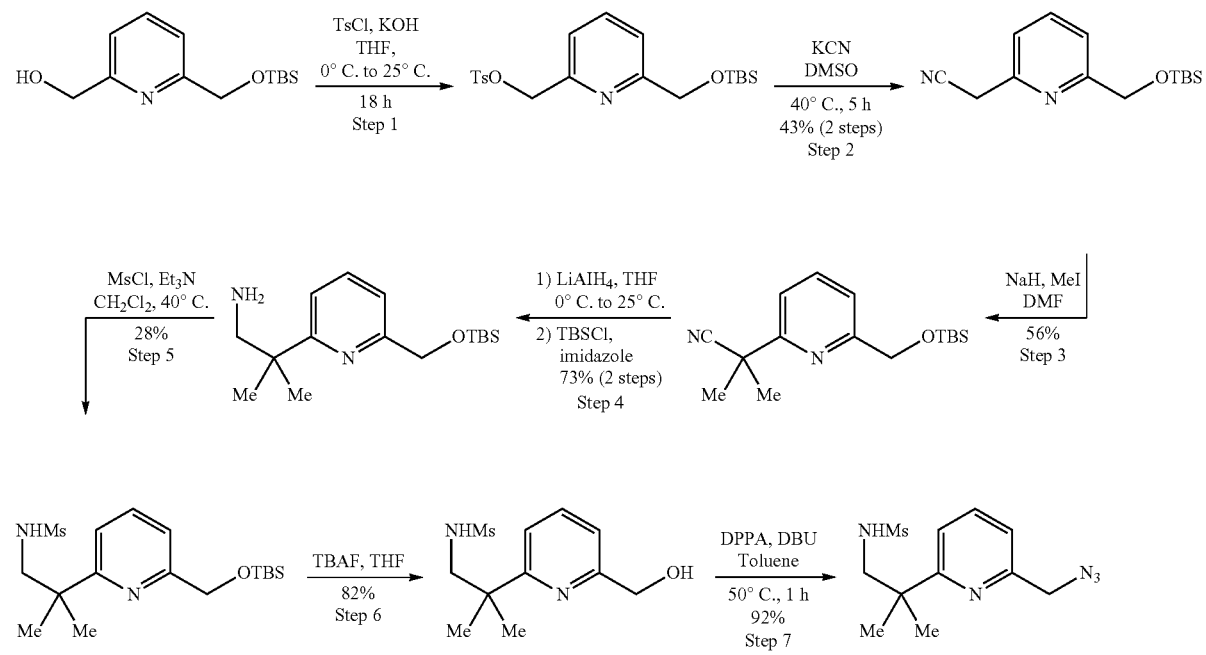

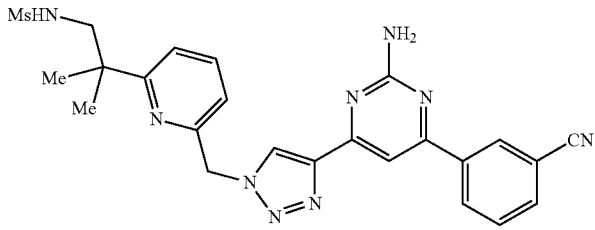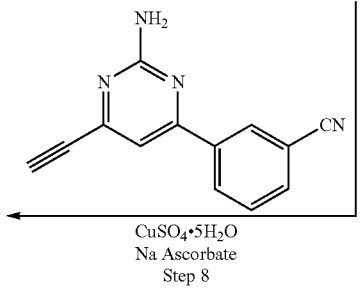

Step 1: To mono-protected 2,6-pyridinedimethanol (19.6 g, 77.4 mmol) in THF (390 ml) at 0° C. was added powdered KOH (8.7 g, 154.8 mmol). The solution was stirred at 0° C. for 30 minutes, then TsCl (19.2 g, 100.7 mmol) was added. The reaction was warmed to room temperature and stirred for 18 hours, filtered, and the filtrate was concentrated to an oil, which was taken on without further purification.

Step 2: To the product of Step 1 (77.4 mmol) in DMSO (150 ml) at room temperature was added KCN (5.2 g, 80 mmol). The reaction was warmed to 40° C. for 5 hours. The resulting solution was cooled to room temperature, washed with MTBE twice. The collected MTBE was washed with water, and the organics were concentrated onto celite. The crude product was purified by flash chromatography over silica gel (ethylacetate/hexanes gradient 5% to 25%). Yield: 8.63 g (43%, 2 steps).

Step 3: The benzyl nitrile product from step 2 (5 g, 19.0 mmol) was dissolved in THF (38 ml) and KOtBu (1.0 M in THF, 41.8 ml, 41.8 mmol) was added at room temperature and stirred for one minute. MeI (2.6 ml, 41.8 mmol) was then added in a single portion, and the reaction was stirred for 10 minutes. The solution was partitioned between ethyl acetate and water, the organic layer was collected, concentrated onto celite, and purified by flash chromatography over silica gel (ethyl acetate/hexanes gradient 0% to 10%). Yield: 2.79 g (51%).

Step 4: A solution of LiAlH$_4$ (2.3 M in 2-Me-THF, 0.87 ml, 2 mmol) was cooled to 0° C., and the tertiary nitrile product of step 3 (500 mg, 1.72 mmol) in THF (3.4 ml) was added slowly. The reaction was stirred 7 hours at room temperature, cooled back down to 0° C., and carefully quenched with water. The reaction was filtered through celite and concentrated. The residue was taken up in methylene chloride (9.0 ml) and cooled to 0° C. before the addition of TBSCl (260 mg, 1.72 mmol) and imidazole (117 mg, 1.72 mmol). After 30 minutes, the solution was concentrated onto celite and the crude material was purified by flash chromatography over silica gel (methanol/ethyl acetate gradient 0% to 70%). Yield: 370 mg (73%, 2 steps).

Step 5: Methanesulfonyl chloride (0.1 ml, 1.26 mmol) was added to a solution of the amine product from step 4 (370 mg, 1.26 mmol) and triethylamine (0.176 ml, 1.26 mmol) in methylene chloride (2.5 ml). The reaction was warmed to 40° C. and stirred for 16 h. The resulting solution was partitioned between ethyl acetate and water, the organic layer was concentrated onto celite, and the crude material was purified by flash chromatography over silica gel (ethyl acetate/hexanes gradient 20% to 100%). Yield: 130.3 mg (28%).

Step 6: TBAF (1.0 M in THF, 0.35 ml, 0.35 mmol) was added to a solution of the sulfonamide product from step 5 (130.3 mg, 0.35 mmol) in THF (1.8 ml). The reaction was concentrated on celite, and the resulting crude product was purified by flash chromatography over silica gel (ethyl acetate/hexanes gradient 30% to 100%). Yield: 74.3 mg (82%).

Step 7: The pyridyl alcohol product from step 5 (74.3 mg, 0.29 mmol) was dissolved in toluene, and DPPA (0.075 ml, 0.35 mmol) and DBU (0.053 ml, 0.35 mmol) were added sequentially. The solution was heated to 50° C. for one hour. The reaction was then partitioned between ethyl acetate and water, and the organic layer was concentrated onto celite. The resulting crude product was purified by flash chromatography over silica gel (ethyl acetate/hexanes gradient 20% to 40%). Yield: 75.2 mg (92%).

Step 8: This step was performed according step 6 of example 1. $^1$H NMR (400 MHz, CCl$_3$) δ 8.47 (s, 1H), 8.34-8.31 (m, 2H), 7.90 (s, 1H), 7.77-7.69 (m, 2H), 7.61 (dd, J=7.8, 7.8 Hz, 1H), 7.33 (d, J=8.0 Hz, 1H), 7.17 (d, J=7.8 Hz, 1H), 5.72 (s, 2H), 5.28 (brt, J=6.6 Hz, 1H), 5.18 (brs, 2H), 3.35 (d, J 6.6 Hz, 2H), 2.94 (s, 3H), 1.36 (s, 6H). ESI MS [M+H]$^+$ for C$_{24}$H$_{25}$N$_9$O$_2$S, calcd 504.2, found 504.3.

Example 223: 3-{2-Amino-6-[1-({6-[1,1-dimethyl-2-(methylsulfonylamino)ethyl]-2-pyridyl}methyl)-1H-1,2,3-triazol-4-yl]-4-pyrimidinyl}-2-fluorobenzonitrile

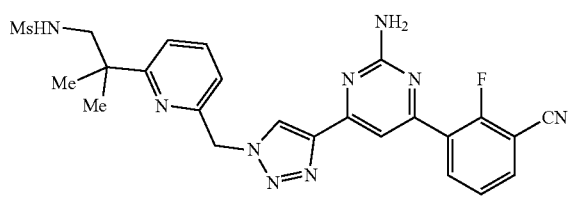

The title compound was synthesized similar to example 222. $^1$H NMR (400 MHz, CDCl$_3$) δ 8.35 (s, 1H), 8.30 (dd, J=7.6, 7.6 Hz, 1H), 7.91 (s, 1H), 7.75-7.70 (m, 2H), 7.40 (dd, J=7.8, 7.8 Hz, 1H), 7.32 (d, J=8.0 Hz, 1H), 7.16 (d, J=7.6 Hz, 1H), 5.72 (s, 2H), 5.28 (bs, 2H), 5.20 (brs, 1H), 3.34 (d, J=5.3 Hz, 2H), 2.94 (s, 3H), 1.36 (s, 6H). ESI MS [M+H]$^+$ for C$_{24}$H$_{24}$FN$_9$O$_2$S, calcd 522.2, found 522.2.

Example 224: m-[2-Amino-6-(1-{[m-(methoxymethyl)phenyl]methyl}-1H-1,2,3-triazol-4-yl)-4-pyrimidinyl]benzonitrile

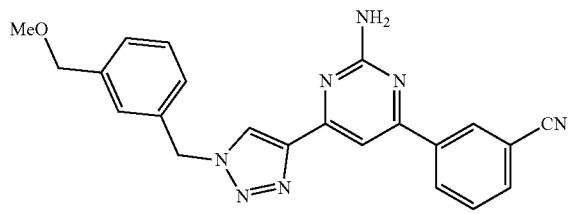

The title compound was prepared similar to example 20 from the corresponding azide and alkyne. $^1$H NMR (400 MHz, CDCl$_3$) δ 8.49-8.44 (m, 1H), 8.31 (ddd, J=8.0, 1.8, 1.2 Hz, 2H), 8.09 (s, 1H), 7.90 (s, 1H), 7.76 (dt, J=7.8, 1.3 Hz, 1H), 7.64-7.57 (m, 1H), 7.41-7.31 (m, 3H), 5.61 (s, 2H), 5.11 (s, 2H), 4.46 (s, 2H), 3.42 (s, 3H); ESI MS [M+H]$^+$ for C$_{22}$H$_{19}$N$_7$O, calcd 398.2, found 398.3.

Example 225: m-[2-Amino-6-(1-{[p-(2-methoxyethoxy)phenyl]methyl}-1H-1,2,3-triazol-4-yl)-4-pyrimidinyl]benzonitrile

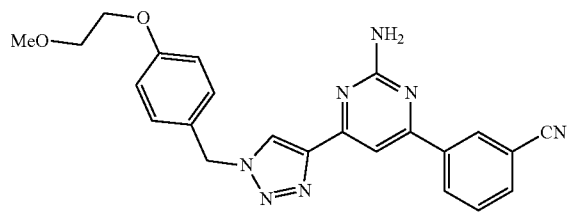

The title compound was prepared similar to example 20 from the corresponding azide and alkyne. $^1$H NMR (400 MHz, CDCl$_3$) δ 8.46 (td, J=1.7, 0.6 Hz, 1H), 8.31 (ddd, J=8.0, 1.8, 1.2 Hz, 1H), 8.04 (s, 1H), 7.89 (s, 1H), 7.76 (ddd, J=7.7, 1.7, 1.2 Hz, 1H), 7.60 (td, J=7.8, 0.6 Hz, 1H), 7.28 (d, J=8.8 Hz, 2H), 6.96 (d, J=8.7 Hz, 2H), 5.54 (s, 2H), 5.10 (s, 2H), 4.21-4.03 (m, 2H), 3.89-3.66 (m, 2H), 3.46 (s, 3H). ESI MS [M+H]$^+$ for C$_{23}$H$_{21}$N$_7$O$_2$, calcd 428.2, found 428.3.

Example 226: m-(2-Amino-6-{1-[(2,4-difluorophenyl)methyl]-1H-1,2,3-triazol-4-yl}-4-pyrimidinyl)benzonitrile

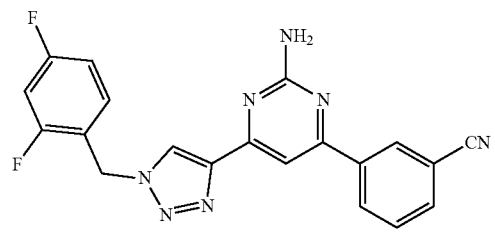

The title compound was prepared similar to example 20 from the corresponding azide and alkyne. $^1$H NMR (400 MHz, CDCl$_3$) δ 8.46 (td, J=1.8, 0.6 Hz, 1H), 8.31 (ddd, J=8.0, 1.8, 1.2 Hz, 1H), 8.17 (d, J=0.6 Hz, 1H), 7.90 (s, 1H), 7.76 (ddd, J=7.7, 1.7, 1.2 Hz, 1H), 7.61 (td, J=7.8, 0.6 Hz, 1H), 7.37 (td, J=8.6, 8.2, 6.1 Hz, 1H), 6.93 (dddd, J=10.8, 7.8, 4.2, 2.5 Hz, 2H), 5.64 (s, 2H), 5.12 (s, 2H); ESI MS [M+H]$^+$ for C$_{20}$H$_{13}$F$_2$N$_7$, calcd 390.1, found 390.2.

Example 227: m-({4-[2-Amino-6-(m-cyanophenyl)-4-pyrimidinyl]-1H-1,2,3-triazol-1-yl}methyl)benzoic acid

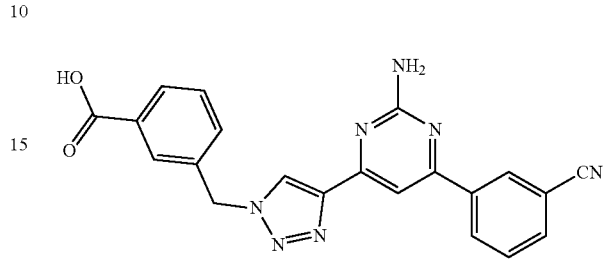

The title compound was prepared similar to example 125 from the corresponding azide and alkyne. $^1$H NMR (400 MHz, DMSO-d$_6$) δ 8.66 (s, 1H), 8.51 (s, 1H), 8.40 (d, J=8.1 Hz, 1H), 7.96-7.83 (m, 3H), 7.73 (s, 1H), 7.67 (t, J=7.9 Hz, 1H), 7.58 (d, J=7.7 Hz, 1H), 7.48 (t, J=7.9 Hz, 1H), 6.85 (s, 2H), 5.75 (s, 2H), 5.70 (d, J=2.1 Hz, 1H); ESI MS [M−H]$^-$ for C$_{21}$H$_{15}$N$_7$O$_2$, calcd 396.1, found 396.1.

Example 228: o-({4-[2-Amino-6-(m-cyanophenyl)-4-pyrimidinyl]-1H-1,2,3-triazol-1-yl}methyl)benzoic acid

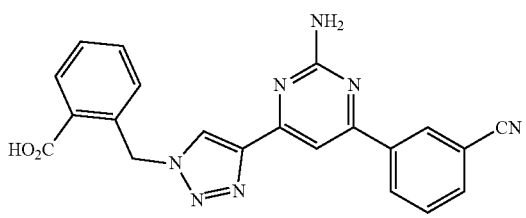 [SMILES: N#Cc1cccc(-c2cc(-c3cn(Cc4ccccc4C(=O)O)nn3)nc(N)n2)c1]

The title compound was prepared similar to example 125 from the corresponding azide and alkyne. ESI MS [M−H]$^-$ for C$_{21}$H$_{15}$N$_7$O$_2$, calcd 396.1, found 396.1.

Example 229: [o-({4-[2-Amino-6-(m-cyanophenyl)-4-pyrimidinyl]-1H-1,2,3-triazol-1-yl}methyl)phenyl]acetic acid

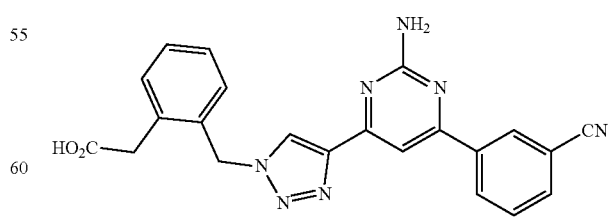

The title compound was prepared similar to example 125 from the corresponding azide and alkyne. $^1$H NMR (400 MHz, DMSO-d$_6$) δ 8.58 (dt, J=1.8, 1.0 Hz, 1H), 8.51 (s, 1H), 8.46 (ddd, J=8.0, 1.8, 1.1 Hz, 1H), 8.00 (dt, J=7.7, 1.3 Hz, 1H), 7.79 (s, 1H), 7.77-7.69 (m, 1H), 7.38-7.26 (m, 3H), 7.22 (dd, J=7.9, 2.0 Hz, 1H), 6.90 (s, 2H), 5.75 (s, 2H), 3.80 (s, 2H); ESI MS [M+H]⁺ for $C_{22}H_{17}N_7O_2$, calcd 412.1, found 412.2.

Example 230: [m-({4-[2-Amino-6-(m-cyanophenyl)-4-pyrimidinyl]-1H-1,2,3-triazol-1-yl}methyl)phenyl]acetic acid

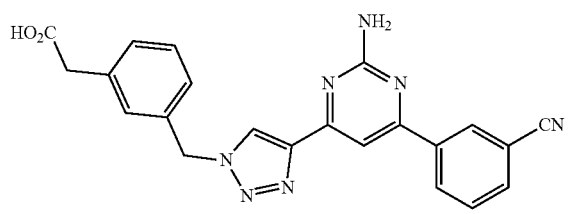

Cycloaddition and hydrolysis reactions were performed in a similar fashion to example 125 to afford the title compound as a tan solid. ¹H NMR (400 MHz, CDCl₃) δ 8.40 (s, 1H), 8.27 (d, J=8.0 Hz, 1H), 8.13 (s, 1H), 7.87 (s, 1H), 7.76 (d, J=7.6 Hz, 1H), 7.60 (t, J=7.8 Hz, 1H), 7.40-7.28 (m, 3H), 5.58 (s, 2H), 3.67 (s, 2H). One aromatic hydrogen is obscured by residual solvent. ESI MS [M+H]⁺ for $C_{22}H_{17}N_7O_2$, calcd 412.2, found 412.3.

Example 231: 2-[m-({4-[2-Amino-6-(m-cyanophenyl)-4-pyrimidinyl]-1H-1,2,3-triazol-1-yl}methyl)phenyl]-2-methylpropionic acid

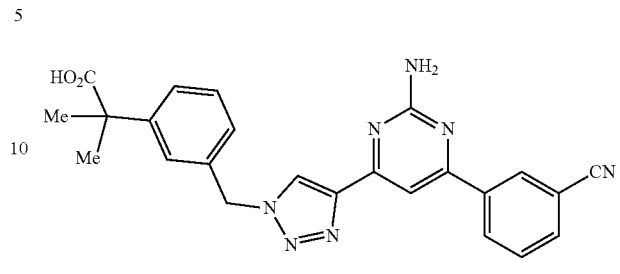

The title compound was prepared similar to example 125 from the corresponding azide and alkyne ¹H NMR (400 MHz, Chloroform-d) δ 8.32 (s, 1H), 8.21 (d, J=8.0 Hz, 1H), 8.01 (s, 1H), 7.86 (s, 1H), 7.79-7.73 (m, 1H), 7.59 (t, J=7.8 Hz, 1H), 7.48-7.34 (m, 2H), 7.31 (s, 1H), 7.16 (d, J=7.4 Hz, 1H), 6.18 (s, 2H), 5.53 (s, 2H), 1.59 (s, 6H); LC-MS retention time 2.50 min LC-MS, Method A, ESI MS [M−H]⁻ for $C_{24}H_{21}N_7O_2$, calcd 439.2, found 440.3.

Example 232: 3-[3-({4-[2-Amino-6-(m-cyanophenyl)-4-pyrimidinyl]-1H-1,2,3-triazol-1-yl}methyl)-2-fluorophenyl]-3-methylbutyric acid

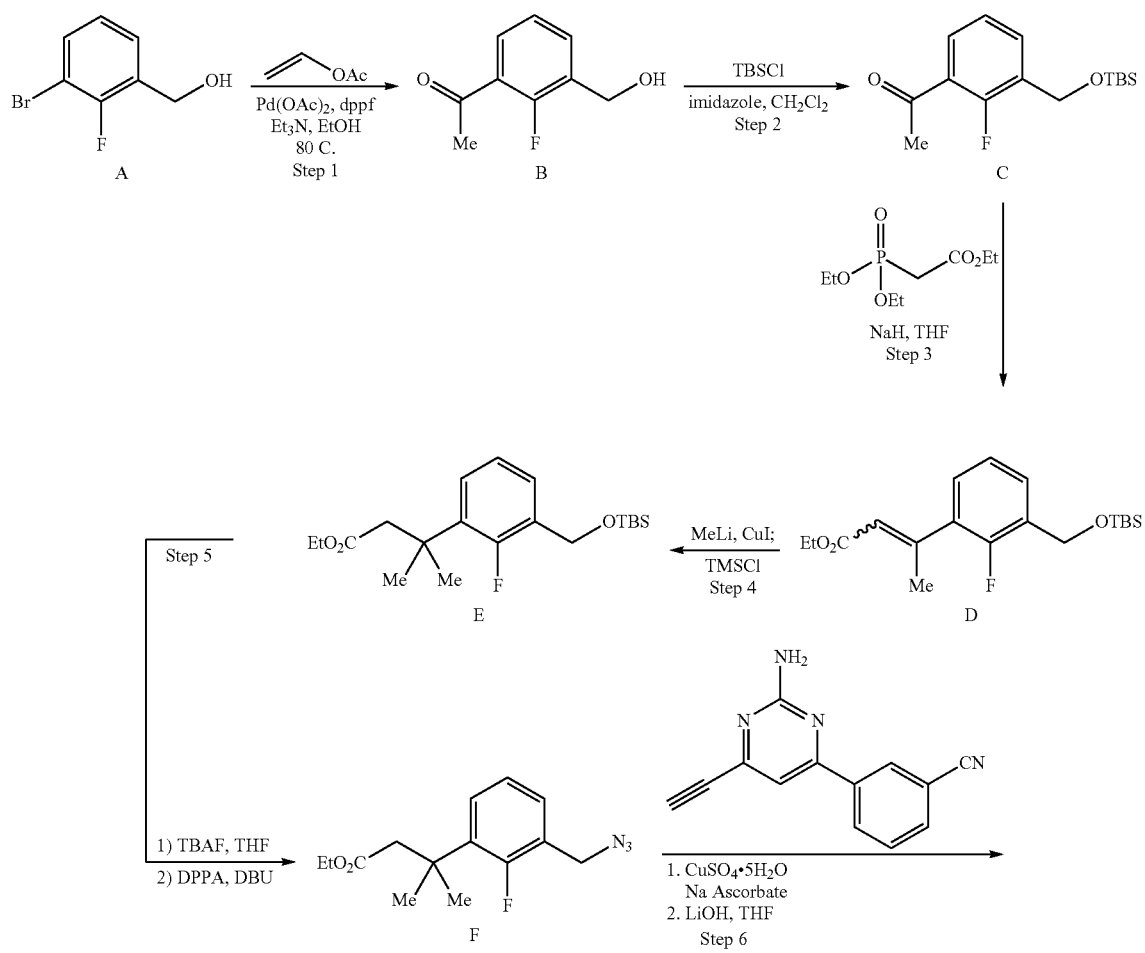

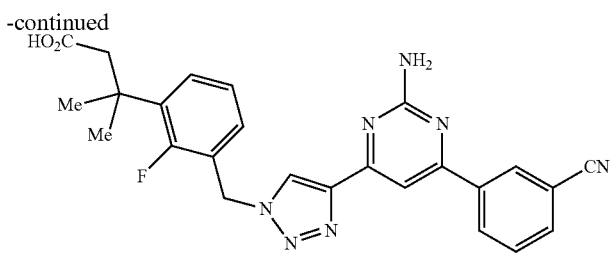

Step 1: Bromide A (1.03 g, 5 mmol), Pd(OAc)$_2$ (34 mg, 0.15 mmol, 3 mol %), dppf (166 mg, 0.3 mmol, 6 mol %), Et$_3$N (1.4 mL, 10 mmol, 2 equiv.), and butyl vinyl ether (1.94 mL, 15 mmol, 3 equiv.) were dissolved in EtOH (10 mL) under a balloon of N$_2$ and heated to 80° C. The reaction mixture was stirred overnight and cooled to ambient temperature, filtered through Celite®, and concentrated. The residue was dissolved in 30 mL CH$_2$Cl$_2$ and 30 mL 5% HCl, and the biphasic mixture was stirred vigorously for ca. 1 hour. The layers were separated, and the organic layer was dried, concentrated, and purified by flash chromatography on SiO$_2$ to afford ketone B (519 mg) as an oil.

Step 2: TBSCl (558 mg, 3.7 mmol, 1.2 equiv.) was added to a solution of ketone B (519 mg) and imidazole (315 mg, 4.6 mmol, 1.5 equiv.) in CH$_2$Cl$_2$ (10 mL). After 30 minutes, ~3 drops of MeOH was added, followed by H$_2$O and CH$_2$Cl$_2$. The layers were separated, and the organic layer was dried and concentrated to afford crude ketone C.

Step 3: NaH (60% dispersion in mineral oil, 136 mg, 3.4 mmol, 1.1 equiv.) was added to a solution of triethyl phosphonoacetate (0.67 mL, 3.4 mmol, 1.1 equiv.) in THF (10 mL) cooled in an ice-water bath. After 20 minutes, a solution of ketone C (ca. 3.09 mmol) in THF (3 mL) was added. The reaction mixture stirred overnight, was concentrated onto Celite®, and purified by flash chromatography on SiO$_2$ to afford ester D (999 mg, ~3:1 E:Z) as an oil.

Step 4: MeLi (1.6 M in THF, 5 mL, 8 mmol) was added to a solution of CuI (1.08 g, 5.7 mmol, 2 equiv.) in Et$_2$O (6 mL) cooled in an ice-water bath. After 15 minutes, the Et$_2$O was removed by passing N$_2$ over the solution. The residue was redissolved in CH$_2$Cl$_2$ (6 mL), and a solution of ester D (705 mg, 2 mmol) in CH$_2$Cl$_2$ (10 mL) was added. TMSCl (0.72 mL, 5.7 mmol, 2 equiv.) was then added and the mixture was allowed to warm to room temperature overnight. The mixture was cooled in an ice-water bath, and the reaction was quenched with 20 mL of 1:1 NH$_4$Cl/NH$_4$OH in H$_2$O. The layers were separated, and the organic layer was dried and concentrated to afford crude ester E Step 5. The above crude ester E was converted corresponding azide F using example 79 procedure.

Step 6. Cycloaddition and hydrolysis reactions were performed in a similar fashion to example 125 to afford the title compound (66 mg). $^1$H NMR (400 MHz, DMSO-d$_6$) 11.89 (s, 1H), 8.62 (s, 1H), 8.58 (t, J=1.7 Hz, 1H), 8.46 (dt, J=8.1, 1.4 Hz, 1H), 7.99 (dt, J=7.7, 1.3 Hz, 1H), 7.79 (s, 1H), 7.74 (t, J=7.8 Hz, 1H), 7.39-7.31 (m, 1H), 7.23-7.11 (m, 2H), 6.91 (s, 2H), 5.77 (s, 2H), 2.68 (s, 2H), 1.42 (s, 6H). ESI MS [M+H]$^+$ for C$_{25}$H$_{22}$FN$_7$O$_2$, calcd 472.2, found 472.4.

Example 233: [m-({4-[2-Amino-6-(m-cyanophenyl)-4-pyrimidinyl]-1H-1,2,3-triazol-1-yl}methyl)phenyl]glycolic acid

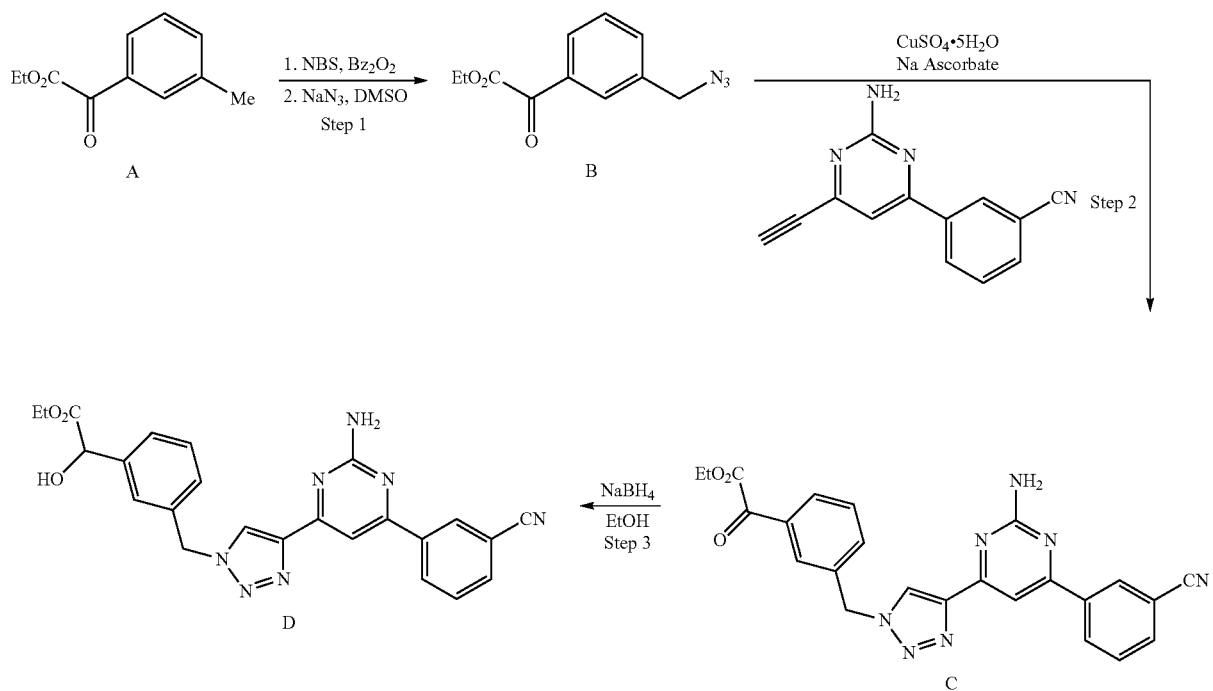

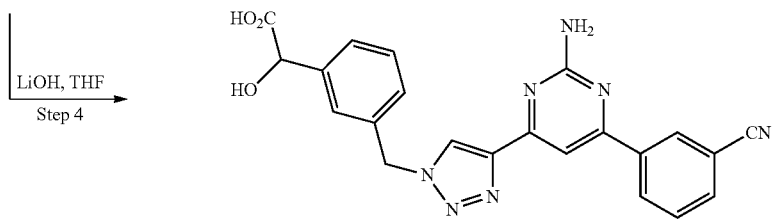

Step 1: Keto-ester A (961 mg, 5 mmol) was dissolved in MeCN (13.5 mL), and the resulting solution was degassed with $N_2$ for 15 minutes. NBS (935 mg, 5.25 mmol, 1.05 equiv.) and $Bz_2O_2$ (61 mg, 0.25 mmol, 0.05 equiv.) were added and the reaction mixture was heated to 70° C. for 2.5 hours. The reaction mixture was cooled to ambient temperature and concentrated. The residue was purified by flash chromatography on $SiO_2$ (0-20% EtOAc/hexanes) to afford bromide (543 mg). the benzylic bromide (543 mg) was converted to azide B with $NaN_3$ in DMSO (ca. 400 mg).

Step 3: Following the General Procedure for CuAAC (example 1, step 6) using azide B, triazole C was synthesized to afford 36 mg of an orange wax.

Step 4: To a solution of triazole D (35 mg, 0.08 mmol) in EtOH (1 mL) was added $NaBH_4$ (4.4 mg, 0.12 mmol, 1.5 equiv.) at ambient temperature. The reaction mixture stirred for 80 minutes and was concentrated. The residue was diluted with $CH_2Cl_2$, washed with $H_2O$, dried, and concentrated to afford alcohol E (7.8 mg).

Step 5: To a solution of alcohol E (7.8 mg, 0.017 mmol) in THF was added 1 M LiGH (34 μL, 0.034 mmol, 2 equiv.). The reaction mixture stirred overnight and was concentrated to afford the title compound (7.7 mg) as a white solid. $^1$H NMR (400 MHz, DMSO-$d_6$) δ 8.62-8.53 (m, 2H), 8.47 (d, J=7.2 Hz, 1H), 7.98 (d, J=7.2 Hz, 1H), 7.80 (d, J=6.0 Hz, 1H), 7.73 (t, J=7.5 Hz, 1H), 7.42 (s, 1H), 7.35 (d, J=6.7 Hz, 1H), 7.24 (t, J=7.3 Hz, 1H), 7.13 (d, J=7.3 Hz, 1H), 6.90 (s, 2H), 5.67 (d, J=5.6 Hz, 2H), 5.16 (s, 1H), 4.36 (d, J=4.7 Hz, 1H). ESI MS [M+H]$^+$ for $C_{22}H_{17}N_7O_3$, calcd 428.2, found 428.2.

Example 234: {[6-({4-[2-Amino-6-(m-cyanophenyl)-4-pyrimidinyl]-1H-1,2,3-triazol-1-yl}methyl)-2-pyridyl]methoxy}acetic acid

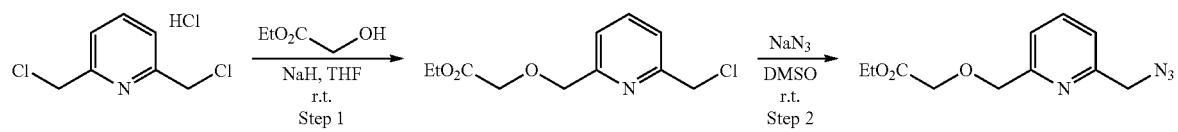

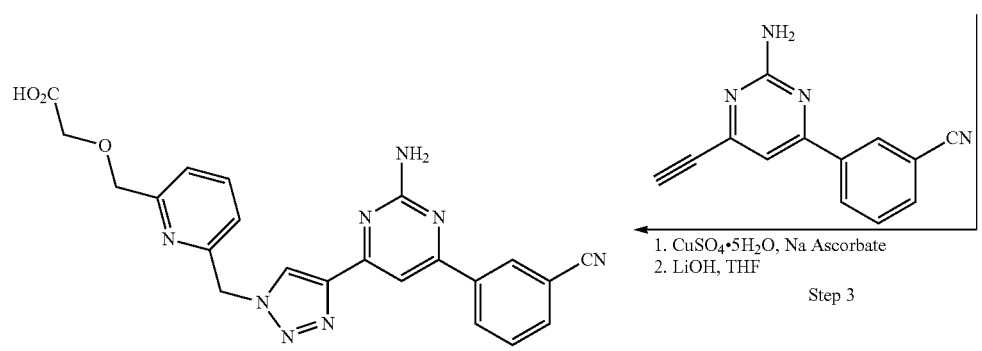

Step 1: To a solution of ethyl glycolate (476 μL, 5.00 mmol) in THF (10 mL) at 0° C. was added NaH (400 mg, 10.0 mmol, 60% in oil) in one portion. The mixture was stirred at r.t. for 15 minutes. The dichloride (1.06 g; 5.00 mmol) was then added and the mixture stirred at r.t. for 14 hours. The mixture was concentrated and purified by silica gel chromatography (0 to 75% EtOAc in hexanes) to afford the desired product as a colorless oil (534 mg; 44%).

Step 2: A mixture of the step 1 product (534 mg, 2.51 mmol), sodium azide (195 mg, 3.01 mmol), and DMSO (5 mL) was stirred at r.t. for 2 hours. MTBE (50 mL) was added, the organic phase washed with water (4×50 mL), and dried over Na$_2$SO$_4$ to afford the desired product as a colorless oil (719 mg; 100%).

Step 3: Cycloaddition and hydrolysis reactions were performed in a similar fashion to example 125 to afford the title compound: White solid (67 mg, 51%). $^1$H NMR (400 MHz, DMSO-d$_6$) δ 12.71 (br s, 1H), 8.69 (s, 1H), 8.58 (s, 1H), 8.47 (d, J=8.0 Hz, 1H), 7.99 (d, J=7.7 Hz, 1H), 7.87 (t, J=7.8, 2.3 Hz, 1H), 7.81 (s, 1H), 7.74 (t, J=7.8, 2.4 Hz, 1H), 7.45 (d, J=7.6 Hz, 1H), 7.23 (d, J=7.6 Hz, 1H), 6.90 (s, 2H), 5.82 (s, 2H), 4.61 (s, 2H), 4.14 (s, 2H). ESI MS [M+H]$^+$ for C$_{22}$H$_{19}$N$_8$O$_3$, calcd 443.2, found 443.2.

Example 235: {1-[6-({4-[2-Amino-6-(m-cyanophenyl)-4-pyrimidinyl]-1H-1,2,3-triazol-1-yl}methyl)-2-pyridyl]ethoxy}acetic acid Step 1. A solution of alcohol (660 mg, 2.47 mmol) in DMF (6 mL) was treated with NaH (60% in mineral oil, 118 mg, 2.96 mmol). The mixture was stirred for 10 minutes before methyl bromoacetate (280 μL, 2.96 mmol). After 2 hours the reaction was worked-up (EtOAc/H$_2$O) and the residue was purified by silica gel chromatography (hexanes/EtOAc 95:5 to 85:15) to afford the alkylated alcohol (316 mg, 38%).

The silylether (316 mg, 0.94 mmol) was dissolved in THF (3 mL) and acetic acid (20 μL) was added followed by TBAF (1 M in THF, 1.5 mL). The mixture was stirred for 2 hours at room temperature and after usual work-up the residue was purified by silica gel chromatography (dichlormethane/hexanes (1:1)/EtOAc 95:5 to 50:50) to furnish the primary alcohol (210 mg, quant.).

Step 2. This step was performed according example 79 to afford the azide (165 mg, 71%).

Step 3. The title compound was prepared similar to example 125 from the corresponding azide and alkyne. $^1$H NMR (400 MHz, Chloroform-d) δ 8.44 (s, 1H), 8.30 (d, J=7.9 Hz, 1H), 8.10 (s, 1H), 7.89 $^1$H NMR (400 MHz, DMSO-d$_6$) δ 8.69 (s, 1H), 8.57 (s, 1H), 8.45 (d, J=7.8 Hz, 1H), 7.97 (d, J=7.8 Hz, 1H), 7.84 (dd, J=7.8, 7.8 Hz, 1H), 7.80 (s, 1H), 7.72 (dd, J=7.8, 7.8 Hz, 1H), 7.43 (dd, J=7.8 Hz, 1H), 7.15 (d, J=7.8 Hz, 1H), 6.89 (s, 1H), 5.82 (s, 2H), 4.60-4.52 (m, 1H), 3.95 (d, J=16.3 Hz, 1H), 3.85 (d, J=16.3 Hz, 1H), 3.30 (s, 1H), 2.10-2.04 (m, 1H), 1.34 (d, J=6.5 Hz, 3H). MS [M+H]$^+$ for C$_{23}$H$_{20}$N$_8$O$_3$, calcd 457.2, found: 457.2.

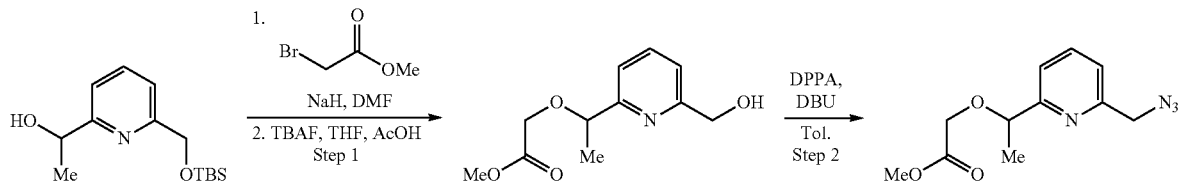

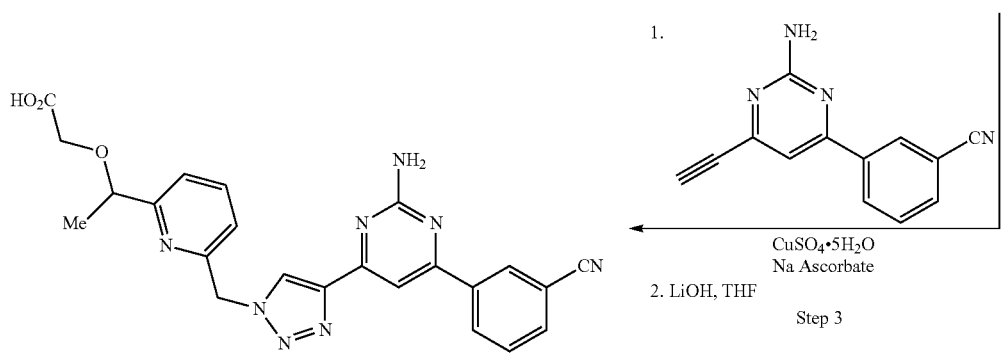

Example 236: [m-({4-[2-Amino-6-(m-cyanophenyl)-4-pyrimidinyl]-1H-1,2,3-triazol-1-yl}methyl)phenoxy]acetic acid

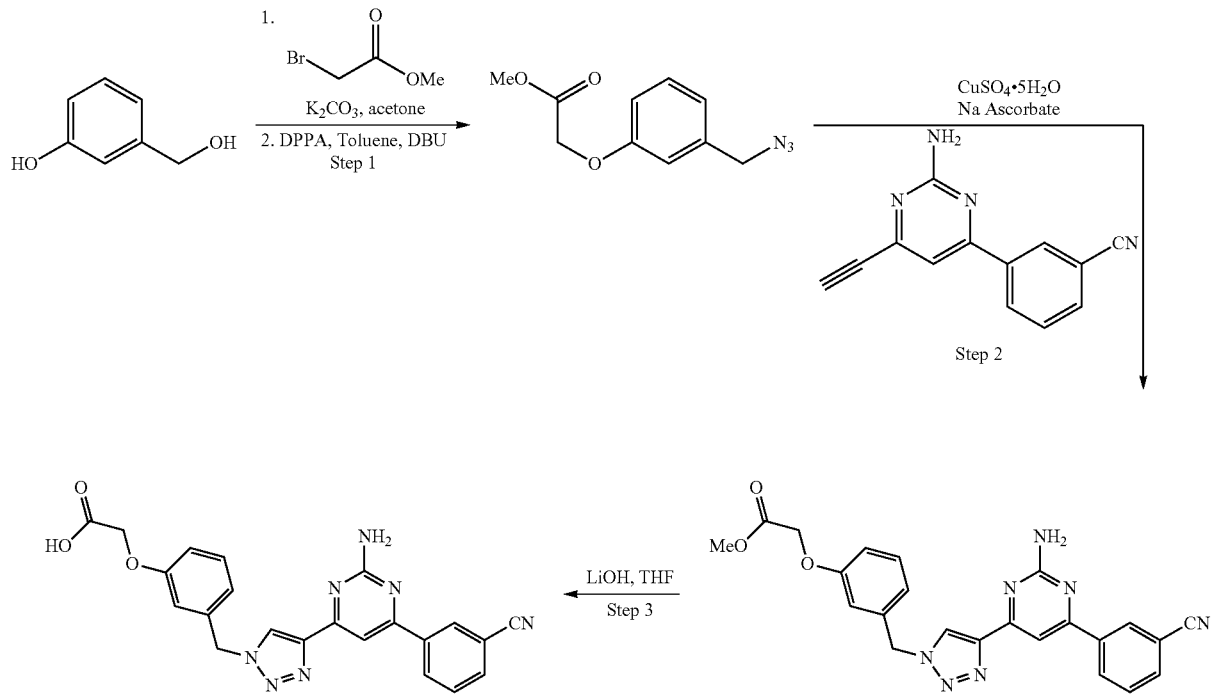

Step 1. A mixture of diol (2.4 g, 19 mmol), K₂CO₃ (4.0 g, 28.5 mmol) and methyl bromoacetate (1.80 mL, 19 mmol) in acetone (15 mL) was stirred overnight at 65 C. The crude mixture was filtered, evaporated to dryness and purified by silica gel chromatography (hexanes/EtOAc 90:10 to 65:35) to deliver the alkylated phenol (1.4 g, 38%).

To a mixture of the above alcohol (1.4 g, 7.1 mmol) and DPPA (1.68 mL, 7.81 mmol) in toluene (15 mL) was added DBU (1.17 mL, 7.81 mmol). The resulting solution was stirred at 65° C. for 4 hours and then purified by silica gel chromatography (hexanes/EtOAc 95:5 to 90:10) to afford the azide (1.18 g, 75%).

Step 2. Methyl [m-({4-[2-amino-6-(m-cyanophenyl)-4-pyrimidinyl]-1H-1,2,3-triazol-1-yl}methyl)phenoxy]acetate was synthesized in a similar fashion to example 125. ¹H NMR (400 MHz, Chloroform-d) δ 8.44 (s, 1H), 8.30 (d, J=7.9 Hz, 1H), 8.10 (s, 1H), 7.89 (d, J=1.5 Hz, 1H), 7.75 (d, J=7.7 Hz, 1H), 7.59 (dd, J=7.7, 7.7 Hz, 1H), 7.32 (dd, J=7.7, 7.7 Hz, 1H), 6.96 (d, J=7.7 Hz, 1H), 6.89 (d, J=7.7 Hz, 1H), 7.88 (s, 2H), 5.57 (s, 2H), 5.16 (s, 2H), 4.63 (s, 2H), 3.79 (s, 3H). MS [M+H]⁺ for $C_{23}H_{19}N_7O_3$, calcd 442.2, found: 442.3.

Step 3. Methyl [m-({4-[2-amino-6-(m-cyanophenyl)-4-pyrimidinyl]-1H-1,2,3-triazol-1-yl}methyl)phenoxy]acetate was hydrolyzed using LiGH to afford the title compound. ¹H NMR (400 MHz, DMSO-d₆) δ 8.63 (s, 1H), 8.56 (s, 1H), 8.44 (d, J=8.0 Hz, 1H), 7.97 (d, J=8.0 Hz, 1H), 7.77 (s, 1H), 7.72 (dd, J=7.8, 7.8 Hz, 1H), 7.28 (dd, J=7.8, 7.8 Hz, 1H), 6.95 (s, 1H), 6.92 (d, J=7.8 Hz, 1H) 6.90-6.79 (m, 3H), 5.65 (s, 2H), 4.59 (s, 3H). MS [M+H]⁺ for $C_{22}H_{17}N_7O_3$, calcd 428.1, found: 428.2.

Example 237: 1-[m-({4-[2-Amino-6-(m-cyanophenyl)-4-pyrimidinyl]-1H-1,2,3-triazol-1-yl}methyl)phenylsulfonyl]-3-azetidinecarboxylic acid

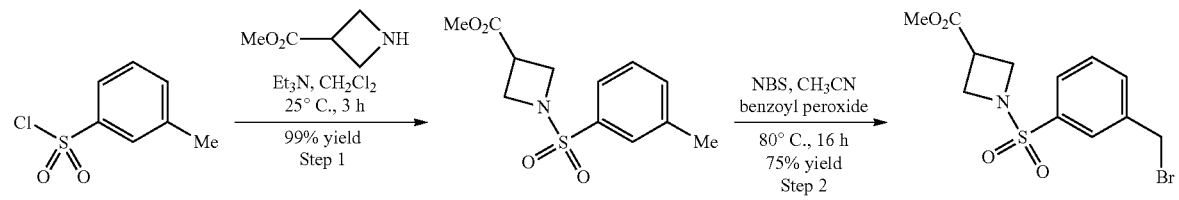

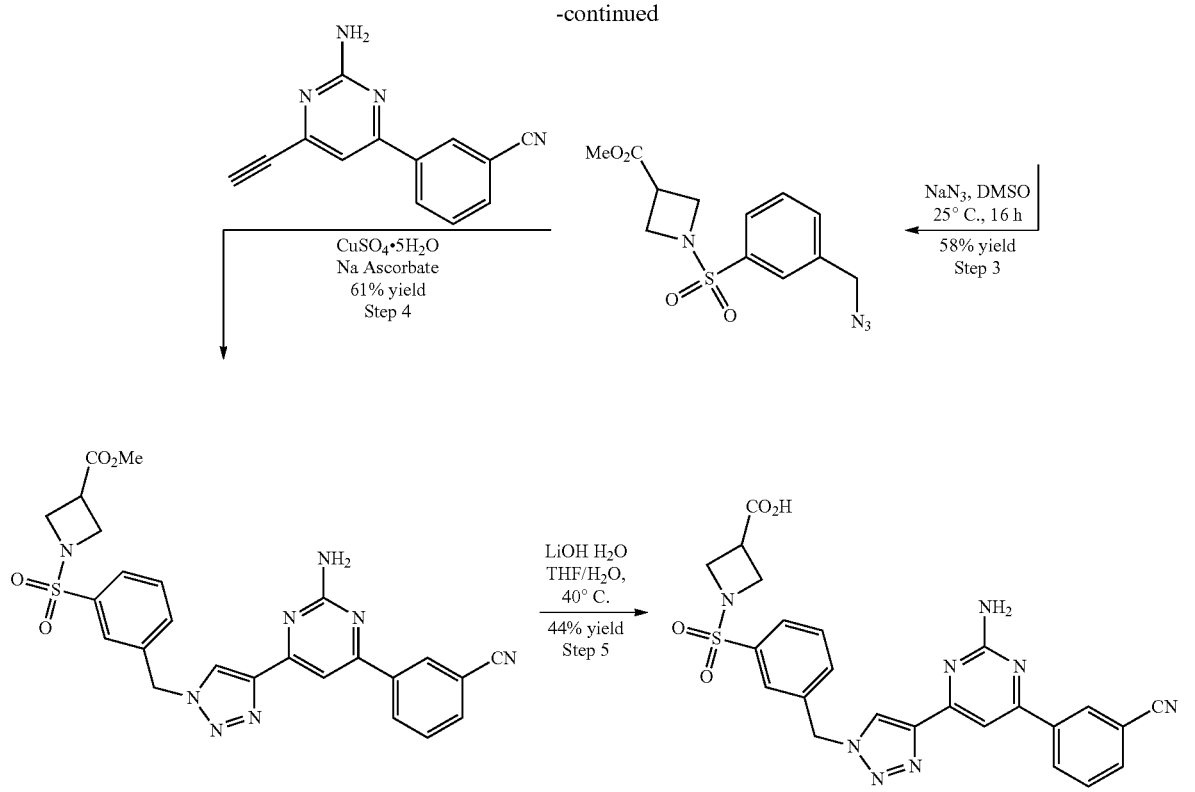

Step 1: The sulfonyl chloride (1 g, 5.24 mmol, 1.0 equiv) and the azetidine hydrochloride (914 mg, 6.03 mmol, 1.15 equiv) were combined in $CH_2Cl_2$ (5.24 mL, 1 M) at room temperature and $Et_3N$ (2.56 mL, 18.4 mmol, 3.5 equiv) was added. The resulting mixture was stirred for 3 h at room temperature. Upon completion, the reaction mixture was concentrated in vacuo to afford the crude product, which was used without further purification.

Step 2: To a solution of the arene (1.40 g, 5.22 mmol, 1.0 equiv) in $CH_3CN$ (74 mL, 0.07 M) was added NBS (1.02 g, 5.74 mmol, 1.10 equiv) followed by benzoyl peroxide (75% pure, 269 mg, 0.834 mmol, 0.16 equiv). The resulting mixture was degassed by bubbling $N_2$ for 10 minutes and then the mixture was heated at reflux for 18 h. Upon completion, the reaction mixture was cooled to room temperature, diluted with 1:1 $CH_2Cl_2$/brine (150 mL) and extracted with $CH_2Cl_2$ (3×). The combined extracts were dried ($MgSO_4$), filtered, and concentrated in vacuo. The resulting residue was purified by flash column chromatography over silica (hexanes/EtOAc gradient) to afford the product (1.36 g, 75% yield).

Step 3: A solution of the benzyl bromide (1.36 g, 3.92 mmol, 1.0 equiv) in DMSO (6.5 mL, 0.6 M) was added to a solution of $NaN_3$ (382 mg, 5.88 mmol, 1.5 equiv) in DMSO (9.19 mL, 0.64 M) at room temperature. The resulting mixture was stirred at room temperature for 24 h. Upon completion, the reaction mixture was diluted with 1:1 $H_2O$/EtOAc (50 mL) and the mixture was extracted with EtOAc (3×). The combined extracts were washed with $H_2O$ (50 mL), brine (50 mL), dried ($MgSO_4$), filtered and concentrated in vacuo. The resulting residue was purified by flash column chromatography over silica (hexanes/EtOAc gradient) to afford the product (699 mg, 58% yield).

Steps 4 and 5: Performed the same as in example 125. $^1H$ NMR (400 MHz, $CDCl_3$) δ 8.46 (s, 1H), 8.33 (d, J=8.0 Hz, 1H), 8.06 (s, 1H), 8.04-7.99 (m, 2H), 7.98 (d, J=1.2 Hz, 1H), 7.84-7.78 (m, 1H), 7.78-7.67 (m, 2H), 7.63 (t, J=7.9 Hz, 1H), 5.74 (s, 2H), 5.30 (s, 2H), 4.24-4.13 (m, 2H), 3.87 (t, J=7.9 Hz, 2H), 3.54-3.39 (m, 1H); LC-MS retention time 2.61 min LC-MS, Method A, ESI MS $[M-H+^+]^-$ for $C_{24}H_{19}N_8O_4S$, calcd 515.1, found 515.3.

Example 238: m-(2-Amino-6-{1-[(o-aminophenyl)methyl]-1H-1,2,3-triazol-4-yl}-4-pyrimidinyl)benzonitrile

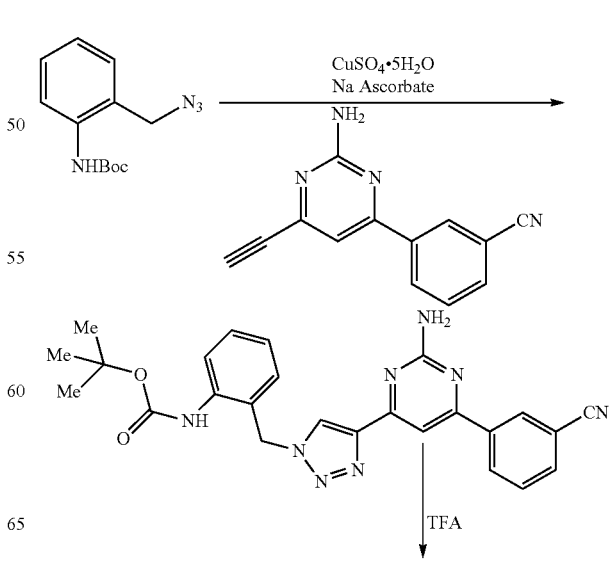

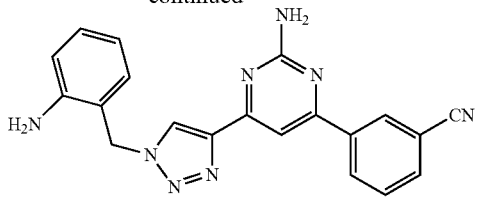

Step 1. 4-[2-Amino-6-(m-cyanophenyl)-4-pyrimidinyl]-1-{[o-(tert butoxycarbonylamino)phenyl]methyl}-1H-1,2,3-triazole was synthesized in a similar fashion to example 1, step 6 to afford 41 mg of a white solid. $^1$H NMR (400 MHz, DMSO-$d_6$) δ 8.98 (s, 1H), 8.58 (td, J=1.8, 0.6 Hz, 1H), 8.49-8.43 (m, 2H), 7.99 (ddd, J=7.7, 1.7, 1.1 Hz, 1H), 7.79 (s, 1H), 7.77-7.71 (m, 1H), 7.38 (dd, J=8.1, 1.6 Hz, 1H), 7.34 (td, J=8.0, 7.5, 1.6 Hz, 1H), 7.18 (td, J=7.4, 1.6 Hz, 1H), 7.14-7.09 (m, 1H), 6.88 (s, 2H), 5.73 (s, 2H), 1.43 (s, 9H). ESI MS [M+H]$^+$ for $C_{25}H_{24}N_8O_2$, calcd 469.2, found 469.4.

Step 2. To a suspension of 4-[2-Amino-6-(m-cyanophenyl)-4-pyrimidinyl]-1-{[o-(tert-butoxycarbonylamino)phenyl]methyl}-1H-1,2,3-triazole (20 mg, 0.04 mmol) in CH$_2$Cl$_2$ (0.4 mL) was added TFA (40 µL) at room temperature. The mixture stirred overnight and was concentrated to dryness. The residue was dissolved in EtOAc and washed with NaHCO$_3$. The organic layer was dried and concentrated to afford 16 mg of a white solid. $^1$H NMR (400 MHz, DMSO-$d_6$) δ 8.57 (td, J=1.8, 0.6 Hz, 1H), 8.45 (ddd, J=8.0, 1.8, 1.1 Hz, 1H), 8.43 (s, 1H), 7.99 (ddd, J=7.7, 1.7, 1.1 Hz, 1H), 7.78 (s, 1H), 7.77-7.70 (m, 1H), 7.11-7.03 (m, 2H), 6.92 (s, 2H), 6.72 (dd, J=8.5, 1.2 Hz, 1H), 6.57 (td, J=7.4, 1.2 Hz, 1H), 5.76 (s, 1H), 5.58 (s, 2H), 5.35 (s, 2H). ESI MS [M+H]$^+$ for $C_{20}H_{16}N_8$, calcd 369.2, found 369.3.

Example 239: m-[2-Amino-6-(1-{[o-(methylsulfonylamino)phenyl]methyl}-1H-1,2,3-triazol-4-yl)-4-pyrimidinyl]benzonitrile

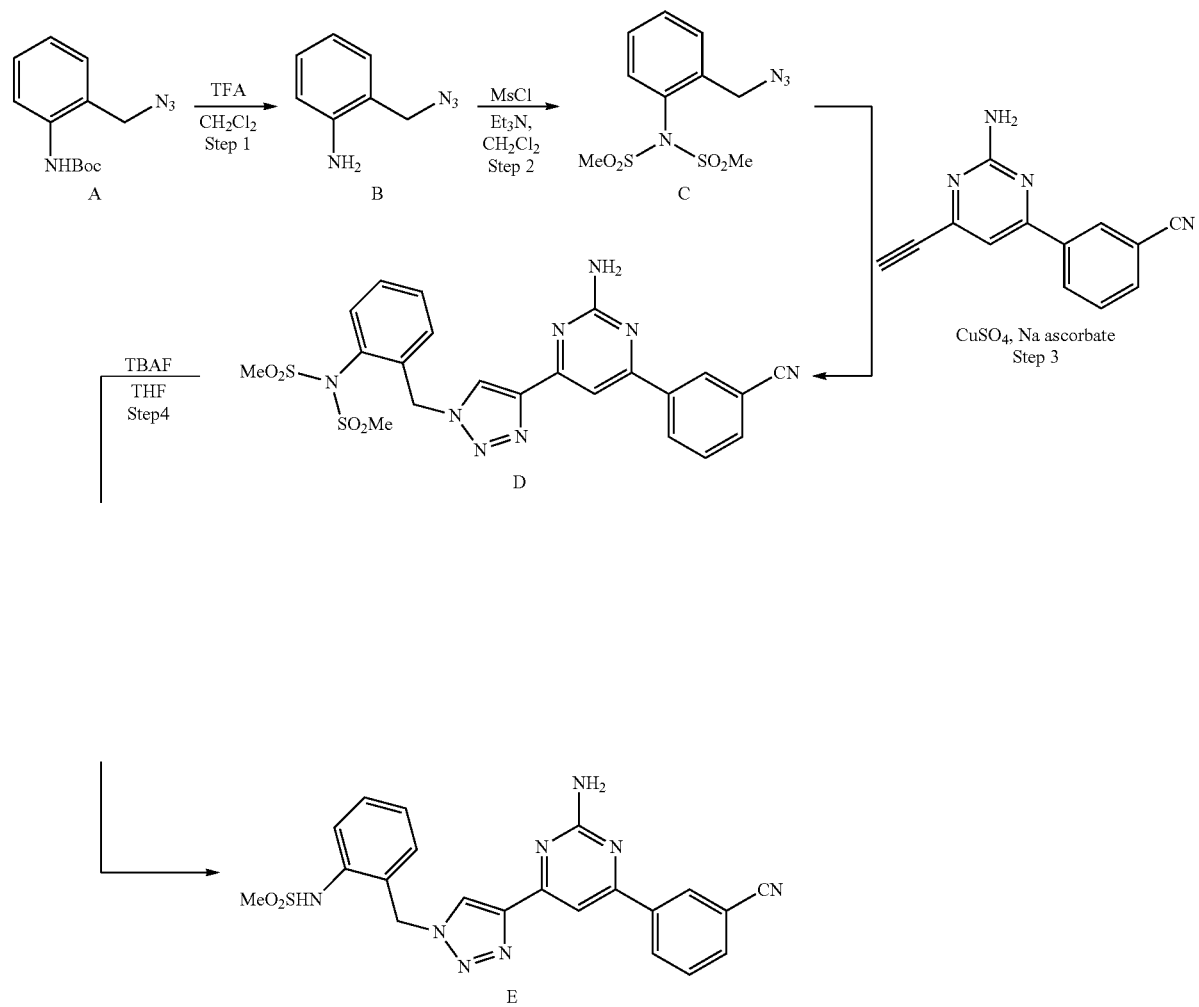

Step 1: Protected aniline substrate A (750 mg) was dissolved in CH₂Cl₂ (12 mL), and TFA (1.5 mL) was added at room temperature. The mixture stirred for three hours and was concentrated to dryness. The residue was dissolved in EtOAc and washed with NaHCO₃. The organic layer was dried and concentrated to afford aniline B (490 mg) as a yellow oil.

Step 2: Aniline B (148 mg, 1 mmol) was dissolved in CH₂Cl₂ (10 mL), and Et₃N (0.56 mL, 4 mmol, 4 equiv.) was added. The mixture was cooled in an ice-water bath and MsCl (0.23 mL, 3 mmol, 3 equiv.) was added. After 15 minutes, the reaction was quenched with 1 M HCl and extracted with CH₂Cl₂. The combined organic layers were dried, concentrated, and purified by flash chromatography on SiO₂ to afford sulfonamide C (190 mg) as a colorless oil.

Step 3: Following the example 1, step 6 procedure for CuAAC using sulfonamide C, triazole D was synthesized to afford 100 mg of a white solid.

Step 4: Triazole D (100 mg, 0.19 mmol) was dissolved in THF (2 mL), and TBAF (1 M in THF, 0.22 mL, 0.22 mmol, 1.2 equiv) was added at room temperature. After the reaction was complete as determined by TLC analysis, the reaction mixture was concentrated and purified by flash chromatography on SiO₂ (0-10% MeOH/CH₂Cl₂) to afford the title compound as a white solid (30 mg). ¹H NMR (400 MHz, DMSO-d₆) δ 9.45 (s, 1H), 8.58 (s, 2H), 8.46 (d, J=3.2 Hz, 1H), 7.99 (d, J=3.6 Hz, 1H), 7.80 (s, 1H), 7.74 (t, J=8 Hz, 1H), 7.43-7.41 (m, 2H), 7.32-7.30 (m, 1H), 7.14 (d, J=8 Hz, 1H), 6.92 (bs, 2H), 5.85 (s, 2H), 3.02 (s, 3H). ESI MS [M+H]⁺ for C₂₁H₁₈N₈O₂S, calcd 447.1, found 447.3.

Example 240: 3-[2-Amino-6-(1-{[o-(methylsulfonylamino)phenyl]methyl}-1H-1,2,3-triazol-4-yl)-4-pyrimidinyl]-2-anisonitrile

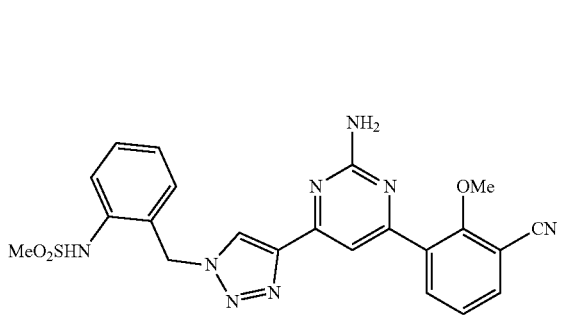

The title compound was prepared similar to example 239 from the corresponding azide and alkyne to afford 41 mg of a pink foam. ¹H NMR (400 MHz, DMSO-d₆) 9.47 (s, 1H), 8.54 (d, J=1.2 Hz, 1H), 8.06 (dd, J=7.8, 1.7 Hz, 1H), 7.94 (dt, J=7.7, 1.5 Hz, 1H), 7.62 (d, J=1.1 Hz, 1H), 7.46-7.40 (m, 2H), 7.35-7.26 (m, 1H), 7.15 (d, J=7.7 Hz, 1H), 6.94-6.83 (m, 2H), 5.83 (s, 2H), 3.84 (d, J=1.2 Hz, 3H), 3.02 (d, J=1.2 Hz, 3H). ESI MS [M+H]⁺ for C₂₂H₂₀N₈O₃S, calcd 477.1, found 477.3.

Example 241: 1-[5-({4-[2-Amino-6-(m-cyanophenyl)-4-pyrimidinyl]-1H-1,2,3-triazol-1-yl}methyl)-1,3-thiazol-2-yl]-4-piperidinecarboxylic acid

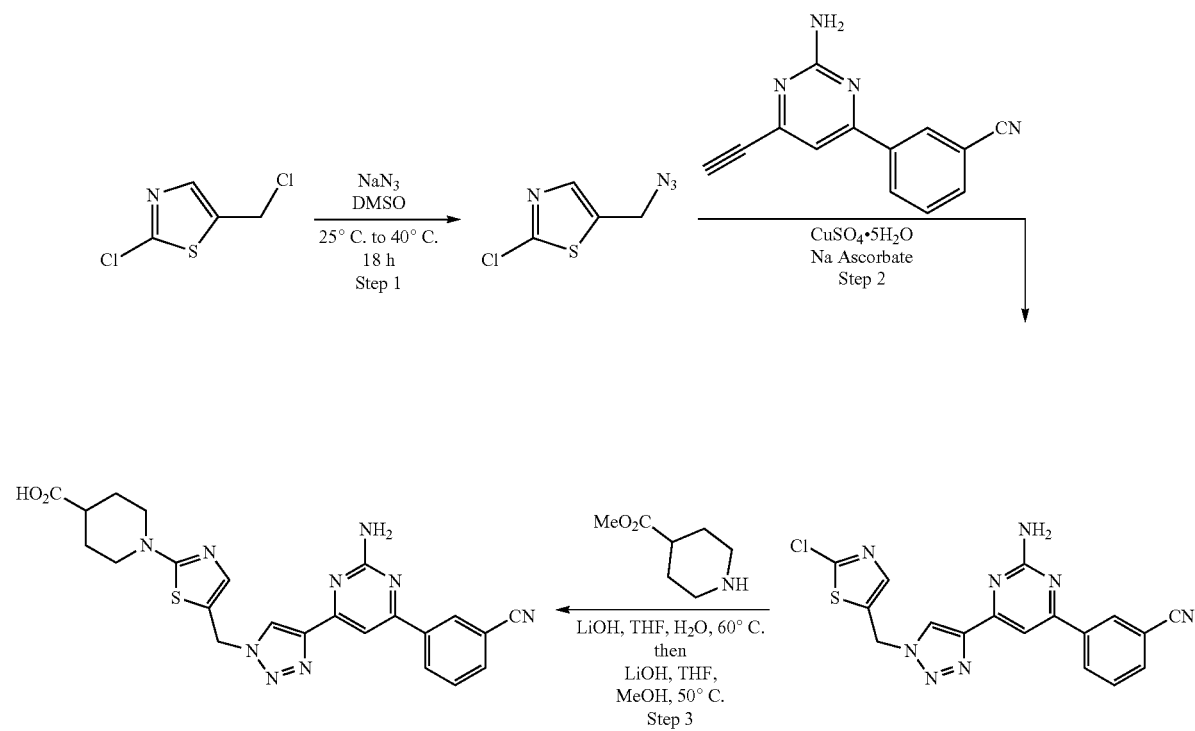

243

Step 1: 2-Chloro-5-(chloromethyl)-thiazole (1.0 g, 6.0 mmol) was dissolved in DMSO (30 ml) and NaN₃ (506 mg, 7.8 mmol) was added. The reaction was stirred at room temperature overnight, partitioned between MTBE and water, and the organic layer was concentrated onto celite. The resulting crude product was purified by flash chromatography over silica gel (ethyl acetate/hexanes 10%) to yield the desired product as a white solid.

Step 2: The azide-alkyne cycloaddition was performed similar to example 1 (step 6).

Step 3: To a solution of the triazole product from step 2 (24 mg, 0.06 mmol) in wet THF (4% H₂O, 0.6 ml) was added the methyl piperidine-4-carboxylate (20.5 µl, 0.152 mmol) and LiGH (1M in H₂O, 7 µl). The reaction was heated to 60° C. An additional portion of the piperidine (61.5 µl, 0.456 mmol) was added after 36 h, and the reaction was stirred a total of 48 h. The resulting solution was concentrated and re-dissolved in THF (1.0 ml) and methanol (1.0 ml). LiGH (1M in H₂O, 250 µl) was added and the solution was heated to 50° C. for 4 hours. The solution was concentrated, taken up in a minimal volume of DMSO and purified by preparative HPLC to yield the title compound. $^1$H NMR (400 MHz, DMSO-d$_6$) δ 8.56 (s, 1H), 8.53 (s, 1H), 8.45 (d, J=8.0 Hz, 1H), 7.98 (d, J=8.0 Hz, 1H), 7.78 (s, 1H), 7.72 (dd, J=8.0, 8.0 Hz, 1H), 6.88 (brs, 2H), 6.80 (s, 1H), 5.53 (s, 2H), 3.76 (d, J=12.0 Hz, 2H), 3.04 (dd, J=12.0, 12.0 Hz, 2H), 2.46-2.43 (m, 1H), 1.88 (d, J=12.0 Hz, 2H), 1.55 (dd, J=12.0, 12.0 Hz, 2H). ESI MS [M+H]⁺ for C$_{23}$H$_{21}$N$_9$O$_2$S, calcd 488.2, found 488.2.

Example 242: 1-[4-({4-[2-Amino-6-(m-cyanophenyl)-4-pyrimidinyl]-1H-1,2,3-triazol-1-yl}methyl)-1,3-thiazol-2-yl]-4-piperidinecarboxylic acid Example 243: m-(2-Amino-6-{1-[(1H-imidazol-2-yl)methyl]-1H-1,2,3-triazol-4-yl}-4-pyrimidinyl)benzonitrile

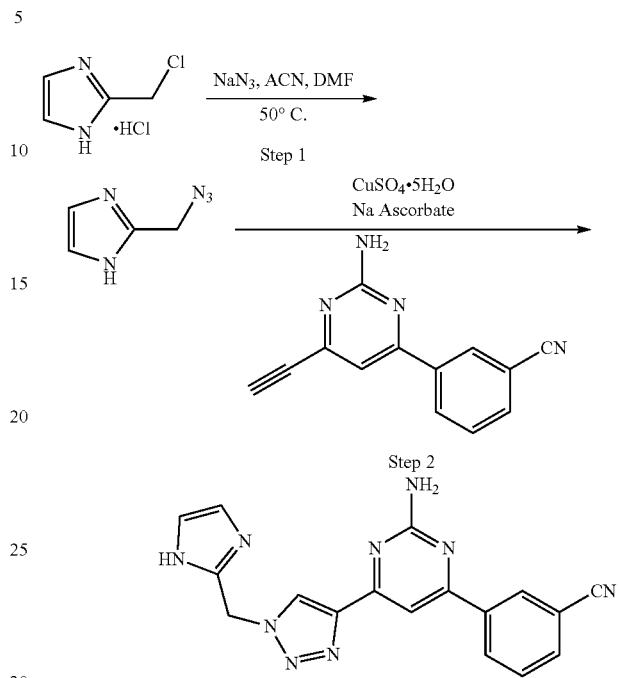

Step 1: A mixture of the commercial chloride derivative (306 mg, 2 mmol) and sodium azide (390 mg, 6 mmol) in MeCN (6 mL) and DMF (1 mL) was stirred at 50° C. for 2

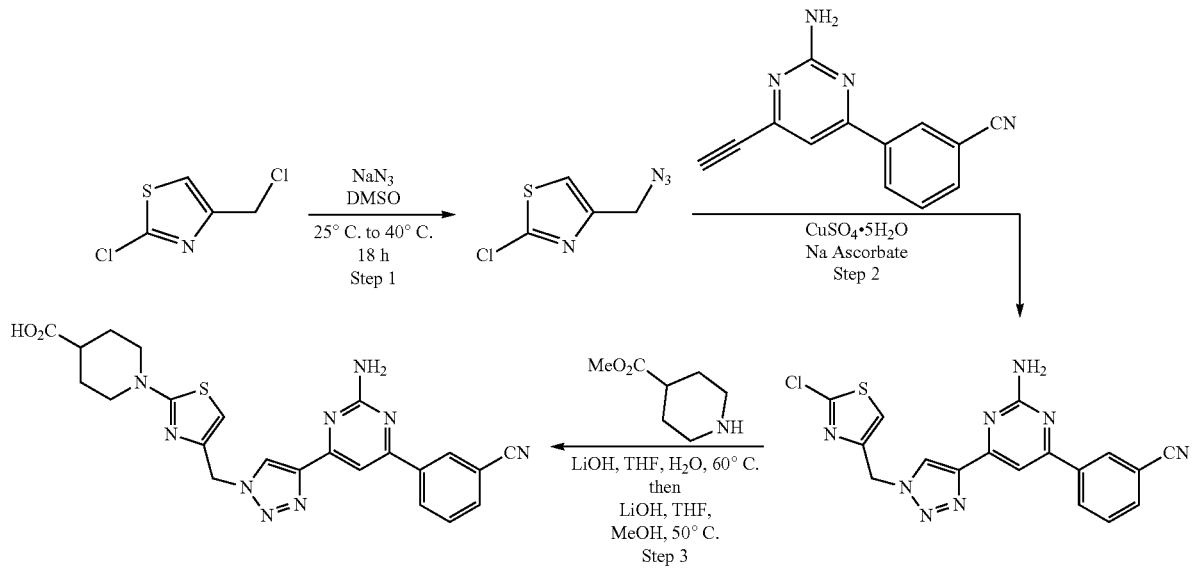

The title compound was prepared in identical fashion to example 241, beginning from 2-chloro-4-(chloromethyl)-thiazole. $^1$H NMR (400 MHz, DMSO-d$_6$) δ 8.58-8.55 (overlap, 2H), 8.44 (d, J=8.0 Hz, 1H), 7.98 (d, J=7.6 Hz, 1H), 7.77 (s, 1H), 7.72 (dd, J=8.0, 7.6 Hz, 1H), 7.32 (s, 1H), 5.77 (s, 2H), 3.78-3.74 (m, 2H), 3.10-3.04 (m, 2H), 1.88-1.86 (m, 2H), 1.55-1.53 (m, 2H). ESI MS [M+H]⁺ for C$_{23}$H$_{21}$N$_9$O$_2$S, calcd 488.2, found 488.2.

hours. It was then cooled to room temperature and the acetonitrile was evaporated. The residue was directly purified by silica gel chromatography (Hex/EtOAc 50:50 to 0:100) to afford the desired azide (150 mg, 61%).

Step 2: The title compound was synthesized in a similar fashion to step 6 of example 1 using the azide derivative and m-(2-amino-6-ethynyl-4-pyrimidinyl)benzonitrile (from example 4). $^1$H NMR (400 MHz, DMSO-d$_6$) δ 8.61-8.58 (m, 1H), 8.57 (s, 1H) 8.48-8.42 (m, 1H), 8.00 (ddd, J=7.7, 1.7, 1.1 Hz, 1H), 7.80 (s, 1H), 7.75 (dd, J=7.7, 7.7 Hz, 1H), 7.18 (brs, 1H), 6.93 (s, 3H), 5.74 (s, 2H). MS [M+H]⁺ for $C_{17}H_{13}N_9$, calcd 344.4, found 344.2.

Example 244: m-(2-Amino-6-{1-[(1H-pyrazol-4-yl)methyl]-1H-1,2,3-triazol-4-yl}-4-pyrimidinyl)benzonitrile

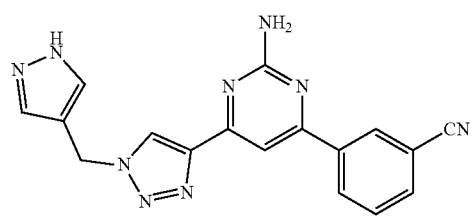

The title compound was synthesized in a similar fashion to step 6 of example 1 using 4-(azidomethyl)-1H-pyrazole and m-(2-amino-6-ethynyl-4-pyrimidinyl)benzonitrile. ¹H NMR (400 MHz, DMSO-d₆) δ 8.58 (brs, 2H), 8.46 (d, J=7.6 Hz, 1H), 8.01 (d, J=7.6 Hz, 1H), 7.81 (s, 2H), 7.75 (dd, J=7.9, 7.9 Hz, 2H), 6.90 (s, 2H), 5.60 (s, 2H). MS [M+H]⁺ for $C_{17}H_{13}N_9$, calcd 344.4, found 344.3.

Example 245: m-[2-(Isopropylamino)-6-(1-{[6-(methoxymethyl)-2-pyridyl]methyl}-1H-1,2,3-triazol-4-yl)-4-pyrimidinyl]benzonitrile

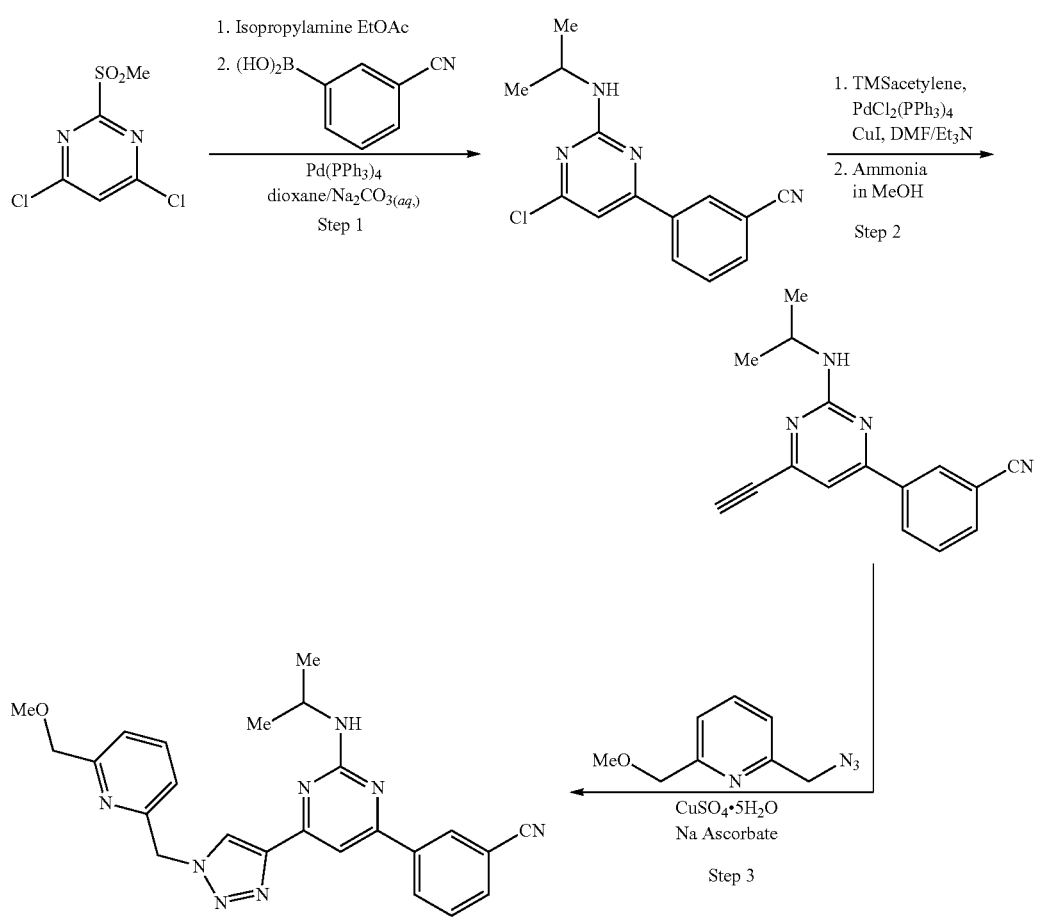

Step 1. Isopropylamine (1.48 mL, 18 mmol) was added dropwise to a solution of dichlorosulfone (3.4 g, 15 mmol) in EtOAc (20 mL) at 0° C. The resulting mixture was stirred at 0° C. for one hour and then at room temperature for one hour. The crude mixture was partitioned between water and EtOAc. The organics were evaporated to dryness and purified by silica gel chromatography (hexanes/EtOAc 95:5 to 85:15) to afford the dichloroaminopyrimidine (2.0 g, 65%).

The dichloride (930 mg, 4.5 mmol) and boronic acid (667 mg, 4.5 mmol) were taken in dioxanne (15 mL) and sodium carbonate (2M in water, 5 mL) and the mixture was degassed with nitrogen for 10 minutes. Pd(PPh$_3$)$_4$ (255 mg, 0.23 mmol) was added and the mixture was heated to 75° C. for 3 hours. After usual work-up the residue was purified by silica gel chromatography (CH$_2$Cl$_2$/EtOAc 100:0 to 90:10) to afford the targeted mono-chloride (520 mg, 42%)

Step 2. This step was performed similar to steps 2-3 of example 1, NH$_3$ was used instead of TBAF in TMS deprotection step (380 mg, 36% from the chloride).

Step 3. The title compounds was synthesized in a similar fashion to step 6 of example 1 using 2-(azidomethyl)-6-(methoxymethyl)pyridine and m-[6-ethynyl-2-(isopropylamino)-4-pyrimidinyl]benzonitrile. $^1$H NMR (400 MHz, CDCl$_3$) δ 8.48 (s, 1H), 8.32 (d, J=8.0 Hz, 1H), 8.30 (s, 1H), 7.81 (s, 1H), 7.77-7.73 (m, 1H), 7.71 (dd, J=8.0 Hz, 1H), 7.59 (dd, J=7.8 Hz, 1H), 7.40 (d, J=8.0 Hz, 1H), 7.11 (d, J=8.0 Hz, 1H), 5.73 (s, 2H), 5.08 (d, J=7.9 Hz, 1H), 4.58 (s, 2H), 4.30 (h, J=6.7 Hz, 1H), 3.49 (s, 3H), 1.29 (d, J=6.5 Hz, 6H). MS [M+H]$^+$ for C$_{24}$H$_{24}$N$_8$O, calcd 441.2, found 441.3.

Example 246: m-[6-(1-{[6-(Methoxymethyl)-2-pyridyl]methyl}-1H-1,2,3-triazol-4-yl)-2-(methylamino)-4-pyrimidinyl]benzonitrile

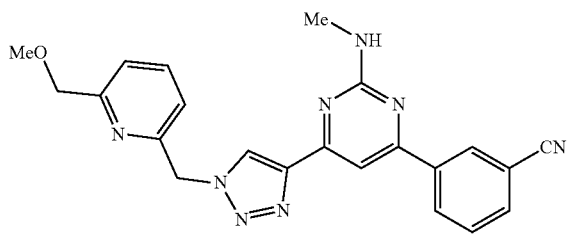

The title compound was synthesized in a similar fashion to example 245 using 2-(azidomethyl)-6-(methoxymethyl)pyridine and m-[6-ethynyl-2-(methylamino)-4-pyrimidinyl]benzonitrile. $^1$H NMR (400 MHz, CDCl$_3$) δ 8.51 (s, 1H), 8.34 (s, 1H), 8.33 (s, 1H), 7.84 (s, 1H), 7.78-7.73 (m, 1H), 7.71 (dd, J=7.6 Hz, 1H), 7.60 (dd, J=7.6 Hz, 1H), 7.41 (d, J=8.0 Hz, 1H), 7.12 (d, J=8.0 Hz, 1H), 5.73 (s, 2H), 5.21 (q, J=5.2 Hz, 1H), 4.59 (s, 2H), 3.50 (s, 3H), 3.11 (d, J=5.2 Hz, 3H). MS [M+H]$^+$ for C$_{22}$H$_{20}$N$_8$O, calcd 413.2, found 413.2.

Example 247: m-[2-(Dimethylamino)-6-(1-{[6-(methoxymethyl)-2-pyridyl]methyl}-1H-1,2,3-triazol-4-yl)-4-pyrimidinyl]benzonitrile

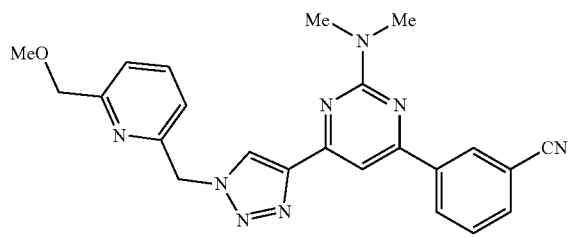

The title compound was synthesized in a similar fashion to example 245. $^1$H NMR (400 MHz, CDCl$_3$) δ 8.51 (s, 1H), 8.37-8.30 (m, 2H), 7.76 (s, 1H), 7.75-7.67 (m, 2H), 7.57 (dd, J=7.9, 7.9 Hz, 1H), 7.40 (d, J=8.0 Hz, 1H), 7.11 (d, J=8.0 Hz, 1H), 5.73 (s, 2H), 4.58 (s, 2H), 3.48 (s, 3H), 3.28 (s, 6H). MS [M+H]$^+$ for C$_{23}$H$_{22}$N$_8$O, calcd 427.2, found 427.3.

Example 248: m-[2-(Cyclopropylamino)-6-(1-{[6-(methoxymethyl)-2-pyridyl]methyl}-1H-1,2,3-triazol-4-yl)-4-pyrimidinyl]benzonitrile

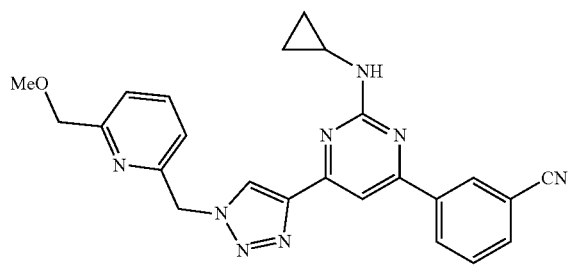 [SMILES: COCc1cccc(Cn2cc(-c3cc(-c4cccc(C#N)c4)nc(NC4CC4)n3)nn2)n1]

The title compound was synthesized in a similar fashion to example 245. $^1$H NMR (400 MHz, CDCl$_3$) δ 8.51 (s, 1H), 8.34 (d, J=8.0 Hz, 1H), 8.32 (s, 1H), 7.88 (s, 1H), 7.78-7.66 (m, 2H), 7.59 (dd, J=7.9, 7.9 Hz, 1H), 7.40 (dd, J=7.6 Hz, 1H), 7.11 (d, J=7.9 Hz, 1H), 5.72 (s, 2H), 5.43 (d, J=2.6 Hz, 1H), 4.58 (s, 2H), 3.49 (s, 3H), 2.95-2.85 (m, 1H), 0.91-0.81 (m, 2H), 0.64-0.55 (m, 2H). MS [M+H]$^+$ for C$_{24}$H$_{22}$N$_8$O, calcd 439.2, found 439.3.

Example 249: m-{2-[(R)-3-Hydroxy-1-pyrrolidinyl]-6-(1-{[6-(methoxymethyl)-2-pyridyl]methyl}-1H-1,2,3-triazol-4-yl)-4-pyrimidinyl}benzonitrile

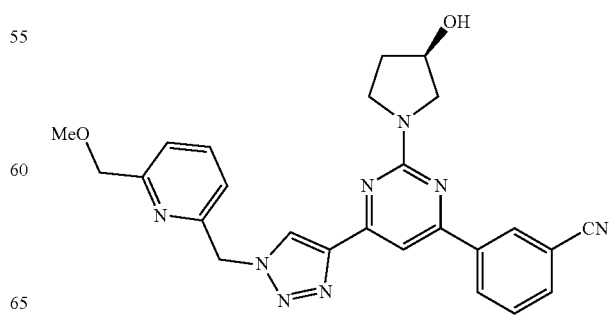

The title compound was synthesized in a similar fashion to example 245. $^1$H NMR (400 MHz, CDCl$_3$) δ 8.48 (s, 1H), 8.32 (s, 1H), 8.31 (s, 1H), 7.77 (s, 1H), 7.73-7.66 (m, 2H), 7.55 (dd, J=7.9, 7.9 Hz, 1H), 7.40 (d, J=7.8 Hz, 1H), 7.11 (d, J=7.8 Hz, 1H), 5.72 (s, 2H), 4.63 (brs, 1H), 4.58 (s, 2H), 3.78 (brs, 4H), 3.48 (s, 3H), 2.22-2.02 (m, 3H). MS [M+H]$^+$ for C$_{25}$H$_{24}$N$_8$O$_2$, calcd 469.2, found 469.3.

Example 250: [6-(m-Cyanophenyl)-4-{1-[(6-cyclopropyl-2-pyridyl)methyl]-1H-1,2,3-triazol-4-yl}-2-pyrimidinylamino]acetic acid

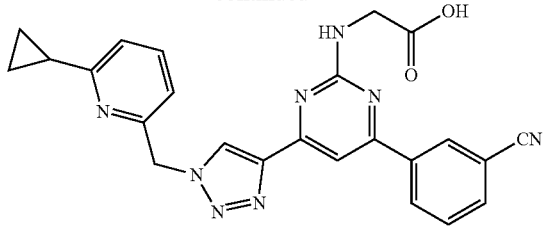

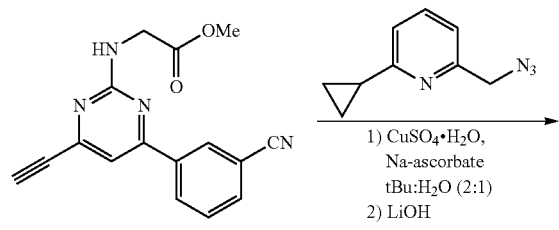

The title compound was synthesized in a similar fashion to example 245 and the hydrolysis reaction was carried out similar to example 125. $^1$H NMR (400 MHz, DMSO-d$_6$) δ 12.49 (s, 1H), 8.70 (s, 1H), 8.60 (d, J=1.7 Hz, 1H), 8.54-8.42 (m, 1H), 7.99 (d, J=7.7 Hz, 1H), 7.87 (s, 1H), 7.73 (t, J=7.9 Hz, 1H), 7.65 (t, J=7.6 Hz, 1H), 7.22 (d, J=7.7 Hz, 1H), 7.01 (d, J=7.7 Hz, 1H), 5.73 (s, 2H), 4.05 (m, 2H), 2.05 (m, 1H), 0.95-0.85 (m, 2H), 0.80 (m, 2H). ESI MS [M+H]$^+$ for C$_{24}$H$_{20}$N$_8$O$_2$, calcd 453.2, found 453.3.

Example 251: [6-(m-Cyanophenyl)-4-(1-{[6-(methoxymethyl)-2-pyridyl]methyl}-1H-1,2,3-triazol-4-yl)-2-pyrimidinylamino]acetic acid

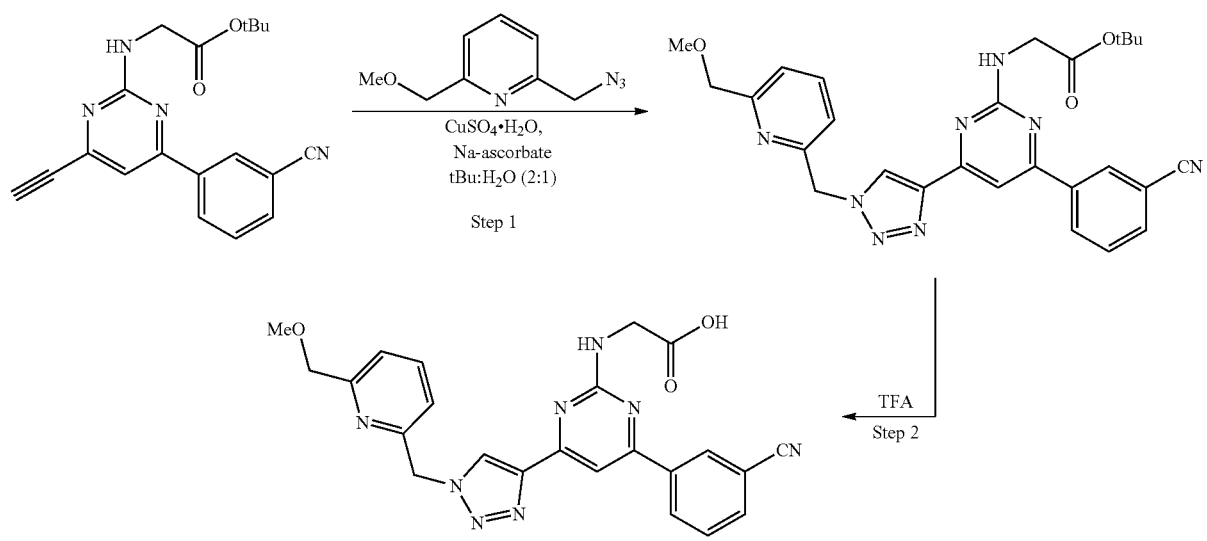 [SMILES: C#Cc1cc(-c2cccc(C#N)c2)nc(NCC(=O)OC(C)(C)C)n1 ; COCc1cccc(CN=[N+]=[N-])n1 ; COCc1cccc(Cn2cc(-c3cc(-c4cccc(C#N)c4)nc(NCC(=O)OC(C)(C)C)n3)nn2)n1 ; COCc1cccc(Cn2cc(-c3cc(-c4cccc(C#N)c4)nc(NCC(=O)O)n3)nn2)n1]

Step 1: tert-Butyl [6-(m-cyanophenyl)-4-(1-{[6-(methoxymethyl)-2-pyridyl]methyl}-1H-1,2,3-triazol-4-yl)-2-pyrimidinylamino]acetate was synthesized similar to example 245. $^1$H NMR (400 MHz, CDCl$_3$) δ 8.52-8.43 (m, 1H), 8.31 (m, 2H), 7.88 (d, J=2.2 Hz, 1H), 7.76-7.65 (m, 2H), 7.57 (t, J=7.9, 1H), 7.44-7.36 (m, 1H), 7.08 (d, J=7.7 Hz, 1H), 5.79 (m, 1H), 5.71 (s, 2H), 4.57 (s, 2H), 4.16 (s, 2H), 3.47 (s, 3H), 1.46 (s, 9H). ESI MS [M+H]$^+$ for C$_{27}$H$_{28}$N$_8$O$_3$, calcd 513.2, found 513.3.

Step 2: tert-Butyl [6-(m-cyanophenyl)-4-(1-{[6-(methoxymethyl)-2-pyridyl]methyl}-1H-1,2,3-triazol-4-yl)-2-pyrimidinylamino]acetate) obtained above was hydrolyzed with TFA to give the title compound. $^1$H NMR (400 MHz, DMSO-d$_6$) δ 8.75 (s, 1H), 8.60 (d, J=1.7 Hz, 1H), 8.52-8.43 (m, 1H), 7.99 (d, J=7.6 Hz, 1H), 7.84 (m, 2H), 7.73 (t, J=7.7 Hz, 1H), 7.65 (s, 1H), 7.37 (d, J=7.8 Hz, 1H), 7.21 (d, J=7.7 Hz, 1H), 5.82 (s, 2H), 4.45 (s, 2H), 4.06 (m, 2H), 3.33 (s, 3H). ESI MS [M+H]$^+$ for C$_{23}$H$_{20}$N$_8$O$_3$, calcd 457.2, found 457.3.

Example 252: [6-(m-Cyanophenyl)-4-(1-{[6-(1-hydroxycyclopentyl)-2-pyridyl]methyl}-1H-1,2,3-triazol-4-yl)-2-pyrimidinylamino]acetic acid

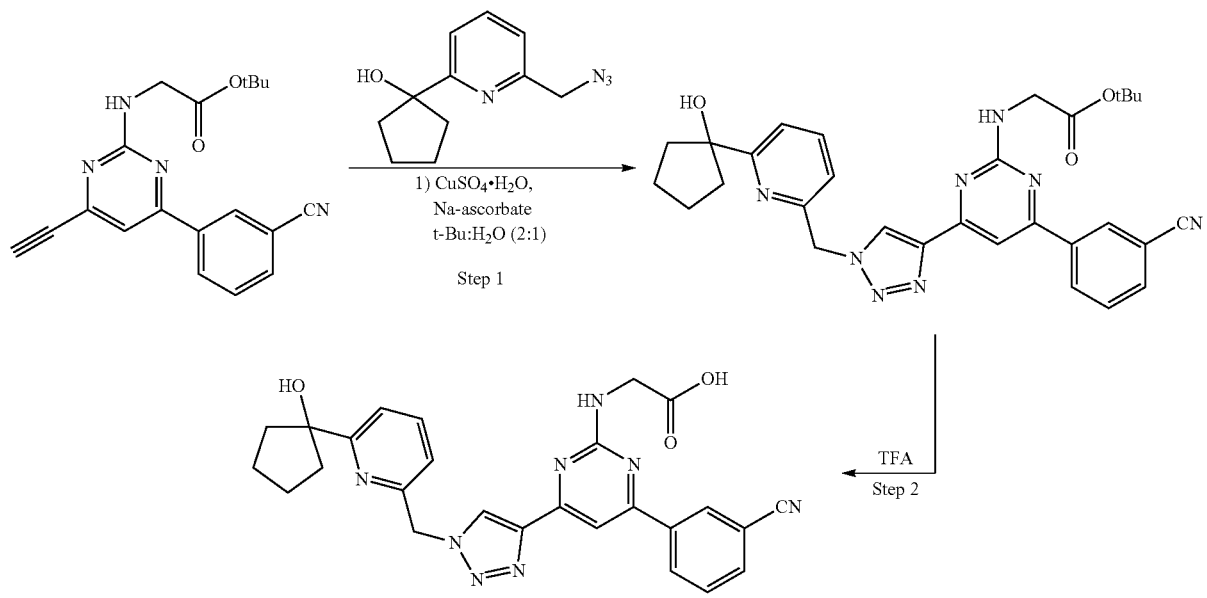 [SMILES: C#Cc1cc(-c2cccc(C#N)c2)nc(NCC(=O)OC(C)(C)C)n1 ; [N-]=[N+]=NCc1cccc(C2(O)CCCC2)n1 ; CC(C)(C)OC(=O)CNc1nc(-c2cccc(C#N)c2)cc(-c2cn(Cc3cccc(C4(O)CCCC4)n3)nn2)n1 ; N#Cc1cccc(-c2cc(-c3cn(Cc4cccc(C5(O)CCCC5)n4)nn3)nc(NCC(=O)O)n2)c1]

Step 1. tert-Butyl [6-(m-cyanophenyl)-4-(1-{[6-(1-hydroxycyclopentyl)-2-pyridyl]methyl}-1H-1,2,3-triazol-4-yl)-2-pyrimidinylamino]acetate was synthesized similar to example 245. $^1$H NMR (400 MHz, CDCl$_3$) δ 8.52-8.45 (m, 1H), 8.37-8.27 (m, 2H), 7.89 (s, 1H), 7.77-7.66 (m, 2H), 7.61-7.55 (m, 1H), 7.38 (d, J=8.0 Hz, 1H), 7.07 (d, J=7.6 Hz, 1H), 5.74 (s, 2H), 4.56 (s, 1H), 4.17 (s, 2H), 2.17-1.62 (m, 8H), 1.47 (s, 9H). ESI MS [M+H]$^+$ for C$_{30}$H$_{32}$N$_8$O$_3$, calcd 553.3, found 553.3.

Step 2. tert-Butyl [6-(m-cyanophenyl)-4-(1-{[6-(1-hydroxycyclopentyl)-2-pyridyl]methyl}-1H-1,2,3-triazol-4-yl)-2-pyrimidinylamino]acetate obtained above was hydrolyzed with TFA to give the title compound: $^1$H NMR (400 MHz, DMSO-d$_6$) δ 8.75 (s, 1H), 8.60 (s, 1H), 8.52-8.45 (m, 1H), 8.03-7.94 (m, 1H), 7.87 (s, 1H), 7.82-7.70 (m, 2H), 7.62 (d, J=7.9 Hz, 2H), 7.11 (d, J=7.6 Hz, 1H), 5.81 (s, 2H), 4.06 (s, 2H), 2.00 (m, 2H), 1.80 (m, 2H), 1.69 (m, 4H). ESI MS [M+H]$^+$ for C$_{26}$H$_{24}$N$_8$O$_3$, calcd 497.2, found 497.3.

Example 253: [6-(m-Cyanophenyl)-4-(1-{[6-(1-methoxyethyl)-2-pyridyl]methyl}-1H-1,2,3-triazol-4-yl)-2-pyrimidinylamino]acetic acid

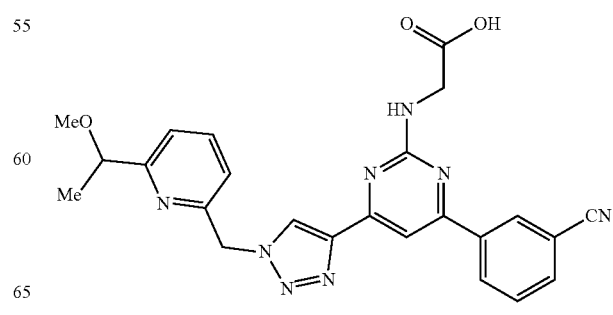

The title compound was synthesized in a similar fashion to example 251. $^1$H NMR (400 MHz, DMSO-$d_6$) δ 8.76 (s, 1H), 8.63-8.53 (m, 1H), 8.53-8.40 (m, 1H), 7.99 (d, J=7.6 Hz, 1H), 7.90-7.80 (m, 2H), 7.73 (t, J=7.8 Hz, 1H), 7.69-7.55 (m, 1H), 7.37 (d, J=7.8 Hz, 1H), 7.16 (d, J=7.8 Hz, 1H), 5.83 (s, 2H), 4.33 (q, J=6.4 Hz, 1H), 4.06 (m, 2H), 3.18 (s, 3H), 1.31 (d, J=5.6 Hz, 3H). ESI MS [M+H]$^+$ for $C_{24}H_{22}N_8O_3$, calcd 471.2, found 471.2.

Example 254: [6-(m-Cyanophenyl)-4-(1-{[6-(trifluoromethyl)-2-pyridyl]methyl}-1H-1,2,3-triazol-4-yl)-2-pyrimidinylamino]acetic acid

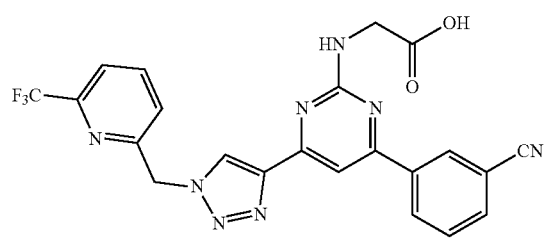 [SMILES: N#Cc1cccc(-c2cc(-c3cn(Cc4cccc(C(F)(F)F)n4)nn3)nc(NCC(=O)O)n2)c1]

The title compound was synthesized in a similar fashion to example 251. $^1$H NMR (400 MHz, DMSO-$d_6$) δ 8.82 (s, 1H), 8.60 (s, 1H), 8.52-8.45 (m, 1H), 8.14 (t, J=7.9 Hz, 1H), 7.99 (d, J=7.7 Hz, 1H), 7.89 (d, J=8.0 Hz, 2H), 7.73 (t, J=7.8 Hz, 1H), 7.69-7.63 (m, 1H), 7.59 (d, J=8.0 Hz, 1H), 5.97 (s, 2H), 4.05 (s, 3H). ESI MS [M+H]$^+$ for $C_{22}H_{15}F_3N_8O_2$, calcd 481.2, found 481.2.

Example 255: [6-(m-Cyanophenyl)-4-{1-[(6-isopropyl-2-pyridyl)methyl]-1H-1,2,3-triazol-4-yl}-2-pyrimidinylamino]acetic acid

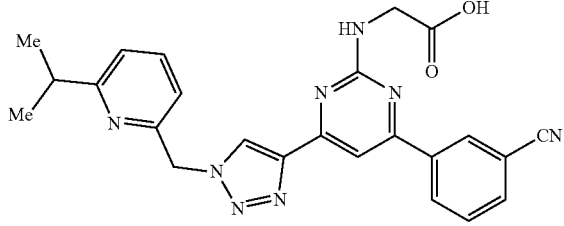

The title compound was synthesized in a similar fashion to example 251. $^1$H NMR (400 MHz, DMSO-$d_6$) δ 8.76 (s, 1H), 8.60 (d, J=1.7 Hz, 1H), 8.52-8.45 (m, 1H), 7.99 (d, J=7.6 Hz, 1H), 7.91-7.82 (m, 1H), 7.77-7.68 (m, 2H), 7.62 (s, 1H), 7.24 (d, J=7.8 Hz, 1H), 7.06 (d, J=7.7 Hz, 1H), 5.80 (s, 2H), 4.10-3.88 (m, 2H), 2.97 (sep, J=6.9 Hz, 1H), 1.18 (d, J=6.9 Hz, 6H). ESI MS [M+H]$^+$ for $C_{24}H_{22}N_8O_2$, calcd 455.2, found 455.3.

Example 256: [6-(m-Cyanophenyl)-4-(1-{[6-(tert-butyl)-2-pyridyl]methyl}-1H-1,2,3-triazol-4-yl)-2-pyrimidinylamino]acetic acid

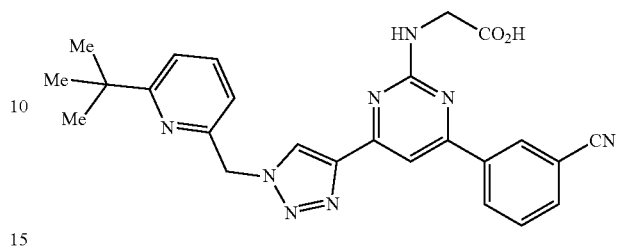

The title compound was synthesized in a similar fashion to example 251. $^1$H NMR (400 MHz, Methanol-$d_4$) δ 8.69 (s, 1H), 8.54 (s, 1H), 8.45 (d, J=8.0 Hz, 1H), 7.91-7.82 (m, 2H), 7.78-7.63 (m, 2H), 7.39 (d, J=7.9 Hz, 1H), 7.16 (d, J=7.7 Hz, 1H), 5.79 (s, 2H), 4.20 (s, 2H), 1.32 (s, 9H); LC-MS retention time 3.20 min LC-MS, Method A, ESI MS [M+H]$^+$ for $C_{25}H_{25}N_8O_2$, calcd 469.2, found 469.3.

Example 257: 3-[6-(m-Cyanophenyl)-4-(1-{[6-(tert-butyl)-2-pyridyl]methyl}-1H-1,2,3-triazol-4-yl)-2-pyrimidinylamino]propionic acid

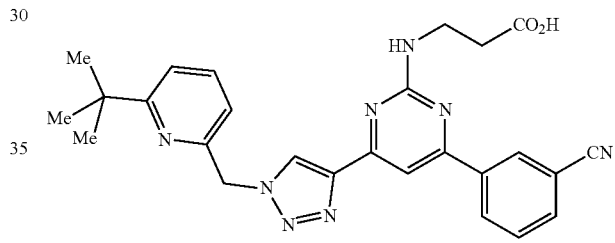

The title compound was synthesized in a similar fashion to example 250 to afford 53 mg of a white solid. $^1$H NMR (400 MHz, DMSO-$d_6$) 8.79 (d, J=32.6 Hz, 1H), 8.61 (s, 1H), 8.50 (s, 1H), 8.00 (dq, J=8.1, 1.2 Hz, 1H), 7.84 (s, 1H), 7.80-7.71 (m, 2H), 7.50-7.35 (m, 2H), 7.11 (s, 1H), 5.83 (s, 2H), 3.63 (s, 2H), 2.60 (t, J=6.8 Hz, 2H), 1.31-1.22 (m, 9H). ESI MS [M+H]$^+$ for $C_{26}H_{26}N_8O_2$, calcd 483.2, found 483.4.

Example 258: (S)-2-[6-(m-Cyanophenyl)-4-(1-{[6-(tert-butyl)-2-pyridyl]methyl}-1H-1,2,3-triazol-4-yl)-2-pyrimidinylamino]propionic acid

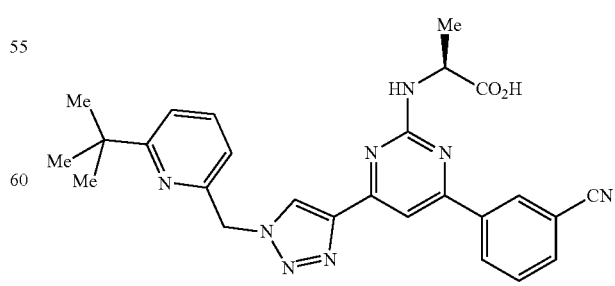

The title compound was synthesized in a similar fashion to example 250 to afford 121 mg of a white solid. $^1$H NMR (400 MHz, DMSO-$d_6$) 8.73 (d, J=1.2 Hz, 1H), 8.63 (d, J=1.4 Hz, 1H), 8.51 (d, J=8.0 Hz, 1H), 8.01 (d, J=7.7 Hz, 1H), 7.94-7.85 (m, 1H), 7.76 (td, J=7.9, 7.2, 3.9 Hz, 2H), 7.40 (d, J=7.9 Hz, 1H), 7.10 (d, J=7.6 Hz, 1H), 5.84 (s, 2H), 4.49 (d, J=35.1 Hz, 1H), 1.45 (d, J=7.2 Hz, 3H), 1.26 (s, 9H). ESI MS [M+H]$^+$ for $C_{26}H_{26}N_8O_2$, calcd 483.2, found 483.4.

Example 259: (R)-2-[6-(m-Cyanophenyl)-4-(1-{[6-(tert-butyl)-2-pyridyl]methyl}-1H-1,2,3-triazol-4-yl)-2-pyrimidinylamino]propionic acid

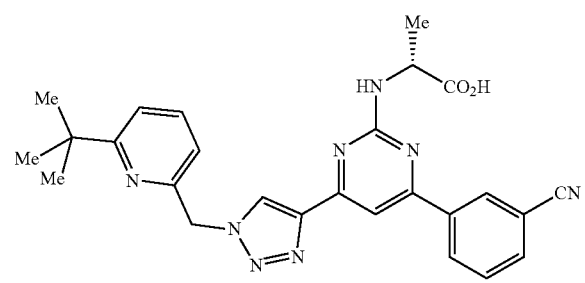

The title compound was synthesized in a similar fashion to example 250 to afford 121 mg of a white solid. $^1$H NMR (400 MHz, DMSO-$d_6$) 8.73 (d, J=1.2 Hz, 1H), 8.63 (d, J=1.4 Hz, 1H), 8.51 (d, J=8.0 Hz, 1H), 8.01 (d, J=7.7 Hz, 1H), 7.94-7.85 (m, 1H), 7.76 (td, J=7.9, 7.2, 3.9 Hz, 2H), 7.40 (d, J=7.9 Hz, 1H), 7.10 (d, J=7.6 Hz, 1H), 5.84 (s, 2H), 4.49 (d, J=35.1 Hz, 1H), 1.45 (d, J=7.2 Hz, 3H), 1.26 (s, 9H). ESI MS [M+H]$^+$ for $C_{26}H_{26}N_8O_2$, calcd 483.2, found 483.4.

Example 260: 3-[6-(m-Cyanophenyl)-4-(1-{[6-(trifluoromethyl)-2-pyridyl]methyl}-1H-1,2,3-triazol-4-yl)-2-pyrimidinylamino]propionic acid

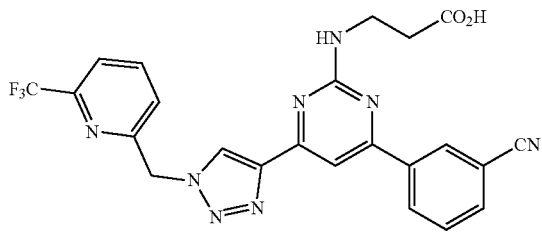

The title compound was synthesized in a similar fashion to example 250 to afford 54 mg of a white solid. $^1$H NMR (400 MHz, DMSO-$d_6$) 8.85 (d, J=33.0 Hz, 1H), 8.62 (s, 1H), 8.51 (s, 1H), 8.16 (t, J=7.9 Hz, 1H), 8.05-7.97 (m, 1H), 7.91 (d, J=7.8 Hz, 1H), 7.85 (s, 1H), 7.76 (t, J=7.9 Hz, 1H), 7.61 (d, J=8.0 Hz, 1H), 7.44 (s, 1H), 5.99 (s, 2H), 3.64 (s, 2H), 2.61 (t, J=7.0 Hz, 2H). ESI MS [M+H]$^+$ for $C_{23}H_{17}F3N_8O_2$, calcd 495.2, found 495.2.

Example 261: (S)-2-[6-(m-Cyanophenyl)-4-(1-{[6-(trifluoromethyl)-2-pyridyl]methyl}-1H-1,2,3-triazol-4-yl)-2-pyrimidinylamino]propionic acid

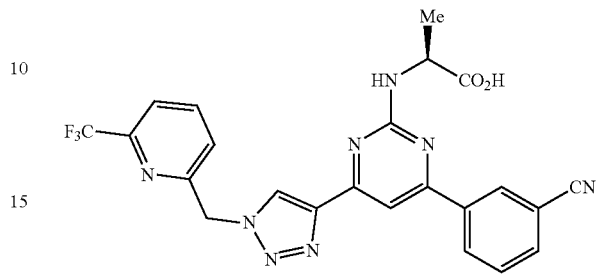

The title compound was synthesized in a similar fashion to example 250 to afford 38 mg of a tan solid. $^1$H NMR (400 MHz, DMSO-$d_6$) 8.78 (s, 1H), 8.63 (td, J=1.8, 0.6 Hz, 1H), 8.55-8.47 (m, 1H), 8.16 (t, J=7.9 Hz, 1H), 8.01 (d, J=7.7 Hz, 1H), 7.94-7.86 (m, 2H), 7.83-7.70 (m, 1H), 7.61 (d, J=7.9 Hz, 1H), 6.00 (s, 2H), 4.50 (d, J=37.7 Hz, 1H), 1.45 (d, J=7.3 Hz, 3H). ESI MS [M+H]$^+$ for $C_{23}H_{17}F3N_8O_2$, calcd 495.2, found 495.3.

Example 262: (R)-2-[6-(m-Cyanophenyl)-4-(1-{[6-(trifluoromethyl)-2-pyridyl]methyl}-1H-1,2,3-triazol-4-yl)-2-pyrimidinylamino]propionic acid

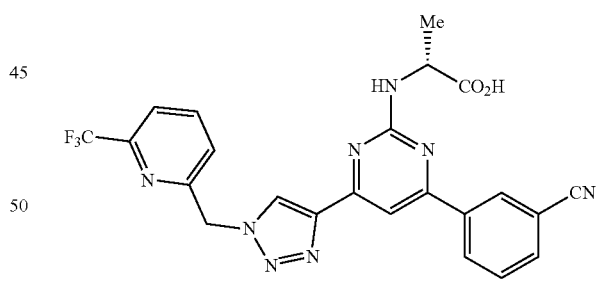

The title compound was synthesized in a similar fashion to example 250 to afford 50 mg of a tan solid. $^1$H NMR (400 MHz, DMSO-$d_6$) 8.78 (s, 1H), 8.63 (td, J=1.8, 0.6 Hz, 1H), 8.55-8.47 (m, 1H), 8.16 (t, J=7.9 Hz, 1H), 8.01 (d, J=7.7 Hz, 1H), 7.94-7.86 (m, 2H), 7.83-7.70 (m, 1H), 7.61 (d, J=7.9 Hz, 1H), 6.00 (s, 2H), 4.50 (d, J=37.7 Hz, 1H), 1.45 (d, J=7.3 Hz, 3H). ESI MS [M+H]$^+$ for $C_{23}H_{17}F3N_8O_2$, calcd 495.2, found 495.3.

Example 263: 3-[6-(m-Cyanophenyl)-4-(1-{[6-(tert-butyl)-2-pyridyl]methyl}-1H-1,2,3-triazol-4-yl)-2-pyrimidinylamino]-3-methylbutyric acid

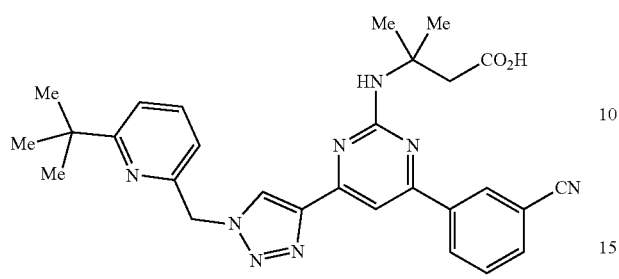

The title compound was synthesized in a similar fashion to example 250. ¹H NMR (400 MHz, DMSO-d₆) δ 11.98 (brs, 1H), 8.74 (s, 1H), 8.59 (s, 1H), 8.47 (d, J=7.9 Hz, 1H), 7.99 (d, J=7.6 Hz, 1H), 7.82 (s, 1H), 7.76-7.72 (m, 2H), 7.38 (d, J=7.9 Hz, 1H), 7.01 (s, 1H), 5.82 (s, 2H), 2.91 (s, 2H), 1.53 (s, 6H), 1.23 (s, 9H). ESI MS [M+H]⁺ for $C_{28}H_{30}N_8O_2$, calcd 511.2, found 511.4.

Example 264: 1-[6-(m-Cyanophenyl)-4-(1-{[6-(tert-butyl)-2-pyridyl]methyl}-1H-1,2,3-triazol-4-yl)-2-pyrimidinylamino]cyclopropanecarboxylic acid

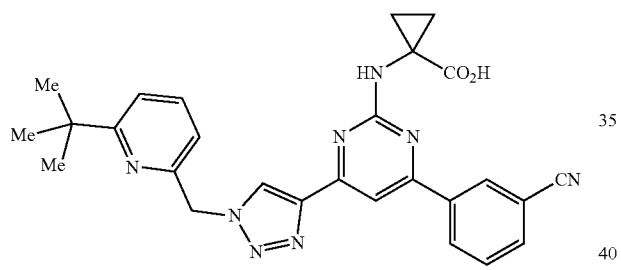

The title compound was synthesized in a similar fashion to example 250. ¹H NMR (400 MHz, CDCl₃) δ 8.48-8.34 (m, 2H), 8.34-8.18 (m, 1H), 8.00-7.84 (m, 1H), 7.77-7.66 (m, 1H), 7.66-7.48 (m, 2H), 7.34-7.20 (m, 1H), 7.01 (d, J=9.9 Hz, 1H), 6.36-6.03 (m, 1H), 5.72-5.55 (m, 2H), 1.77-1.61 (m, 2H), 1.45-1.13 (m, 11H); LC-MS retention time 3.35 min LC-MS, Method A, ESI MS [M+H]⁺ for $C_{27}H_{27}N_8O_2$, calcd 495.2, found 495.3.

Example 265: 1-[6-({4-[6-(m-cyanophenyl)-2-(isopropylamino)-4-pyrimidinyl]-1H-1,2,3-triazol-1-yl}methyl)-2-pyridyl]-3-azetidinecarboxylic acid

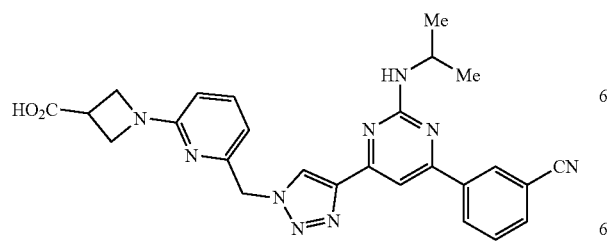

The title compound was synthesized in a similar fashion to example 250. ¹H NMR (400 MHz, DMSO-d₆) δ 8.61 (s, 1H), 8.53-8.42 (m, 1H), 8.00 (d, J=7.9 Hz, 1H), 7.80-7.70 (m, 2H), 7.54 (t, J=7.7 Hz, 1H), 7.29 (d, J=7.6 Hz, 1H), 6.54-6.50 (m, 1H), 6.38 (d, J=8.4 Hz, 1H), 5.64 (s, 2H), 4.28-4.18 (m, 1H), 4.08 (t, J=8.7 Hz, 2H), 3.95 (t, J=7.1 Hz, 2H), 3.52-3.44 (m, 1H), 1.22 (d, J=6.4 Hz, 6H). ESI MS [M+H]⁺ for $C_{26}H_{25}N_9O_2$, calcd 496.2, found 496.3.

Example 266: 1-{6-[(4-{2-[(R)-tetrahydrofur-3-ylamino]-6-(m-cyanophenyl)-4-pyrimidinyl}-1H-1,2,3-triazol-1-yl)methyl]-2-pyridyl}-3-azetidinecarboxylic acid

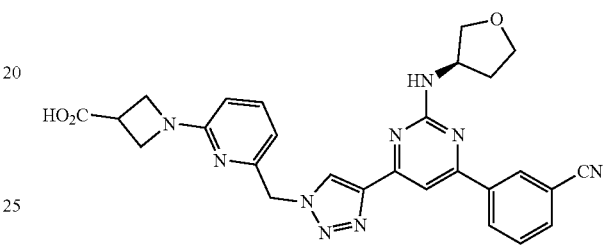

The title compound was synthesized in a similar fashion to example 250. ¹H NMR (400 MHz, DMSO-d₆) δ 8.62 (s, 1H), 8.55-8.44 (m, 1H), 8.01 (d, J=7.9 Hz, 1H), 7.84 (s, 1H), 7.80-7.67 (m, 2H), 7.55 (t, J=7.9 Hz, 1H), 6.52 (d, J=7.3 Hz, 1H), 6.38 (d, J=8.3 Hz, 1H), 5.65 (s, 2H), 4.55 (s, 1H), 4.13-3.91 (m, 5H), 3.87 (q, J=7.8 Hz, 1H), 3.75 (q, J=7.6 Hz, 1H), 3.64-3.57 (m, 1H), 3.54-3.46 (m, 1H), 2.51 (s, 1H), 2.26-2.17 (dd, J=13.1, 7.1 Hz, 1H), 2.00-1.93 (m, 1H). ESI MS [M+H]⁺ for $C_{27}H_{25}N_9O_3$, calcd 524.2, found 524.3.

Example 266: Methyl (S)-1-[6-({4-[6-(m-cyanophenyl)-2-(2-hydroxy-2-methylpropylamino)-4-pyrimidinyl]-1H-1,2,3-triazol-1-yl}methyl)-2-pyridyl]-2-pyrrolidinecarboxylate

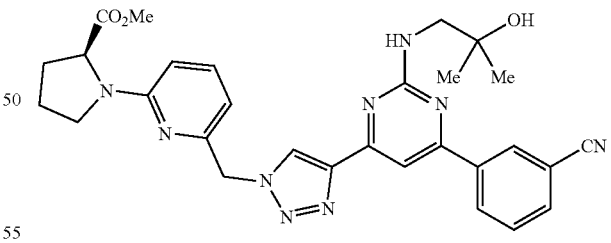

The title compound was synthesized in a similar fashion to example 250. ¹H NMR (400 MHz, CDCl₃) δ 8.43 (s, 1H), 8.38 (s, 1H), 8.30 (d, J=8.0 Hz, 1H), 7.84 (s, 1H), 7.73 (d, J=7.2 Hz, 1H), 7.58 (dd, J=8.0, 8.0 Hz, 1H), 7.44 (dd, J=8.0, 8.0 Hz, 1H), 6.56 (d, J=7.2 Hz, 1H), 6.37 (d, J=8.0 Hz, 1H), 5.73 (brs 1H), 5.52-5.36 (m, 2H), 4.56-4.47 (m, 1H), 3.64 (s, 3H), 3.62-3.54 (m, 2H), 3.48-3.38 (m, 2H), 2.38-2.04 (m, 4H), 1.30 (s, 6H). MS [M+H]⁺ for $C_{29}H_{31}N_9O_3$, calcd 554.3, found 554.4.

Example 267: (S)-1-[6-({4-[6-(m-Cyanophenyl)-2-(2-hydroxy-2-methylpropylamino)-4-pyrimidinyl]-1H-1,2,3-triazol-1-yl}methyl)-2-pyridyl]-2-pyrrolidinecarboxylic acid

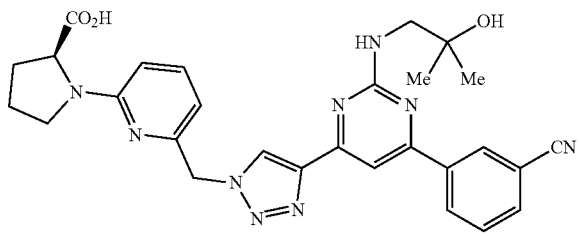

The title compound was synthesized in a similar fashion to example 250. $^1$H NMR (400 MHz, DMSO-d$_6$) δ 12.39 (brs, 1H), 8.60 (s, 1H), 8.49 (d, J=7.9 Hz, 1H), 7.98 (d, J=7.6 Hz, 1H), 7.79 (s, 1H), 7.73 (dd, J=7.7 Hz, 1H), 7.50 (dd, J=7.7 Hz, 1H), 7.00 (brs, 1H), 6.47 (d, J=6.0 Hz, 1H), 6.39 (d, J=8.5 Hz, 1H), 5.59 (d, J=15.2 Hz, 1H), 5.53 (d, J=15.2 Hz, 1H), 4.60 (brs, 1H), 4.34 (d, J=8.7 Hz, 1H), 3.53-3.33 (m, 3H), 2.27-2.12 (m, 1H), 2.06 (s, 1H), 2.04-1.84 (m, 2H), 1.14 (s, 6H). MS [M+H]$^+$ for C$_{28}$H$_{29}$N$_9$O$_3$, calcd 540.3, found 540.3.

Example 268: Methyl (R)-1-{6-[(4-{2-[(R)-tetrahydrofur-3-ylamino]-6-(m-cyanophenyl)-4-pyrimidinyl}-1H-1,2,3-triazol-1-yl)methyl]-2-pyridyl}-2-pyrrolidinecarboxylate

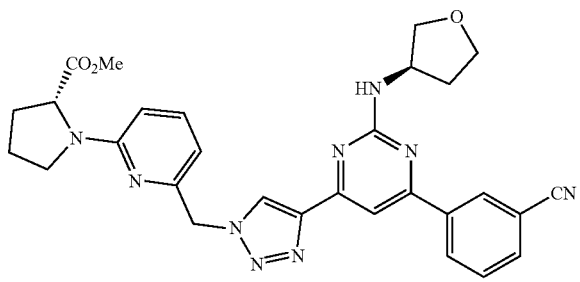

The title compound was synthesized in a similar fashion to example 250. $^1$H NMR (400 MHz, CDCl$_3$) δ 8.48 (s, 1H), 8.39 (s, 1H), 8.34 (d, J=7.8 Hz, 2H), 7.86 (s, 1H), 7.74 (d, J=7.8 Hz, 1H), 7.59 (dd, J=7.8, 7.8 Hz, 1H), 7.46 (dd, J=7.8 Hz, 1H), 6.58 (d, J=7.8 Hz, 1H), 6.39 (d, J=7.8 Hz, 1H), 5.53-5.39 (m, 2H), 4.80 (brs, 1H), 4.54 (d, J=8.0 Hz, 1H), 4.18-3.85 (m, 3H), 3.81-3.72 (m, 1H), 3.63-3.57 (m, 1H), 3.65 (s, 3H), 3.50-3.39 (m, 1H), 2.46-2.34 (m, 1H), 2.34-2.22 (m, 1H), 2.22-2.00 (m, 3H), 2.01-1.89 (m, 1H). MS [M+H]$^+$ for C$_{29}$H$_{29}$N$_9$O$_3$, calcd 552.3, found: 552.4.

Example 269: (R)-1-{6-[(4-{2-[(R)-Tetrahydrofur-3-ylamino]-6-(m-cyanophenyl)-4-pyrimidinyl}-1H-1,2,3-triazol-1-yl)methyl]-2-pyridyl}-2-pyrrolidinecarboxylic acid

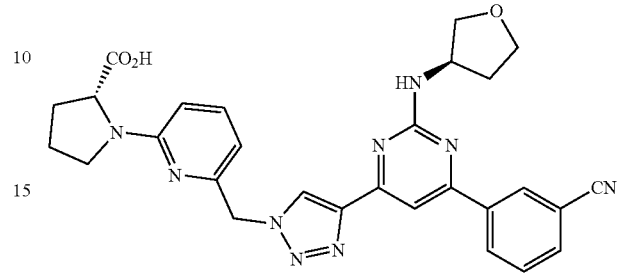

The title compound was synthesized in a similar fashion to example 250. $^1$H NMR (400 MHz, CDCl$_3$) δ 8.53 (s, 1H), 8.41 (s, 1H), 8.28 (d, J=8.0 Hz, 1H), 7.84 (s, 1H), 7.78-7.69 (m, 1H), 7.56 (dd, J=7.8, 7.8 Hz, 1H), 7.48 (dd, J=7.2, 7.2 Hz, 1H), 6.67 (d, J=7.2 Hz, 1H), 6.45 (dd, J=8.0 Hz, 1H), 5.68 (d, J=6.8 Hz, 1H), 5.53 (dd, J=15.2 Hz, 1H), 5.41 (dd, J=15.2 Hz, 1H), 5.29 (s, 2H), 4.77-4.65 (m, 1H), 4.59-4.50 (m, 1H), 4.11-3.95 (m, 2H), 3.95-3.84 (m, 1H), 3.72 (dd, J=9.5, 3.8 Hz, 1H), 3.58-3.32 (m, 2H), 2.42-2.95 (m, 3H), 1.99-1.85 (m, 1H). MS [M+H]$^+$ for C$_{28}$H$_{27}$N$_9$O$_3$, calcd 538.2, found: 538.3.

Example 270: (R)-1-{6-[(4-{2-[(S)-Tetrahydrofur-3-ylamino]-6-(m-cyanophenyl)-4-pyrimidinyl}-1H-1,2,3-triazol-1-yl)methyl]-2-pyridyl}-2-pyrrolidinecarboxylic acid

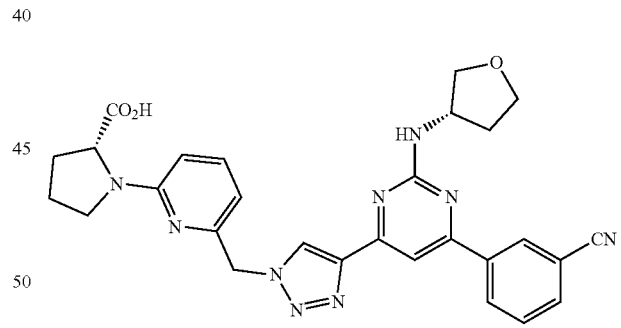

The title compound was synthesized in a similar fashion to example 250. $^1$H NMR (400 MHz, Acetone-d$_6$) δ 11.48 (brs, 1H), 8.67 (brs, 1H), 8.59 (s, 1H), 8.51 (d, J=8.0 Hz, 1H), 7.94-7.88 (m, 1H), 7.87 (s, 1H), 7.74 (dd, J=8.0, 8.0 Hz, 1H), 7.56 (dd, J=8.5, 7.2 Hz, 1H), 6.76 (d, J=6.6 Hz, 1H), 6.66 (d, J=7.2 Hz, 1H), 6.50 (d, J=8.5 Hz, 1H), 5.63 (s, 1H), 5.58 (s, 2H), 4.76-4.67 (m, 1H), 4.54-4.47 (m, 1H), 4.12-4.02 (m, 1H), 3.95 (q, J=7.4 Hz, 1H), 3.86-3.68 (m, 2H), 3.61-3.50 (m, 1H), 3.44 (q, J=8.2 Hz, 1H), 2.39-2.12 (m, 4H), 2.03-1.96 (m, 1H). MS [M+H]$^+$ for C$_{28}$H$_{27}$N$_9$O$_3$, calcd 538.2, found 538.3.

Example 271: (S)-1-{6-[(4-{2-[(S)-Tetrahydrofur-3-ylamino]-6-(m-cyanophenyl)-4-pyrimidinyl}-1H-1,2,3-triazol-1-yl)methyl]-2-pyridyl}-2-pyrrolidinecarboxylic acid

Example 273: (S)-1-[6-({4-[6-(m-Cyanophenyl)-2-(cyclopropylamino)-4-pyrimidinyl]-1H-1,2,3-triazol-1-yl}methyl)-2-pyridyl]-2-pyrrolidinecarboxylic acid

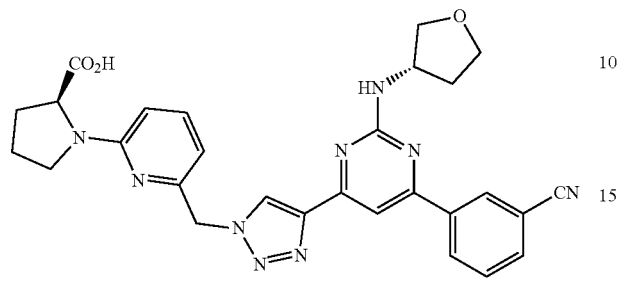

The title compound was synthesized in a similar fashion to example 250. $^1$H NMR (400 MHz, CD$_3$OD) δ 10.42 (s, 1H), 10.16 (s, 1H), 10.07 (d, J=8.0 Hz, 1H), 9.47 (s, 1H), 9.43-9.34 (m, 1H), 9.25 (t, J=7.8 Hz, 1H), 8.99 (t, J=7.9 Hz, 1H), 8.07 (d, J=7.1 Hz, 1H), 7.94 (d, J=8.5 Hz, 1H), 7.11 (s, 2H), 6.29 (s, 1H), 5.79 (s, 1H), 5.71-5.63 (m, 1H), 5.58 (q, J=7.6 Hz, 1H), 5.46 (q, J=7.6 Hz, 1H), 5.33 (dd, J=9.0, 3.9 Hz, 1H), 5.29-5.17 (m, 1H), 5.11-4.97 (m, 1H), 4.00-3.76 (m, 2H), 3.76-3.41 (m, 4H); LC-MS retention time 3.15 min LC-MS, Method A, ESI MS [M+H]$^+$ for C$_{28}$H$_{28}$N$_9$O$_3$, calcd 538.2, found 538.4.

The title compound was synthesized in a similar fashion to example 250. $^1$H NMR (400 MHz, Acetone-d6) δ 8.66 (brs, 1H), 8.63 (brs, 1H), 8.54 (d, J=8.0 Hz, 1H), 7.98-7.88 (m, 1H), 7.90 (s, 1H), 7.74 (dd, J=8.0, 8.0 Hz, 1H), 7.55 (dd, J=8.0, 8.0 Hz, 1H), 6.77 (s, 1H), 6.66 (d, J=8.0 Hz, 1H), 6.50 (d, J=8.0 Hz, 1H), 5.62 (s, 2H), 5.58 (s, 1H), 4.49 (dd, J=8.6, 3.1 Hz, 1H), 3.61-3.39 (m, 2H), 3.05-2.92 (m, 1H), 2.34-2.01 (m, 4H), 0.90-0.75 (m, 2H), 0.69-0.57 (m, 2H). MS [M+H]$^+$ for C$_{27}$H$_{25}$N9O$_2$, calcd 508.2, found 508.4.

Example 274: (R)-1-[6-({4-[6-(m-Cyanophenyl)-2-(cyclopropylamino)-4-pyrimidinyl]-1H-1,2,3-triazol-1-yl}methyl)-2-pyridyl]-2-pyrrolidinecarboxylic acid

Example 272: (S)-1-{6-[(4-{2-[(R)-Tetrahydrofur-3-ylamino]-6-(m-cyanophenyl)-4-pyrimidinyl}-1H-1,2,3-triazol-1-yl)methyl]-2-pyridyl}-2-pyrrolidinecarboxylic acid

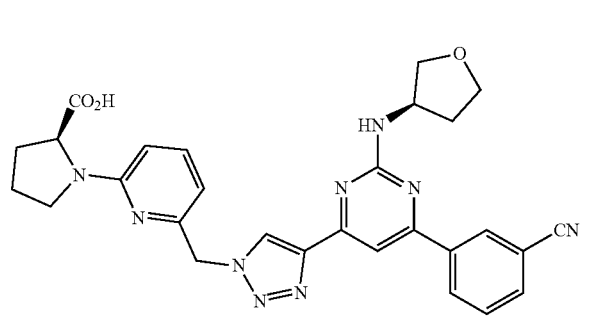

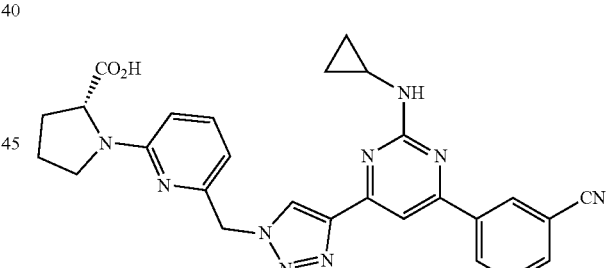

The title compound was synthesized in a similar fashion to example 250. $^1$H NMR (400 MHz, CD$_3$OD) δ 10.42 (s, 1H), 10.16 (s, 1H), 10.07 (d, J=8.0 Hz, 1H), 9.47 (s, 1H), 9.43-9.34 (m, 1H), 9.25 (t, J=7.8 Hz, 1H), 8.99 (t, J=7.9 Hz, 1H), 8.07 (d, J=7.1 Hz, 1H), 7.94 (d, J=8.5 Hz, 1H), 7.11 (s, 2H), 6.29 (s, 1H), 5.79 (s, 1H), 5.71-5.63 (m, 1H), 5.58 (q, J=7.6 Hz, 1H), 5.46 (q, J=7.6 Hz, 1H), 5.33 (dd, J=9.0, 3.9 Hz, 1H), 5.29-5.17 (m, 1H), 5.11-4.97 (m, 1H), 4.00-3.76 (m, 2H), 3.76-3.41 (m, 4H); LC-MS retention time 3.15 min LC-MS, Method A, ESI MS [M+H]$^+$ for C$_{28}$H$_{28}$N$_9$O$_3$, calcd 538.2, found 538.3.

The title compound was synthesized in a similar fashion to example 250. $^1$H NMR (400 MHz, Acetone-d$_6$) δ 8.67 (s 1H), 8.64 (s, 1H), 8.56 (d, J=8.0 Hz, 1H), 7.95-7.93 (m, 1H), 7.92 (s, 1H), 7.76 (dd, J=8.0, 8.0 Hz, 1H), 7.56 (dd, J=8.5, 7.2 Hz, 1H), 6.78 (s, 1H), 6.67 (d, J=7.2 Hz, 1H), 6.51 (d, J=8.5 Hz, 1H), 5.63 (s, 2H), 5.59 (s, 1H), 4.54-4.46 (m, 1H), 3.60-3.51 (m, 2H), 3.46 (q, J=8.0 Hz, 1H), 3.31 (d, J=0.9 Hz, 1H), 3.05-2.94 (m, 1H), 2.35-2.12 (m, 3H), 0.88-0.78 (m, 2H), 0.68-0.59 (m, 2H). MS [M+H]$^+$ for C$_{27}$H$_{25}$N9O$_2$, calcd 508.2, found 508.3.

Example 275: (S)-1-{6-[(4-{6-(m-Cyanophenyl)-2-[(cyclopropylmethyl)amino]-4-pyrimidinyl}-1H-1,2,3-triazol-1-yl)methyl]-2-pyridyl}-2-pyrrolidinecarboxylic acid

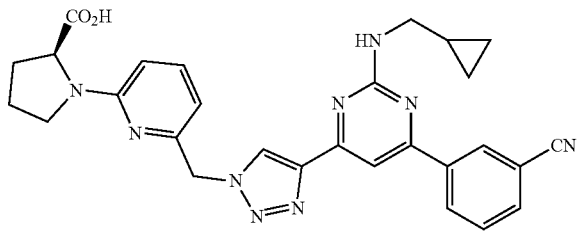 [SMILES: N#Cc1cccc(-c2cc(-c3cn(Cc4cccc(N5CCC[C@H]5C(=O)O)n4)nn3)nc(NCC3CC3)n2)c1]

The title compound was synthesized in a similar fashion to example 250. $^1$H NMR (400 MHz, CD$_3$OD) δ 8.69 (s, 1H), 8.53 (s, 1H), 8.45 (d, J=7.9 Hz, 1H), 7.85 (d, J=7.7 Hz, 1H), 7.76 (s, 1H), 7.72-7.64 (m, 1H), 7.59-7.45 (m, 1H), 6.65 (d, J=7.2 Hz, 1H), 6.49 (d, J=8.4 Hz, 1H), 5.55 (s, 2H), 4.47 (d, J=8.6 Hz, 1H), 3.58 (s, 1H), 3.51-3.36 (m, 2H), 2.39-2.22 (m, 1H), 2.20-1.95 (m, 3H), 1.37-1.10 (m, 2H), 0.57-0.49 (m, 2H), 0.37-0.28 (m, 2H); LC-MS retention time 3.50 min LC-MS, Method A, ESI MS [M+H]$^+$ for C$_{28}$H$_{28}$N$_9$O$_2$, calcd 522.2, found 522.3.

Example 276: (S)-1-[6-({4-[6-(m-Cyanophenyl)-2-(isopropylamino)-4-pyrimidinyl]-1H-1,2,3-triazol-1-yl}methyl)-2-pyridyl]-2-pyrrolidinecarboxylic acid

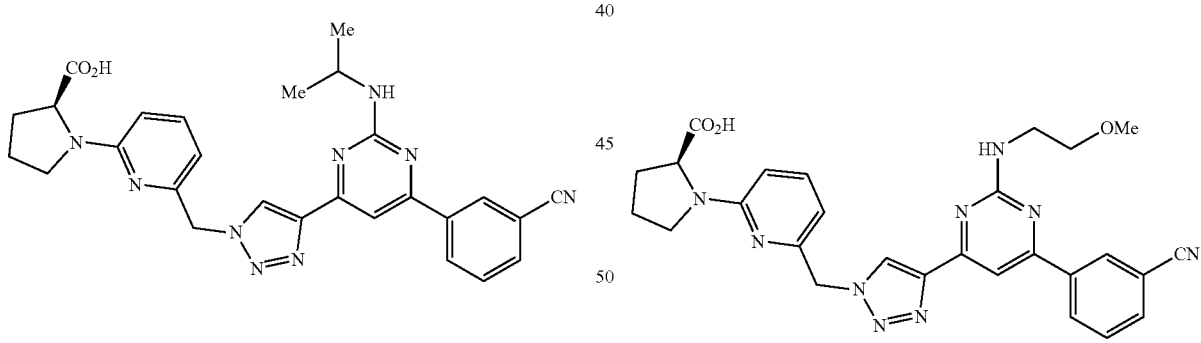

The title compound was synthesized in a similar fashion to example 250. $^1$H NMR (400 MHz, Acetone-d$_6$) δ 8.67 (brs, 1H), 8.61 (s, 1H), 8.53 (d, J=7.7 Hz, 1H), 7.92 (d, J=7.7 Hz, 1H), 7.84 (s, 1H), 7.76 (dd, J=7.2, 7.2 Hz, 1H), 7.56 (dd, J=8.5, 8.5 Hz, 1H), 6.65 (d, J=7.2 Hz, 1H), 6.51 (d, J=8.5 Hz, 1H), 6.34 (s, 1H), 5.59 (s, 2H), 4.54-4.46 (m, 1H), 4.46-4.33 (m, 1H), 3.61-3.52 (m, 1H), 3.45 (q, J=8.2 Hz, 1H), 2.36-2.10 (m, 2H), 2.09-2.00 (m, 2H), 1.31 (d, J=6.5 Hz, 1H). MS [M+H]$^+$ for C$_{27}$H$_{27}$N$_9$O$_2$, calcd 510.2, found 510.3.

Example 277: (R)-1-[6-({4-[6-(m-Cyanophenyl)-2-(isopropylamino)-4-pyrimidinyl]-1H-1,2,3-triazol-1-yl}methyl)-2-pyridyl]-2-pyrrolidinecarboxylic acid

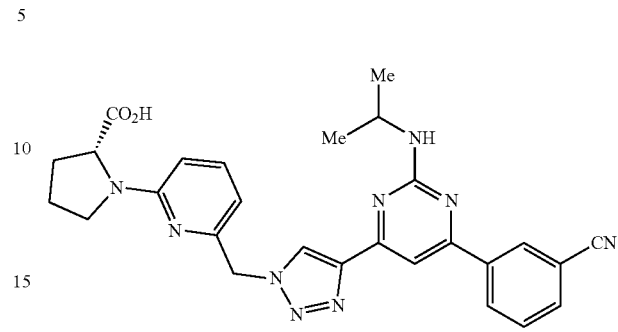

The title compound was synthesized in a similar fashion to example 250. $^1$H NMR (400 MHz, Acetone-d$_6$) δ 11.33 (s, 1H), 8.67 (s, 1H), 8.61 (s, 1H), 8.52 (d, J=8.0 Hz, 1H), 7.92 (d, J=7.8 Hz, 1H), 7.84 (s, 1H), 7.75 (dd, J=7.8, 7.8 Hz, 1H), 7.56 (dd, J=7.8, 7.8 Hz, 1H), 6.65 (d, J=7.2 Hz, 1H), 6.50 (d, J=8.5 Hz, 1H), 6.34 (brs, 1H), 5.59 (s, 2H), 4.54-4.46 (m, 1H), 4.46-4.33 (m, 1H), 3.62-3.38 (m, 2H), 2.33-2.14 (m, 2H), 2.14-2.01 (m, 2H), 1.31 (d, J=6.6 Hz, 6H). ESI MS [M+H]$^+$ for C$_{27}$H$_{27}$N$_9$O$_2$, calcd 510.6, found 510.4.

Example 278: (S)-1-[6-({4-[6-(m-Cyanophenyl)-2-(2-methoxyethylamino)-4-pyrimidinyl]-1H-1,2,3-triazol-1-yl}methyl)-2-pyridyl]-2-pyrrolidinecarboxylic acid The title compound was synthesized in a similar fashion to example 250. $^1$H NMR (400 MHz, DMSO-d$_6$) δ 8.78 (s, 1H), 8.61 (s, 1H), 8.55-8.44 (m, 1H), 8.00 (d, J=7.4 Hz, 1H), 7.88-7.79 (m, 1H), 7.75 (dd, J=8.0, 8.0 Hz, 1H), 7.55 (s, 1H), 7.59-7.49 (m, 1H), 6.55-6.38 (m, 2H), 5.62 (s, 2H), 4.47-4.34 (m, 1H), 3.67-3.34 (m, 7H), 3.28 (s, 3H), 2.30-1.89 (m, 2H). MS [M+H]$^+$ for C$_{27}$H$_{27}$N$_9$O$_3$, calcd 526.2, found 526.3.

Example 279: (R)-1-[6-({4-[6-(m-Cyanophenyl)-2-(2-methoxyethylamino)-4-pyrimidinyl]-1H-1,2,3-triazol-1-yl}methyl)-2-pyridyl]-2-pyrrolidinecarboxylic acid

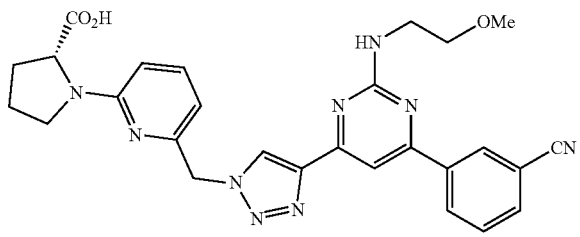

The title compound was synthesized in a similar fashion to example 250. $^1$H NMR (400 MHz, Acetone-$d_6$) δ 11.54 (brs, 1H), 8.69 (s, 1H), 8.63 (s, 1H), 8.54 (d, J=8.0 Hz, 1H), 7.96-7.89 (m, 1H), 7.87 (s, 1H), 7.76 (dd, J=8.0, 8.0 Hz, 1H), 7.56 (dd, J=8.5, 7.2 Hz, 1H), 6.66 (d, J=7.2 Hz, 1H), 6.51 (d, J=8.5 Hz, 1H), 5.59 (s, 2H), 4.51 (d, J=7.4 Hz, 1H), 3.76 (q, J=5.6 Hz, 2H), 3.64 (dd, J=5.6, 5.6 Hz, 2H), 3.59-3.51 (m, 1H), 3.51-3.41 (m, 1H), 3.35 (s, 3H), 2.37-2.10 (m, 2H), 2.10-2.01 (m, 2H). MS [M+H]$^+$ for $C_{27}H_{27}N_9O_3$, calcd 526.2, found 526.4.

Example 280: 3-{6-[(4-{2-[(R)-Tetrahydrofur-3-ylamino]-6-(m-cyanophenyl)-4-pyrimidinyl}-1H-1,2,3-triazol-1-yl)methyl]-2-pyridyl}propionic acid

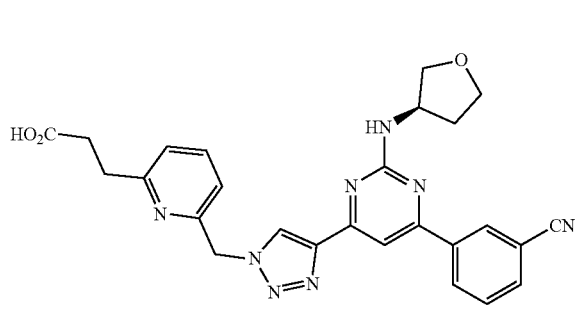

The title compound was synthesized in a similar fashion to example 250. $^1$H NMR (400 MHz, Acetone-$d_6$) δ 8.62 (s, 1H), 8.54 (d, J=7.9 Hz, 1H), 7.93 (dq, J=7.7 Hz, 1H), 7.90 (s, 1H), 7.82-7.71 (m, 2H), 7.30 (d, J=7.9 Hz, 1H), 7.21 (d, J=7.7 Hz, 1H), 6.75 (brs, 1H), 5.80 (s, 2H), 4.72 (brs, 1H), 4.11-4.03 (m, 1H), 3.95 (q, J=7.6 Hz, 1H), 3.86-3.68 (m, 2H), 3.09 (t, J=7.3 Hz, 2H), 2.77 (t, J=7.3 Hz, 2H), 2.41-2.29 (m, 1H), 2.07-1.99 (m, 2H). MS [M+H]$^+$ for $C_{26}H_{24}N_8O_3$, calcd 497.2, found 497.3.

Example 281: 3-{6-[(4-{2-[(S)-Tetrahydrofur-3-ylamino]-6-(m-cyanophenyl)-4-pyrimidinyl}-1H-1,2,3-triazol-1-yl)methyl]-2-pyridyl}butyric acid

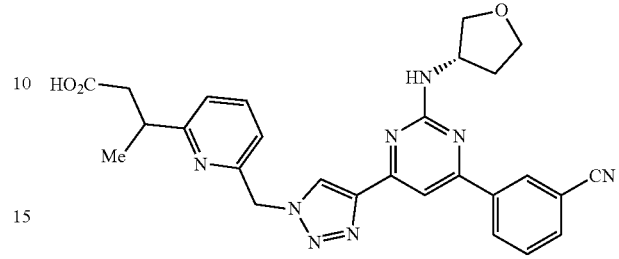

The title compound was synthesized in a similar fashion to example 250. $^1$H NMR (400 MHz, Acetone-$d_6$) δ 10.66 (brs, 1H), 8.72 (brs, 1H), 8.61 (s, 1H), 8.54 (d, J=7.8 Hz, 1H), 7.93 (d, J=7.8 Hz, 1H), 7.90 (s, 1H), 7.77 (dd, J=7.8, 7.8 Hz, 1H), 7.31 (d, J=7.8 Hz, 1H), 7.21 (d, J=7.8 Hz, 1H), 6.74 (s, 1H), 5.81 (s, 2H), 4.69 (s, 1H), 4.11-3.90 (m, 3H), 3.86-3.67 (m, 2H), 3.46-3.34 (m, 1H), 2.87 (dd, J=16.0, 7.6 Hz, 1H), 2.59 (dd, J=16.0, 6.8 Hz, 1H), 2.41-2.27 (m, 1H), 2.11-1.92 (m, 1H), 1.29 (d, J=6.9 Hz, 3H). MS [M+H]$^+$ for $C_{27}H_{26}N_8O_3$, calcd 511.2, found 511.4.

Example 282: 3-{6-[(4-{2-[(R)-Tetrahydrofur-3-ylamino]-6-(m-cyanophenyl)-4-pyrimidinyl}-1H-1,2,3-triazol-1-yl)methyl]-2-pyridyl}butyric acid

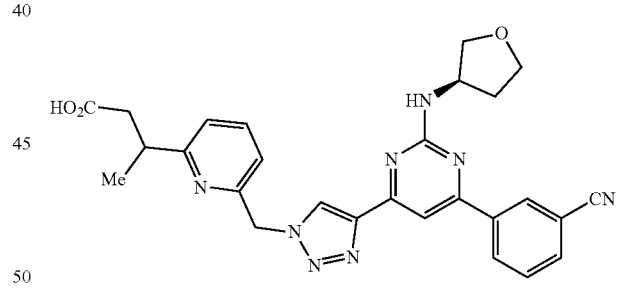

The title compound was synthesized in a similar fashion to example 250. $^1$H NMR (400 MHz, Acetone-$d_6$) δ 10.70 (brs, 1H), 8.72 (brs, 1H), 8.61 (s, 1H), 8.54 (d, J=7.8 Hz, 1H), 7.93 (d, J=7.8 Hz, 1H), 7.90 (s, 1H), 7.77 (dd, J=7.8, 7.8 Hz, 1H), 7.31 (d, J=7.8 Hz, 1H), 7.21 (d, J=7.8 Hz, 1H), 6.74 (s, 1H), 5.81 (s, 2H), 4.69 (s, 1H), 4.11-3.90 (m, 3H), 3.86-3.67 (m, 2H), 3.46-3.34 (m, 1H), 2.87 (dd, J=16.0, 7.6 Hz, 1H), 2.59 (dd, J=16.0, 6.8 Hz, 1H), 2.41-2.27 (m, 1H), 2.11-1.92 (m, 1H), 1.29 (d, J=6.9 Hz, 3H). MS [M+H]$^+$ for $C_{27}H_{26}N_8O_3$, calcd 511.2, found 511.3.

Example 283: 3-[6-({4-[6-(m-Cyanophenyl)-2-(2-methoxyethylamino)-4-pyrimidinyl]-1H-1,2,3-triazol-1-yl}methyl)-2-pyridyl]-3-methylbutyric acid

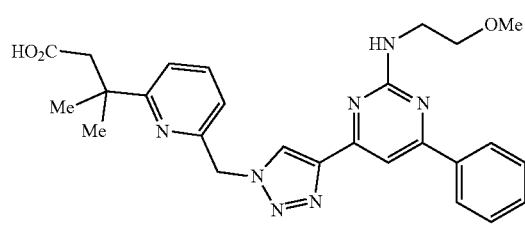

The title compound was synthesized in a similar fashion to example 250. $^1$H NMR (400 MHz, Acetone-d$_6$) δ 8.63 (s, 1H), 8.56 (s, 1H), 7.94 (d, J=8.0 Hz, 1H), 7.88 (s, 1H), 7.83-7.73 (m, 2H), 7.45 (d, J=8.0 Hz, 1H), 7.22 (d, J=8.0 Hz, 1H), 6.47 (brs, 1H), 5.82 (s, 2H), 5.62 (s, 1H), 3.82-3.59 (m, 4H), 3.34 (s, 3H), 2.80 (s, 2H), 1.95 (s, 6H). MS [M+H]$^+$ for C$_{27}$H$_{28}$N$_8$O$_3$, calcd 513.2, found 513.4.

Example 284: 3-{6-[(4-{2-[(S)-2-Methoxy-1-methylethylamino]-6-(m-cyanophenyl)-4-pyrimidinyl}-1H-1,2,3-triazol-1-yl)methyl]-2-pyridyl}-3-methylbutyric acid

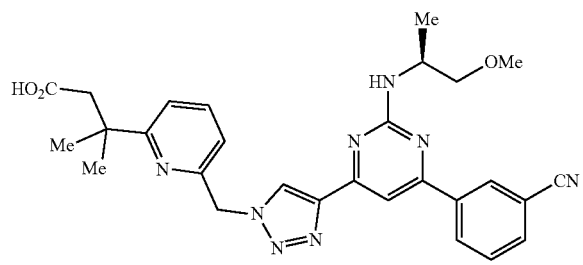

The title compound was synthesized in a similar fashion to example 250. $^1$H NMR (400 MHz, Acetone-d$_6$) δ 10.70 (brs, 1H), 8.66 (s, 1H), 8.61 (s, 1H), 8.53 (d, J=8.0 Hz, 1H), 7.92 (d, J=8.0 Hz, 1H), 7.86 (s, 1H), 7.82-7.70 (m, 1H), 7.45 (d, J=8.0 Hz, 1H), 7.22 (d, J=7.6 Hz, 1H), 6.31 (s, 1H), 5.81 (s, 2H), 4.56-4.41 (m, 1H), 3.56 (dd, J=11.4, 6.1 Hz, 1H), 3.45 (dd, J=11.4, 5.8 Hz, 1H), 3.35 (s, 3H), 2.81 (s, 2H), 1.44 (s, 6H), 1.29 (d, J=6.7 Hz, 3H). MS [M+H]$^+$ for C$_{28}$H$_{30}$N$_8$O$_3$, calcd 427.2, found 427.4.

Example 285: 3-{6-[(4-{2-[(R)-2-Methoxy-1-methylethylamino]-6-(m-cyanophenyl)-4-pyrimidinyl}-1H-1,2,3-triazol-1-yl)methyl]-2-pyridyl}-3-methylbutyric acid

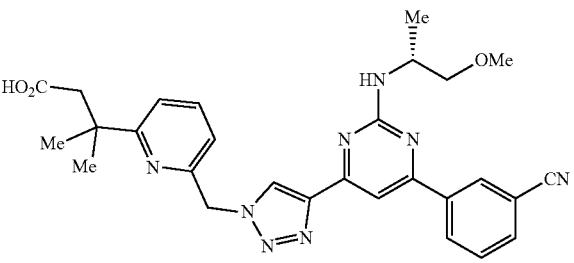

The title compound was synthesized in a similar fashion to example 250. $^1$H NMR (400 MHz, Acetone-d$_6$) δ 8.66 (s, 1H), 8.61 (s, 1H), 8.53 (d, J=8.0 Hz, 1H), 7.92 (d, J=8.0 Hz, 1H), 7.86 (s, 1H), 7.82-7.70 (m, 1H), 7.45 (d, J=8.0 Hz, 1H), 7.22 (d, J=7.6 Hz, 1H), 6.31 (s, 1H), 5.81 (s, 2H), 4.56-4.41 (m, 1H), 3.56 (dd, J=11.4, 6.1 Hz, 1H), 3.45 (dd, J=11.4, 5.8 Hz, 1H), 3.35 (s, 3H), 2.81 (s, 2H), 1.44 (s, 6H), 1.29 (d, J=6.7 Hz, 3H). MS [M+H]$^+$ for C$_{28}$H$_{30}$N$_8$O$_3$, calcd 427.2, found 427.3.

Example 286: (4-{6-[(4-{2-[(R)-Tetrahydrofur-3-ylamino]-6-(m-cyanophenyl)-4-pyrimidinyl}-1H-1,2,3-triazol-1-yl)methyl]-2-pyridyl}-1-piperidyl)acetic acid

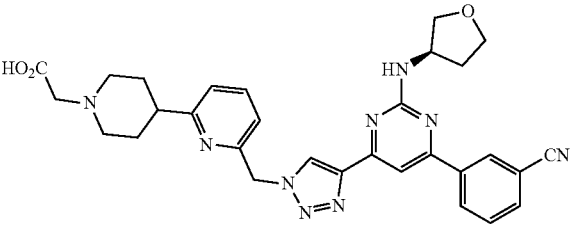 [SMILES: N#Cc1cccc(-c2cc(-c3cn(Cc4cccc(C5CCN(CC(=O)O)CC5)n4)nn3)nc(N[C@@H]3CCOC3)n2)c1]

The title compound was synthesized in a similar fashion to example 250. $^1$H NMR (400 MHz, CD$_3$OD) δ 8.63 (s, 1H), 8.42 (s, 1H), 8.36 (d, J=8.0 Hz, 1H), 7.77 (dd, J=8.0, 8.0 Hz, 1H), 7.71 (s, 1H), 7.62 (dd, J=8.0 Hz, 1H), 7.28 (dd, J=8.0, 8.0 Hz, 2H), 5.78 (s, 2H), 4.62 (brs, 1H), 4.11-3.93 (m, 2H), 3.92-3.81 (m, 1H), 3.78-3.64 (m, 4H), 3.62 (s, 2H), 3.21-2.97 (m, 3H), 2.39-2.25 (m, 1H), 2.17-2.08 (m, 1H), 2.17-1.93 (m, 4H). MS [M+H]$^+$ for C$_{30}$H$_{31}$N$_9$O$_3$, calcd 566.3, found 566.4.

Example 287: (4-{6-[(4-{2-[(R)-2-Methoxy-1-methylethylamino]-6-(m-cyanophenyl)-4-pyrimidinyl}-1H-1,2,3-triazol-1-yl)methyl]-2-pyridyl}-1-piperidyl)acetic acid

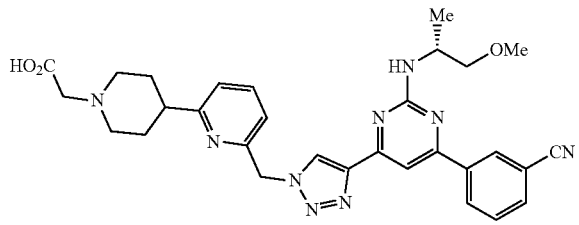

The title compound was synthesized in a similar fashion to example 250. ¹H NMR (400 MHz, CD₃OD) δ 8.64 (s, 1H), 8.47 (s, 1H), 8.40 (d, J=7.9 Hz, 1H), 7.86-7.73 (m, 2H), 7.73 (s, 1H), 7.76-7.62 (m, 1H), 7.66 (dd, J=8.0, 8.0 Hz, 1H), 5.79 (s, 2H), 4.50-4.38 (m, 1H), 3.73-3.49 (m, 4H), 3.45 (dd, J=7.4, 5.4 Hz, 1H), 3.39 (s, 2H), 3.34 (s, 3H), 3.21-2.98 (m, 3H), 2.21-2.05 (m, 4H), 1.29 (d, J=6.7 Hz, 3H). MS [M+H]⁺ for $C_{30}H_{33}N_9O_3$, calcd 568.3, found 568.4.

Example 288: 2-{6-[(4-{2-[(R)-Tetrahydrofur-3-ylamino]-6-(m-cyanophenyl)-4-pyrimidinyl}-1H-1,2,3-triazol-1-yl)methyl]-2-pyridyl}cyclopentanecarboxylic acid

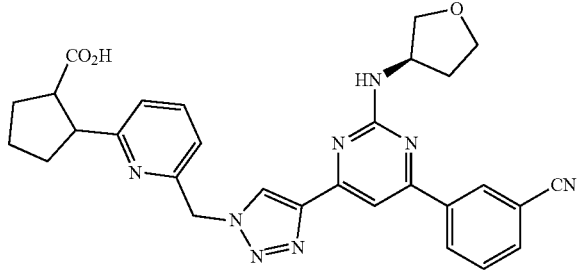 [SMILES: N#Cc1cccc(-c2cc(-c3cn(Cc4cccc(C5CCCC5C(=O)O)n4)nn3)nc(N[C@@H]3CCOC3)n2)c1]

The title compound was synthesized in a similar fashion to example 250. ¹H NMR (400 MHz, CD₃OD) δ 8.73-8.71 (m, 1H), 8.58 (s, 1H), 8.47-8.41 (m, 1H), 7.87-7.85 (m, 1H), 7.82-7.80 (m, 1H), 7.74-7.68 (m, 2H), 7.27-7.20 (m, 2H), 5.79 (s, 1H), 5.74 (s, 1H), 4.77-4.69 (m, 1H), 4.13-4.01 (m, 1H), 4.04-3.98 (m, 1H), 3.91-3.86 (m, 1H), 3.76 (dd, J=8.9, 3.9 Hz, 1H), 3.64-3.59 (m, 0.5H), 3.51-3.47 (m, 0.5H), 3.26-3.21 (m, 0.5H), 3.14-3.08 (m, 0.5H), 2.41-2.31 (m, 1H), 2.19-1.65 (m, 8H). ESI MS [M+H]⁺ for $C_{29}H_{28}N_8O_3$, calcd 537.2, found 537.3.

Example 289: m-[6-(1-{[6-(Methoxymethyl)-2-pyridyl]methyl}-1H-1,2,3-triazol-4-yl)-2-(1-pyrrolidinyl)-4-pyrimidinyl]benzonitrile

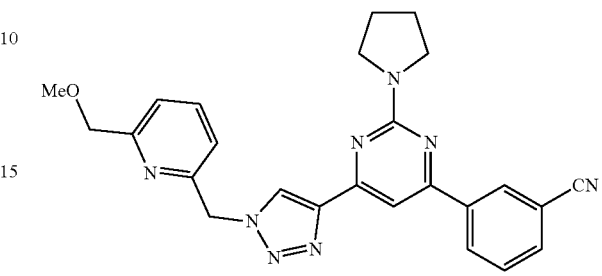

The title compound was synthesized in a similar fashion to example 250. ¹H NMR (400 MHz, CDCl₃) δ 8.57-8.50 (m, 1H), 8.40-8.29 (m, 2H), 7.78 (s, 1H), 7.76-7.66 (m, 2H), 7.62-7.54 (m, 1H), 7.40 (d, J=7.8 Hz, 1H), 7.11 (d, J=7.4 Hz, 1H), 5.73 (s, 2H), 4.59 (s, 2H), 3.69 (m, 4H), 3.50 (s, 3H), 2.03 (s, 4H). ESI MS [M+H]⁺ for $C_{25}H_{24}N_8O$, calcd 453.2, found 453.3.

Example 290: m-{2-[(Cyclopropylmethyl)amino]-6-(1-{[6-(methoxymethyl)-2-pyridyl]methyl}-1H-1,2,3-triazol-4-yl)-4-pyrimidinyl}benzonitrile

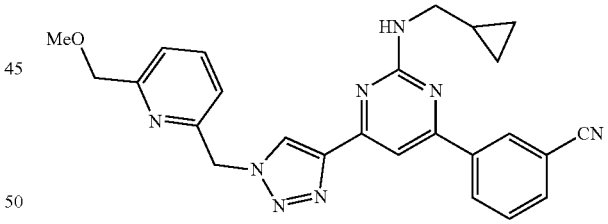

The title compound was synthesized in a similar fashion to example 250. ¹H NMR (400 MHz, DMSO-d₆) δ 8.77 (s, 1H), 8.59 (s, 1H), 8.48 (d, J=8.1 Hz, 1H), 7.99 (dt, J=7.6, 1.3 Hz, 1H), 7.85 (t, J=7.7 Hz, 1H), 7.79 (s, 1H), 7.74 (t, J=7.8 Hz, 1H), 7.38 (d, J=7.8 Hz, 1H), 7.22 (d, J=7.8 Hz, 1H), 5.82 (s, 2H), 4.45 (s, 2H), 3.33 (s, 3H), 3.30 (d, J=7.1 Hz, 2H), 3.16-3.13 (m, 1H), 1.13 (s, 1H), 0.49-0.35 (m, 2H), 0.26 (dd, J=5.8, 4.3 Hz, 2H); LC-MS retention time 3.48 min LC-MS, Method A, ESI MS [M+H]⁺ for $C_{25}H_{25}N_8O$, calcd 453.2, found 453.2.

Example 291: m-[2-(Cyclopentylamino)-6-(1-{[6-(methoxymethyl)-2-pyridyl]methyl}-1H-1,2,3-triazol-4-yl)-4-pyrimidinyl]benzonitrile

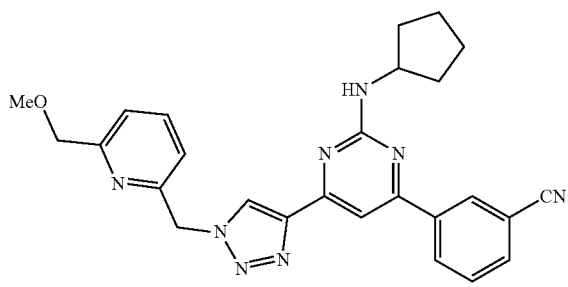 [SMILES: COCc1cccc(Cn2cc(-c3cc(-c4cccc(C#N)c4)nc(NC4CCCC4)n3)nn2)n1]

The title compound was synthesized in a similar fashion to example 250. $^1$H NMR (400 MHz, CDCl$_3$) δ 8.48 (s, 1H), 8.36-8.26 (m, 2H), 7.81 (d, J=3.9 Hz, 1H), 7.78-7.66 (m, 2H), 7.59 (td, J=7.8, 3.4 Hz, 1H), 7.44-7.36 (m, 1H), 7.14-7.08 (m, 1H), 5.73 (s, 2H), 5.30-5.11 (m, 1H), 4.59 (s, 2H), 4.41 (m, 1H), 3.50 (s, 3H), 2.19-2.03 (m, 2H), 1.83-1.63 (m, 4H), 1.62-1.40 (m, 2H). ESI MS [M+H]$^+$ for C$_{26}$H$_{26}$N$_8$O, calcd 467.2, found 467.3.

Example 292: m-[2-(2-Hydroxy-2-methylpropylamino)-6-(1-{[6-(methoxymethyl)-2-pyridyl]methyl}-1H-1,2,3-triazol-4-yl)-4-pyrimidinyl]benzonitrile

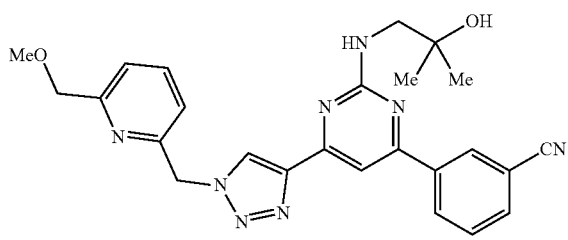

The title compound was synthesized in a similar fashion to example 250. $^1$H NMR (400 MHz, CDCl$_3$) δ 8.39 (s, 1H), 8.33 (s, 1H), 8.27 (dd, J=8.0, 1.1 Hz, 1H), 7.82 (s, 1H), 7.75-7.65 (m, 2H), 7.56 (t, J=7.8 Hz, 1H), 7.39 (d, J=7.7 Hz, 1H), 7.08 (d, J=7.7 Hz, 1H), 5.77 (s, 1H), 5.70 (s, 2H), 4.57 (s, 2H), 3.53 (d, J=5.3 Hz, 2H), 3.46 (s, 3H), 1.29 (s, 6H). ESI MS [M+H]$^+$ for C$_{25}$H$_{26}$N$_8$O$_2$, calcd 471.2, found 471.3.

Example 293: m-[2-(2-Methoxyethylamino)-6-(1-{[6-(methoxymethyl)-2-pyridyl]methyl}-1H-1,2,3-triazol-4-yl)-4-pyrimidinyl]benzonitrile

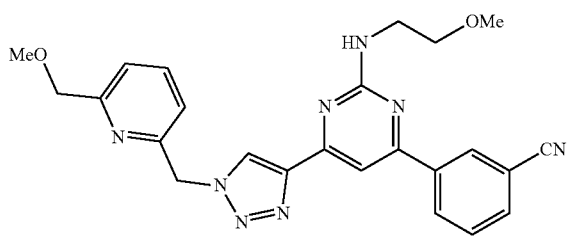

The title compound was synthesized in a similar fashion to example 250. $^1$H NMR (400 MHz, CDCl$_3$) δ 8.46 (s, 1H), 8.34-8.26 (m, 2H), 7.82 (s, 1H), 7.76-7.65 (m, 2H), 7.57 (t, J=7.8 Hz, 1H), 7.40 (d, J=7.7 Hz, 1H), 7.10 (d, J=7.5 Hz, 1H), 5.71 (s, 2H), 5.58 (t, J=5.7 Hz, 1H), 4.57 (s, 2H), 3.73 (q, J=5.3 Hz, 2H), 3.65-3.56 (m, 2H), 3.48 (s, 3H), 3.39 (s, 3H). ESI MS [M+H]$^+$ for C$_{24}$H$_{24}$N$_8$O$_2$, calcd 457.2, found 457.3.

Example 294: m-{2-[(S)-Tetrahydrofur-3-ylamino]-6-(1-{[6-(methoxymethyl)-2-pyridyl]methyl}-1H-1,2,3-triazol-4-yl)-4-pyrimidinyl}benzonitrile


The title compound was synthesized in a similar fashion to example 250. $^1$H NMR (400 MHz, CDCl$_3$) δ 8.47 (s, 1H), 8.36-8.26 (m, 2H), 7.87 (s, 1H), 7.79-7.67 (m, 2H), 7.64-7.54 (m, 1H), 7.41 (d, J=7.8 Hz, 1H), 7.13 (d, J=7.7 Hz, 1H), 5.73 (s, 2H), 5.38 (d, J=7.1 Hz, 1H), 4.74 (s, 1H), 4.59 (s, 2H), 4.10-3.97 (m, 2H), 3.90 (td, J=8.4, 5.5 Hz, 1H), 3.77 (dd, J=9.3, 3.5 Hz, 1H), 3.50 (s, 3H), 2.38 (m, 1H), 1.94 (m, 1H). ESI MS [M+H]$^+$ for C$_{25}$H$_{24}$N$_8$O$_2$, calcd 469.2, found 469.3.

Example 295: m-{2-[(R)-Tetrahydrofur-3-ylamino]-6-(1-{[6-(methoxymethyl)-2-pyridyl]methyl}-1H-1,2,3-triazol-4-yl)-4-pyrimidinyl}benzonitrile

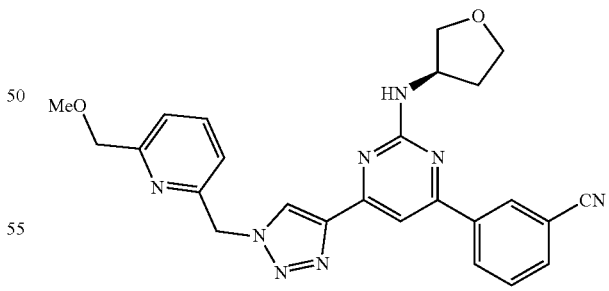

The title compound was synthesized in a similar fashion to example 250. $^1$H NMR (400 MHz, CDCl$_3$) δ 8.49-8.42 (m, 1H), 8.35-8.26 (m, 2H), 7.89-7.84 (m, 1H), 7.77-7.68 (m, 2H), 7.63-7.53 (m, 1H), 7.40 (d, J=7.7 Hz, 1H), 7.12 (d, J=8.2 Hz, 1H), 5.72 (s, 2H), 5.41 (s, 1H), 4.74 (m, 1H), 4.58 (s, 2H), 4.10-3.95 (m, 2H), 3.90 (m, 1H), 3.82-3.71 (m, 1H), 3.48 (m, 1H), 2.37 (m, 1H), 1.94 (m, 1H). ESI MS [M+H]$^+$ for C$_{25}$H$_{24}$N$_8$O$_2$, calcd 469.2, found 469.3.

Example 296: m-[2-(4-Hydroxycyclohexylamino)-6-(1-{[6-(methoxymethyl)-2-pyridyl]methyl}-1H-1,2,3-triazol-4-yl)-4-pyrimidinyl]benzonitrile

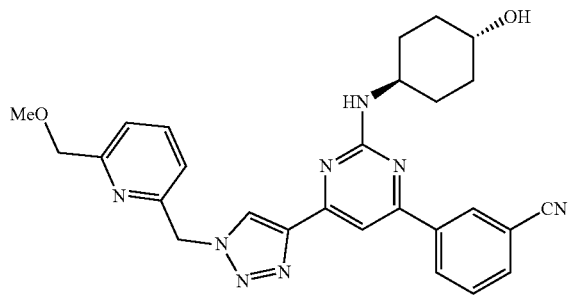 [SMILES: COCc1cccc(Cn2cc(-c3cc(-c4cccc(C#N)c4)nc(N[C@H]4CC[C@H](O)CC4)n3)nn2)n1]

The title compound was synthesized in a similar fashion to example 250. ¹H NMR (400 MHz, CDCl₃) δ 8.46-8.40 (m, 1H), 8.30 (d, J=5.0 Hz, 2H), 7.80 (s, 1H), 7.76-7.66 (m, 2H), 7.61-7.54 (m, 1H), 7.43-7.36 (m, 1H), 7.11 (d, J=7.8 Hz, 1H), 5.72 (s, 2H), 5.14 (d, J=7.8 Hz, 1H), 4.57 (s, 2H), 4.02-3.87 (m, 1H), 3.70 (m, 1H), 3.48 (s, 3H), 2.25-2.11 (m, 2H), 2.10-1.96 (m, 2H), 1.57-1.43 (m, 2H), 1.40-1.26 (m, 2H). ESI MS [M+H]⁺ for $C_{27}H_{28}N_8O_2$, calcd 497.3, found 497.3.

Example 297: m-{2-[(1R,2R)-2-Methoxycyclopentylamino]-6-(1-{[6-(methoxymethyl)-2-pyridyl]methyl}-1H-1,2,3-triazol-4-yl)-4-pyrimidinyl}benzonitrile

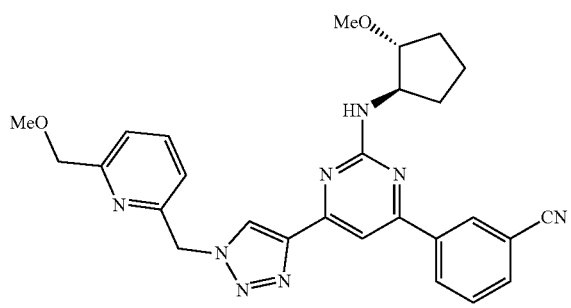 [SMILES: COCc1cccc(Cn2cc(-c3cc(-c4cccc(C#N)c4)nc(N[C@@H]4CCC[C@H]4OC)n3)nn2)n1]

The title compound was synthesized in a similar fashion to example 250. ¹H NMR (400 MHz, CDCl₃) δ 8.47 (s, 1H), 8.32 (d, J=8.2 Hz, 1H), 8.28 (s, 1H), 7.83 (s, 1H), 7.77-7.66 (m, 2H), 7.61-7.53 (m, 1H), 7.43-7.37 (m, 1H), 7.11 (d, J=7.7 Hz, 1H), 5.72 (s, 2H), 5.29-5.13 (m, 1H), 4.57 (s, 2H), 4.46-4.30 (m, 1H), 3.73 (m, 1H), 3.48 (s, 3H), 3.41 (s, 3H), 2.27 (m, 1H), 1.94 (m, 1H), 1.88-1.65 (m, 3H), 1.60-1.44 (m, 1H). ESI MS [M+H]⁺ for $C_{27}H_{28}N_8O_2$, calcd 497.3, found 497.3.

Example 298: m-{2-[(R)-Tetrahydrofur-3-ylamino]-6-(1-{[6-(1-methoxyethyl)-2-pyridyl]methyl}-1H-1,2,3-triazol-4-yl)-4-pyrimidinyl}benzonitrile

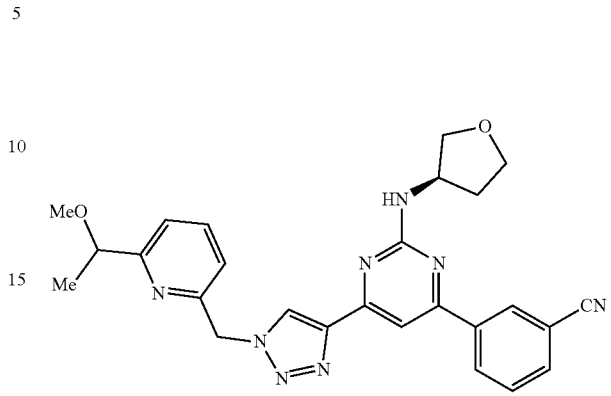

The title compound was synthesized in a similar fashion to example 250. ¹H NMR (400 MHz, CDCl₃) δ 8.45 (s, 1H), 8.32 (m, 2H), 7.87 (s, 1H), 7.76-7.68 (m, 2H), 7.62-7.55 (m, 1H), 7.41-7.36 (m, 1H), 7.10 (d, J=7.7 Hz, 1H), 5.73 (s, 2H), 5.40 (d, J=7.0 Hz, 1H), 4.72 (s, 1H), 4.49-4.37 (m, 1H), 4.07-3.98 (m, 2H), 3.94-3.85 (m, 1H), 3.76 (dd, J=9.3, 3.4 Hz, 1H), 3.32 (s, 3H), 2.45-2.27 (m, 1H), 1.94 (dddd, J=13.0, 7.4, 5.7, 4.0 Hz, 1H), 1.46 (d, J=6.5 Hz, 3H). ESI MS [M+H]⁺ for $C_{26}H_{26}N_8O_2$, calcd 483.2, found 483.3.

Example 299: m-[2-(2-Hydroxyethylamino)-6-(1-{[6-(1-methoxyethyl)-2-pyridyl]methyl}-1H-1,2,3-triazol-4-yl)-4-pyrimidinyl]benzonitrile

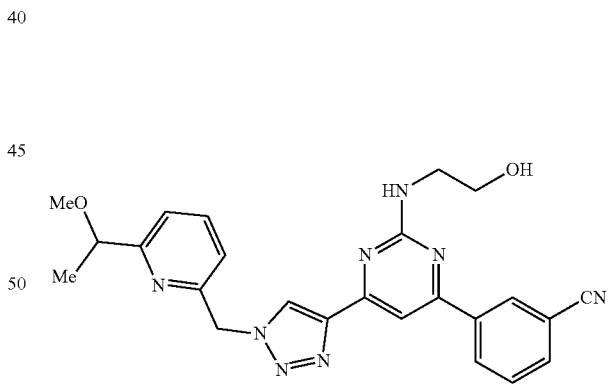

The title compound was synthesized in a similar fashion to example 250. ¹H NMR (400 MHz, CDCl₃) δ 8.41 (s, 1H), 8.35 (s, 1H), 8.31-8.23 (m, 1H), 7.84 (s, 1H), 7.76-7.64 (m, 2H), 7.57 (m, 1H), 7.39 (d, J=7.6 Hz, 1H), 7.08 (d, J=7.7 Hz, 1H), 5.72 (m, 3H), 4.48-4.35 (m, 1H), 3.88 (m, 2H), 3.78-3.63 (m, 2H), 3.32 (s, 3H), 1.45 (d, J=6.6 Hz, 3H). ESI MS [M+H]⁺ for $C_{24}H_{24}N_8O_2$, calcd 457.2, found 457.3.

Example 300: m-{2-[(1R,2R)-2-Hydroxycyclopentylamino]-6-(1-{[6-(1-methoxyethyl)-2-pyridyl]methyl}-1H-1,2,3-triazol-4-yl)-4-pyrimidinyl}benzonitrile

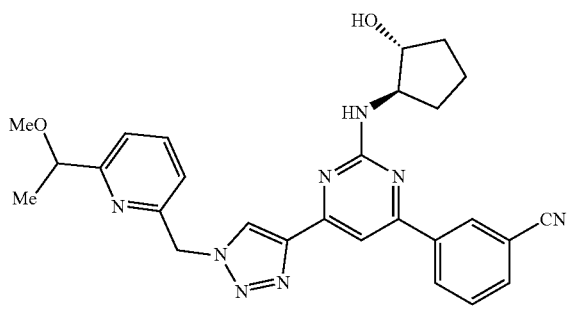 [SMILES: COC(C)c1cccc(Cn2cc(-c3cc(-c4cccc(C#N)c4)nc(N[C@@H]4CCC[C@H]4O)n3)nn2)n1]

The title compound was synthesized in a similar fashion to example 250. ¹H NMR (400 MHz, CDCl₃) δ 8.36 (m, 2H), 8.27 (d, J=8.0 Hz, 1H), 7.86 (s, 1H), 7.75 (dd, J=7.7, 1.4 Hz, 1H), 7.69 (t, J=7.8 Hz, 1H), 7.60 (t, J=7.8 Hz, 1H), 7.39 (d, J=7.8 Hz, 1H), 7.08-7.00 (m, 1H), 5.72 (s, 2H), 5.49 (s, 1H), 4.43 (m, 1H), 4.18-4.06 (m, 1H), 4.00 (s, 1H), 3.32 (s, 3H), 2.26 (m, 1H), 2.12 (m, 1H), 1.94-1.68 (m, 3H), 1.61 (m, 1H), 1.46 (d, J=6.6 Hz, 6H). ESI MS [M+H]⁺ for $C_{27}H_{28}N_8O_2$, calcd 497.2, found 497.3.

Example 301: m-[6-(1-{[6-(1-Methoxyethyl)-2-pyridyl]methyl}-1H-1,2,3-triazol-4-yl)-2-(2-methoxy-1-phenylethylamino)-4-pyrimidinyl]benzonitrile

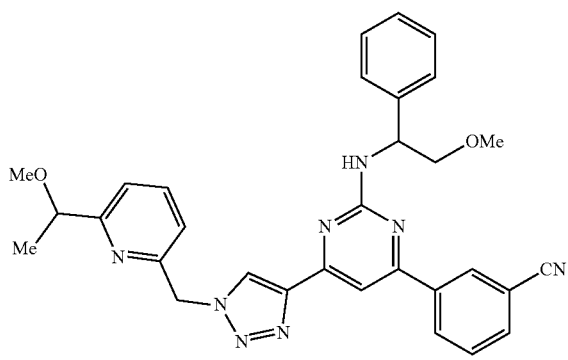 [SMILES: COCC(Nc1nc(-c2cccc(C#N)c2)cc(-c2cn(Cc3cccc(C(C)OC)n3)nn2)n1)c1ccccc1]

The title compound was synthesized in a similar fashion to example 250. ¹H NMR (400 MHz, CDCl₃) δ 8.17 (s, 2H), 7.80 (s, 1H), 7.74-7.61 (m, 2H), 7.52 (m, 1H), 7.45 (d, J=7.4 Hz, 3H), 7.42-7.38 (m, 1H), 7.37-7.31 (m, 2H), 7.29-7.22 (m, 1H), 7.06 (d, J=7.6 Hz, 1H), 6.06 (d, J=5.9 Hz, 1H), 5.70 (s, 2H), 5.25 (m, 1H), 4.43 (q, J=6.4 Hz, 1H), 3.80-3.62 (m, 2H), 3.40 (s, 3H), 3.33 (s, 3H), 1.48 (d, J=5.6 Hz, 1H). ESI MS [M+H]⁺ for $C_{31}H_{30}N_8O_2$, calcd 547.3, found 547.3.

Example 302: m-[2-(2-Methoxyethylamino)-6-(1-{[6-(1-methoxyethyl)-2-pyridyl]methyl}-1H-1,2,3-triazol-4-yl)-4-pyrimidinyl]benzonitrile

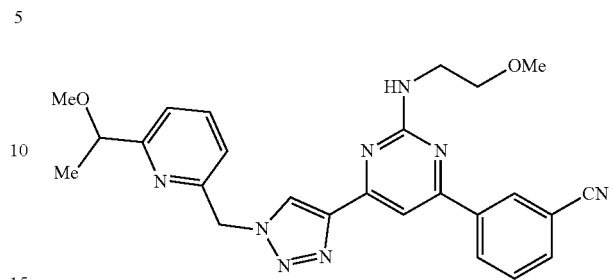

The title compound was synthesized in a similar fashion to example 250. ¹H NMR (400 MHz, CDCl₃) δ 8.47 (d, J=1.6 Hz, 1H), 8.31 (d, J=7.9 Hz, 2H), 7.83 (d, J=1.4 Hz, 1H), 7.75-7.67 (m, 2H), 7.61-7.52 (m, 1H), 7.39 (d, J=7.8 Hz, 1H), 7.08 (d, J=7.8 Hz, 1H), 5.72 (s, 2H), 5.57 (t, J=5.7 Hz, 1H), 4.43 (m, 1H), 3.73 (t, J=5.2 Hz, 2H), 3.61 (t, J=5.3 Hz, 2H), 3.39 (s, 3H), 3.32 (s, 3H), 1.46 (d, J=6.6 Hz, 3H). ESI MS [M+H]⁺ for $C_{25}H_{26}N_8O_2$, calcd 471.2, found 471.3.

Example 303: m-[6-(1-{[6-(1-Methoxyethyl)-2-pyridyl]methyl}-1H-1,2,3-triazol-4-yl)-2-(2-phenoxyethylamino)-4-pyrimidinyl]benzonitrile

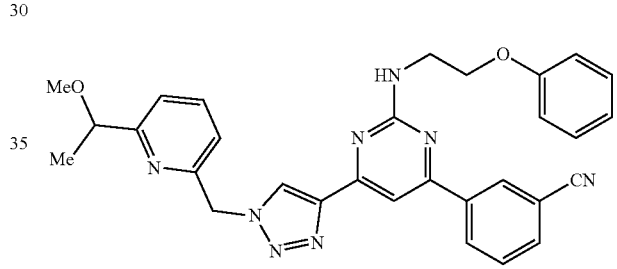

The title compound was synthesized in a similar fashion to example 250. ¹H NMR (400 MHz, DMSO-d₆) δ 8.79 (s, 1H), 8.61 (s, 1H), 8.49 (d, J=8.0 Hz, 1H), 8.04-7.96 (m, 1H), 7.91-7.81 (m, 2H), 7.75 (t, J=7.8 Hz, 1H), 7.39 (d, J=7.8 Hz, 1H), 7.31-7.23 (m, 2H), 7.20 (d, J=7.7 Hz, 1H), 6.97 (d, J=8.8 Hz, 2H), 6.91 (t, J=7.3, 1.1 Hz, 1H), 5.85 (s, 2H), 4.34 (q, J=6.5 Hz, 1H), 4.20 (t, J=6.0 Hz, 2H), 3.82 (s, 2H), 3.19 (s, 3H), 1.32 (d, J=6.5 Hz, 3H). ESI MS [M+H]⁺ for $C_{30}H_{29}N_8O_2$, calcd 533.2, found 533.3.

Example 304: m-[2-(Dimethylamino)-6-(1-{[6-(1-hydroxycyclopentyl)-2-pyridyl]methyl}-1H-1,2,3-triazol-4-yl)-4-pyrimidinyl]benzonitrile

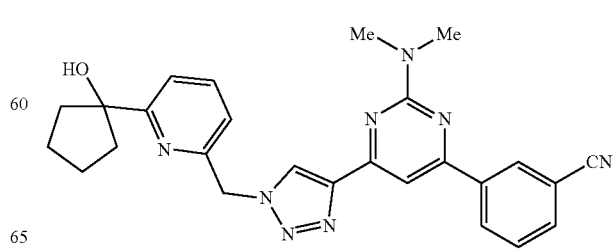

The title compound was synthesized in a similar fashion to example 250. ¹H NMR (400 MHz, CDCl₃) δ 8.53 (s, 1H), 8.42-8.31 (m, 2H), 7.78 (s, 1H), 7.77-7.68 (m, 2H), 7.59 (dd, J=8.0 Hz, 1H), 7.39 (d, J=8.0 Hz, 1H), 7.11 (d, J=8.0 Hz, 1H), 5.76 (s, 2H), 4.55 (s, 1H), 3.30 (m, 6H), 2.14-1.81 (m, 8H). MS [M+H]⁺ for $C_{26}H_{26}N_8O$, calcd 467.2, found 467.3.

Example 305: m-[2-(Cyclopropylamino)-6-(1-{[6-(1-hydroxycyclopentyl)-2-pyridyl]methyl}-1H-1,2,3-triazol-4-yl)-4-pyrimidinyl]benzonitrile

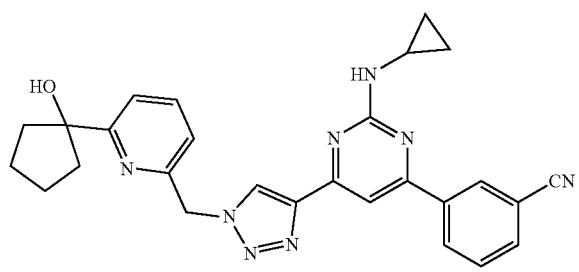

The title compound was synthesized in a similar fashion to example 250. ¹H NMR (400 MHz, CDCl₃) δ 8.51 (s, 1H), 8.35 (d, J=8.0 Hz, 1H), 8.32 (s, 1H), 7.89 (s, 1H), 7.77-7.72 (m, 1H), 7.71 (dd, J=7.6 Hz, 1H) 7.59 (dd, J=7.6 Hz, 1H), 7.38 (d, J=8.0 Hz, 1H), 7.11 (d, J=7.6 Hz, 1H), 5.75 (s, 2H), 5.42 (s, 1H), 4.60 (s, 1H), 2.90 (p, J=7.9 Hz, 1H), 2.07-1.80 (m, 8H), 0.97-0.76 (m, 2H), 0.63-0.57 (m, 2H). MS [M+H]⁺ for $C_{27}H_{26}N_8O$, calcd 479.2, found 479.3.

Example 306: m-[6-(1-{[6-(1-Hydroxycyclopentyl)-2-pyridyl]methyl}-1H-1,2,3-triazol-4-yl)-2-(1-pyrrolidinyl)-4-pyrimidinyl]benzonitrile

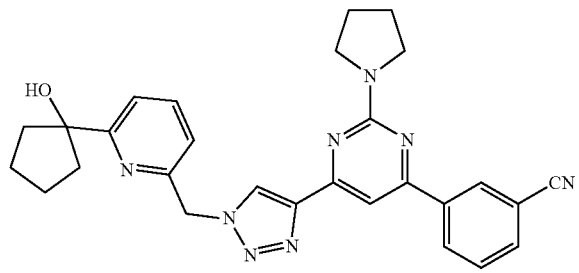

The title compound was synthesized in a similar fashion to example 250. ¹H NMR (400 MHz, CDCl₃) δ 8.57-8.52 (m, 1H), 8.38-8.30 (m, 2H), 7.78 (s, 1H), 7.76-7.67 (m, 2H), 7.62-7.55 (m, 1H), 7.38 (d, J=7.9 Hz, 1H), 7.10 (d, J=7.6 Hz, 1H), 5.75 (s, 2H), 4.56 (s, 1H), 3.69 (m, 4H), 2.08-1.74 (m, 12H). ESI MS [M+H]⁺ for $C_{28}H_{28}N_8O$, calcd 493.2, found 493.3.

Example 307: m-[2-(Cyclopentylamino)-6-(1-{[6-(1-hydroxycyclopentyl)-2-pyridyl]methyl}-1H-1,2,3-triazol-4-yl)-4-pyrimidinyl]benzonitrile

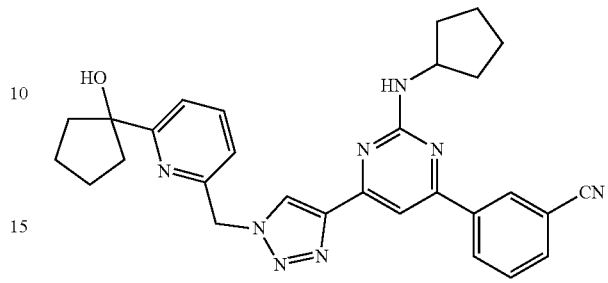

The title compound was synthesized in a similar fashion to example 250. ¹H NMR (400 MHz, CDCl₃) δ 8.48 (s, 1H), 8.36-8.25 (m, 2H), 7.81 (s, 1H), 7.77-7.68 (m, 2H), 7.64-7.53 (m, 1H), 7.38 (d, J=7.9 Hz, 1H), 7.11 (d, J=7.6 Hz, 1H), 5.75 (s, 2H), 5.21 (d, J=7.2 Hz, 1H), 4.59 (s, 1H), 4.42 (m, 1H), 2.18-2.07 (m, 2H), 2.07-1.92 (m, 4H), 1.87 (m, 6H), 1.73 (m, 2H), 1.54 (m, 2H). ESI MS [M+H]⁺ for $C_{29}H_{30}N_8O$, calcd 507.3, found 507.3.

Example 308: m-[6-(1-{[6-(1-Hydroxycyclopentyl)-2-pyridyl]methyl}-1H-1,2,3-triazol-4-yl)-2-(tetrahydro-2H-pyran-4-ylamino)-4-pyrimidinyl]benzonitrile

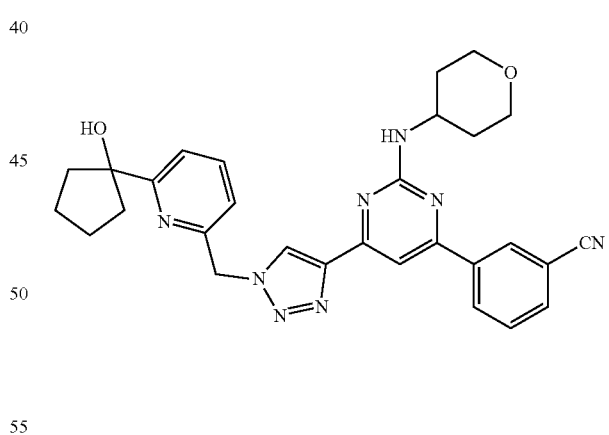

The title compound was synthesized in a similar fashion to example 250. ¹H NMR (400 MHz, DMSO-d₆) δ 8.75 (s, 1H), 8.63-8.54 (m, 1H), 8.52-8.42 (m, 1H), 8.04-7.91 (m, 1H), 7.85-7.69 (m, 3H), 7.64 (t, J=6.7 Hz, 1H), 7.20-7.05 (m, 1H), 5.85-5.79 (m, 2H), 5.77-5.70 (m, 1H), 4.16-4.00 (m, 1H), 3.94-3.81 (m, 2H), 3.43 (s, 2H), 2.05-1.49 (m, 12H), 1.22 (d, J=5.0 Hz, 1H); LC-MS retention time 3.03 min LC-MS, Method A, ESI MS [M+H]⁺ for $C_{29}H_{31}N_8O_2$, calcd 523.3, found 523.3.

Example 309: m-[6-(1-{[6-(1-Hydroxycyclopentyl)-2-pyridyl]methyl}-1H-1,2,3-triazol-4-yl)-2-(2-hydroxy-2-methylpropylamino)-4-pyrimidinyl]benzonitrile

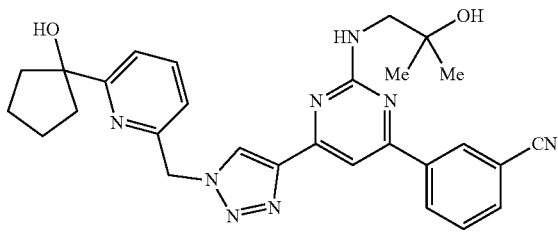 [SMILES: CC(C)(O)CNc1nc(-c2cccc(C#N)c2)cc(-c2cn(Cc3cccc(C4(O)CCCC4)n3)nn2)n1]

The title compound was synthesized in a similar fashion to example 250. $^1$H NMR (400 MHz, CDCl$_3$) δ 8.43-8.33 (m, 2H), 8.31-8.22 (m, 1H), 7.83 (s, 1H), 7.75-7.64 (m, 2H), 7.56 (dd, J=8.3, 7.3 Hz, 1H), 7.36 (d, J=8.0 Hz, 1H), 7.09 (d, J=7.6 Hz, 1H), 5.76 (s, 1H), 5.72 (s, 2H), 4.63 (s, 1H), 3.53 (d, J=6.1 Hz, 2H), 2.02-1.75 (m, 8H), 1.29 (s, 6H). ESI MS [M+H]$^+$ for C$_{28}$H$_{30}$N$_8$O$_2$, calcd 511.3, found 511.3.

Example 310: m-[6-(1-{[6-(1-Hydroxycyclopentyl)-2-pyridyl]methyl}-1H-1,2,3-triazol-4-yl)-2-(2-methoxyethylamino)-4-pyrimidinyl]benzonitrile

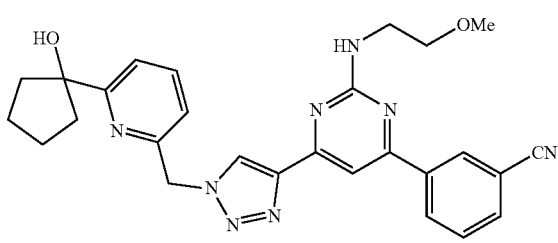 [SMILES: COCCNc1nc(-c2cccc(C#N)c2)cc(-c2cn(Cc3cccc(C4(O)CCCC4)n3)nn2)n1]

The title compound was synthesized in a similar fashion to example 250. $^1$H NMR (400 MHz, CDCl$_3$) δ 8.46 (s, 1H), 8.36-8.27 (m, 2H), 7.82 (s, 1H), 7.75-7.65 (m, 2H), 7.60-7.52 (m, 1H), 7.38 (d, J=8.0 Hz, 1H), 7.09 (d, J=7.6 Hz, 1H), 5.73 (s, 2H), 5.59 (t, J=5.7 Hz, 1H), 4.60 (s, 1H), 3.73 (m, 2H), 3.66-3.55 (m, 2H), 3.39 (s, 3H), 2.10-1.73 (m, 8H). ESI MS [M+H]$^+$ for C$_{24}$H$_{28}$N$_8$O$_2$, calcd 597.2, found 597.2.

Example 311: m-{2-[(S)-Tetrahydrofur-3-ylamino]-6-(1-{[6-(1-hydroxycyclopentyl)-2-pyridyl]methyl}-1H-1,2,3-triazol-4-yl)-4-pyrimidinyl}benzonitrile

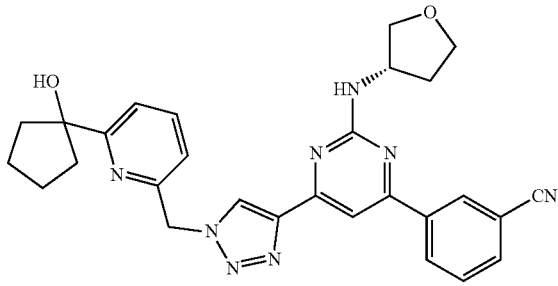 [SMILES: N#Cc1cccc(-c2cc(-c3cn(Cc4cccc(C5(O)CCCC5)n4)nn3)nc(N[C@H]3CCOC3)n2)c1]

The title compound was synthesized in a similar fashion to example 250. $^1$H NMR (400 MHz, CDCl$_3$) δ 8.44 (s, 1H), 8.31 (d, J=9.7 Hz, 2H), 7.86 (s, 1H), 7.78-7.66 (m, 2H), 7.58 (dd, J=8.5, 7.2 Hz, 1H), 7.38 (d, J=7.9 Hz, 1H), 7.11 (d, J=7.6 Hz, 1H), 5.74 (s, 2H), 5.43 (d, J=7.1 Hz, 1H), 4.72 (m, 1H), 4.59 (s, 1H), 4.07-3.95 (m, 2H), 3.89 (ddd, J=9.9, 7.8, 5.8 Hz, 1H), 3.76 (dd, J=9.3, 3.4 Hz, 1H), 2.43-2.26 (m, 1H), 2.01-1.76 (m, 9H). ESI MS [M+H]$^+$ for C$_{28}$H$_{28}$N$_8$O$_2$, calcd 509.2, found 509.2.

Example 312: m-{2-[(R)-Tetrahydrofur-3-ylamino]-6-(1-{[6-(1-hydroxycyclopentyl)-2-pyridyl]methyl}-1H-1,2,3-triazol-4-yl)-4-pyrimidinyl}benzonitrile

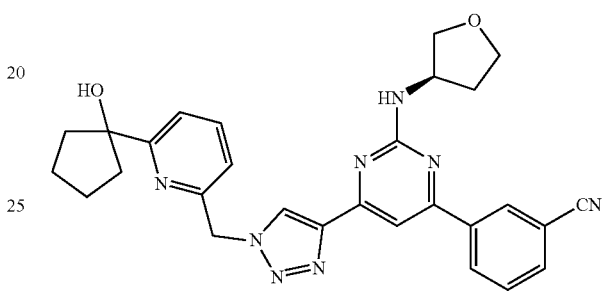

The title compound was synthesized in a similar fashion to example 250. $^1$H NMR (400 MHz, CDCl$_3$) δ 8.45 (s, 1H), 8.34-8.24 (m, 2H), 7.85 (s, 1H), 7.78-7.66 (m, 2H), 7.62-7.54 (m, 1H), 7.38 (d, J=8.0 Hz, 1H), 7.11 (d, J=7.7 Hz, 1H), 5.74 (s, 2H), 5.55-5.33 (m, 1H), 4.73 (s, 1H), 4.60 (s, 1H), 4.09-3.95 (m, 2H), 3.89 (m, 1H), 3.76 (dd, J=9.3, 3.5 Hz, 1H), 2.44-2.28 (m, 1H), 2.08-1.76 (m, 9H). ESI MS [M+H]$^+$ for C$_{28}$H$_{28}$N$_8$O$_2$, calcd 509.2, found 509.3.

Example 313: m-[2-(4-Hydroxycyclohexylamino)-6-(1-{[6-(1-hydroxycyclopentyl)-2-pyridyl]methyl}-1H-1,2,3-triazol-4-yl)-4-pyrimidinyl]benzonitrile

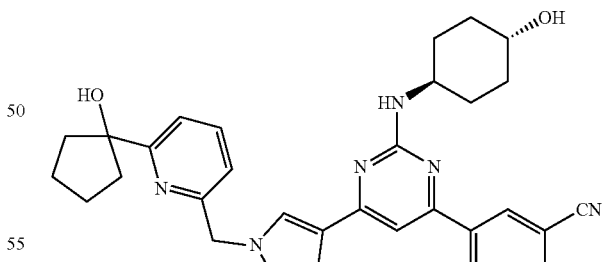

The title compound was synthesized in a similar fashion to example 250. $^1$H NMR (400 MHz, CDCl$_3$) δ 8.44 (s, 1H), 8.30 (m, 2H), 7.81 (s, 1H), 7.77-7.67 (m, 2H), 7.63-7.55 (m, 1H), 7.42-7.34 (m, 1H), 7.12 (d, J=7.6 Hz, 1H), 5.75 (s, 2H), 5.10 (d, J=7.9 Hz, 1H), 4.62 (s, 1H), 3.96 (m, 1H), 3.76-3.63 (m, 1H), 2.20 (s, 1H), 2.11-1.26 (m, 16H). ESI MS [M+H]$^+$ for C$_{30}$H$_{32}$N$_8$O$_2$, calcd 537.3, found 537.3.

Example 314: m-{2-[(1R,2R)-2-Methoxycyclopentylamino]-6-(1-{[6-(1-hydroxycyclopentyl)-2-pyridyl]methyl}-1H-1,2,3-triazol-4-yl)-4-pyrimidinyl}benzonitrile

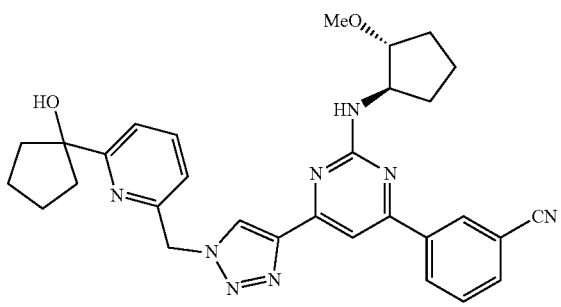 [SMILES: CO[C@@H]1CCC[C@H]1Nc1nc(-c2cccc(C#N)c2)cc(-c2cn(Cc3cccc(C4(O)CCCC4)n3)nn2)n1]

The title compound was synthesized in a similar fashion to example 250. $^1$H NMR (400 MHz, CDCl$_3$) δ 8.48 (s, 1H), 8.33 (d, J=8.0 Hz, 1H), 8.30-8.23 (m, 1H), 7.84 (s, 1H), 7.77-7.67 (m, 2H), 7.58 (t, J=7.8 Hz, 1H), 7.38 (d, J=8.0 Hz, 1H), 7.11 (d, J=7.6 Hz, 1H), 5.75 (s, 2H), 5.21 (d, J=7.2 Hz, 1H), 4.60 (s, 1H), 4.47-4.31 (m, 1H), 3.73 (dt, J=6.5, 3.5 Hz, 1H), 3.41 (s, 3H), 2.35-2.17 (m, 1H), 2.08-1.65 (m, 12H), 1.54 (m, 1H). ESI MS [M+H]$^+$ for C$_{30}$H$_{32}$N$_8$O$_2$, calcd 537.3, found 537.4.

Example 315: m-{2-[(1R,2R)-2-Hydroxycyclopentylamino]-6-(1-{[6-(1-hydroxycyclopentyl)-2-pyridyl]methyl}-1H-1,2,3-triazol-4-yl)-4-pyrimidinyl}benzonitrile

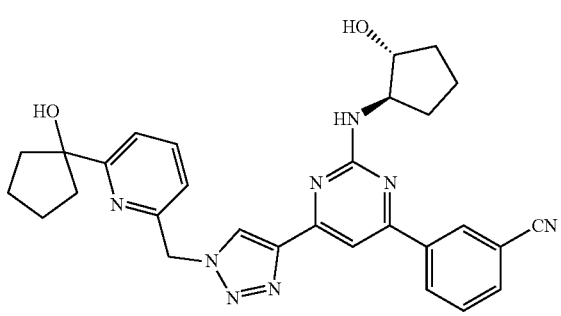 [SMILES: N#Cc1cccc(-c2cc(-c3cn(Cc4cccc(C5(O)CCCC5)n4)nn3)nc(N[C@@H]3CCC[C@H]3O)n2)c1]

The title compound was synthesized in a similar fashion to example 250. $^1$H NMR (400 MHz, CDCl$_3$) δ 8.43 (m, 2H), 8.26 (d, J=7.7 Hz, 1H), 7.84 (s, 1H), 7.77-7.72 (m, 1H), 7.72-7.65 (m, 1H), 7.62-7.55 (m, 1H), 7.41-7.33 (m, 1H), 7.11 (d, J=7.6 Hz, 1H), 6.38 (s, 1H), 5.72 (s, 2H), 5.53 (m, 1H), 4.66 (m, 1H), 3.98 (s, 1H), 2.34-2.21 (m, 2H), 2.12 (m, 2H), 2.04-1.68 (m, 8H), 1.61 (m, 2H). ESI MS [M+H]$^+$ for C$_{29}$H$_{30}$N$_8$O$_2$, calcd 523.3, found 523.4.

Example 316: m-[6-(1-{[6-(1-Hydroxycyclopentyl)-2-pyridyl]methyl}-1H-1,2,3-triazol-4-yl)-2-(2-hydroxyethylamino)-4-pyrimidinyl]benzonitrile

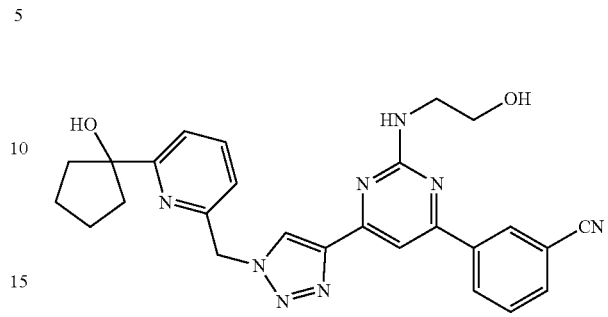

The title compound was synthesized in a similar fashion to example 250. $^1$H NMR (400 MHz, CDCl$_3$) δ 8.48-8.38 (m, 2H), 8.35-8.26 (m, 1H), 7.87 (s, 1H), 7.80-7.68 (m, 2H), 7.60 (t, J=7.9 Hz, 1H), 7.38 (d, J=8.0 Hz, 1H), 7.13 (d, J=7.6 Hz, 1H), 5.75 (s, 2H), 5.68 (s, 1H), 3.89 (t, J=4.9 Hz, 2H), 3.72 (t, J=5.4 Hz, 2H), 2.01 (m, 4H), 1.88 (m, 2H), 1.61 (m, 2H). ESI MS [M+H]$^+$ for C$_{26}$H$_{26}$N$_8$O$_2$, calcd 483.2, found 483.3.

Example 317: (S)-1-{6-[(4-{2-[(S)-2-Methoxy-1-phenylethylamino]-6-(m-cyanophenyl)-4-pyrimidinyl}-1H-1,2,3-triazol-1-yl)methyl]-2-pyridyl}-3-pyrrolidinecarboxylic acid

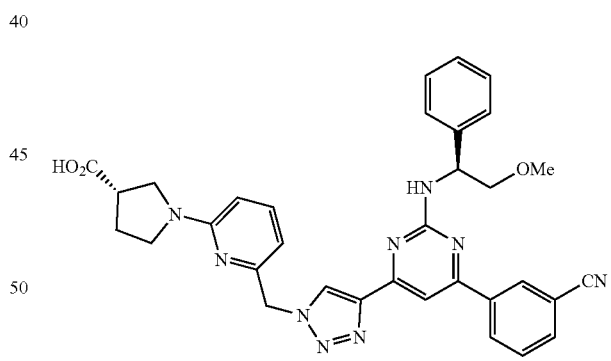

The title compound was synthesized in a similar fashion to example 250. $^1$H NMR (400 MHz, DMSO-d$_6$) δ 8.78-8.36 (m, 4H), 7.95 (s, 1H), 7.73 (d, J=19.9 Hz, 2H), 7.51 (m, 2H), 7.47-7.40 (m, 1H), 7.29 (m, 2H), 7.19 (s, 1H), 6.38 (s, 1H), 6.32 (dd, J=8.6, 3.3 Hz, 1H), 5.57 (s, 1H), 5.36 (s, 1H), 3.73 (s, 1H), 3.55 (m, 2H), 3.28 (m, 5H), 2.65 (s, 1H), 1.99 (m, 2H), 1.29-1.07 (m, 1H). ESI MS [M+H]$^+$ for C$_{33}$H$_{31}$N$_9$O$_3$, calcd 602.3, found 602.4.

Example 318: (S)-1-{6-[(4-{2-[(R)-2-Methoxy-1-phenylethylamino]-6-(m-cyanophenyl)-4-pyrimidinyl}-1H-1,2,3-triazol-1-yl)methyl]-2-pyridyl}-3-pyrrolidinecarboxylic acid

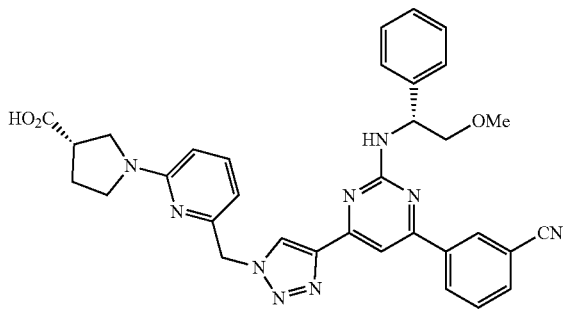 [SMILES: COC[C@H](Nc1nc(-c2cccc(C#N)c2)cc(-c2cn(Cc3cccc(N4CC[C@H](C(=O)O)C4)n3)nn2)n1)c1ccccc1]

The title compound was synthesized in a similar fashion to example 250. ¹H NMR (400 MHz, DMSO-d₆) δ 8.78-8.36 (m, 4H), 7.95 (s, 1H), 7.73 (d, J=19.9 Hz, 2H), 7.51 (m, 2H), 7.47-7.40 (m, 1H), 7.29 (m, 2H), 7.19 (s, 1H), 6.38 (s, 1H), 6.32 (dd, J=8.6, 3.3 Hz, 1H), 5.57 (s, 2H), 5.36 (s, 1H), 3.73 (s, 1H), 3.55 (m, 2H), 3.28 (m, 5H), 2.65 (s, 1H), 1.99 (m, 2H), 1.29-1.07 (m, 1H). ESI MS [M+H]⁺ for $C_{33}H_{31}N_9O_3$, calcd 602.3, found 602.4.

Example 319: 3-[6-({4-[6-(m-Cyanophenyl)-2-(isopropylamino)-4-pyrimidinyl]-1H-1,2,3-triazol-1-yl}methyl)-2-pyridyl]-3-methylbutyric acid

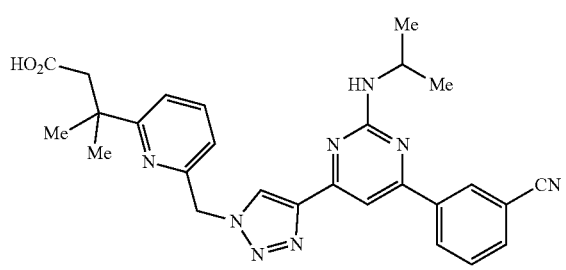 [SMILES: CC(C)Nc1nc(-c2cccc(C#N)c2)cc(-c2cn(Cc3cccc(C(C)(C)CC(=O)O)n3)nn2)n1]

The title compound was synthesized in a similar fashion to example 250. ¹H NMR (400 MHz, DMSO-d₆) δ 8.78 (s, 1H), 8.61 (s, 1H), 8.49 (d, J=8.0 Hz, 1H), 8.00 (d, J=7.8 Hz, 1H), 7.83-7.70 (m, 3H), 7.43-7.34 (m, 1H), 7.12 (d, J=7.6 Hz, 1H), 5.82 (s, 2H), 4.34-4.16 (m, 1H), 2.66 (s, 2H), 1.33 (s, 6H), 1.22 (d, J=6.3 Hz, 6H). ESI MS [M+H]⁺ for $C_{27}H_{28}N_8O_2$, calcd 497.2, found 497.4.

Example 320: 3-[6-({4-[6-(m-Cyanophenyl)-2-(cyclopropylamino)-4-pyrimidinyl]-1H-1,2,3-triazol-1-yl}methyl)-2-pyridyl]-3-methylbutyric acid

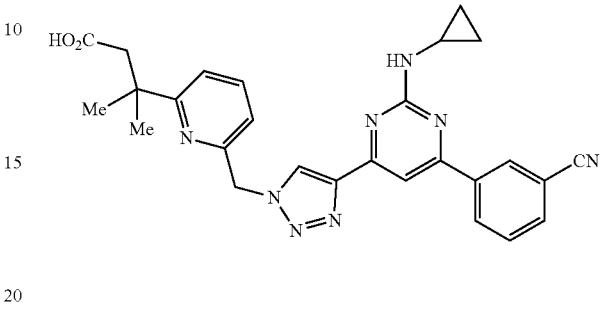

The title compound was synthesized in a similar fashion to example 250. ¹H NMR (400 MHz, DMSO-d₆) δ 8.84-8.68 (m, 1H), 8.63 (s, 1H), 8.57-8.47 (m, 1H), 8.00 (d, J=7.7 Hz, 1H), 7.86 (s, 1H), 7.80-7.72 (m, 2H), 7.65 (s, 1H), 7.39 (d, J=8.0 Hz, 1H), 7.11 (d, J=7.7 Hz, 1H), 5.82 (s, 2H), 2.95-2.87 (m, 1H), 2.66 (s, 2H), 1.33 (s, 6H), 0.77-0.70 (m, 2H), 0.59-0.52 (m, 2H). ESI MS [M+H]⁺ for $C_{27}H_{26}N_8O_2$, calcd 495.2, found 495.3.

Example 321: 3-{6-[(4-{2-[(R)-Tetrahydrofur-3-ylamino]-6-(m-cyanophenyl)-4-pyrimidinyl}-1H-1,2,3-triazol-1-yl)methyl]-2-pyridyl}-3-methylbutyric acid

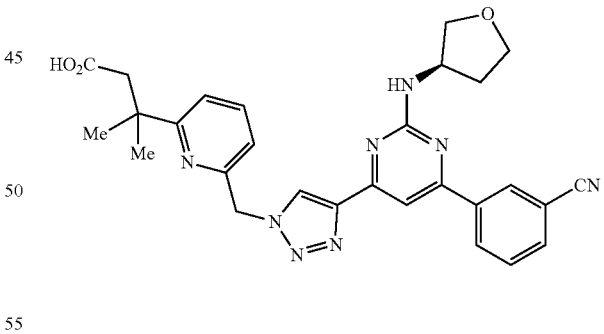

The title compound was synthesized in a similar fashion to example 250. ¹H NMR (400 MHz, DMSO-d₆) δ 8.62 (s, 1H), 8.50 (s, 1H), 8.01 (d, J=7.8 Hz, 1H), 7.85 (s, 1H), 7.80-7.72 (m, 2H), 7.39 (d, J=8.0 Hz, 1H), 7.11 (d, J=7.6 Hz, 1H), 5.82 (s, 2H), 4.56 (s, 1H), 4.01 (dd, J=8.8, 6.2 Hz, 1H), 3.87 (q, J=7.5 Hz, 1H), 3.80-3.71 (m, 1H), 3.67-3.55 (m, 1H), 2.66 (s, 2H), 2.29-2.16 (m, 1H), 2.05-1.90 (m, 1H), 1.33 (s, 6H). ESI MS [M+H]⁺ for $C_{28}H_{29}N_8O_3$, calcd 525.2, found 525.3.

Example 322: 3-{6-[(4-{2-[(S)-Tetrahydrofur-3-ylamino]-6-(m-cyanophenyl)-4-pyrimidinyl}-1H-1,2,3-triazol-1-yl)methyl]-2-pyridyl}-3-methylbutyric acid

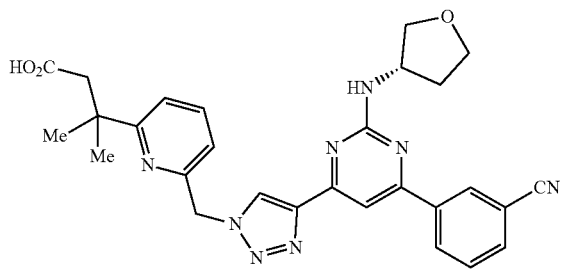 [SMILES: CC(C)(CC(=O)O)c1cccc(Cn2cc(-c3cc(-c4cccc(C#N)c4)nc(N[C@H]4CCOC4)n3)nn2)n1]

The title compound was synthesized in a similar fashion to example 250. $^1$H NMR (400 MHz, DMSO-$d_6$) δ 8.62 (s, 1H), 8.55-8.46 (m, 1H), 8.01 (d, J=6.5 Hz, 1H), 7.85 (s, 1H), 7.82-7.71 (m, 2H), 7.39 (d, J=7.9 Hz, 1H), 7.11 (d, J=7.6 Hz, 1H), 5.82 (s, 2H), 4.63-4.47 (m, 1H), 4.01 (dd, J=8.8, 6.2 Hz, 1H), 3.92-3.82 (m, 1H), 3.81-3.71 (m, 1H), 3.67-3.56 (m, 1H), 2.66 (s, 2H), 2.29-2.16 (m, 1H), 2.04-1.90 (m, 1H), 1.33 (s, 6H). ESI MS [M+H]$^+$ for $C_{28}H_{29}N_8O_3$, calcd 525.2, found 525.3.

Example 323: 3-[6-({4-[6-(m-Cyanophenyl)-2-{[(5-oxo-2-pyrrolidinyl)methyl]amino}-4-pyrimidinyl]-1H-1,2,3-triazol-1-yl}methyl)-2-pyridyl]-3-methylbutyric acid

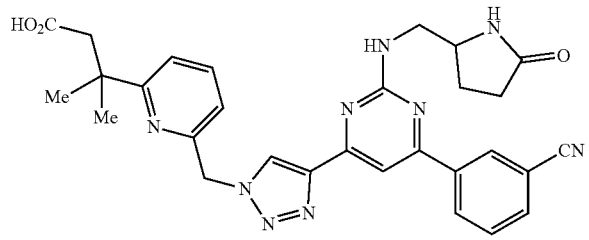 [SMILES: CC(C)(CC(=O)O)c1cccc(Cn2cc(-c3cc(-c4cccc(C#N)c4)nc(NCC4CCC(=O)N4)n3)nn2)n1]

The title compound was synthesized in a similar fashion to example 250. $^1$H NMR (400 MHz, DMSO-$d_6$) δ 8.79 (m, 1H), 8.60 (s, 1H), 8.49 (m, 3H), 7.99 (dd, J=7.7, 1.4 Hz, 1H), 7.82 (s, 1H), 7.74 (m, 2H), 7.50 (s, 1H), 7.36 (d, J=8.0 Hz, 1H), 7.06 (d, J=7.5 Hz, 1H), 5.79 (s, 2H), 3.63 (m, 3H), 2.68-2.60 (m, 2H), 2.24-2.02 (m, 3H), 1.82 (m, 1H), 1.37-1.24 (s, 6H). ESI MS [M+H]$^+$ for $C_{29}H_{29}N_9O_3$, calcd 552.2, found 552.3.

Example 324: m-[6-(1-{[6-(Methoxymethyl)-2-pyridyl]methyl}-1H-1,2,3-triazol-4-yl)-2-(2-phenoxyacetylamino)-4-pyrimidinyl]benzonitrile

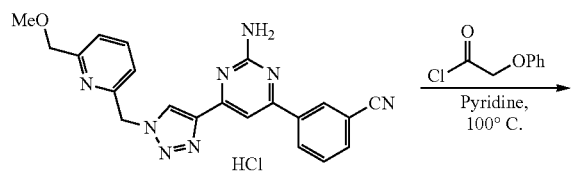

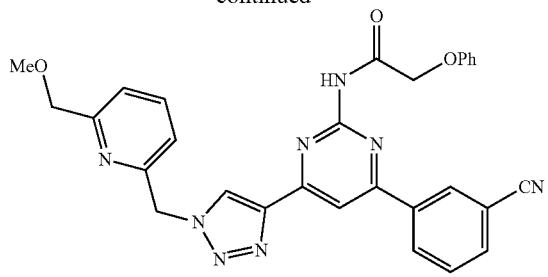

A room temperature stirred reaction mixture of m-[2-amino-6-(1-{[6-(methoxymethyl)-2-pyridyl]methyl}-1H-1,2,3-triazol-4-yl)-4-pyrimidinyl]benzonitrile (20 mg, 0.045 mmol) and phenoxyacetyl chloride (8 mg, 0.045 mmol) in pyridine was heated at 100° C. for 30 minutes. It was cooled to room temperature, diluted with water, extracted with ethyl acetate, purified by reverse phase HPLC and then by flash column to get the pure compound (20 mg, 81%). $^1$H NMR (400 MHz, DMSO-$d_6$) δ 10.92 (s, 1H), 8.89 (d, J=2.1 Hz, 1H), 8.74 (d, J=1.9 Hz, 1H), 8.66-8.56 (m, 1H), 8.44-8.33 (m, 1H), 8.20-7.91 (m, 1H), 7.75-787 (m, 2H), 7.37 (d, J=7.8 Hz, 1H), 7.30-7.15 (m, 3H), 6.98-6.90 (m, 2H), 5.85 (d, J=2.0 Hz, 2H), 5.78-5.67 (m, 1H), 5.17 (d, J=1.9 Hz, 2H), 4.43 (d, J=1.9 Hz, 2H), 3.31 (s, 3H); ESI MS [M+H]$^+$ for $C_{29}H_{24}N_8O_3$, calcd 533.2, found 533.3.

Example 325: m-[2-Acetylamino-6-(1-{[6-(methoxymethyl)-2-pyridyl]methyl}-1H-1,2,3-triazol-4-yl)-4-pyrimidinyl]benzonitrile

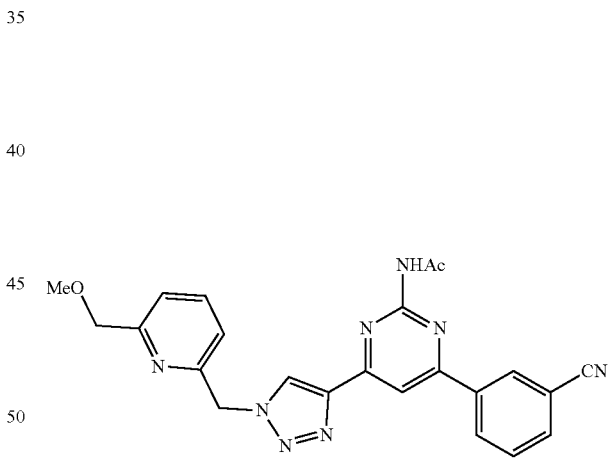

The title compound was synthesized in a similar fashion to example 324. $^1$H NMR (400 MHz, CDCl$_3$) δ 8.46 (s, 1H), 8.40 (s, 1H), 8.39-8.33 (m, 1H), 8.26 (s, 1H), 8.07 (brs, 1H), 7.84-7.78 (m, 1H), 7.73 (dd, J=7.6, 7.6 Hz, 1H), 7.65 (dd, J=7.8, 7.8 Hz, 1H), 7.43 (d, J=8.0 Hz, 1H), 7.16 (d, J=8.0 Hz, 1H), 7.20-7.13 (m, 1H), 5.74 (s, 2H), 4.59 (s, 2H), 4.12 (qd, J=7.2, 1.6 Hz, 1H), 3.50 (s, 3H), 2.65 (s, 3H). MS [M+H]$^+$ for $C_{23}H_{20}N_8O_2$, calcd 441.2, found: 441.3.

Example 326: m-[2-(2-Methoxyacetylamino)-6-(1-{[6-(methoxymethyl)-2-pyridyl]methyl}-1H-1,2,3-triazol-4-yl)-4-pyrimidinyl]benzonitrile

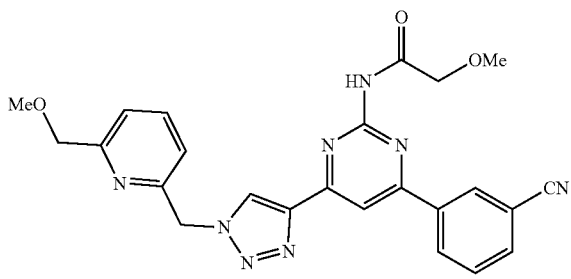 [SMILES: COCC(=O)Nc1nc(-c2cccc(C#N)c2)cc(-c2cn(Cc3cccc(COC)n3)nn2)n1]

The title compound was synthesized in a similar fashion to example 324. LC-MS retention time 2.91 min LC-MS, Method A, ESI MS [M+H]$^+$ for $C_{24}H_{23}N_8O_3$, calcd 471.2, found 471.3.

Example 327: m-[2-(2-Ethoxyacetylamino)-6-(1-{[6-(methoxymethyl)-2-pyridyl]methyl}-1H-1,2,3-triazol-4-yl)-4-pyrimidinyl]benzonitrile

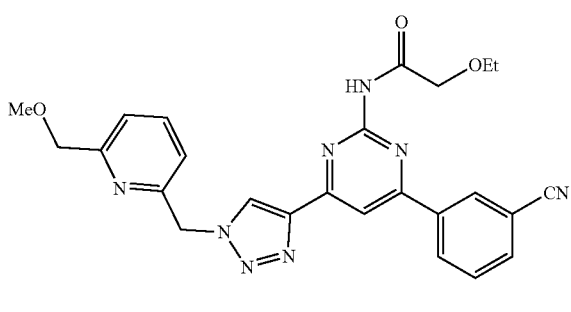 [SMILES: CCOCC(=O)Nc1nc(-c2cccc(C#N)c2)cc(-c2cn(Cc3cccc(COC)n3)nn2)n1]

The title compound was synthesized in a similar fashion to example 324. $^1$H NMR (400 MHz, CDCl$_3$) δ 9.07 (s, 1H), 8.56-8.51 (m, 1H), 8.47 (d, J=0.7 Hz, 1H), 8.43 (ddt, J=8.0, 1.8, 0.9 Hz, 1H), 8.34-8.28 (m, 1H), 7.84-7.77 (m, 1H), 7.71 (t, J=7.8 Hz, 1H), 7.65 (t, J=7.8 Hz, 1H), 7.42 (d, J=7.8 Hz, 1H), 7.12 (d, J=7.7 Hz, 1H), 5.74 (s, 2H), 4.59 (s, 2H), 4.18 (s, 2H), 3.78-3.64 (m, 2H), 3.49 (s, 3H), 1.36 (td, J=7.0, 0.7 Hz, 3H); LC-MS retention time 3.03 min LC-MS, Method A, ESI MS [M+H]$^+$ for $C_{25}H_{25}N_8O_3$, calcd 485.2, found 485.3.

Example 328: m-[6-(1-{[6-(Methoxymethyl)-2-pyridyl]methyl}-1H-1,2,3-triazol-4-yl)-2-[(tetrahydrofur-2-yl)carbonylamino]-4-pyrimidinyl]benzonitrile

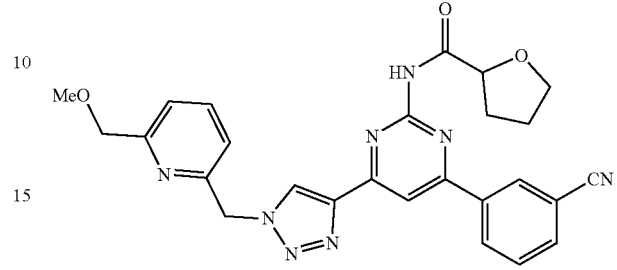

The title compound was synthesized in a similar fashion to example 324. $^1$H NMR (400 MHz, CDCl$_3$) δ 9.31 (s, 1H), 8.55 (t, J=1.7 Hz, 1H), 8.47 (s, 1H), 8.45-8.40 (m, 1H), 8.31 (d, J=1.3 Hz, 1H), 7.80 (dt, J=7.7, 1.4 Hz, 1H), 7.71 (t, J=7.8 Hz, 1H), 7.64 (t, J=7.8 Hz, 1H), 7.42 (d, J=7.8 Hz, 1H), 7.11 (d, J=7.7 Hz, 1H), 5.74 (s, 2H), 4.59 (s, 2H), 4.57-4.51 (m, 1H), 4.14 (q, J=7.0 Hz, 1H), 4.06-3.97 (m, 1H), 3.50 (s, 3H), 2.45-2.19 (m, 2H), 1.99 (dp, J=13.3, 6.1 Hz, 2H); LC-MS retention time 3.03 min LC-MS, Method A, ESI MS [M+H]$^+$ for $C_{26}H_{25}N_8O_3$, calcd 497.2, found 497.3.

Example 329: m-[6-(1-{[6-(Methoxymethyl)-2-pyridyl]methyl}-1H-1,2,3-triazol-4-yl)-2-[(tetrahydro-2H-pyran-2-yl)carbonylamino]-4-pyrimidinyl]benzonitrile

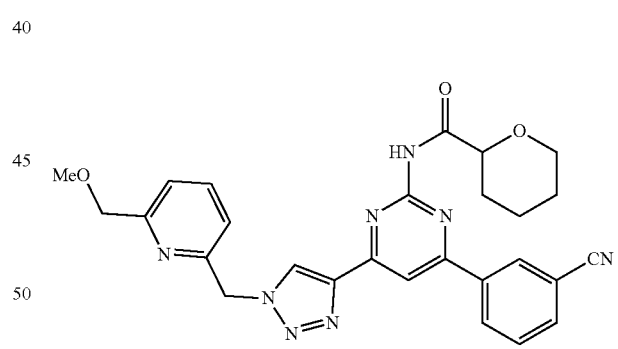

The title compound was synthesized in a similar fashion to example 324. $^1$H NMR (400 MHz, CDCl$_3$) δ 9.22 (s, 1H), 8.56 (tt, J=1.7, 0.8 Hz, 1H), 8.48 (d, J=1.3 Hz, 1H), 8.44 (ddd, J=8.0, 1.9, 1.2 Hz, 1H), 8.30 (d, J=1.3 Hz, 1H), 7.82-7.68 (m, 3H), 7.67-7.61 (m, 1H), 7.42 (d, J=7.7 Hz, 1H), 7.10 (d, J=7.7 Hz, 1H), 5.78-5.60 (s, 2H), 4.59 (s, 2H), 3.50 (s, 3H), 2.23 (d, J=11.8 Hz, 1H), 1.94 (d, J=28.3 Hz, 2H), 1.76-1.44 (m, 6H); LC-MS retention time 3.33 min LC-MS, Method A, ESI MS [M+H]$^+$ for $C_{27}H_{27}N_8O_3$, calcd 511.2, found 511.3.

Example 330: m-[6-(1-{[6-(Methoxymethyl)-2-pyridyl]methyl}-1H-1,2,3-triazol-4-yl)-2-(2-phenoxypropionylamino)-4-pyrimidinyl]benzonitrile

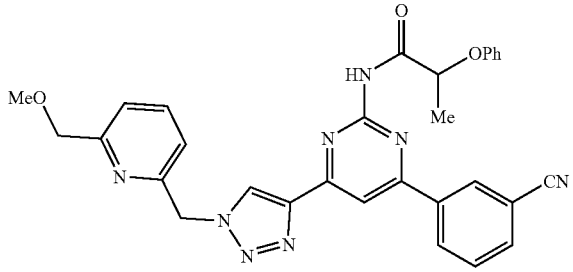 [SMILES: COCc1cccc(Cn2cc(-c3cc(-c4cccc(C#N)c4)nc(NC(=O)C(C)Oc4ccccc4)n3)nn2)n1]

The title compound was synthesized in a similar fashion to example 324. $^1$H NMR (400 MHz, Chloroform-d) δ 9.06 (s, 1H), 8.53 (s, 1H), 8.48 (s, 1H), 8.45-8.37 (m, 1H), 8.32 (s, 1H), 7.84-7.76 (m, 1H), 7.72 (dd, J=7.8, 7.8 Hz, 1H), 7.64 (dd, J=7.8, 7.8 Hz, 1H), 7.42 (d, J=7.8 Hz, 1H), 7.39-7.30 (m, 2H), 7.12 (d, J=7.8 Hz, 1H), 7.09-6.99 (m, 3H), 5.74 (s, 2H), 4.89 (brs, 1H), 4.59 (s, 2H), 3.50 (s, 3H), 1.72 (d, J=6.4 Hz, 3H). MS [M+H]$^+$ for $C_{30}H_{26}N_8O_3$, calcd 547.2, found: 547.3.

Example 331: m-[2-(2-Hydroxy-2-methylpropionylamino)-6-(1-{[6-(methoxymethyl)-2-pyridyl]methyl}-1H-1,2,3-triazol-4-yl)-4-pyrimidinyl]benzonitrile

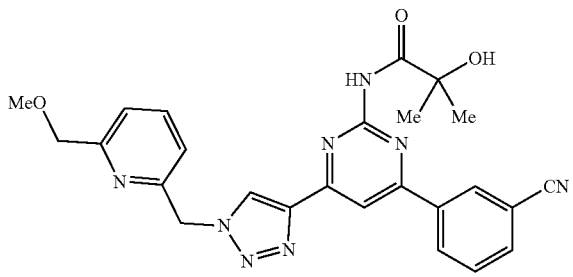 [SMILES: COCc1cccc(Cn2cc(-c3cc(-c4cccc(C#N)c4)nc(NC(=O)C(C)(C)O)n3)nn2)n1]

The title compound was synthesized in a similar fashion to example 324. $^1$H NMR (400 MHz, DMSO-d$_6$) δ 9.78 (s, 1H), 8.93 (s, 1H), 8.76 (s, 1H), 8.64 (d, J=8.0 Hz, 1H), 8.40 (s, 1H), 8.04 (d, J=7.8 Hz, 1H), 7.86 (t, J=7.8 Hz, 1H), 7.77 (t, J=7.9 Hz, 1H), 7.38 (d, J=7.8 Hz, 1H), 7.25 (d, J=7.7 Hz, 1H), 5.84 (s, 2H), 4.45 (s, 2H), 3.33 (s, 3H), 1.39 (s, 6H); LC-MS retention time 2.85 min LC-MS, Method A, ESI MS [M+H]$^+$ for $C_{25}H_{25}N_8O_3$, calcd 485.2, found 485.3.

Example 332: 2-Fluoro-3-[6-(1-{[6-(methoxymethyl)-2-pyridyl]methyl}-1H-1,2,3-triazol-4-yl)-2-(2-phenoxyacetylamino)-4-pyrimidinyl]benzonitrile

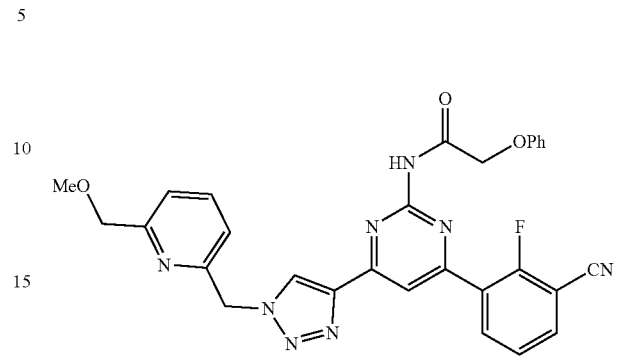

The title compound was synthesized in a similar fashion to example 324. $^1$H NMR (400 MHz, CDCl$_3$) δ 8.99 (brs, 1H), 8.51 (dd, J=7.8, 7.8 Hz, 1H), 8.46 (s, 1H) 8.40 (s, 1H), 7.78 (dd, J=7.6, 7.6 Hz, 1H), 7.72 (dd, J=7.8, 7.8 Hz, 1H), 7.50-7.39 (m, 2H), 7.36 (dd, J=7.8, 7.8 Hz, 1H), 7.14 (d, J=7.8 Hz, 1H), 7.09-6.99 (m, 2H), 5.74 (s, 2H), 4.79 (s, 2H), 4.59 (s, 2H), 3.50 (s, 2H). MS [M+H]$^+$ for $C_{29}H_{23}FN_8O_3$, calcd 551.2, found: 551.3.

Example 333: 1-[6-(2-Furyl)-4-(1-{[6-(methoxymethyl)-2-pyridyl]methyl}-1H-1,2,3-triazol-4-yl)-2-pyrimidinylamino]-2-phenoxy-1-ethanone

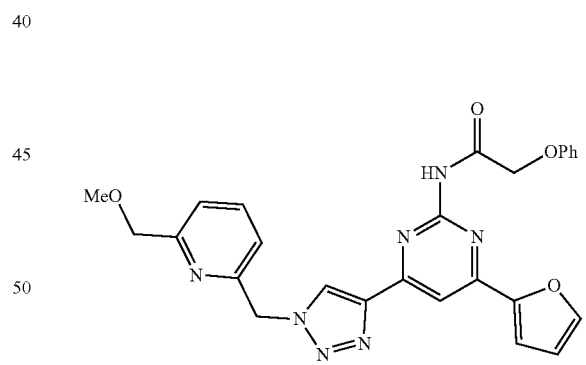

The title compound was synthesized in a similar fashion to example 324. $^1$H NMR (400 MHz, CDCl$_3$) δ 8.85 (s, 1H), 8.45-8.40 (m, 1H), 8.20-8.18 (m, 1H), 7.71 (td, J=7.9, 2.1 Hz, 1H), 7.67-7.64 (m, 1H), 7.44-7.39 (m, 1H), 7.39-7.30 (m, 3H), 7.11 (d, J=7.7 Hz, 1H), 7.08-7.00 (m, 3H), 6.61 (ddd, J=3.5, 2.6, 1.6 Hz, 1H), 5.74 (d, J=2.0 Hz, 2H), 4.83 (s, 2H), 4.59 (d, J=1.9 Hz, 2H), 3.49 (s, 3H); ESI MS [M+H]$^+$ for $C_{26}H_{23}N_7O_4$, calcd 498.2, found 498.3.

Example 334: m-[2-(2-Methoxyacetylamino)-6-(1-{[6-(1-methoxyethyl)-2-pyridyl]methyl}-1H-1,2,3-triazol-4-yl)-4-pyrimidinyl]benzonitrile

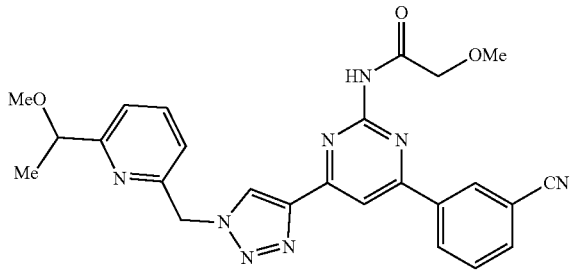 [SMILES: COCC(=O)Nc1nc(-c2cccc(C#N)c2)cc(-c2cn(Cc3cccc(C(C)OC)n3)nn2)n1]

The title compound was synthesized in a similar fashion to example 324. $^1$H NMR (400 MHz, CDCl$_3$) δ 9.02 (s, 1H), 8.56-8.51 (m, 1H), 8.49 (s, 1H), 8.42 (dt, J=7.9, 1.5 Hz, 1H), 8.32 (s, 1H), 7.80 (dq, J=7.7, 1.4 Hz, 1H), 7.68 (dtd, J=27.0, 7.8, 1.1 Hz, 2H), 7.41 (d, J=7.8 Hz, 1H), 7.09 (dd, J=7.8, 1.2 Hz, 1H), 5.74 (s, 2H), 4.43 (q, J=6.5 Hz, 1H), 4.16 (s, 2H), 3.56 (s, 3H), 3.33 (s, 3H), 1.46 (dd, J=6.5, 1.2 Hz, 3H); LC-MS retention time 3.00 min LC-MS, Method A, ESI MS [M+H]$^+$ for C$_{25}$H$_{25}$N$_8$O$_3$, calcd 485.2, found 485.3.

Example 335: m-[6-(1-{[6-(1-Methoxyethyl)-2-pyridyl]methyl}-1H-1,2,3-triazol-4-yl)-2-(2-phenoxyacetylamino)-4-pyrimidinyl]benzonitrile

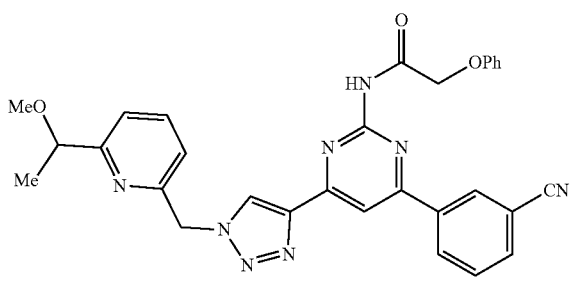 [SMILES: COC(C)c1cccc(Cn2cc(-c3cc(-c4cccc(C#N)c4)nc(NC(=O)COc4ccccc4)n3)nn2)n1]

The title compound was synthesized in a similar fashion to example 324. $^1$H NMR (400 MHz, DMSO-d$_6$) δ 10.93 (s, 1H), 8.91 (s, 1H), 8.74 (s, 1H), 8.60 (d, J=8.0 Hz, 1H), 8.37 (d, J=0.9 Hz, 1H), 8.04 (d, J=7.5 Hz, 1H), 7.82 (dt, J=25.2, 7.8 Hz, 2H), 7.36 (d, J=7.8 Hz, 1H), 7.27 (dd, J=8.4, 7.0 Hz, 2H), 7.19 (d, J=7.7 Hz, 1H), 6.93 (ddd, J=12.2, 6.6, 3.8 Hz, 3H), 5.86 (s, 2H), 5.18 (s, 2H), 4.30 (q, J=6.5 Hz, 1H), 3.16 (d, J=0.9 Hz, 3H), 1.42-1.21 (m, 3H); ESI MS [M+H]$^+$ for C$_{30}$H$_{26}$N$_8$O$_3$, calcd 547.2, found 548.3.

Example 336: 1-[4-(1-{[6-(1-Methoxyethyl)-2-pyridyl]methyl}-1H-1,2,3-triazol-4-yl)-6-(1,3-oxazol-2-yl)-2-pyrimidinylamino]-2-phenoxy-1-ethanone

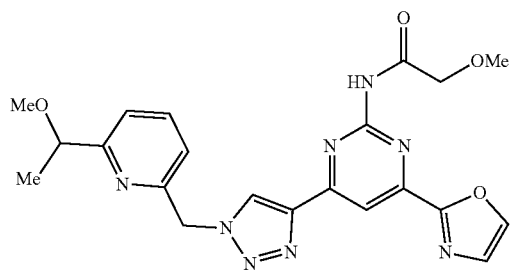 [SMILES: COCC(=O)Nc1nc(-c2cn(Cc3cccc(C(C)OC)n3)nn2)cc(-c2ncco2)n1]

The title compound was synthesized in a similar fashion to example 324. $^1$H NMR (400 MHz, CD$_3$OD) δ 8.86 (s, 1H), 8.42 (s, 1H), 8.22 (s, 1H), 7.85 (t, J=8.0 Hz, 1H), 7.52 (s, 1H), 7.44 (d, J=8.6 Hz, 1H), 7.34-7.25 (m, 3H), 7.05 (d, J=7.9 Hz, 2H), 6.98 (t, J=7.4 Hz, 1H), 5.82 (s, 2H), 5.13 (s, 2H), 4.40 (q, J=6.5 Hz, 1H), 3.26 (s, 3H), 1.38 (d, J=6.5 Hz, 3H). ESI MS [M+H]$^+$ for C$_{26}$H$_{25}$N$_8$O$_4$, calcd 513.2, found 513.3.

Example 337: m-[2-(2-Methoxyacetylamino)-6-(1-{[6-(1-methoxypropyl)-2-pyridyl]methyl}-1H-1,2,3-triazol-4-yl)-4-pyrimidinyl]benzonitrile The title compound was synthesized in a similar fashion to example 324 to afford 16 mg of a tan solid. $^1$H NMR (400 MHz, DMSO-d$_6$) δ 10.54 (s, 1H), 8.90 (d, J=1.1 Hz, 1H), 8.75 (d, J=1.5 Hz, 1H), 8.66-8.56 (m, 1H), 8.37 (d, J=1.1 Hz, 1H), 8.12-7.98 (m, 1H), 7.87 (t, J=7.8 Hz, 1H), 7.80 (t, J=7.9 Hz, 1H), 7.35 (d, J=7.8 Hz, 1H), 7.21 (d, J=7.7 Hz, 1H), 5.88 (s, 2H), 4.38 (s, 2H), 4.13 (t, J=6.2 Hz, 1H), 3.39 (s, 3H), 3.18 (s, 3H), 1.68 (p, J=7.0 Hz, 2H), 0.84-0.72 (m, 3H). ESI MS [M+H]$^+$ for C$_{26}$H$_{26}$N$_8$O$_3$, calcd 499.2, found 499.3.

Example 338: m-[6-(1-{[6-(1-Methoxypropyl)-2-pyridyl]methyl}-1H-1,2,3-triazol-4-yl)-2-(2-phenoxyacetylamino)-4-pyrimidinyl]benzonitrile

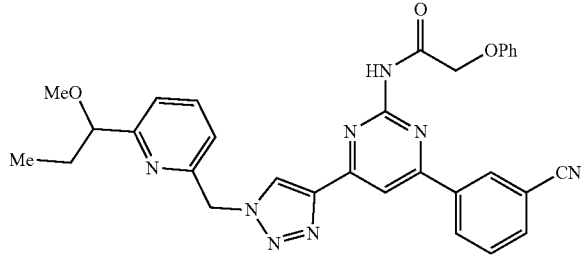 [SMILES: CCC(OC)c1cccc(Cn2cc(-c3cc(-c4cccc(C#N)c4)nc(NC(=O)COc4ccccc4)n3)nn2)n1]

The title compound was synthesized in a similar fashion to example 324 to afford 31 mg of a tan solid. $^1$H NMR (400 MHz, CDCl$_3$) δ 9.03 (s, 1H), 8.56-8.46 (m, 2H), 8.45-8.39 (m, 1H), 8.38-8.26 (m, 1H), 7.80 (dq, J=7.7, 1.3 Hz, 1H), 7.71 (td, J=7.9, 1.9 Hz, 1H), 7.64 (td, J=7.7, 1.7 Hz, 1H), 7.41-7.31 (m, 3H), 7.12-7.01 (m, 4H), 5.79-5.68 (m, 2H), 4.80 (s, 2H), 4.21 (dd, J=7.0, 5.4 Hz, 1H), 3.31 (s, 3H), 1.87-1.72 (m, 2H), 0.97-0.84 (m, 3H). ESI MS [M+H]$^+$ for C$_{31}$H$_{28}$N$_8$O$_3$, calcd 561.2, found 561.4.

Example 339: m-[2-(2-Methoxyacetylamino)-6-(1-{[6-(1-methoxy-2-methylpropyl)-2-pyridyl]methyl}-1H-1,2,3-triazol-4-yl)-4-pyrimidinyl]benzonitrile

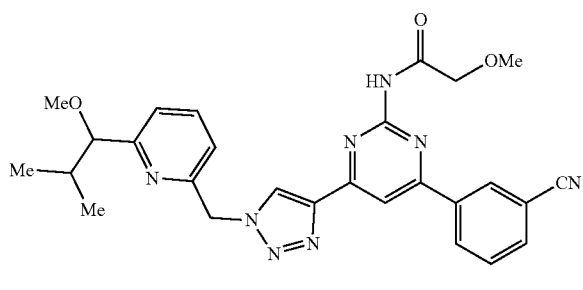 [SMILES: COCC(=O)Nc1nc(-c2cccc(C#N)c2)cc(-c2cn(Cc3cccc(C(OC)C(C)C)n3)nn2)n1]

The title compound was synthesized in a similar fashion to example 324 to afford 16 mg of a tan solid. $^1$H NMR (400 MHz, DMSO-d$_6$) δ 10.53 (s, 1H), 8.89 (d, J=1.3 Hz, 1H), 8.75 (d, J=1.7 Hz, 1H), 8.61 (d, J=8.0 Hz, 1H), 8.37 (d, J=1.4 Hz, 1H), 8.12-7.99 (m, 1H), 7.87 (t, J=7.8 Hz, 1H), 7.80 (t, J=7.8 Hz, 1H), 7.31 (d, J=7.8 Hz, 1H), 7.22 (d, J=7.7 Hz, 1H), 5.88 (s, 2H), 4.38 (s, 2H), 3.92 (d, J=5.8 Hz, 1H), 3.39 (s, 3H), 3.16 (s, 3H), 1.94 (q, J=6.7 Hz, 1H), 0.80 (dd, J=6.7, 1.3 Hz, 3H), 0.71 (dd, J=6.9, 1.3 Hz, 3H). ESI MS [M+H]$^+$ for C$_{27}$H$_{28}$N$_8$O$_3$, calcd 513.2, found 513.4.

Example 340: m-[6-(1-{[6-(1-Methoxy-2-methylpropyl)-2-pyridyl]methyl}-1H-1,2,3-triazol-4-yl)-2-(2-phenoxyacetylamino)-4-pyrimidinyl]benzonitrile

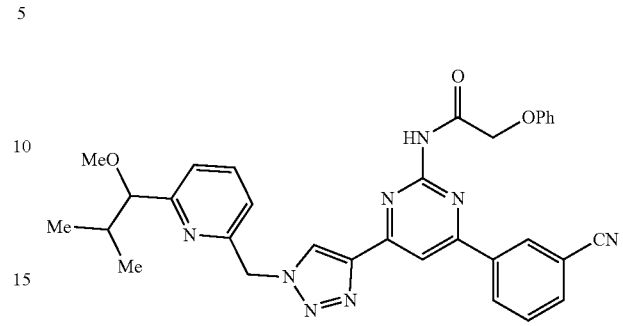

The title compound was synthesized in a similar fashion to example 324 to afford 33 mg of a tan solid. $^1$H NMR (400 MHz, CDCl$_3$) δ 9.00 (s, 1H), 8.55-8.51 (m, 1H), 8.50 (d, J=1.6 Hz, 1H), 8.46-8.40 (m, 1H), 8.33 (d, J=1.6 Hz, 1H), 7.81 (dt, J=7.7, 1.4 Hz, 1H), 7.74-7.60 (m, 2H), 7.40-7.31 (m, 3H), 7.26 (d, J=2.7 Hz, 1H), 7.11-7.01 (m, 3H), 5.75 (s, 2H), 4.80 (s, 2H), 4.00 (dd, J=6.3, 1.7 Hz, 1H), 3.28 (s, 3H), 2.10-1.97 (m, 1H), 0.92 (dd, J=6.8, 1.7 Hz, 3H), 0.82 (dd, J=6.8, 1.7 Hz, 3H). ESI MS [M+H]$^+$ for C$_{32}$H$_{30}$N$_8$O$_3$, calcd 575.3, found 575.4.

Example 341: m-[6-(1-{[6-(Cyclopropylmethoxymethyl)-2-pyridyl]methyl}-1H-1,2,3-triazol-4-yl)-2-(2-methoxyacetylamino)-4-pyrimidinyl]benzonitrile

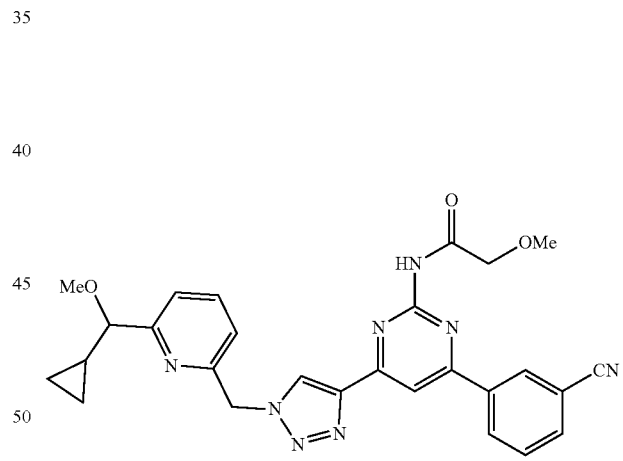

The title compound was synthesized in a similar fashion to example 324 to afford 17 mg of a tan solid. $^1$H NMR (400 MHz, DMSO-d$_6$) δ 10.53 (s, 1H), 8.90 (d, J=1.4 Hz, 1H), 8.75 (s, 1H), 8.61 (d, J=7.7 Hz, 1H), 8.37 (d, J=1.3 Hz, 1H), 8.11-8.03 (m, 1H), 7.90-7.83 (m, 1H), 7.80 (t, J=7.8 Hz, 1H), 7.39 (d, J=7.8 Hz, 1H), 7.24 (d, J=7.7 Hz, 1H), 5.89 (s, 2H), 4.38 (s, 2H), 3.67 (d, J=7.7 Hz, 1H), 3.39 (s, 3H), 3.19 (s, 3H), 1.16-0.97 (m, 1H), 0.55-0.37 (m, 2H), 0.35-0.16 (m, 2H). ESI MS [M+H]$^+$ for C$_{27}$H$_{26}$N$_8$O$_3$, calcd 511.2, found 511.3.

Example 342: m-[6-(1-{[6-(Cyclopropylmethoxymethyl)-2-pyridyl]methyl}-1H-1,2,3-triazol-4-yl)-2-(2-phenoxyacetylamino)-4-pyrimidinyl]benzonitrile

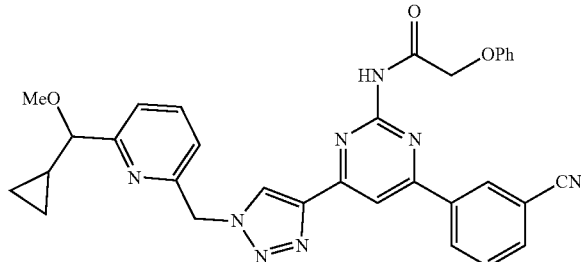

The title compound was synthesized in a similar fashion to example 324 to afford 31 mg of a tan solid. $^1$H NMR (400 MHz, CDCl$_3$) δ 9.01 (s, 1H), 8.54-8.48 (m, 2H), 8.41 (ddt, J=8.0, 1.8, 1.1 Hz, 1H), 8.32 (d, J=1.1 Hz, 1H), 7.79 (dq, J=7.7, 1.3 Hz, 1H), 7.71 (td, J=7.8, 1.1 Hz, 1H), 7.67-7.60 (m, 1H), 7.40 (dt, J=7.8, 1.0 Hz, 1H), 7.37-7.31 (m, 2H), 7.12 (dt, J=7.7, 1.1 Hz, 1H), 7.08-7.00 (m, 3H), 5.75 (s, 2H), 4.79 (s, 2H), 3.72 (dd, J=7.9, 1.0 Hz, 1H), 3.32 (s, 3H), 1.18-1.08 (m, 1H), 0.91-0.79 (m, 1H), 0.62 (dddd, J=12.1, 8.6, 5.7, 1.1 Hz, 1H), 0.54-0.34 (m, 3H). ESI MS [M+H]$^+$ for C$_{32}$H$_{28}$N$_8$O$_3$, calcd 573.2, found 573.3.

Example 343: m-[6-(1-{[6-(Cyclopentylmethoxymethyl)-2-pyridyl]methyl}-1H-1,2,3-triazol-4-yl)-2-(2-methoxyacetylamino)-4-pyrimidinyl]benzonitrile

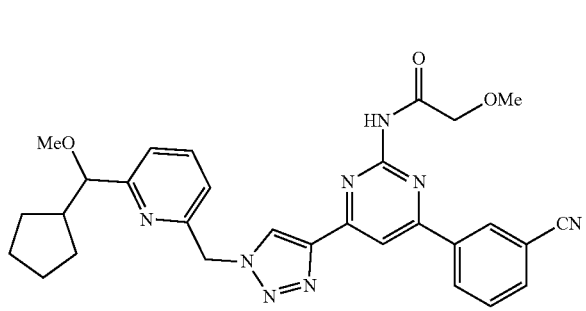 [SMILES: COCC(=O)Nc1nc(-c2cccc(C#N)c2)cc(-c2cn(Cc3cccc(C(OC)C4CCCC4)n3)nn2)n1]

The title compound was synthesized in a similar fashion to example 324 to afford 15 mg of a tan solid. $^1$H NMR (400 MHz, DMSO-d$_6$) δ 10.52 (s, 1H), 8.89 (d, J=1.4 Hz, 1H), 8.74 (dd, J=2.4, 1.1 Hz, 1H), 8.61 (d, J=8.1 Hz, 1H), 8.36 (d, J=1.3 Hz, 1H), 8.05 (dd, J=7.5, 1.4 Hz, 1H), 7.88-7.76 (m, 2H), 7.34 (d, J=7.8 Hz, 1H), 7.23 (d, J=7.7 Hz, 1H), 5.88 (s, 2H), 4.37 (d, J=1.3 Hz, 2H), 3.96 (d, J=7.8 Hz, 1H), 3.39 (s, 3H), 3.13 (s, 3H), 2.21-2.09 (m, 1H), 1.59 (d, J=10.3 Hz, 1H), 1.51-1.09 (m, 7H). ESI MS [M+H]$^+$ for C$_{29}$H$_3$N$_8$O$_3$, calcd 539.3, found 539.3.

Example 344: m-[6-(1-{[6-(Cyclopentylmethoxymethyl)-2-pyridyl]methyl}-1H-1,2,3-triazol-4-yl)-2-(2-phenoxyacetylamino)-4-pyrimidinyl]benzonitrile

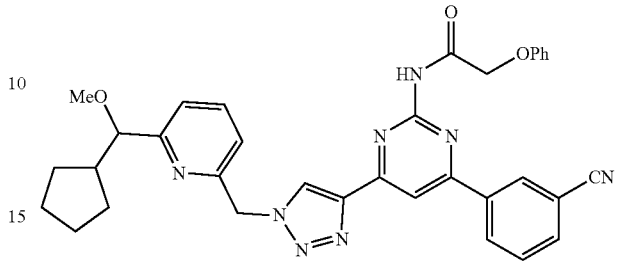

The title compound was synthesized in a similar fashion to example 324 to afford 15 mg of a tan solid. $^1$H NMR (400 MHz, DMSO-d$_6$) δ 10.94 (s, 1H), 8.92 (d, J=1.4 Hz, 1H), 8.76 (d, J=1.7 Hz, 1H), 8.66-8.53 (m, 1H), 8.38 (d, J=1.3 Hz, 1H), 8.06 (dd, J=7.8, 1.4 Hz, 1H), 7.94-7.73 (m, 2H), 7.37-7.17 (m, 4H), 7.04-6.85 (m, 3H), 5.88 (s, 2H), 5.19 (s, 2H), 3.95 (d, J=7.6 Hz, 1H), 3.11 (s, 3H), 2.14 (q, J=7.7 Hz, 1H), 1.58 (d, J=9.6 Hz, 1H), 1.53-1.08 (m, 7H). ESI MS [M+H]$^+$ for C$_{34}$H$_{32}$N$_8$O$_3$, calcd 601.3.

Example 345: m-[2-(2-Methoxyacetylamino)-6-(1-{[6-(methoxyphenylmethyl)-2-pyridyl]methyl}-1H-1,2,3-triazol-4-yl)-4-pyrimidinyl]benzonitrile

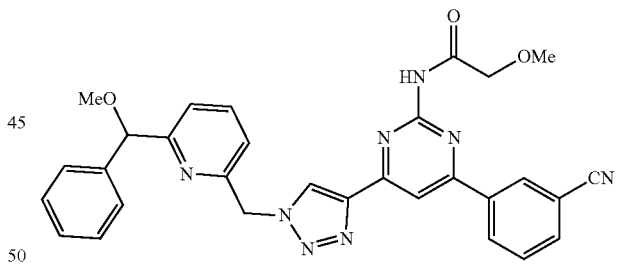

The title compound was synthesized in a similar fashion to example 324 to afford 17 mg of a tan solid. $^1$H NMR (400 MHz, DMSO-d$_6$) δ 10.54 (s, 1H), 8.86 (d, J=1.4 Hz, 1H), 8.76 (d, J=1.5 Hz, 1H), 8.62 (d, J=7.7 Hz, 1H), 8.37 (d, J=1.5 Hz, 1H), 8.06 (d, J=7.9 Hz, 1H), 7.89-7.76 (m, 2H), 7.49 (d, J=7.9 Hz, 1H), 7.33 (d, J=7.9 Hz, 2H), 7.27-7.14 (m, 4H), 5.85 (s, 2H), 5.32 (s, 1H), 4.38 (s, 2H), 3.39 (s, 3H), 3.30 (s, 3H). ESI MS [M+H]$^+$ for C$_{30}$H$_{26}$N$_8$O$_3$, calcd 547.2, found 547.3.

Example 346: m-[6-(1-{[6-(Methoxyphenylmethyl)-2-pyridyl]methyl}-1H-1,2,3-triazol-4-yl)-2-(2-phenoxyacetylamino)-4-pyrimidinyl]benzonitrile

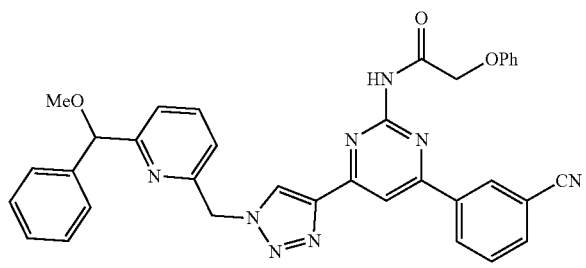 [SMILES: COC(c1ccccc1)c1cccc(Cn2cc(-c3cc(-c4cccc(C#N)c4)nc(NC(=O)COc4ccccc4)n3)nn2)n1]

The title compound was synthesized in a similar fashion to example 324 to afford 31 mg of a tan solid. $^1$H NMR (400 MHz, CDCl$_3$) δ 9.01 (s, 1H), 8.54 (td, J=1.7, 0.9 Hz, 1H), 8.48-8.39 (m, 2H), 8.37-8.29 (m, 1H), 7.81 (dq, J=8.6, 1.2 Hz, 1H), 7.73-7.61 (m, 2H), 7.52-7.47 (m, 1H), 7.40 (dtd, J=6.8, 1.3, 0.7 Hz, 2H), 7.38-7.32 (m, 2H), 7.32-7.27 (m, 2H), 7.24-7.18 (m, 1H), 7.10-7.02 (m, 4H), 5.70 (d, J=2.1 Hz, 2H), 5.37 (s, 1H), 4.81 (s, 2H), 3.43 (s, 3H). ESI MS [M+H]$^+$ for C$_{35}$H$_{28}$N$_8$O$_3$, calcd 609.2, found 609.4.

Example 347: m-[6-(1-{[6-(1-Hydroxycyclobutyl)-2-pyridyl]methyl}-1H-1,2,3-triazol-4-yl)-2-(2-phenoxyacetylamino)-4-pyrimidinyl]benzonitrile

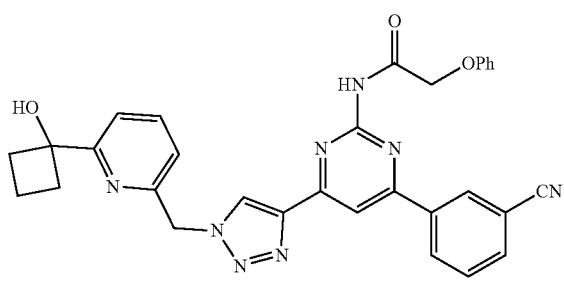 [SMILES: N#Cc1cccc(-c2cc(-c3cn(Cc4cccc(C5(O)CCC5)n4)nn3)nc(NC(=O)COc3ccccc3)n2)c1]

The title compound was synthesized in a similar fashion to example 324. $^1$H NMR (400 MHz, CDCl$_3$) δ 9.02 (brs, 1H), 8.54 (s, 1H), 8.46 (s, 1H), 8.43 (d, J=7.8 Hz, 1H) 8.34 (s, 1H), 7.85-7.75 (m, 2H), 7.66 (dd, J=7.8, 7.8 Hz, 1H), 7.59 (d, J=7.8 Hz, 1H), 7.36 (dd, J=7.8, 7.8 Hz, 2H), 7.15 (d, J=7.8 Hz, 1H), 7.12-6.97 (m, 3H), 5.77 (s, 2H), 4.79 (s, 2H), 2.66-2.43 (m, 4H), 2.20-2.01 (m, 1H), 1.96-1.80 (m, 1H). MS [M+H]$^+$ for C$_{31}$H$_{26}$N$_8$O$_3$, calcd 559.2, found: 559.4.

Example 348: m-[6-(1-{[6-(1-Hydroxycyclopentyl)-2-pyridyl]methyl}-1H-1,2,3-triazol-4-yl)-2-(2-phenoxyacetylamino)-4-pyrimidinyl]benzonitrile

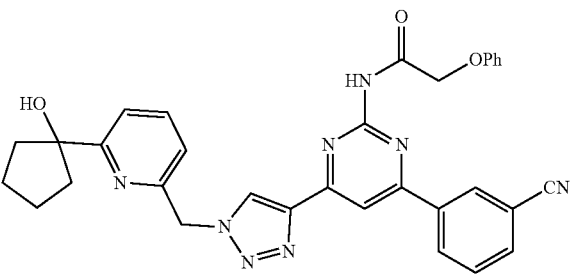 [SMILES: N#Cc1cccc(-c2cc(-c3cn(Cc4cccc(C5(O)CCCC5)n4)nn3)nc(NC(=O)COc3ccccc3)n2)c1]

The title compound was synthesized in a similar fashion to example 324. $^1$H NMR (400 MHz, CDCl$_3$) δ 9.02 (brs, 1H), 8.54 (s, 1H), 8.46 (s, 1H), 8.46-8.40 (m, 1H), 8.34 (s, 1H), 7.82 (d, J=7.8 Hz, 1H), 7.73 (dd, J=7.8, 7.8 Hz, 2H), 7.66 (dd, J=7.8, 7.8 Hz, 2H), 7.44-7.27 (m, 2H), 7.14-6.97 (m, 3H), 5.77 (s, 2H), 4.79 (brs, 2H), 2.07-1.91 (m, 8H). MS [M+H]$^+$ for C$_{32}$H$_{28}$N$_8$O$_3$, calcd 573.2, found: 573.4.

Example 349: 6-(1-{[6-(Methoxymethyl)-2-pyridyl]methyl}-1H-pyrazol-3-yl)-4-phenyl-2-pyrimidinylamine

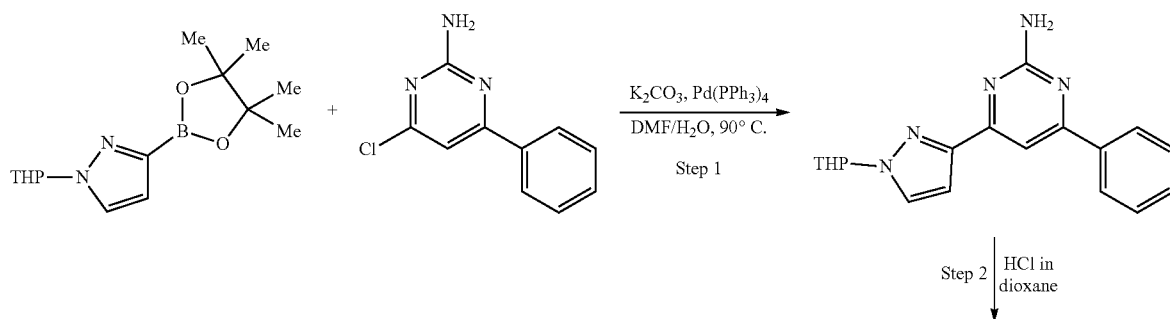

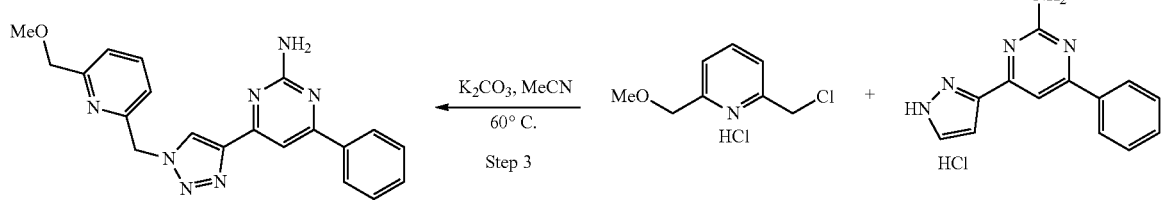

Step 1: A mixture of 3-pyrazole boronate derivative (875 mg, 3.2 mmol), chloropyrimidine derivative (500 mg, 2.5 mmol) and K$_2$CO$_3$ (1.04 g, 7.5 mmol) was suspended in 10 mL DMF and 2.5 mL H$_2$O. The content was degassed by bubbling N$_2$ through the solution. To this degassed reaction mixture was added Pd(PPh$_3$)$_4$ (290 mg, 0.25 mmol) and heated at 90° C. for 10 h. After cooling the reaction to room temperature, 10 mL brine was added and the aqueous layer was extracted using EtOAc (2×25 mL). The pooled organic layer was dried over Na$_2$SO$_4$, concentrated and purified by silica gel chromatography to yield the desired product (522 mg, 65%).

Step 2: To a solution of THP-pyrazole from step 1 (114 mg, 0.36 mmol) in 2 mL MeOH was added 2 mL of 4N HCl in dioxane. The reaction was stirred at room temperature for 1 h. Solvents were evaporated under pressure and the crude product was used in next step without further purification.

Step 3: To a mixture of the crude product from step 2 (0.36 mmol), chloromethylpyridine derivative (112.4 mg, 0.54 mmol) in dry 2 mL MeCN was added K$_2$CO$_3$ (248 mg, 1.8 mmol). The reaction mixture was heated at 60° C. for 5 h. After cooling the reaction to room temperature, 10 mL brine was added and the aqueous layer was extracted using EtOAc (2×10 mL). The pooled organic layer was dried over Na$_2$SO$_4$, concentrated and purified by silica gel chromatography to yield the desired product A0001028 (94 mg, 70%). $^1$H NMR (400 MHz, CDCl$_3$) δ 8.10-8.01 (m, 1H), 7.68-7.61 (m, 2H), 7.58 (d, J=2.4 Hz, 1H), 7.48-7.44 (m, 3H), 7.34 (d, J=7.7 Hz, 1H), 6.98 (d, J=2.4 Hz, 1H), 6.92-6.87 (m, 1H), 5.56 (s, 4H), 5.43 (s, 2H), 4.58 (s, 2H), 3.48 (s, 3H). ESI MS [M+H]$^+$ for C$_{21}$H$_{20}$N6O, calcd 373.2, found 373.2.

Example 350: 6-[2-Amino-6-(1-{[6-(1-hydroxy-1-methylethyl)-2-pyridyl]methyl}-1H-pyrazol-4-yl)-4-pyrimidinyl]-2-toluonitrile

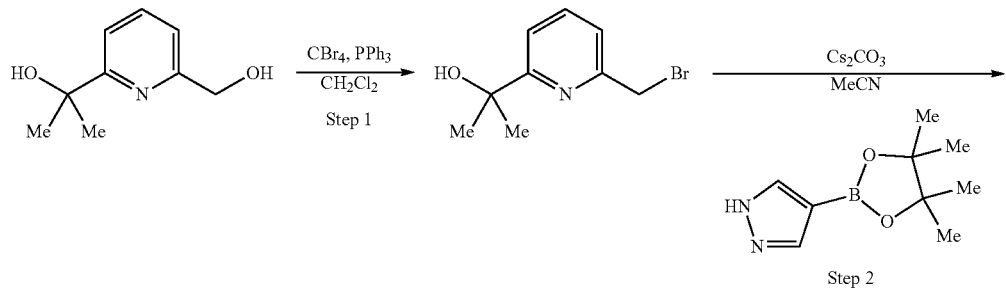

-continued

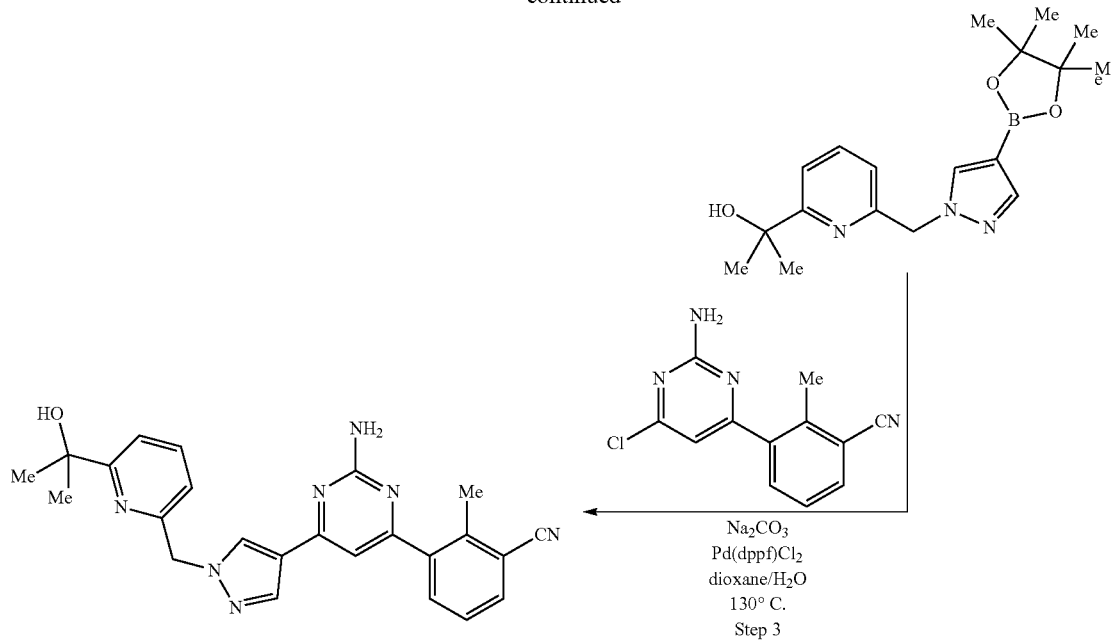

Na₂CO₃
Pd(dppf)Cl₂
dioxane/H₂O
130° C.
Step 3

Step 1: To a solution of 2-(6-(hydroxymethyl)pyridin-2-yl)propan-2-ol (2.13 g, 12.7 mmol, 1.0 equiv) in CH₂Cl₂ (127 mL, 0.1 M) under N2 was added CBr₄ (4.7 g, 14.0 mmol, 1.1 equiv) followed by triphenylphosphine (3.7 g, 14.0 mmol, 1.1 equiv). The resulting mixture was stirred at room temperature for 4 h. Following this time, the reaction mixture was transferred to a separatory funnel and washed with saturated aqueous NaHCO₃ (150 mL). The organic phase was collected, dried over MgSO₄, and concentrated in vacuo. The resulting oil was purified by column chromatography (CH₂Cl₂→9:1 CH₂Cl₂:MeOH) to give 2-(6-(bromomethyl)pyridin-2-yl)propan-2-ol (2.0 g, 69% yield) as a yellow oil.

Step 2: 2-(6-(bromomethyl)pyridin-2-yl)propan-2-ol (1.0 g, 4.3 mmol, 1.0 equiv) and 4-pyrazoleboronic acid pinacol ester (928 mg, 4.8 mmol, 1.1 equiv) were taken up in MeCN (23 mL, 0.2 M) and Cs₂CO₃ (1.6 g, 4.8 mmol, 1.1 equiv) was added. The resulting mixture was stirred at room temperature for 3 h. Upon completion, the mixture was diluted with CH₂Cl₂ (20 mL) and filtered through a fritted funnel. The filtrate was concentrated in vacuo to afford 2-(6-((4-(4,4,5,5-tetramethyl-1,3,2-dioxaborolan-2-yl)-1H-pyrazol-1-yl)methyl)pyridin-2-yl)propan-2-ol which was used in subsequent reactions without further purification.

Step 3. 2-(6-{[4-(4,4,5,5-Tetramethyl-1,3,2-dioxaborolan-2-yl)-1H-pyrazol-1-yl]methyl}-2-pyridyl)-2-propanol (86 mg, 0.25 mmol, 1 equiv.), 6-(2-amino-6-chloro-4-pyrimidinyl)-2-toluonitrile (67 mg, 0.28 mmol, 1.1 equiv.), and Na₂CO₃ (53 mg, 0.5 mmol, 2 equiv.) were weighed directly into a vial. H₂O (0.5 mL) and dioxane (1 mL) were added, and the resulting suspension was degassed with N₂ for ca. 15 minutes. Pd(dppf)Cl₂ (9.2 mg, 0.013 mmol, 5 mol %) was added, and the vial was heated in an aluminum heating block set to 130° C. for 1.5 hours. The reaction mixture was cooled to room temperature, diluted with EtOAc and H₂O, and extracted. The combined organic layers were dried and concentrated. Purification by HPLC (2-100% H₂O/MeCN+ 0.1% TFA) afforded 33 mg of a white solid. ¹H NMR (400 MHz, CD₃OD) 8.48 (t, J=0.8 Hz, 1H), 8.16 (t, J=0.8 Hz, 1H), 7.79-7.72 (m, 2H), 7.68 (d, J=7.7 Hz, 1H), 7.55 (d, J=7.8 Hz, 1H), 7.47 (dd, J=8.3, 7.4 Hz, 1H), 7.09-6.92 (m, 2H), 5.49 (d, J=7.3 Hz, 2H), 2.57 (s, 3H), 1.49 (d, J=0.9 Hz, 6H). ESI MS [M+H]⁺ for C₂₄H₂₃N₇O, calcd 426.2, found 426.3.

Example 351: 6-(1-{[6-(Methoxymethyl)-2-pyridyl]methyl}-1H-pyrazol-4-yl)-4-phenyl-2-pyrimidinylamine

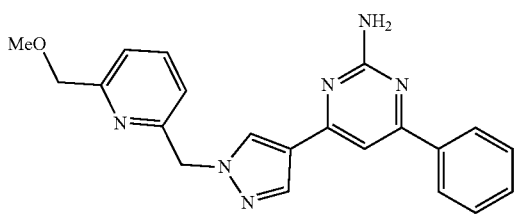 [SMILES: COCc1cccc(Cn2cc(-c3cc(-c4ccccc4)nc(N)n3)cn2)n1]

The title compound was synthesized in a similar fashion to example 350 from the corresponding boronate and chloropyrimidine derivatives. ¹H NMR (400 MHz, CDCl₃) δ 8.16 (d, J=0.7 Hz, 1H), 8.12 (d, J=0.7 Hz, 1H), 8.05-7.96 (m, 2H), 7.67 (t, J=7.8 Hz, 1H), 7.54-7.44 (m, 3H), 7.39-7.33 (m, 1H), 7.20 (s, 1H), 6.98-6.93 (m, 1H), 5.50 (s, 2H), 5.07 (s, 2H), 4.59 (s, 2H), 3.49 (s, 3H); ESI MS [M+H]⁺ for C₂₁H₂₀N₆O, calcd 373.2, found 373.2.

Example 352: 3-[2-Amino-6-(1-{[6-(tert-butyl)-2-pyridyl]methyl}-1H-pyrazol-4-yl)-4-pyrimidinyl]-2-anisonitrile

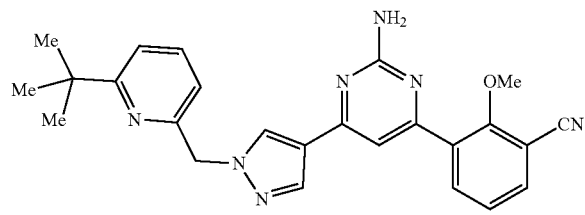 [SMILES: COc1c(C#N)cccc1-c1cc(-c2cnn(Cc3cccc(C(C)(C)C)n3)c2)nc(N)n1]

The title compound was synthesized in a similar fashion to example 350 from the corresponding boronate and chloropyrimidine derivatives. $^1$H NMR (400 MHz, CDCl$_3$) δ 8.20 s, 1H), 8.08 (s, 1H), 8.03 (dd, J=7.8, 1.8 Hz, 1H), 7.70-7.64 (m, 1H), 7.59-7.53 (m, 1H), 7.35-7.27 (m, 2H), 7.25 (d, J=6.8 Hz, 1H), 6.88 (d, J=7.6 Hz, 1H), 5.45 (s, 2H), 5.07 (s, 2H), 3.87 (s, 3H), 1.34 (s, 9H). ESI MS [M+H]$^+$ for C$_{25}$H$_{25}$N$_7$O, calcd 440.2, found 440.3.

Example 353: 3-[2-Amino-6-(1-{[6-(tert-butyl)-2-pyridyl]methyl}-1H-pyrazol-4-yl)-4-pyrimidinyl]-2-fluorobenzonitrile

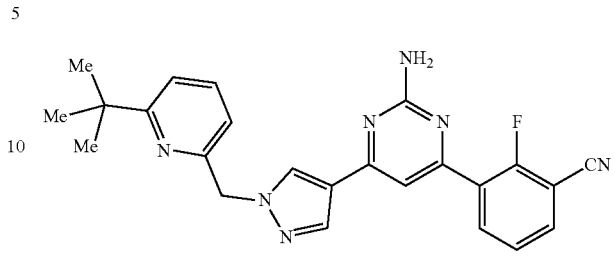

The title compound was synthesized in a similar fashion to example 350 from the corresponding boronate and chloropyrimidine derivatives. $^1$H NMR (400 MHz, CDCl$_3$) δ 8.32 (t, J=7.7, 1H), 8.22 (s, 1H), 8.09 (s, 1H), 7.71 (ddd, J=7.7, 5.8, 1.8 Hz, 1H), 7.56 (t, J=7.8 Hz, 1H), 7.38 (t, J=7.8 Hz, 1H), 7.30-7.22 (m, 2H), 6.87 (d, J=7.7 Hz, 1H), 5.45 (s, 2H), 5.12 (s, 2H), 1.35 (s, 9H). ESI MS [M+H]$^+$ for C$_{24}$H$_{22}$FN$_7$, calcd 428.2, found 428.4.

Example 354: m-[6-Amino-4-(1-{[6-(methoxymethyl)-2-pyridyl]methyl}-1H-1,2,3-triazol-4-yl)-2-pyridyl]benzonitrile

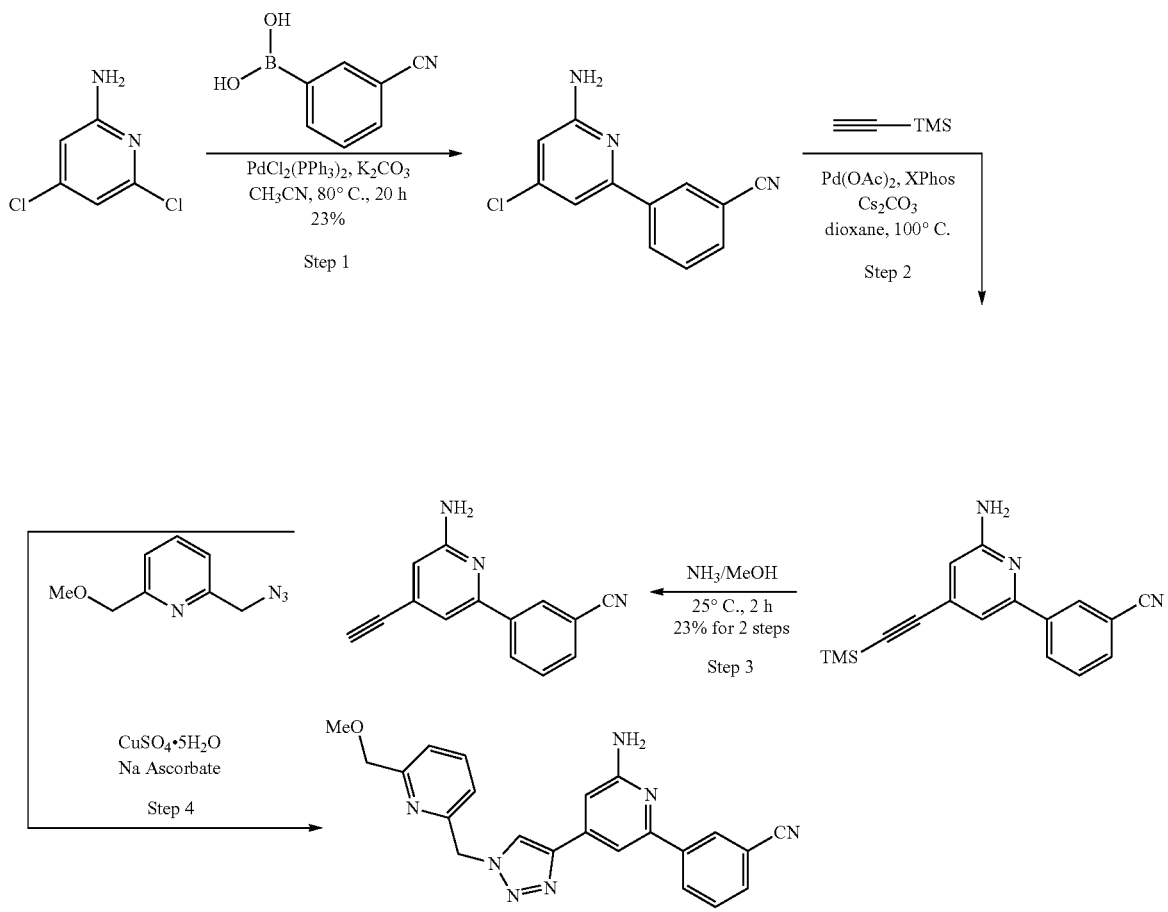

Step 1: The dichloropyridine (652 mg, 4.0 mmol, 1.0 equiv) and the boronic acid (588 mg, 4.0 mmol, 1.0 equiv) were dissolved in CH$_3$CN (16 mL, 0.25 M) in a 40 mL vial equipped with a magnetic stir bar. An aqueous solution of K$_2$CO$_3$ (2 M, 2 mL, 4.0 mmol, 1.0 equiv) was added and the resulting solution was degassed by bubbling N$_2$ for 10 minutes. Pd(PPh$_3$)$_4$ (231 mg, 0.2 mmol, 5 mol %) was then added and the mixture was heated to 80° C. for 20 hours under a nitrogen atmosphere. Upon completion, the reaction mixture was diluted with EtOAc (20 mL), filtered over Celite, and concentrated in vacuo. The crude residue was purified by flash column chromatography over silica (hexanes/EtOAc gradient 0% to 100%) to afford the product as a white solid (211 mg, 23% yield).

Step 2: The aryl chloride (336 mg, 1.5 mmol, 1.0 equiv), Pd(OAc)$_2$ (16.8 mg, 0.075 mmol, 5 mol %), XPhos (71.5 mg, 0.15 mmol, 10 mol %), and Cs$_2$CO$_3$ (1.47 g, 4.5 mmol, 3.0 equiv) were suspended in dioxane (7.5 mL, 0.2 M). The solution was degassed by bubbling N$_2$ for 5 minutes, and then stirred at room temperature for 20 minutes. TMSA (1.04 mL, 7.5 mmol, 5.0 equiv) was added via syringe and the resulting mixture was stirred at 100° C. for 3 h. Upon completion, the reaction mixture was cooled to room temperature, diluted with EtOAc (30 mL), filtered over Celite, and concentrated in vacuo to afford the crude product, which was used without further purification in step 3.

Step 3: In a 40 mL vial, the crude TMS-protected alkyne from step 2 was suspended in MeOH (2.9 mL) and a solution of ammonia in MeOH (7 N, 0.42 mL) was added. The resulting mixture was allowed to stir at room temperature for 2 h. Upon completion, the reaction mixture was concentrated in vacuo. The crude brown residue was purified by flash column chromatography over silica (hexanes/EtOAc, gradient 0% to 100%) to afford the alkyne as a pale beige solid (73.6 mg, 23% yield over two steps).

Step 4: Performed the same as in example 1. $^1$H NMR (400 MHz, DMSO-d$_6$) δ 9.09 (d, J=5.5 Hz, 1H), 8.51 (dd, J=4.6, 2.8 Hz, 1H), 8.37 (t, J=6.4 Hz, 1H), 8.06 (t, J=6.5 Hz, 1H), 7.91-7.78 (m, 2H), 7.78-7.71 (m, 1H), 7.55 (d, J=5.1 Hz, 1H), 7.40 (t, J=6.6 Hz, 1H), 7.29 (t, J=6.7 Hz, 1H), 5.86-5.80 (m, 2H), 4.47-4.41 (m, 2H), 3.35-3.29 (m, 3H); LC-MS retention time 2.290 min LC-MS, Method A, ESI MS [M+H]$^+$ for C$_{22}$H$_{20}$N$_7$O, calcd 398.2, found 398.1.

Example 355: m-[6-Amino-4-(1-{[6-(1-methoxy-ethyl)-2-pyridyl]methyl}-1H-1,2,3-triazol-4-yl)-2-pyridyl]benzonitrile

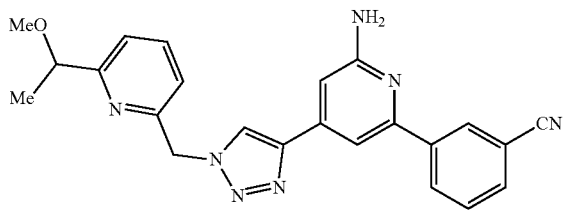 [SMILES: COC(C)c1cccc(Cn2cc(-c3cc(N)nc(-c4cccc(C#N)c4)c3)nn2)n1]

The title compound was synthesized in a similar fashion to example 354. $^1$H NMR (400 MHz, CDCl$_3$) δ 8.36-8.29 (m, 1H), 8.26-8.18 (m, 1H), 8.13-8.05 (m, 1H), 7.73 (td, J=7.7, 4.5 Hz, 1H), 7.69-7.61 (m, 1H), 7.59-7.48 (m, 2H), 7.41 (dd, J=7.9, 4.0 Hz, 1H), 7.13 (dd, J=7.7, 4.0 Hz, 1H), 7.03-6.98 (m, 1H), 5.77-5.68 (m, 2H), 4.64 (brs, 2H), 4.51-4.36 (m, 1H), 3.39-3.28 (m, 3H), 1.51-1.43 (m, 3H); LC-MS retention time 2.30 min LC-MS, Method A, ESI MS [M+H]$^+$ for C$_{23}$H$_{22}$N$_7$O, calcd 412.2, found 412.3.

Example 356: (R)-1-[6-({4-[2-Amino-6-(m-cyano-phenyl)-4-pyridyl]-1H-1,2,3-triazol-1-yl}methyl)-2-pyridyl]-2-pyrrolidinecarboxylic acid

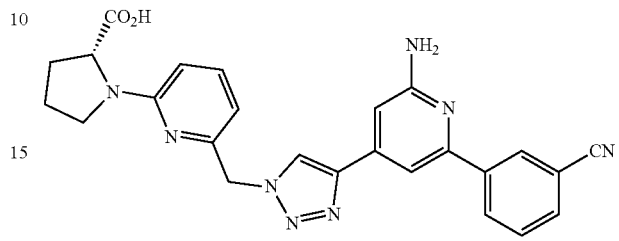

The title compound was synthesized in a similar fashion to example 354. $^1$H NMR (400 MHz, CDCl$_3$) δ 8.35 (s, 1H), 7.85 (s, 1H), 7.58-7.47 (m, 2H), 7.46-7.35 (m, 2H), 7.12 (t, J=7.8 Hz, 1H), 6.89 (d, J=1.2 Hz, 1H), 6.68 (d, J=7.2 Hz, 1H), 6.52 (d, J=8.5 Hz, 1H), 5.47 (d, J=14.1 Hz, 1H), 5.15 (d, J=14.1 Hz, 1H), 4.63 (t, J=5.8 Hz, 1H), 3.66-3.57 (m, 1H), 3.49-3.38 (m, 1H), 2.39-2.18 (m, 3H), 2.17-2.05 (m, 1H); LC-MS retention time 2.29 min LC-MS, Method A, ESI MS [M+H]$^+$ for C$_{25}$H$_{23}$N$_8$O$_2$, calcd 467.2, found 467.3.

Example 357: 1-[6-({4-[2-Amino-6-(m-cyanophenyl)-4-pyridyl]-1H-1,2,3-triazol-1-yl}methyl)-2-pyridyl]-3-pyrrolidinecarboxylic acid

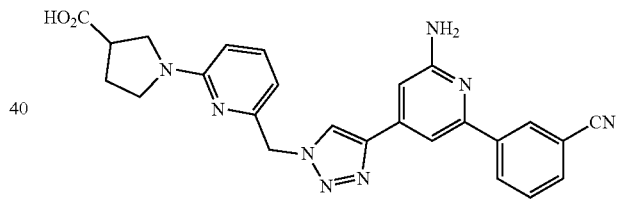

The title compound was synthesized in a similar fashion to example 354. $^1$H NMR (400 MHz, DMSO-d$_6$) δ 8.79 (s, 1H), 8.48 (s, 1H), 8.39 (d, J=8.0 Hz, 1H), 7.83 (s, 1H), 7.70-7.62 (m, 1H), 7.61 (s, 1H), 7.48 (dd, J=8.0, 8.0 Hz, 1H), 7.05 (s, 1H), 6.49-6.35 (m, 2H), 6.26 (s, 2H), 5.56 (s, 2H), 3.62-3.20 (m, 5H), 2.20-2.02 (m, 2H). MS [M+H]$^+$ for C$_{25}$H$_{22}$N$_8$O$_2$, calcd 467.2, found: 467.3.

Example 358: 1-[6-({4-[2-Amino-6-(m-cyanophenyl)-4-pyridyl]-1H-1,2,3-triazol-1-yl}methyl)-2-pyridyl]-4-piperidinecarboxylic acid

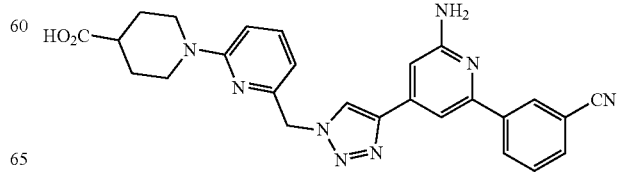

The title compound was synthesized in a similar fashion to example 354. $^1$H NMR (400 MHz, CDCl$_3$) δ 8.35 (s, 1H), 8.16 (s, 1H), 8.10-8.01 (m, 1H), 7.71-7.63 (m, 1H), 7.57-7.49 (m, 2H), 7.49-7.42 (m, 1H), 6.92-6.87 (m, 1H), 6.69 (d, J=8.7 Hz, 1H), 6.62 (d, J=7.1 Hz, 1H), 5.49 (s, 2H), 4.45-4.34 (m, 2H), 3.14-3.01 (m, 2H), 2.72-2.59 (m, 1H), 2.11-1.93 (m, 2H), 1.79-1.60 (m, 2H); LC-MS retention time 2.27 min LC-MS, Method A, ESI MS [M+H]$^+$ for C$_{26}$H$_{25}$N$_8$O$_2$, calcd 481.2, found 481.3.

Example 359: 1—[(R)-1-[6-({4-[2-Amino-6-(m-cyanophenyl)-4-pyridyl]-1H-1,2,3-triazol-1-yl}methyl)-2-pyridyl]ethyl]-4-piperidinecarboxylic acid tion, the reaction mixture was concentrated in vacuo and the resulting residue was purified by flash column chromatography over silica (CH$_2$Cl$_2$/MeOH) to afford the product (292 mg, 71% yield).

Step 2: To an ice-cooled solution of the TBS-protected alcohol (292 mg, 0.744 mmol, 1.0 equiv) in THF (1.9 mL, 0.4 M) was added TBAF (1 M solution in THF, 0.74 mL, 0.74 mmol, 1.0 equiv) dropwise. The resulting solution was stirred at 0° C. for 30 minutes. Upon completion, the reaction mixture was concentrated in vacuo and the resulting residue was purified by flash column chromatography over silica (CH$_2$Cl$_2$/MeOH gradient) to afford the product as a colorless oil (190 mg, 92% yield).

Step 3: To a solution of the alcohol (180 mg, 0.647 mmol, 1.0 equiv) in 1,2-DCE (0.72 mL, 0.9 M) at room temperature

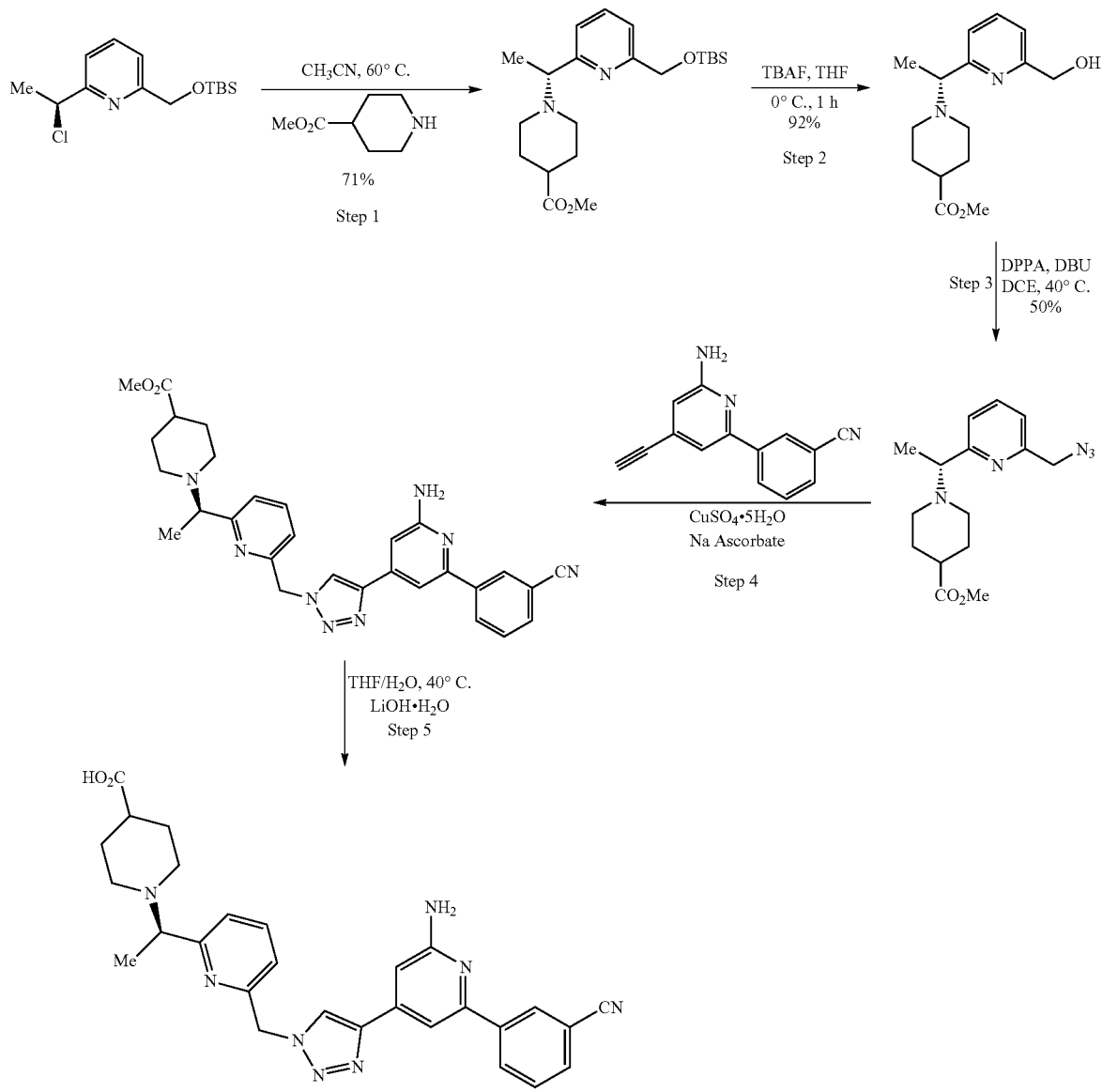

Step 1: The pyridyl chloride (297 mg, 1.04 mmol, 1.0 equiv) and the piperidine (476 mg, 3.33 mmol, 3.2 equiv) were dissolved in dry CH$_3$CN (1.73 mL). The reaction mixture was then stirred at 60° C. for 3.5 h. Upon complewas added DPPA (0.17 mL, 0.776 mmol, 1.2 equiv), followed by DBU (0.12 mL, 0.776 mmol, 1.2 equiv). The resulting mixture was stirred at room temperature for 10 minutes and then at 40° C. for 4 h. Upon completion, the reaction mixture was concentrated in vacuo and the resulting residue was purified by flash column chromatography over silica (hexanes/EtOAc) to afford the product as a pale beige oil (98.6 mg, 50% yield).

Steps 4 and 5: Performed the same as in example 125. $^1$H NMR (400 MHz, DMSO-$d_6$) δ 10.44 (s, 1H), 8.97 (s, 1H), 8.46 (s, 1H), 8.38 (d, J=8.0 Hz, 1H), 7.97 (t, J=7.8 Hz, 1H), 7.84 (d, J=7.7 Hz, 1H), 7.70-7.61 (m, 2H), 7.58 (d, J=7.7 Hz, 1H), 7.46 (d, J=8.0 Hz, 1H), 7.06 (s, 1H), 6.27 (s, 2H), 5.87 (s, 2H), 4.64-4.45 (m, 1H), 3.62-3.46 (m, 1H), 3.24-3.05 (m, 1H), 2.88-2.54 (m, 2H), 2.45-2.20 (m, 1H), 1.96-1.64 (m, 4H), 1.56 (d, J=6.8 Hz, 3H); LC-MS retention time 2.02 min LC-MS, Method A, ESI MS [M+H]$^+$ for $C_2H_{29}N_8O_2$, calcd 509.2, found 509.3.

Example 360: 1—[(S)-1-[6-({4-[2-Amino-6-(m-cyanophenyl)-4-pyridyl]-1H-1,2,3-triazol-1-yl}methyl)-2-pyridyl]ethyl]-4-piperidinecarboxylic acid

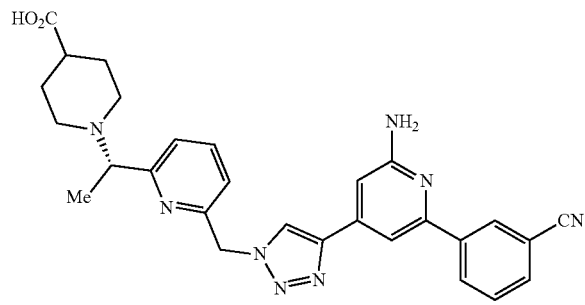 [SMILES: C[C@@H](c1cccc(Cn2cc(-c3cc(N)nc(-c4cccc(C#N)c4)c3)nn2)n1)N1CCC(C(=O)O)CC1]

The title compound was synthesized in a similar fashion to example 359. $^1$H NMR (400 MHz, DMSO-$d_6$) δ 10.26 (s, 1H), 9.01 (s, 1H), 8.46 (s, 1H), 8.37 (d, J=8.1 Hz, 1H), 7.97 (t, J=7.8 Hz, 1H), 7.92-7.82 (m, 1H), 7.73-7.63 (m, 2H), 7.56 (d, J=7.7 Hz, 1H), 7.48 (d, J=7.8 Hz, 1H), 7.15 (s, 1H), 5.88 (s, 2H), 4.63-4.49 (m, 1H), 3.61-3.50 (m, 1H), 3.21-3.10 (m, 1H), 2.88-2.56 (m, 2H), 2.38-2.22 (m, 1H), 1.96-1.63 (m, 4H), 1.56 (d, J=6.7 Hz, 3H); LC-MS retention time 2.02 min LC-MS, Method A, ESI MS [M+H]$^+$ for $C_{28}H_{29}N_8O_2$, calcd 509.2, found 509.3.

Example 361: 1—[(S)-1-[6-({4-[2-Amino-6-(m-cyanophenyl)-4-pyridyl]-1H-1,2,3-triazol-1-yl}methyl)-2-pyridyl]propyl]-4-piperidinecarboxylic acid

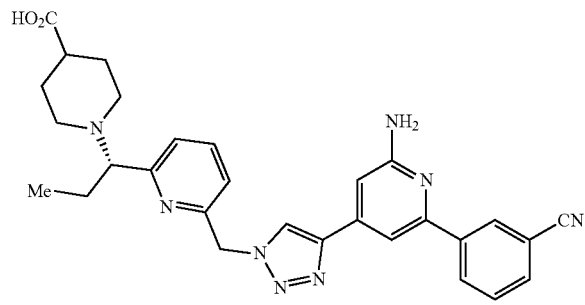 [SMILES: CC[C@@H](c1cccc(Cn2cc(-c3cc(N)nc(-c4cccc(C#N)c4)c3)nn2)n1)N1CCC(C(=O)O)CC1]

The title compound was synthesized in a similar fashion to example 359. $^1$H NMR (400 MHz, DMSO-$d_6$) δ 10.96 (s, 1H), 9.31 (s, 1H), 8.54 (d, J=1.9 Hz, 1H), 8.42 (d, J=8.1 Hz, 1H), 8.06-7.95 (m, 2H), 7.85 (s, 1H), 7.77 (t, J=7.8 Hz, 1H), 7.58 (dd, J=7.9, 3.3 Hz, 2H), 5.98-5.91 (m, 2H), 4.34 (d, J=10.8 Hz, 1H), 3.63-3.52 (m, 1H), 3.21-3.09 (m, 1H), 2.80-2.63 (m, 1H), 2.27-1.61 (m, 8H), 0.59 (t, J=7.3 Hz, 3H); LC-MS retention time 2.08 min LC-MS, Method A, ESI MS [M+H]$^+$ for $C_{29}H_{31}N_8O_2$, calcd 523.3, found 523.3.

Example 362: [6-(m-Cyanophenyl)-4-(1-{[6-(tert-butyl)-2-pyridyl]methyl}-1H-1,2,3-triazol-4-yl)-2-pyridylamino]acetic acid

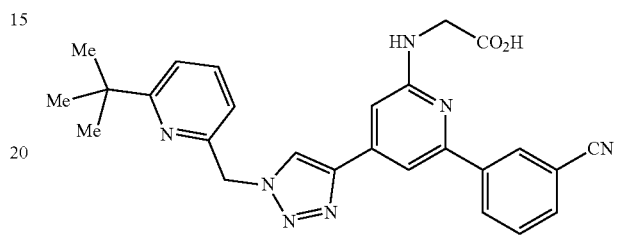

The title compound was synthesized in a similar fashion to example 354. $^1$H NMR (400 MHz, CDCl$_3$) δ 8.33-8.09 (m, 2H), 7.63-7.33 (m, 4H), 7.04-6.86 (m, 3H), 5.63 (s, 2H), 4.21 (s, 2H), 1.31 (s, 9H); LC-MS retention time 3.35 min LC-MS, Method A, ESI MS [M+H]$^+$ for $C_{26}H_{26}N_7O_2$, calcd 468.2, found 468.3.

Example 363: (S)-1-{6-[(4-{2-[(S)-2-Methoxy-1-phenylethylamino]-6-(m-cyanophenyl)-4-pyridyl}-1H-1,2,3-triazol-1-yl)methyl]-2-pyridyl}-3-pyrrolidinecarboxylic acid

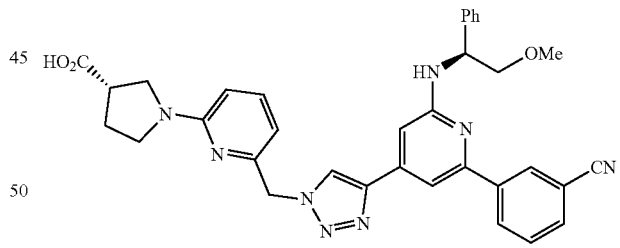

The title compound was synthesized in a similar fashion to example 354. $^1$H NMR (400 MHz, CDCl$_3$) δ 8.45 (s, 1H), 8.12-8.02 (m, 2H), 7.64-7.53 (m, 2H), 7.52-7.34 (m, 5H), 7.33-7.22 (m, 2H), 6.84 (s, 1H), 6.65-6.56 (m, 1H), 6.34 (d, J=8.5 Hz, 1H), 5.62-5.39 (m, 2H), 5.30 (s, 2H), 5.21 (dd, J=8.4, 3.9 Hz, 1H), 4.01-3.65 (m, 2H), 3.60-3.48 (m, 1H), 3.46 (s, 3H), 3.37-3.14 (m, 1H), 2.44-2.23 (m, 2H), 1.32-1.17 (m, 1H); LC-MS retention time 3.25 min LC-MS, Method A, ESI MS [M+H]$^+$ for $C_{34}H_{33}N_8O_3$, calcd 601.3, found 601.4.

Example 364: (S)-1-{6-[(4-{2-[(R)-2-Methoxy-1-phenylethylamino]-6-(m-cyanophenyl)-4-pyridyl}-1H-1,2,3-triazol-1-yl)methyl]-2-pyridyl}-3-pyrrolidinecarboxylic acid

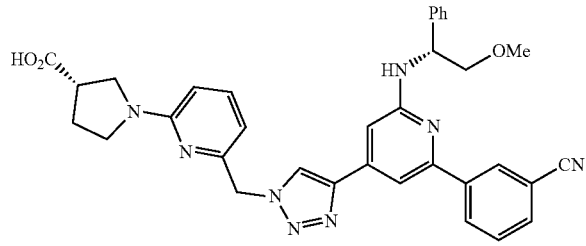 [SMILES: COC[C@H](Nc1cc(-c2cn(Cc3cccc(N4CC[C@H](C(=O)O)C4)n3)nn2)cc(-c2cccc(C#N)c2)n1)c1ccccc1]

The title compound was synthesized in a similar fashion to example 354. $^1$H NMR (400 MHz, CDCl$_3$) δ 8.47 (s, 1H), 8.11-8.04 (m, 2H), 7.62-7.53 (m, 2H), 7.51-7.35 (m, 5H), 7.33-7.23 (m, 2H), 6.84 (s, 1H), 6.62-6.55 (m, 1H), 6.36-6.30 (m, 1H), 5.60-5.40 (m, 2H), 5.30 (s, 2H), 5.19 (dd, J=8.2, 4.0 Hz, 1H), 3.96-3.70 (m, 2H), 3.65-3.47 (m, 1H), 3.46 (s, 3H), 3.37-3.12 (m, 1H), 2.43-2.18 (m, 2H), 1.33-1.18 (m, 1H); LC-MS retention time 3.25 min LC-MS, Method A, ESI MS [M+H]$^+$ for C$_{34}$H$_{33}$N$_8$O$_3$, calcd 601.3, found 601.4.

Example 365: m-[4-(1-{[6-(Methoxymethyl)-2-pyridyl]methyl}-1H-1,2,3-triazol-4-yl)-6-(2-phenoxyacetylamino)-2-pyridyl]benzonitrile

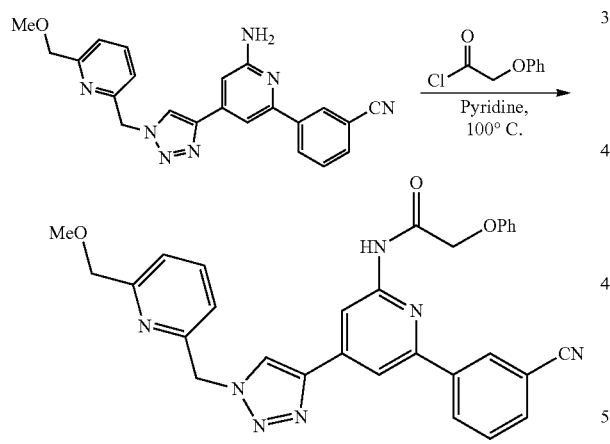

Experimental: To a solution of the aminopyridine (30.6 mg, 76.9 μmol, 1.0 equiv) in pyridine (0.3 mL) in a glass vial was added 2-phenoxyacetyl chloride (0.01 mL, 76.9 μmol, 1.0 equiv). The resulting solution was stirred at 100° C. for 1 h. Upon completion, the reaction mixture was cooled to 25° C. and concentrated in vacuo. The crude residue was purified by flash column chromatography (CH$_2$Cl$_2$/MeOH) to afford the product (15 mg, 25% yield). $^1$H NMR (400 MHz, CDCl$_3$) δ 9.10-8.97 (m, 1H), 8.56-8.48 (m, 1H), 8.47-8.40 (m, 1H), 8.33-8.25 (m, 2H), 8.25-8.18 (m, 1H), 7.79-7.67 (m, 2H), 7.65-7.55 (m, 1H), 7.48-7.35 (m, 3H), 7.17 (t, J=7.0 Hz, 1H), 7.12-7.03 (m, 3H), 5.75 (s, 2H), 4.68 (s, 2H), 4.61 (s, 2H), 3.51 (s, 3H); LC-MS retention time 3.38 min LC-MS, Method A, ESI MS [M+H]$^+$ for C$_{30}$H$_{26}$N$_7$O$_3$, calcd 532.2, found 532.3.

Example 366: 1-[6-({4-[6-(m-Cyanophenyl)-2-(2-methoxyacetylamino)-4-pyridyl]-1H-1,2,3-triazol-1-yl}methyl)-2-pyridyl]-4-piperidinecarboxylic acid

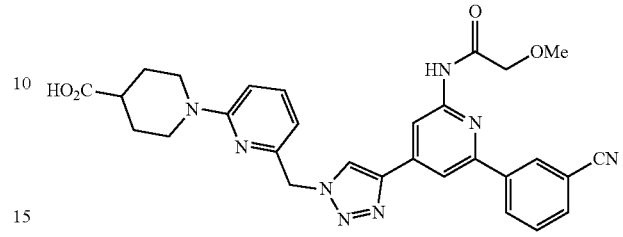

The title compound was synthesized in a similar fashion to example 365. $^1$H NMR (400 MHz, Acetone-d6) δ 9.22 (s, 1H), 8.84-8.77 (m, 2H), 8.57-8.54 (m, 1H), 8.53-8.46 (m, 1H), 8.32-8.26 (m, 1H), 7.89-7.81 (m, 1H), 7.74 (t, J=7.9 Hz, 1H), 7.57-7.47 (m, 1H), 6.79 (d, J=8.5 Hz, 1H), 6.60 (d, J=7.3 Hz, 1H), 5.65 (s, 2H), 4.34-4.20 (m, 2H), 4.13 (s, 2H), 3.55 (s, 3H), 3.07-2.92 (m, 2H), 2.66-2.48 (m, 1H), 1.99-1.82 (m, 2H), 1.71-1.51 (m, 2H); LC-MS retention time 3.13 min LC-MS, Method A, ESI MS [M+H]$^+$ for C$_{29}$H$_{29}$N$_8$O$_4$, calcd 553.2, found 553.4.

Example 367: m-[6-(2-Methoxyacetylamino)-4-(1-{[6-(1-methoxyethyl)-2-pyridyl]methyl}-1H-1,2,3-triazol-4-yl)-2-pyridyl]benzonitrile

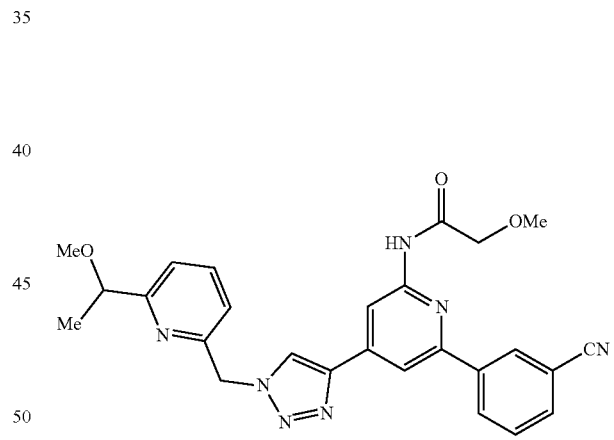

The title compound was synthesized in a similar fashion to example 365. $^1$H NMR (400 MHz, CDCl$_3$) δ 8.98 (s, 1H), 8.50-8.36 (m, 2H), 8.32-8.18 (m, 3H), 7.77-7.67 (m, 2H), 7.58 (tt, J=7.8, 0.8 Hz, 1H), 7.41 (d, J=7.8 Hz, 1H), 7.11 (dd, J=7.6, 1.2 Hz, 1H), 5.73 (s, 2H), 4.48-4.37 (m, 1H), 4.07 (s, 2H), 3.56 (s, 3H), 1.47 (d, J=6.6 Hz, 3H); LC-MS retention time 2.25 min LC-MS, Method A, ESI MS [M+H]$^+$ for C$_{26}$H$_{26}$N$_7$O$_3$, calcd 484.2, found 484.3.

Example 368: m-[6-(2-Ethoxyacetylamino)-4-(1-{[6-(1-methoxyethyl)-2-pyridyl]methyl}-1H-1,2,3-triazol-4-yl)-2-pyridyl]benzonitrile

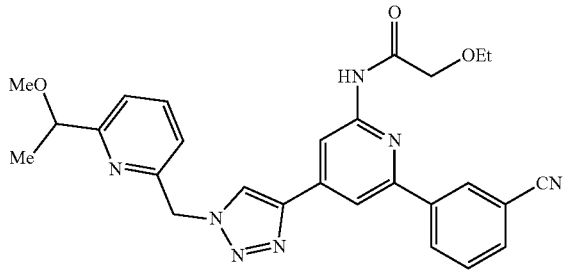 [SMILES: CCOCC(=O)Nc1cc(-c2cn(Cc3cccc(C(C)OC)n3)nn2)cc(-c2cccc(C#N)c2)n1]

The title compound was synthesized in a similar fashion to example 365. ¹H NMR (400 MHz, CDCl₃) δ 9.02 (s, 1H), 8.48 (d, J=1.2 Hz, 1H), 8.44 (t, J=1.7 Hz, 1H), 8.29 (dt, J=8.1, 1.5 Hz, 1H), 8.27 (d, J=1.2 Hz, 1H), 8.22 (s, 1H), 7.76-7.68 (m, 2H), 7.59 (t, J=7.8 Hz, 1H), 7.45-7.38 (m, 1H), 7.11 (d, J=7.6 Hz, 1H), 5.74 (s, 2H), 4.44 (q, J=6.5 Hz, 1H), 4.11 (s, 2H), 3.72 (q, J=7.0 Hz, 2H), 3.34 (s, 3H), 1.47 (d, J=6.5 Hz, 3H), 1.37 (t, J=7.0 Hz, 3H); LC-MS retention time 3.27 min LC-MS, Method A, ESI MS [M+H]⁺ for $C_{27}H_{29}N_7O_3$, calcd 499.2, found 499.3.

Example 369: m-[4-(1-{[6-(1-Methoxyethyl)-2-pyridyl]methyl}-1H-1,2,3-triazol-4-yl)-6-(2-phenoxyacetylamino)-2-pyridyl]benzonitrile

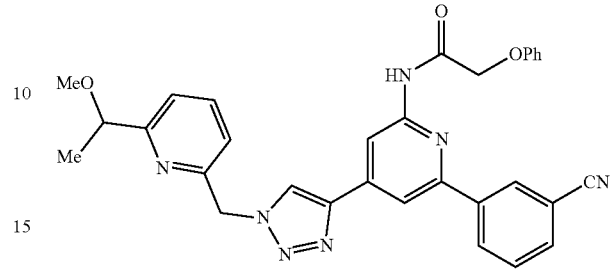

The title compound was synthesized in a similar fashion to example 365. ¹H NMR (400 MHz, CDCl₃) δ 9.05 (s, 1H), 8.52 (d, J=1.2 Hz, 1H), 8.43 (t, J=1.8 Hz, 1H), 8.32-8.20 (m, 3H), 7.78-7.66 (m, 2H), 7.60 (t, J=7.8 Hz, 1H), 7.45-7.32 (m, 2H), 7.15-6.99 (m, 4H), 5.75 (s, 2H), 4.68 (s, 2H), 4.45 (q, J=6.5 Hz, 1H), 3.35 (s, 3H), 1.48 (d, J=6.8 Hz, 2H); LC-MS retention time 3.59 min LC-MS, Method A, ESI MS [M+H]⁺ for $C_{31}H_{28}N_7O_3$, calcd 546.2, found 546.3.

Example 370: m-[6-Amino-2-(1-{[6-(methoxymethyl)-2-pyridyl]methyl}-1H-1,2,3-triazol-4-yl)-4-pyridyl]benzonitrile

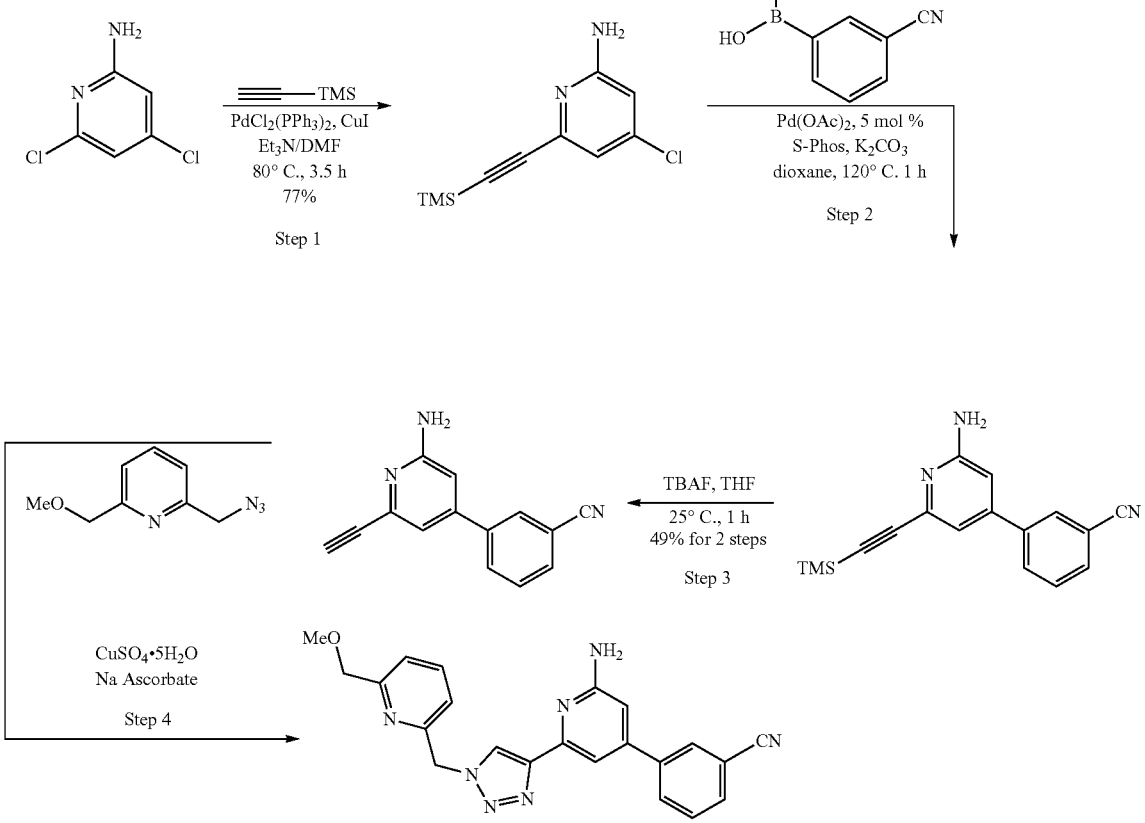

Step 1: The dichloropyridine (652 mg, 4.0 mmol, 1.0 equiv), PdCl$_2$(PPh$_3$)$_2$ (140 mg, 0.2 mmol, 5 mol %), and CuI (76 mg, 0.4 mmol, 10 mol %) were combined in Et$_3$N/DMF (1:1, 16 mL, 0.25 M) in a 40 mL vial equipped with a magnetic stir bar. The resulting mixture was degassed by bubbling N$_2$ for 10 minutes. Then, TMSA (2.2 mL, 16 mmol, 4.0 equiv) was added via syringe and the resulting mixture was stirred at 80° C. for 3 h. Upon completion, the reaction mixture was cooled to room temperature and concentrated in vacuo. The resulting mixture was re-dissolved in EtOAc (30 mL) and filtered over Celite. The mixture was again concentrated in vacuo and the resulting residue was purified by flash column chromatography over silica (hexanes/EtOAc, gradient 0% to 100%) to afford the TMS-protected alkyne (692 mg, 77% yield).

Step 2: The chloropyridine (334 mg, 1.34 mmol, 1.0 equiv) and the boronic acid (196 mg, 1.34 mmol, 1.0 equiv) were combined in dioxane (4.5 mL, 0.3 M). An aqueous solution of K$_2$CO$_3$ (2 M, 0.67 mL, 1.34 mmol, 1.0 equiv) was added and the resulting solution was degassed by bubbling N$_2$ for 10 minutes. Pd(OAc)$_2$ (15 mg, 0.067 mmol, 5 mol %) and S-Phos (55 mg, 0.134 mmol, 10 mol %) were added and the reaction mixture was stirred at 120° C. for 1 h. Upon completion, the reaction mixture was cooled to room temperature, diluted with EtOAc (20 mL), filtered over Celite, and concentrated in vacuo to afford the crude product, which was used without further purification in step 3.

Step 3: In a 40 mL vial, the crude TMS-protected alkyne from step 2 was dissolved in THF (2.7 mL) and a solution of TBAF (1 M, 1.34 mL) was added dropwise at room temperature. The resulting mixture was stirred at room temperature for 1 h. Upon completion, the reaction mixture was concentrated in vacuo and the crude residue was purified by flash column chromatography over silica (hexanes/EtOAc, gradient 0% to 100%) to afford the product as a beige solid (145 mg, 49% yield over two steps).

Step 4: Performed the same as in example 1. $^1$H NMR (400 MHz, CDCl$_3$) δ 8.18 (s, 1H), 7.97-7.87 (m, 2H), 7.76 (d, J=1.4 Hz, 1H), 7.73-7.66 (m, 2H), 7.58 (td, J=7.8, 0.7 Hz, 1H), 7.40 (d, J=7.7 Hz, 1H), 7.08 (d, J=7.6 Hz, 1H), 6.61 (d, J=1.5 Hz, 1H), 5.72 (s, 2H), 4.62-4.54 (m, 4H), 3.50 (s, 3H); LC-MS retention time 2.25 min LC-MS, Method A, ESI MS [M+H]$^+$ for C$_{22}$H$_{20}$N$_7$O, calcd 398.2, found 398.2.

Example 371: m-[6-Amino-4-(1-{[6-(methoxymethyl)-2-pyridyl]methyl}-1H-1,2,3-triazol-4-yl)-2-pyrimidinyl]benzonitrile

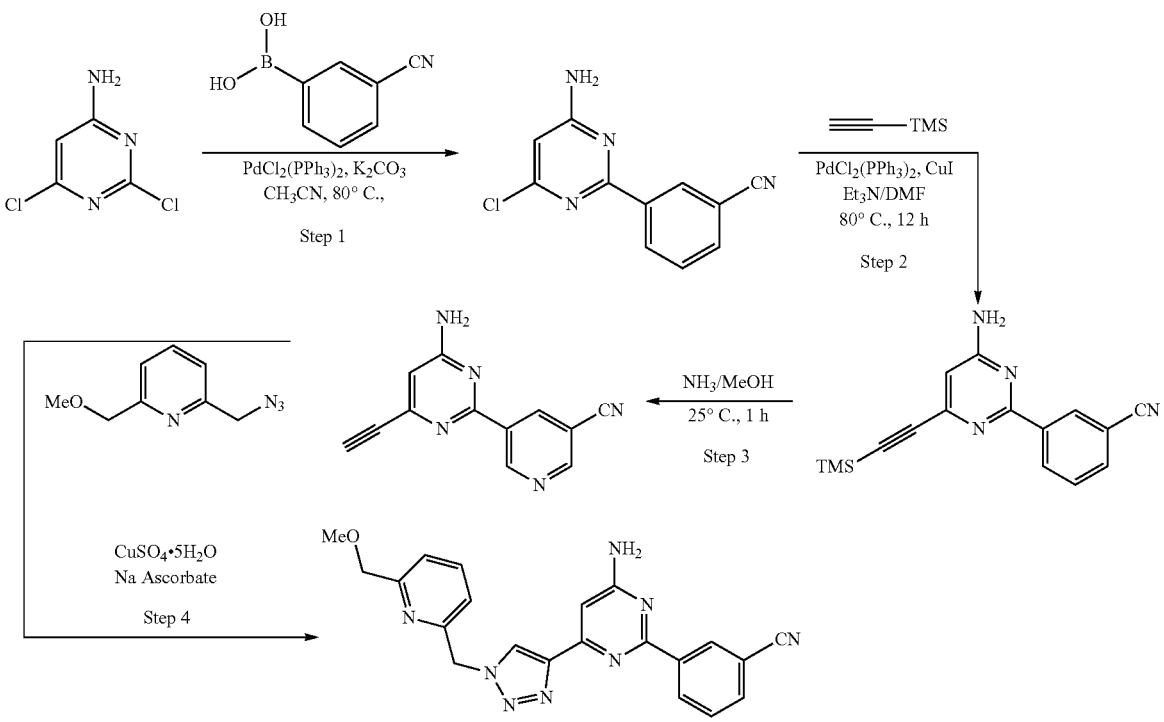

Step 1: The dichloropyridine (656 mg, 4.0 mmol, 1.0 equiv) and the boronic acid (588 mg, 4.0 mmol, 1.0 equiv) were dissolved in CH$_3$CN (16 mL, 0.25 M) in a 40 mL vial equipped with a magnetic stir bar. An aqueous solution of K$_2$CO$_3$ (2 M, 2 mL, 4.0 mmol, 1.0 equiv) was added and the resulting solution was degassed by bubbling N$_2$ for 10 minutes. Pd(PPh$_3$)$_4$ (231 mg, 0.2 mmol, 5 mol %) was then added and the mixture was heated to 80° C. for 12 hours under a nitrogen atmosphere. Upon completion, the reaction mixture was diluted with EtOAc (20 mL), filtered over Celite, and concentrated in vacuo. The crude residue was purified by flash column chromatography over silica (hexanes/EtOAc gradient 0% to 100%) to afford the product as a white solid (360.4 mg, 39% yield).

Step 2: The diaryl chloride (360 mg, 1.56 mmol, 1.0 equiv), PdCl$_2$(PPh$_3$)$_2$ (54.8 mg, 0.0781 mmol, 5 mol %), and CuI (29.8 mg, 0.156 mmol, 10 mol %) were combined in Et$_3$N/DMF (1:1, 6.24 mL, 0.25 M) in a 40 mL vial equipped with a magnetic stir bar. The resulting mixture was degassed by bubbling N$_2$ for 10 minutes. Then, TMSA (0.86 mL, 6.25 mmol, 4.0 equiv) was added via syringe and the resulting mixture was stirred at 80° C. for 3 h. Upon completion, the reaction mixture was cooled to room temperature and concentrated in vacuo. The resulting mixture was re-dissolved in EtOAc (10 mL) and filtered over Celite. The mixture was again concentrated in vacuo and the resulting residue was used directly in the next step without further purification.

Step 3: In a 40 mL vial, the crude TMS-protected alkyne from step 2 was suspended in MeOH (3.12 mL) and a solution of ammonia in MeOH (7 N, 0.90 mL) was added. The resulting mixture was allowed to stir at room temperature for 2 h. Upon completion, the reaction mixture was concentrated in vacuo. The crude brown residue was purified by flash column chromatography over silica (hexanes/EtOAc, gradient 0% to 100%) to afford the alkyne as a pale brown solid (59.7 mg, 17% yield over two steps).

Step 4: Performed the same as in example 1. $^1$H NMR (400 MHz, DMSO-$d_6$) δ 8.99 (s, 1H), 8.74 (s, 1H), 8.65 (dt, J=8.0, 1.4 Hz, 1H), 7.98 (dt, J=7.7, 1.4 Hz, 1H), 7.87 (t, J=7.7 Hz, 1H), 7.73 (t, J=7.8 Hz, 1H), 7.40 (d, J=7.7 Hz, 1H), 7.23 (d, J=7.7 Hz, 1H), 7.12 (s, 1H), 5.81 (s, 2H), 4.48 (s, 2H), 3.35 (s, 3H); LC-MS retention time 2.07 min LC-MS, Method A, ESI MS [M+H]$^+$ for $C_{21}H_{19}N_8O$, calcd 399.2, found 399.2.

Example 372: 2-({4-[2-Amino-6-(3-cyano-2-methylphenyl)pyrimidin-4-yl]-1H-1,2,3-triazol-1-yl}methyl)-6-(2-hydroxypropan-2-yl)pyridin-1-ium-1-olate

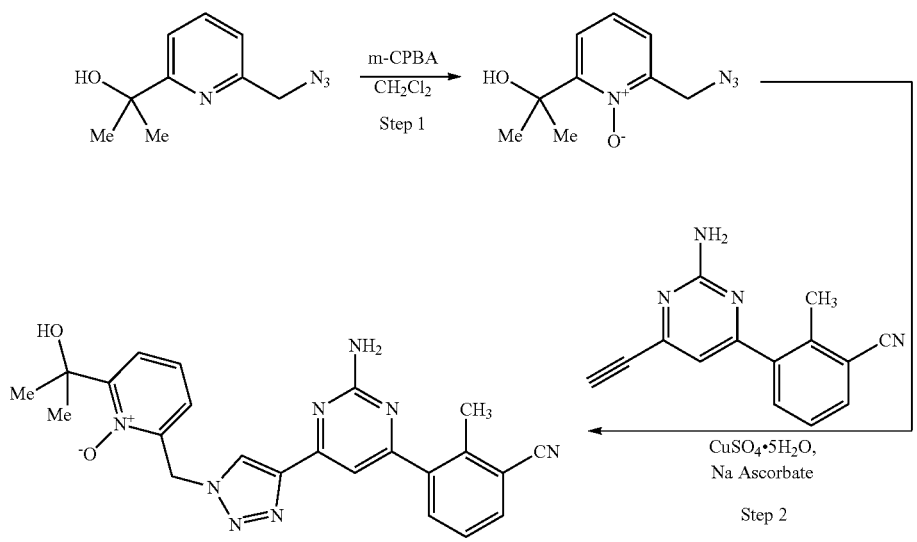

Step 1. m-CPBA (~75 wt. %, 507 mg, 2.2 mmol, 1.1 equiv.) was added to a stirring solution of the azide (example 1, step 5 product, 384 mg, 2 mmol, 1 equiv.) at room temperature. The mixture stirred until the reaction was complete as determined by LC-MS analysis. The mixture was concentrated and purified by flash chromatography on $SiO_2$ to afford the N-oxide derivative as yellow oil (366 mg, 88% yield).

Step 2. Performed the same as in example 1, step 6 to afford the title compound as a light brown solid. $^1$H NMR (400 MHz, CDCl$_3$) δ 8.58 (s, 1H), 7.72-7.68 (m, 1H), 7.68-7.64 (m, 1H), 7.52 (d, J=1.2 Hz, 1H), 7.48-7.33 (m, 4H), 7.16 (dd, J=7.7, 2.0 Hz, 1H), 5.91 (s, 2H), 5.17 (bs, 2H), 2.66-2.57 (m, 3H), 1.69 (d, J=1.1 Hz, 6H). ESI MS [M+H]$^+$ for $C_{23}H_{22}N_8O_2$, calcd 443.2, found 443.4.

Example 373: 3-{2-Amino-6-[1-({6-[2-hydroxy($^2H_6$)propan-2-yl]pyridin-2-yl}methyl)-1H-1,2,3-triazol-4-yl]pyrimidin-4-yl}-2-methylbenzonitrile

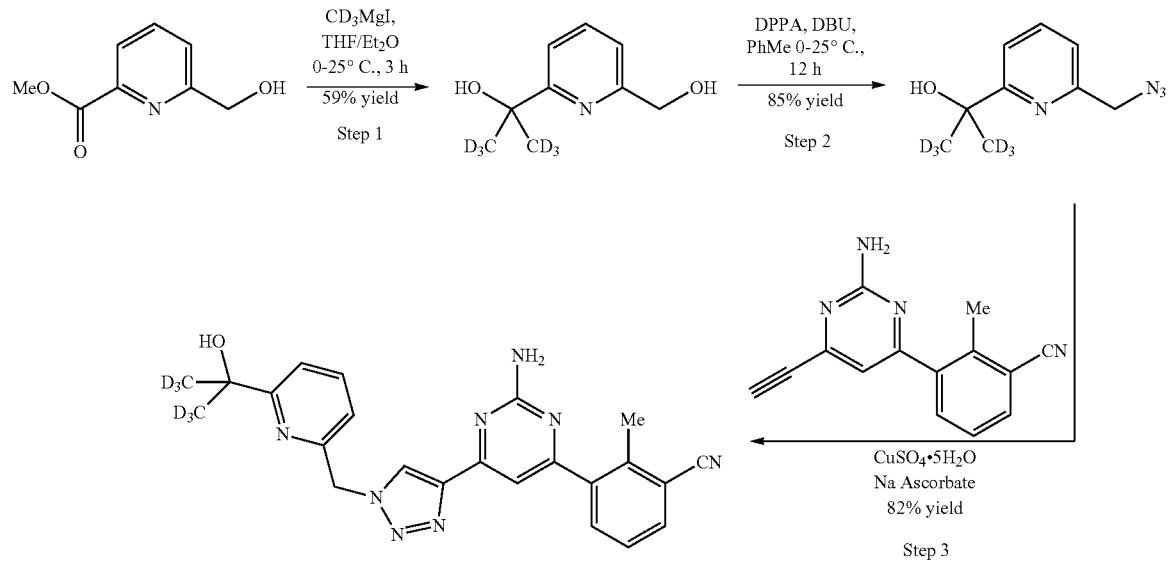

Step 1: To an ice-cooled solution of methyl-d$_3$-magnesium iodide (47.9 mL, 47.8 mmol, 1 M, 4.0 equiv.) under N2 was added a solution of the pyridyl ester (2.00 g, 12.0 mmol, 1.0 equiv) in THF (22.0 mL, 0.54 M) over the course of 30 minutes. The ice bath was then removed and the reaction mixture was allowed to stir at 25° C. for 3 h. Upon completion, the reaction mixture was cooled to 0° C. and quenched by dropwise addition of saturated aqueous NH$_4$Cl (50 mL). The mixture was extracted with EtOAc (3×50 mL). The combined organic extracts were dried (Na$_2$SO$_4$), filtered, and concentrated in vacuo. The resulting residue was purified by flash column chromatography over silica (1:1 hexanes/EtOAc) to afford the product (1.22 g, 59% yield).

Steps 2 and 3: Performed the same as in example 1. $^1$H NMR (400 MHz, CDCl$_3$) δ 8.31 (s, 1H), 7.77-7.62 (m, 3H), 7.54 (s, 1H), 7.43-7.34 (m, 2H), 7.14 (d, J=7.6 Hz, 1H), 5.75 (s, 2H), 5.11 (s, 2H), 4.69 (s, 1H), 2.63 (s, 3H); LC-MS retention time 2.71 min LC-MS, Method A, ESI MS [M+H+]$^+$ for C$_{23}$H$_{17}$D6N$_8$O, calcd 433.2, found 433.3.

Biological Example

Particular compounds were evaluated for adenosine A$_{2A}$ receptor activity as described for the cAMP assay above. K$_B$ is a measure of antagonism/inhibition (similar to an IC$_{50}$). Results are provided in Table 1.

TABLE 1

Specific Examples (Potency: A$_{2A}$R IC$_{50}$/K$_B$: + means >1 μM, ++ means 100 nM to 1 μM, +++ means <100 nM)

TABLE 1-continued
Specific Examples (Potency: A$_{2A}$R IC$_{50}$/K$_B$: + means >1 µM, ++ means 100 nM to 1 µM, +++ means <100 nM)
| | Potency |
|---|---|
| 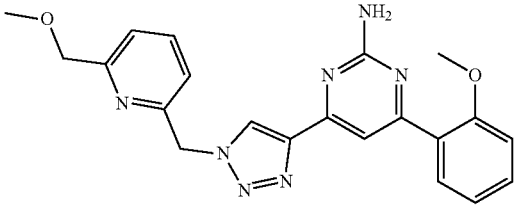 [SMILES: COCc1cccc(Cn2cc(-c3cc(-c4ccccc4OC)nc(N)n3)nn2)n1] | ++ |
| 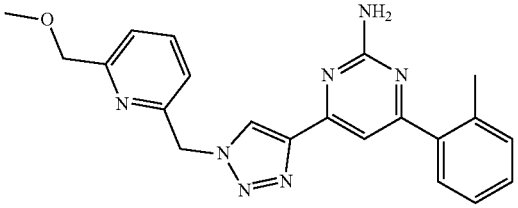 [SMILES: COCc1cccc(Cn2cc(-c3cc(-c4ccccc4C)nc(N)n3)nn2)n1] | ++ |
| 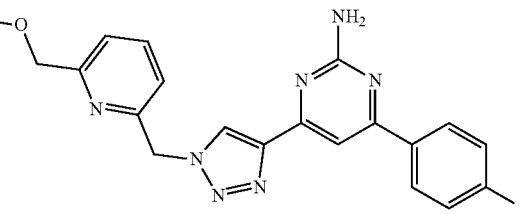 | +++ |
| 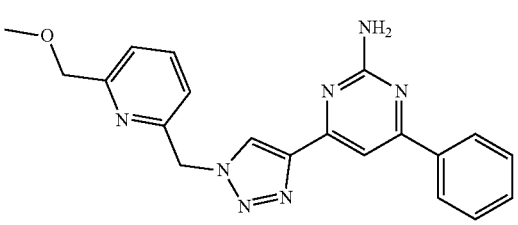 [SMILES: COCc1cccc(Cn2cc(-c3cc(-c4ccccc4)nc(N)n3)nn2)n1] | +++ |
| 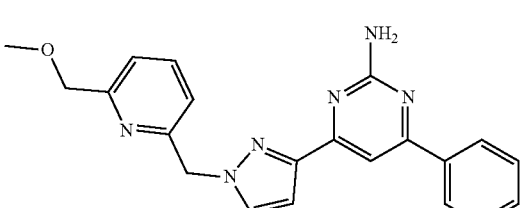 | ++ |
| 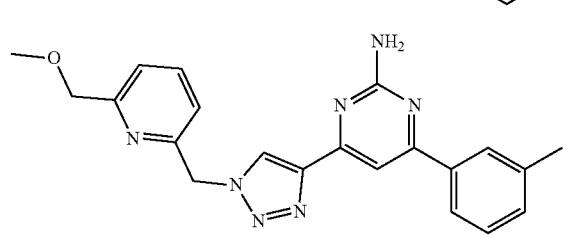 | +++ |
| 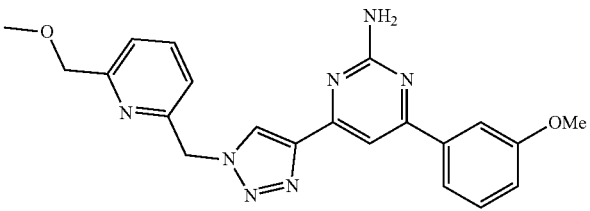 [SMILES: COCc1cccc(Cn2cc(-c3cc(-c4cccc(OC)c4)nc(N)n3)nn2)n1] | +++ |

TABLE 1-continued
Specific Examples (Potency: $A_{2A}R$ $IC_{50}/K_B$: + means >1 µM, ++ means 100 nM to 1 µM, +++ means <100 nM)
| Structure | Potency |
|---|---|
| 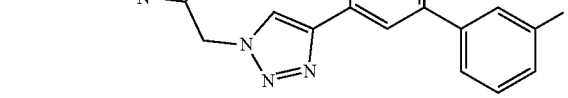 | +++ |
|  | +++ |
| 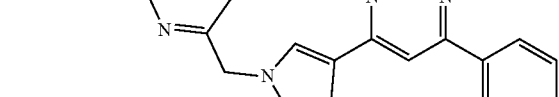 | +++ |
| 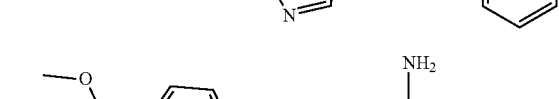 | +++ |
| 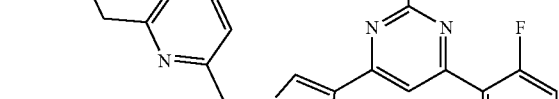 | +++ |
| 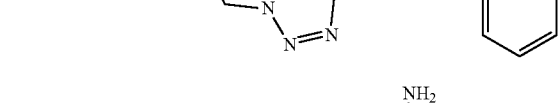 | ++ |
|  | ++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 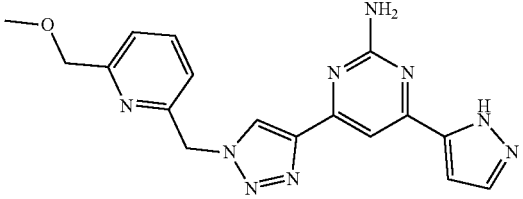 [SMILES: COCc1cccc(Cn2cc(-c3cc(-c4ccn[nH]4)nc(N)n3)nn2)n1] | ++ |
| 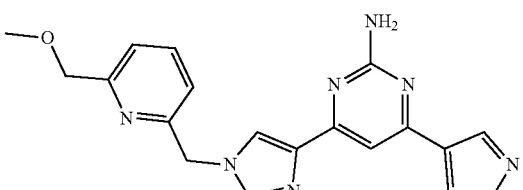 | ++ |
| 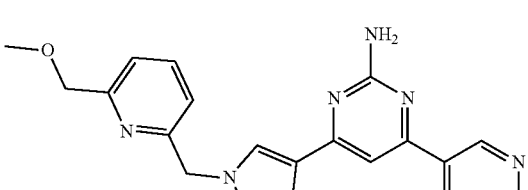 | +++ |
| 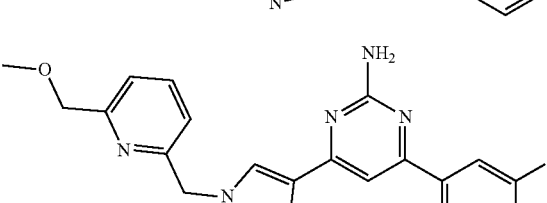 | ++ |
| 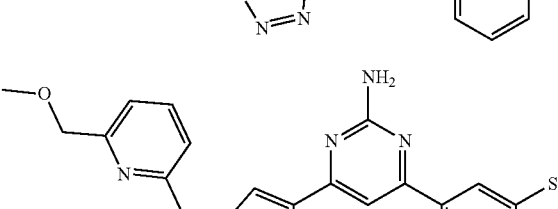 | + |
| 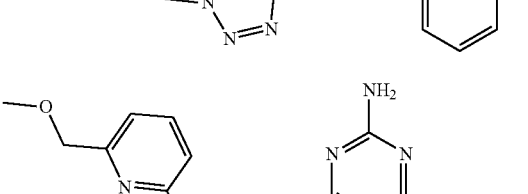 | +++ |
| 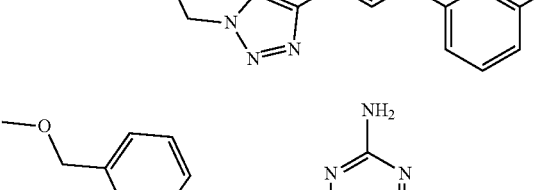 | ++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 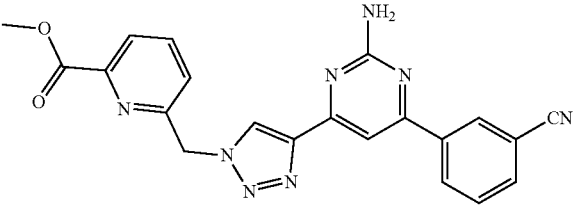 [SMILES: COC(=O)c1cccc(Cn2cc(-c3cc(-c4cccc(C#N)c4)nc(N)n3)nn2)n1] | +++ |
| 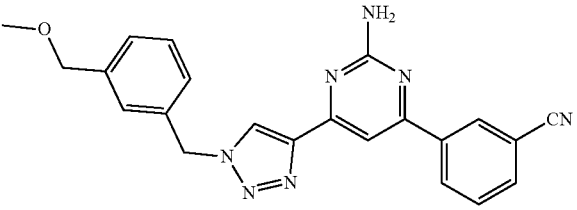 | +++ |
| 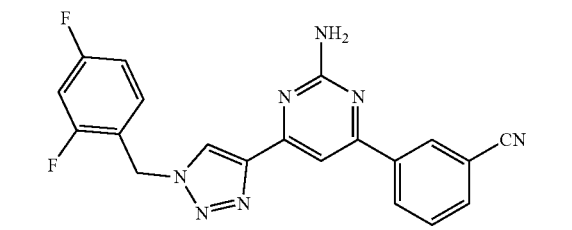 [SMILES: N#Cc1cccc(-c2cc(-c3cn(Cc4ccc(F)cc4F)nn3)nc(N)n2)c1] | +++ |
| 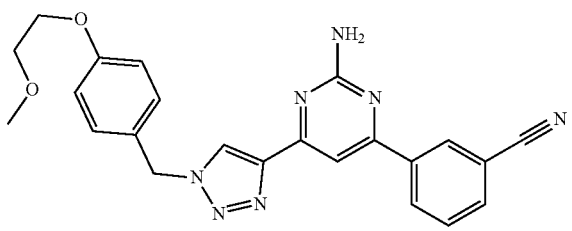 [SMILES: COCCOc1ccc(Cn2cc(-c3cc(-c4cccc(C#N)c4)nc(N)n3)nn2)cc1] | ++ |
| 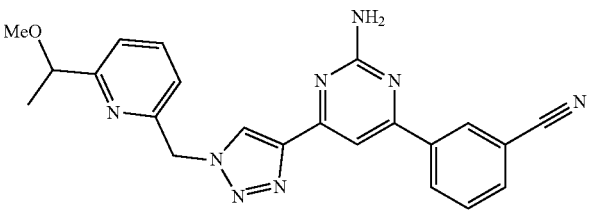 [SMILES: COC(C)c1cccc(Cn2cc(-c3cc(-c4cccc(C#N)c4)nc(N)n3)nn2)n1] | +++ |
| 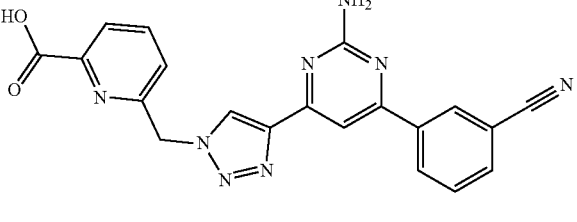 | ++ |
| 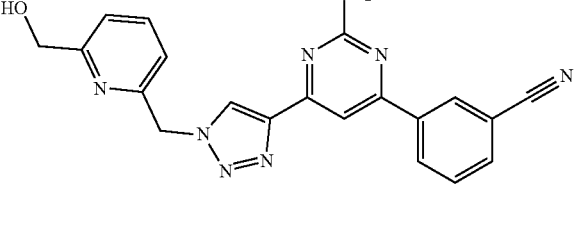 | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (pyridin-2-ylmethyl-triazolyl)-(2-amino-pyrimidinyl)-(3-cyanophenyl) | +++ |
| (6-methoxymethyl-pyridin-2-ylmethyl)-(5-methyl-triazolyl)-(2-amino-pyrimidinyl)-(3-cyanophenyl) | +++ |
| (4-CO₂Me-pyridin-2-ylmethyl)-triazolyl-(2-amino-pyrimidinyl)-(3-cyanophenyl) | + |
| (imidazol-2-ylmethyl)-triazolyl-(2-amino-pyrimidinyl)-(3-cyanophenyl) | +++ |
| (4-CO₂H-pyridin-2-ylmethyl)-triazolyl-(2-amino-pyrimidinyl)-(3-cyanophenyl) | + |
| (3-HO₂C-benzyl)-triazolyl-(2-amino-pyrimidinyl)-(3-cyanophenyl) | ++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (MeO₂C-pyridine-CH₂-triazole-pyrimidine(NH₂)-phenyl-CN) | ++ |
| (HO₂C-pyridine-CH₂-triazole-pyrimidine(NH₂)-phenyl-CN) | + |
| (HO₂C-phenyl-CH₂-triazole-pyrimidine(NH₂)-phenyl-CN) | +++ |
| (pyrazole-CH₂-triazole-pyrimidine(NH₂)-phenyl-CN) | ++ |
| (MeO₂C-CH₂CH₂-pyridine-CH₂-triazole-pyrimidine(NH₂)-phenyl-CN) | +++ |
| (HOOC-CH₂CH₂-pyridine-CH₂-triazole-pyrimidine(NH₂)-phenyl-CN) | +++ |

333
334
TABLE 1-continued
Specific Examples (Potency: $A_{2A}R$ $IC_{50}/K_B$: + means >1 µM, ++ means 100 nM to 1 µM, +++ means <100 nM)
| Structure | Potency |
|---|---|
| 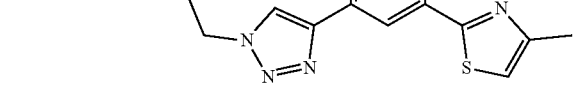 | +++ |
| 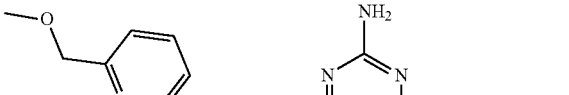 | + |
| 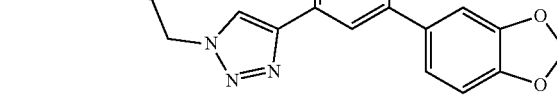 | + |
|  | +++ |
| 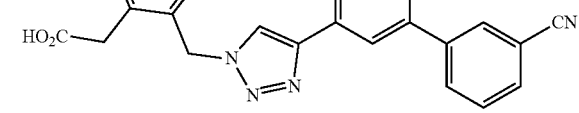 | +++ |
|  | +++ |
| 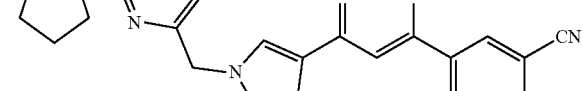 | ++ |

TABLE 1-continued
Specific Examples (Potency: $A_{2A}R$ $IC_{50}/K_B$: + means >1 µM, ++ means 100 nM to 1 µM, +++ means <100 nM)
| Structure | Potency |
|---|---|
| 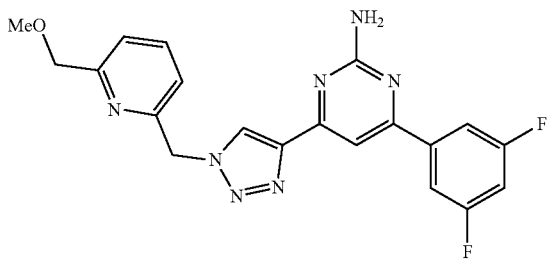 [SMILES: COCc1cccc(Cn2cc(-c3cc(-c4cc(F)cc(F)c4)nc(N)n3)nn2)n1] | +++ |
| 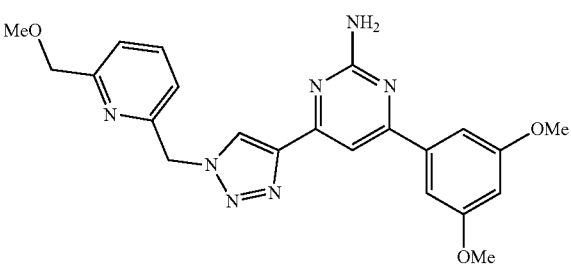 [SMILES: COCc1cccc(Cn2cc(-c3cc(-c4cc(OC)cc(OC)c4)nc(N)n3)nn2)n1] | + |
| 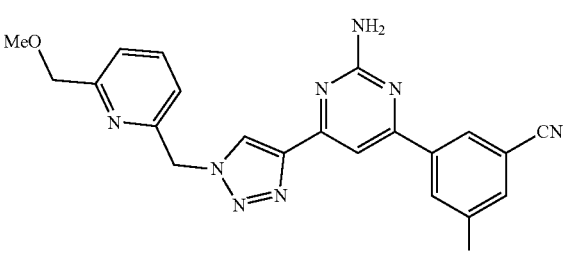 | +++ |
| 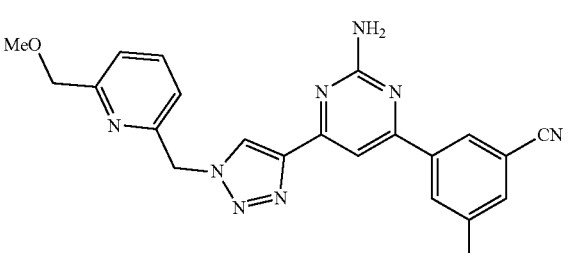 | +++ |
| 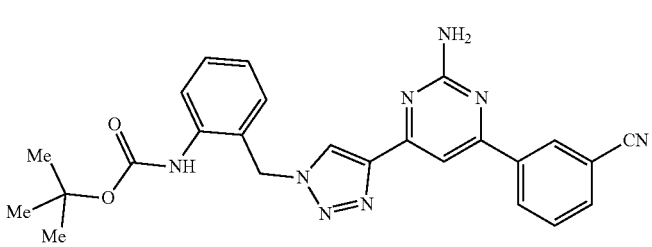 [SMILES: CC(C)(C)OC(=O)Nc1ccccc1Cn1cc(-c2cc(-c3cccc(C#N)c3)nc(N)n2)nn1] | +++ |
| 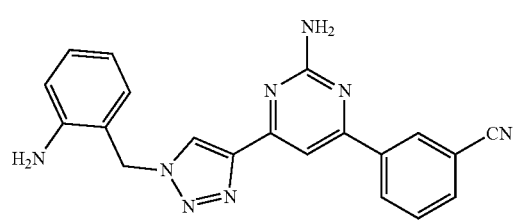 [SMILES: N#Cc1cccc(-c2cc(-c3cn(Cc4ccccc4N)nn3)nc(N)n2)c1] | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (chemical structure) | +++ |
| (chemical structure) | +++ |
| (chemical structure) | +++ |
| (chemical structure) | +++ |
| (chemical structure) | +++ |
| (chemical structure) | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 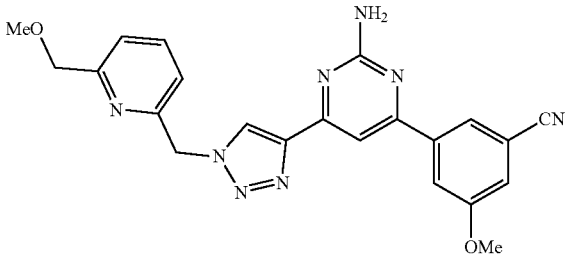 [SMILES: COCc1cccc(Cn2cc(-c3cc(-c4cc(C#N)cc(OC)c4)nc(N)n3)nn2)n1] | + |
| 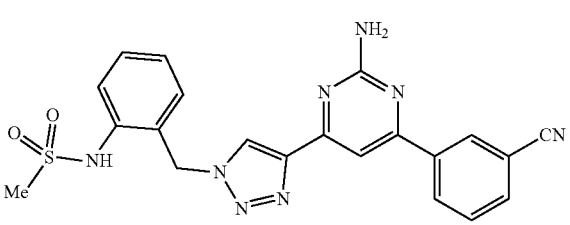 [SMILES: CS(=O)(=O)Nc1ccccc1Cn1cc(-c2cc(-c3cccc(C#N)c3)nc(N)n2)nn1] | +++ |
| 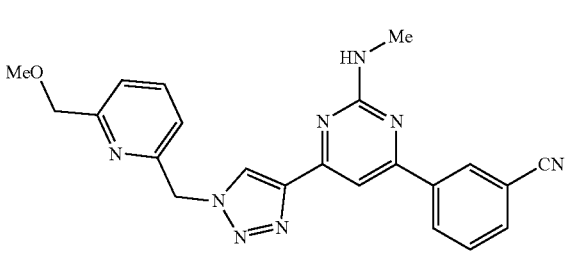 [SMILES: CNc1nc(-c2cccc(C#N)c2)cc(-c2cn(Cc3cccc(COC)n3)nn2)n1] | +++ |
| 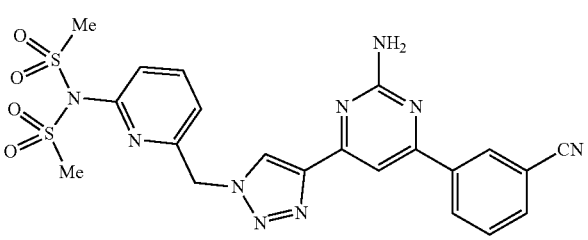 [SMILES: CS(=O)(=O)N(c1cccc(Cn2cc(-c3cc(-c4cccc(C#N)c4)nc(N)n3)nn2)n1)S(C)(=O)=O] | ++ |
| 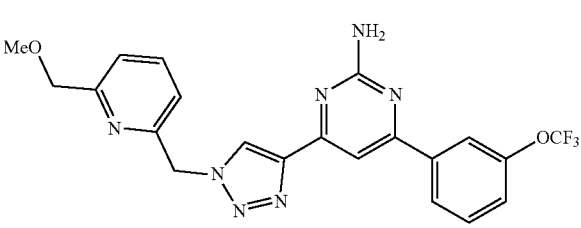 [SMILES: COCc1cccc(Cn2cc(-c3cc(-c4cccc(OC(F)(F)F)c4)nc(N)n3)nn2)n1] | + |
| 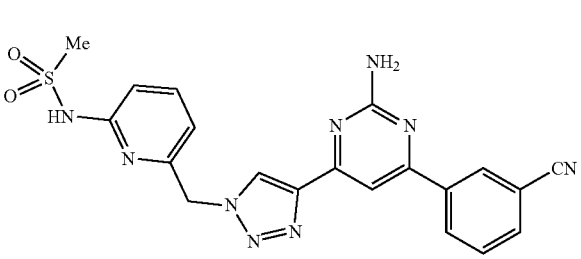 [SMILES: CS(=O)(=O)Nc1cccc(Cn2cc(-c3cc(-c4cccc(C#N)c4)nc(N)n3)nn2)n1] | ++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 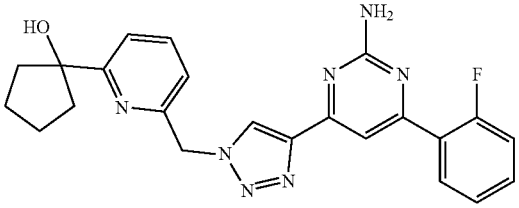 [SMILES: Nc1nc(-c2cn(Cc3cccc(C4(O)CCCC4)n3)nn2)cc(-c2ccccc2F)n1] | +++ |
| 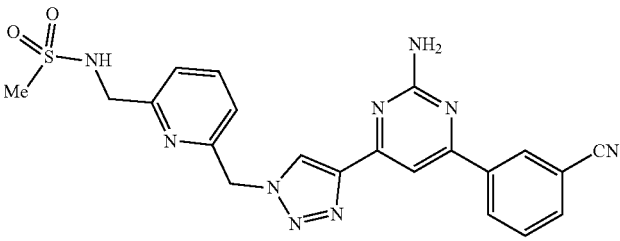 [SMILES: CS(=O)(=O)NCc1cccc(Cn2cc(-c3cc(-c4cccc(C#N)c4)nc(N)n3)nn2)n1] | +++ |
| 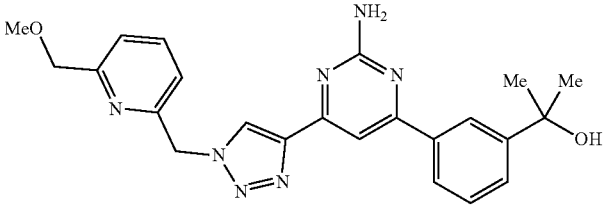 [SMILES: COCc1cccc(Cn2cc(-c3cc(-c4cccc(C(C)(C)O)c4)nc(N)n3)nn2)n1] | + |
| 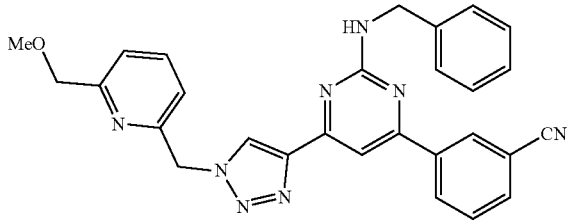 [SMILES: COCc1cccc(Cn2cc(-c3cc(-c4cccc(C#N)c4)nc(NCc4ccccc4)n3)nn2)n1] | ++ |
| 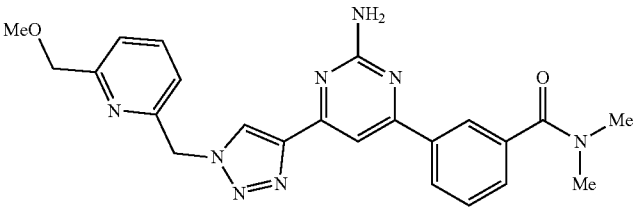 [SMILES: COCc1cccc(Cn2cc(-c3cc(-c4cccc(C(=O)N(C)C)c4)nc(N)n3)nn2)n1] | + |
| 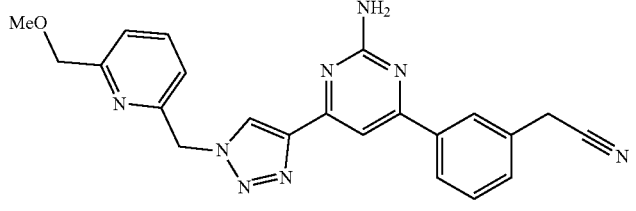 [SMILES: COCc1cccc(Cn2cc(-c3cc(-c4cccc(CC#N)c4)nc(N)n3)nn2)n1] | ++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 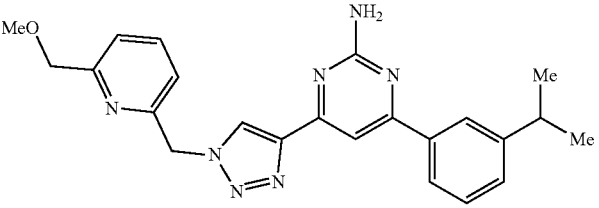 [SMILES: COCc1cccc(Cn2cc(-c3cc(-c4cccc(C(C)C)c4)nc(N)n3)nn2)n1] | + |
| 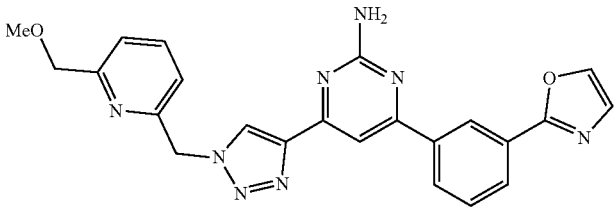 [SMILES: COCc1cccc(Cn2cc(-c3cc(-c4cccc(-c5ncco5)c4)nc(N)n3)nn2)n1] | + |
| 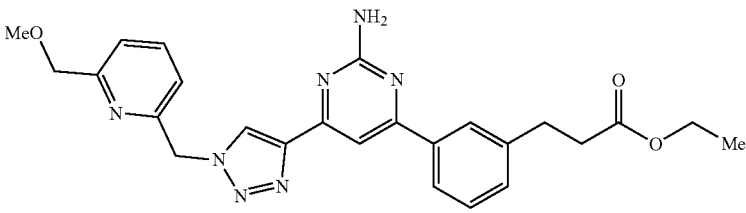 [SMILES: CCOC(=O)CCc1cccc(-c2cc(-c3cn(Cc4cccc(COC)n4)nn3)nc(N)n2)c1] | + |
| 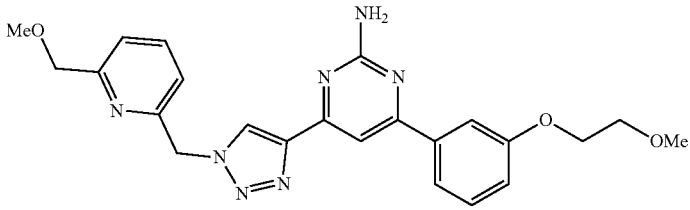 [SMILES: COCCOc1cccc(-c2cc(-c3cn(Cc4cccc(COC)n4)nn3)nc(N)n2)c1] | + |
| 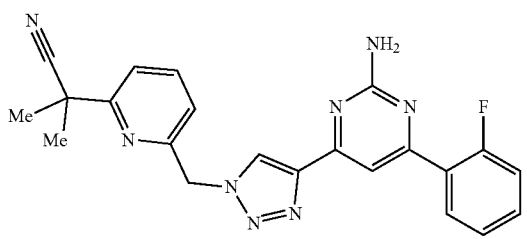 [SMILES: CC(C)(C#N)c1cccc(Cn2cc(-c3cc(-c4ccccc4F)nc(N)n3)nn2)n1] | +++ |
| 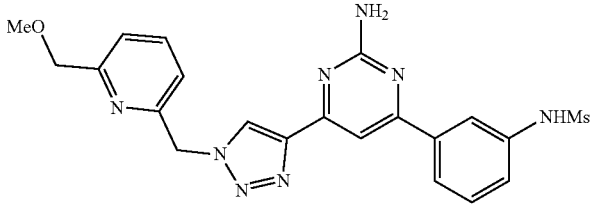 | + |
| 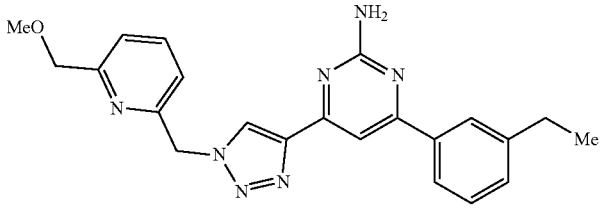 [SMILES: CCc1cccc(-c2cc(-c3cn(Cc4cccc(COC)n4)nn3)nc(N)n2)c1] | + |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 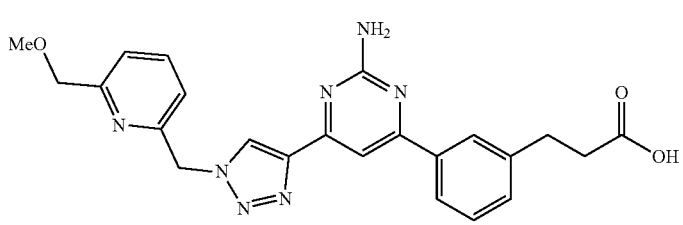 [SMILES: COCc1cccc(Cn2cc(-c3cc(-c4cccc(CCC(=O)O)c4)nc(N)n3)nn2)n1] | + |
| 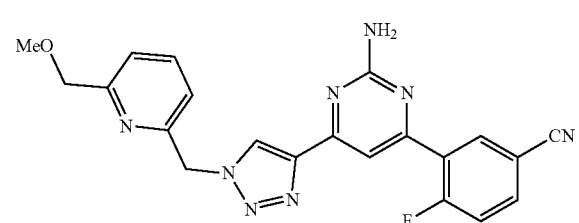 | ++ |
| 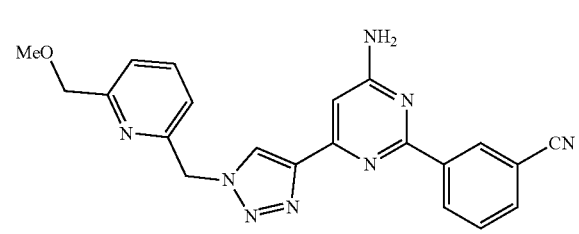 [SMILES: COCc1cccc(Cn2cc(-c3cc(N)nc(-c4cccc(C#N)c4)n3)nn2)n1] | +++ |
| 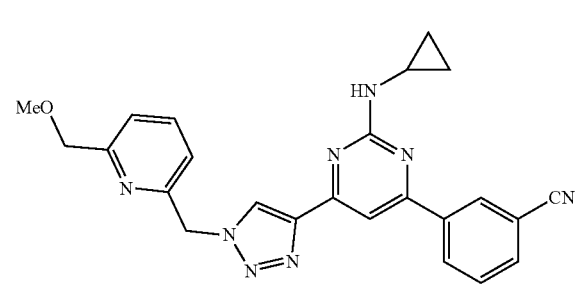 [SMILES: COCc1cccc(Cn2cc(-c3cc(-c4cccc(C#N)c4)nc(NC4CC4)n3)nn2)n1] | +++ |
| 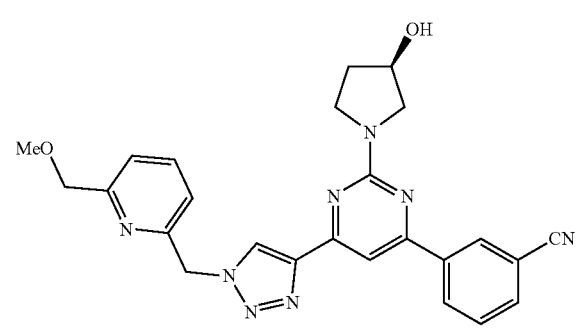 [SMILES: COCc1cccc(Cn2cc(-c3cc(-c4cccc(C#N)c4)nc(N4CC[C@@H](O)C4)n3)nn2)n1] | ++ |
| 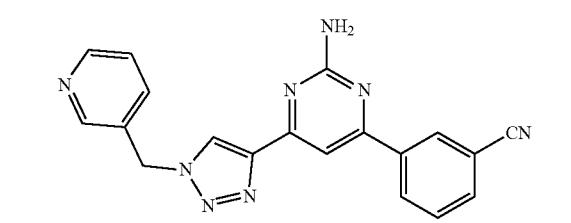 [SMILES: N#Cc1cccc(-c2cc(-c3cn(Cc4cccnc4)nn3)nc(N)n2)c1] | +++ |

TABLE 1-continued
Specific Examples (Potency: $A_{2A}R$ $IC_{50}/K_B$: + means >1 μM, ++ means 100 nM to 1 μM, +++ means <100 nM)
| Structure | Potency |
|---|---|
| 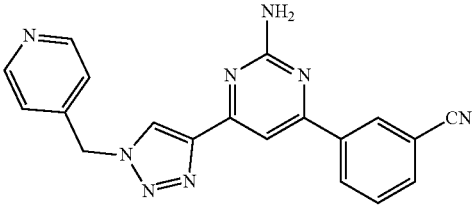 [SMILES: N#Cc1cccc(-c2cc(-c3cn(Cc4ccncc4)nn3)nc(N)n2)c1] | ++ |
| 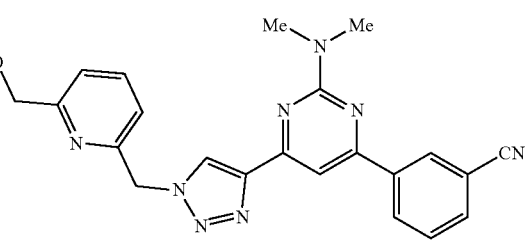 | ++ |
| 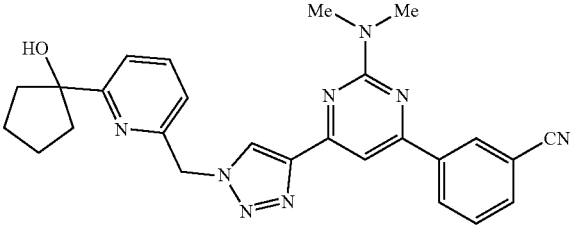 [SMILES: CN(C)c1nc(-c2cccc(C#N)c2)cc(-c2cn(Cc3cccc(C4(O)CCCC4)n3)nn2)n1] | ++ |
| 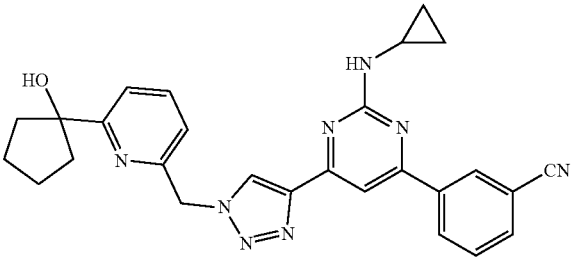 [SMILES: N#Cc1cccc(-c2cc(-c3cn(Cc4cccc(C5(O)CCCC5)n4)nn3)nc(NC3CC3)n2)c1] | +++ |
| 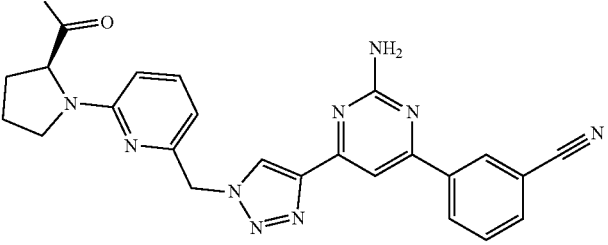 | +++ |
| 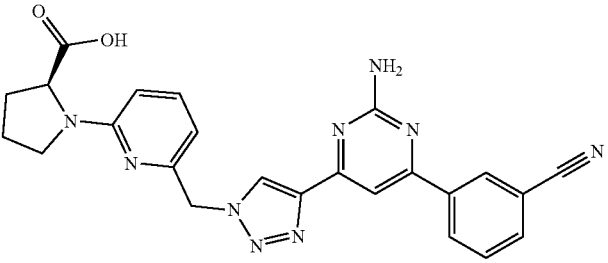 [SMILES: N#Cc1cccc(-c2cc(-c3cn(Cc4cccc(N5CCC[C@H]5C(=O)O)n4)nn3)nc(N)n2)c1] | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (pyridine-CH2OMe / triazole / pyrimidine with NHC(O)CH2OPh and furan) | +++ |
| (3-methylpyridine / triazole / pyrimidine-NH2 / 3-cyanophenyl) | +++ |
| (pyridine-CH2OMe / triazole / pyrimidine with NHC(O)C(CH3)2OH / 3-cyanophenyl) | +++ |
| (pyridine-CH2OMe / triazole / pyrimidine-NH-cyclopentyl / 3-cyanophenyl) | +++ |
| (pyridine-C(OH)(cyclopentyl) / triazole / pyrimidine-NH-cyclopentyl / 3-cyanophenyl) | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 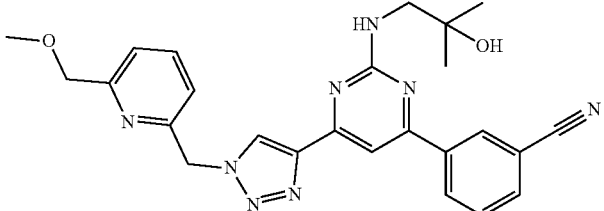 | +++ |
| 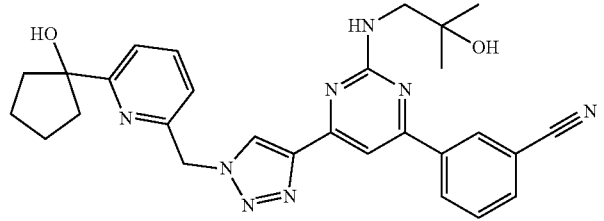 [SMILES: CC(C)(O)CNc1nc(-c2cccc(C#N)c2)cc(-c2cn(Cc3cccc(C4(O)CCCC4)n3)nn2)n1] | +++ |
| 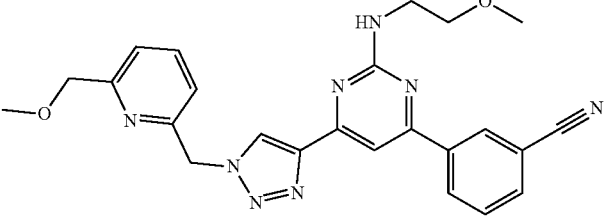 | +++ |
| 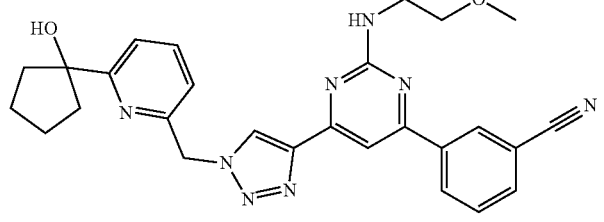 | +++ |
| 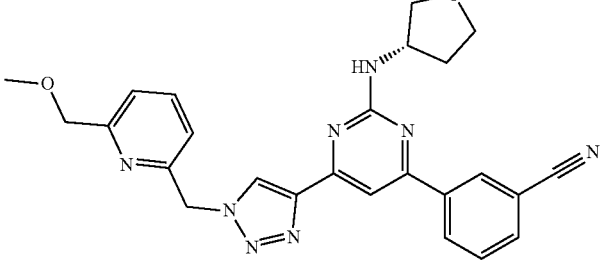 | +++ |
| 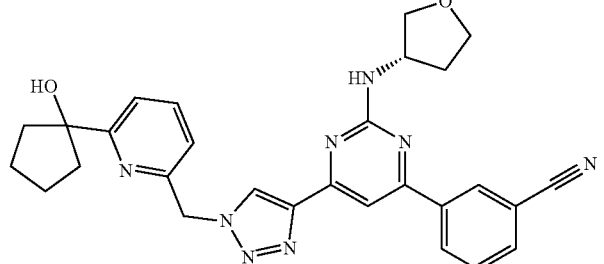 | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 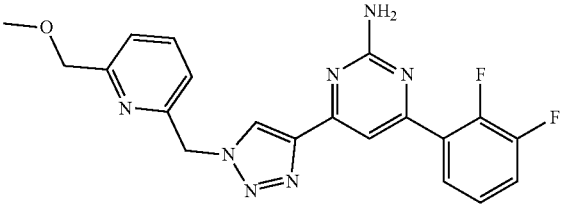 [SMILES: COCc1cccc(Cn2cc(-c3cc(-c4cccc(F)c4F)nc(N)n3)nn2)n1] | +++ |
| 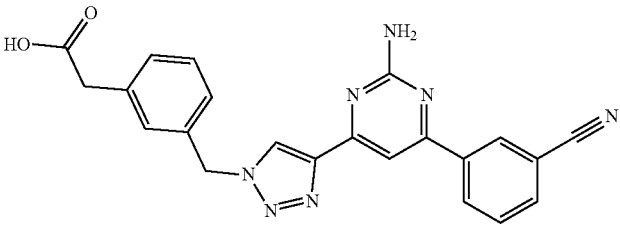 [SMILES: N#Cc1cccc(-c2cc(-c3cn(Cc4cccc(CC(=O)O)c4)nn3)nc(N)n2)c1] | +++ |
| 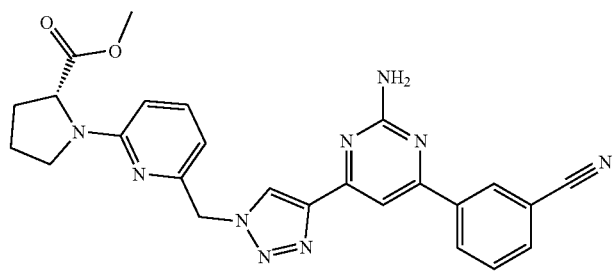 [SMILES: COC(=O)[C@H]1CCCN1c1cccc(Cn2cc(-c3cc(-c4cccc(C#N)c4)nc(N)n3)nn2)n1] | +++ |
| 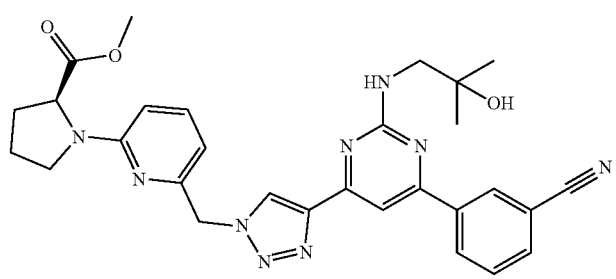 [SMILES: COC(=O)[C@@H]1CCCN1c1cccc(Cn2cc(-c3cc(-c4cccc(C#N)c4)nc(NCC(C)(C)O)n3)nn2)n1] | +++ |
| 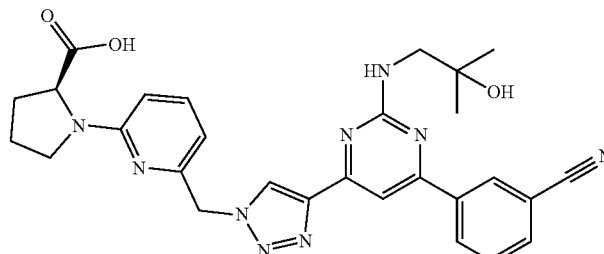 | +++ |
| 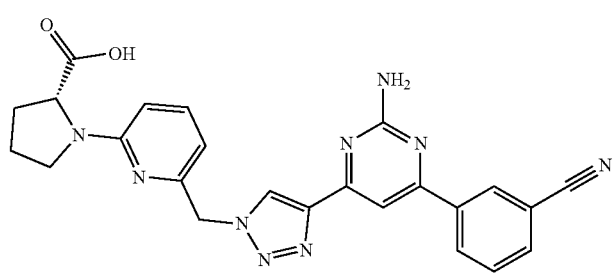 [SMILES: N#Cc1cccc(-c2cc(-c3cn(Cc4cccc(N5CCC[C@@H]5C(=O)O)n4)nn3)nc(N)n2)c1] | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 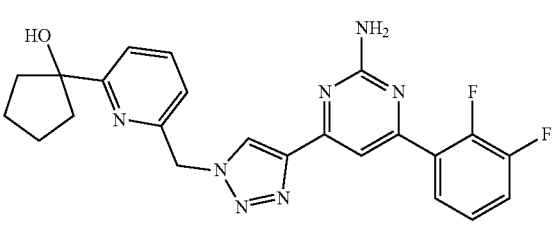 [SMILES: Nc1nc(-c2cn(Cc3cccc(C4(O)CCCC4)n3)nn2)cc(-c2cccc(F)c2F)n1] | +++ |
| 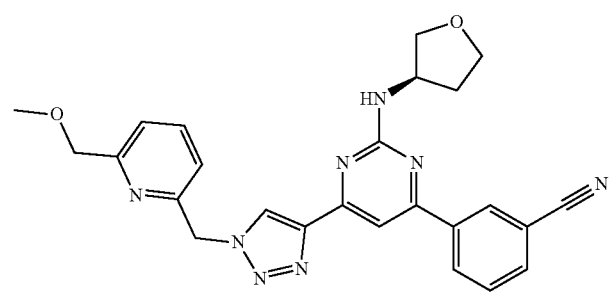 [SMILES: COCc1cccc(Cn2cc(-c3cc(-c4cccc(C#N)c4)nc(N[C@@H]4CCOC4)n3)nn2)n1] | +++ |
| 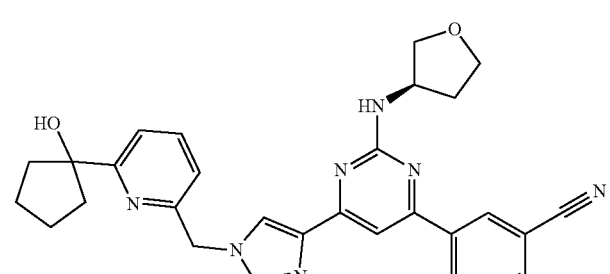 | +++ |
| 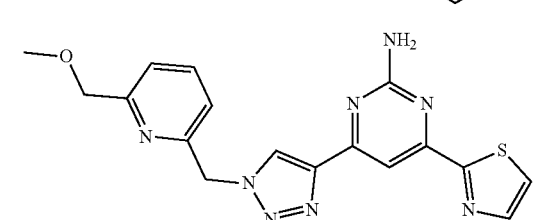 | +++ |
| 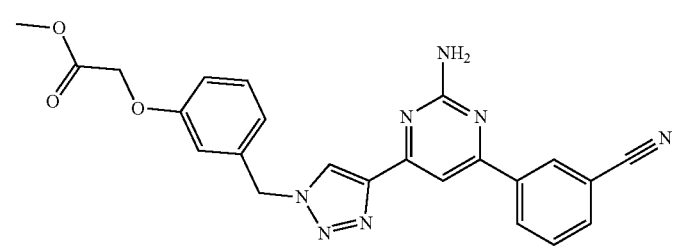 [SMILES: COC(=O)COc1cccc(Cn2cc(-c3cc(-c4cccc(C#N)c4)nc(N)n3)nn2)c1] | +++ |
| 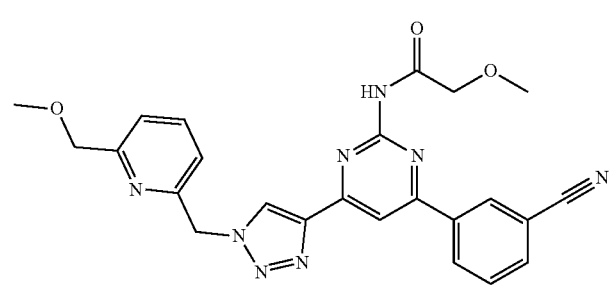 [SMILES: COCC(=O)Nc1nc(-c2cccc(C#N)c2)cc(-c2cn(Cc3cccc(COC)n3)nn2)n1] | +++ |

TABLE 1-continued
Specific Examples (Potency: A$_{2A}$R IC$_{50}$/K$_B$: + means >1 µM, ++ means 100 nM to 1 µM, +++ means <100 nM)
| | Potency |
|---|---|
| 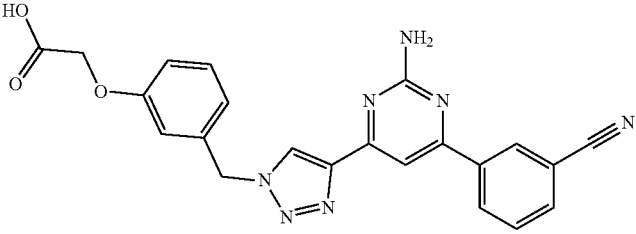 [SMILES: N#Cc1cccc(-c2cc(-c3cn(Cc4cccc(OCC(=O)O)c4)nn3)nc(N)n2)c1] | ++ |
| 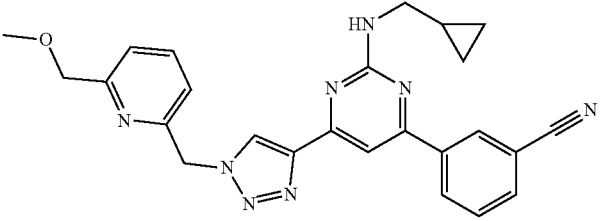 [SMILES: COCc1cccc(Cn2cc(-c3cc(-c4cccc(C#N)c4)nc(NCC4CC4)n3)nn2)n1] | +++ |
| 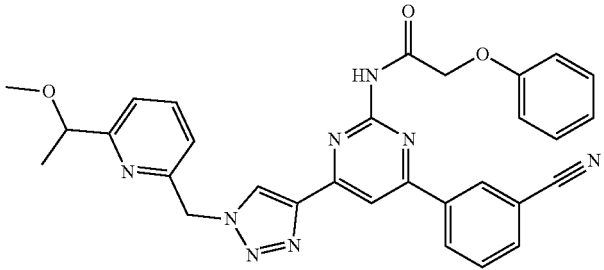 [SMILES: COC(C)c1cccc(Cn2cc(-c3cc(-c4cccc(C#N)c4)nc(NC(=O)COc4ccccc4)n3)nn2)n1] | +++ |
| 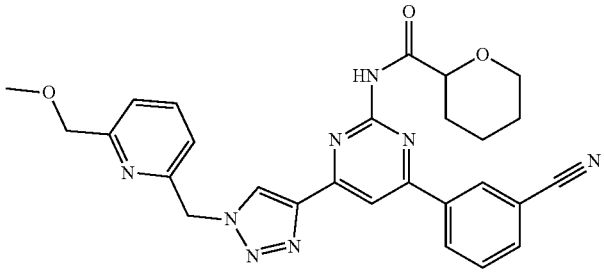 [SMILES: COCc1cccc(Cn2cc(-c3cc(-c4cccc(C#N)c4)nc(NC(=O)C4CCCCO4)n3)nn2)n1] | +++ |
| 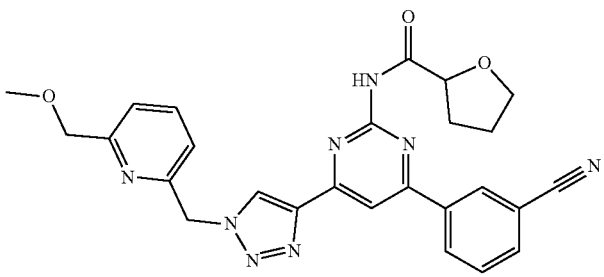 [SMILES: COCc1cccc(Cn2cc(-c3cc(-c4cccc(C#N)c4)nc(NC(=O)C4CCCO4)n3)nn2)n1] | +++ |

US 12,195,447 B2
TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 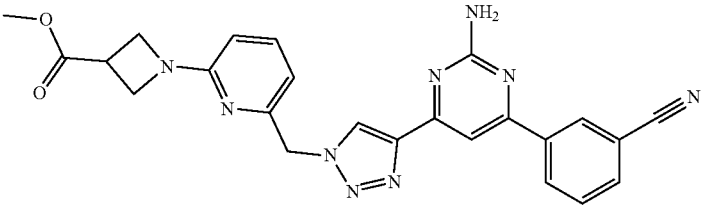 [SMILES: COC(=O)C1CN(c2cccc(Cn3cc(-c4cc(-c5cccc(C#N)c5)nc(N)n4)nn3)n2)C1] | +++ |
| 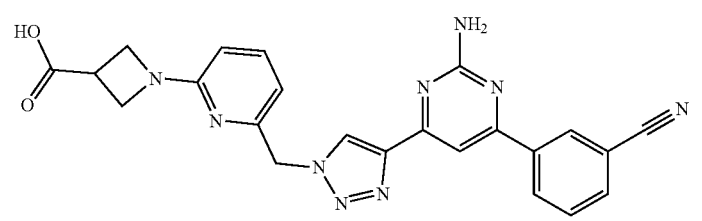 [SMILES: N#Cc1cccc(-c2cc(-c3cn(Cc4cccc(N5CC(C(=O)O)C5)n4)nn3)nc(N)n2)c1] | +++ |
| 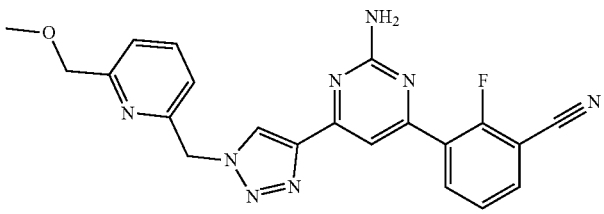 [SMILES: COCc1cccc(Cn2cc(-c3cc(-c4cccc(C#N)c4F)nc(N)n3)nn2)n1] | +++ |
| 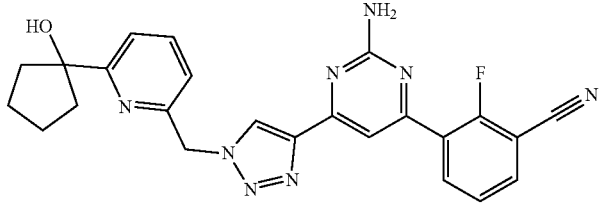 [SMILES: N#Cc1cccc(-c2cc(-c3cn(Cc4cccc(C5(O)CCCC5)n4)nn3)nc(N)n2)c1F] | +++ |
| 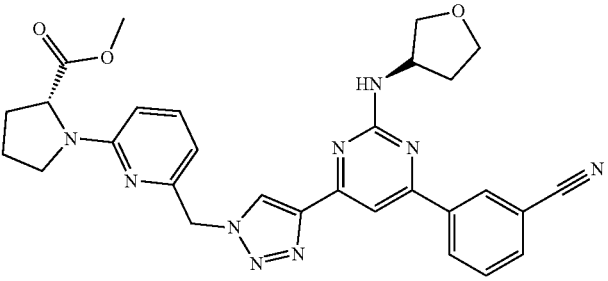 | +++ |
| 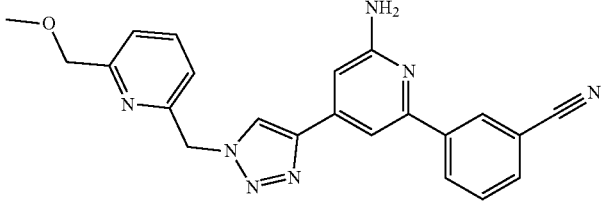 [SMILES: COCc1cccc(Cn2cc(-c3cc(N)nc(-c4cccc(C#N)c4)c3)nn2)n1] | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 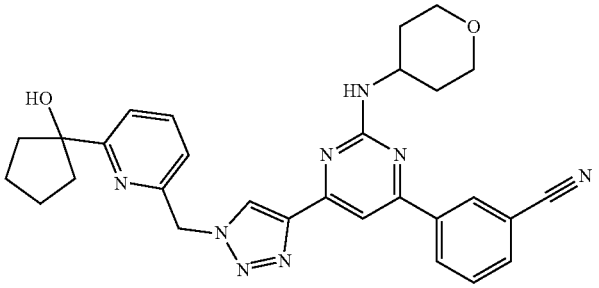 [SMILES: N#Cc1cccc(-c2cc(-c3cn(Cc4cccc(C5(O)CCCC5)n4)nn3)nc(NC3CCOCC3)n2)c1] | +++ |
| 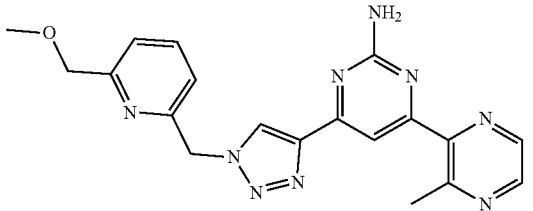 [SMILES: COCc1cccc(Cn2cc(-c3cc(-c4nccnc4C)nc(N)n3)nn2)n1] | ++ |
| 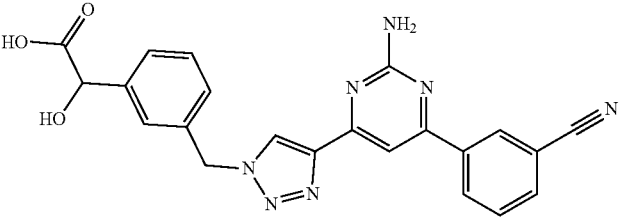 [SMILES: N#Cc1cccc(-c2cc(-c3cn(Cc4cccc(C(O)C(=O)O)c4)nn3)nc(N)n2)c1] | ++ |
| 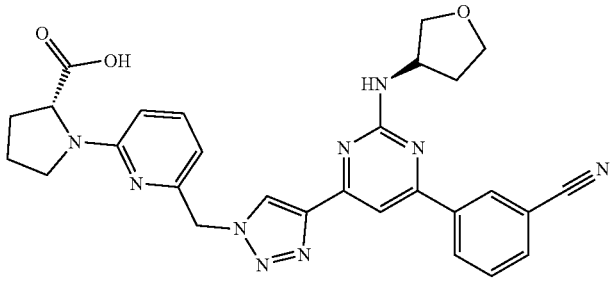 | +++ |
| 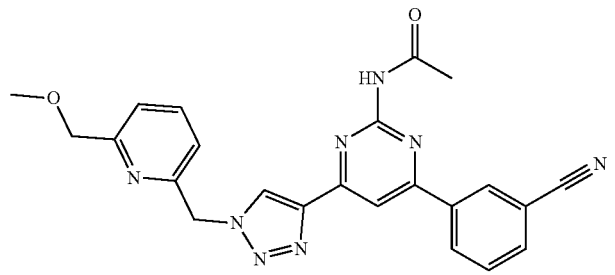 [SMILES: COCc1cccc(Cn2cc(-c3cc(-c4cccc(C#N)c4)nc(NC(C)=O)n3)nn2)n1] | +++ |

TABLE 1-continued
Specific Examples (Potency: $A_{2A}R$ $IC_{50}/K_B$: + means >1 µM, ++ means 100 nM to 1 µM, +++ means <100 nM)
| Structure | Potency |
|---|---|
| 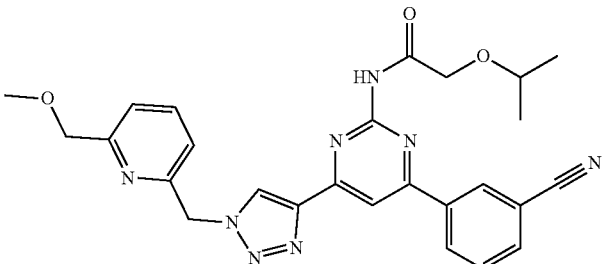 | +++ |
| 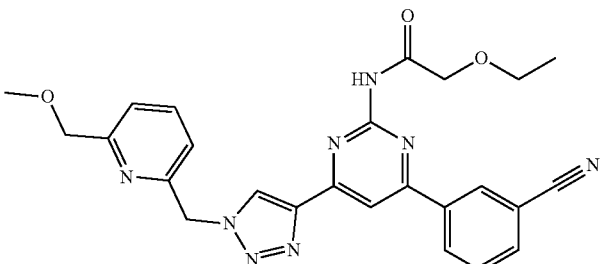 | +++ |
| 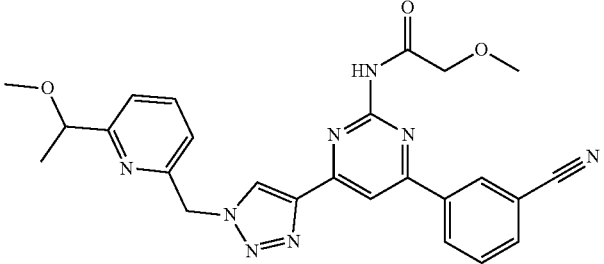 [SMILES: COCC(=O)Nc1nc(-c2cccc(C#N)c2)cc(-c2cn(Cc3cccc(C(C)OC)n3)nn2)n1] | +++ |
| 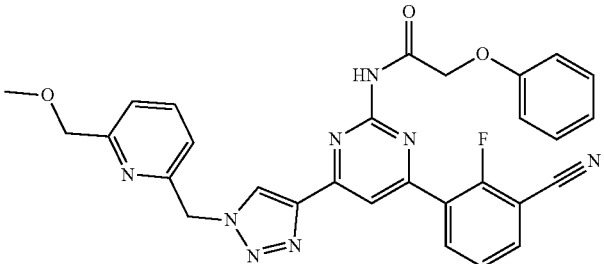 | +++ |
| 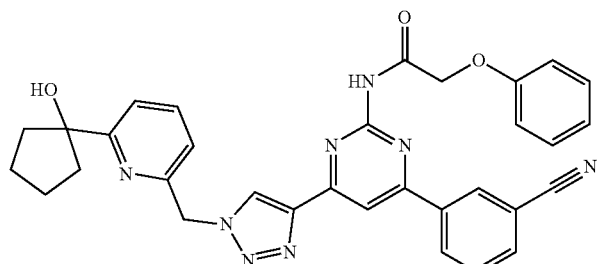 | +++ |

TABLE 1-continued

Specific Examples (Potency: $A_{2A}R$ $IC_{50}/K_B$: + means >1 µM, ++ means 100 nM to 1 µM, +++ means <100 nM)

| | Potency |
|---|---|
| [structure] | +++ |
| [structure] | +++ |
| [structure] | ++ |
| [structure] | ++ |
| [structure] | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 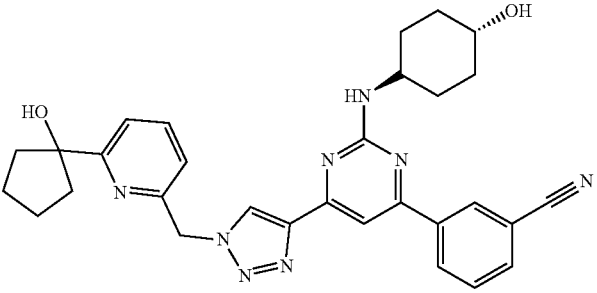 | +++ |
| 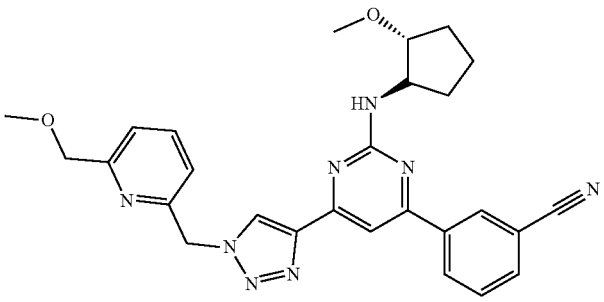 | +++ |
| 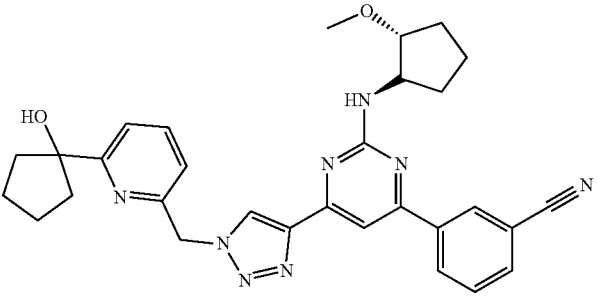 | +++ |
| 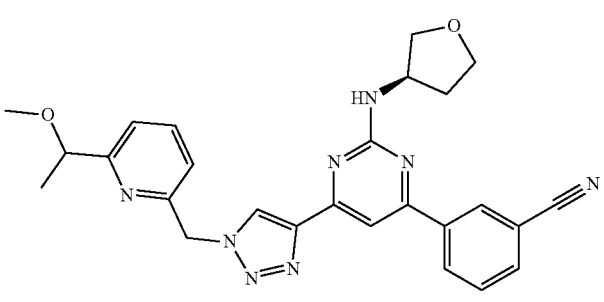 [SMILES: COC(C)c1cccc(Cn2cc(-c3cc(-c4cccc(C#N)c4)nc(N[C@@H]4CCOC4)n3)nn2)n1] | +++ |
| 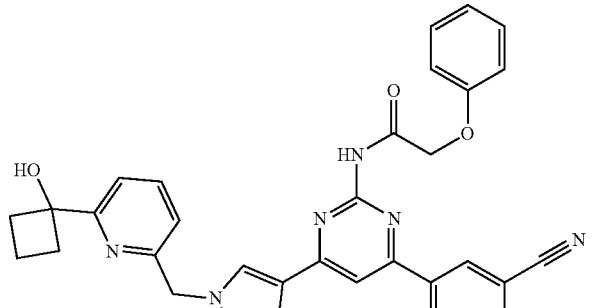 | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (pyrrolidine-3-carboxylic acid linked to pyridine-CH2-triazole-pyrimidine(NH2)-3-cyanophenyl) | +++ |
| (methoxymethyl-pyridine-CH2-triazole-pyrimidine(NH2)-4-cyanophenyl) | ++ |
| (1-methoxyethyl-pyridine-CH2-triazole-pyridine-3-cyanophenyl) | +++ |
| (HOOC-CH2-NH-pyridine-CH2-triazole-pyrimidine(NH2)-3-cyanophenyl) | +++ |
| (methoxymethyl-pyridine-CH2-triazole-pyrimidine-NH-CH2-COOH, 3-cyanophenyl) | ++ |

TABLE 1-continued

Specific Examples (Potency: $A_{2A}R$ $IC_{50}/K_B$: + means >1 µM, ++ means 100 nM to 1 µM, +++ means <100 nM)

| | Potency |
|---|---|
| (structure) | ++ |
| (structure) | + |
| (structure) | +++ |
| (structure) | +++ |
| (structure) | +++ |

US 12,195,447 B2
373
374
TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 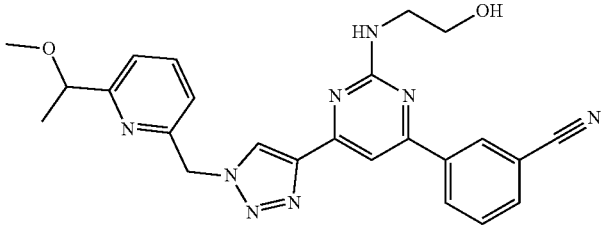 [SMILES: COC(C)c1cccc(Cn2cc(-c3cc(-c4cccc(C#N)c4)nc(NCCO)n3)nn2)n1] | +++ |
| 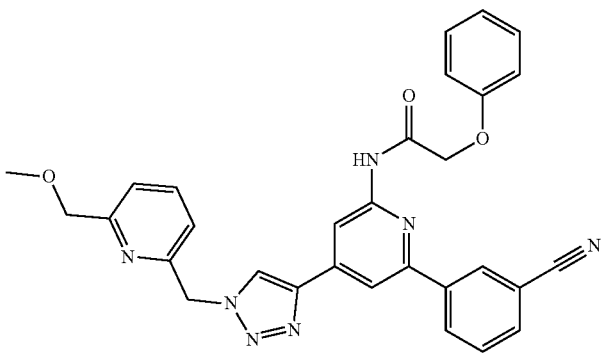 [SMILES: COCc1cccc(Cn2cc(-c3cc(NC(=O)COc4ccccc4)nc(-c4cccc(C#N)c4)c3)nn2)n1] | +++ |
| 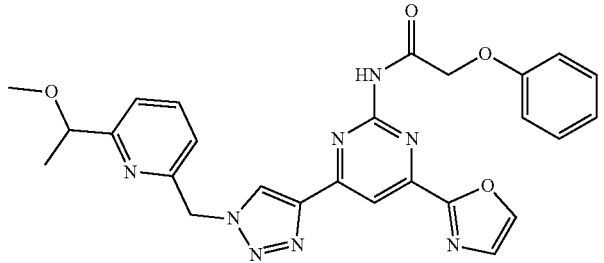 [SMILES: COC(C)c1cccc(Cn2cc(-c3cc(-c4ncco4)nc(NC(=O)COc4ccccc4)n3)nn2)n1] | +++ |
| 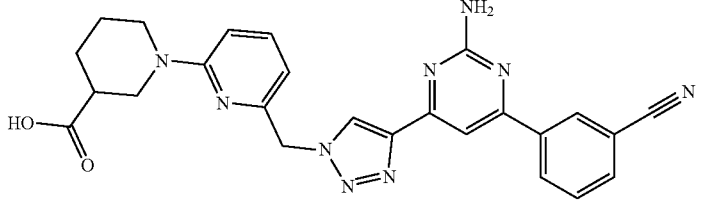 [SMILES: N#Cc1cccc(-c2cc(-c3cn(Cc4cccc(N5CCCC(C(=O)O)C5)n4)nn3)nc(N)n2)c1] | +++ |
| 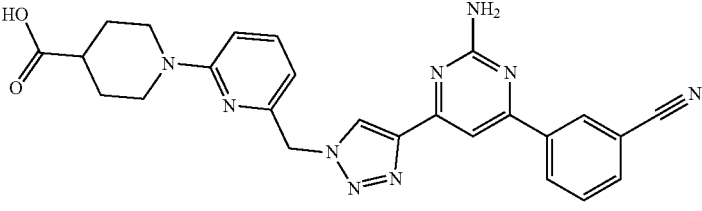 [SMILES: N#Cc1cccc(-c2cc(-c3cn(Cc4cccc(N5CCC(C(=O)O)CC5)n4)nn3)nc(N)n2)c1] | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (structure) | +++ |
| (structure) | +++ |
| (structure) | +++ |
| (structure) | +++ |
| (structure) | +++ |
| (structure) | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 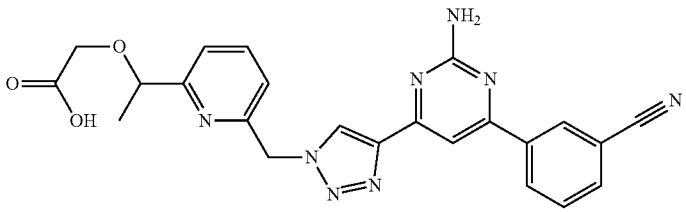 [SMILES: CC(OCC(=O)O)c1cccc(Cn2cc(-c3cc(-c4cccc(C#N)c4)nc(N)n3)nn2)n1] | +++ |
| 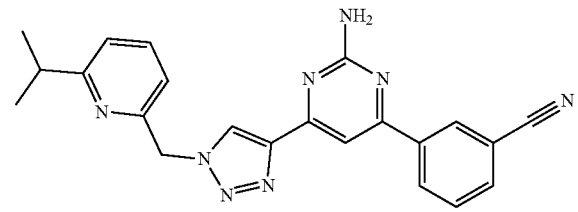 [SMILES: CC(C)c1cccc(Cn2cc(-c3cc(-c4cccc(C#N)c4)nc(N)n3)nn2)n1] | +++ |
| 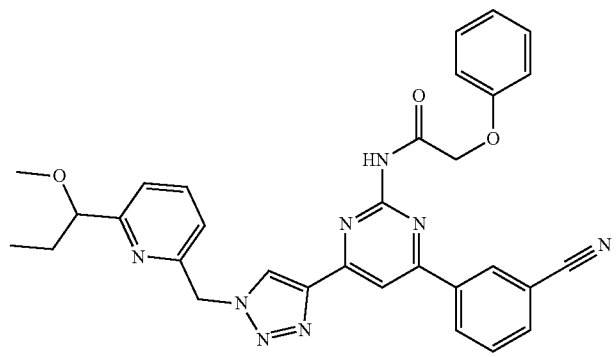 [SMILES: CCC(OC)c1cccc(Cn2cc(-c3cc(-c4cccc(C#N)c4)nc(NC(=O)COc4ccccc4)n3)nn2)n1] | +++ |
| 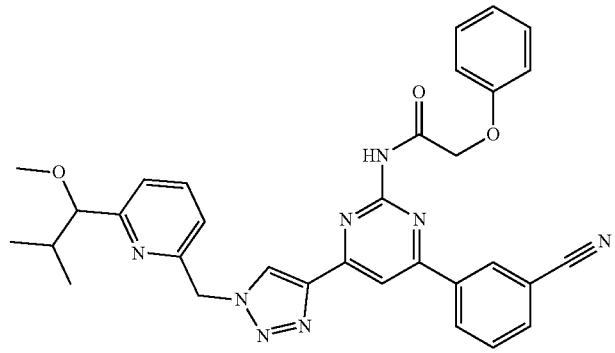 [SMILES: COC(c1cccc(Cn2cc(-c3cc(-c4cccc(C#N)c4)nc(NC(=O)COc4ccccc4)n3)nn2)n1)C(C)C] | +++ |
| 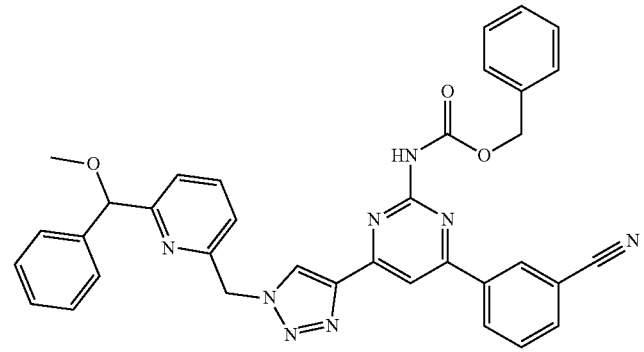 [SMILES: COC(c1ccccc1)c1cccc(Cn2cc(-c3cc(-c4cccc(C#N)c4)nc(NC(=O)OCc4ccccc4)n3)nn2)n1] | ++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 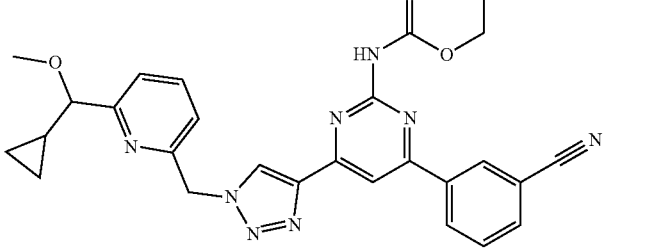 | +++ |
| 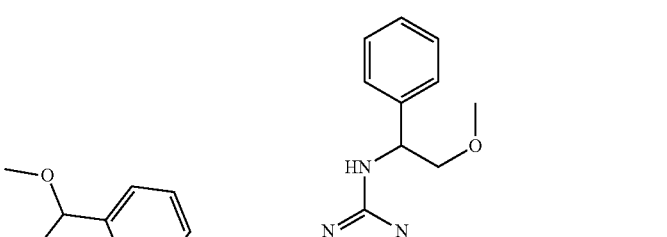 | +++ |
| 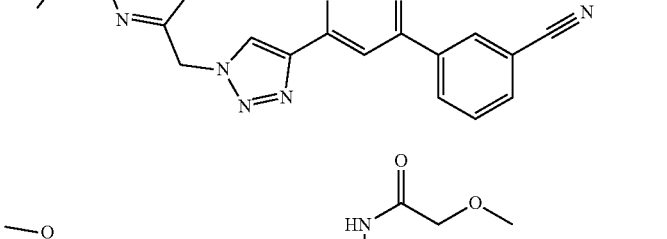 | +++ |
| 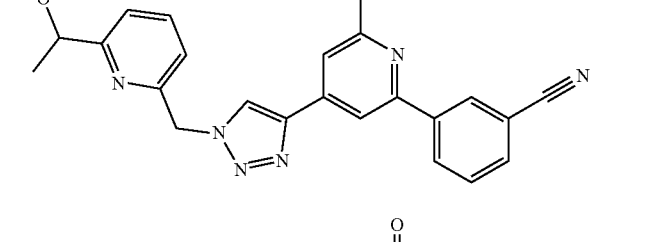 | +++ |
| 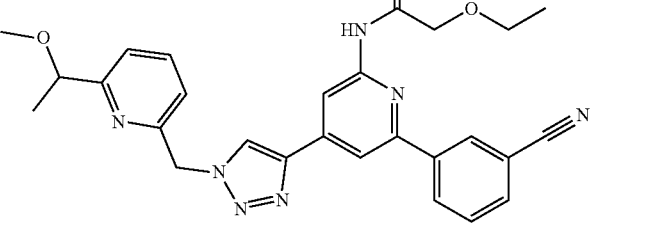 | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (pyridine with –CH₂OCH₂COOH substituent, linked via CH₂-triazole to 2-amino-6-(3-cyanophenyl)pyrimidin-4-yl) | ++ |
| (pyridine with –CH₂OEt substituent, linked via CH₂-triazole to 2-amino-6-(3-cyanophenyl)pyrimidin-4-yl) | +++ |
| (pyridine with –CH₂O-iBu substituent, linked via CH₂-triazole to 2-amino-6-(3-cyanophenyl)pyrimidin-4-yl) | +++ |
| (pyridine with 2-carboxypiperidin-1-yl substituent, linked via CH₂-triazole to 2-amino-6-(3-cyanophenyl)pyrimidin-4-yl) | +++ |
| (pyridine with 3-carboxymorpholin-4-yl substituent, linked via CH₂-triazole to 2-amino-6-(3-cyanophenyl)pyrimidin-4-yl) | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (structure with methoxyethyl-pyridine, triazole, pyrimidine with NH-CH2-CO2H, 3-cyanophenyl) | +++ |
| (structure with (3S)-pyrrolidine-3-carboxylic acid on pyridine, triazole, 2-aminopyrimidine, 3-cyanophenyl) | +++ |
| (structure with 2-methyl-2-(pyridinylamino)propanoic acid, triazole, 2-aminopyrimidine, 3-cyanophenyl) | ++ |
| (structure with pyrrolidine-3-carboxylic acid on pyridine, triazole, 2-aminopyrimidine, 3-cyanophenyl) | +++ |
| (structure with (3R)-pyrrolidine-3-carboxylic acid on pyridine, triazole, 2-aminopyrimidine, 3-cyanophenyl) | +++ |
| (structure with methoxypropyl-pyridine, triazole, pyrimidine with NH-C(O)-CH2-OMe, 3-cyanophenyl) | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 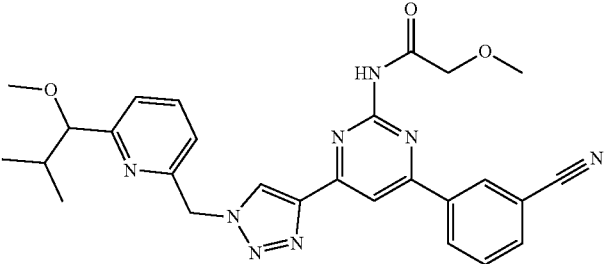 [SMILES: COCC(=O)Nc1nc(-c2cccc(C#N)c2)cc(-c2cn(Cc3cccc(C(OC)C(C)C)n3)nn2)n1] | +++ |
| 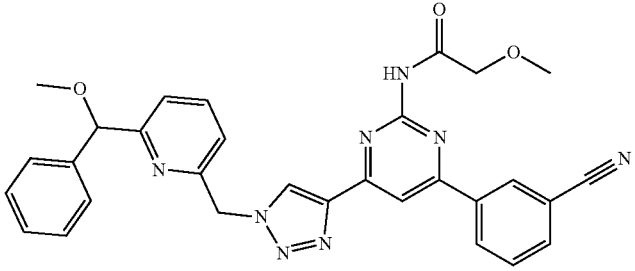 [SMILES: COCC(=O)Nc1nc(-c2cccc(C#N)c2)cc(-c2cn(Cc3cccc(C(OC)c4ccccc4)n3)nn2)n1] | +++ |
| 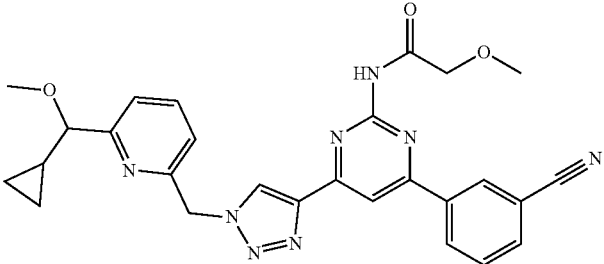 [SMILES: COCC(=O)Nc1nc(-c2cccc(C#N)c2)cc(-c2cn(Cc3cccc(C(OC)C4CC4)n3)nn2)n1] | +++ |
| 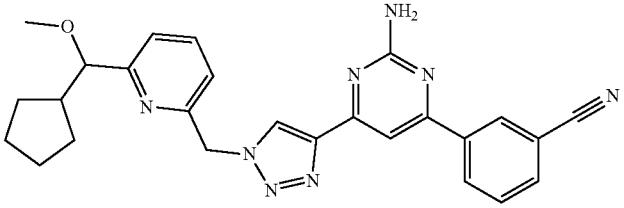 [SMILES: COC(c1cccc(Cn2cc(-c3cc(-c4cccc(C#N)c4)nc(N)n3)nn2)n1)C1CCCC1] | +++ |
| 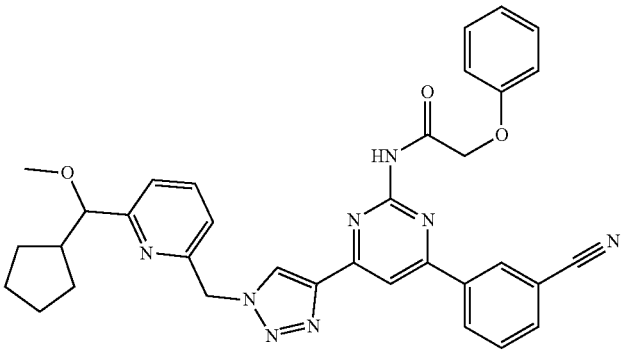 [SMILES: COC(c1cccc(Cn2cc(-c3cc(-c4cccc(C#N)c4)nc(NC(=O)COc4ccccc4)n3)nn2)n1)C1CCCC1] | ++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 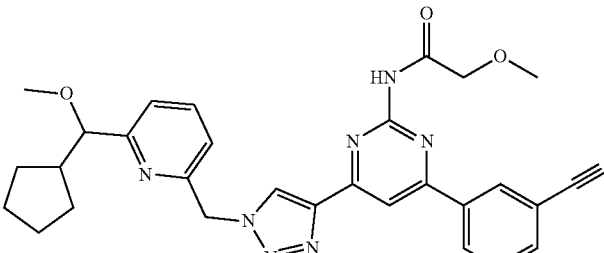 | +++ |
| 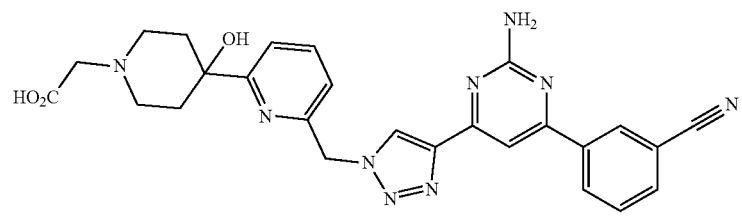 [SMILES: N#Cc1cccc(-c2cc(-c3cn(Cc4cccc(C5(O)CCN(CC(=O)O)CC5)n4)nn3)nc(N)n2)c1] | +++ |
| 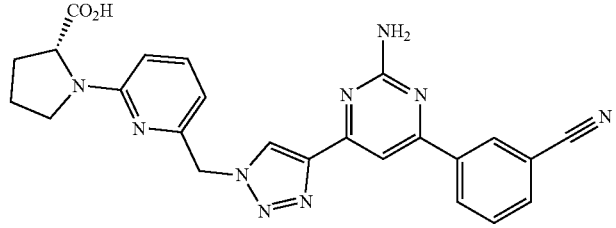 [SMILES: N#Cc1cccc(-c2cc(-c3cn(Cc4cccc(N5CCC[C@@H]5C(=O)O)n4)nn3)nc(N)n2)c1] | ++ |
| 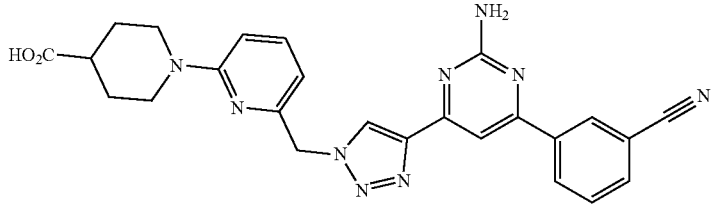 [SMILES: N#Cc1cccc(-c2cc(-c3cn(Cc4cccc(N5CCC(C(=O)O)CC5)n4)nn3)nc(N)n2)c1] | +++ |
| 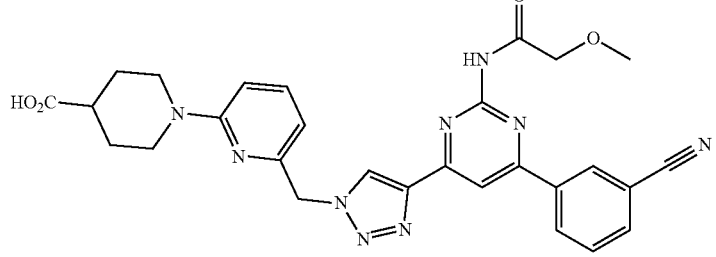 | +++ |
| 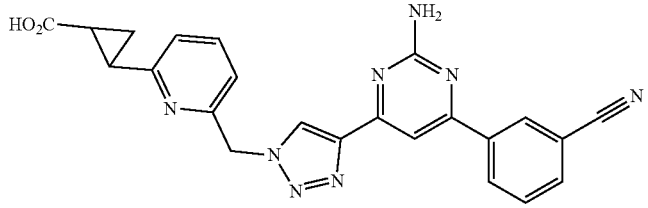 [SMILES: N#Cc1cccc(-c2cc(-c3cn(Cc4cccc(C5CC5C(=O)O)n4)nn3)nc(N)n2)c1] | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 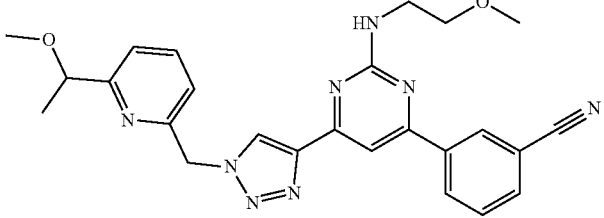 | +++ |
| 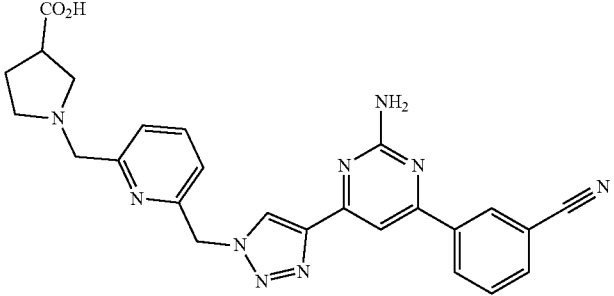 [SMILES: N#Cc1cccc(-c2cc(-c3cn(Cc4cccc(CN5CCC(C(=O)O)C5)n4)nn3)nc(N)n2)c1] | +++ |
| 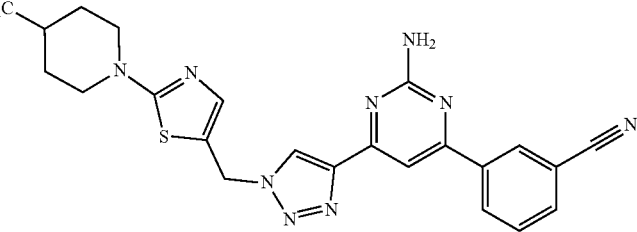 | +++ |
| 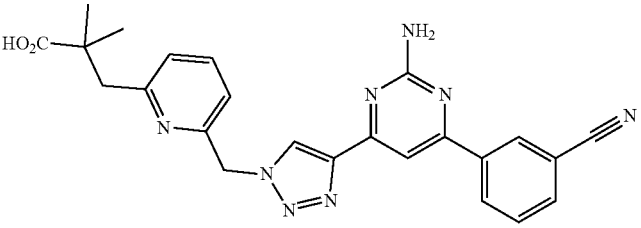 [SMILES: CC(C)(Cc1cccc(Cn2cc(-c3cc(-c4cccc(C#N)c4)nc(N)n3)nn2)n1)C(=O)O] | +++ |
| 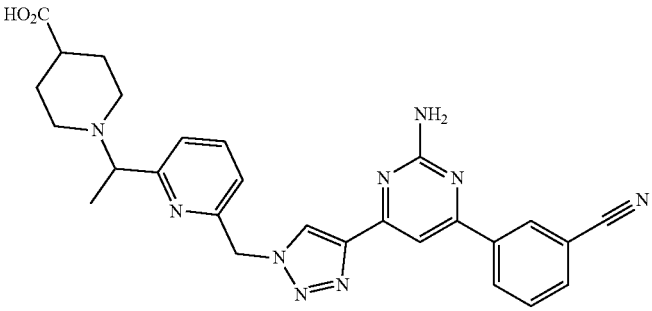 [SMILES: CC(c1cccc(Cn2cc(-c3cc(-c4cccc(C#N)c4)nc(N)n3)nn2)n1)N1CCC(C(=O)O)CC1] | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 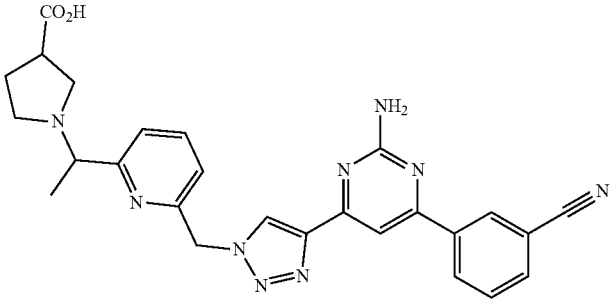 [SMILES: CC(c1cccc(Cn2cc(-c3cc(-c4cccc(C#N)c4)nc(N)n3)nn2)n1)N1CCC(C(=O)O)C1] | +++ |
| 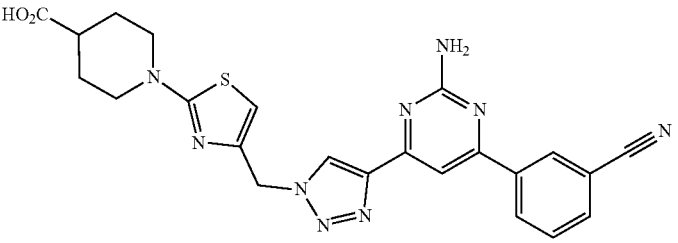 [SMILES: N#Cc1cccc(-c2cc(-c3cn(Cc4csc(N5CCC(C(=O)O)CC5)n4)nn3)nc(N)n2)c1] | + |
| 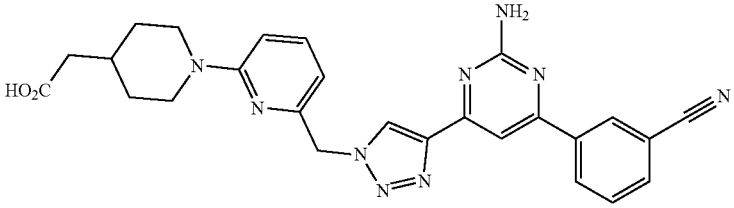 [SMILES: N#Cc1cccc(-c2cc(-c3cn(Cc4cccc(N5CCC(CC(=O)O)CC5)n4)nn3)nc(N)n2)c1] | +++ |
| 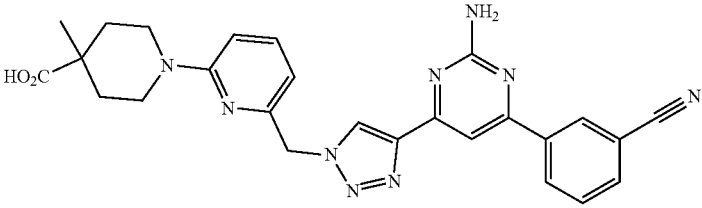 [SMILES: CC1(C(=O)O)CCN(c2cccc(Cn3cc(-c4cc(-c5cccc(C#N)c5)nc(N)n4)nn3)n2)CC1] | +++ |
| 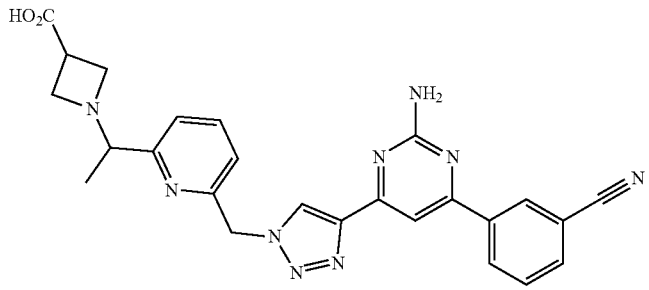 [SMILES: CC(c1cccc(Cn2cc(-c3cc(-c4cccc(C#N)c4)nc(N)n3)nn2)n1)N1CC(C(=O)O)C1] | ++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 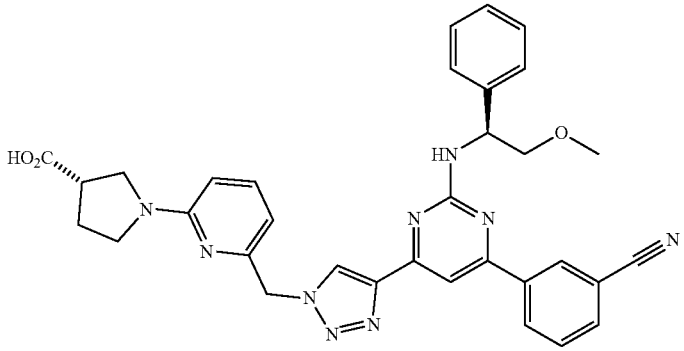 [SMILES: COC[C@@H](Nc1nc(-c2cccc(C#N)c2)cc(-c2cn(Cc3cccc(N4CC[C@H](C(=O)O)C4)n3)nn2)n1)c1ccccc1] | +++ |
| 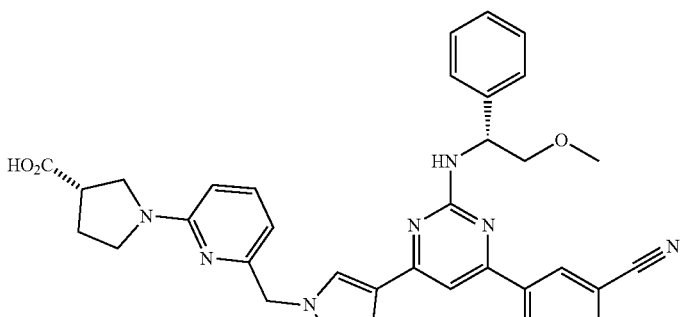 | +++ |
| 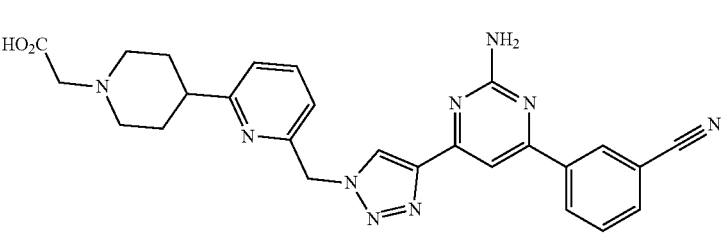 [SMILES: N#Cc1cccc(-c2cc(-c3cn(Cc4cccc(C5CCN(CC(=O)O)CC5)n4)nn3)nc(N)n2)c1] | +++ |
| 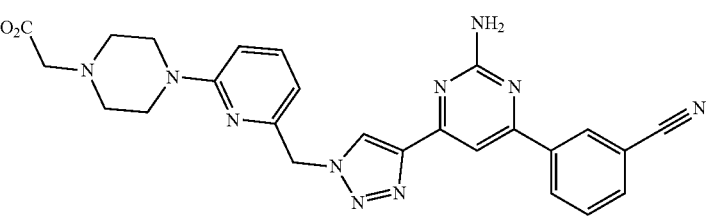 | +++ |
| 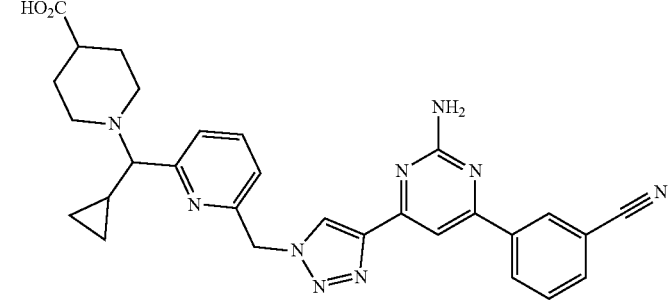 [SMILES: N#Cc1cccc(-c2cc(-c3cn(Cc4cccc(C(C5CC5)N5CCC(C(=O)O)CC5)n4)nn3)nc(N)n2)c1] | +++ |

TABLE 1-continued
Specific Examples (Potency: $A_{2A}R\ IC_{50}/K_B$: + means >1 μM, ++ means 100 nM to 1 μM, +++ means <100 nM)
| Structure | Potency |
|---|---|
| 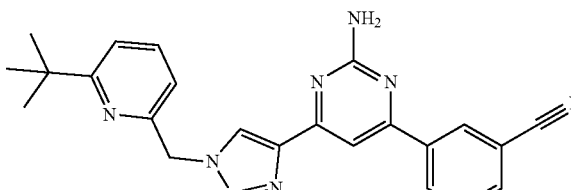 | +++ |
| 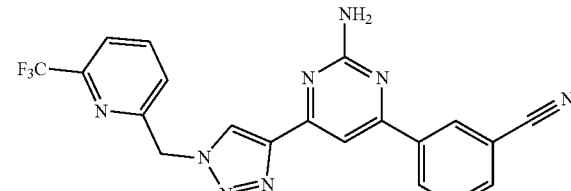 | +++ |
| 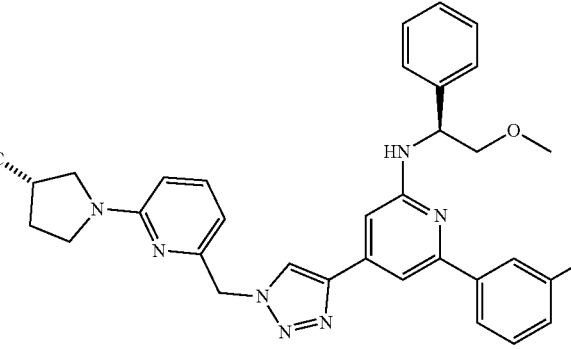 | ++ |
| 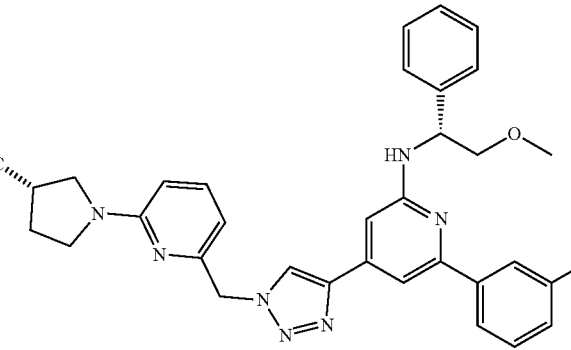 | +++ |
| 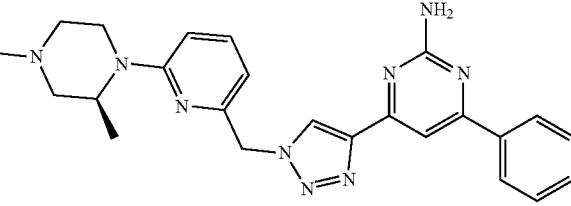 | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (structure) | +++ |
| (structure) | +++ |
| (structure) | +++ |
| (structure) | +++ |
| (structure) | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (structure) | +++ |
| (structure) | +++ |
| (structure) | +++ |
| (structure) | +++ |
| (structure) | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 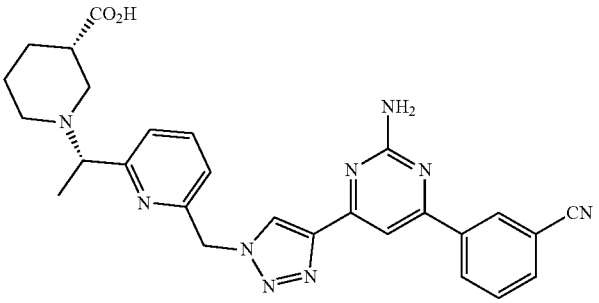 [SMILES: C[C@@H](c1cccc(Cn2cc(-c3cc(-c4cccc(C#N)c4)nc(N)n3)nn2)n1)N1CCC[C@H](C(=O)O)C1] | |
| 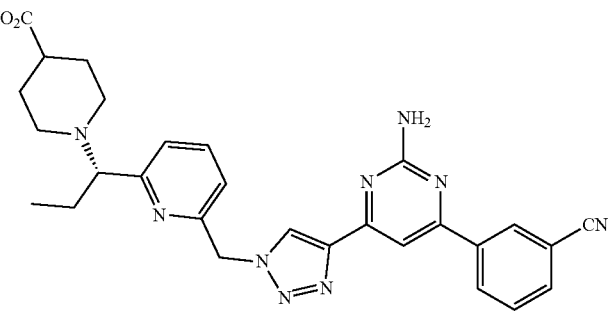 | +++ |
| 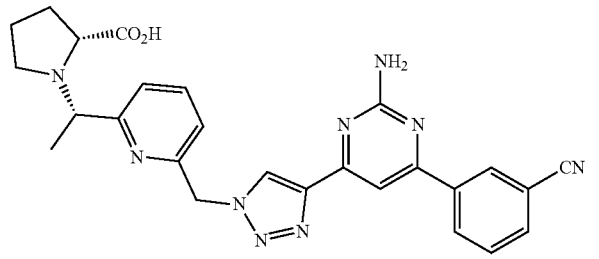 [SMILES: C[C@@H](c1cccc(Cn2cc(-c3cc(-c4cccc(C#N)c4)nc(N)n3)nn2)n1)N1CCC[C@@H]1C(=O)O] | +++ |
| 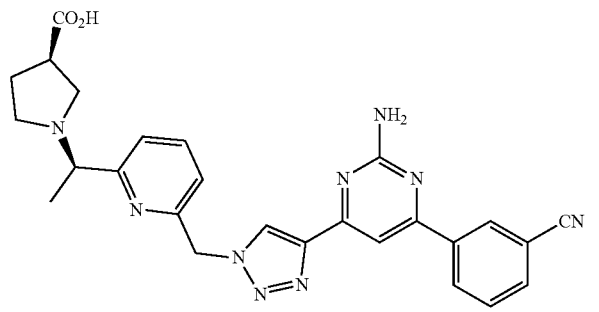 [SMILES: C[C@H](c1cccc(Cn2cc(-c3cc(-c4cccc(C#N)c4)nc(N)n3)nn2)n1)N1CC[C@@H](C(=O)O)C1] | +++ |
| 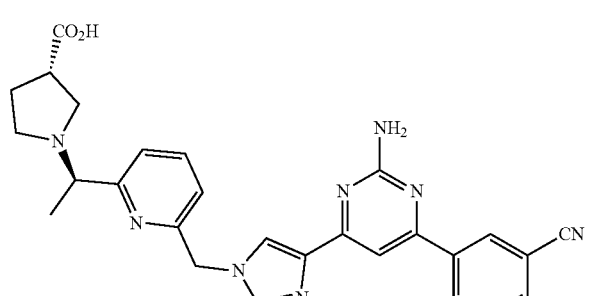 | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (pyridine with HO₂C-C(Me)₂- substituent, linked via CH₂-triazole to 2-amino-pyrimidine bearing 3-cyanophenyl) | +++ |
| ((R)-piperidine-3-carboxylic acid N-linked via CH(Me) to pyridine, CH₂-triazole, 2-amino-pyrimidine, 3-cyanophenyl) | +++ |
| (piperidine-4-carboxylic acid N-linked via CH(Et) to pyridine, CH₂-triazole, 2-amino-pyrimidine, 3-cyanophenyl) | +++ |
| (piperidine-4-carboxylic acid N-linked via CH(Et) to pyridine, CH₂-triazole, 2-amino-pyridine, 3-cyanophenyl) | +++ |
| ((S)-proline N-linked to pyridine, CH₂-triazole, 2-cyclopropylamino-pyrimidine, 3-cyanophenyl) | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 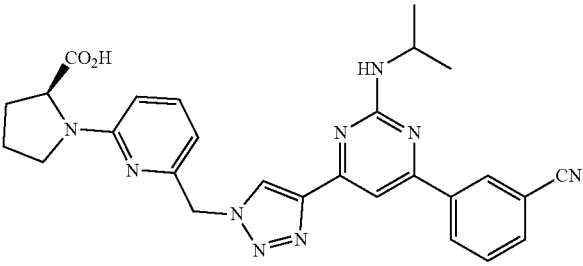 [SMILES: CC(C)Nc1nc(-c2cccc(C#N)c2)cc(-c2cn(Cc3cccc(N4CCC[C@H]4C(=O)O)n3)nn2)n1] | +++ |
| 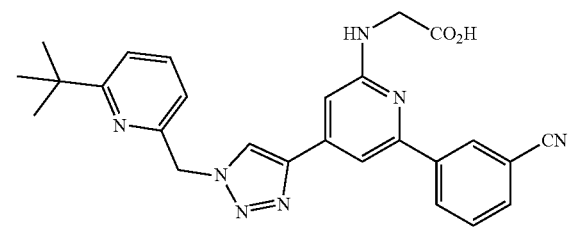 [SMILES: CC(C)(C)c1cccc(Cn2cc(-c3cc(NCC(=O)O)nc(-c4cccc(C#N)c4)c3)nn2)n1] | +++ |
| 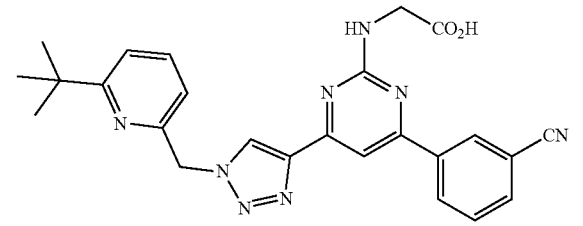 [SMILES: CC(C)(C)c1cccc(Cn2cc(-c3cc(-c4cccc(C#N)c4)nc(NCC(=O)O)n3)nn2)n1] | +++ |
| 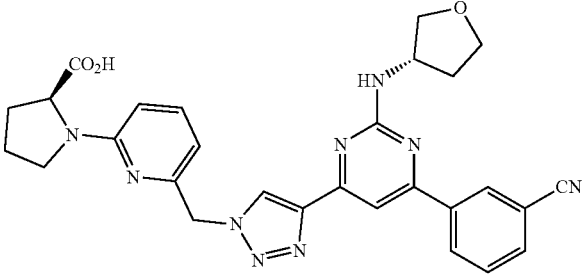 [SMILES: N#Cc1cccc(-c2cc(-c3cn(Cc4cccc(N5CCC[C@H]5C(=O)O)n4)nn3)nc(N[C@H]3CCOC3)n2)c1] | +++ |
| 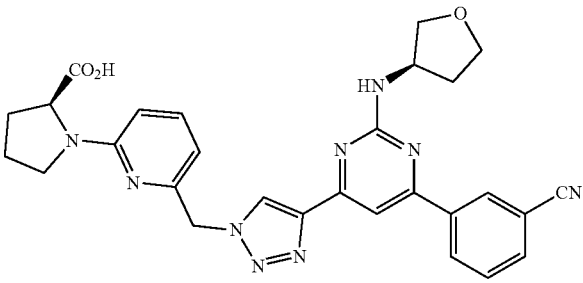 [SMILES: N#Cc1cccc(-c2cc(-c3cn(Cc4cccc(N5CCC[C@H]5C(=O)O)n4)nn3)nc(N[C@@H]3CCOC3)n2)c1] | +++ |
| 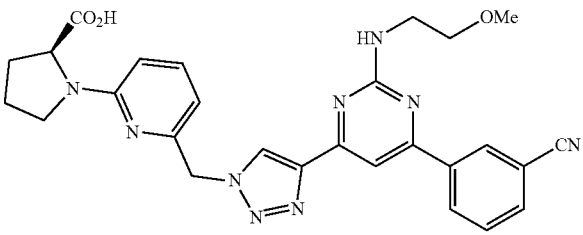 [SMILES: COCCNc1nc(-c2cccc(C#N)c2)cc(-c2cn(Cc3cccc(N4CCC[C@H]4C(=O)O)n3)nn2)n1] | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (pyrrolidine-CO2H)-pyridine-CH2-triazole-pyrimidine(NHcyclopropyl)-phenyl-CN | ++ |
| (pyrrolidine-CO2H)-pyridine-CH2-triazole-pyrimidine(NHisopropyl)-phenyl-CN | ++ |
| (pyrrolidine-CO2H)-pyridine-CH2-triazole-pyrimidine(NH-tetrahydrofuran-3-yl)-phenyl-CN | +++ |
| (CF3-pyridine)-CH2-triazole-pyrimidine(NH-CH(CH3)-CO2H)-phenyl-CN | ++ |
| (azetidine-CO2H)-pyridine-CH2-triazole-pyrimidine(NHcyclopropyl)-phenyl-CN | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 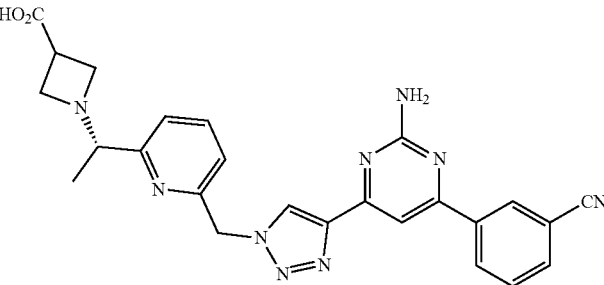 | +++ |
| 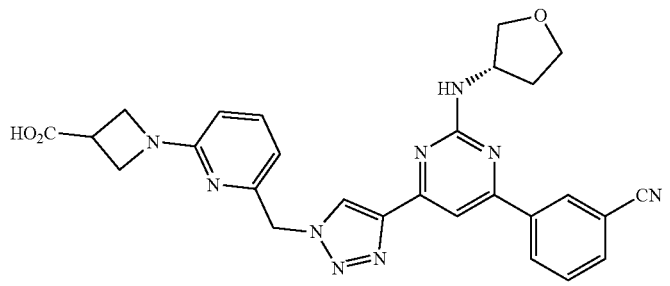 [SMILES: N#Cc1cccc(-c2cc(-c3cn(Cc4cccc(N5CC(C(=O)O)C5)n4)nn3)nc(N[C@H]3CCOC3)n2)c1] | +++ |
| 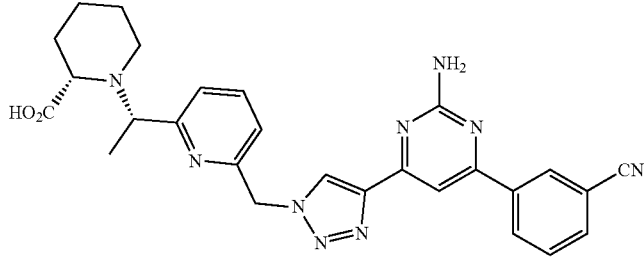 [SMILES: C[C@@H](c1cccc(Cn2cc(-c3cc(-c4cccc(C#N)c4)nc(N)n3)nn2)n1)N1CCCC[C@H]1C(=O)O] | +++ |
| 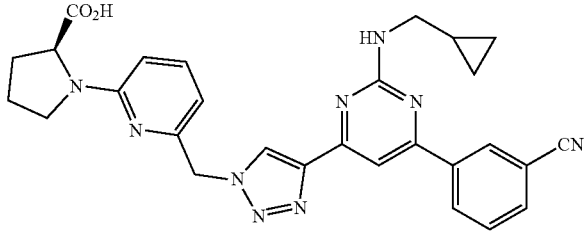 [SMILES: N#Cc1cccc(-c2cc(-c3cn(Cc4cccc(N5CCC[C@H]5C(=O)O)n4)nn3)nc(NCC3CC3)n2)c1] | +++ |
| 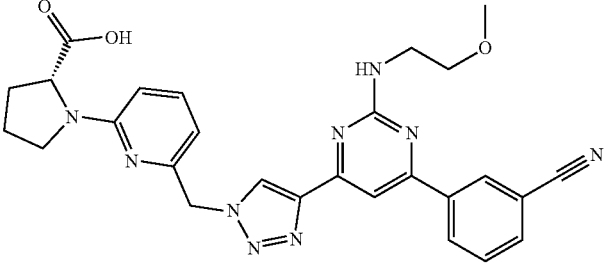 [SMILES: COCCNc1nc(-c2cccc(C#N)c2)cc(-c2cn(Cc3cccc(N4CCC[C@@H]4C(=O)O)n3)nn2)n1] | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (structure) | +++ |
| (structure) | +++ |
| (structure) | ++ |
| (structure) | +++ |
| (structure) | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 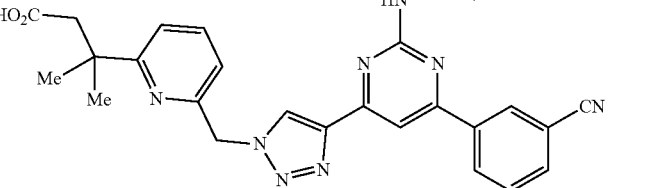 | +++ |
| 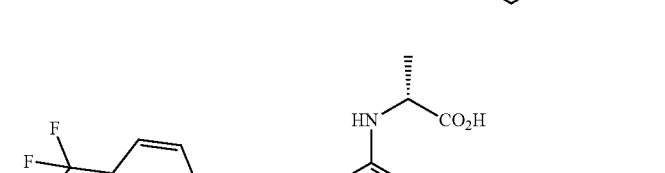 | ++ |
| 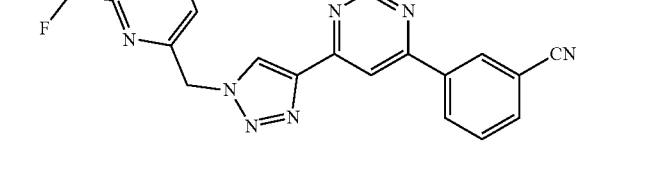 | +++ |
| 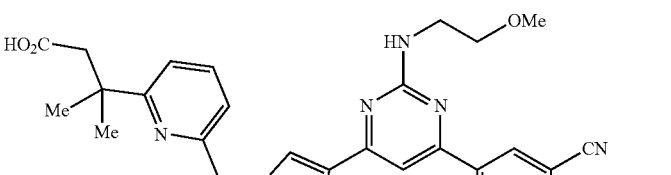 | +++ |
| 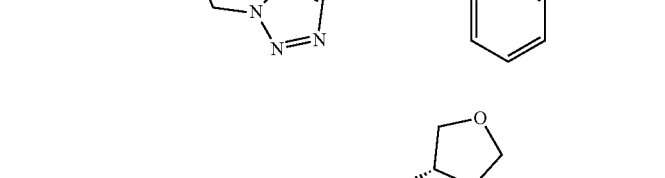 | +++ |

TABLE 1-continued

Specific Examples (Potency: A$_{2A}$R IC$_{50}$/K$_B$: + means >1 μM, ++ means 100 nM to 1 μM, +++ means <100 nM)

| Structure | Potency |
|---|---|
| (structure) | +++ |
| (structure) | +++ |
| (structure) | ++ |
| (structure) | +++ |
| (structure) | +++ |
| (structure) | +++ |

TABLE 1-continued

Specific Examples (Potency: A$_{2A}$R IC$_{50}$/K$_B$: + means >1 µM, ++ means 100 nM to 1 µM, +++ means <100 nM)

| | Potency |
|---|---|
| (structure) | +++ |
| (structure) | +++ |
| (structure) | +++ |
| (structure) | +++ |
| (structure) | +++ |

US 12,195,447 B2
419                                                                                                                                      420
TABLE 1-continued
Specific Examples (Potency: A$_{2A}$R IC$_{50}$/K$_B$: + means >1 µM, ++ means 100 nM to 1 µM, +++ means <100 nM)
| | Potency |
|---|---|
| 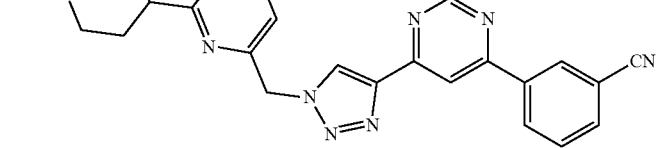 | +++ |
|  | +++ |
| 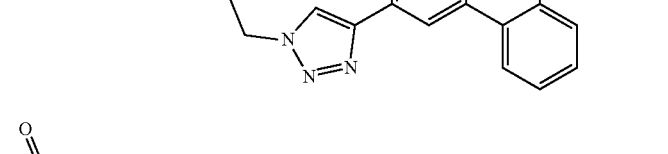 | +++ |
| 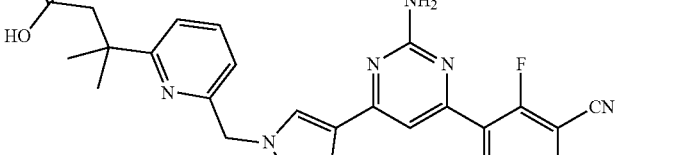 | +++ |
| 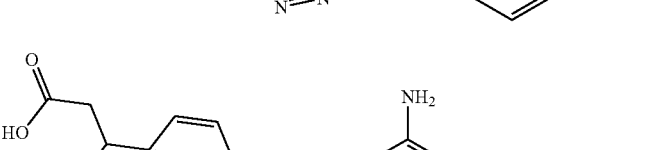 | +++ |
| 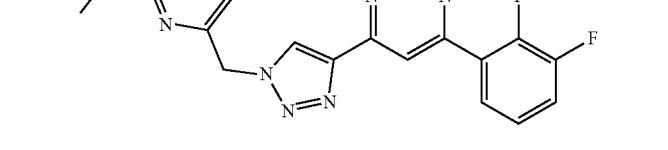 | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (chemical structure) | ++ |
| (chemical structure) | +++ |
| (chemical structure) | +++ |
| (chemical structure) | +++ |
| (chemical structure) | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 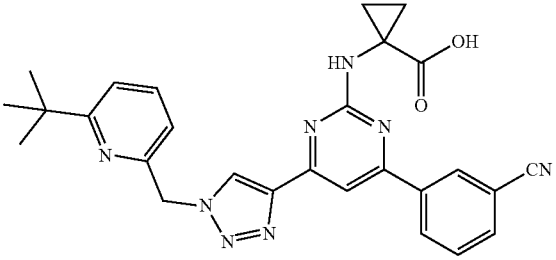 [SMILES: CC(C)(C)c1cccc(Cn2cc(-c3cc(-c4cccc(C#N)c4)nc(NC4(C(=O)O)CC4)n3)nn2)n1] | ++ |
| 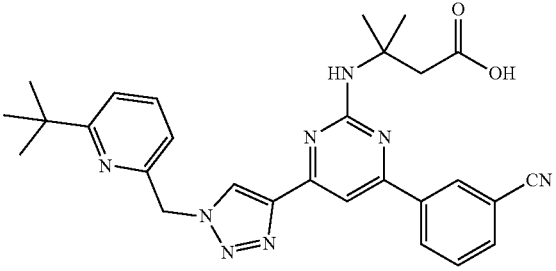 [SMILES: CC(C)(CC(=O)O)Nc1nc(-c2cccc(C#N)c2)cc(-c2cn(Cc3cccc(C(C)(C)C)n3)nn2)n1] | ++ |
| 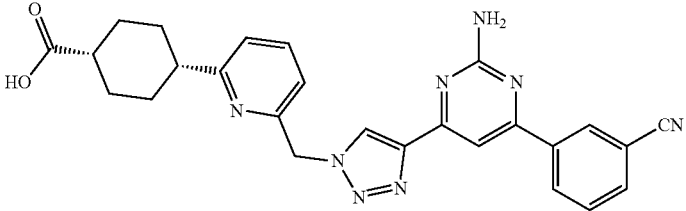 [SMILES: N#Cc1cccc(-c2cc(-c3cn(Cc4cccc([C@H]5CC[C@@H](C(=O)O)CC5)n4)nn3)nc(N)n2)c1] | +++ |
| 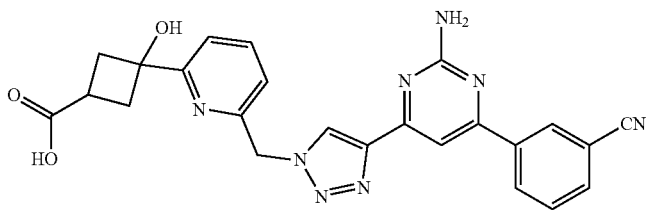 [SMILES: N#Cc1cccc(-c2cc(-c3cn(Cc4cccc(C5(O)CC(C(=O)O)C5)n4)nn3)nc(N)n2)c1] | +++ |
| 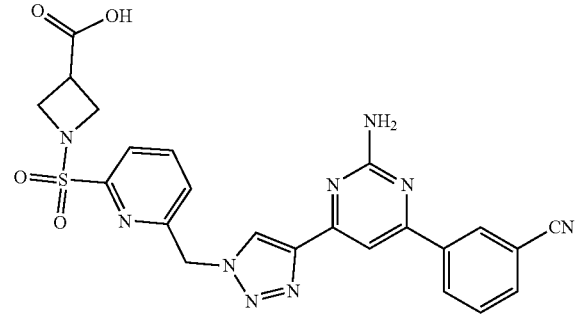 [SMILES: N#Cc1cccc(-c2cc(-c3cn(Cc4cccc(S(=O)(=O)N5CC(C(=O)O)C5)n4)nn3)nc(N)n2)c1] | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 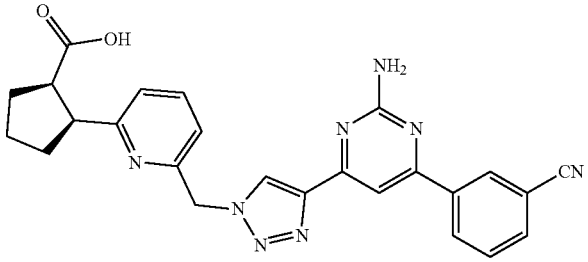 [SMILES: N#Cc1cccc(-c2cc(-c3cn(Cc4cccc([C@H]5CCC[C@H]5C(=O)O)n4)nn3)nc(N)n2)c1] | +++ |
| 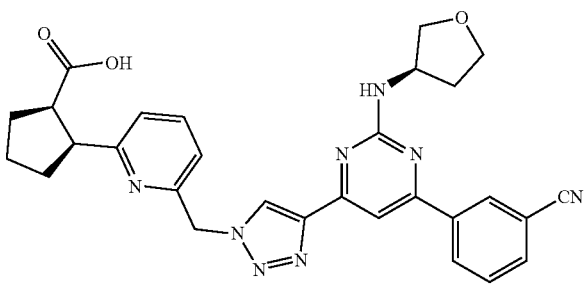 [SMILES: N#Cc1cccc(-c2cc(-c3cn(Cc4cccc([C@H]5CCC[C@H]5C(=O)O)n4)nn3)nc(N[C@@H]3CCOC3)n2)c1] | +++ |
| 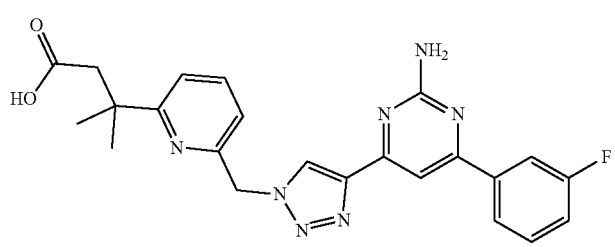 [SMILES: CC(C)(CC(=O)O)c1cccc(Cn2cc(-c3cc(-c4cccc(F)c4)nc(N)n3)nn2)n1] | +++ |
| 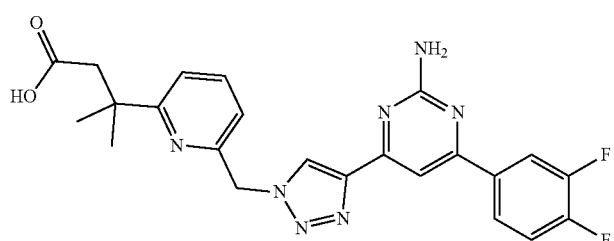 [SMILES: CC(C)(CC(=O)O)c1cccc(Cn2cc(-c3cc(-c4cccc(F)c4)nc(N)n3)nn2)n1] | +++ |
| 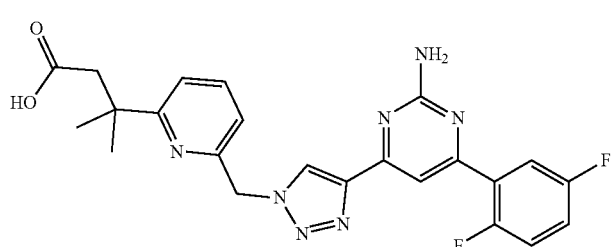 | ++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (cyclopentane-carboxylic acid, pyridine, triazole-CH2, pyrimidine-NH2, 3-cyanophenyl) | +++ |
| (cyclopentane-carboxylic acid, pyridine, triazole-CH2, pyrimidine-NH-(tetrahydrofuran-3-yl), 3-cyanophenyl) | +++ |
| (gem-dimethyl propanoic acid, pyridine, triazole-CH2, pyrimidine-NH2, 3-fluorophenyl) | +++ |
| (gem-dimethyl propanoic acid, pyridine, triazole-CH2, pyrimidine-NH2, 3,4-difluorophenyl) | +++ |
| (gem-dimethyl propanoic acid, pyridine, triazole-CH2, pyrimidine-NH2, 2,5-difluorophenyl) | ++ |
| (cyclopentane-carboxylic acid, pyridine, triazole-CH2, pyrimidine-NH2, 3-cyanophenyl) | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (compound) | +++ |
| (compound) | +++ |
| (compound) | ++ |
| (compound) | +++ |
| (compound) | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 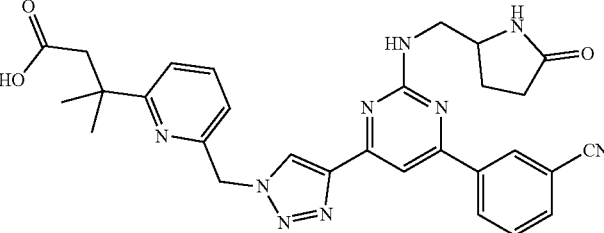 | +++ |
| 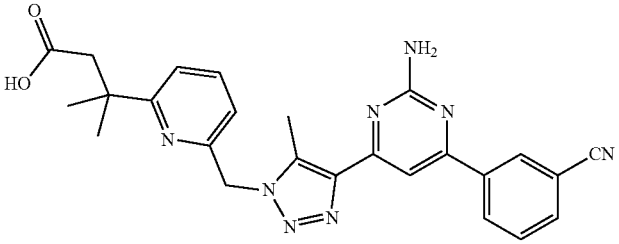 [SMILES: Cc1c(-c2cc(-c3cccc(C#N)c3)nc(N)n2)nnn1Cc1cccc(C(C)(C)CC(=O)O)n1] | ++ |
| 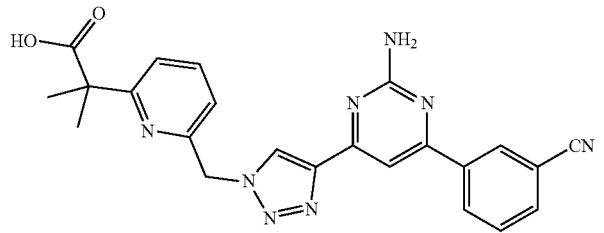 [SMILES: CC(C)(C(=O)O)c1cccc(Cn2cc(-c3cc(-c4cccc(C#N)c4)nc(N)n3)nn2)n1] | +++ |
| 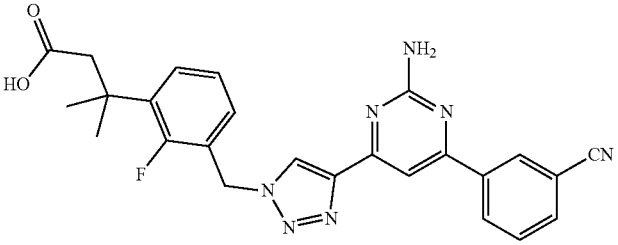 [SMILES: CC(C)(CC(=O)O)c1cccc(Cn2cc(-c3cc(-c4cccc(C#N)c4)nc(N)n3)nn2)c1F] | +++ |
| 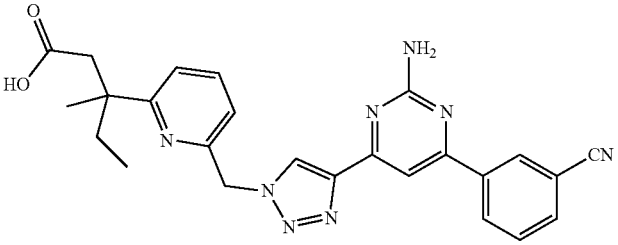 [SMILES: CCC(C)(CC(=O)O)c1cccc(Cn2cc(-c3cc(-c4cccc(C#N)c4)nc(N)n3)nn2)n1] | +++ |
| 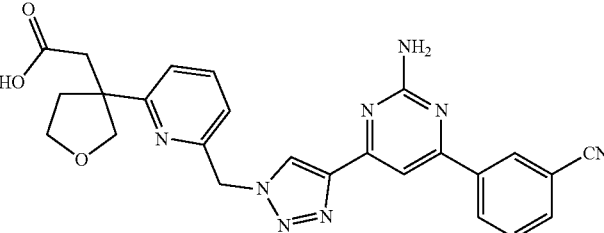 | +++ |

TABLE 1-continued

Specific Examples (Potency: $A_{2A}R$ $IC_{50}/K_B$: + means >1 μM, ++ means 100 nM to 1 μM, +++ means <100 nM)

| | Potency |
|---|---|
| [structure] | +++ |
| [structure] | +++ |
| [structure] | +++ |
| [structure] | +++ |
| [structure] | +++ |
| [structure] | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 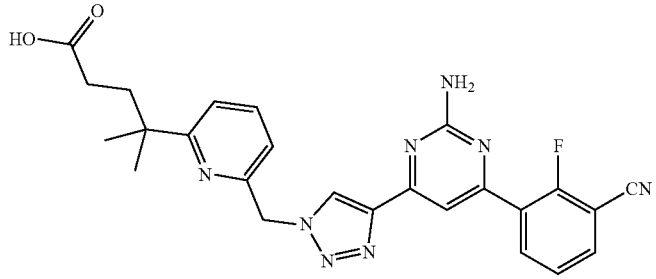 [SMILES: CC(C)(CCC(=O)O)c1cccc(Cn2cc(-c3cc(-c4cccc(C#N)c4F)nc(N)n3)nn2)n1] | +++ |
| 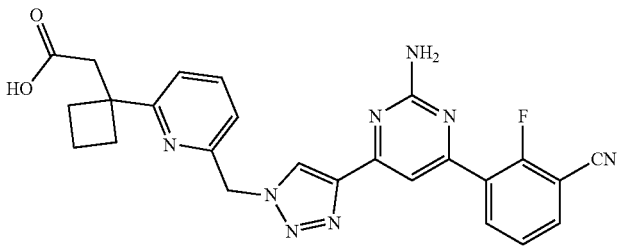 [SMILES: N#Cc1cccc(-c2cc(-c3cn(Cc4cccc(C5(CC(=O)O)CCC5)n4)nn3)nc(N)n2)c1F] | +++ |
| 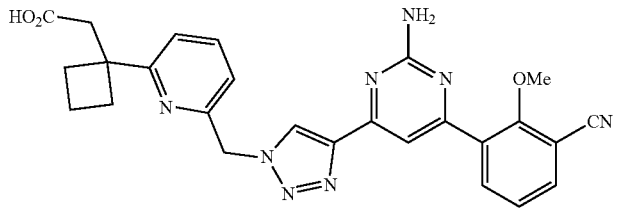 [SMILES: COc1c(C#N)cccc1-c1cc(-c2cn(Cc3cccc(C4(CC(=O)O)CCC4)n3)nn2)nc(N)n1] | +++ |
| 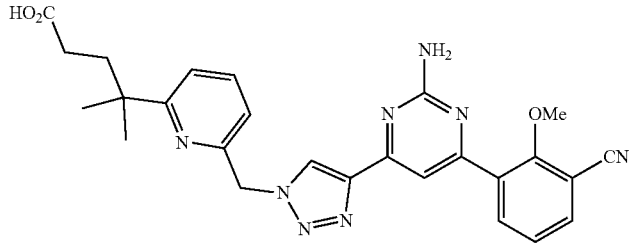 [SMILES: COc1c(C#N)cccc1-c1cc(-c2cn(Cc3cccc(C(C)(C)CCC(=O)O)n3)nn2)nc(N)n1] | +++ |
| 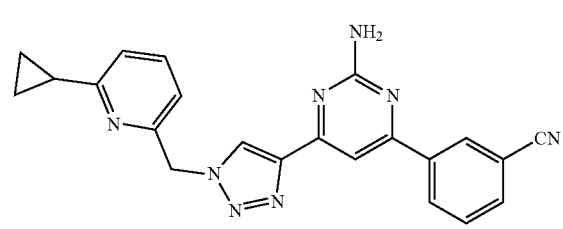 [SMILES: N#Cc1cccc(-c2cc(-c3cn(Cc4cccc(C5CC5)n4)nn3)nc(N)n2)c1] | +++ |
|  | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (6-cyclopropylpyridin-2-yl)methyl-triazole linked to 2-amino-pyrimidine with 2-fluoro-3-cyanophenyl | +++ |
| (6-tert-butylpyridin-2-yl)methyl-triazole linked to 2-amino-pyrimidine with 2,3-difluorophenyl | +++ |
| (6-cyclopropylpyridin-2-yl)methyl-triazole linked to 2-amino-pyrimidine with 2,3-difluorophenyl | +++ |
| (6-(1-methoxyethyl)pyridin-2-yl)methyl-triazole linked to 2-amino-pyrimidine with 3-cyanophenyl | +++ |
| (6-(1-methoxyethyl)pyridin-2-yl)methyl-triazole linked to 2-amino-pyrimidine with 2-fluoro-3-cyanophenyl | +++ |
| (6-(1-methoxyethyl)pyridin-2-yl)methyl-triazole linked to 2-amino-pyrimidine with 3-cyanophenyl | +++ |

TABLE 1-continued

Specific Examples (Potency: $A_{2A}R$ $IC_{50}/K_B$: + means >1 μM, ++ means 100 nM to 1 μM, +++ means <100 nM)

| Structure | Potency |
|---|---|
| (6-(1-methoxyethyl)pyridin-2-yl)methyl triazole linked to 2-amino-pyrimidine with 2-fluoro-3-cyanophenyl | +++ |
| (6-tert-butylpyridin-2-yl)methyl triazole linked to 2-amino-pyrimidine with 2-fluoro-3-cyanophenyl | +++ |
| (6-tert-butylpyridin-2-yl)methyl triazole linked to 2-amino-pyrimidine with 2-methoxy-3-cyanophenyl | +++ |
| (6-isopropylpyridin-2-yl)methyl triazole linked to 2-amino-pyrimidine with 2-methoxy-3-cyanophenyl | +++ |
| (6-cyclopropylpyridin-2-yl)methyl triazole linked to 2-amino-pyrimidine with 2-methoxy-3-cyanophenyl | +++ |
| (6-isopropylpyridin-2-yl)methyl triazole linked to 2-amino-pyrimidine with 2-fluoro-3-cyanophenyl | +++ |
| (6-isopropylpyridin-2-yl)methyl triazole linked to 2-amino-pyrimidine with 2,3-difluorophenyl | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (structure) | +++ |
| (structure) | +++ |
| (structure) | +++ |
| (structure) | +++ |
| (structure) | +++ |
| (structure) | +++ |

TABLE 1-continued
Specific Examples (Potency: $A_{2A}R$ $IC_{50}/K_B$: + means >1 μM, ++ means 100 nM to 1 μM, +++ means <100 nM)
| | Potency |
|---|---|
| 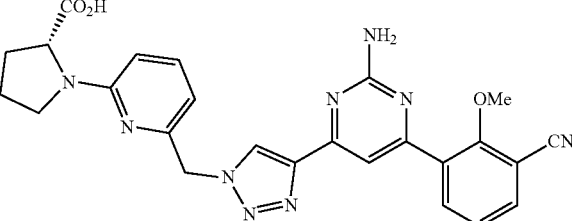 | ++ |
| 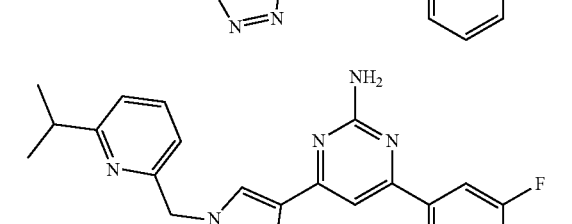 | +++ |
| 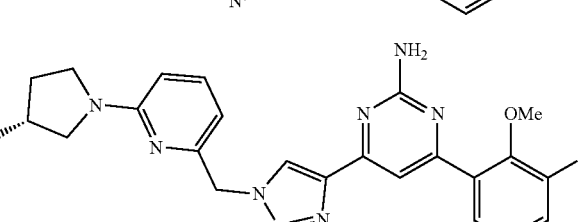 | +++ |
| 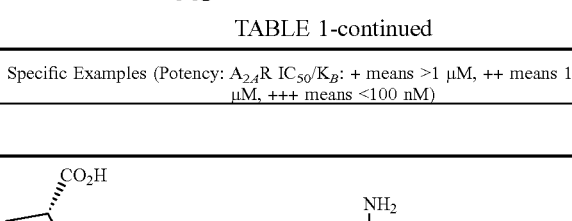 | +++ |
| 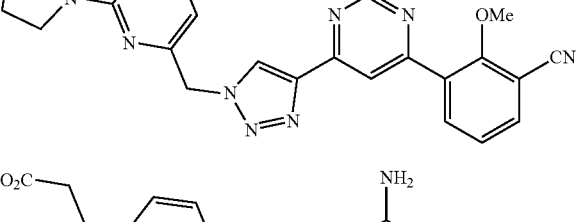 | +++ |
| 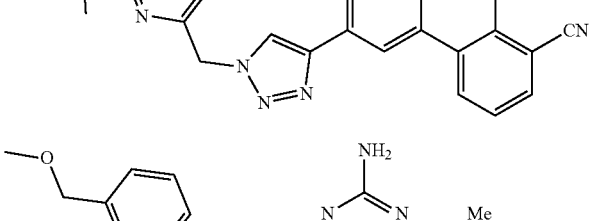 | +++ |
| 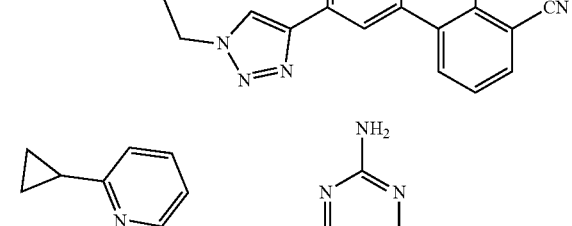 | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 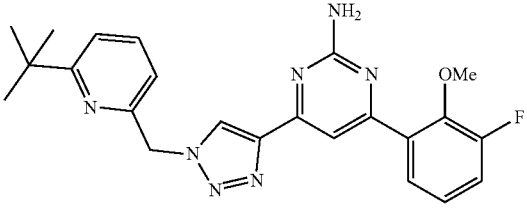 [SMILES: COc1c(F)cccc1-c1cc(-c2cn(Cc3cccc(C(C)(C)C)n3)nn2)nc(N)n1] | +++ |
| 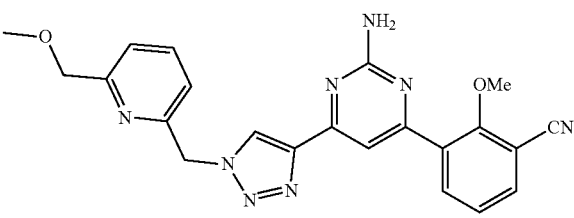 [SMILES: COCc1cccc(Cn2cc(-c3cc(-c4cccc(C#N)c4OC)nc(N)n3)nn2)n1] | +++ |
| 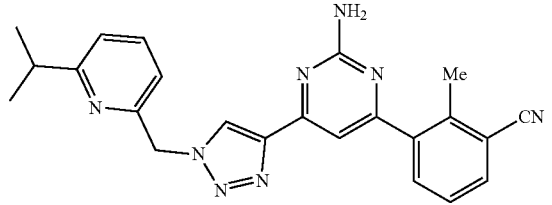 [SMILES: Cc1c(C#N)cccc1-c1cc(-c2cn(Cc3cccc(C(C)C)n3)nn2)nc(N)n1] | +++ |
| 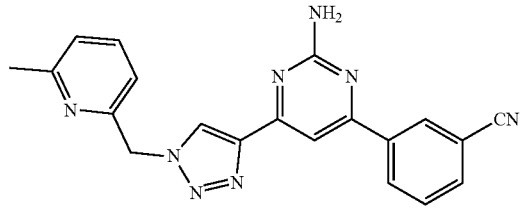 [SMILES: Cc1cccc(Cn2cc(-c3cc(-c4cccc(C#N)c4)nc(N)n3)nn2)n1] | +++ |
| 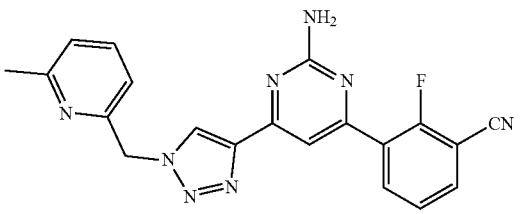 [SMILES: Cc1cccc(Cn2cc(-c3cc(-c4cccc(C#N)c4F)nc(N)n3)nn2)n1] | +++ |
| 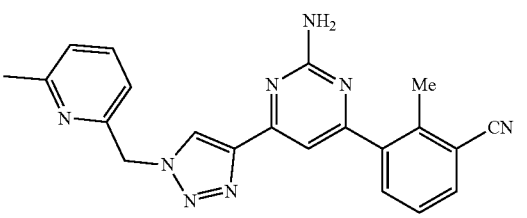 [SMILES: Cc1cccc(Cn2cc(-c3cc(-c4cccc(C#N)c4C)nc(N)n3)nn2)n1] | +++ |
| 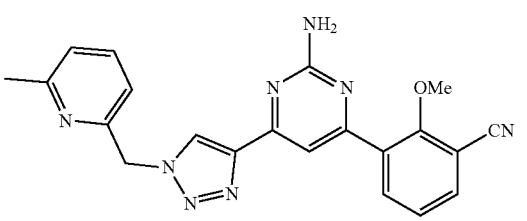 [SMILES: COc1c(C#N)cccc1-c1cc(-c2cn(Cc3cccc(C)n3)nn2)nc(N)n1] | +++ |

447                                                                                                                               448
TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 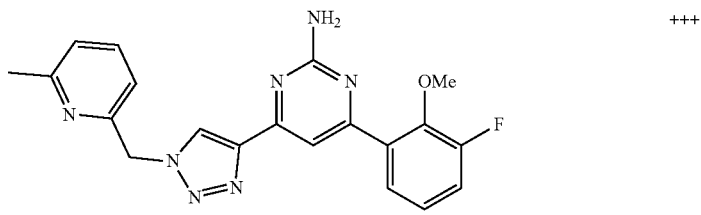 | +++ |
| 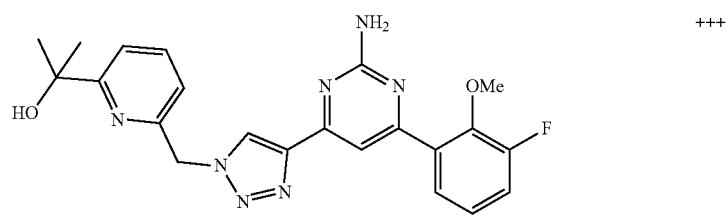 | +++ |
| 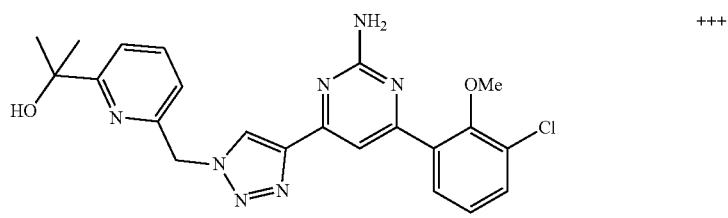 | +++ |
| 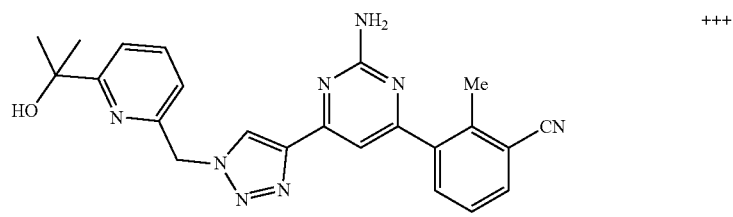 | +++ |
| 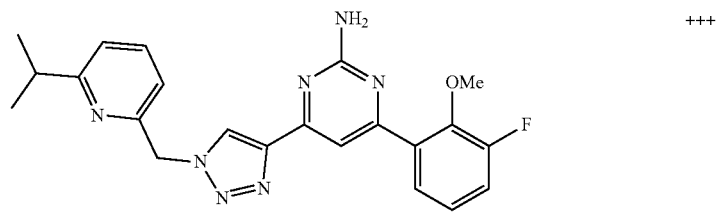 | +++ |
| 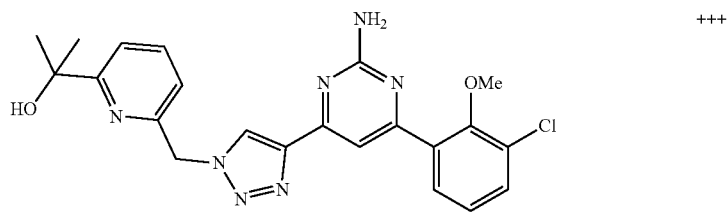 | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| (chemical structure) | +++ |
| (chemical structure) | ++ |
| (chemical structure) | +++ |
| (chemical structure) | +++ |
| (chemical structure) | +++ |
| (chemical structure) | +++ |

TABLE 1-continued
Specific Examples (Potency: $A_{2A}R$ $IC_{50}/K_B$: + means >1 µM, ++ means 100 nM to 1 µM, +++ means <100 nM)
| | Potency |
|---|---|
| 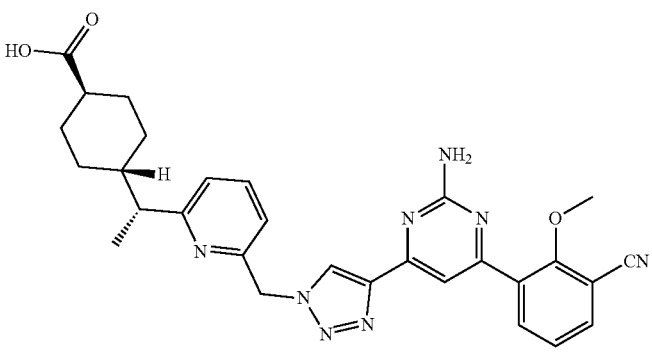 [SMILES: COc1c(C#N)cccc1-c1cc(-c2cn(Cc3cccc([C@H](C)[C@H]4CC[C@H](C(=O)O)CC4)n3)nn2)nc(N)n1] | +++ |
| 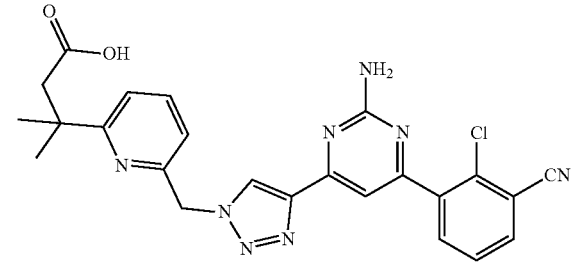 [SMILES: CC(C)(CC(=O)O)c1cccc(Cn2cc(-c3cc(-c4cccc(C#N)c4Cl)nc(N)n3)nn2)n1] | +++ |
| 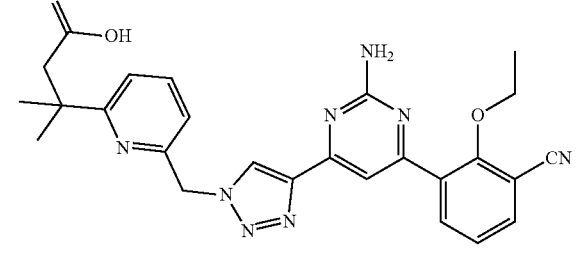 | +++ |
| 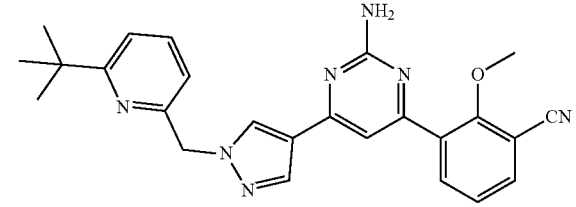 [SMILES: COc1c(C#N)cccc1-c1cc(-c2cnn(Cc3cccc(C(C)(C)C)n3)c2)nc(N)n1] | ++ |
| 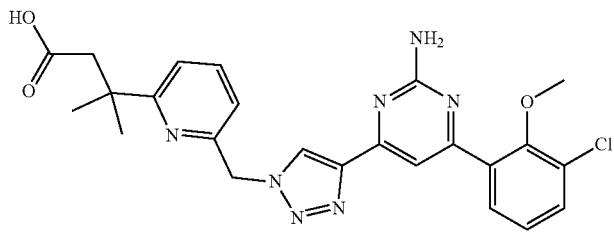 [SMILES: COc1c(Cl)cccc1-c1cc(-c2cn(Cc3cccc(C(C)(C)CC(=O)O)n3)nn2)nc(N)n1] | +++ |

TABLE 1-continued

Specific Examples (Potency: $A_{2A}R$ $IC_{50}/K_B$: + means >1 µM, ++ means 100 nM to 1 µM, +++ means <100 nM)

| | Potency |
|---|---|
| [chemical structure] | +++ |
| [chemical structure] | |
| [chemical structure] | |
| [chemical structure] | +++ |
| [chemical structure] | +++ |
| [chemical structure] | +++ |

TABLE 1-continued

Specific Examples (Potency: $A_{2A}R$ $IC_{50}/K_B$: + means >1 µM, ++ means 100 nM to 1 µM, +++ means <100 nM)

| Structure | Potency |
|---|---|
| | +++ |
| | +++ |
| | +++ |
| | +++ |
| | +++ |
| | +++ |

TABLE 1-continued
Specific Examples (Potency: $A_{2A}R$ $IC_{50}/K_B$: + means >1 µM, ++ means 100 nM to 1 µM, +++ means <100 nM)
| Structure | Potency |
|---|---|
| 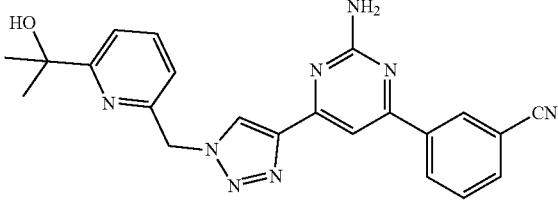 [SMILES: CC(C)(O)c1cccc(Cn2cc(-c3cc(-c4cccc(C#N)c4)nc(N)n3)nn2)n1] | +++ |
| 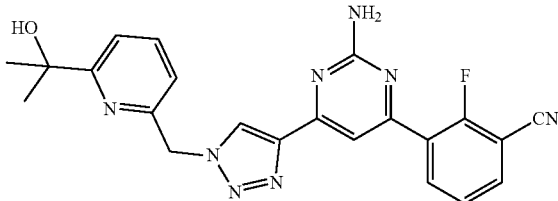 | +++ |
| 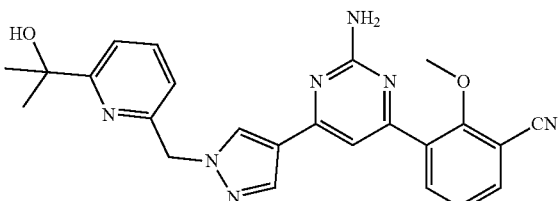 | +++ |
| 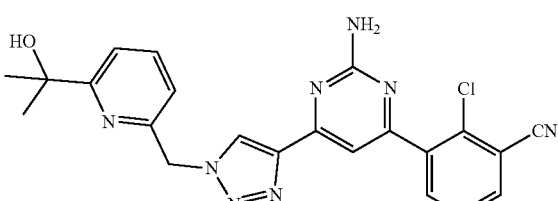 | +++ |
| 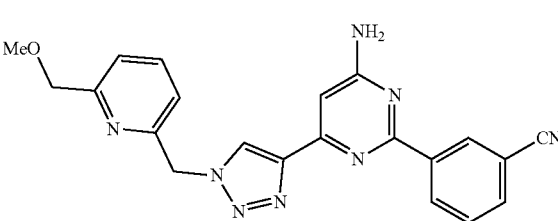 | +++ |
| 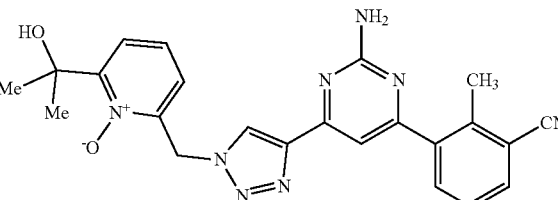 | +++ |
| 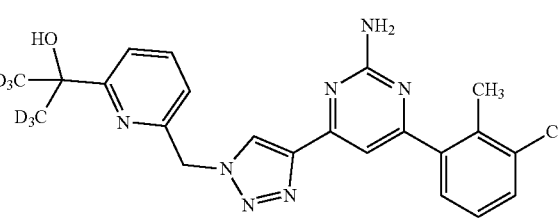 | +++ |

TABLE 1-continued

Specific Examples (Potency: $A_{2A}R$ $IC_{50}/K_B$: + means >1 µM, ++ means 100 nM to 1 µM, +++ means <100 nM)

| | Potency |
|---|---|
| 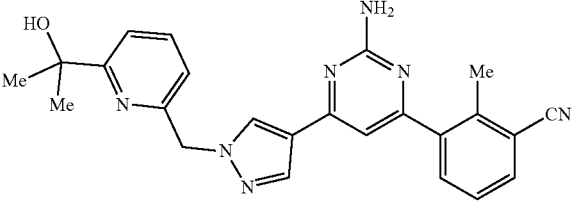 [SMILES: Cc1c(C#N)cccc1-c1cc(-c2cnn(Cc3cccc(C(C)(C)O)n3)c2)nc(N)n1] | +++ |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound selected from the group consisting of:

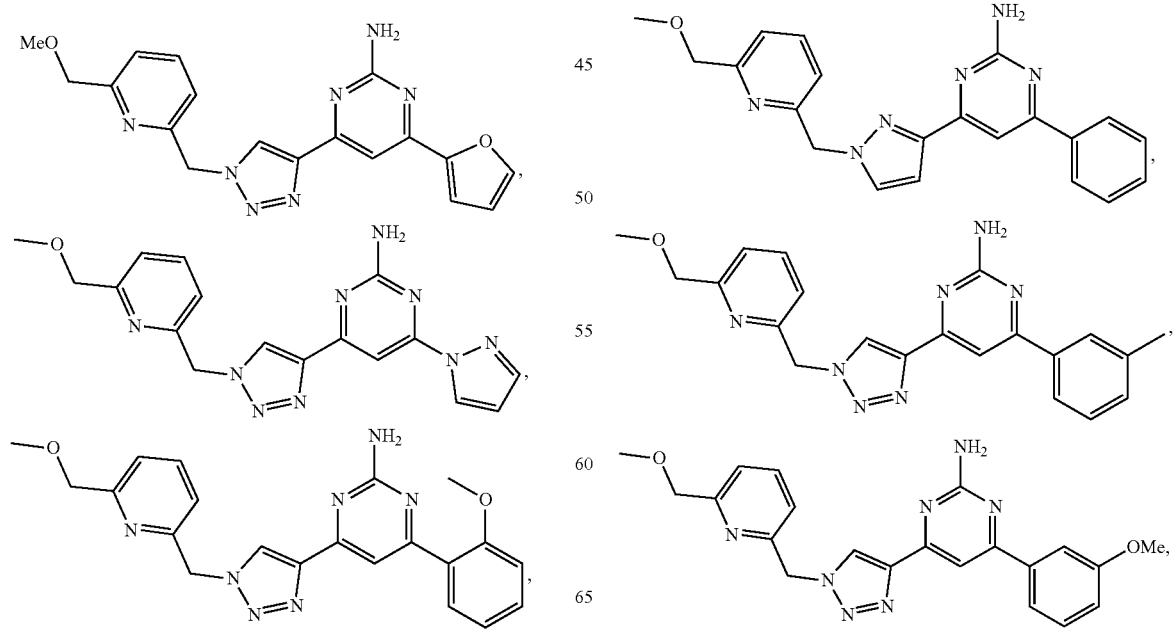

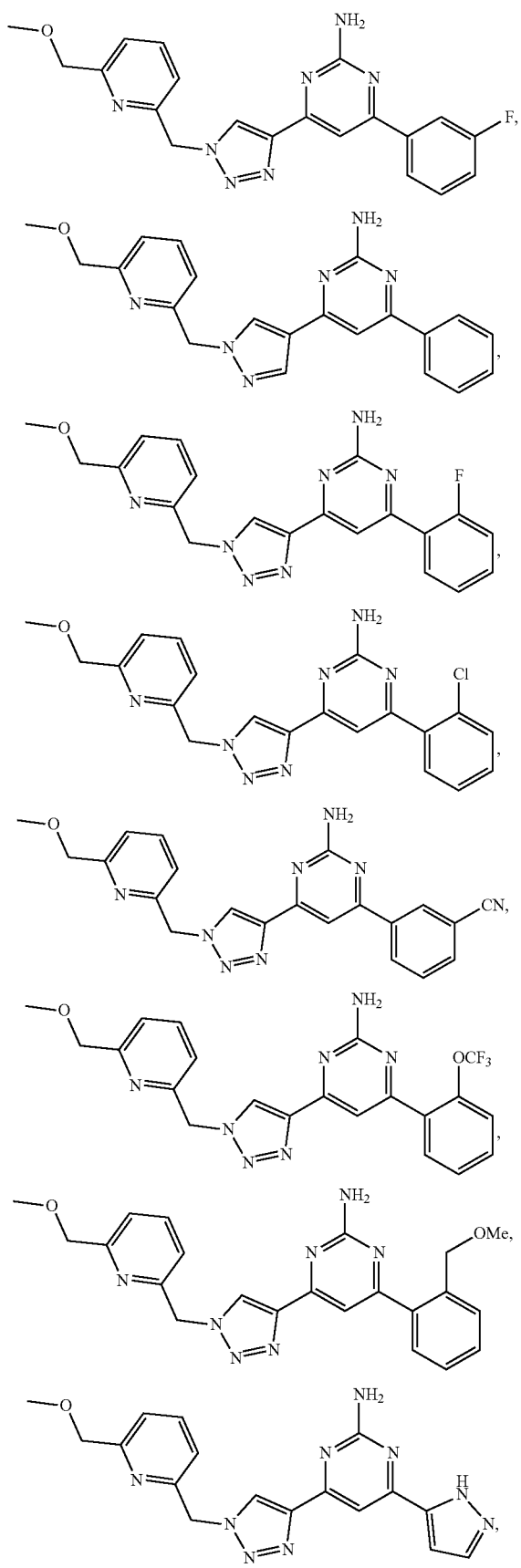
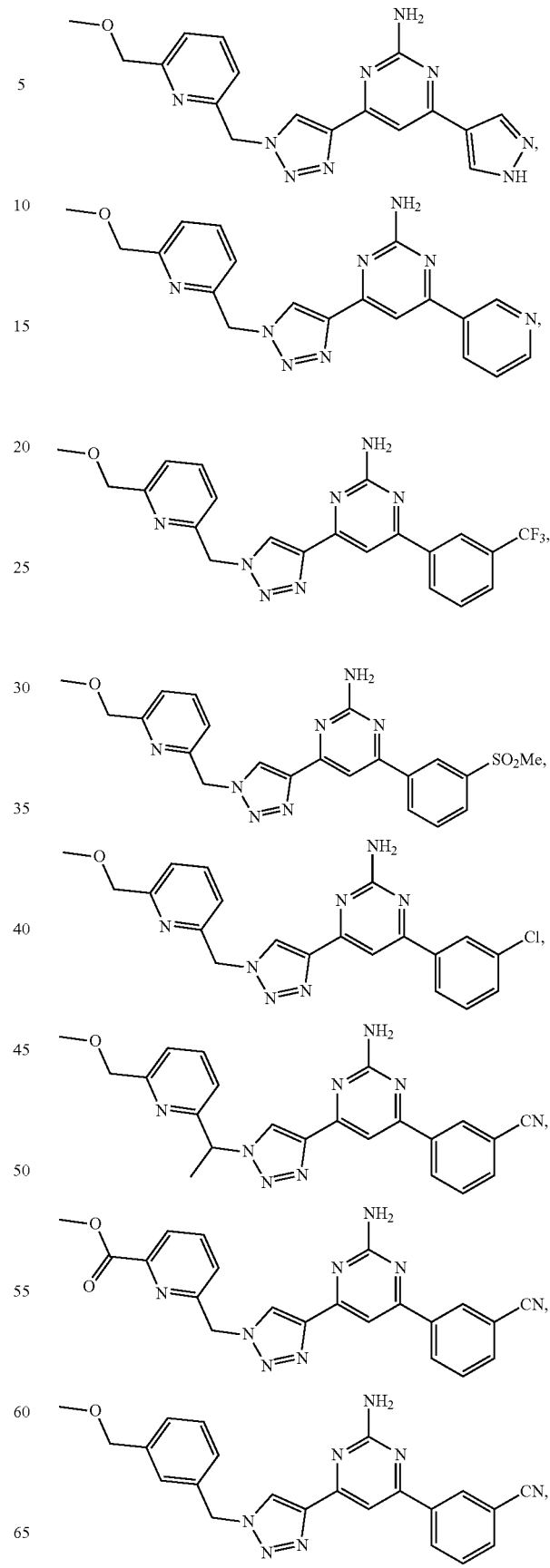

463
-continued
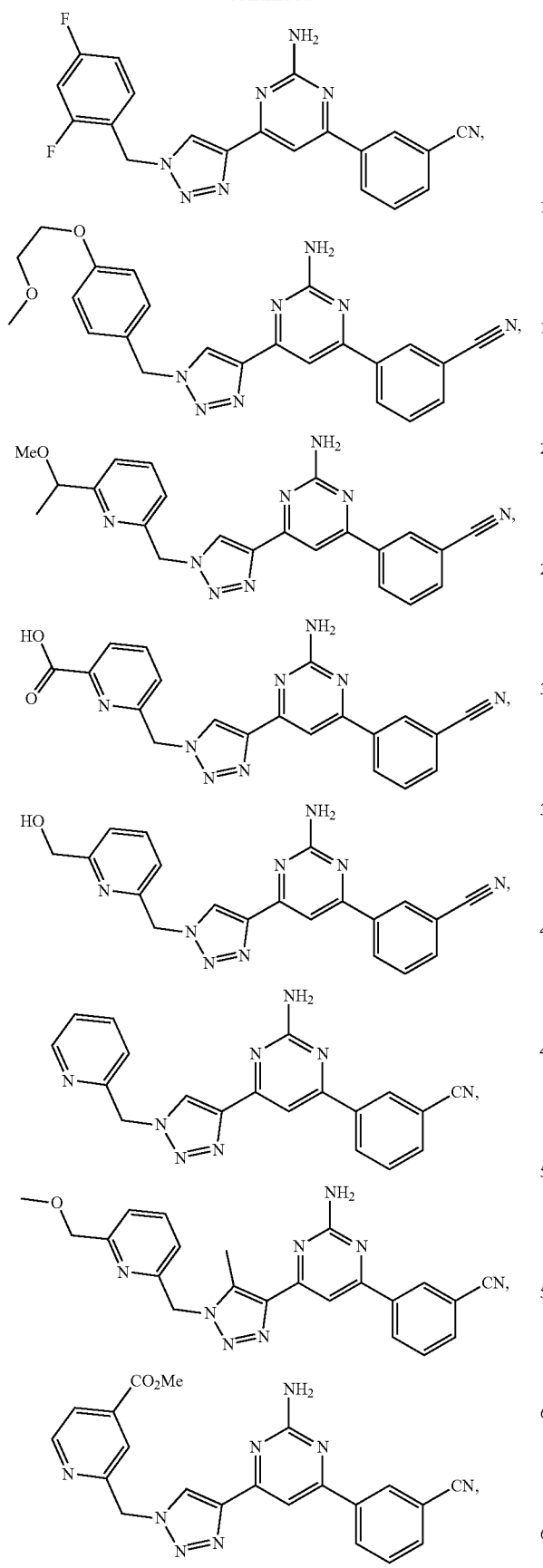
464
-continued
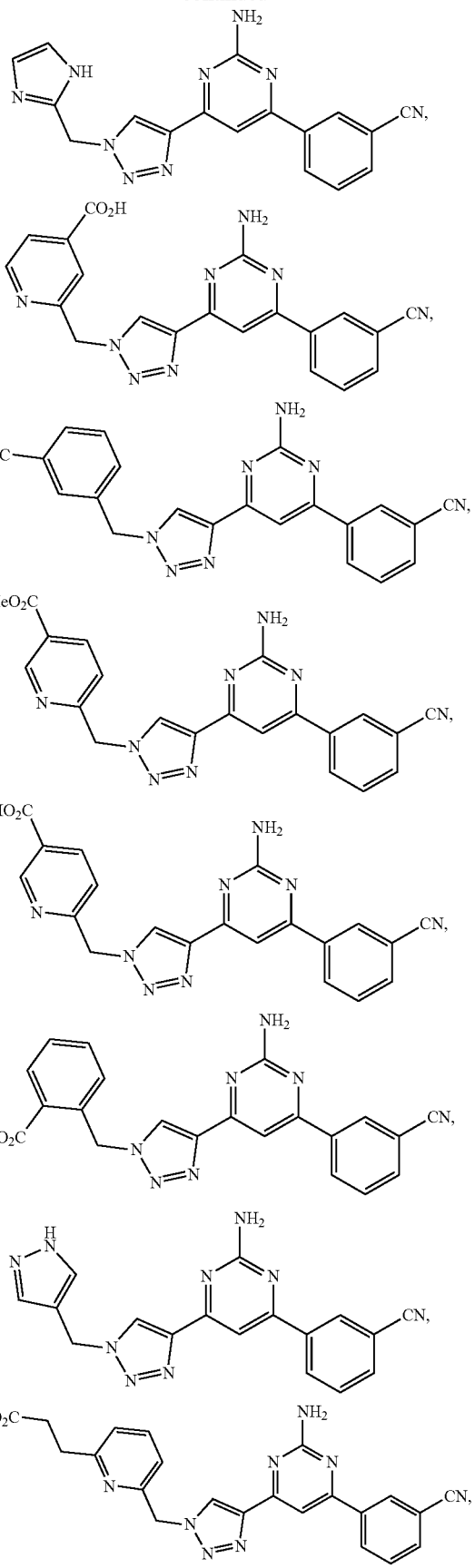

465
-continued
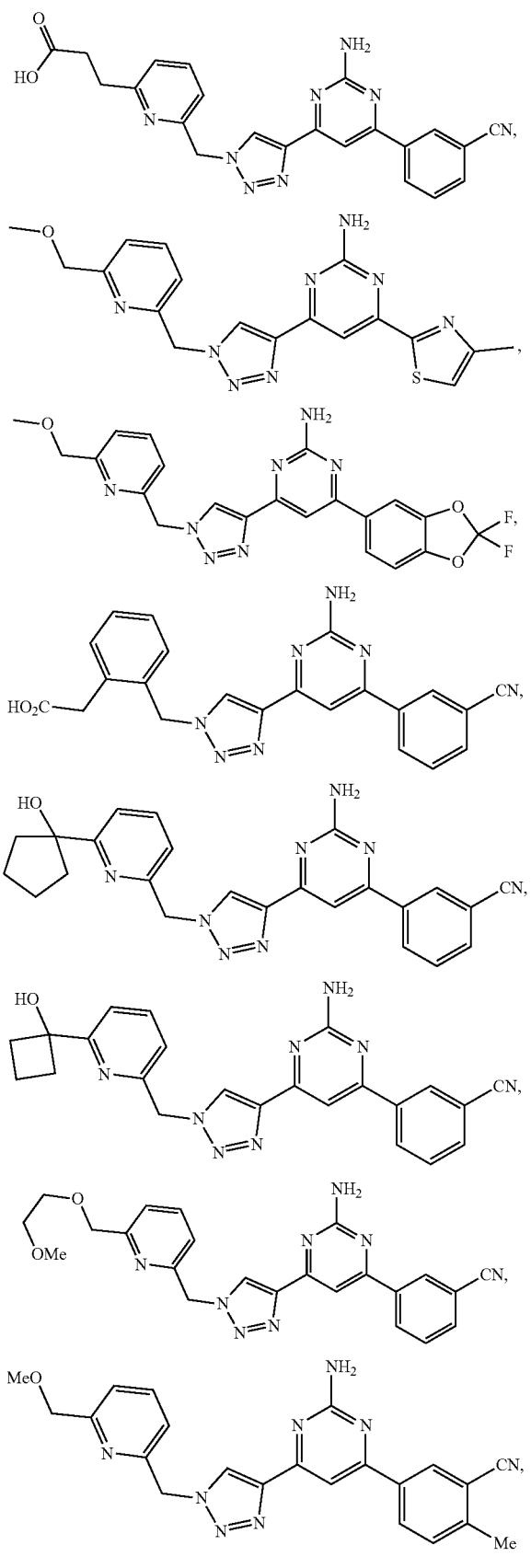
466
-continued
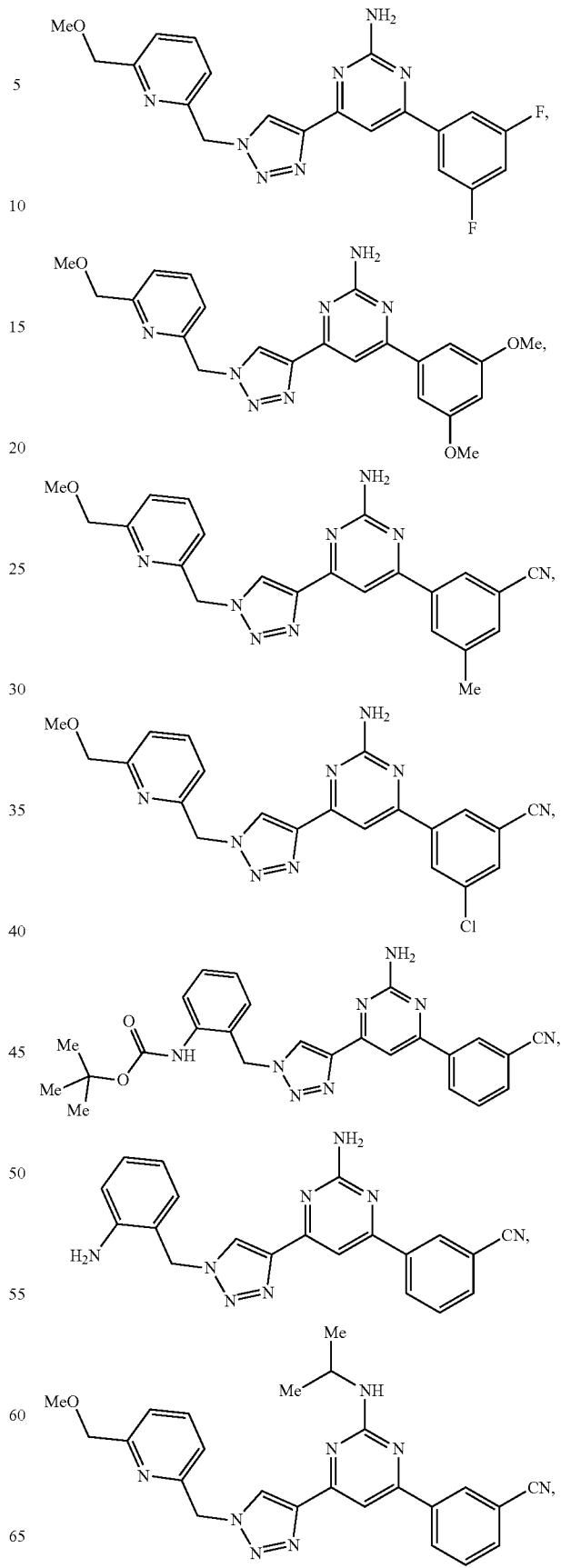

467
-continued
468
-continued
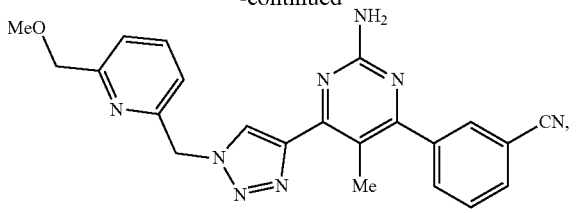
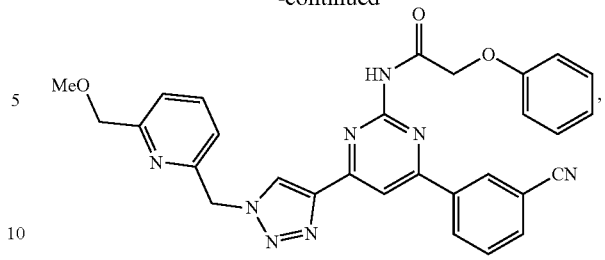
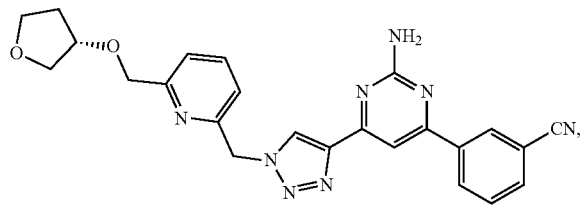
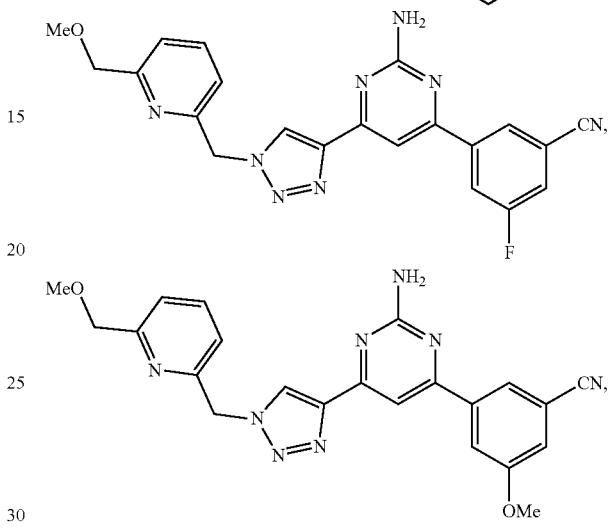
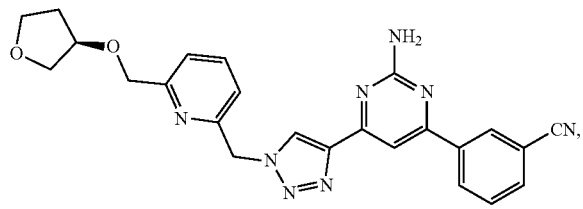
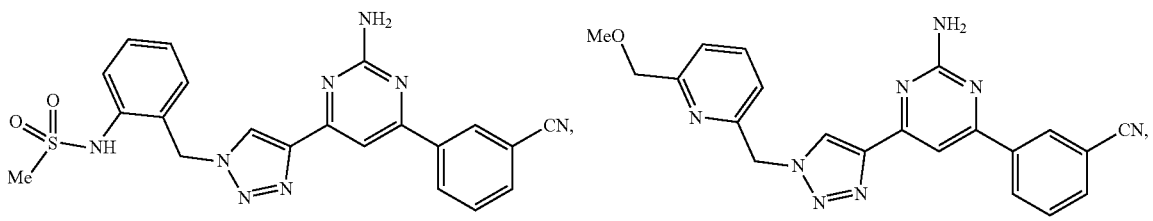
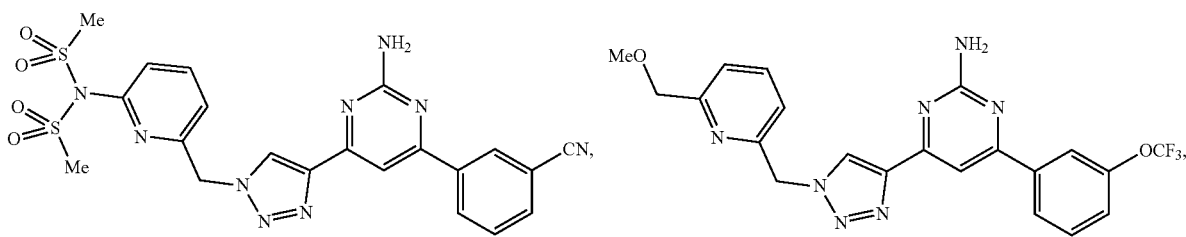
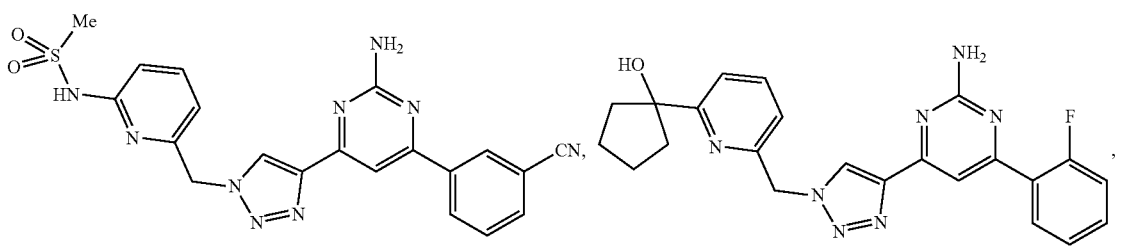

-continued
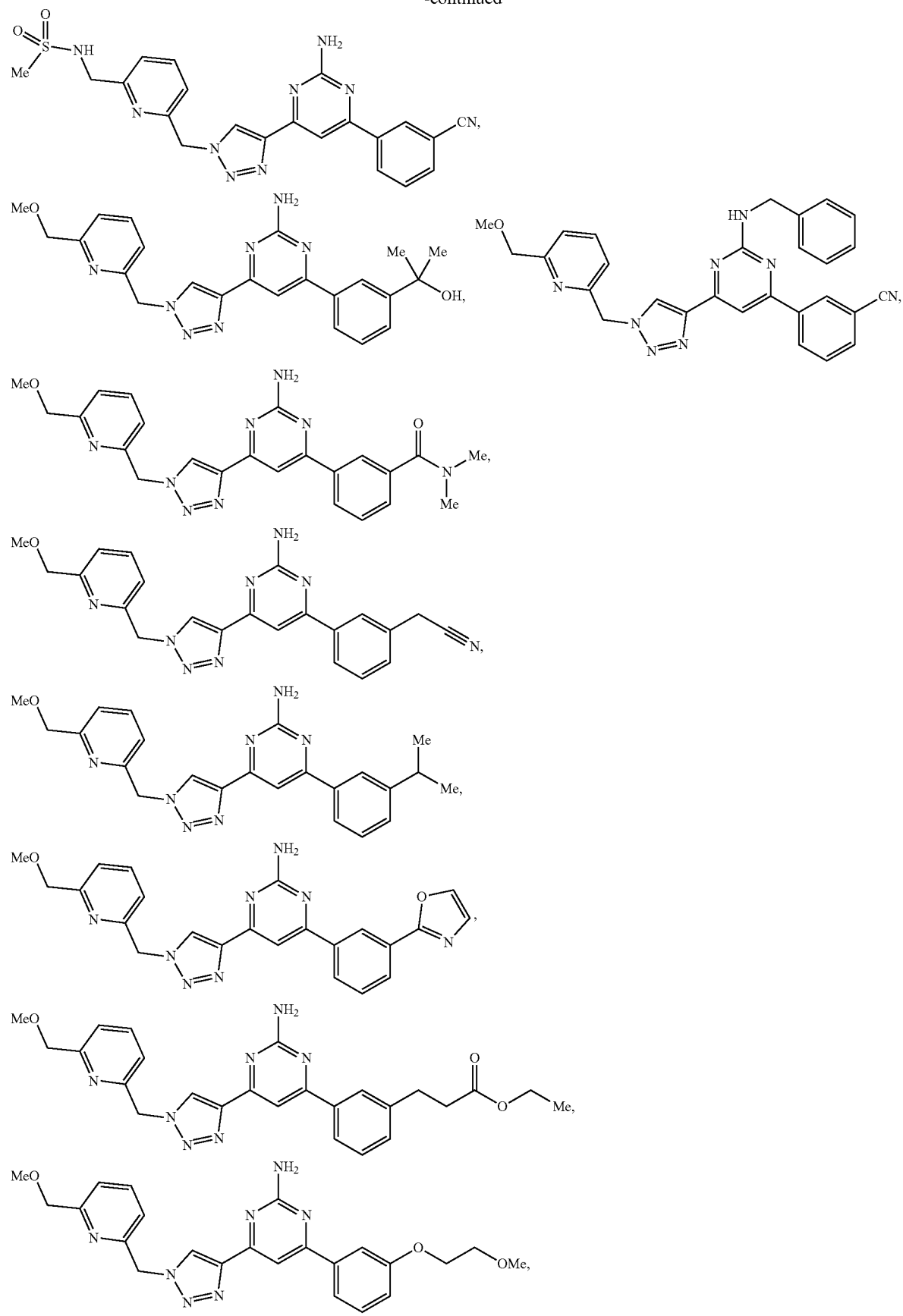

471 472
-continued
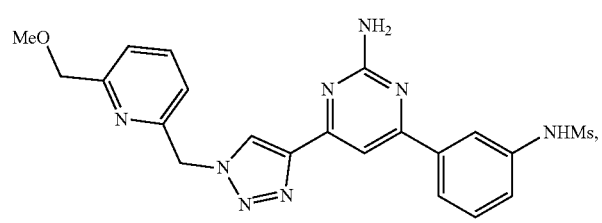
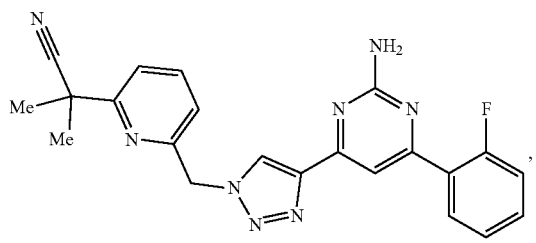
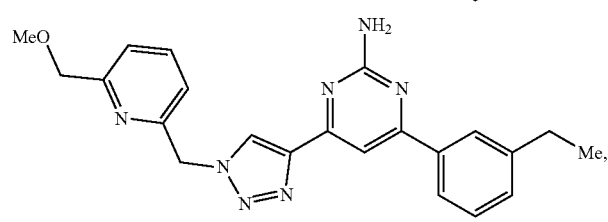
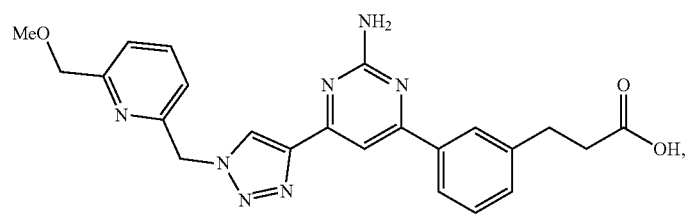
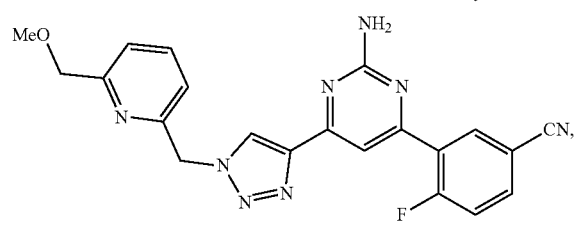
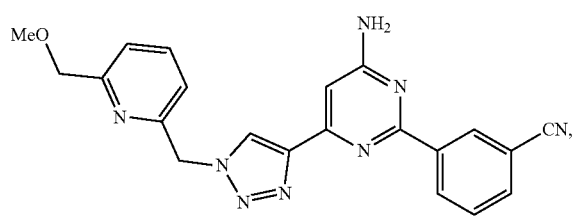
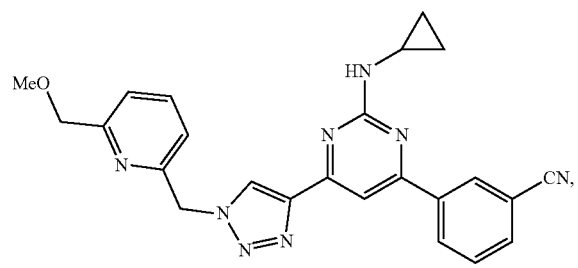
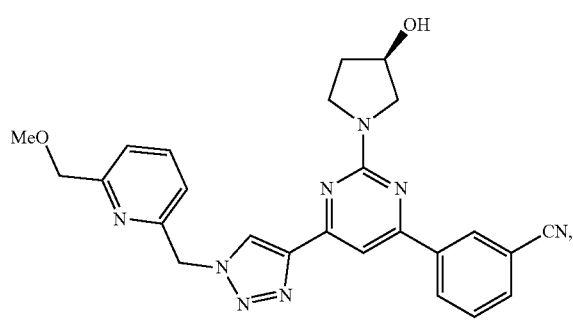
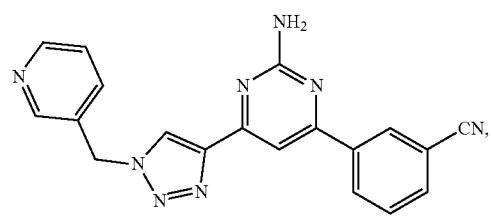
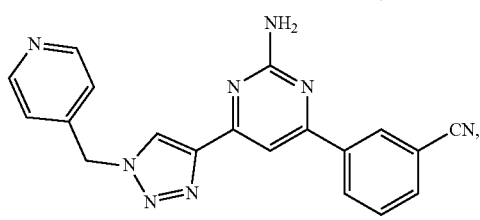
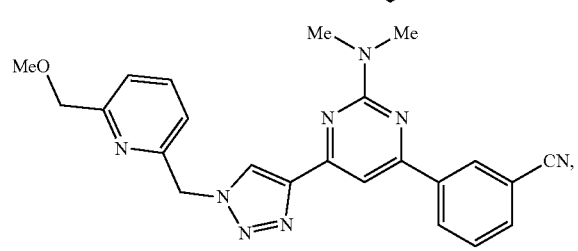
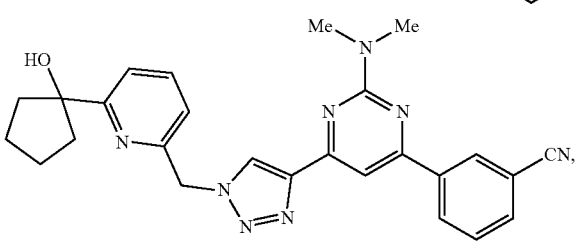

473 474
-continued
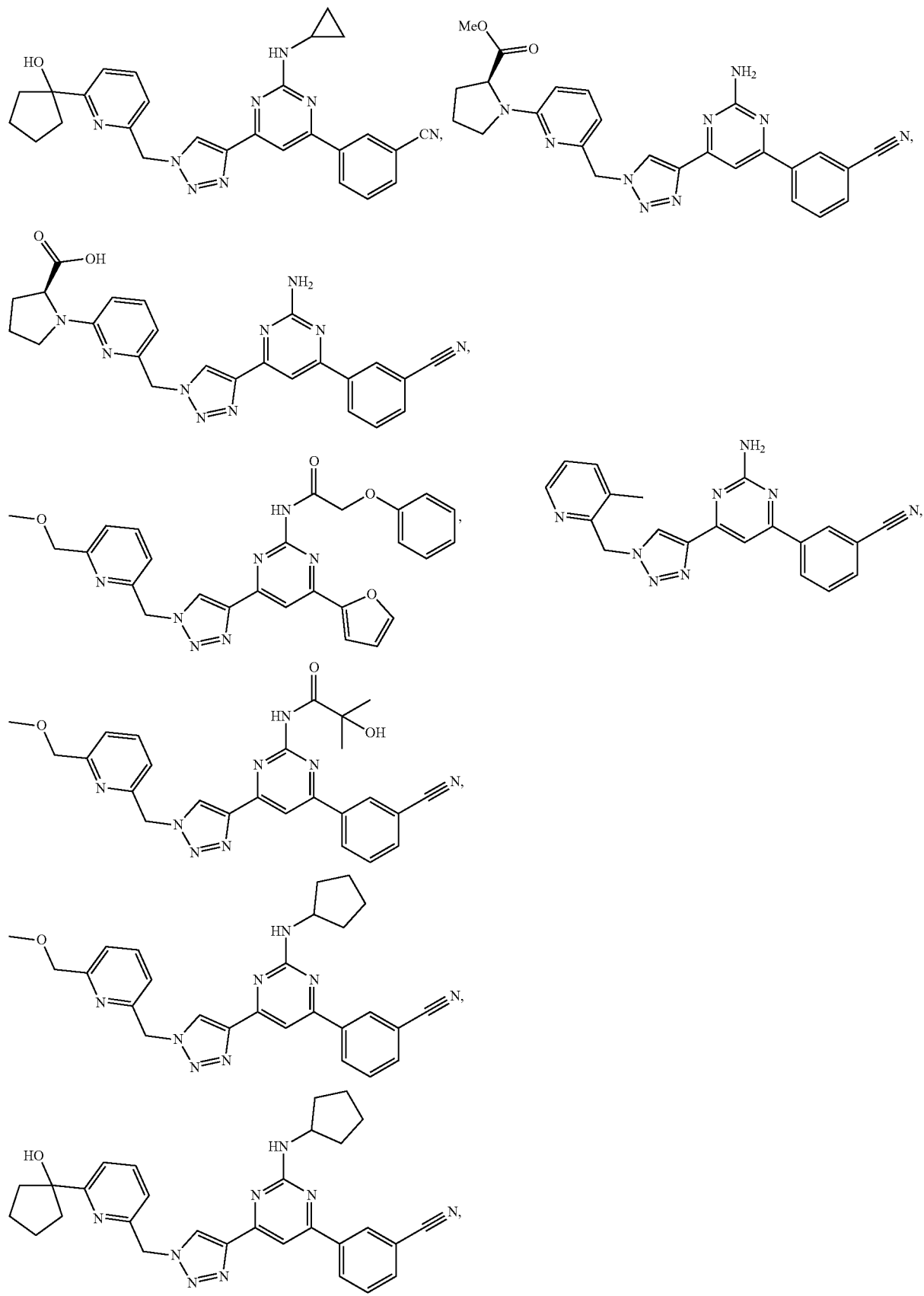

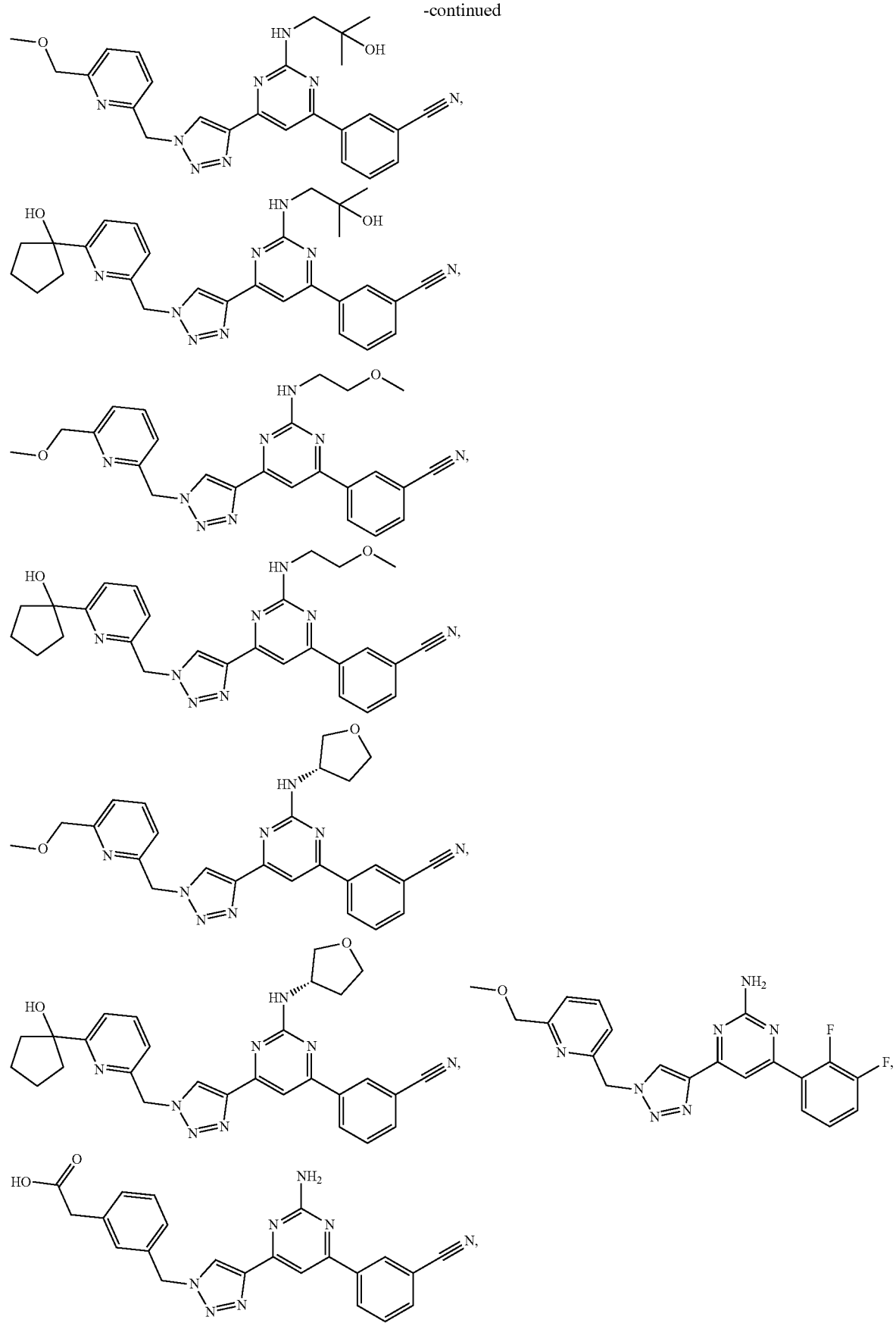

477
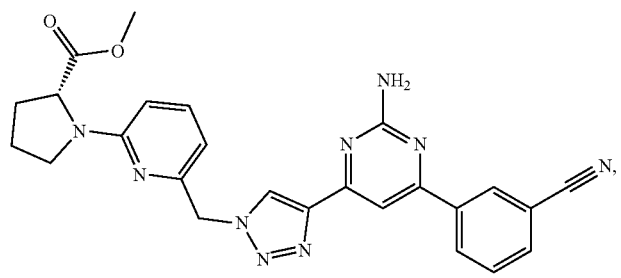
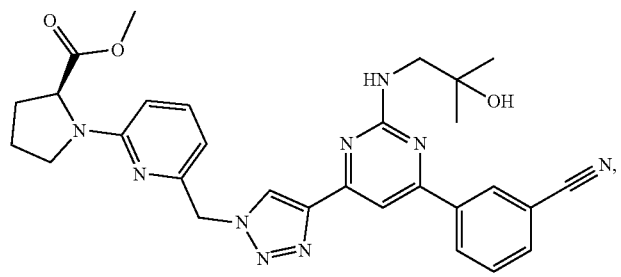
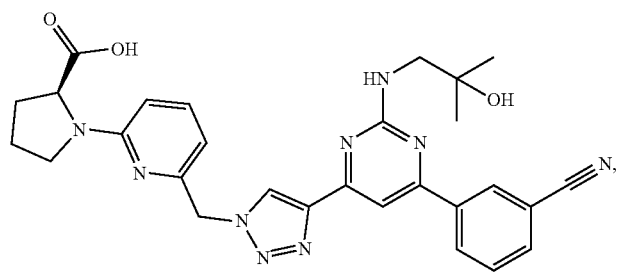
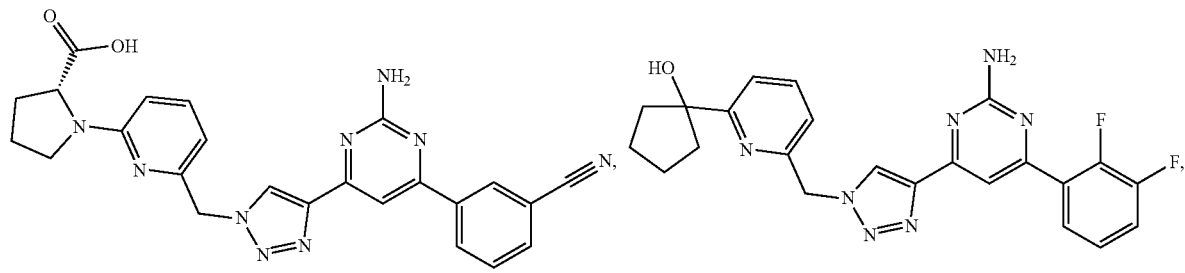
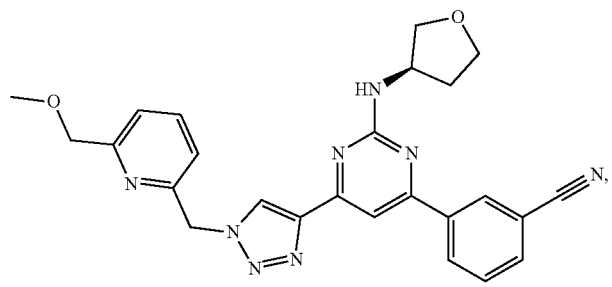
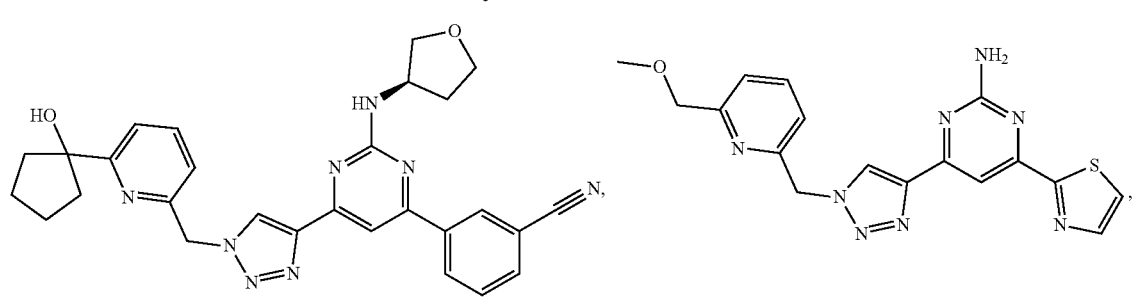
478
-continued -continued
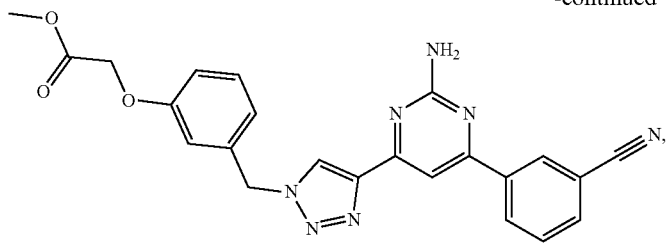
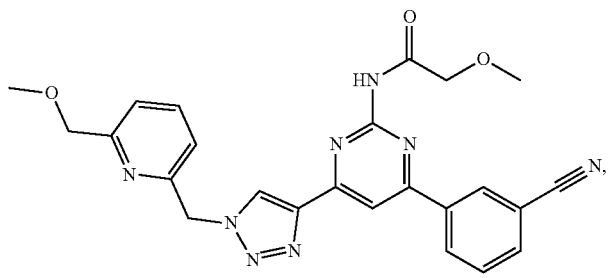
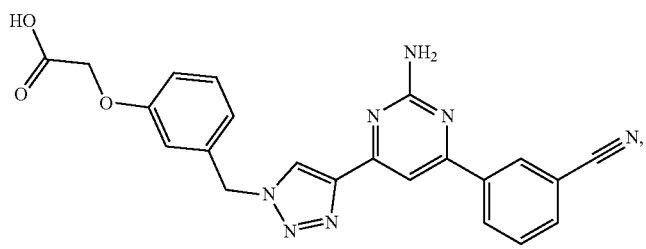
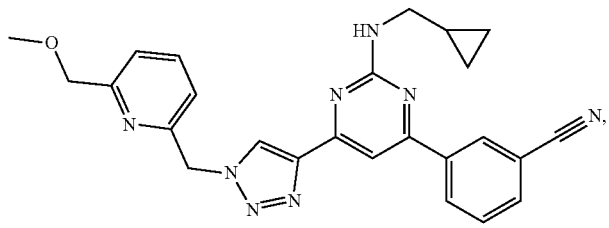
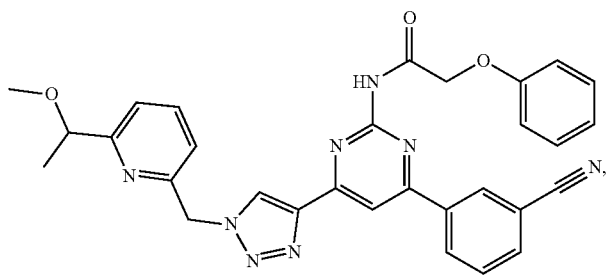
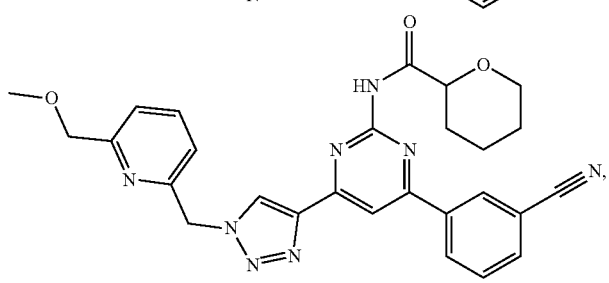

-continued
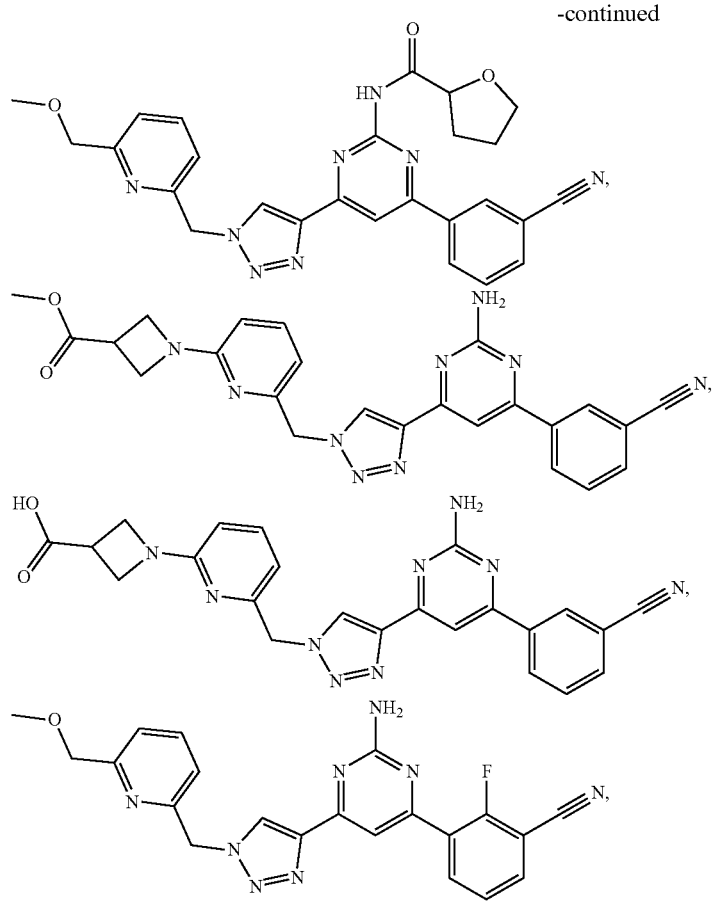
-continued
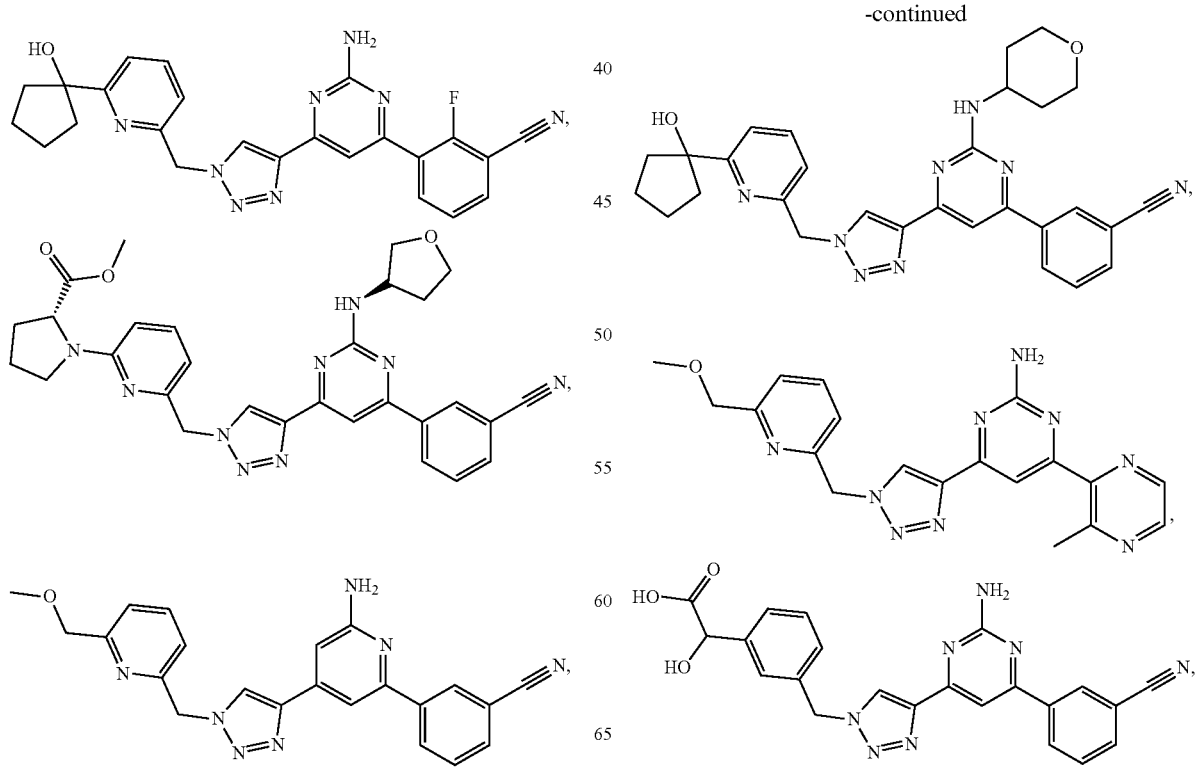

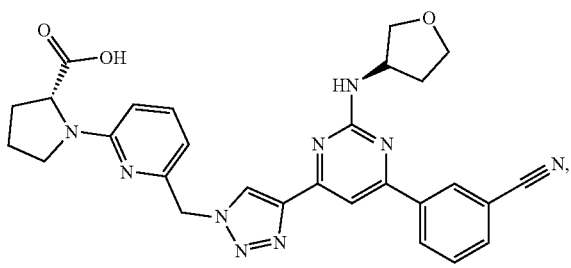
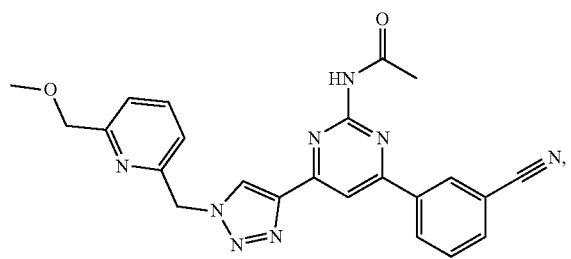
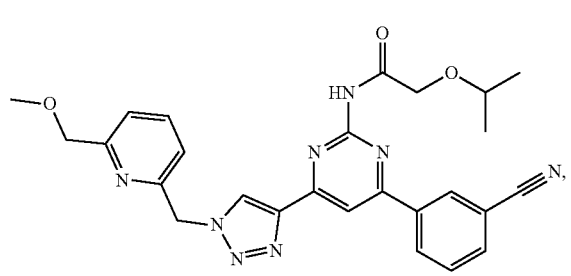
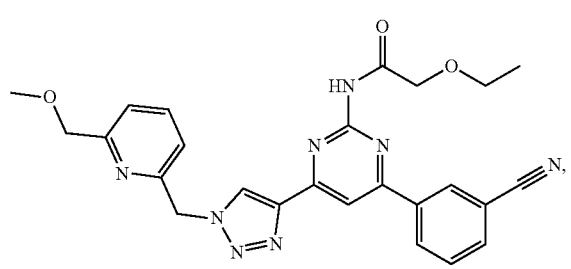
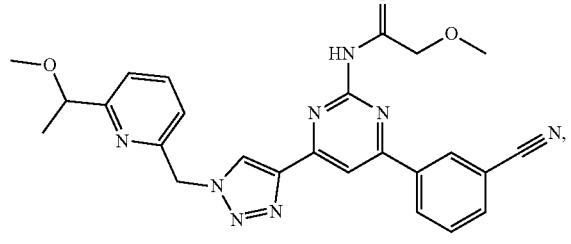
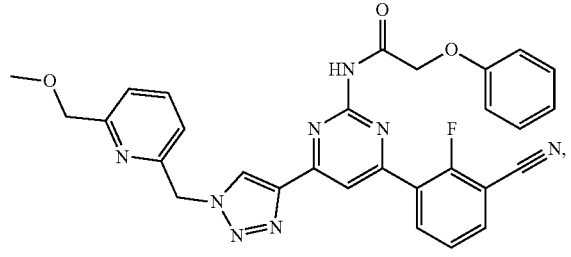
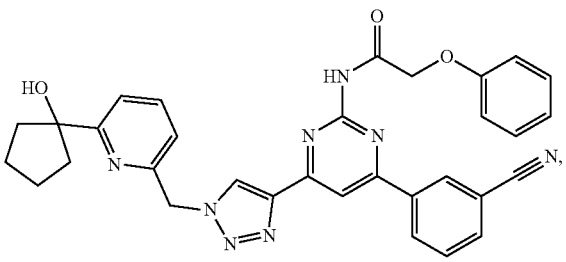
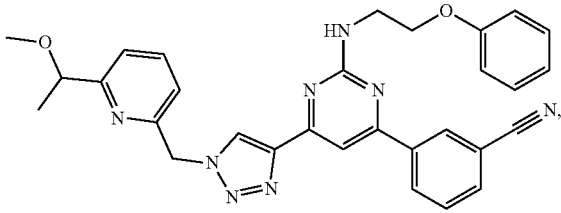
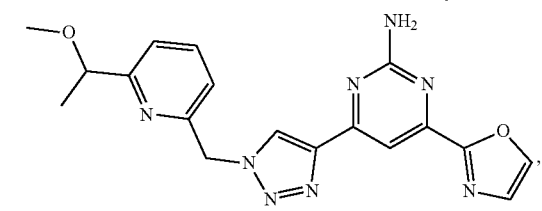
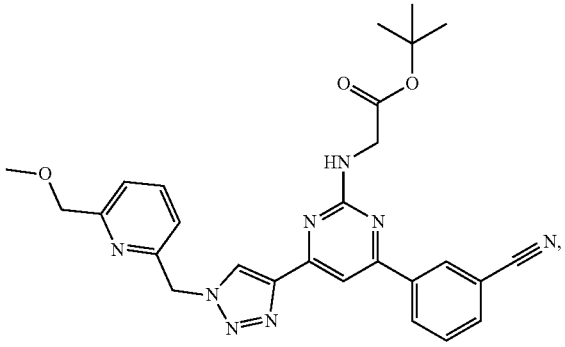
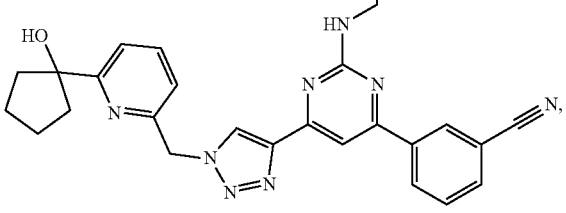
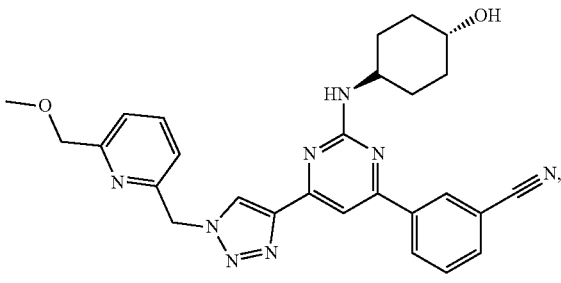

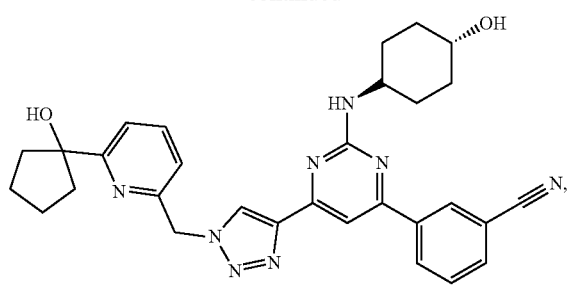

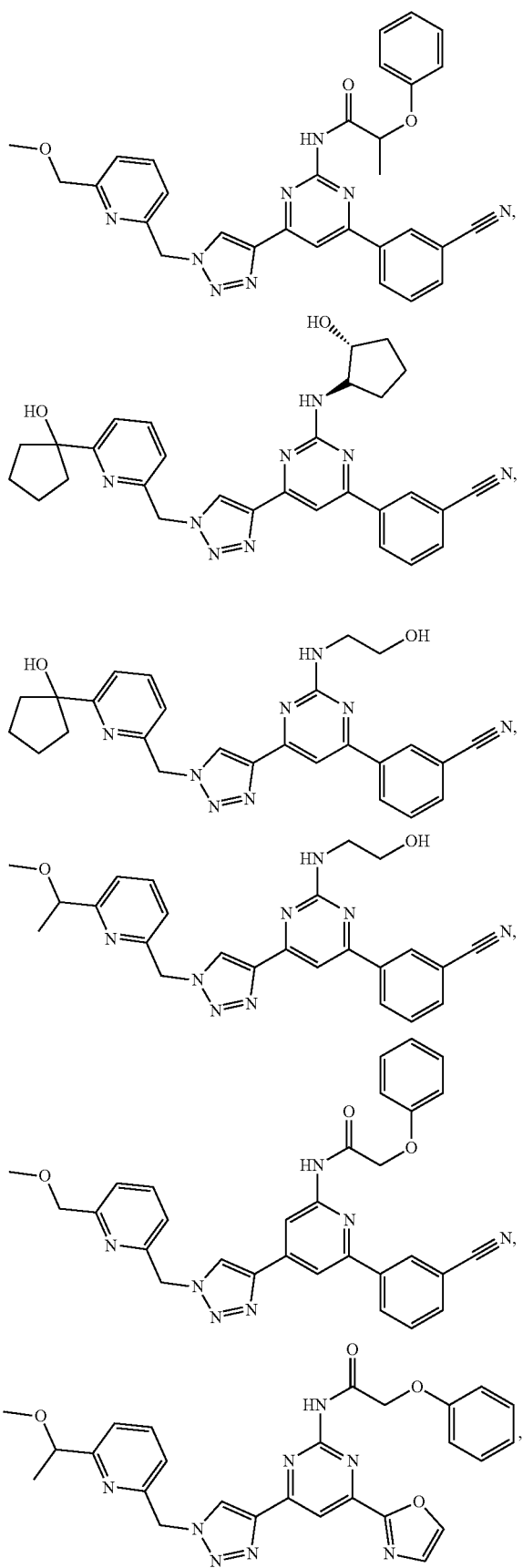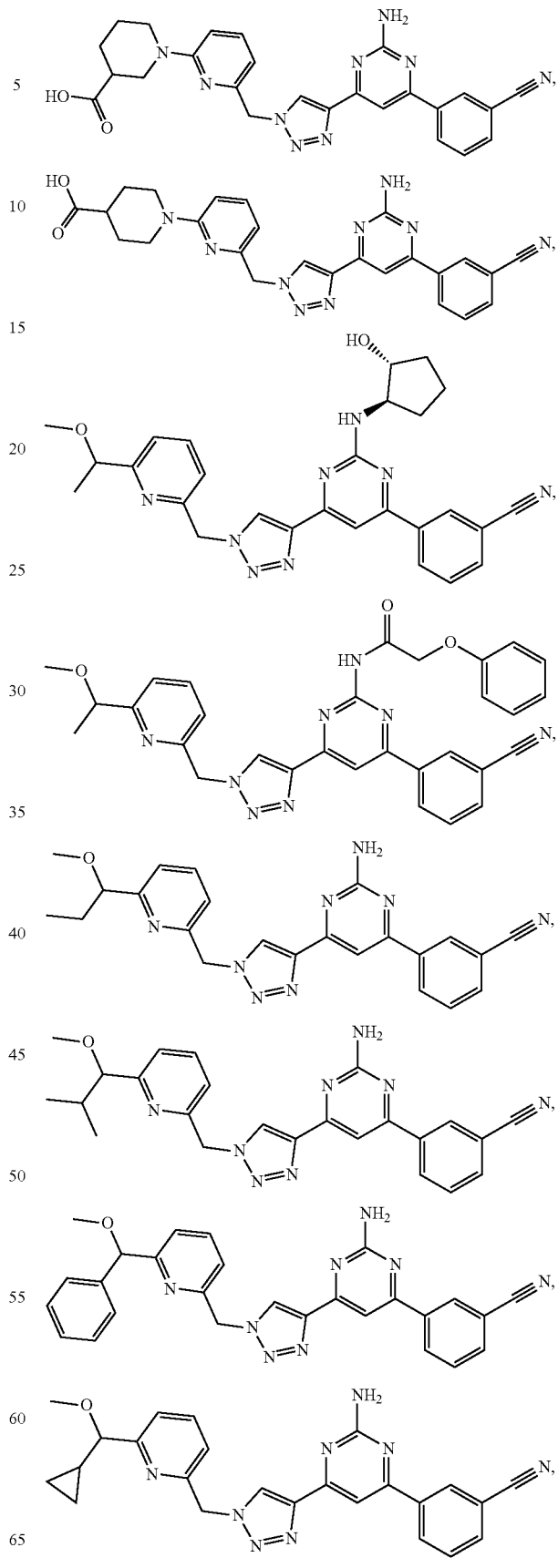

489
-continued
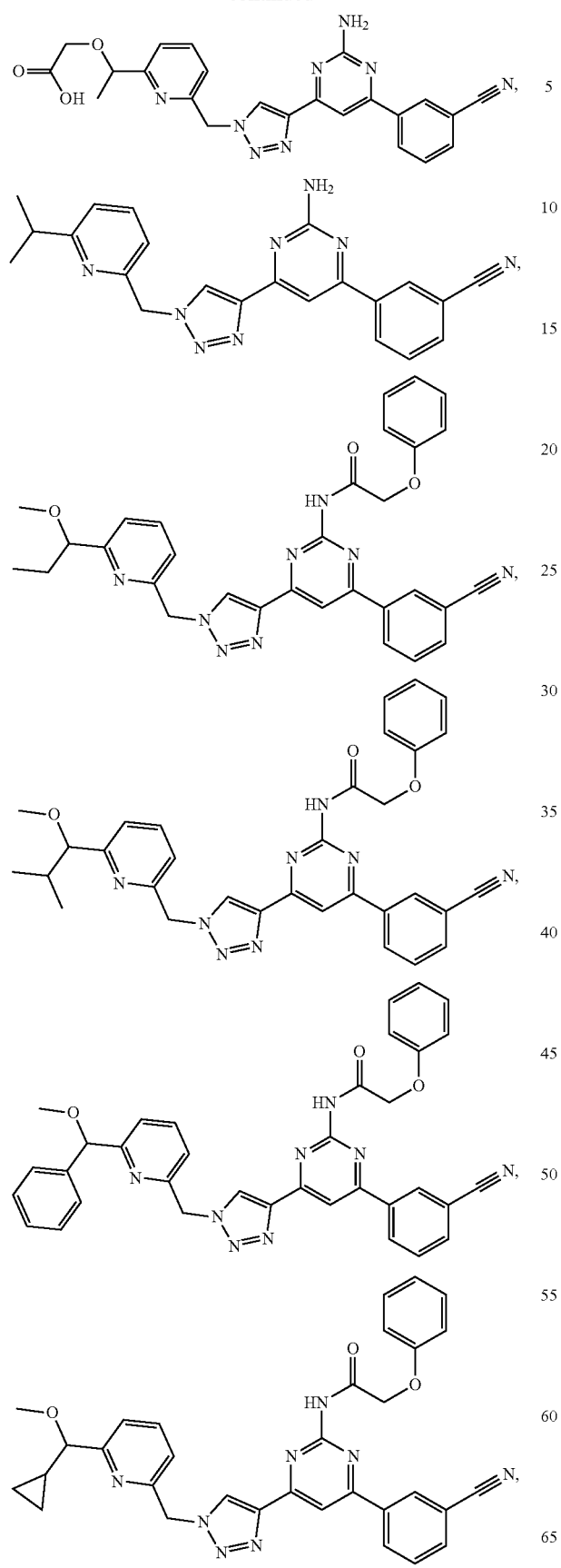
490
-continued
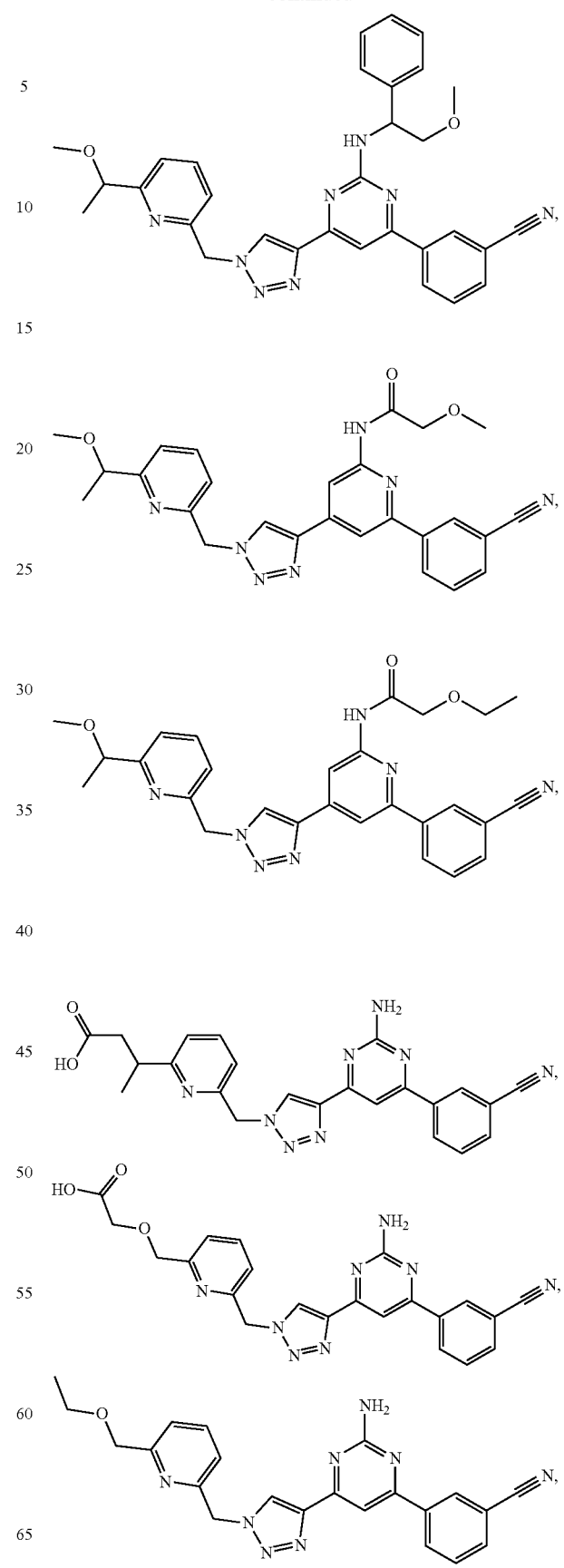

491
-continued
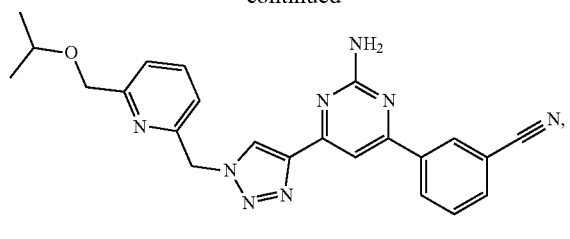
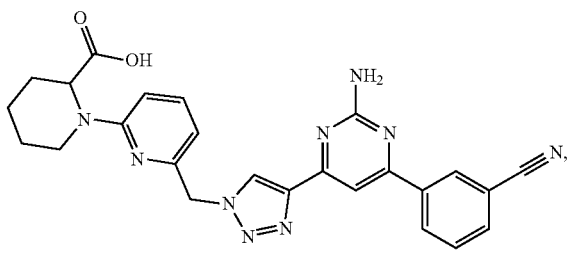
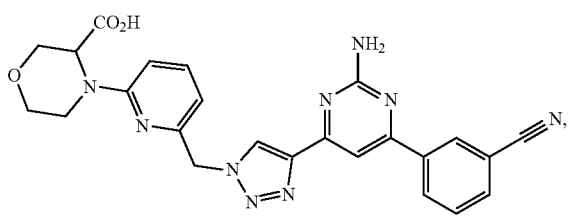
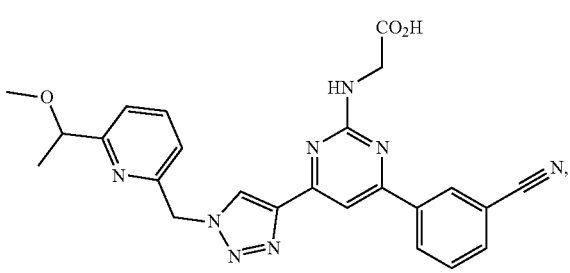
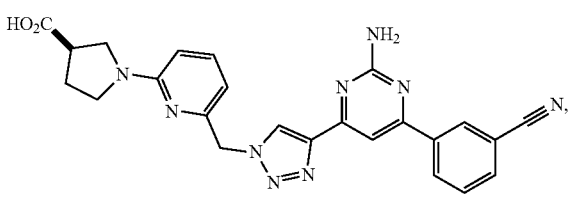
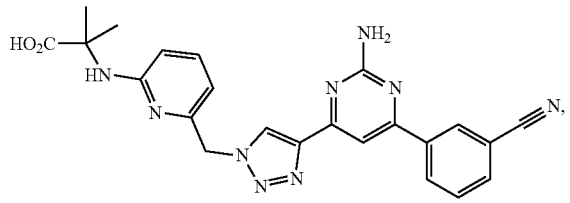
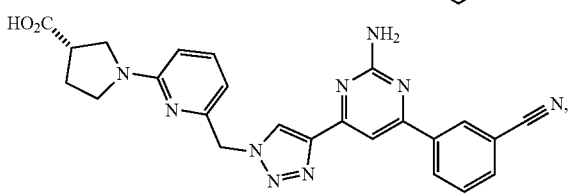
492
-continued
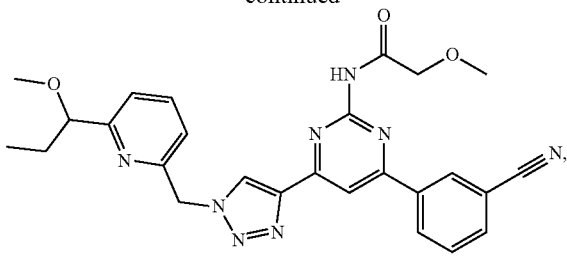
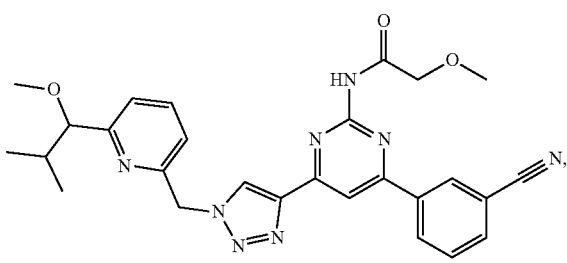
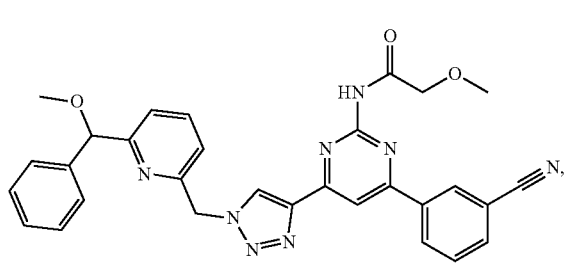
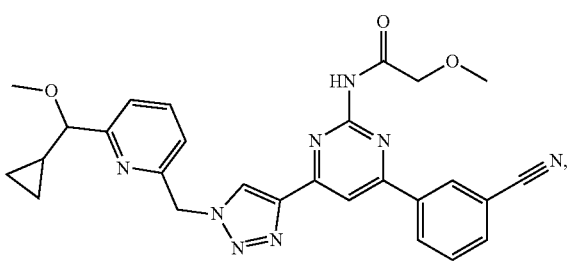
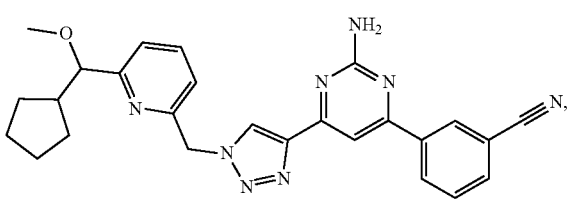
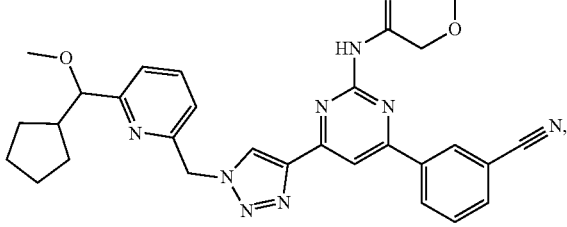

493
-continued
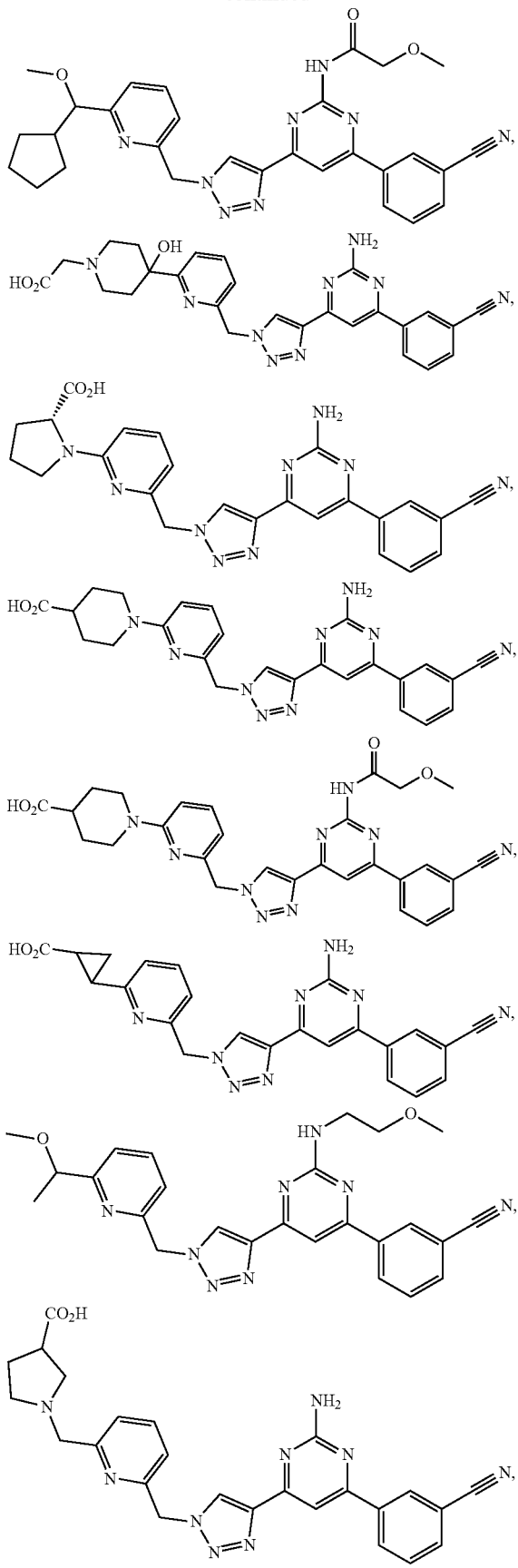
494
-continued
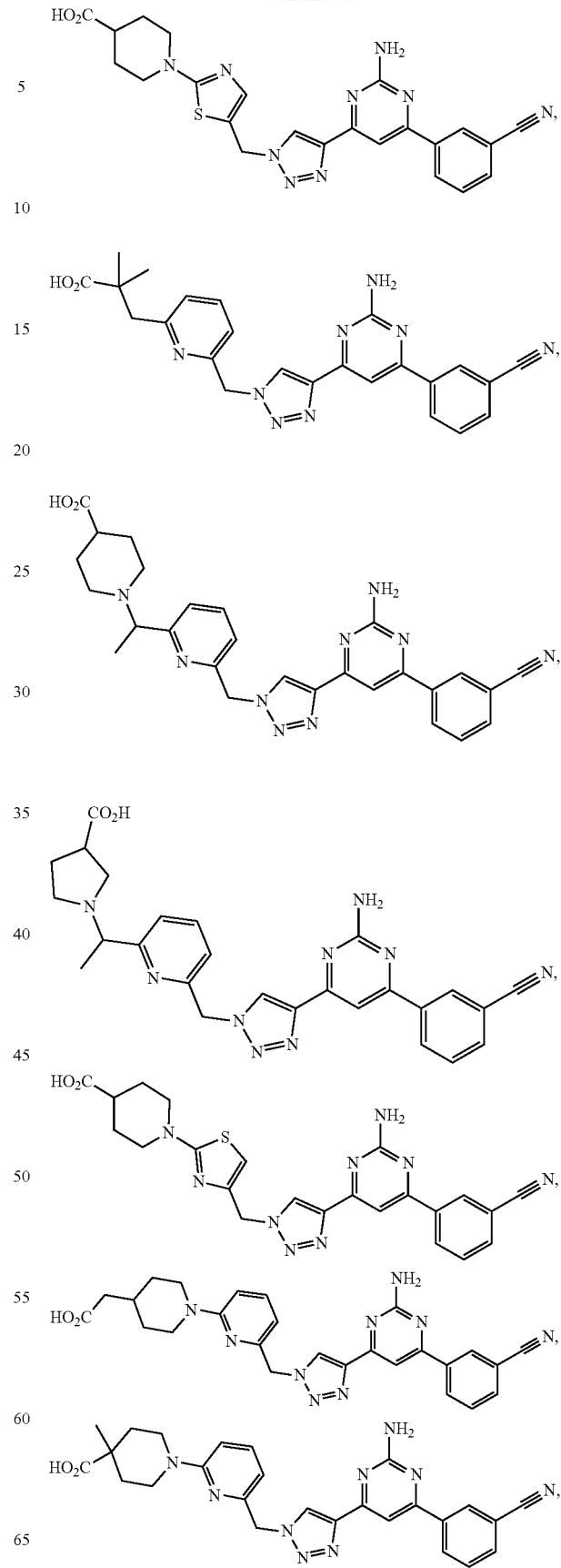

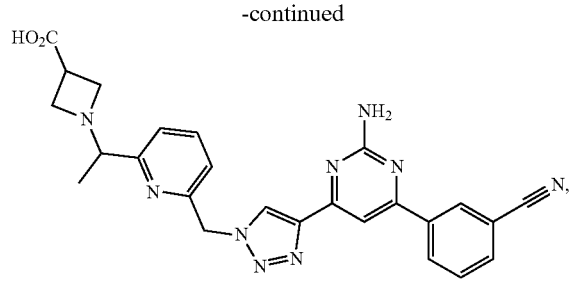
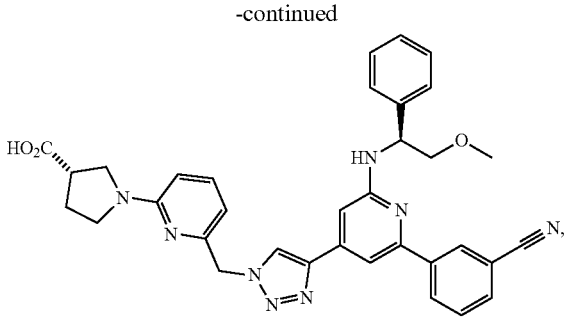
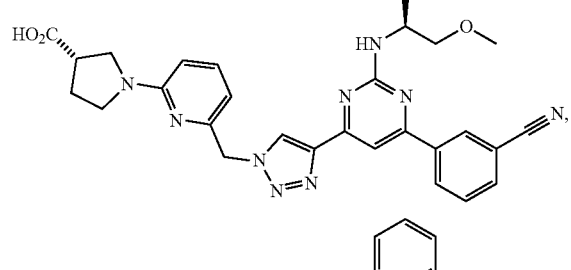
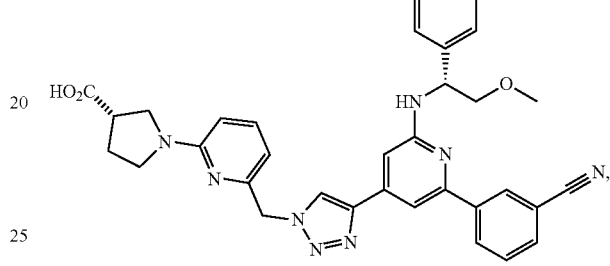
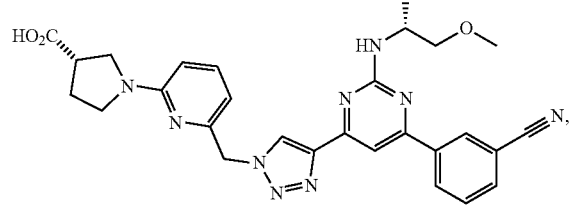
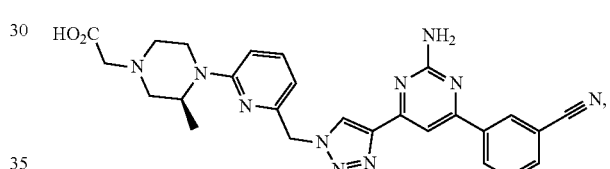
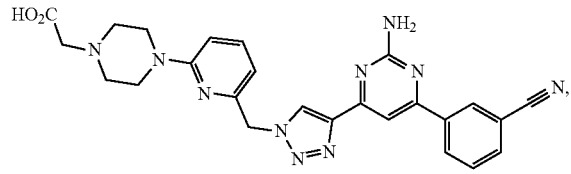
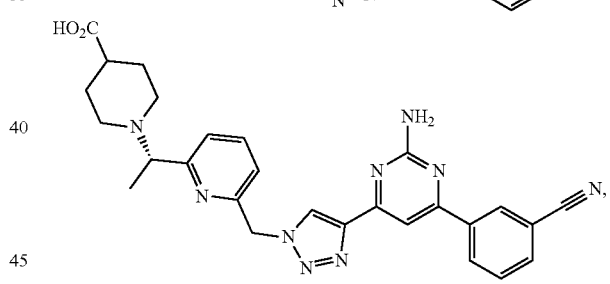
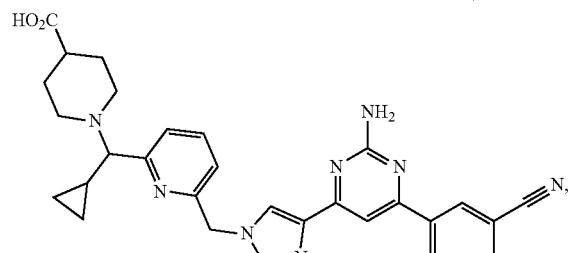
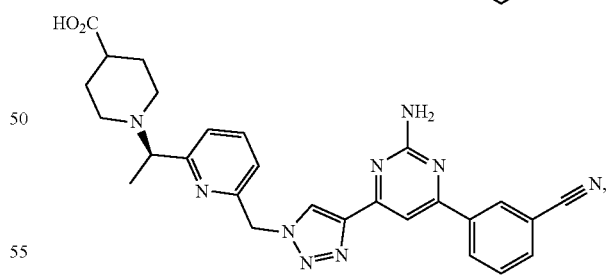
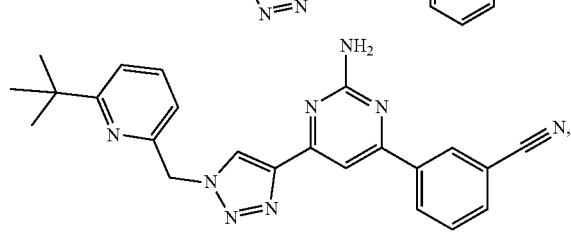
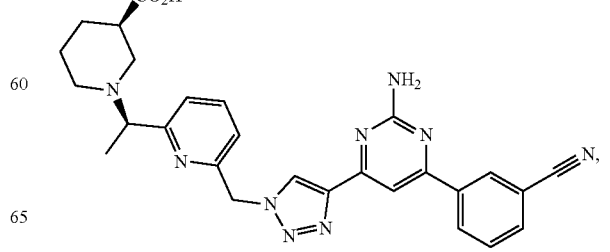
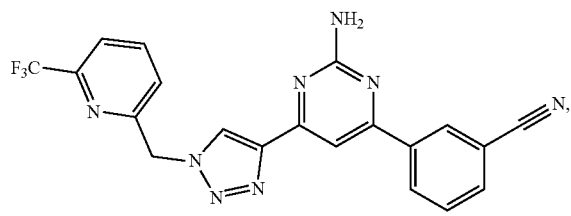

497
-continued
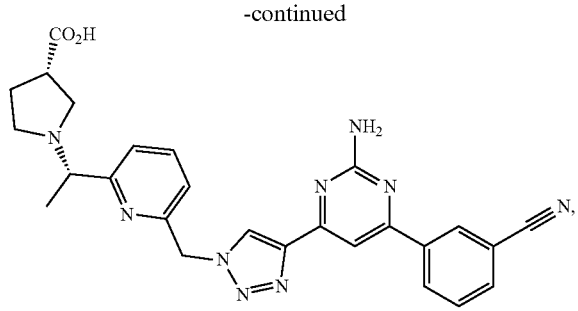
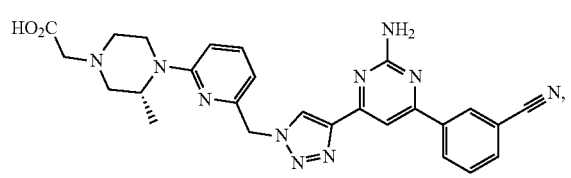
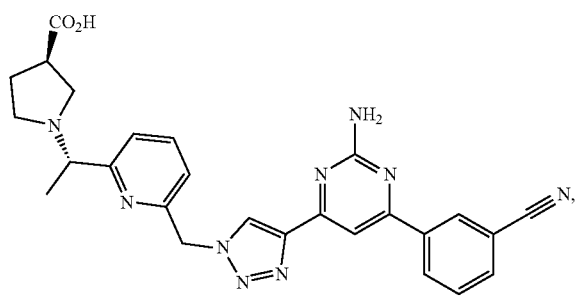
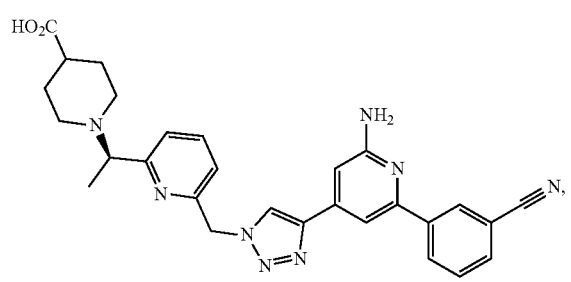
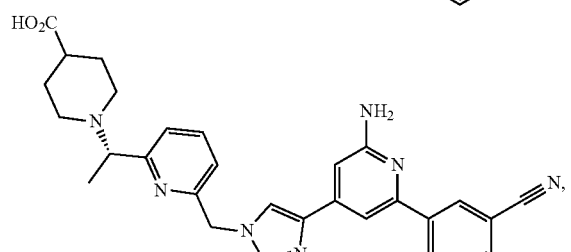
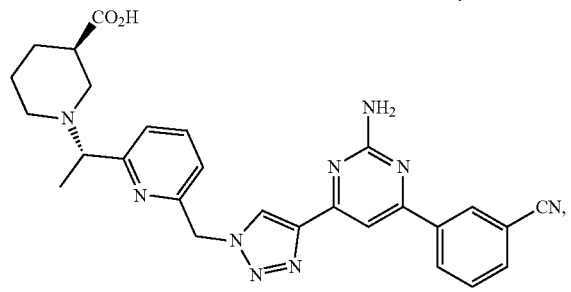
498
-continued
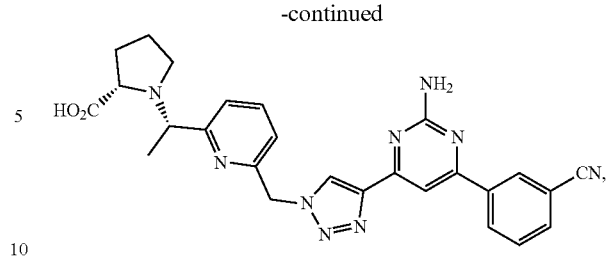
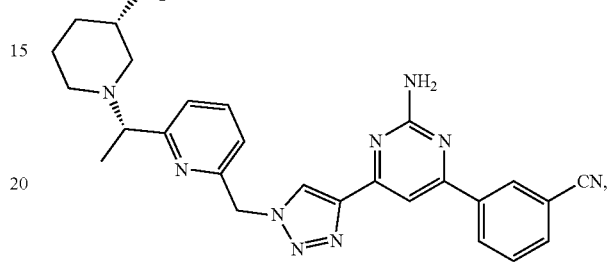
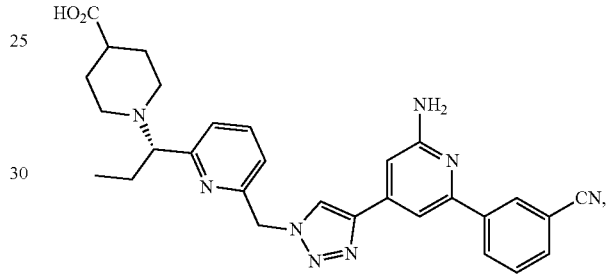
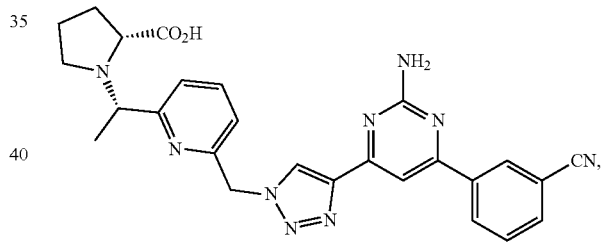
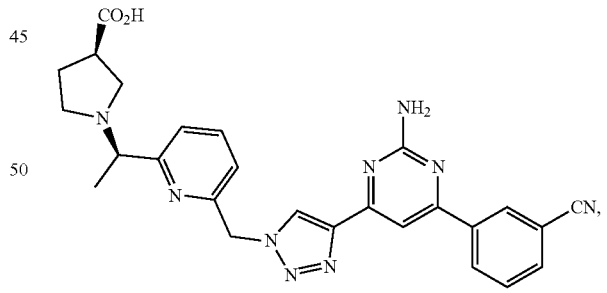
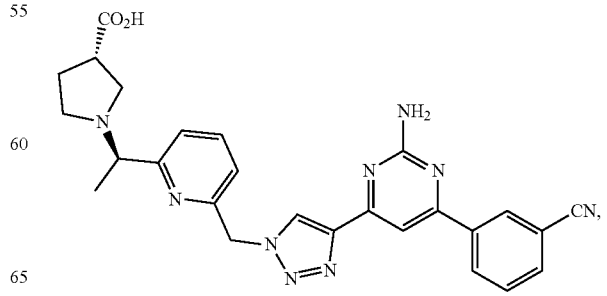

499
-continued
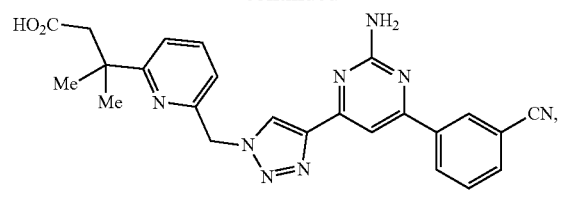
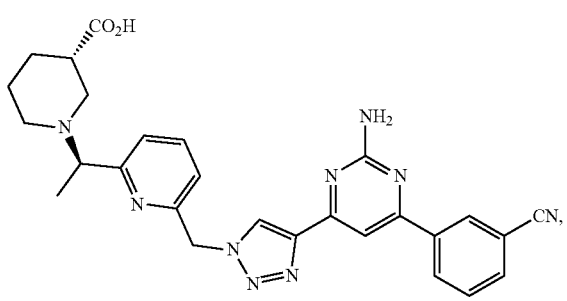
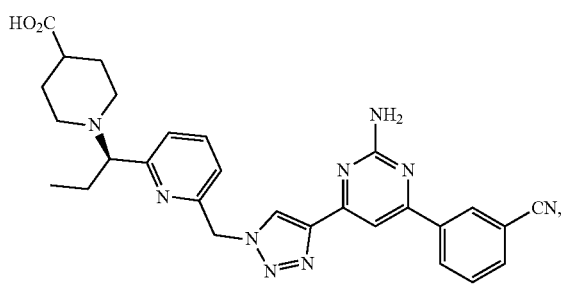
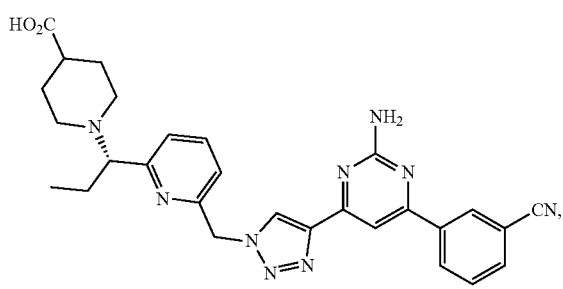
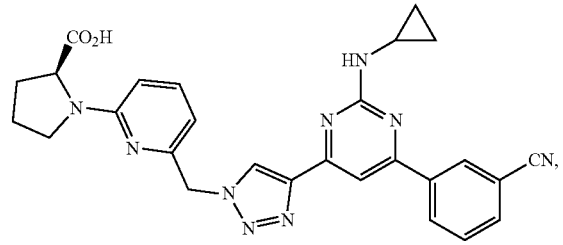
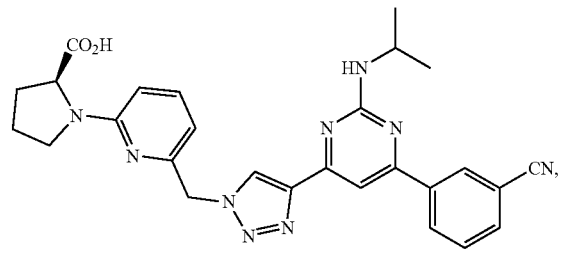
500
-continued
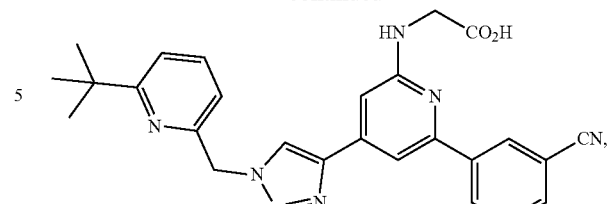
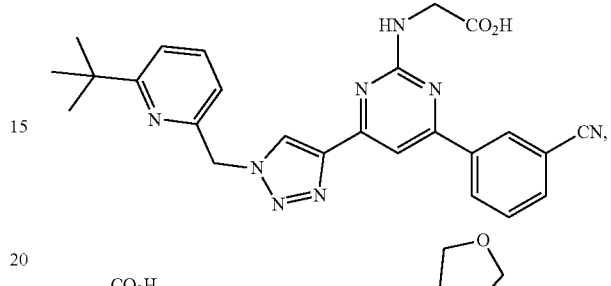
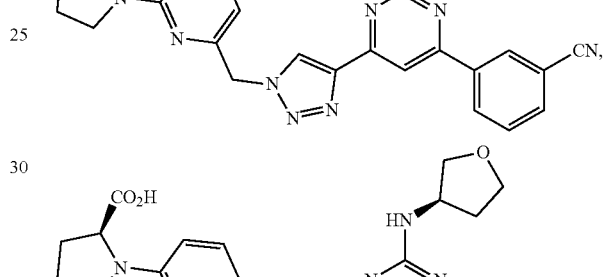
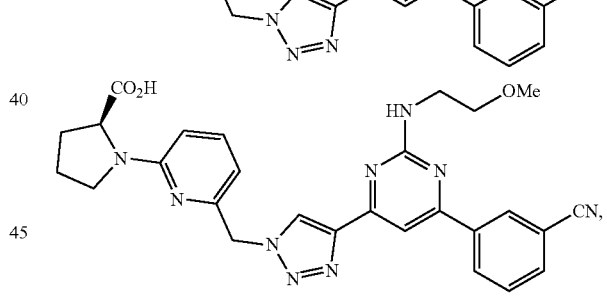
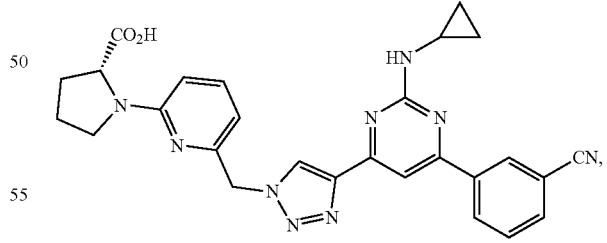
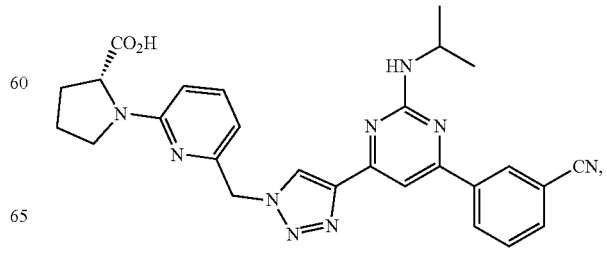

-continued
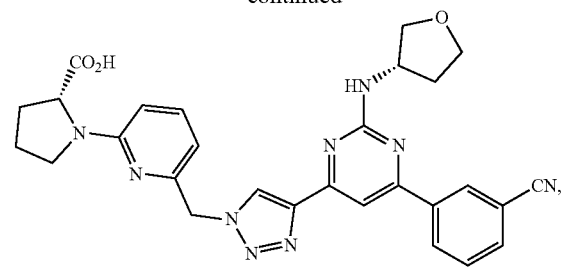
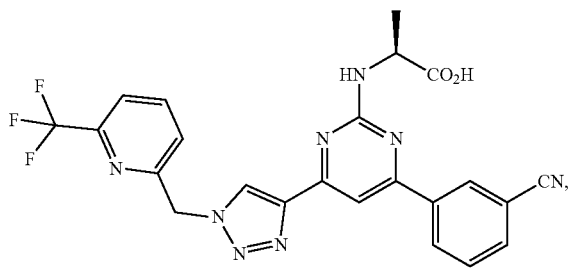
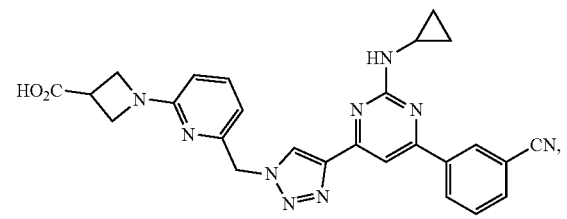
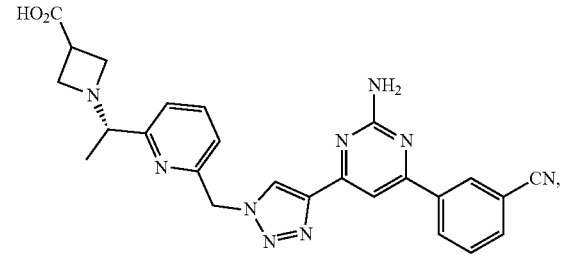
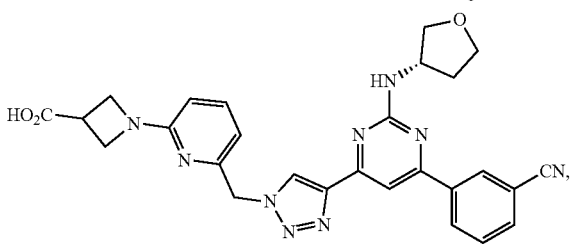
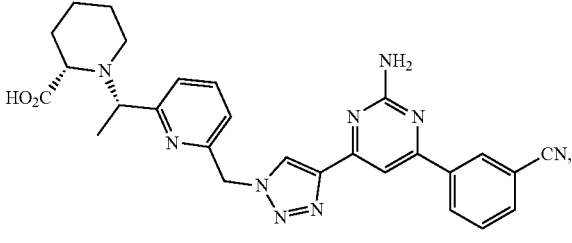
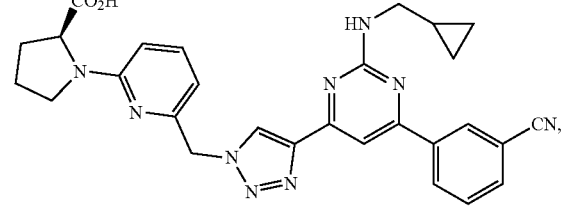
-continued
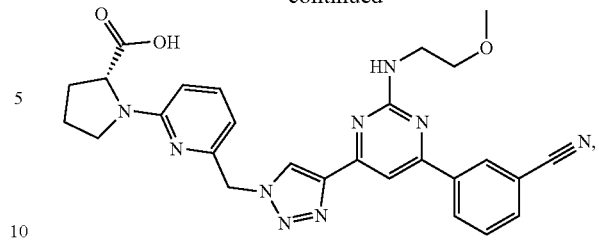
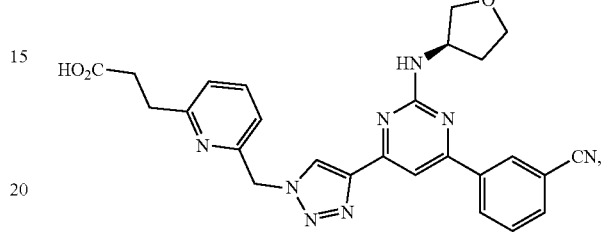
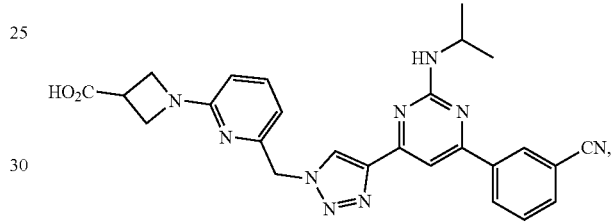
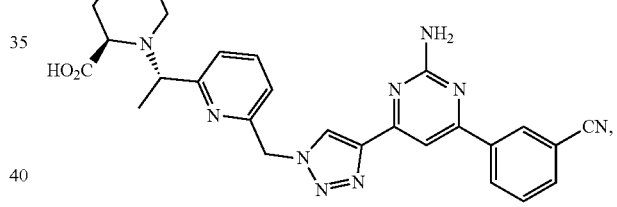
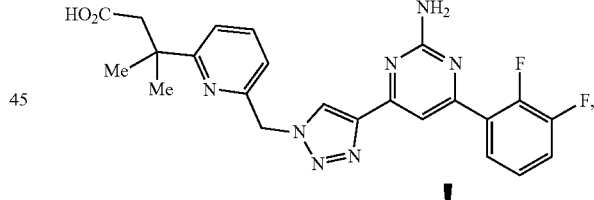
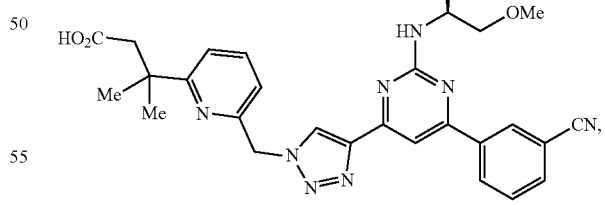
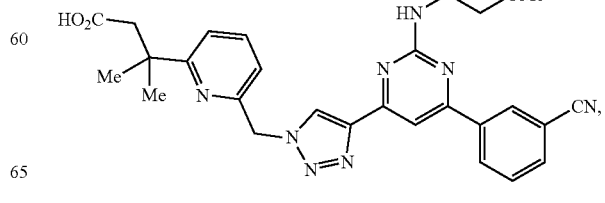

503
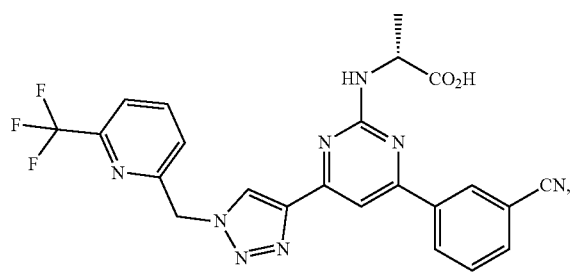
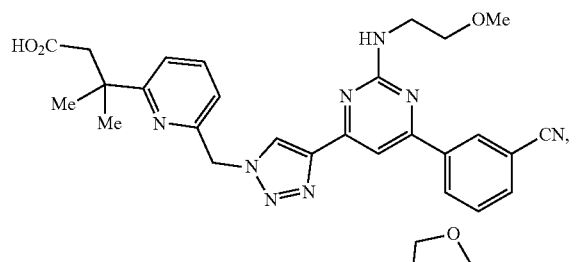
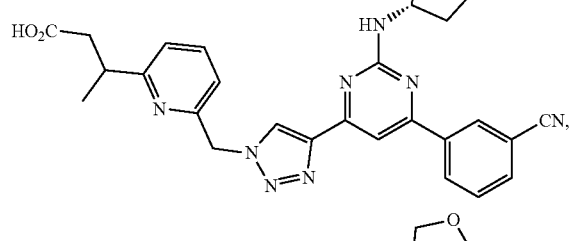
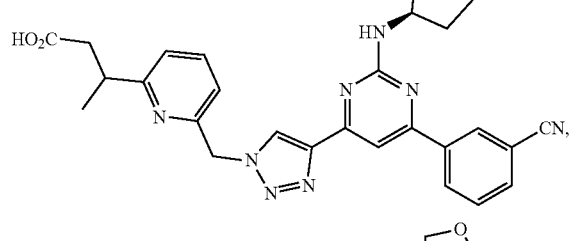
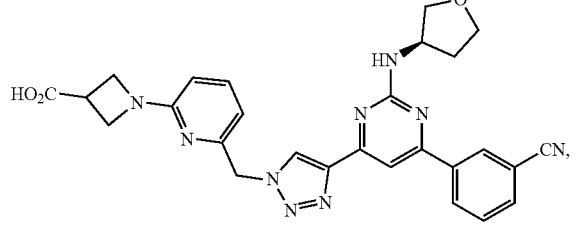
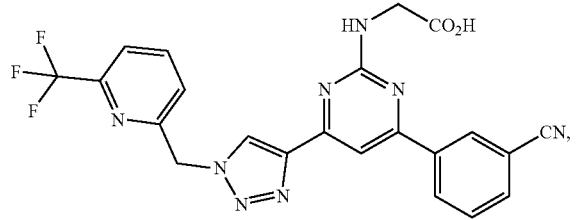
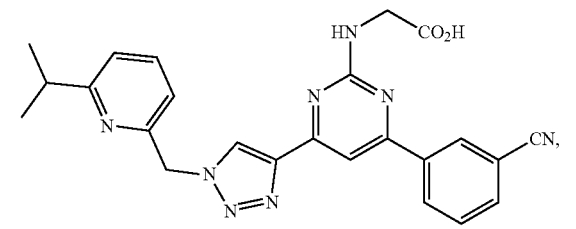
504
-continued
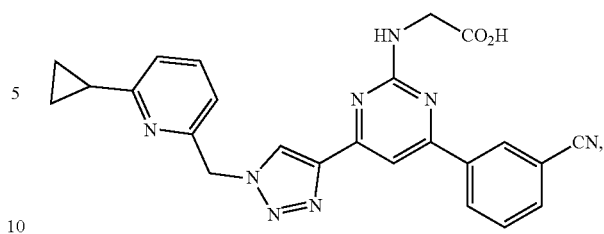
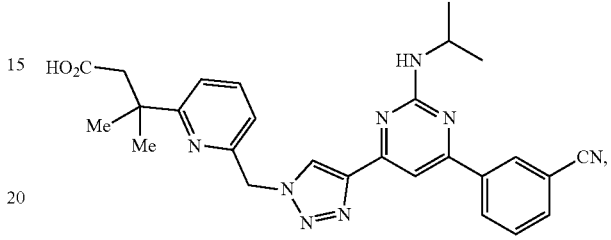
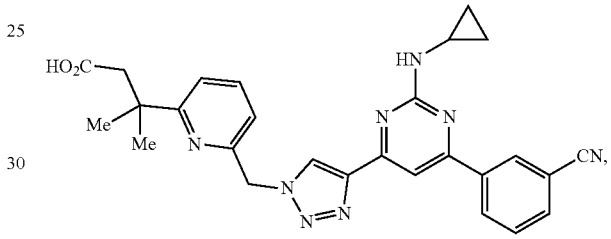
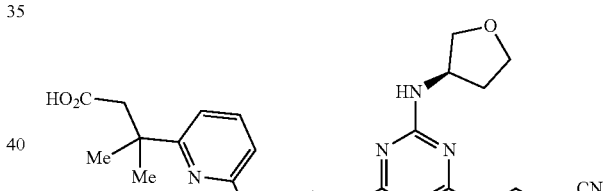
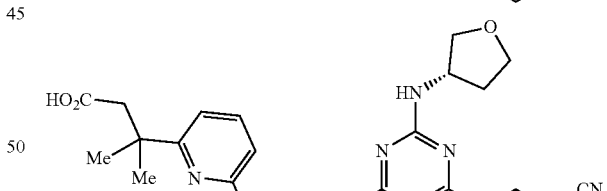
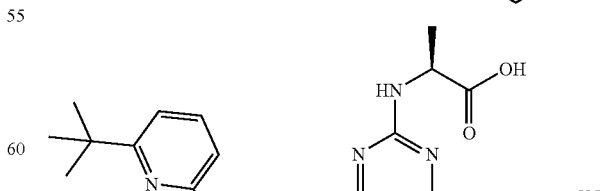
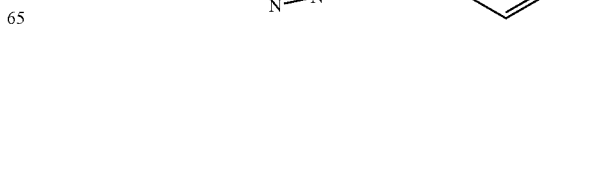

505
-continued
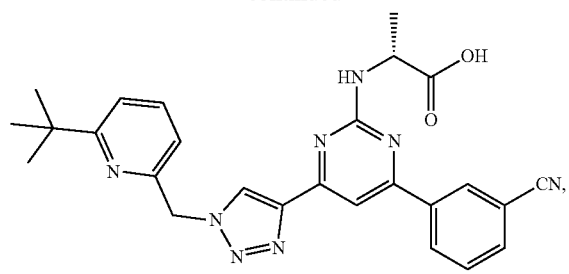
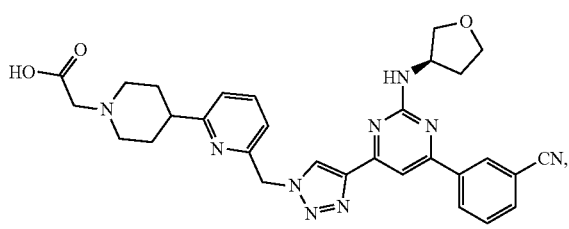
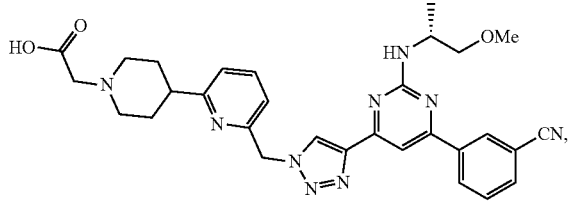
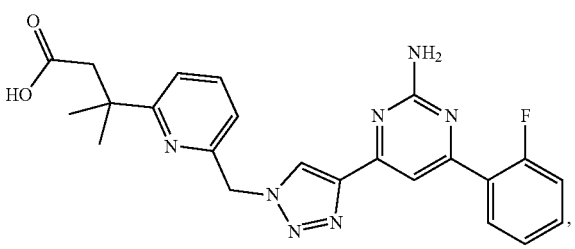
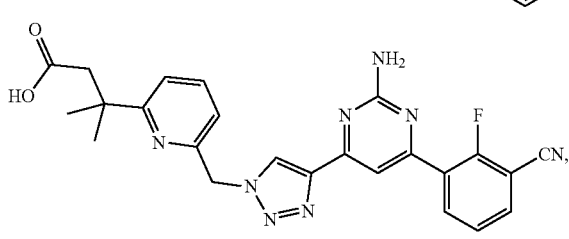
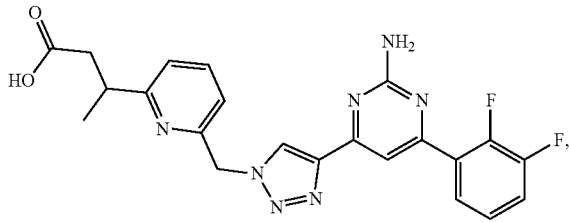
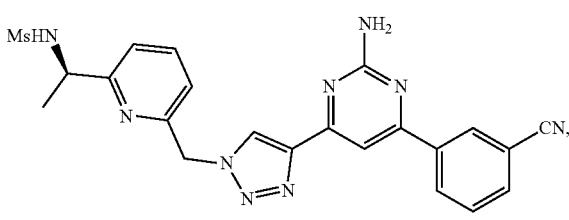
506
-continued
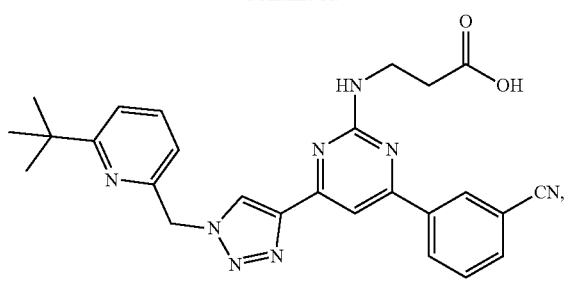
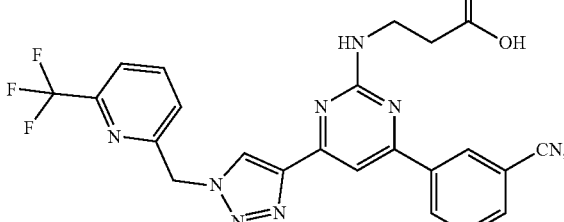
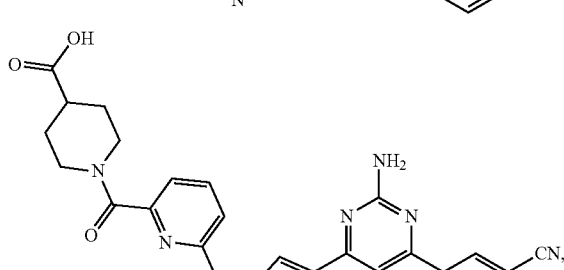
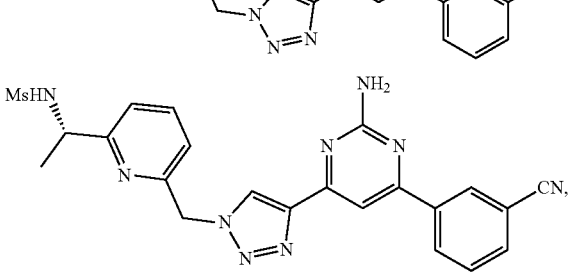
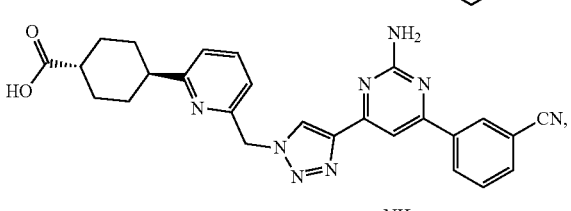
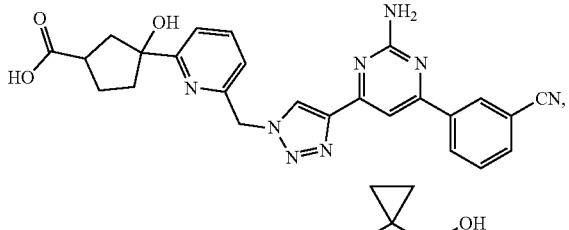
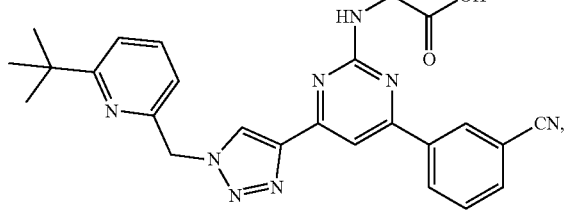

507
-continued
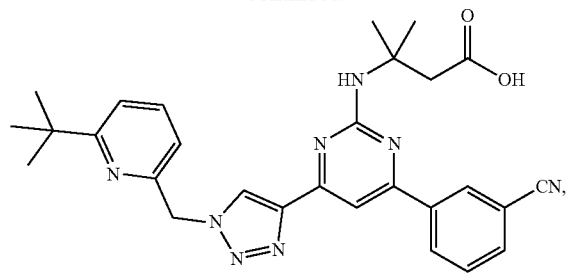
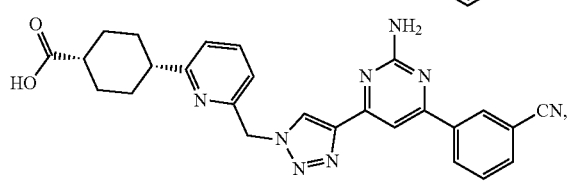
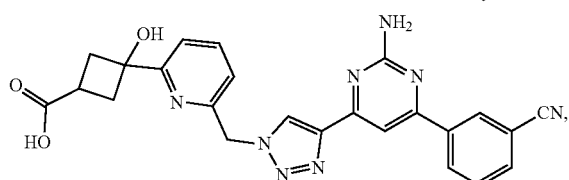
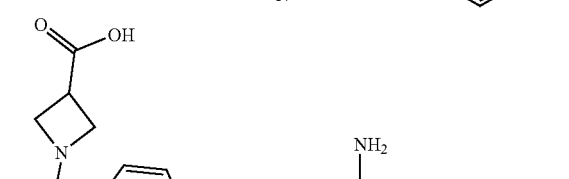
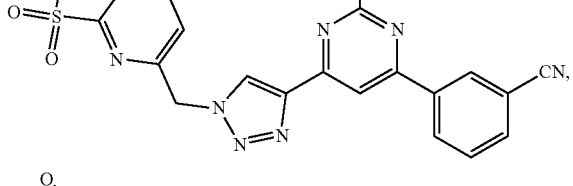
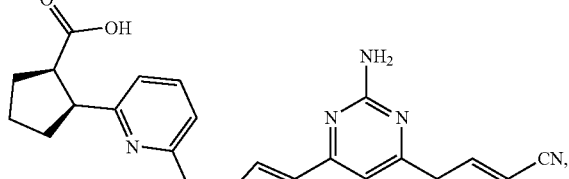
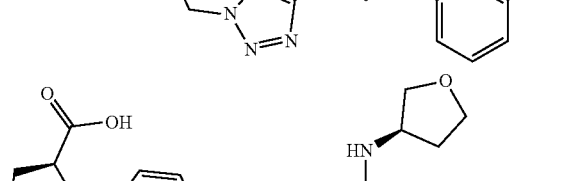
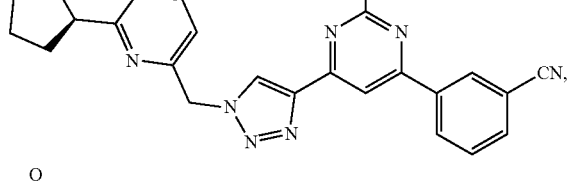
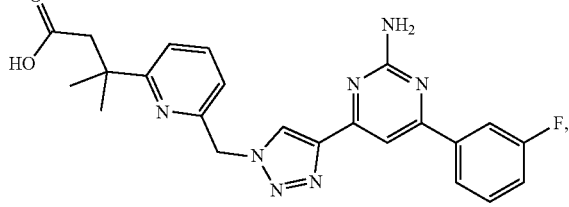
508
-continued
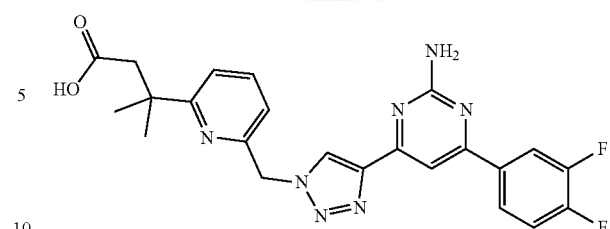
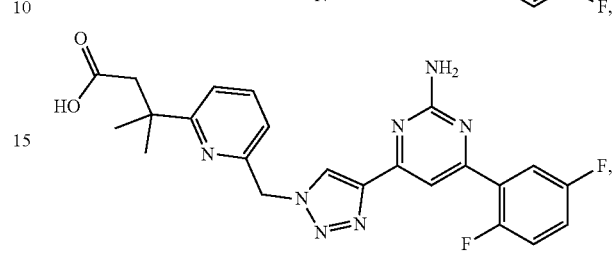
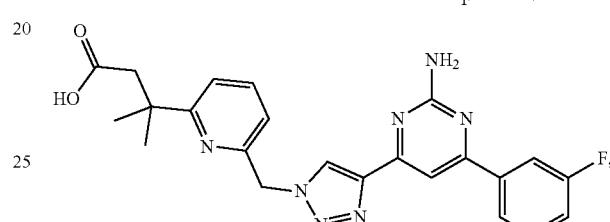
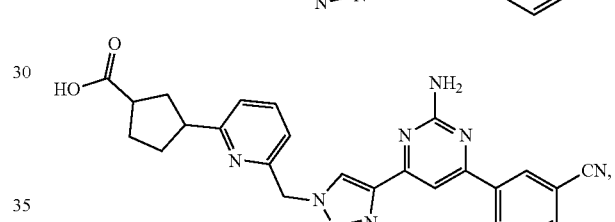
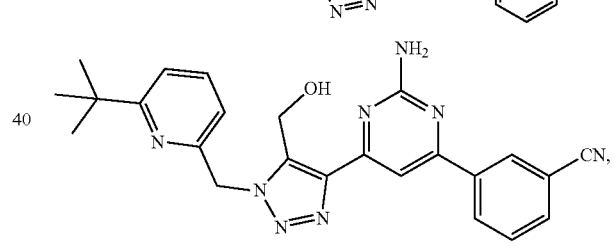
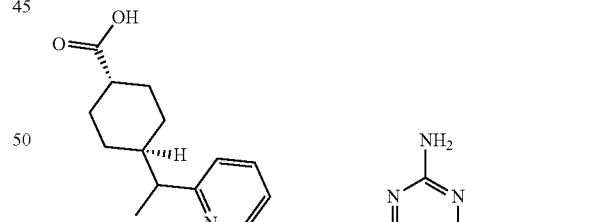
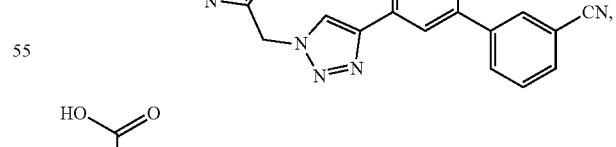
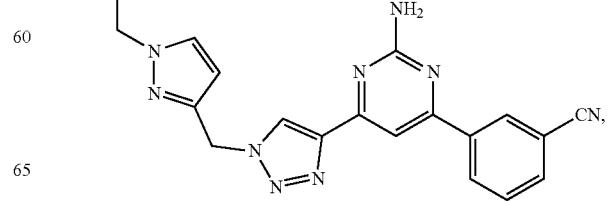

509
-continued
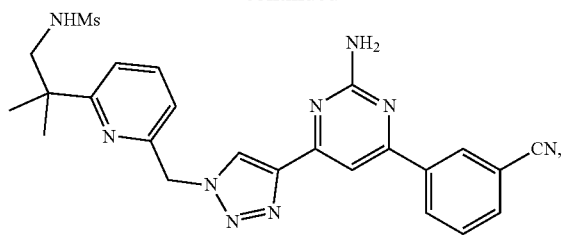
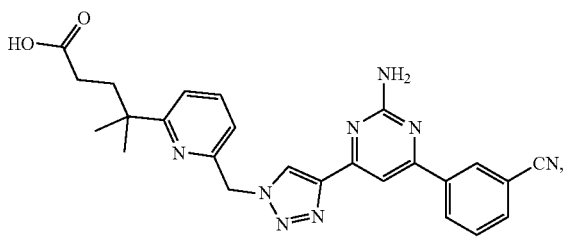
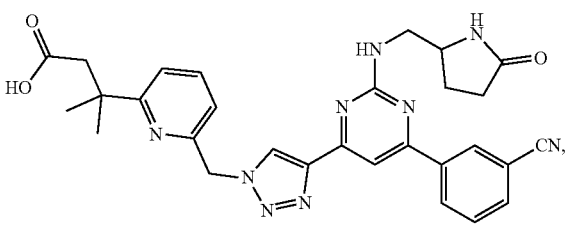
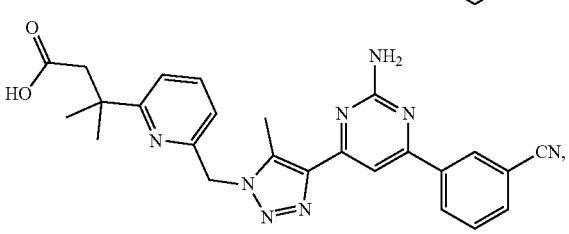
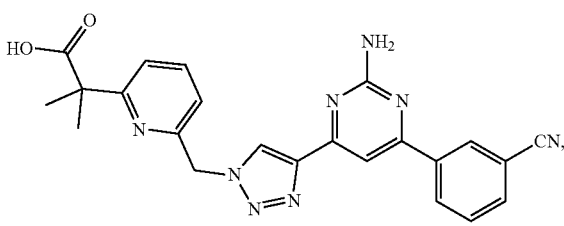
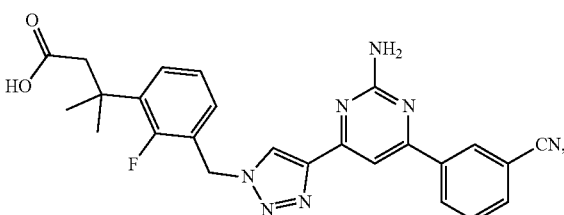
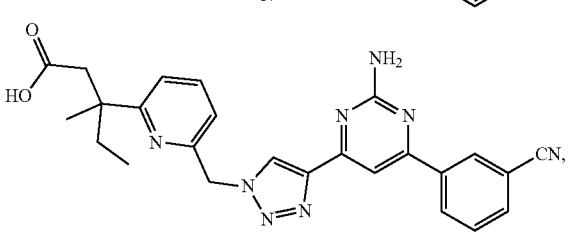
510
-continued
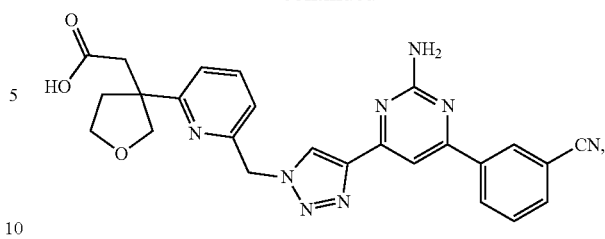
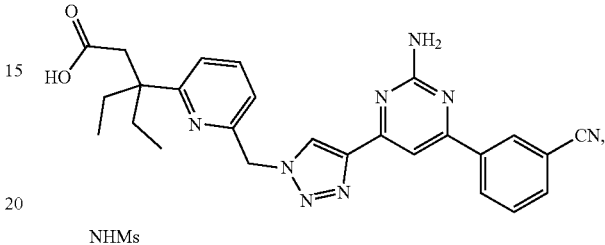
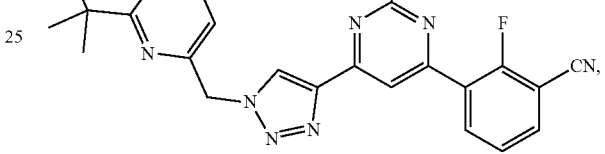
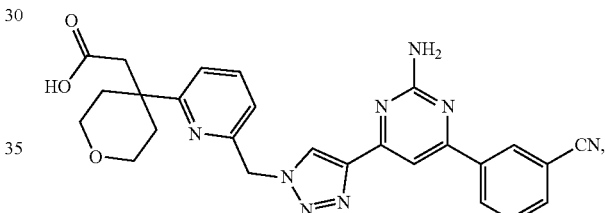
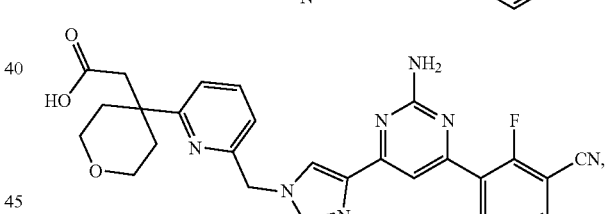
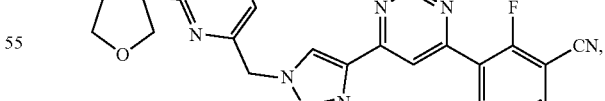
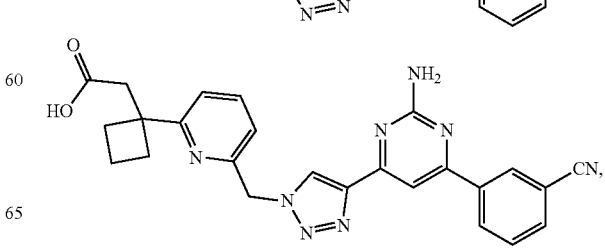

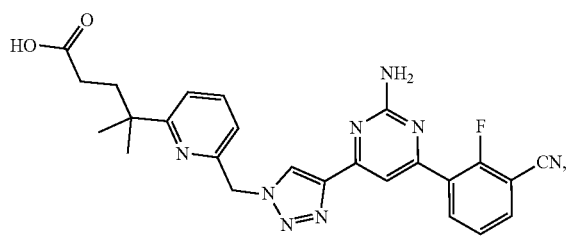
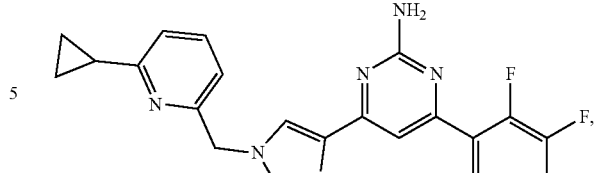
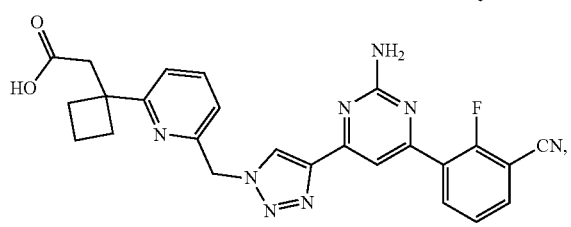
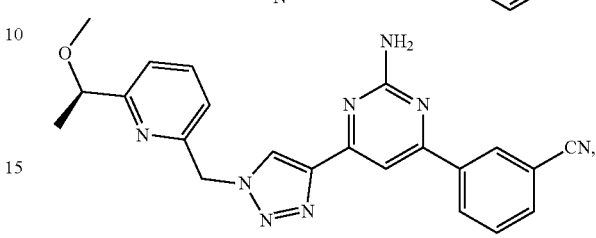
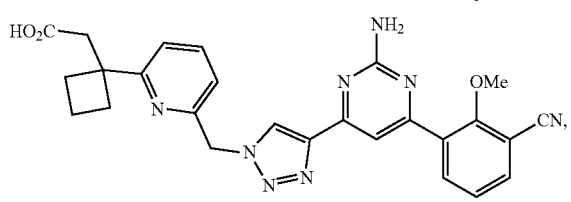
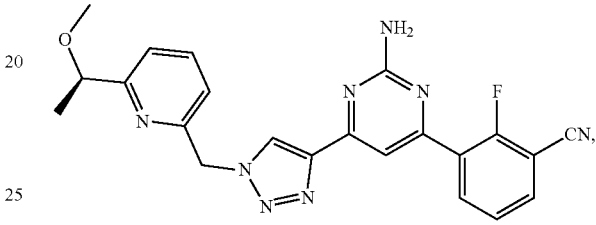
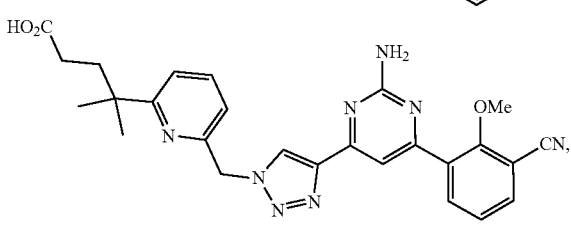
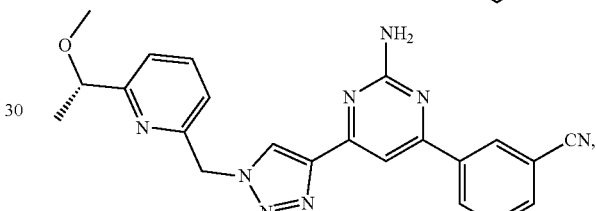
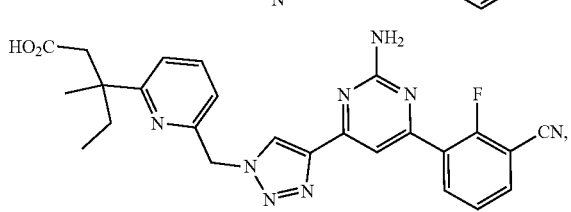
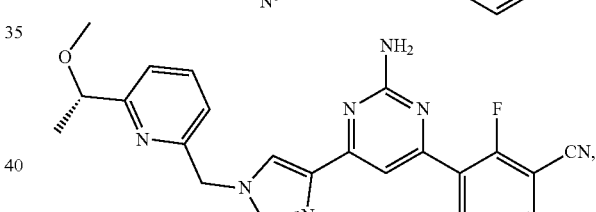
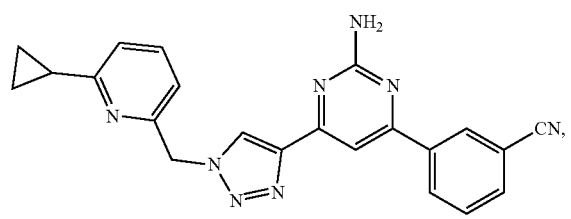
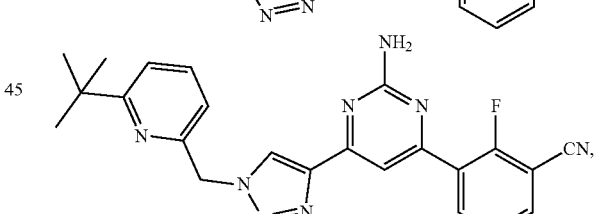
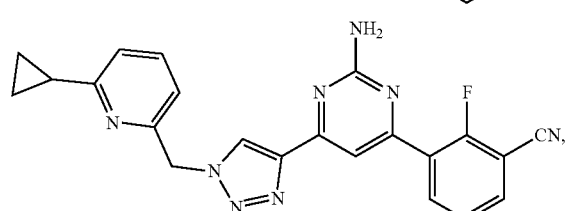
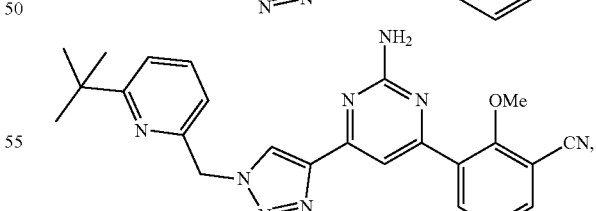
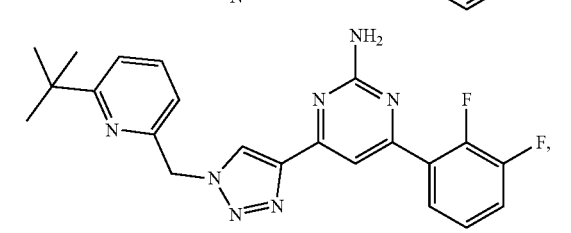
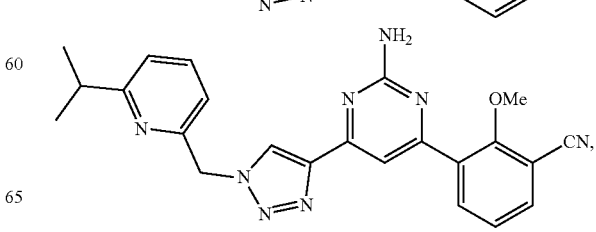

513
-continued
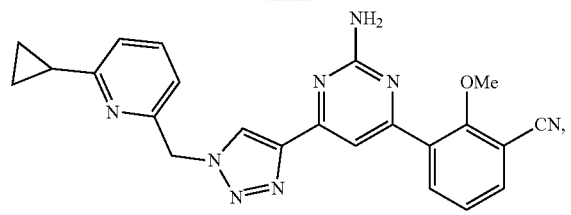
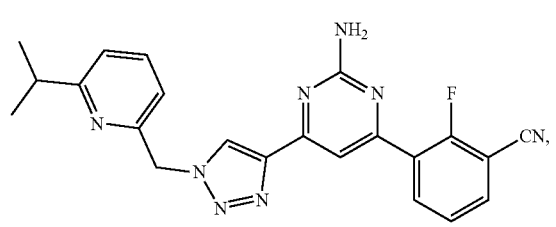
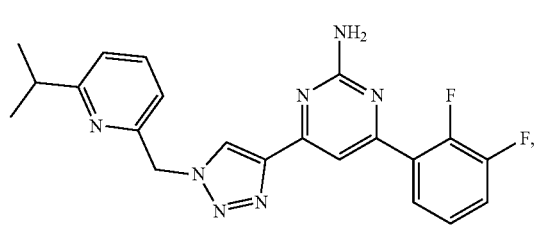
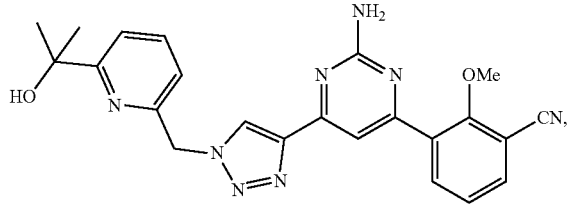
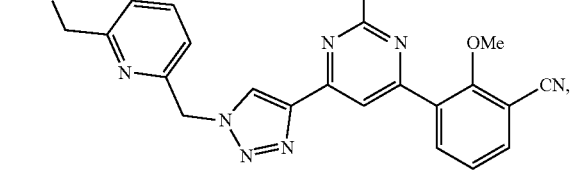
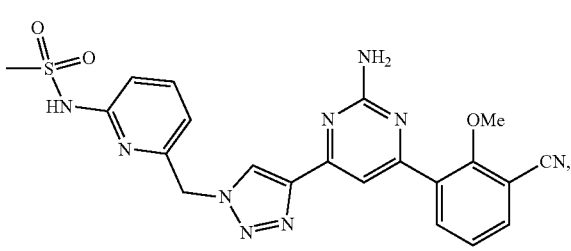
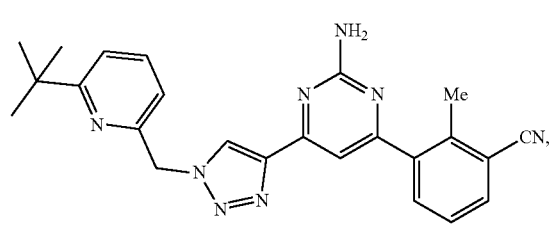
514
-continued
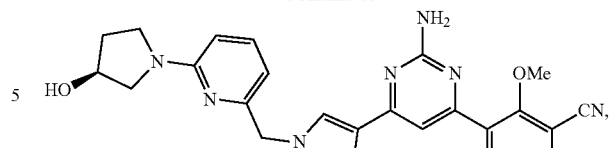
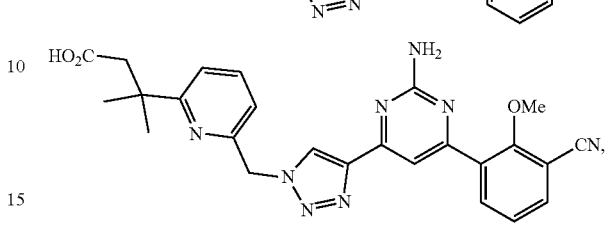
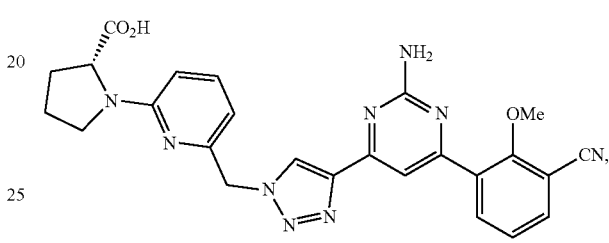
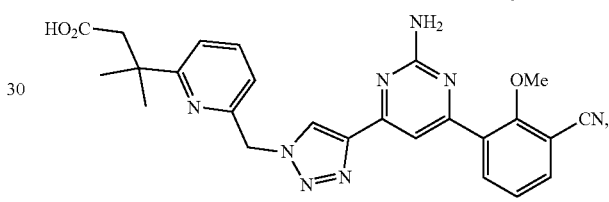
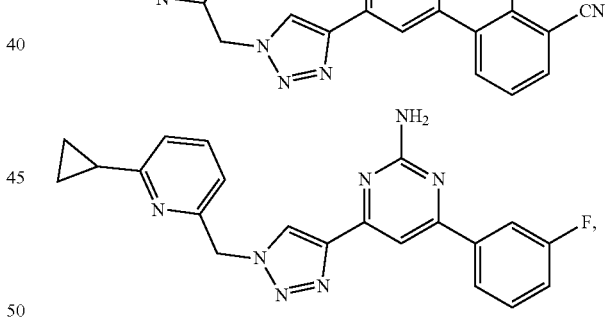
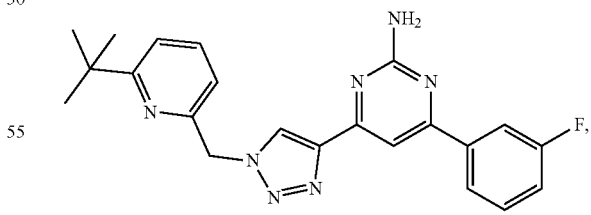
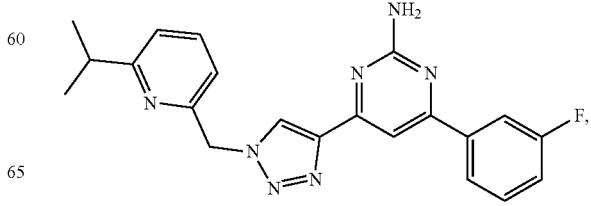

515
-continued
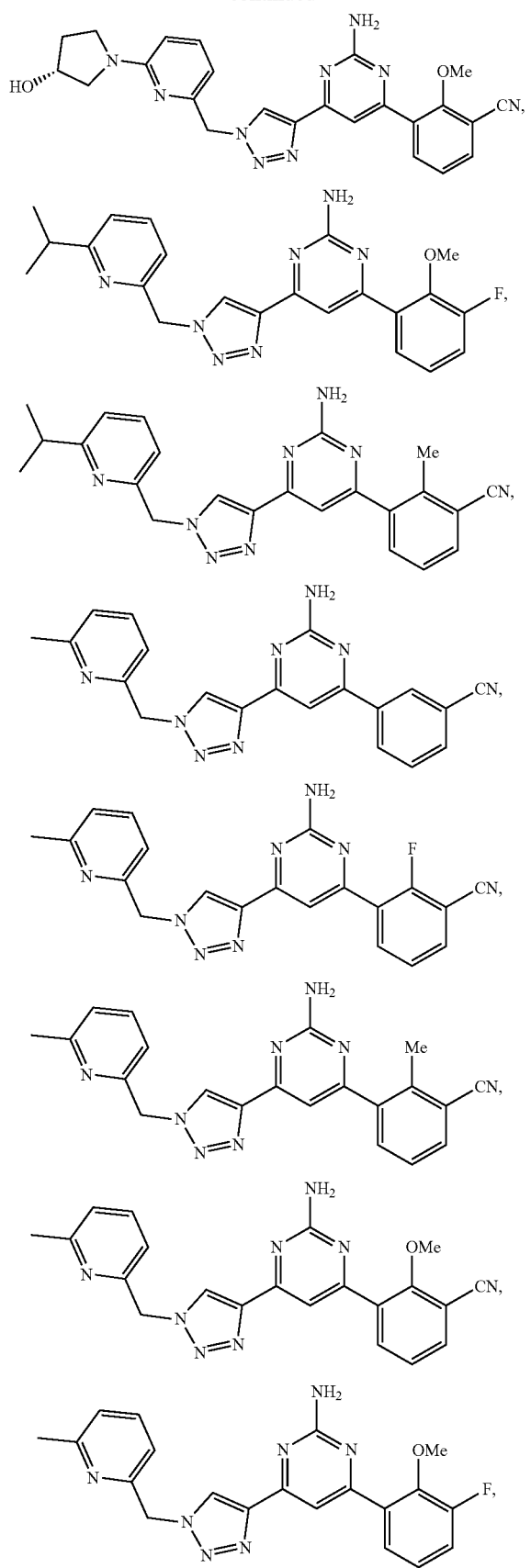
516
-continued
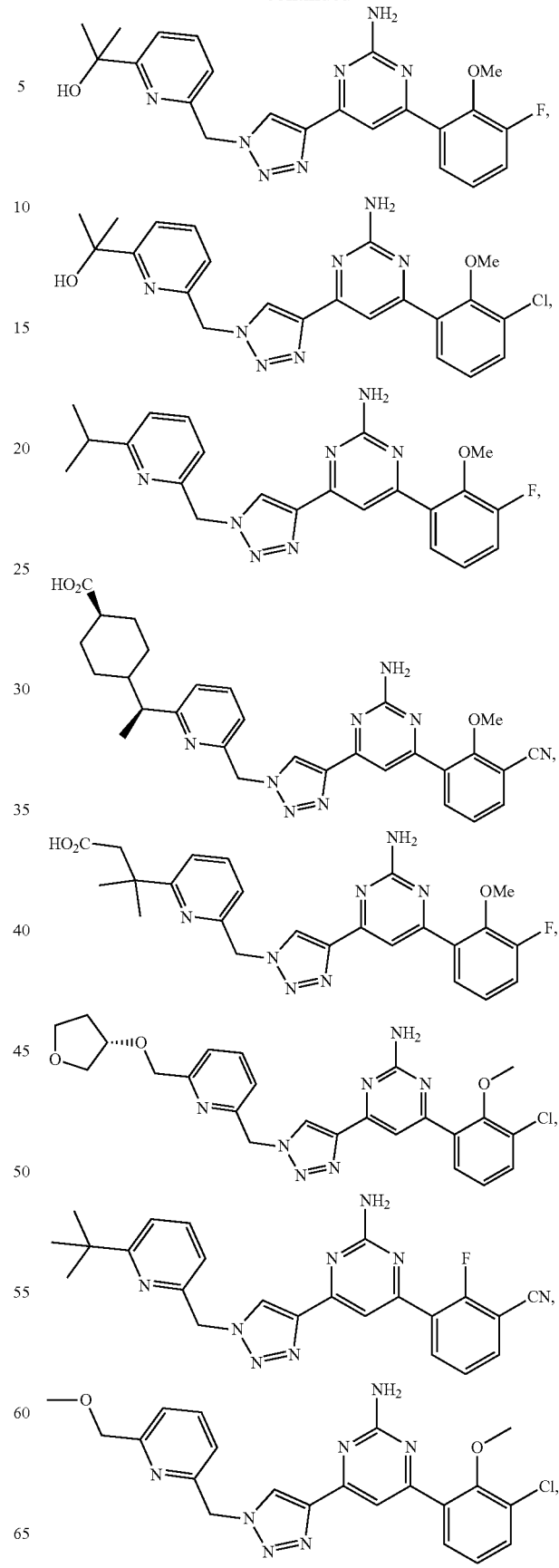

517
-continued
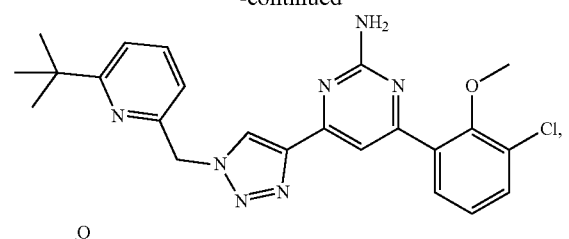
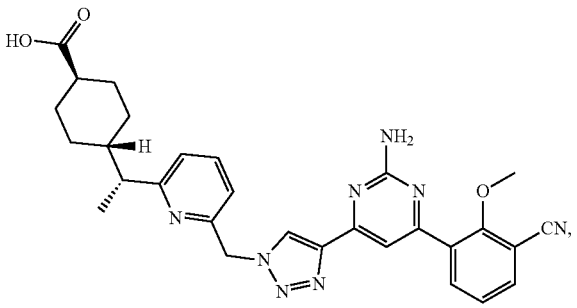
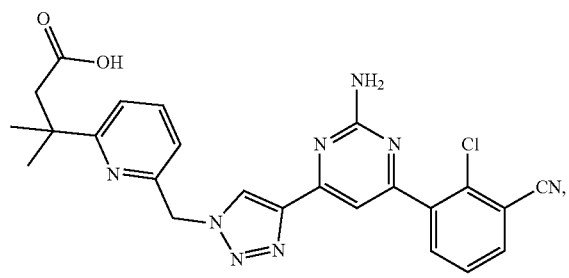
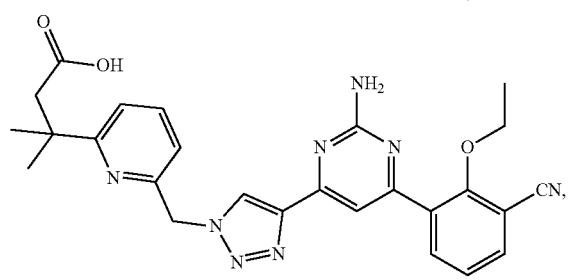
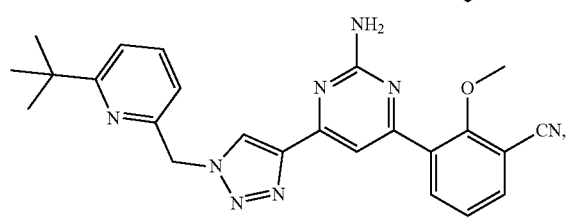
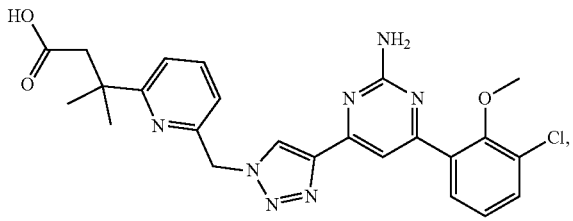
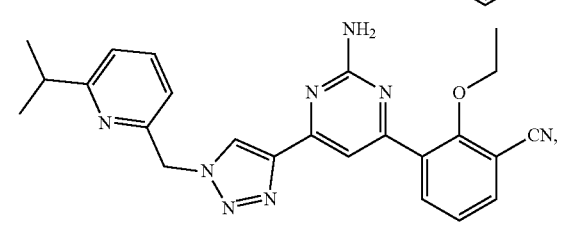
518
-continued
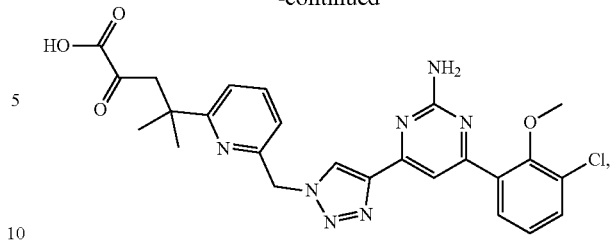
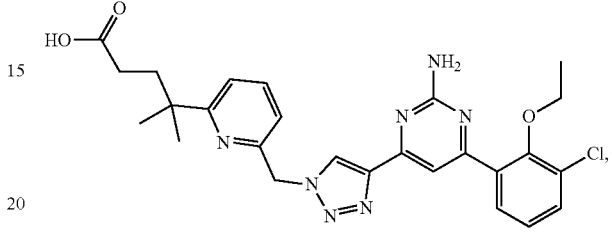
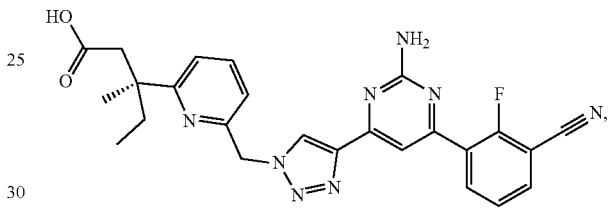
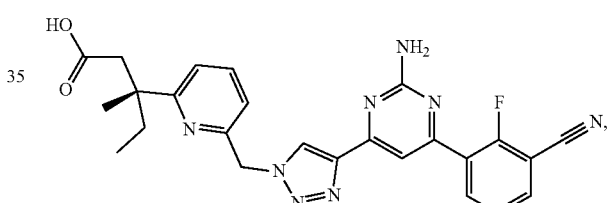
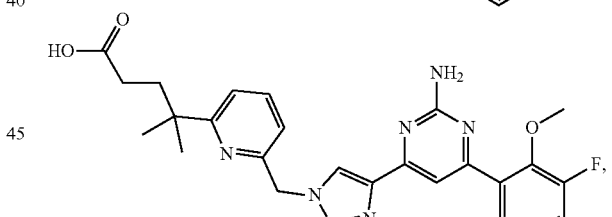
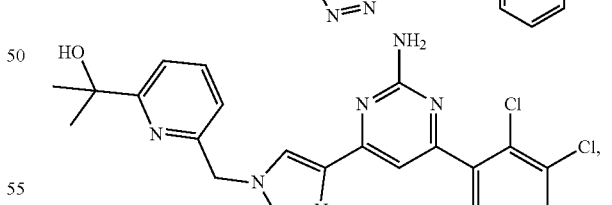
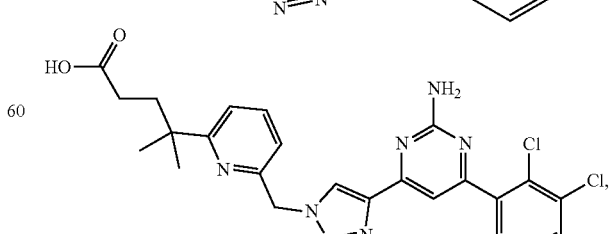

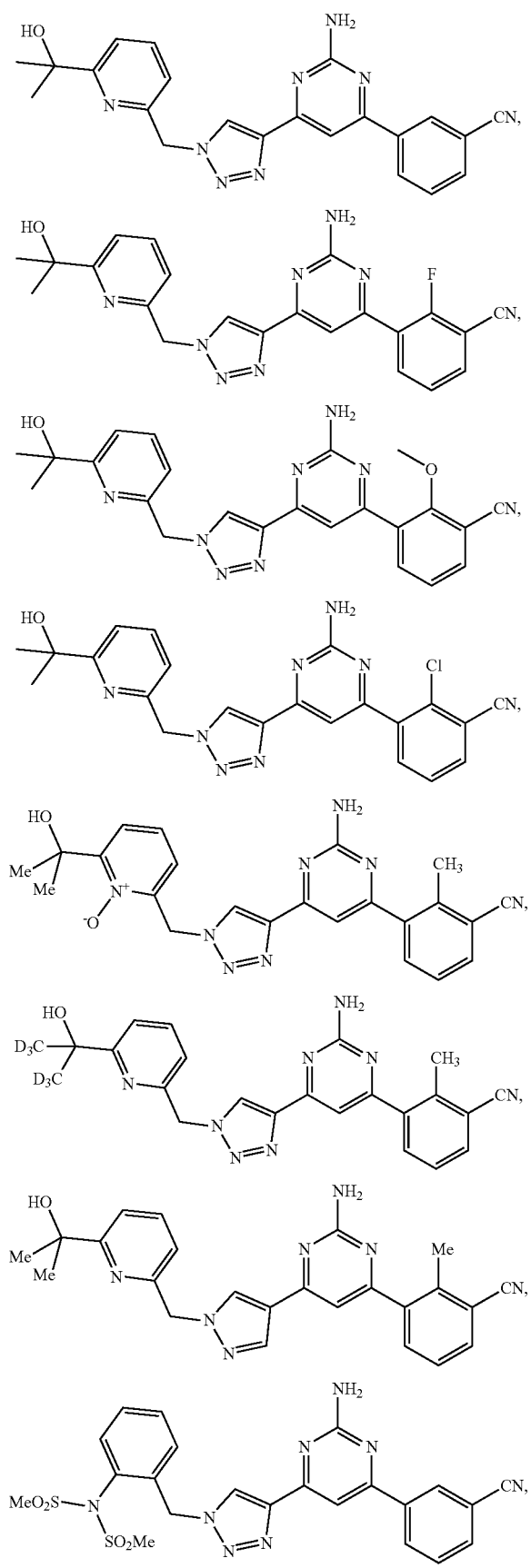
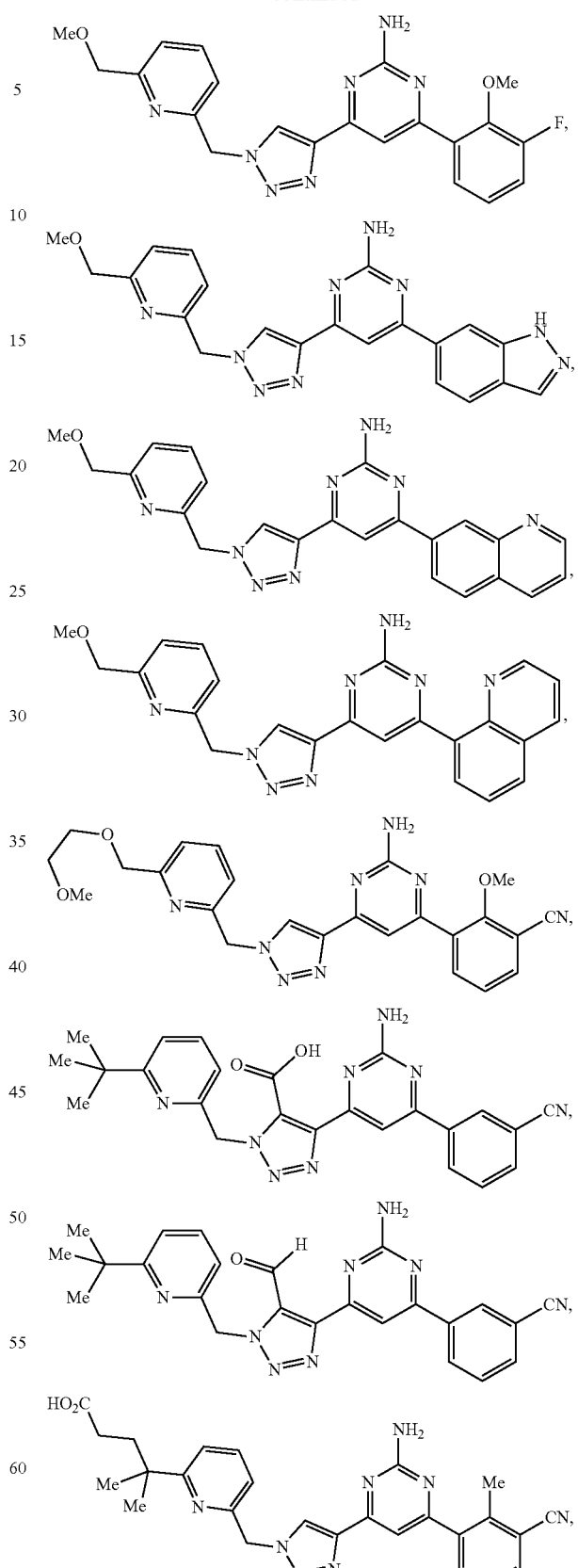

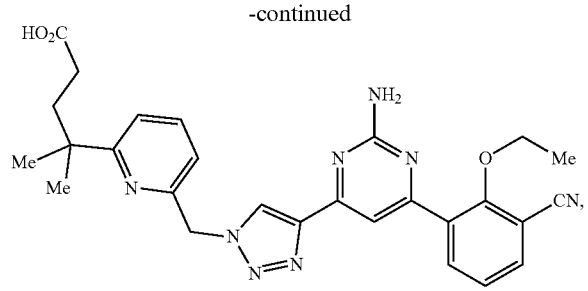
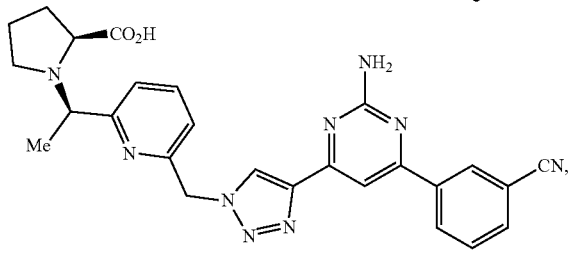
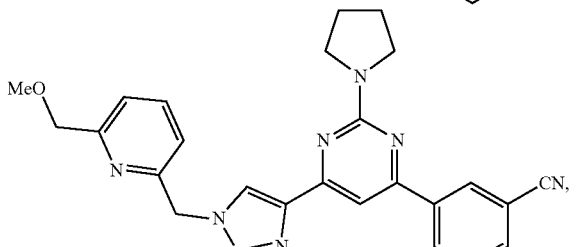
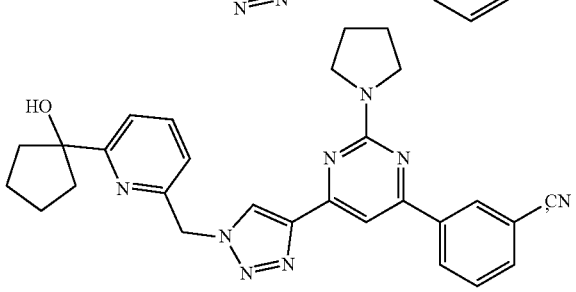
or a pharmaceutically acceptable salt thereof.
2. A pharmaceutical composition comprising a compound of claim 1, or a pharmaceutically acceptable salt thereof, and a pharmaceutically acceptable excipient.
* * * * *

UNITED STATES PATENT AND TRADEMARK OFFICE
CERTIFICATE OF CORRECTION

PATENT NO. : 12,195,447 B2
APPLICATION NO. : 17/507921
DATED : January 14, 2025
INVENTOR(S) : Joel Beatty et al.

Page 1 of 7

It is certified that error appears in the above-identified patent and that said Letters Patent is hereby corrected as shown below:

In the Claims

In Claim 1, Column 468, Lines 31 to 41, please replace:

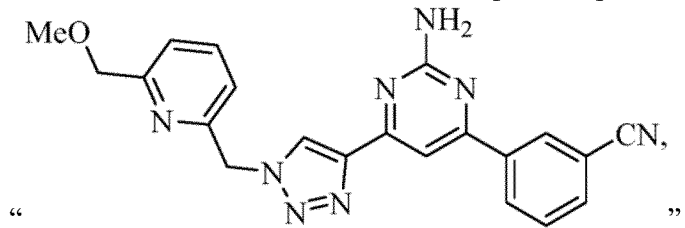

" "

With:

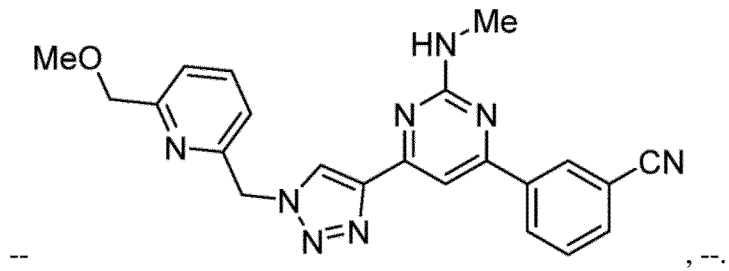

-- , --.

In Claim 1, Column 485, Lines 12 to 23, please replace:

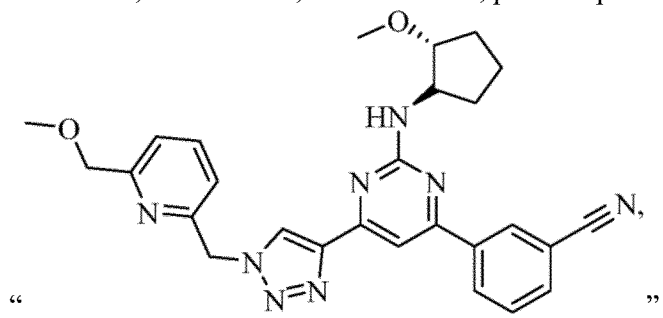

" "

Signed and Sealed this
Twenty-ninth Day of April, 2025

Coke Morgan Stewart
*Acting Director of the United States Patent and Trademark Office*

With:
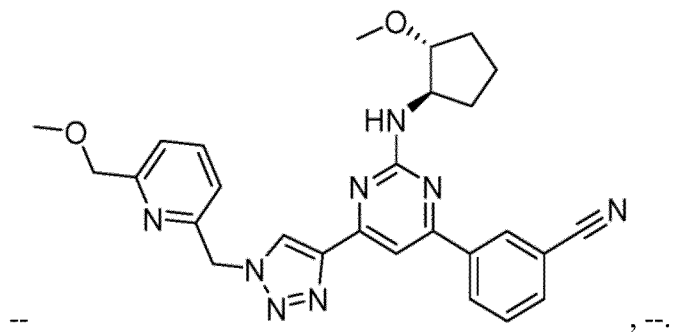
--, --.
In Claim 1, Column 485, Lines 24 to 34, please replace:
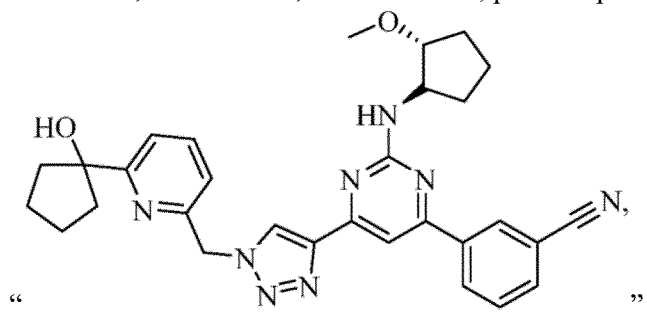
" "
With:
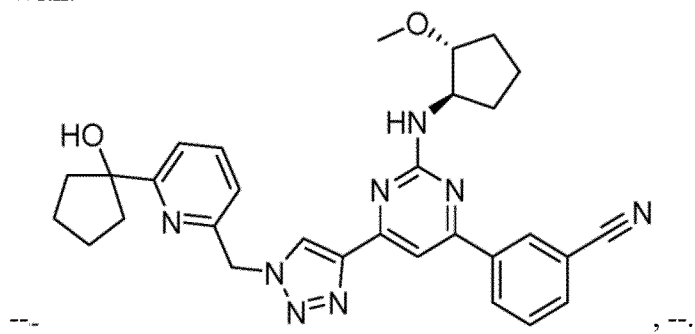
--, --.
In Claim 1, Column 485, Lines 35 to 44, please replace:
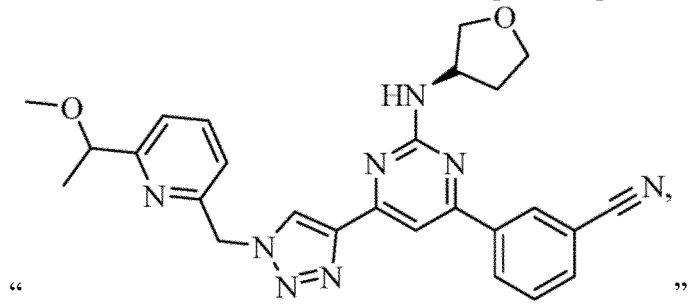
" "

CERTIFICATE OF CORRECTION (continued)
U.S. Pat. No. 12,195,447 B2

Page 3 of 7

With:

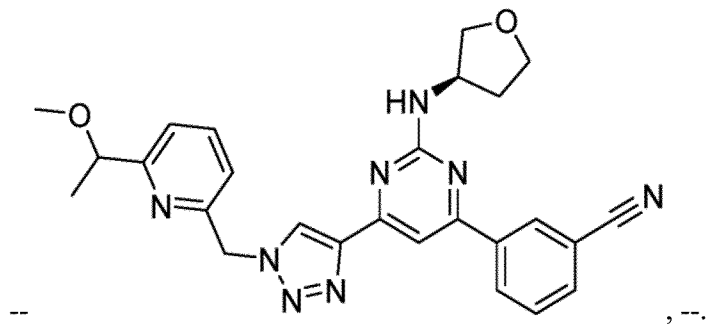

--    , --.

In Claim 1, Column 487, Lines 15 to 25, please replace:

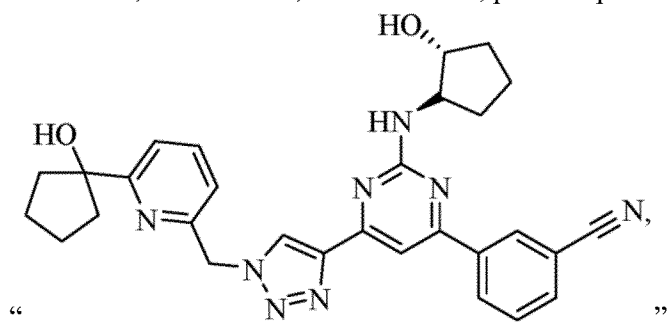

"    "

With:

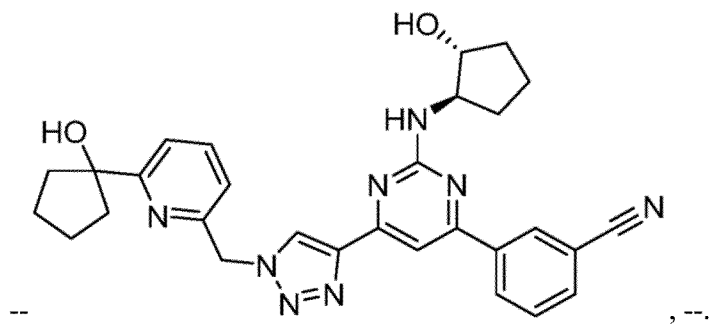

--    , --.

In Claim 1, Column 488, Lines 26 to 36, please replace:

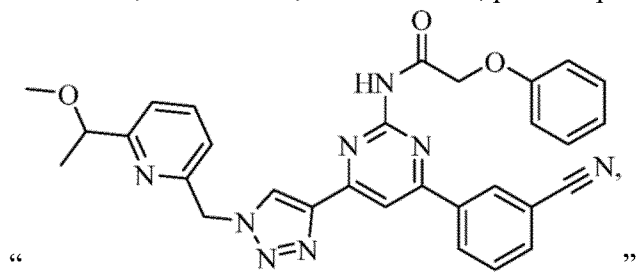

"    "

With:
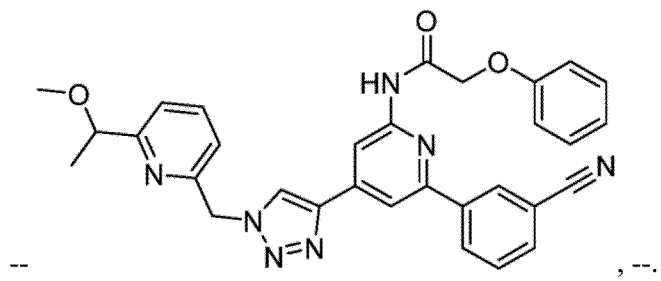
, --.
In Claim 1, Column 498, Lines 23 to 34, please replace:
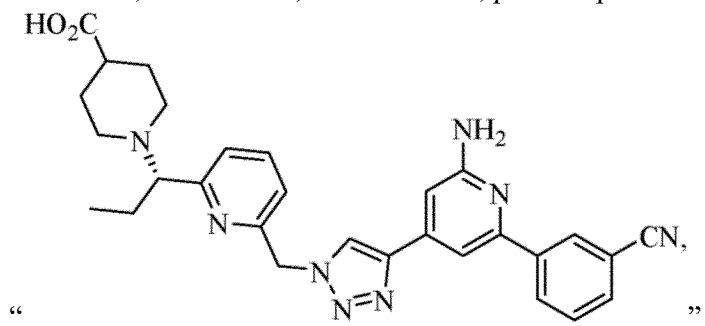
"  ,"
With:
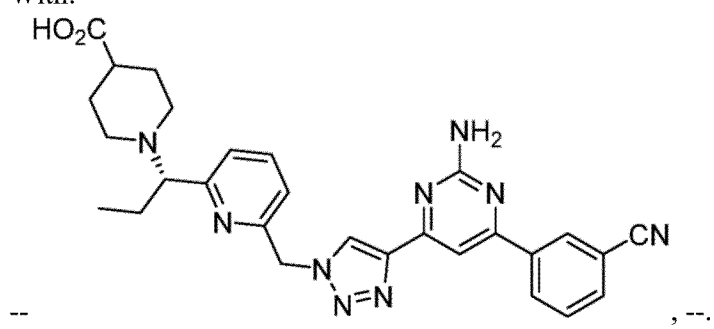
-- , --.
In Claim 1, Column 499, Lines 36 to 47, please replace:
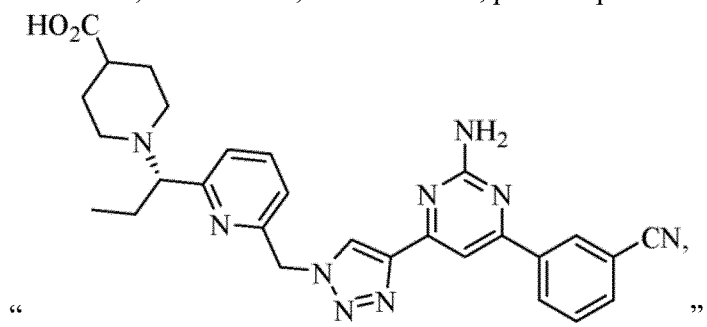
"  ,"

CERTIFICATE OF CORRECTION (continued)
U.S. Pat. No. 12,195,447 B2

With:

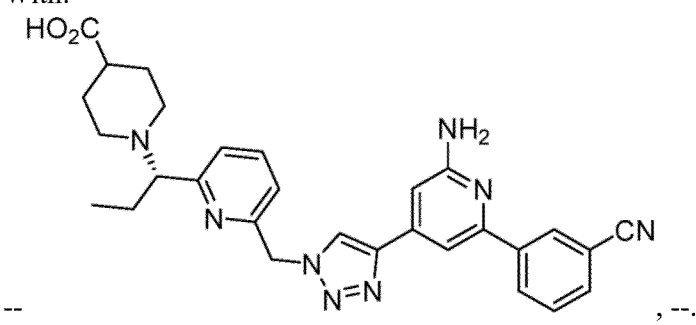

--                                                                                    , --.

In Claim 1, Column 514, Lines 27 to 34, please replace:

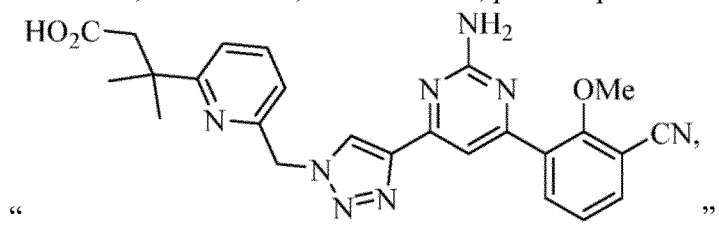

"                                                                                    "

With:

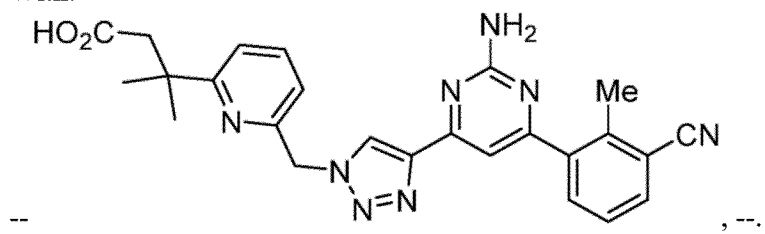

--                                                                                    , --.

In Claim 1, Column 515, Lines 9 to 17, please replace:

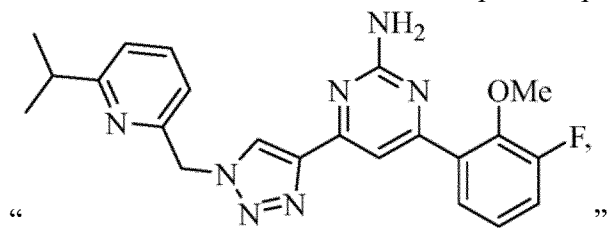

"                                                                                    "

With:

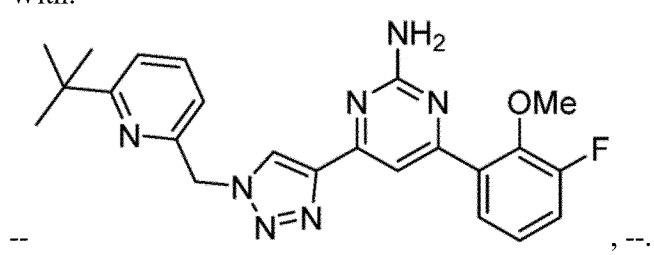

--                                                                                    , --.

CERTIFICATE OF CORRECTION (continued)
U.S. Pat. No. 12,195,447 B2

In Claim 1, Column 516, Lines 51 to 59, please replace:

"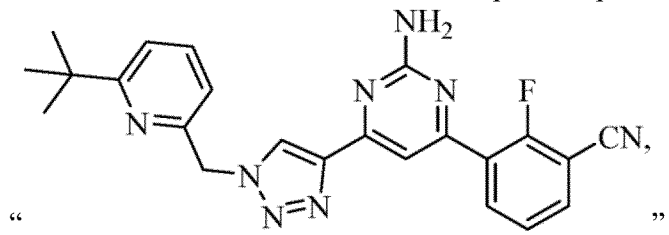"

With:

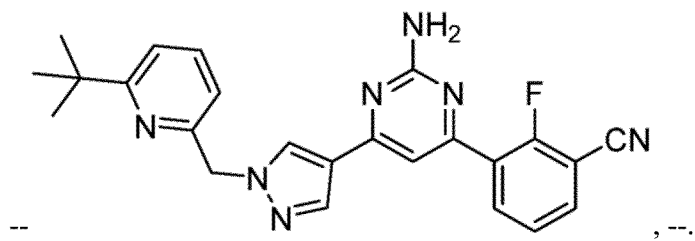

, --.

In Claim 1, Column 517, Lines 42 to 50, please replace:

"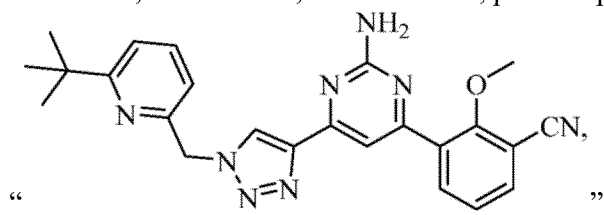"

With:

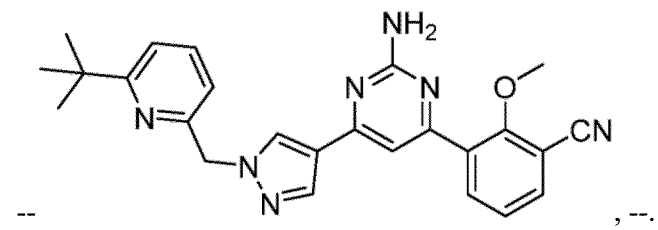

, --.

In Claim 1, Column 518, Lines 2 to 11, please replace:

"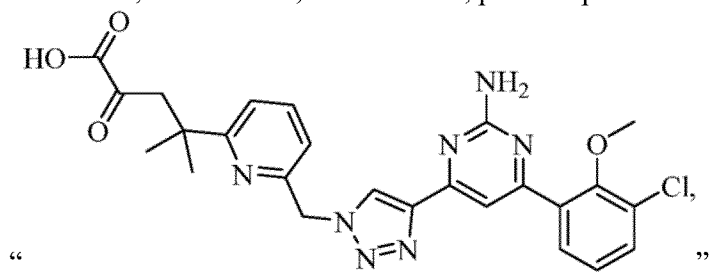"

With:
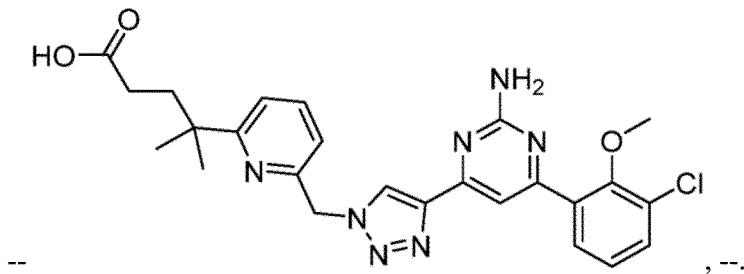
--                                                 , --.
In Claim 1, Column 519, Lines 18 to 26, please replace:
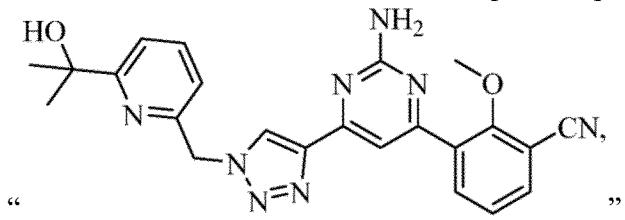
"                                                 "
With:
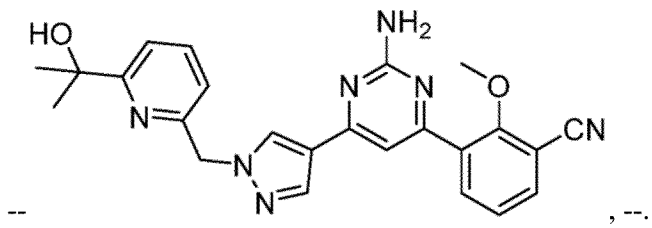
--                                                 , --.